US011028052B2

United States Patent
Chumakova et al.

(10) Patent No.: US 11,028,052 B2
(45) Date of Patent: Jun. 8, 2021

(54) COMPOUNDS USEFUL AS MODULATORS OF TRPM8

(71) Applicant: Firmenich Incorporated, Plainsboro, NJ (US)

(72) Inventors: Lyudmyla Chumakova, San Diego, CA (US); Andrew Patron, San Marcos, CA (US); Chad Priest, Cardiff, CA (US); Donald Karanewsky, Escondido, CA (US); Rachel Kimmich, San Diego, CA (US); Brant Clayton Boren, San Diego, CA (US); Jeffrey Robert Hammaker, San Diego, CA (US); Volodymyr Chumakov, San Diego, CA (US); Wen Zhao, San Diego, CA (US); Alain Noncovich, San Diego, CA (US); Jane Ung, San Diego, CA (US)

(73) Assignee: Firmenich Incorporated, Plainsboro, NJ (US)

( * ) Notice: Subject to any disclaimer, the term of this patent is extended or adjusted under 35 U.S.C. 154(b) by 0 days.

(21) Appl. No.: 16/574,657

(22) Filed: Sep. 18, 2019

(65) Prior Publication Data
US 2020/0010425 A1 Jan. 9, 2020

Related U.S. Application Data

(62) Division of application No. 15/697,301, filed on Sep. 6, 2017, now Pat. No. 10,421,727, which is a division
(Continued)

(51) Int. Cl.
| | | |
|---|---|---|
| *C07D 231/20* | (2006.01) | |
| *C07D 333/22* | (2006.01) | |
| *C07D 333/78* | (2006.01) | |
| *C07D 235/02* | (2006.01) | |
| *C07D 401/06* | (2006.01) | |

(Continued)

(52) U.S. Cl.
CPC ............... *C07D 231/20* (2013.01); *A23L 2/52* (2013.01); *A23L 33/10* (2016.08); *C07C 233/31* (2013.01); *C07D 207/26* (2013.01); *C07D 207/32* (2013.01); *C07D 207/333* (2013.01); *C07D 213/50* (2013.01); *C07D 233/78* (2013.01); *C07D 235/02* (2013.01); *C07D 239/22* (2013.01); *C07D 239/62* (2013.01); *C07D 333/22* (2013.01); *C07D 401/06* (2013.01); *C07D 403/06* (2013.01); *C07D 405/06* (2013.01); *C07D 409/06* (2013.01); *A23V 2002/00* (2013.01); *C07C 2601/04* (2017.05);
(Continued)

(58) Field of Classification Search
CPC ... C07D 239/22; C07D 239/62; C07D 235/02
See application file for complete search history.

(56) References Cited

U.S. PATENT DOCUMENTS

| | | | |
|---|---|---|---|
| 2,552,978 | A | 5/1951 | Kreuz |
| 4,443,616 | A | 4/1984 | Hofer |

(Continued)

FOREIGN PATENT DOCUMENTS

| | | |
|---|---|---|
| CA | 2474456 | 8/2001 |
| DE | 102008045220 | 3/2010 |

(Continued)

OTHER PUBLICATIONS

Henz et al, Journal of the American Chemical Society (1941), 63, 3360-3.*
Atkinson et al., Jan. 2013, Intromolecular arylation of amino acid enolates, Chemical Communications; 49(84):9734.
Bellucci et al., Dec. 21, 2011, Three-component, one-pot sequential synthesis of glyco-hydantoin conjugates, Organic & Biomolecular Chemistry, p. 8379.
(Continued)

*Primary Examiner* — Kamal A Saeed
(74) *Attorney, Agent, or Firm* — Knobbe Martens, Olson & Bear, LLP

(57) ABSTRACT

The present invention includes compounds useful as modulators of TRPM8, such as compounds of Formulae (Ia), (Ib) and (Ic), and the subgenus and species thereof; personal products containing those compounds; and the use of those compounds and the personal products, particularly the use of increasing or inducing chemesthetic sensations, such as cooling or cold sensations.

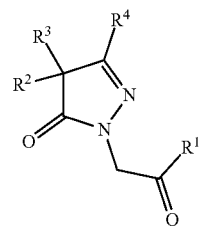

(Ia)

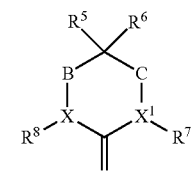

(Ib)

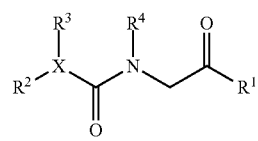

(Ic)

12 Claims, No Drawings

Related U.S. Application Data of application No. 14/768,146, filed as application No. PCT/US2014/017212 on Feb. 19, 2014, now Pat. No. 9,840,471.

(60) Provisional application No. 61/766,458, filed on Feb. 19, 2013, provisional application No. 61/829,530, filed on May 31, 2013, provisional application No. 61/829,367, filed on May 31, 2013.

(51) Int. Cl.
| | | |
|---|---|---|
| *C07D 403/06* | (2006.01) | |
| *C07D 239/22* | (2006.01) | |
| *C07D 405/06* | (2006.01) | |
| *C07D 409/06* | (2006.01) | |
| *C07D 207/32* | (2006.01) | |
| *C07D 213/50* | (2006.01) | |
| *A23L 2/52* | (2006.01) | |
| *C07C 233/31* | (2006.01) | |
| *C07D 207/26* | (2006.01) | |
| *C07D 207/33* | (2006.01) | |
| *C07D 239/62* | (2006.01) | |
| *A23L 33/10* | (2016.01) | |
| *C07D 233/78* | (2006.01) | |
| *C07D 207/333* | (2006.01) | |

(52) U.S. Cl.
CPC ...... *C07C 2601/14* (2017.05); *C07C 2601/16* (2017.05)

(56) References Cited

U.S. PATENT DOCUMENTS

| | | | |
|---|---|---|---|
| 5,175,191 | A | 12/1992 | Marks et al. |
| 5,391,560 | A | 2/1995 | Fuchs et al. |
| 6,049,006 | A | 4/2000 | Commons |
| 9,840,471 | B2 | 12/2017 | Chumakova et al. |
| 10,421,727 | B2 | 9/2019 | Chumakova et al. |

FOREIGN PATENT DOCUMENTS

| | | |
|---|---|---|
| JP | 10-045588 | 2/1998 |
| WO | WO 03/064394 | 8/2003 |
| WO | WO 11/002067 | 1/2011 |
| WO | WO 12/061698 | 5/2012 |

OTHER PUBLICATIONS

Buba et al., Jan. 2011, Z-selective hydroamidation of terminal alkynes with secondary amides and imides catalyzed by a Ru/Yb-system, Journal of Organometallic Chemistry, 696(1):170-178.

Cousin et al., Feb. 10, 2009, Mono-2,3 or 6-hydroxy methylated [beta]-cyclodextrin (eicosa-0-methyl-[beta]-cyclodextrin) isomers as chiral stationary phases for capillary GC, Chromatographia, 69:9-10.

Hall et al., 1999, Hypolipidemic triazolidine-3, 5-diones, 3,5-pyrazolidinediones, 3.5-isoxazolidinediones, 1,3,5-triazabicyclo[3.1.0]hexanes-2,4-diones as HMG-CoA reductase, ACAT, GPAT, and PP inhibitors and NCEH activators, Recent Research Developments in Lipds Research, 1:297-304.

Menck et al., Dec. 2012, Hollow-fiber liquid-phase microextraction and gas chromatography-mass spectrometry of barbiturates in whole blood samples: sample preparation, Journal of Separation Science, 35(23):3361-3368.

Olimpieri et al., Apr. 17, 2012, Supporting information regioselective multicomponent sequential synthesis of hydantoins, Organic & Biomolecular Chemistry, 10:9538-9555.

Tisse et al., Feb. 23, 2006, Capillary gas chromatographic properties of three new mono-ester permethylated _b-cyclodextrin derivatives, Analytica Chimica Acta, 560(1-2):207-217.

Wen et al., Jun. 4, 2009, Cu(I)-catalyzed diamination of disubstituted terminal olefins: an approach to potent NK 1 antagonist, Organic Letters, 11(11)L2365-2368.

Yuan et al., Jun. 2007, A mild Cu(I)-catalyzed regioselective diamination of conjugated dienes, Organic Letters, 9(13):2589-2591.

Zhao et al., Dec. 28, 2011, Cu(I)-catalyzed diamination of conjugated dienes. Complementary regioselectivity from two distinct mechanistic pathways involving Cu(II) and Cu(III) species, Journal of the American Chemical Society, 133(51):20890-20900.

International Search Report dated Sep. 4, 2014 in PCT/US13/017212.

Extended European Search Report dated Sep. 20, 2016 in patent application No. 14754162.7.

\* cited by examiner

COMPOUNDS USEFUL AS MODULATORS OF TRPM8

CROSS-REFERENCE TO RELATED APPLICATIONS

Any and all priority claims identified in the Application Data Sheet, or any correction thereto, are hereby incorporated by reference under 37 CFR 1.57. For example, this application is a divisional of U.S. patent application Ser. No. 15/697,301 having a filing date of Sep. 6, 2017, which is a divisional of U.S. patent application Ser. No. 14/768,146 having a 371(c)(1) date of Aug. 14, 2015 which is a U.S. National Phase of International Application No. PCT/US2014/017212 filed Feb. 19, 2014 and published on Aug. 28, 2014 as International Publication No. WO 2014/130582, which claims the benefit of U.S. Provisional Application No. 61/766,458 filed on Feb. 19, 2013, and U.S. Provisional Application Nos. 61/829,530 and 61/829,367 both filed on May 31, 2013, the contents of each of which are hereby incorporated by reference in their entireties for all purposes.

FIELD

The present invention relates to compounds useful as modulators of TRPM8.

BACKGROUND

The present invention provides compounds useful as modulators of the Melastatin Transient Receptor Potential Channel 8 (TRPM8). TRPM8 is a channel involved in the chemesthetic sensation, such as cool to cold temperatures as well as the sensation of known cooling agents, such as Menthol and Icilin. However, many of the currently known TRPM8 modulators have deficiencies with regard to strength and/or duration of effect, skin and/or mucosa irritation, odor, taste, solubility, and/or toxicity.

SUMMARY

In one embodiment, the present invention provides a five- or six-membered heterocyclic compound having structural Formula (Ia) or (Ib):

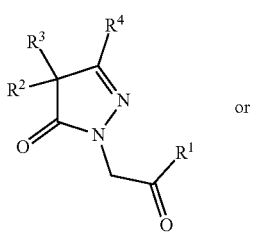

(Ia)

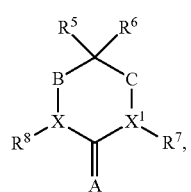

(Ib)

or a salt or solvate thereof;
wherein
$R^1$ is optionally substituted aryl, optionally substituted carbocyclyl, optionally substituted heteroaryl, or optionally substituted heterocyclyl;

$R^2$ and $R^3$ are independently selected from the group consisting of optionally substituted alkyl, optionally substituted alkenyl, optionally substituted aryl, optionally substituted carbocyclyl, optionally substituted heteroaryl, and optionally substituted heterocyclyl;

$R^4$ is optionally substituted alkyl, optionally substituted alkenyl, optionally substituted aryl, optionally substituted carbocyclyl, optionally substituted heteroaryl, or optionally substituted heterocyclyl;

either $R^5$ or $R^6$ is optionally substituted $C_1$-$C_3$ alkyl; and the remaining $R^5$ or $R^6$ is selected from the group consisting of optionally substituted alkyl, optionally substituted alkenyl, optionally substituted alkynyl, optionally substituted alkoxy, optionally substituted alkylaryl, optionally substituted alkoxyaryl, optionally substituted aryl, optionally substituted aryloxy, optionally substituted heteroaryl, optionally substituted heteroaryloxy, optionally substituted heteroalkyl, optionally substituted carbocyclyl, or optionally substituted heterocyclyl; or alternatively, $R^5$ and $R^6$, taken together with the atoms to which they are attached, form an optionally substituted carbocyclyl;

X and $X^1$ are independently CH or N; provided that X and $X^1$ are not both CH;

$R^7$ and $R^8$ are independently selected from the group consisting of hydrogen, halogen, hydroxyl, cyano, carboxy, optionally substituted $C_1$-$C_8$ alkyl, optionally substituted alkenyl, optionally substituted alkynyl, optionally substituted heteroalkyl, optionally substituted alkylaryl, optionally substituted alkoxyaryl, optionally substituted aryl, optionally substituted aryloxy, optionally substituted heteroaryl, optionally substituted heteroaryloxy, optionally substituted carbocyclyl, or optionally substituted heterocyclyl, -alkylene-carbonyl-aryl, -alkylene-carbonyl-heteroaryl, -alkylene-carbonyl-(substituted aryl), -alkylene-carbonyl-(substituted heteroaryl), -alkylene-carbonyl-O-aryl, -alkylene-carbonyl-O-(substituted aryl), -alkylene-carbonyl-$NR^9$-aryl, -alkylene-carbonyl-$NR^9$-(substituted aryl), -alkylene-carbonyl-O-heteroaryl, -alkylene-carbonyl-O-(substituted heteroaryl), -alkylene-carbonyl-$NR^9$-heteroaryl, -alkylene-carbonyl-$NR^9$-(substituted heteroaryl), $OR^9$, and $NR^9R^{10}$; or alternatively, X and $R^8$, or $X^1$ and $R^7$, taken together, is independently O or S;

A is O, S, or $NR^5$;

B and C are independently $CH_2$, C=O, or a covalent bond; provided that B and C are not both covalent bond; and $R^9$ and $R^{10}$ are independently selected from the group consisting of hydrogen, optionally substituted alkyl, optionally substituted aryl, optionally substituted arylalkyl, optionally substituted heteroalkyl, optionally substituted heteroaryl, optionally substituted heteroarylalkyl, optionally substituted acylamido, and optionally substituted diacylamido; or alternatively, $R^9$ and $R^{10}$, together with the atoms to which they are bonded, form an optionally substituted cycloheteroalkyl.

In one embodiment, the present invention provides a compound having structural Formula (Ic):

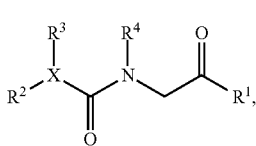

(Ic)

or a salt or solvate thereof;
wherein
    X is $CR^5$ or N;
    $R^1$ is optionally substituted aryl, optionally substituted carbocyclyl, optionally substituted heteroaryl, or optionally substituted heterocyclyl;
    $R^2$ and $R^3$ are the same or different and are independently selected from the group consisting of hydrogen, optionally substituted alkyl, optionally substituted alkenyl, optionally substituted aryl, optionally substituted carbocyclyl, optionally substituted heteroaryl, and optionally substituted heterocyclyl;
    $R^4$ is hydrogen, hydroxyl, alkoxy, optionally substituted alkyl, optionally substituted alkenyl, optionally substituted aryl, optionally substituted carbocyclyl, optionally substituted heteroaryl, or optionally substituted heterocyclyl; and
    $R^5$ is hydrogen, optionally substituted alkyl, optionally substituted alkenyl, optionally substituted aryl, optionally substituted carbocyclyl, optionally substituted heteroaryl, or optionally substituted heterocyclyl; or alternatively, $R^3$ and $R^5$, or $R^3$ and $R^4$, taken together with the atoms to which they are attached, form an optionally substituted carbocyclyl or optionally substituted heterocyclyl.

In another embodiment, the present invention provides a personal product comprising a compound of the present invention, or a salt or solvate thereof.

In another embodiment, the present invention provides a method of modulating transient receptor potential channel melastatin member 8 (TRPM8) comprising contacting the receptor with a compound of the present invention, or a salt or solvate thereof.

In another embodiment, the present invention provides a method of modulating the cooling sensation of a composition comprising combining the composition with a compound of the present invention, or a salt or solvate thereof, to form a modified composition.

In another embodiment, the present invention provides a method of inducing a cooling sensation in a human or animal comprising contacting the human or animal with a compound of the present invention, or a salt or solvate thereof.

In another embodiment, the present invention provides a method of treating a condition, disease, or disorder associated with a TRPM8 receptor comprising administering to a subject in need of such treatment an therapeutically effective amount of a compound of the present invention, or a salt or solvate thereof.

DETAILED DESCRIPTIONS OF THE INVENTION

Various embodiments and advantages of the present invention will be set forth in part in the description that follows, and in part will be obvious from the description, or may be learned by practice of the invention. It is to be understood that both the foregoing general description and the following detailed description are exemplary and explanatory only and are not restrictive of the invention as described.

Definitions

The terms "a" and "an" do not denote a limitation of quantity, but rather denote the presence of at least one of the referenced item. The term "or" or "and/or" is used as a function word to indicate that two words or expressions are to be taken together or individually. The terms "comprising", "having", "including", and "containing" are to be construed as open-ended terms (i.e., meaning "including, but not limited to"). The endpoints of all ranges directed to the same component or property are inclusive and independently combinable.

The term "present compound(s)" or "compound(s) of the present invention" refers to compounds encompassed by structural formula disclosed herein, such as Formula (I), Formula (Ia), and includes any subgenus and specific compounds within the formula whose structure is disclosed herein. Compounds may be identified either by their chemical structure and/or chemical name. When the chemical structure and chemical name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in unsolvated forms as well as solvated forms, including hydrated forms and as N-oxides. In general, compounds may be hydrated, solvated or N-oxides. Certain compounds may exist in multiple crystalline or amorphous forms. In general, all physical forms are equivalent for the uses contemplated herein and are intended to be within the scope of the present invention. Further, it should be understood, when partial structures of the compounds are illustrated, that brackets indicate the point of attachment of the partial structure to the rest of the molecule. The term "tautomer" as used herein refers to isomers that change into one another with great ease so that they can exist together in equilibrium.

"Alkyl," by itself or as part of another substituent, refers to a saturated branched, straight-chain or cyclic monovalent hydrocarbon radical derived by the removal of one hydrogen atom from a single carbon atom of a parent alkane. The term "alkyl" includes "cycloakyl" as defined herein below. Typical alkyl groups include, but are not limited to, methyl; ethyl; propyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl) or 1 to 4 carbon atoms ($C_1$-$C_4$ alkyl). $C_1$-$C_6$ alkyl is also known as "lower alkyl".

It is noted that when an alkyl group is further connected to another atom, it becomes an "alkylene" group. In other words, the term "alkylene" refers to a divalent alkyl. For example, —CH$_2$CH$_3$ is an ethyl, while —CH$_2$CH$_2$— is an ethylene. That is, "Alkylene," by itself or as part of another substituent, refers to a saturated or unsaturated, branched, straight-chain or cyclic divalent hydrocarbon radical derived by the removal of two hydrogen atoms from a single carbon atom or two different carbon atoms of a parent alkane, alkene or alkyne. The term "alkylene" includes "cycloalkylene" as defined herein below. The term "alkylene" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. In some embodiments, an alkylene group comprises from 1 to 20 carbon atoms (C$_1$-C$_{20}$ alkylene). In other embodiments, an alkylene group comprises from 1 to 10 carbon atoms (C$_1$-C$_{10}$ alkylene). In still other embodiments, an alkylene group comprises from 1 to 6 carbon atoms (C$_1$-C$_6$ alkylene).

"Alkenyl," by itself or as part of another substituent, refers to an unsaturated branched, straight-chain or cyclic monovalent hydrocarbon radical having at least one carbon-carbon double bond derived by the removal of one hydrogen atom from a single carbon atom of a parent alkene. The term "alkenyl" includes "cycloalkenyl" as defined herein below. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, an alkenyl group comprises from 1 to 20 carbon atoms (C$_2$-C$_{20}$ alkenyl). In other embodiments, an alkenyl group comprises from 1 to 10 carbon atoms (C$_2$-C$_{10}$ alkenyl). In still other embodiments, an alkenyl group comprises from 1 to 6 carbon atoms (C$_2$-C$_6$ alkenyl) or 1 to 4 carbon atoms (C$_2$-C$_4$ alkenyl). C$_2$-C$_6$ alkenyl is also known as "lower alkenyl".

"Alkynyl," by itself or as part of another substituent refers to an unsaturated branched, straight-chain or cyclic monovalent hydrocarbon radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like. In some embodiments, an alkynyl group comprises from 1 to 20 carbon atoms (C$_2$-C$_{20}$ alkynyl). In other embodiments, an alkynyl group comprises from 1 to 10 carbon atoms (C$_2$-C$_{10}$ alkynyl). In still other embodiments, an alkynyl group comprises from 1 to 6 carbon atoms (C$_2$-C$_6$ alkynyl) or 1 to 4 carbon atoms (C$_2$-C$_4$ alkynyl). C$_2$-C$_6$ alkynyl is also known as "lower alkynyl".

"Alkoxy," by itself or as part of another substituent, refers to a radical of the formula —O—R$^{199}$, where R$^{199}$ is alkyl or substituted alkyl as defined herein.

"Acyl" by itself or as part of another substituent refers to a radical —C(O)R$^{200}$, where R$^{200}$ is hydrogen, alkyl, substituted alkyl, aryl, substituted aryl, arylalkyl, substituted arylalkyl, heteroalkyl, substituted heteroalkyl, heteroarylalkyl or substituted heteroarylalkyl as defined herein. Representative examples include, but are not limited to formyl, acetyl, cyclohexylcarbonyl, cyclohexylmethylcarbonyl, benzoyl, benzylcarbonyl and the like.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms (C$_6$-C$_{20}$ aryl). In other embodiments, an aryl group comprises from 6 to 15 carbon atoms (C$_6$-C$_{15}$ aryl). In still other embodiments, an aryl group comprises from 6 to 10 carbon atoms (C$_6$-C$_{10}$ aryl).

"Arylalkyl," by itself or as part of another substituent, refers to an acyclic alkyl group in which one of the hydrogen atoms bonded to a carbon atom, typically a terminal or sp$^3$ carbon atom, is replaced with an aryl group as, as defined herein. That is, arylakyl can also be considered as an alkyl substituted by aryl. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is (C$_6$-C$_{30}$) arylalkyl, e.g., the alkanyl, alkenyl or alkynyl moiety of the arylalkyl group is (C$_1$-C$_{10}$) alkyl and the aryl moiety is (C$_6$-C$_{20}$) aryl. In other embodiments, an arylalkyl group is (C$_6$-C$_{20}$) arylalkyl, e.g., the alkanyl, alkenyl or alkynyl moiety of the arylalkyl group is (C$_1$-C$_8$) alkyl and the aryl moiety is (C$_6$-C$_{12}$) aryl. In still other embodiments, an arylalkyl group is (C$_6$-C$_{15}$) arylalkyl, e.g., the alkanyl, alkenyl or alkynyl moiety of the arylalkyl group is (C$_1$-C$_5$) alkyl and the aryl moiety is (C$_6$-C$_{10}$) aryl.

"Carbocyclic," or "Carbocyclyl," by itself or as part of another substituent, refers to a saturated or partially saturated, buy not aromatic, cyclic monovalent hydrocarbon radical, including cycloalkyl, cycloalkenyl, and cycloalkynyl as defined herein. Typical carbocyclyl groups include, but are not limited to, groups derived from cyclopropane, cyclobutane, cyclopentane, cyclohexane, and the like. In some embodiments, the cycloalkyl group comprises from 3 to 10 ring atoms (C$_3$-C$_{10}$ cycloalkyl). In other embodiments, the cycloalkyl group comprises from 3 to 7 ring atoms (C$_3$-C$_7$ cycloalkyl). The carbocyclyl may be further substituted by one or more heteroatoms including, but not limited to, N, P, O, S, and Si, which attach to the carbon atoms of the cycloalkyl via monovalent or multivalent bond.

"Heteroalkyl," by themselves or as part of other substituents, refer to alkyl groups, in which one or more of the carbon atoms, are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl group. Typical heteroatomic groups which can be included in these groups include, but are not limited to, —O—, —S—, —O—O—, —S—S—, —O—S—, —NR$^{201}$R$^{202}$—, =N—N=, —N=N—, —N=N—NR$^{203}$R$^{204}$, —PR$^{205}$—, —P(O)$_2$—, —POR$^{206}$—, —O—P $(O)_2$—, —SO—, —$SO_2$—, —$SnR^{207}R^{208}$— and the like, where $R^{201}$, $R^{202}$, $R^{203}$, $R^{204}$, $R^{205}$, $R^{206}$, $R^{207}$ and $R^{208}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heterocyclic," or "Heterocyclyl," by itself or as part of another substituent, refers to a carbocyclic radical in which one or more carbon atoms are independently replaced with the same or different heteroatom. The heterocyclyl may be further substituted by one or more heteroatoms including, but not limited to, N, P, O, S, and Si, which attach to the carbon atoms of the heterocyclyl via monovalent or multivalent bond. Typical heteroatoms to replace the carbon atom(s) include, but are not limited to, N, P, O, S, Si, etc. Typical heterocyclyl groups include, but are not limited to, groups derived from epoxides, azirines, thiiranes, imidazolidine, morpholine, piperazine, piperidine, pyrazolidine, pyrrolidone, quinuclidine, and the like. In some embodiments, the heterocyclyl group comprises from 3 to 10 ring atoms (3-10 membered heterocyclyl) In other embodiments, the heterocyclyl group comprise from 5 to 7 ring atoms (5-7 membered heterocyclyl). A cycloheteroalkyl group may be substituted at a heteroatom, for example, a nitrogen atom, with a ($C_1$-$C_6$) alkyl group. As specific examples, N-methyl-imidazolidinyl, N-methyl-morpholinyl, N-methyl-piperazinyl, N-methyl-piperidinyl, N-methyl-pyrazolidinyl and N-methyl-pyrrolidinyl are included within the definition of "heterocyclyl." A heterocyclyl group may be attached to the remainder of the molecule via a ring carbon atom or a ring heteroatom.

"Halo," by itself or as part of another substituent refers to a radical —F, —Cl, —Br or —I.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from 5 to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl" by itself or as part of another substituent refers to an acyclic alkyl group in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylakenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is ($C_1$-$C_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is ($C_1$-$C_3$) alkyl and the heteroaryl moiety is a 5-10 membered heteroaryl.

"N-oxide", also known as amine oxide or amine-N-oxide, means a compound that derives from a compound of the present invention via oxidation of an amine group of the compound of the present invention. An N-oxide typically contains the functional group $R_3N^+$—$O^-$ (sometimes written as $R_3N$=O or $R_3N{\rightarrow}O$).

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Solvate" means a compound formed by solvation (the combination of solvent molecules with molecules or ions of the solute), or an aggregate that consists of a solute ion or molecule, i.e., a compound of the present invention, with one or more solvent molecules. When water is the solvent, the corresponding solvate is "hydrate".

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include, but are not limited to —$R^a$, halo, —$O^-$, =O, —$OR^b$, —$SR^b$, —$S^-$, =S, —$NR^cR^c$, =$NR^b$, =N—$OR^b$, trihalomethyl, —$CF_3$, —CN, —OCN, —SCN, —NO, —NO$_2$, =N$_2$, —N$_3$, —S(O)$_2^b$, —S(O)$_2$NR$^b$, —S(O)$_2$O—, —S(O)$_2$OR$^b$, —OS(O)$_2$R$^b$, —OS(O)$_2$O$^-$, —OS(O)$_2$OR$^b$, —P(O)(O$^-$)$_2$, —P(O)(OR$^b$)(O$^-$), —P(O)(OR$^b$)(OR$^b$), —C(O)$^b$, —C(S)$^b$, —C(NR$^b$)$^b$, —C(O)O$^-$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)O-, —OC(O)OR$^b$, —OC(S)OR$^b$, —NR$^b$C(O)R$^b$, —NR$^b$C(S)R$^b$, —NR$^b$C(O)O$^-$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$ is selected from the group consisting of alkyl, cycloalkyl, heteroalkyl, cycloheteroalkyl, aryl, arylalkyl, heteroaryl and heteroarylalkyl; each R$^b$ is independently hydrogen or R$^a$; and each R$^c$ is independently R$^b$ or alternatively, the two R$^c$s may be taken together with the nitrogen atom to which they are bonded form a 4-, 5-, 6- or 7-membered cycloheteroalkyl which may optionally include from 1 to 4 of the same or different additional heteroatoms selected from the group consisting of O, N and S. As specific examples, —NR$^c$R$^c$ is meant to include —NH$_2$, —NH-alkyl, N-pyrrolidinyl and N-morpholinyl. As another specific example, a substituted alkyl is meant to include -alkylene-O-alkyl, -alkylene-heteroaryl, -alkylene-cycloheteroalkyl, -alkylene-C(O)OR$^b$, alkylene-C(O)NR$^b$R$^b$, and —CH$_2$—CH$_2$—C(O)—CH$_3$. The one or more substituent groups, taken together with the atoms to which they are bonded, may form a cyclic ring including cycloalkyl and cycloheteroalkyl.

Similarly, substituent groups useful for substituting unsaturated carbon atoms in the specified group or radical include, but are not limited to, —R$^a$, halo, —O-, —OR$^b$, —SR$^b$, —S-, —NR$^c$R$^c$, trihalomethyl, —CF$_3$, —CN, —OCN, —SCN, —NO, —NO$_2$, —N$_3$, —S(O)$_2^b$, —S(O)$_2$O—, —S(O)$_2$OR$^b$, —OS(O)$_2^b$, —OS(O)$_2$O-, —OS(O)$_2$OR$^b$, —P(O)(O$^-$)$_2$, —P(O)(OR$^b$)(O$^-$), —P(O)(OR$^b$)(OR$^b$), —C(O)$^b$, —C(S)$^b$, —C(NR$^b$)$^b$, —C(O)O-, —C(O)OR$^b$, —C(S)OR$^b$, —C(O)NR$^c$R$^c$, —C(NR$^b$)NR$^c$R$^c$, —OC(O)$^b$, —OC(S)$^b$, —OC(O)O-, —OC(O)OR$^b$, —OC(S)OR$^b$, —NR$^b$C(O)$^b$, —NR$^b$C(S)$^b$, —NR$^b$C(O)O$^-$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined.

Substituent groups useful for substituting nitrogen atoms in heteroalkyl and cycloheteroalkyl groups include, but are not limited to, —R$^a$, —O-, —OR$^b$, —SR$^b$, —S-, —NR$^c$R$^c$, trihalomethyl, —CF$_3$, —CN, —NO, —NO$_2$, —S(O)$_2^b$, —S(O)$_2$O-, —S(O)$_2$OR$^b$, —OS(O)$_2^b$, —OS(O)$_2$O$^-$, —OS(O)$_2$OR$^b$, —P(O)(O$^-$)$_2$, —P(O)(OR$^b$)(O$^-$), —P(O)(OR$^b$)(OR$^b$), —C(O)R$^b$, —C(S)R$^b$, —C(NR$^b$)$^b$, —C(O)OR$^b$, —C(S)OR$^b$, —C(O)NR$^c$R$^c$, —C(NR$^b$)NR$^c$R$^c$, —OC(O)$^b$, —OC(S)$^b$, —OC(O)OR$^b$, —OC(S)OR$^b$, —NR$^b$C(O)R$^b$, —NR$^b$C(S)R$^b$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined.

Substituent groups from the above lists useful for substituting other specified groups or atoms will be apparent to those of skill in the art.

The term "substituted" specifically envisions and allows for one or more substitutions that are common in the art. However, it is generally understood by those skilled in the art that the substituents should be selected so as to not adversely affect the useful characteristics of the compound or adversely interfere with its function. Suitable substituents may include, for example, halogen groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, arylalkyl or heteroarylalkyl groups, arylalkoxy or heteroarylalkoxy groups, amino groups, alkyl- and dialkylamino groups, carbamoyl groups, alkylcarbonyl groups, carboxyl groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups, cycloalkyl groups, cyano groups, C$_1$-C$_6$ alkylthio groups, arylthio groups, nitro groups, keto groups, acyl groups, boronate or boronyl groups, phosphate or phosphonyl groups, sulfamyl groups, sulfonyl groups, sulfinyl groups, and combinations thereof. In the case of substituted combinations, such as "substituted arylalkyl," either the aryl or the alkyl group may be substituted, or both the aryl and the alkyl groups may be substituted with one or more substituents. Additionally, in some cases, suitable substituents may combine to form one or more rings as known to those of skill in the art.

The term "optionally substituted" denotes the presence or absence of the substituent group(s). That is, it means "substituted or unsubstituted". For example, optionally substituted alkyl includes both unsubstituted alkyl and substituted alkyl. The substituents used to substitute a specified group can be further substituted, typically with one or more of the same or different groups selected from the various groups specified above.

"Carrier" refers to a diluent, adjuvant, excipient or vehicle with which a compound is administered.

The term "chemesthesis" or "chemesthetic sensation" herein refers to the sensibility of bodily surface, e.g., the skin and/or mucosal surfaces which arise either when the bodily surface is exposed to heat or coldness or when chemical compounds activate receptors associated with senses that mediate pain, touch, and thermal/cold perception. Particularly, these chemical-induced reactions do not fit into the traditional sense categories of taste and smell. Examples of chemesthetic sensations include the burn-like irritation from chili pepper, the coolness of menthol in mouthwashes and topical analgesic creams, the stinging or tingling of carbonation in the nose and mouth, and the tear-induction of onions. That is, chemesthetic sensations can arise by direct chemical activation of ion channels on sensory nerve fibers, e.g. TRPM8. Because chemoresponsive nerve fibers are present in all types of skin, chemesthetic sensations can be aroused from anywhere on the body's surface as well as from mucosal surfaces in the nose, mouth, eyes, etc.

A "chemesthetic sensation modifier" or "chemesthetic sensation modifying agent" herein refers to a compound, or a salt or solvate thereof, which modulates, including enhancing or potentiating, inducing, or blocking, the chemesthetic sensation in an animal or a human.

A "chemesthetic sensation modulating amount" herein refers to an amount of a compound of the present invention that is sufficient to alter (either induce, increase, or decrease) the chemesthetic sensation in a personal product, sufficiently to be perceived by an animal or human subject. In many embodiments of the invention, at least about 0.001 ppm of the present compound would need to be present in order for most animal or human subjects to perceive a modulation of the chemesthetic sensation in a personal product comprising the present compound. A broad range of concentration that would typically be employed in order to economically provide a desirable degree of chemesthetic sensation modulation can be from about 0.001 ppm to 1000 ppm, or from about 0.01 ppm to about 500 ppm, or from about 0.05 ppm to about 300 ppm, or from about 0.1 ppm to about 200 ppm, or from about 0.5 ppm to about 150 ppm, or from about 1 ppm to about 100 ppm.

A "chemesthetic sensation inducing amount" or "chemesthetic sensation increasing amount" herein refers to an amount of a compound that is sufficient to induce or increase a chemesthetic sensation as perceived by an animal or a human. A broad range of a chemesthetic sensation inducing/increasing amount can be from about 0.001 ppm to 100 ppm, or a narrow range from about 0.1 ppm to about 10 ppm. Alternative ranges of chemesthetic sensation inducing/increasing amounts can be from about 0.01 ppm to about 30 ppm, from about 0.05 ppm to about 15 ppm, from about 0.1 ppm to about 5 ppm, or from about 0.1 ppm to about 3 ppm.

As used herein, an "ingestible composition" includes any substance that, either alone or together with another substance, can be taken by mouth whether intended for consumption or not. The ingestible composition includes both "food or beverage products" and "non-edible products". By "Food or beverage products", it is meant any edible product intended for consumption by humans or animals, including solids, semi-solids, or liquids (e.g., beverages). The term "non-edible products" or "noncomestible composition" includes any product or composition that can be taken by humans or animals for purposes other than consumption or as food or beverage. For example, the non-edible product or noncomestible composition includes supplements, nutraceuticals, functional food products (e.g., any fresh or processed food claimed to have a health-promoting and/or disease-preventing properties beyond the basic nutritional function of supplying nutrients), pharmaceutical and over the counter medications, oral care products such as dentifrices and mouthwashes, cosmetic products such as sweetened lip balms and other personal care products that may or may not contain any sweetener.

A "ingestibly acceptable carrier or excipient" is a medium and/or composition that is used to prepare a desired dispersed dosage form of the inventive compound, in order to administer the inventive compound in a dispersed/diluted form, so that the biological effectiveness of the inventive compound is maximized. The medium and/or composition may be in any form depending on the intended use of a product, e.g., solid, semi-solid, liquid, paste, gel, lotion, cream, foamy material, suspension, solution, or any combinations thereof (such as a liquid containing solid contents). Ingestibly acceptable carriers includes many common food ingredients, such as water at neutral, acidic, or basic pH, fruit or vegetable juices, vinegar, marinades, beer, wine, natural water/fat emulsions such as milk or condensed milk, edible oils and shortenings, fatty acids and their alkyl esters, low molecular weight oligomers of propylene glycol, glyceryl esters of fatty acids, and dispersions or emulsions of such hydrophobic substances in aqueous media, salts such as sodium chloride, wheat flours, solvents such as ethanol, solid edible diluents such as vegetable powders or flours, or other liquid vehicles; dispersion or suspension aids; surface active agents; isotonic agents; thickening or emulsifying agents, preservatives; solid binders; lubricants and the like.

A "flavor" herein refers to the perception of taste in a subject, which include sweet, sour, salty, bitter and umami (also known as savory). The subject may be a human or an animal.

A "flavoring agent" herein refers to a compound or the ingestibly acceptable salt or solvate thereof that induces a flavor or taste in an animal or a human. The flavoring agent can be natural, semi-synthetic, or synthetic.

A "modulator" herein refers to a compound that can regulate the activity of TRPM8. Such regulation includes activating TRPM8, blocking TRPM8, or potentiating/reducing the activation of TRPM8. That is, the modulators include agonists, antagonists, enhancers, and etc.

A "personal product", as used herein, refers to any product that is used by or useful for a person or animal, optionally in contact with the person or animal during its intended use, e.g., in surface contact such as skin or mucosa contact with the person or animal during its intended use.

"Treating" or "treatment" of any condition, disease or disorder refers to ameliorating the condition, disease or disorder (i.e., arresting or reducing the development of the condition, disease or disorder or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the condition, disease or disorder, either physically, (e.g., stabilization of a discernible symptom), physiologically, (e.g., stabilization of a physical parameter) or both. In yet other embodiments, "treating" or "treatment" refers to delaying the onset of the condition, disease or disorder.

"Therapeutically effective amount" means the amount of the present compound that, when administered to a patient for treating a condition, disease or disorder, is sufficient to effect such treatment for the condition, disease or disorder. The "therapeutically effective amount" will vary depending on the compound, the condition, disease or disorder and its severity and the age, weight, etc., of the patient to be treated.

Embodiments of the Compounds

In one embodiment, the present invention provides a five- or six-membered heterocyclic compound having structural Formula (Ia) or (Ib):

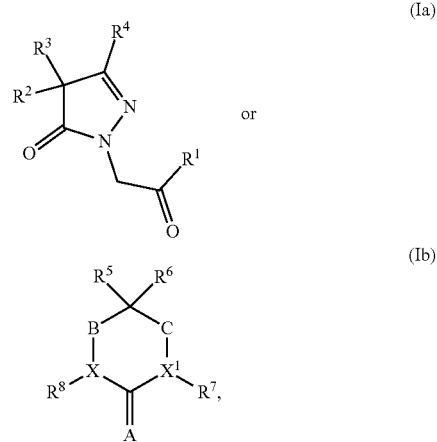

or a salt or solvate thereof;
wherein
$R^1$ is optionally substituted aryl, optionally substituted carbocyclyl, optionally substituted heteroaryl, or optionally substituted heterocyclyl;

$R^2$ and $R^3$ are independently selected from the group consisting of optionally substituted alkyl, optionally substituted alkenyl, optionally substituted aryl, optionally substituted carbocyclyl, optionally substituted heteroaryl, and optionally substituted heterocyclyl;

$R^4$ is optionally substituted alkyl, optionally substituted alkenyl, optionally substituted aryl, optionally substituted carbocyclyl, optionally substituted heteroaryl, or optionally substituted heterocyclyl;

either $R^5$ or $R^6$ is optionally substituted $C_1$-$C_3$ alkyl; and the remaining $R^5$ or $R^6$ is selected from the group consisting of optionally substituted alkyl, optionally substituted alkenyl, optionally substituted alkynyl, optionally substituted alkoxy, optionally substituted alkylaryl, optionally substituted alkoxyaryl, optionally substituted aryl, optionally substituted aryloxy, optionally substituted heteroaryl, optionally substituted heteroaryloxy, optionally substituted heteroalkyl, optionally substituted carbocyclyl, or optionally substituted heterocyclyl; or alternatively, $R^5$ and $R^6$, taken together with the atoms to which they are attached, form an optionally substituted carbocyclyl;

X and $X^1$ are independently CH or N; provided that X and $X^1$ are not both CH;

$R^7$ and $R^8$ are independently selected from the group consisting of hydrogen, halogen, hydroxyl, cyano, carboxy, optionally substituted $C_1$-$C_8$ alkyl, optionally substituted alkenyl, optionally substituted alkynyl, optionally substituted heteroalkyl, optionally substituted alkylaryl, optionally substituted alkoxyaryl, optionally substituted aryl, optionally substituted aryloxy, optionally substituted heteroaryl, optionally substituted heteroaryloxy, optionally substituted carbocyclyl, or optionally substituted heterocyclyl, -alkylene-carbonyl-aryl, -alkylene-carbonyl-heteroaryl, -alkylene-carbonyl-(substituted aryl), -alkylene-carbonyl-(substituted heteroaryl), -alkylene-carbonyl-O-aryl, -alkylene-carbonyl-O-(substituted aryl), -alkylene-carbonyl-$NR^9$-aryl, -alkylene-carbonyl-$NR^9$-(substituted aryl), -alkylene-carbonyl-O-heteroaryl, -alkylene-carbonyl-O-(substituted heteroaryl), -alkylene-carbonyl-$NR^9$-heteroaryl, -alkylene-carbonyl-$NR^9$-(substituted heteroaryl), $OR^9$, and $NR^9R^{10}$; or alternatively, X and $R^8$, or $X^1$ and $R^7$, taken together, is independently O or S;

A is O, S, or $NR^5$;

B and C are independently $CH_2$, C=O, or a covalent bond; provided that B and C are not both covalent bond; and $R^9$ and $R^{10}$ are independently selected from the group consisting of hydrogen, optionally substituted alkyl, optionally substituted aryl, optionally substituted arylalkyl, optionally substituted heteroalkyl, optionally substituted heteroaryl, optionally substituted heteroarylalkyl, optionally substituted acylamido, and optionally substituted diacylamido; or alternatively, $R^9$ and $R^{10}$, together with the atoms to which they are bonded, form an optionally substituted cycloheteroalkyl.

In one embodiment of Formula (Ia) or (Ib), the optionally substituted carbocyclyl or optionally substituted heterocyclyl is optionally substituted cycloalkyl, optionally substituted cycloalkenyl, optionally substituted cycloheteroalkyl, or optionally substituted cycloheteroalkenyl.

In one embodiment, the present invention provides a five-membered heterocyclic compound having structural Formula (Ia) or (Ib):

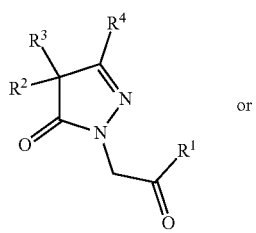

(Ia)

or

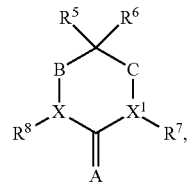

(Ib)

or a salt or solvate thereof;
wherein
$R^1$ is optionally substituted aryl, optionally substituted carbocyclyl, optionally substituted heteroaryl, or optionally substituted heterocyclyl;

$R^2$ and $R^3$ are independently selected from the group consisting of optionally substituted alkyl, optionally substituted alkenyl, optionally substituted aryl, optionally substituted carbocyclyl, optionally substituted heteroaryl, and optionally substituted heterocyclyl;

$R^4$ is optionally substituted alkyl, optionally substituted alkenyl, optionally substituted aryl, optionally substituted carbocyclyl, optionally substituted heteroaryl, or optionally substituted heterocyclyl;

either $R^5$ or $R^6$ is $C_1$-$C_3$ alkyl, and the remaining $R^5$ or $R^6$ is selected from the group consisting of optionally substituted alkyl, optionally substituted alkenyl, optionally substituted alkynyl, optionally substituted alkylaryl, optionally substituted heteroalkyl, optionally substituted carbocyclyl, or optionally substituted heterocyclyl; or alternatively, $R^5$ and $R^6$, taken together with the atoms to which they are attached, form an optionally substituted carbocyclic ring;

X and $X^1$ are N;

$R^7$ is hydrogen, or optionally substituted $C_1$-$C_6$ alkyl;

$R^8$ is selected from the group consisting of optionally substituted $C_1$-$C_8$ alkyl, optionally substituted alkenyl, -alkylene-carbonyl-aryl, -alkylene-carbonyl-heteroaryl, -alkylene-carbonyl-(substituted aryl), -alkylene-carbonyl-(substituted heteroaryl), -alkylene-carbonyl-O-aryl, -alkylene-carbonyl-O-(substituted aryl), -alkylene-carbonyl-$NR^9$-aryl, alkylene-carbonyl-$NR^9$-(substituted aryl), -alkylene-carbonyl-O-heteroaryl, -alkylene-carbonyl-O-(substituted heteroaryl), -alkylene-carbonyl-$NR^9$-heteroaryl, and -alkylene-carbonyl-$NR^9$-(substituted heteroaryl);

$R^9$ is selected from the group consisting of hydrogen, optionally substituted alkyl, optionally substituted aryl, optionally substituted arylalkyl, optionally substituted heteroalkyl, optionally substituted heteroaryl, optionally substituted heteroarylalkyl, optionally substituted acylamido, and optionally substituted diacylamido;

A is O;

B is $CH_2$, or C=O; and

C is a covalent bond.

In one embodiment of Formula (Ia), $R^1$ is optionally substituted aryl or optionally substituted heteroaryl. In one embodiment of $R^1$, the optionally substituted heteroaryl is a five- or six-membered heteroaryl containing one or more heteroatoms selected from nitrogen, oxygen, and sulfur. In one embodiment of $R^1$, the optionally substituted aryl is optionally substituted phenyl; and the optionally substituted heteroaryl is selected from the group consisting of pyrrolyl, thienyl, pyridyl, pyrimidyl, furanyl, and pyrazolyl, each of which is optionally substituted.

In one embodiment of Formula (Ia), $R^2$ is optionally substituted aryl, optionally substituted carbocyclyl, optionally substituted heteroaryl, and optionally substituted heterocyclyl. In one embodiment of $R^2$, the optionally substituted carbocyclyl is an optionally substituted 5- or 6-membered monocyclic carbocyclyl, or an optionally substituted 9- to 12-membered bicyclic carbocyclyl.

In one embodiment of Formula (Ia), $R^3$ is optionally substituted alkyl or optionally substituted alkenyl. In one embodiment of Formula (Ia), $R^3$ is optionally substituted $C_1$-$C_4$ alkyl.

In one embodiment of Formula (Ia), $R^2$ is optionally substituted carbocyclyl; and $R^3$ is optionally substituted alkyl.

In one embodiment of Formula (Ia), $R^4$ is optionally substituted alkyl. In one embodiment of Formula (Ia), $R^4$ is optionally substituted $C_1$-$C_4$ alkyl.

In one embodiment of Formula (Ia), the optional substituent may be one or more substituent(s) selected from the group consisting of alkyl, alkoxy, hydroxyl, amino, N-alkyl amino, N-dialkyl amino, halo, nitro, cyano, acyl, carboxyl, carboxyl ester, or amide; or two substituents, together with the atoms to which they are attached, form an optionally substituted carbocyclyl or heterocyclyl containing one or more heteroatom(s) selected from nitrogen, oxygen, and sulfur.

In some specific embodiments of Formula (Ia), the present compound is selected from the group consisting of:

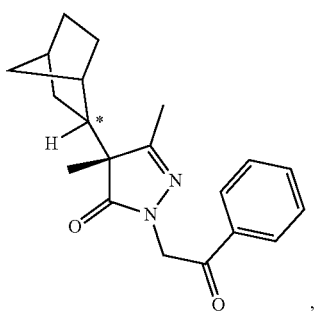

,

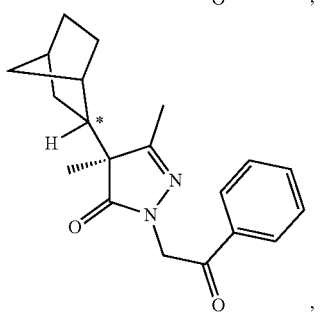

,

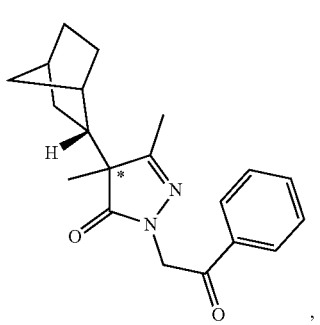

,

-continued

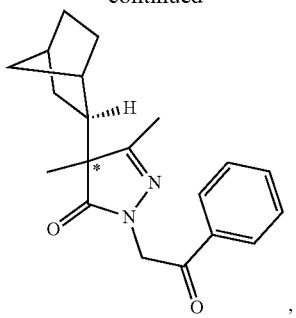

,

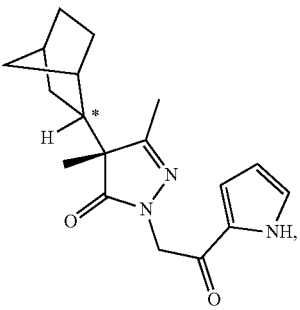

,

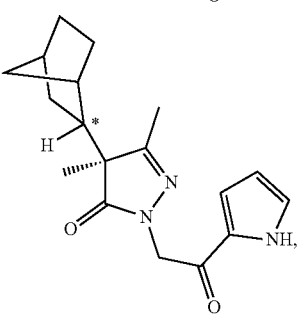

,

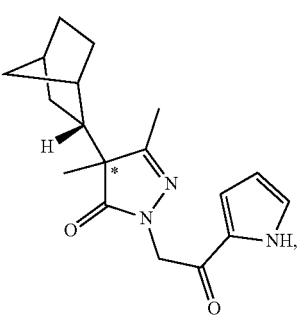

,

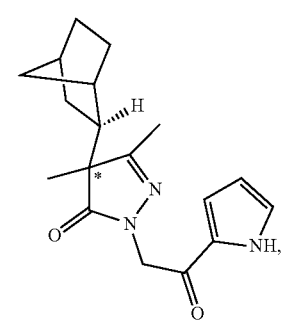

,

-continued
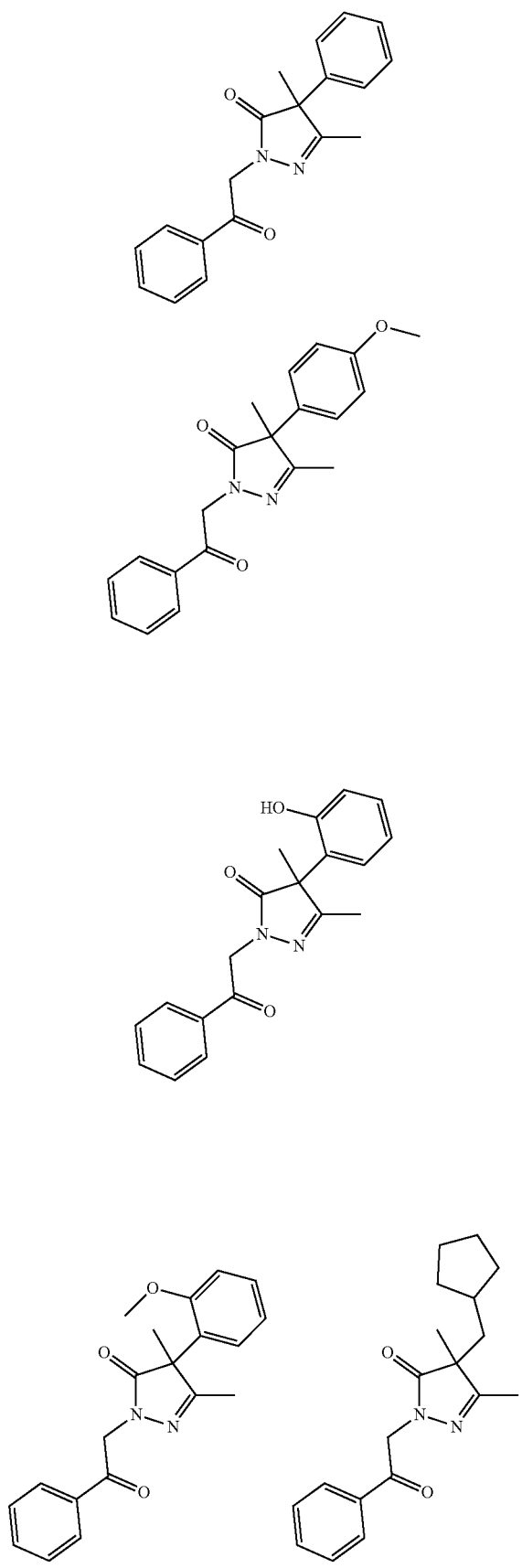
-continued
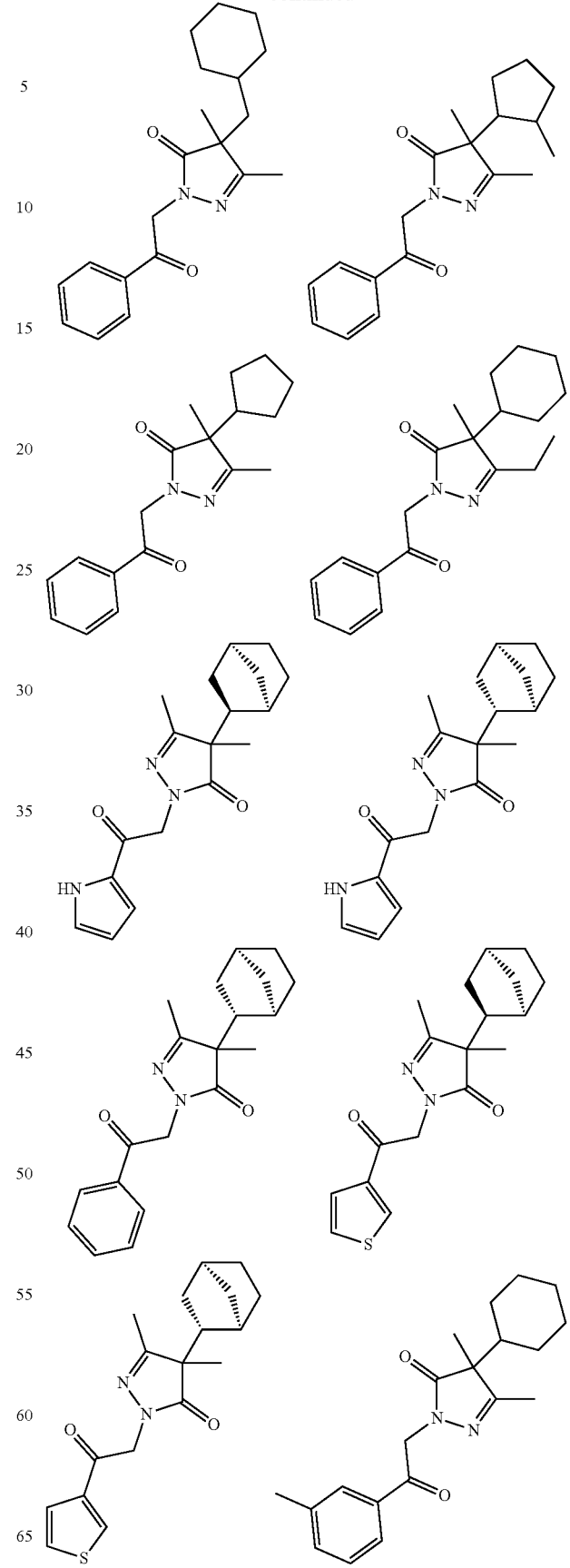

-continued
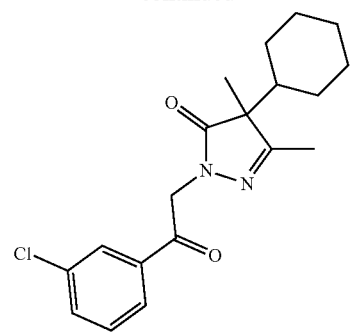
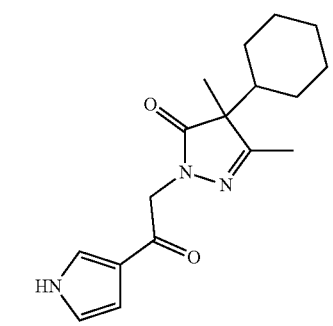
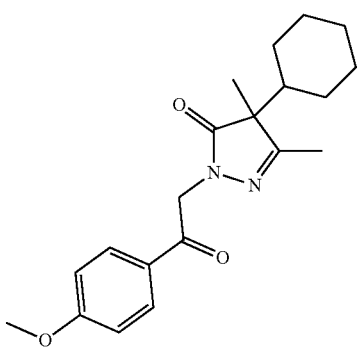
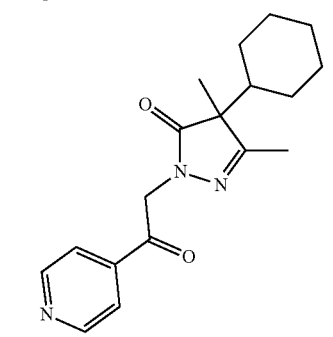
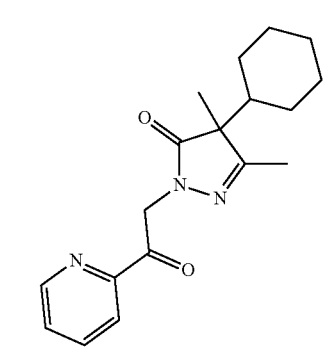
-continued
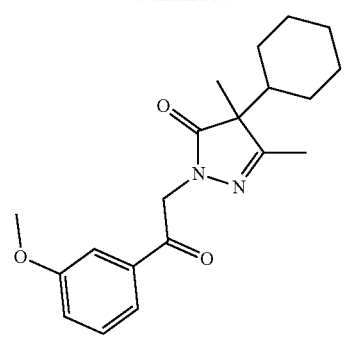
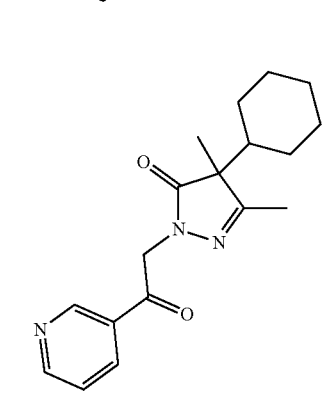
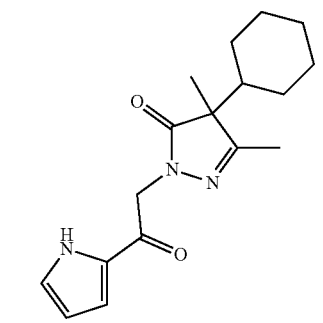
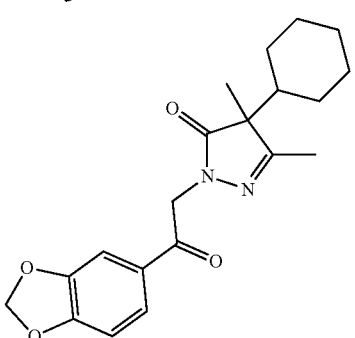
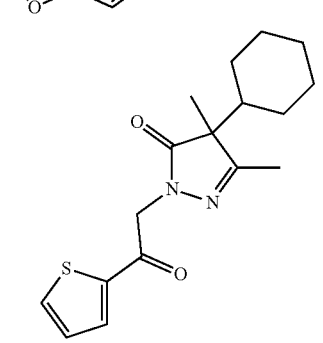

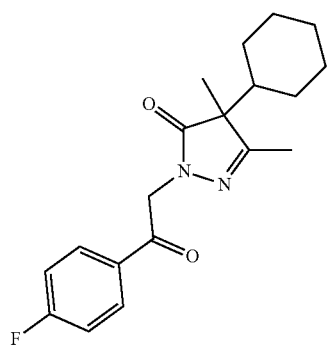

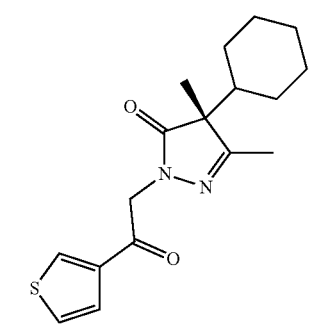

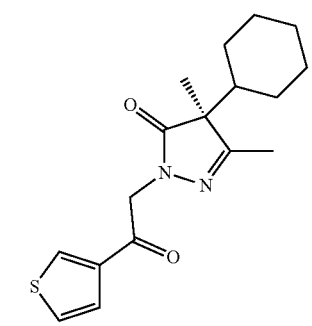

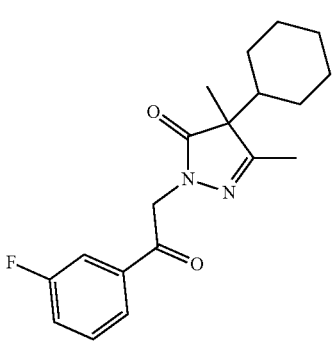

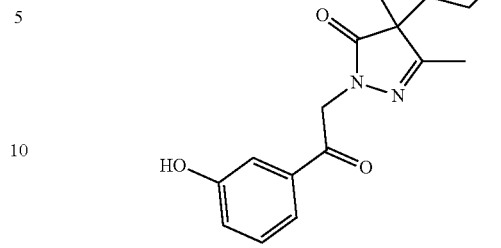

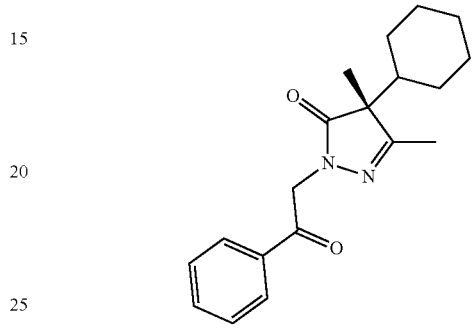

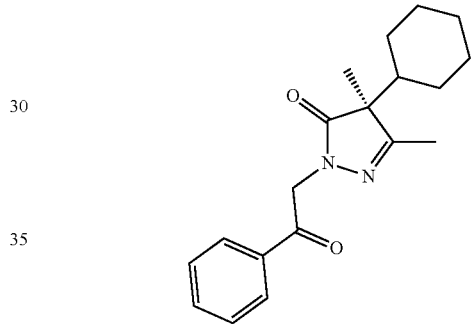

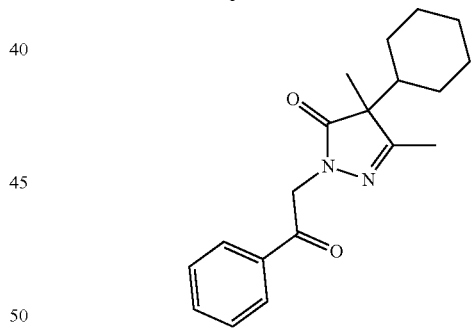

wherein a carbon atom marked with an asterisk indicates a chiral center which may be in a configuration of R, or S, or mixed R and S including racemic R and S. In one embodiment, the carbon atom marked with an asterisk indicates a chiral center, and the compound is a racemic mixture. In other embodiments, the carbon atom marked with an asterisk indicates a chiral center, and the chiral center has an S configuration. In certain embodiments, the carbon atom marked with an asterisk indicates a chiral center, and the compound is a mixture enriched in one isomer relative to the other isomer (e.g., enriched in the R isomer relative to the S isomer; or, enriched in the S isomer relative to the R isomer). In some embodiments, the present compounds may be diastereomeric. In some embodiments, the compound may be a diastereomer and may be optically pure. In other embodiments, the compound may not be optically pure, but may be enriched in one diastereomer. In still other embodiments, the compound may be a mixture of all possible diastereomers.

In one embodiment of Formula (Ib), either $R^5$ or $R^6$, is selected from $C_1$-$C_3$ alkyl, and the remaining $R^5$ or $R^6$ is selected from the group consisting of optionally substituted alkyl, optionally substituted alkenyl, optionally substituted alkynyl, optionally substituted alkylaryl, optionally substituted heteroalkyl, optionally substituted carbocyclyl, or optionally substituted heterocyclyl; or alternatively, $R^5$ and $R^6$, taken together with the atoms to which they are attached, form an optionally substituted carbocyclyl;

X and $X^1$ are N;
$R^7$ is hydrogen, or optionally substituted $C_1$-$C_4$ alkyl;
$R^8$ is represented by (a), (b), or (c):

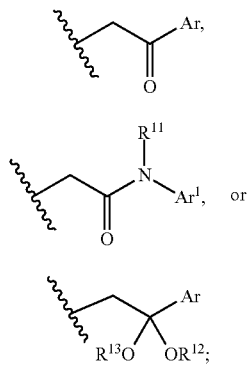

Ar and $Ar^1$ are independently optionally substituted aryl, or optionally substituted heteroaryl;
$R^{11}$ is selected from the group consisting of hydrogen, optionally substituted $C_1$-$C_4$ alkyl, optionally substituted aryl, optionally substituted heteroalkyl, or optionally substituted heteroaryl;
$R^{12}$ and $R^{13}$ are independently $C_1$-$C_4$ alkyl; or alternatively, $R^{12}$ and $R^{13}$, together with the atoms to which they are bonded, form a 5-, 6- or 7-membered optionally substituted cycloheteroalkyl ring;
A is selected from O;
B is selected from $CH_2$ or C=O;
C represents a chemical bond.

In one embodiment of Formula (Ib), either $R^5$ or $R^6$ is selected from $C_1$-$C_3$ alkyl, and the remaining $R^5$ or $R^6$ is selected from the group consisting of optionally substituted $C_3$-$C_8$ cycloalkyl, optionally substituted $C_3$-$C_8$ cycloalkenyl, optionally substituted $C_3$-$C_6$ alkyl, optionally substituted $C_3$-$C_6$ alkenyl, and optionally substituted $C_1$-$C_3$ alkyl-aryl; or alternatively, $R^5$ and $R^6$, taken together with the atoms to which they are attached, form an optionally substituted $C_3$-$C_8$ cycloalkyl or optionally substituted $C_3$-$C_8$ cycloalkenyl ring.

X and $X^1$ are N;
$R^7$ is hydrogen, or $C_1$-$C_4$ alkyl;
$R^8$ is represented by (a), (b) or (c):

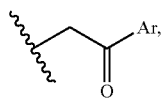

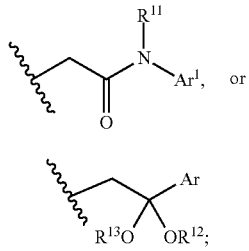

Ar and $Ar^1$ are independently optionally substituted phenyl or optionally substituted heteroaryl; and
$R^{11}$ is hydrogen, optionally substituted $C_1$-$C_4$ alkyl, optionally substituted aryl, optionally substituted heteroalkyl, or optionally substituted heteroaryl;
$R^{12}$ and $R^{13}$ are independently $C_1$-$C_4$ alkyl, or alternatively, $R^{12}$ and $R^{13}$, together with the atoms to which they are bonded, form a 5-, 6- or 7-membered cycloheteroalkyl ring;
A is O;
B is $CH_2$, or CO; and
C is a covalent bond.

In one embodiment of Formula (Ib), either $R^5$ or $R^6$ is $C_1$-$C_3$ alkyl, and the remaining $R^5$ or $R^6$ is selected from the group consisting of optionally substituted alkyl, optionally substituted alkenyl, optionally substituted alkynyl, optionally substituted alkylaryl, optionally substituted heteroalkyl, optionally substituted cycloalkyl, optionally substituted cycloalkenyl, optionally substituted cycloheteroalkyl, and optionally substituted cycloheteroalkenyl;

X and $X^1$ are N;
$R^7$ is $C_1$-$C_4$ alkyl;
$R^8$ is represented by (a), (b) or (c):

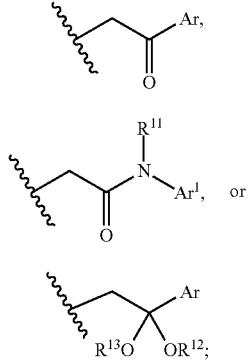

Ar and $Ar^1$ are independently optionally substituted aryl or optionally substituted heteroaryl;
$R^{12}$ is selected from the group consisting of hydrogen, optionally substituted $C_1$-$C_4$ alkyl, optionally substituted aryl, optionally substituted heteroalkyl, or optionally substituted heteroaryl;
$R^{12}$ and $R^{13}$ are independently $C_1$-$C_4$ alkyl, or alternatively, $R^{12}$ and $R^{13}$, together with the atoms to which they are bonded, form a 5-, 6- or 7-membered optionally substituted cycloheteroalkyl ring;
A is O;
B is $CH_2$, or C=O; and
C is $CH_2$, or C=O.

In one embodiment of Formula (Ib), either $R^5$ or $R^6$ is selected from $C_1$-$C_3$ alkyl, and the remaining $R^5$ or $R^6$ is selected from the group consisting of optionally substituted $C_3$-$C_8$ cycloalkyl, optionally substituted $C_3$-$C_8$ cycloalkenyl, optionally substituted $C_3$-$C_6$ alkyl, optionally substituted $C_3$-$C_6$ alkenyl, and optionally substituted $C_1$-$C_3$ alkyl-aryl;

X and $X^1$ are N;
$R^7$ is $C_1$-$C_3$ alkyl;
$R^8$ is represented by (a), (b) or (c):

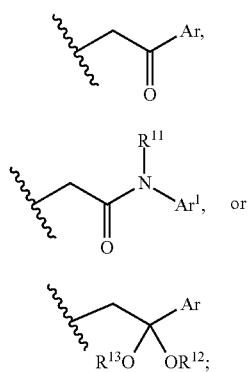

Ar and $Ar^1$ are independently optionally substituted phenyl, or optionally substituted heteroaryl;

$R^{11}$ is selected from the group consisting of hydrogen, optionally substituted $C_1$-$C_4$ alkyl, optionally substituted aryl, optionally substituted heteroalkyl, and optionally substituted heteroaryl;

$R^{12}$ and $R^{13}$ are independently $C_1$-$C_4$ alkyl; or alternatively, $R^{12}$ and $R^{13}$, together with the atoms to which they are bonded, form a 5-, 6- or 7-membered cycloheteroalkyl ring;

A is O;
B is $CH_2$, or C=O; and
C is $CH_2$, or C=O.

In one embodiment of Formula (Ib), the optional substituent may be one or more substituent(s) selected from the group consisting of alkyl, alkoxy, hydroxyl, amino, N-alkyl amino, N-dialkyl amino, halo, nitro, cyano, acyl, carboxyl, carboxyl ester, or amide; or two substituents, together with the atoms to which they are attached, form an optionally substituted carbocyclyl or heterocyclyl containing one or more heteroatom(s) selected from nitrogen, oxygen, and sulfur.

In some specific embodiments of Formula (Ib), the present compounds are selected from the compounds listed in Table X below:

TABLE X

| Example | Structure |
|---------|-----------|
| 2.1 | |
| 2.2 | 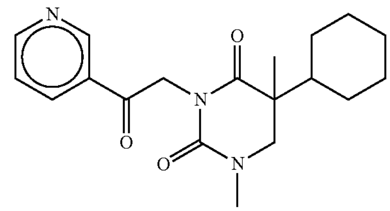 |
| 2.3 | 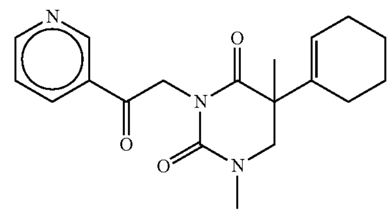 |
| 2.4 | 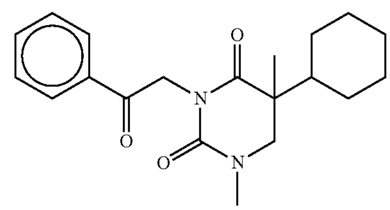 |
| 2.5 | 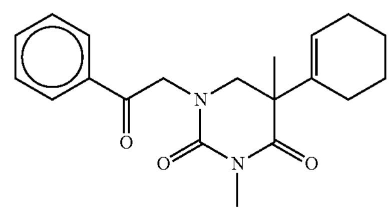 |
| 2.6 | 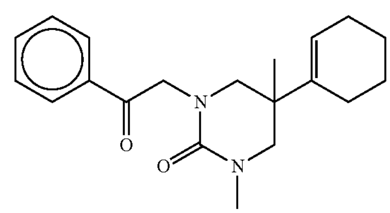 |
| 2.7 | 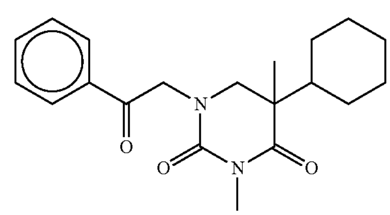 |
| 2.8 | 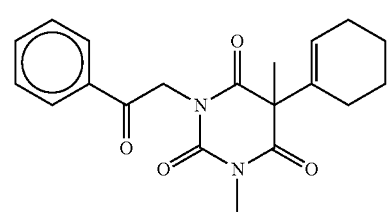 |

TABLE X-continued
| Example | Structure |
|---|---|
| 2.9 | 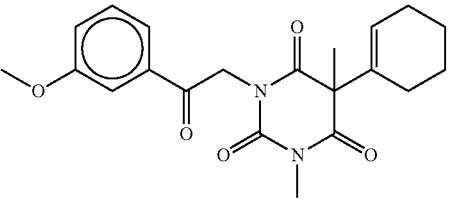 |
| 2.10 | 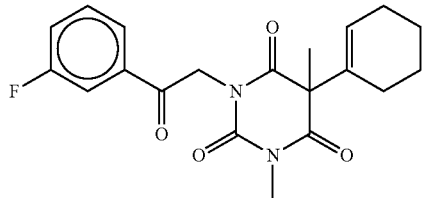 |
| 2.11 | 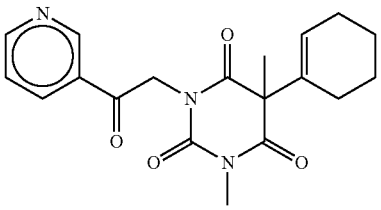 |
| 2.12 | 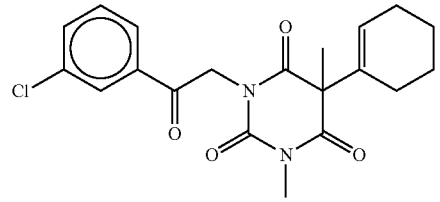 |
| 2.13 | 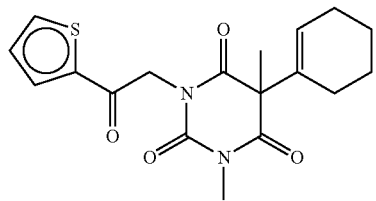 |
| 2.14 | 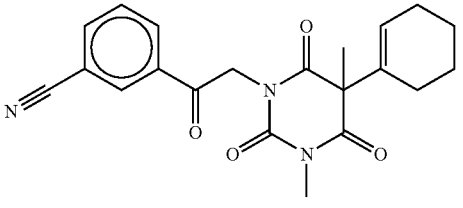 |
| 2.15 | 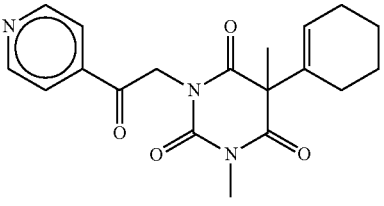 |
| 2.16 | 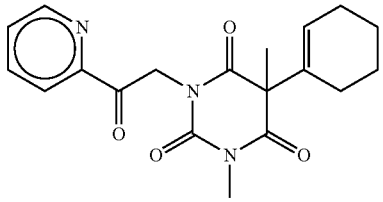 |
| 2.17 | 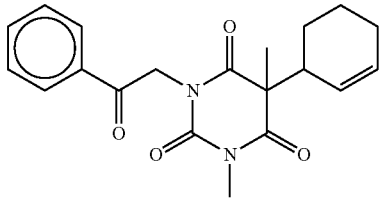 |
| 2.18 | 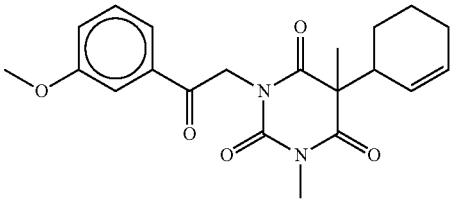 |
| 2.19 | 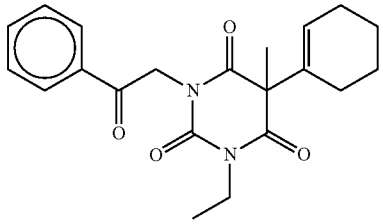 |
| 2.20 | 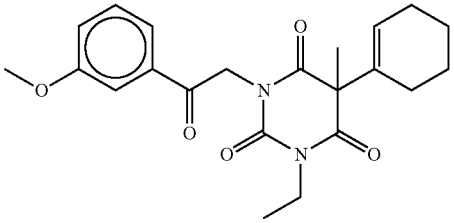 |
| 2.21 | 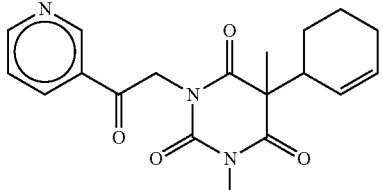 |
| 2.22 | 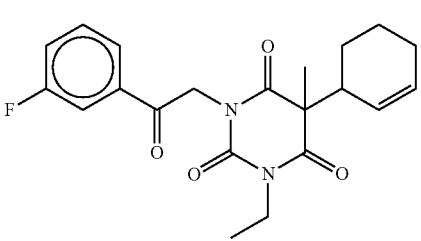 |

TABLE X-continued

| Example | Structure |
|---------|-----------|
| 2.23 | 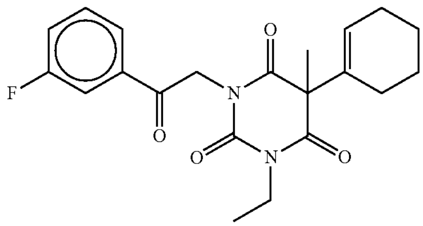 |
| 2.24 | 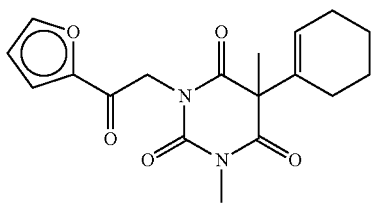 |
| 2.25 | 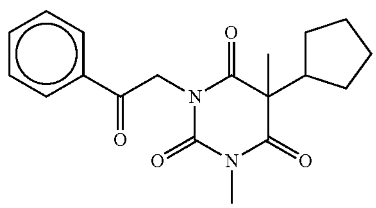 |
| 2.26 | 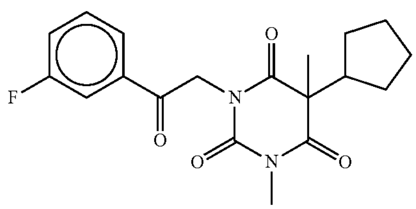 |
| 2.27 | 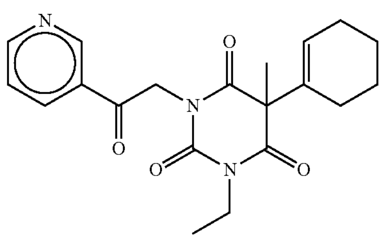 |
| 2.28 | 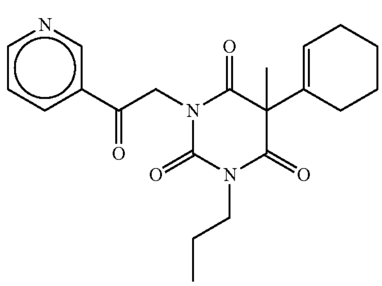 |
| 2.29 | 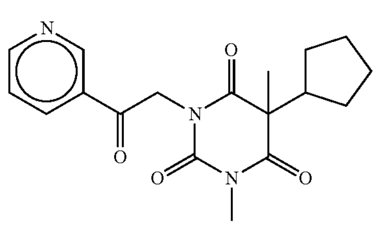 |

TABLE X-continued

| Example | Structure |
|---------|-----------|
| 2.31 | |
| 2.31 | |
| 2.32 | 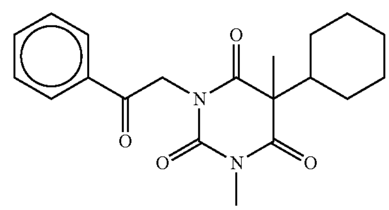 |
| 2.33 | 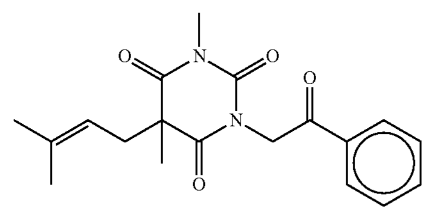 |
| 2.34 | 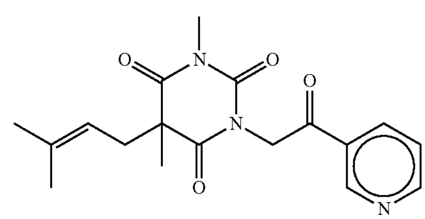 |
| 2.35 | 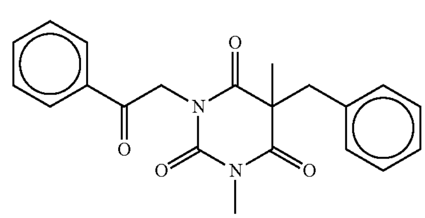 |
| 2.36 | 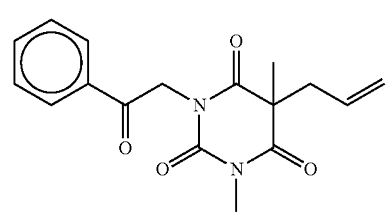 |

TABLE X-continued

| Example | Structure |
|---|---|
| 2.37 | 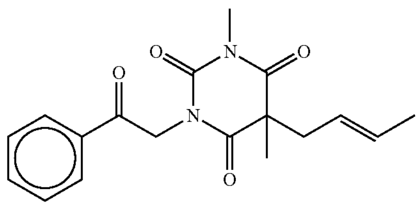 |
| 2.38 | 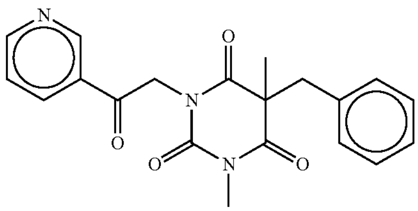 |
| 2.39 | 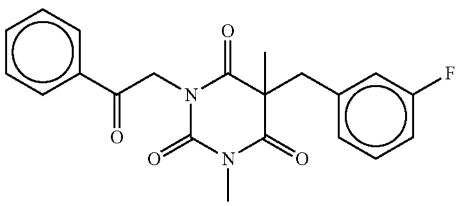 |
| 2.40 | 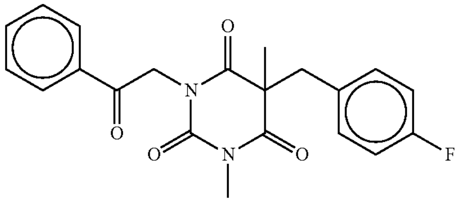 |
| 2.41 | 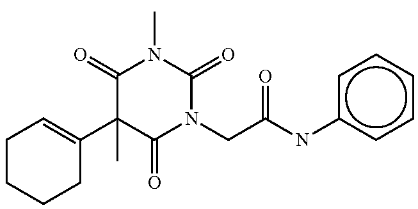 |
| 2.42 | 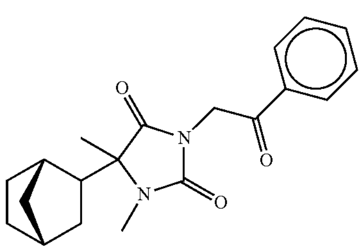 |
| 2.43 | 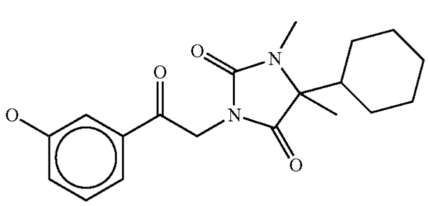 |
| 2.44 | |
| 2.45 | |
| 2.46 | |
| 2.47 | |
| 2.48 | |
| 2.49 | |
| 2.50 | |

TABLE X-continued

| Example | Structure |
|---|---|
| 2.51 | 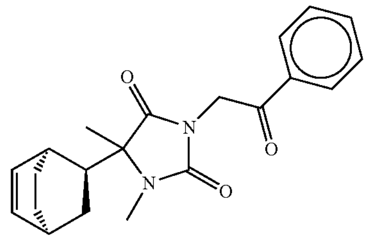 |
| 2.52 | 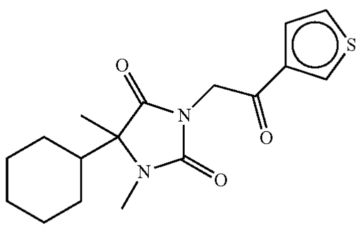 |
| 2.53 | 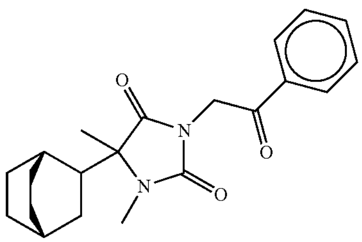 |
| 2.54 | 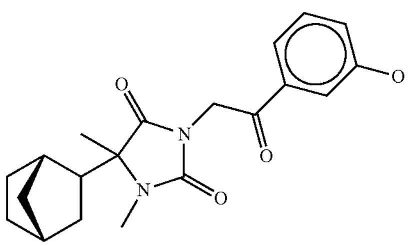 |
| 2.55 | 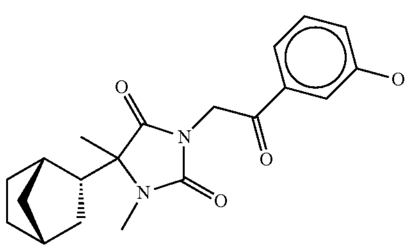 |
| 2.56 | 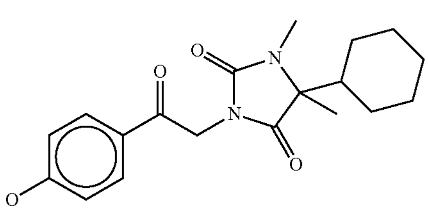 |
| 2.57 | 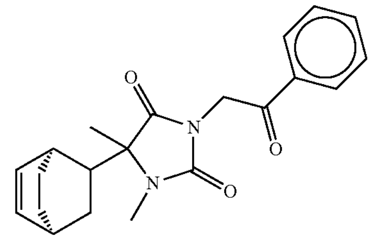 |
| 2.58 | 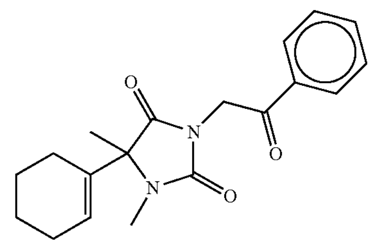 |
| 2.59 | 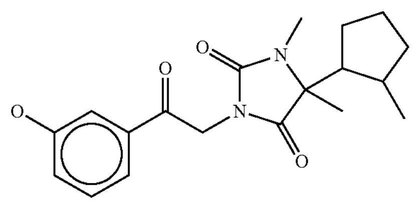 |
| 2.60 | 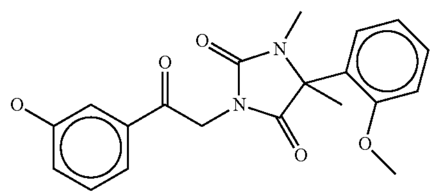 |
| 2.61 | 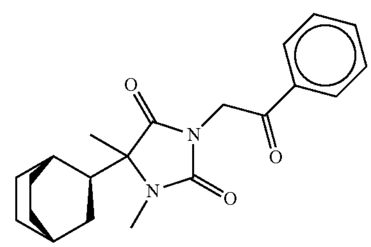 |
| 2.62 | 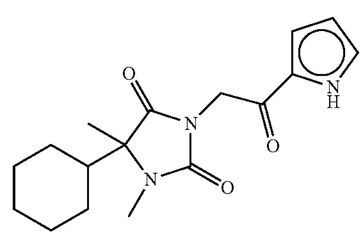 |

TABLE X-continued

| Example | Structure |
|---------|-----------|
| 2.63 | 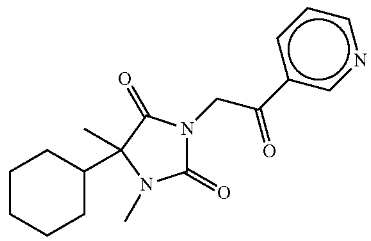 |
| 2.64 | 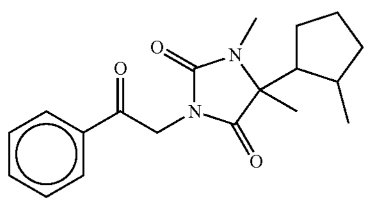 |
| 2.65 | 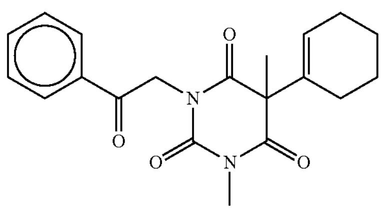 |
| 2.66 | 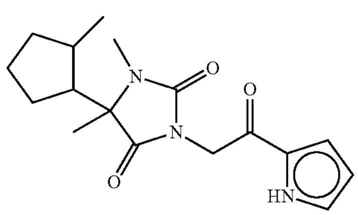 |
| 2.67 | 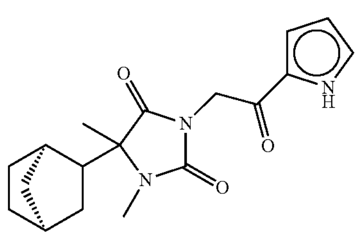 |
| 2.68 | 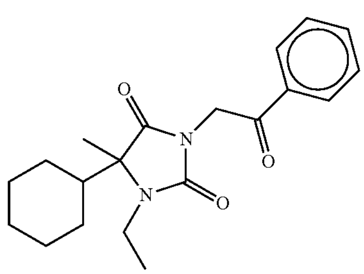 |
| 2.69 | |
| 2.70 | |
| 2.71 | |
| 2.72 | |
| 2.73 | |
| 2.74 | |

TABLE X-continued

| Example | Structure |
|---|---|
| 2.75 | 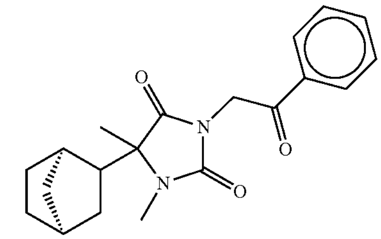 |
| 2.76 | 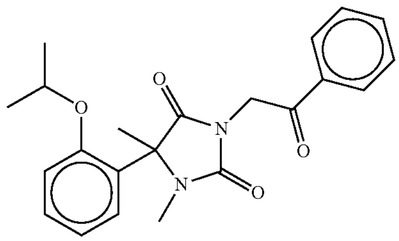 |
| 2.77 | 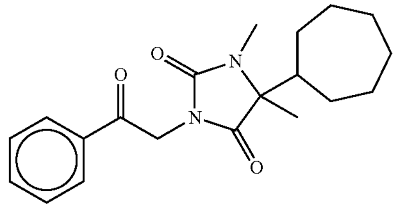 |
| 2.78 | 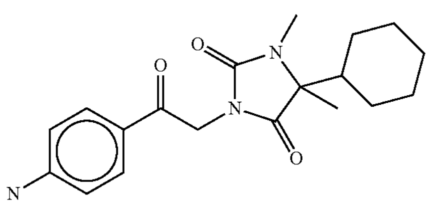 |
| 2.79 | 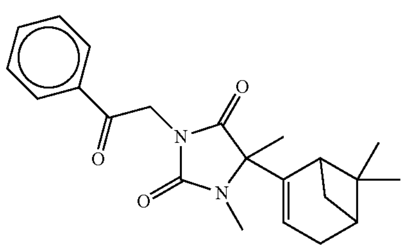 |
| 2.80 | 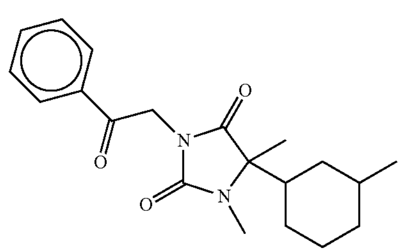 |
| 2.81 | |
| 2.82 | |
| 2.83 | |
| 2.84 | |
| 2.85 | |
| 2.86 | |

TABLE X-continued
| Example | Structure |
|---|---|
| 2.87 | 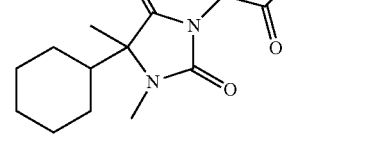 |
| 2.88 | 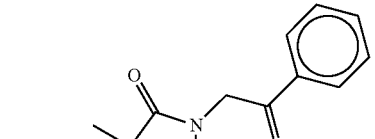 |
| 2.89 | 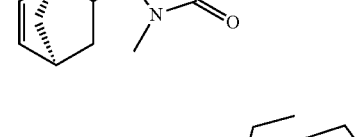 |
| 2.90 | 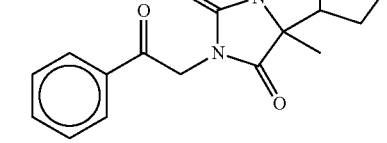 |
| 2.91 | 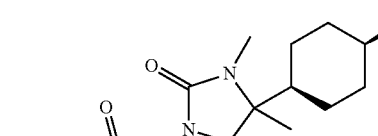 |
| 2.92 | 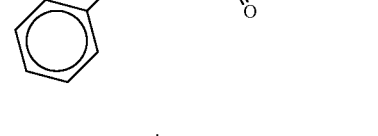 |
| 2.93 | 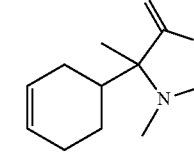 |
| 2.94 | 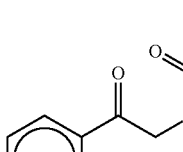 |
| 2.95 |  |
| 2.96 | 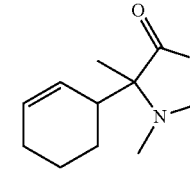 |
| 2.97 | 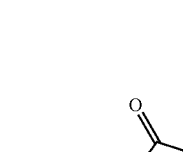 |
| 2.98 | 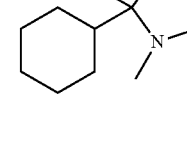 |

TABLE X-continued
| Example | Structure |
|---|---|
| 2.99 | 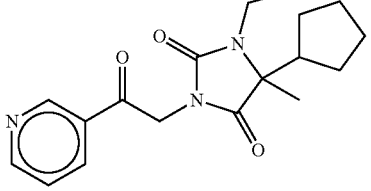 |
| 2.100 | 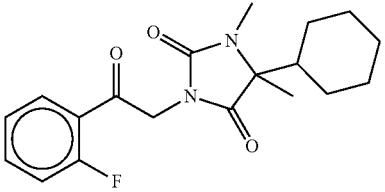 |
| 2.101 | 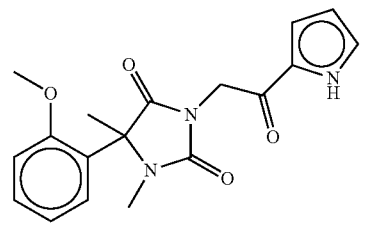 |
| 2.102 | 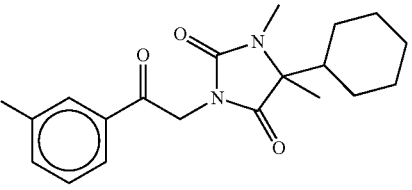 |
| 2.103 | 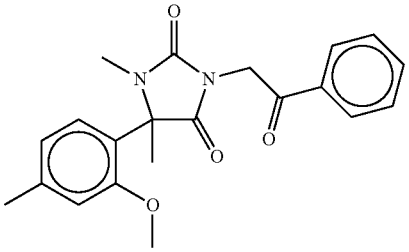 |
| 2.104 | 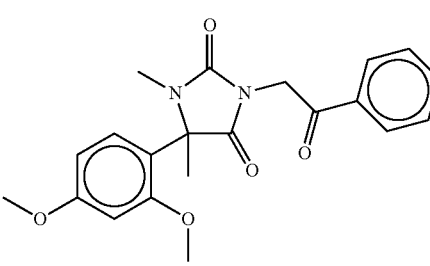 |
| 2.105 | 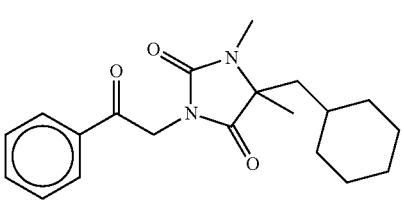 |
| 2.106 | 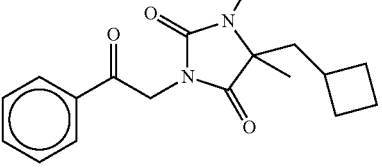 |
| 2.107 | 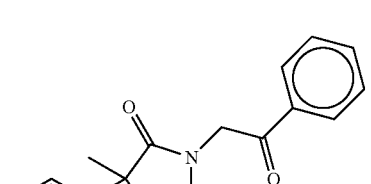 |
| 2.108 | 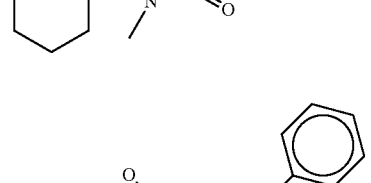 |
| 2.109 | 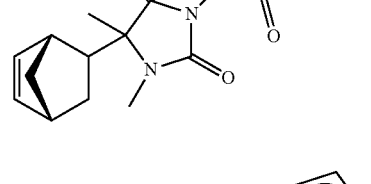 |
| 2.110 | 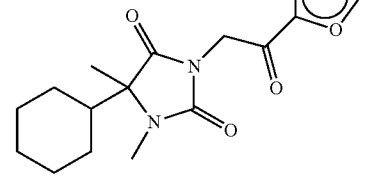 |
| 2.111 | 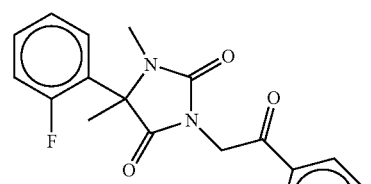 |

TABLE X-continued

| Example | Structure |
|---|---|
| 2.112 | 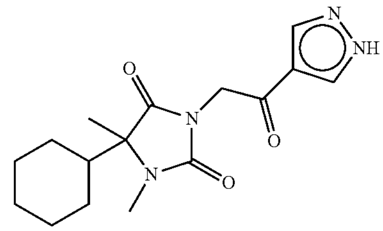 |
| 2.113 | 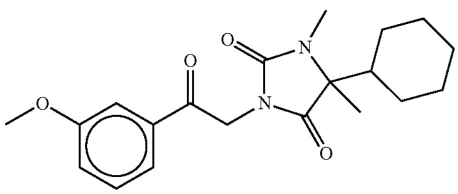 |
| 2.114 | 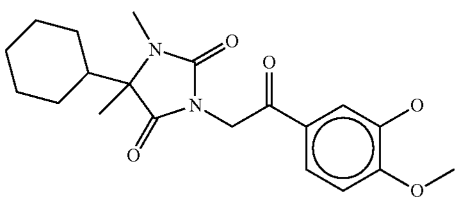 |
| 2.115 | 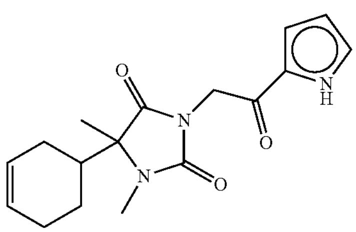 |
| 2.116 | 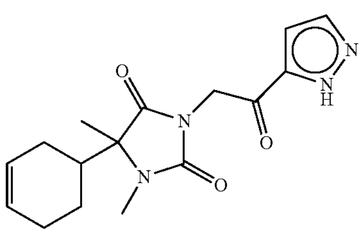 |
| 2.117 | 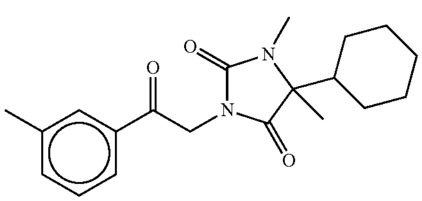 |
| 2.118 | 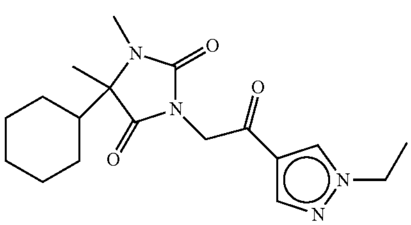 |
| 2.119 | |
| 2.120 | |
| 2.121 | |
| 2.122 | |
| 2.123 | |
| 2.124 | |

TABLE X-continued

| Example | Structure |
|---|---|
| 2.125 | 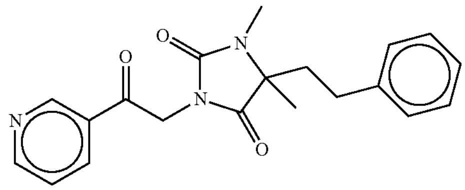 |
| 2.126 | 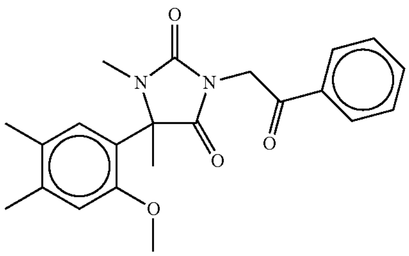 |
| 2.127 | 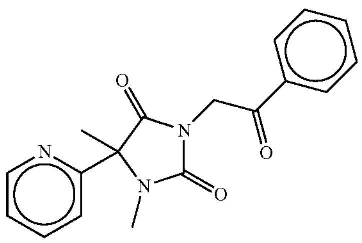 |
| 2.128 | 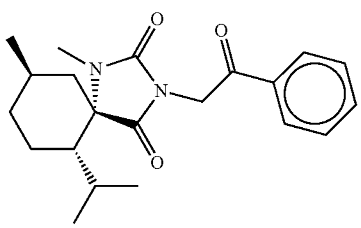 |
| 2.129 | 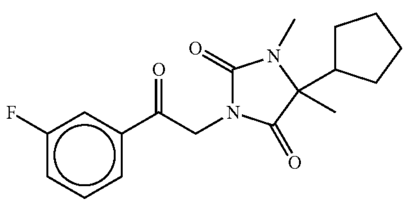 |
| 2.130 | 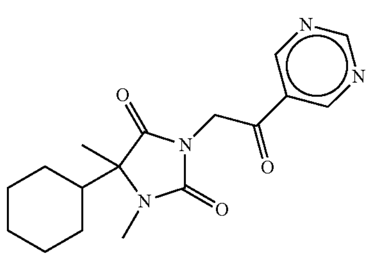 |
| 2.131 | 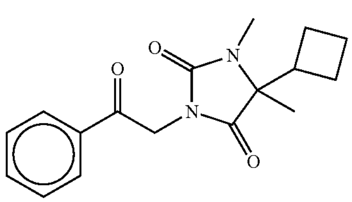 |
| 2.132 | |
| 2.133 | |
| 2.134 | |
| 2.135 | |
| 2.136 | |
| 2.137 | |

TABLE X-continued

| Example | Structure |
|---|---|
| 2.138 | 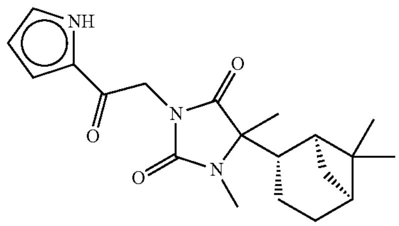 |
| 2.139 | 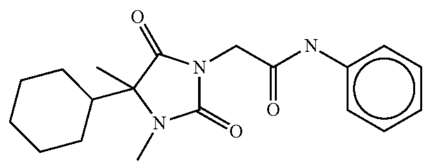 |
| 2.140 | 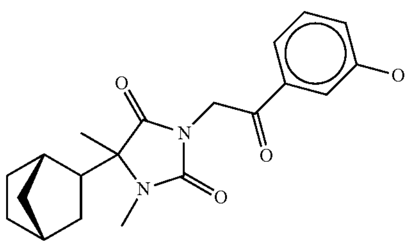 |
| 2.141 | 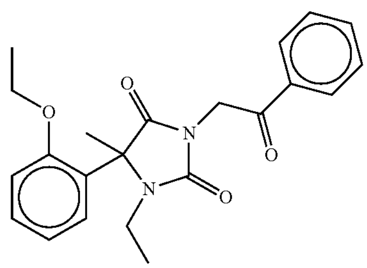 |
| 2.142 | 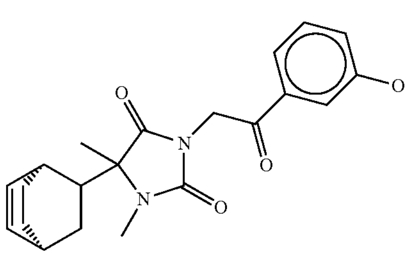 |
| 2.143 | 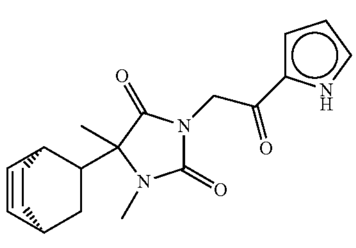 |
| 2.144 | |
| 2.145 | |
| 2.146 | |
| 2.147 | |
| 2.148 | |
| 2.149 | |

In one embodiment, the present invention provides a compound having structural Formula (Ic):

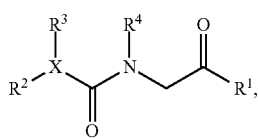

or a salt or solvate thereof;
wherein
X is $CR^5$ or N;
$R^1$ is optionally substituted aryl, optionally substituted carbocyclyl, optionally substituted heteroaryl, or optionally substituted heterocyclyl;
$R^2$ and $R^3$ are the same or different and are independently selected from the group consisting of hydrogen, optionally substituted alkyl, optionally substituted alkenyl, optionally substituted aryl, optionally substituted carbocyclyl, optionally substituted heteroaryl, and optionally substituted heterocyclyl;
$R^4$ is hydrogen, hydroxyl, alkoxy, optionally substituted alkyl, optionally substituted alkenyl, optionally substituted aryl, optionally substituted carbocyclyl, optionally substituted heteroaryl, or optionally substituted heterocyclyl; and
$R^5$ is hydrogen, optionally substituted alkyl, optionally substituted alkenyl, optionally substituted aryl, optionally substituted carbocyclyl, optionally substituted heteroaryl, or optionally substituted heterocyclyl; or alternatively, $R^3$ and $R^5$, or $R^3$ and $R^4$, taken together with the atoms to which they are attached, form an optionally substituted carbocyclyl or optionally substituted heterocyclyl.

In one embodiment of Formula (Ic), X is CH or N;
$R^1$ is optionally substituted aryl, optionally substituted carbocyclyl, optionally substituted heteroaryl, or optionally substituted heterocyclyl;
$R^2$ and $R^3$ are the same or different and are independently selected from the group consisting of optionally substituted alkyl, optionally substituted alkenyl, optionally substituted aryl, optionally substituted carbocyclyl, optionally substituted heteroaryl, and optionally substituted heterocyclyl; and
$R^4$ is hydrogen, hydroxyl, alkoxy, optionally substituted alkyl, optionally substituted alkenyl, optionally substituted aryl, optionally substituted carbocyclyl, optionally substituted heteroaryl, or optionally substituted heterocyclyl.

In one embodiment of Formula (Ic), $R^1$ is optionally substituted aryl or optionally substituted heteroaryl. In one embodiment of $R^1$, the optionally substituted aryl is optionally substituted phenyl. In one embodiment of $R^1$, the optionally substituted heteroaryl is a five- or six-membered heteroaryl containing one or more heteroatoms selected from nitrogen, oxygen, and sulfur. In one embodiment of $R^1$, the optionally substituted heteroaryl is selected from the group consisting of pyrrolyl, thienyl, pyridyl, imidazolyl, triazolyl, thiazolyl, pyrimidyl, furanyl, and pyrazolyl, each of which is optionally substituted.

In one embodiment of Formula (Ic), $R^2$ is optionally substituted aryl, optionally substituted carbocyclyl, optionally substituted heteroaryl, or optionally substituted heterocyclyl. In one embodiment of $R^2$, the optionally substituted carbocyclyl is an optionally substituted 5- or 6-membered monocyclic carbocyclyl.

In one embodiment of Formula (Ic), $R^3$ is hydrogen, optionally substituted alkyl, or optionally substituted alkenyl. In one embodiment of Formula (Ic), $R^3$ is optionally substituted $C_1$-$C_4$ alkyl.

In one embodiment of Formula (Ic), $R^2$ is optionally substituted carbocyclyl; and $R^3$ is optionally substituted alkyl.

In one embodiment of Formula (Ic), $R^4$ is hydrogen, hydroxyl, alkoxy, or optionally substituted alkyl. In one embodiment of Formula (Ic), $R^4$ is optionally substituted $C_1$-$C_4$ alkyl.

In one embodiment of Formula (Ic), X is N or CH.

In one embodiment of Formula (Ic), $R^2$ is optionally substituted aryl, optionally substituted carbocyclyl, optionally substituted heteroaryl, or optionally substituted heterocyclyl; and $R^3$ is optionally substituted alkyl or optionally substituted alkenyl.

In one embodiment of Formula (Ic), X is CH;
$R^1$ is optionally substituted aryl or optionally substituted heteroaryl;
$R^2$ is optionally substituted carbocyclyl;
$R^3$ is optionally substituted alkyl; and
$R^4$ is hydrogen or optionally substituted alkyl.

In one embodiment of Formula (Ic), the optional substituent may be one or more substituent(s) selected from the group consisting of alkyl, alkoxy, hydroxyl, amino, N-alkyl amino, N-dialkyl amino, halo, nitro, cyano, acyl, carboxyl, carboxyl ester, or amide; or two substituents, together with the atoms to which they are attached, form an optionally substituted carbocyclyl or heterocyclyl containing one or more heteroatom(s) selected from nitrogen, oxygen, and sulfur.

In one embodiment of Formula (Ic), the compound has structural Formula (Id):

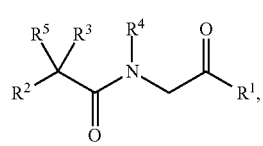

or a salt or solvate thereof;
wherein
$R^1$ is optionally substituted aryl, optionally substituted carbocyclyl, optionally substituted heteroaryl, or optionally substituted heterocyclyl;
$R^2$, $R^3$ and $R^5$ are independently selected from the group consisting of hydrogen, optionally substituted alkyl, optionally substituted alkenyl, optionally substituted aryl, optionally substituted carbocyclyl, optionally substituted heteroaryl, and optionally substituted heterocyclyl, provided that $R^2$ is not hydrogen, and $R^3$ and $R^5$ are not both hydrogen; or alternatively, $R^2$ and $R^3$, taken together with the carbon atom to which they are attached, forms a moiety with a double bond: $=C(R^6R^7)$; or alternatively, $R^3$ and $R^5$, or $R^4$ and $R^5$, taken together with the atoms to which they are attached, form an optionally substituted carbocyclyl or optionally substituted heterocyclyl; and
$R^4$ is hydrogen, hydroxyl, alkoxy, optionally substituted alkyl, optionally substituted alkenyl, optionally substituted aryl, optionally substituted carbocyclyl, optionally substituted heteroaryl, or optionally substituted heterocyclyl;
$R^6$ and $R^7$ are independently hydrogen, optionally substituted alkyl, optionally substituted heteroalkyl, optionally substituted alkenyl, optionally substituted aryl, optionally substituted carbocyclyl, optionally substituted heteroaryl, or optionally substituted heterocyclyl; or alternatively, $R^6$ and $R^7$, taken together with the carbon atom to which they are attached, form an an optionally substituted carbocyclyl or optionally substituted heterocyclyl.

In one embodiment of Formula (Id), $R^1$ is optionally substituted aryl or optionally substituted heteroaryl. In one embodiment of $R^2$, the optionally substituted aryl is optionally substituted phenyl; and the optionally substituted heteroaryl is a five- or six-membered heteroaryl containing one or more heteroatoms selected from nitrogen, oxygen, and sulfur. In one embodiment of $R^2$, the substituted heteroaryl is selected from the group consisting of pyrrolyl, thienyl, pyridyl, imidazolyl, triazolyl, thiazolyl, pyrimidyl, furanyl, and pyrazolyl, each of which is optionally substituted.

In one embodiment of Formula (Id), $R^2$ is optionally substituted alkyl, optionally substituted alkenyl, optionally substituted aryl, optionally substituted carbocyclyl, optionally substituted heteroaryl, or optionally substituted heterocyclyl; and $R^3$ and $R^5$ are independently selected from the group consisting of hydrogen, optionally substituted alkyl, optionally substituted alkenyl, optionally substituted aryl, optionally substituted carbocyclyl, optionally substituted heteroaryl, and optionally substituted heterocyclyl, provided that $R^3$ and $R^5$ are not both hydrogen.

In one embodiment of Formula (Id), $R^3$ is optionally substituted alkyl, or optionally substituted alkenyl; and $R^5$ is optionally substituted alkyl, or optionally substituted alkenyl.

In one embodiment of Formula (Id), $R^3$ is optionally substituted $C_1$-$C_4$ alkyl.

In one embodiment of Formula (Id), $R^5$ is optionally substituted $C_1$-$C_4$ alkyl.

In one embodiment of Formula (Id), $R^3$ and $R^5$, taken together with the carbon atom to which they are attached, form an optionally substituted carbocyclyl. In one embodiment, the optionally substituted carbocyclyl is an optionally substituted 3-, 4-, or 5-membered monocyclic carbocyclyl.

In one embodiment of Formula (Id), $R^2$ is optionally substituted aryl, optionally substituted carbocyclyl, optionally substituted heteroaryl, or optionally substituted heterocyclyl. In one embodiment of $R^2$, the optionally substituted carbocyclyl is an optionally substituted 5- or 6-membered monocyclic carbocyclyl.

In one embodiment of Formula (Id), $R^2$ is optionally substituted aryl, optionally substituted carbocyclyl, optionally substituted heteroaryl, or optionally substituted heterocyclyl;

$R^3$ is optionally substituted alkyl or optionally substituted alkenyl; and $R^5$ is optionally substituted $C_1$-$C_4$ alkyl.

In one embodiment of Formula (Id), $R^2$ is optionally substituted carbocyclyl;

$R^3$ is optionally substituted alkyl; and $R^5$ is optionally substituted $C_1$-$C_4$ alkyl.

In one embodiment of Formula (Id), $R^4$ is hydrogen, hydroxyl, alkoxy, or optionally substituted alkyl. In one embodiment of Formula (Id), $R^4$ is hydrogen or optionally substituted $C_1$-$C_4$ alkyl.

In one embodiment of Formula (Id), $R^1$ is optionally substituted aryl or optionally substituted heteroaryl;

$R^2$ is optionally substituted carbocyclyl;

$R^3$ is optionally substituted alkyl;

$R^5$ is optionally substituted $C_1$-$C_4$ alkyl; and $R^4$ is hydrogen or optionally substituted alkyl.

In one embodiment of Formula (Id), $R^2$ and $R^3$, taken together with the carbon atom to which they are attached, forms a moiety with a double bond: =$C(R^6R^7)$; wherein $R^6$ and $R^7$, taken together with the carbon atom to which they are attached, form an an optionally substituted carbocyclyl.

In one embodiment of Formula (Id), $R^2$ is optionally substituted aryl, optionally substituted carbocyclyl, optionally substituted heteroaryl, or optionally substituted heterocyclyl; $R^3$ is hydrogen, optionally substituted alkyl, or optionally substituted alkenyl; and $R^4$ and $R^5$, taken together with the atoms to which they are attached, form an optionally substituted heterocyclyl.

In some specific embodiments of the present invention, the present compounds are selected from the compounds listed in Table Y below. The "Ex #" below denotes Example number.

TABLE Y

| Ex# | Structure |
|---|---|
| 3.1 | 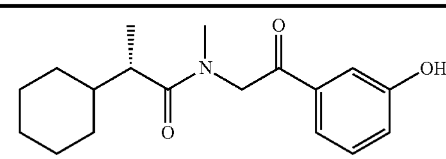 |
| 3.2 | 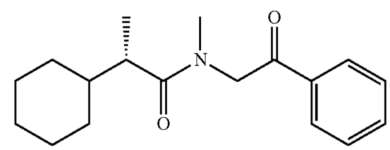 [SMILES: C[C@H](C(=O)N(C)CC(=O)c1ccccc1)C1CCCCC1] |
| 3.3 | 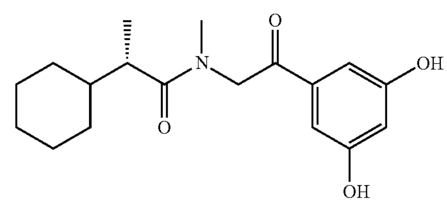 [SMILES: C[C@H](C(=O)N(C)CC(=O)c1cc(O)cc(O)c1)C1CCCCC1] |
| 3.4 | 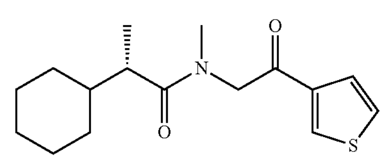 [SMILES: C[C@H](C(=O)N(C)CC(=O)c1ccsc1)C1CCCCC1] |
| 3.5 | 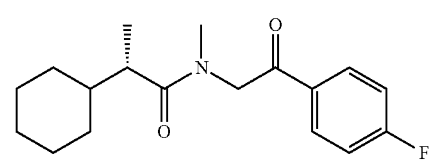 [SMILES: C[C@H](C(=O)N(C)CC(=O)c1ccc(F)cc1)C1CCCCC1] |
| 3.6 | 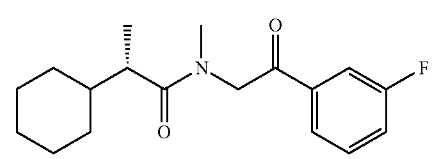 [SMILES: C[C@H](C(=O)N(C)CC(=O)c1cccc(F)c1)C1CCCCC1] |
| 3.7 | 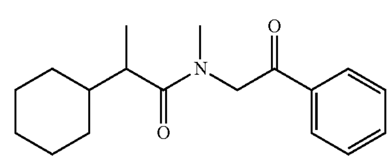 [SMILES: CC(C(=O)N(C)CC(=O)c1ccccc1)C1CCCCC1] |
| 3.8 | 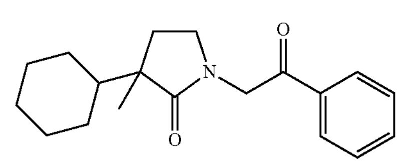 [SMILES: CC1(C2CCCCC2)CCN(CC(=O)c2ccccc2)C1=O] |

TABLE Y-continued
| Ex# | Structure |
|---|---|
| 3.9 | 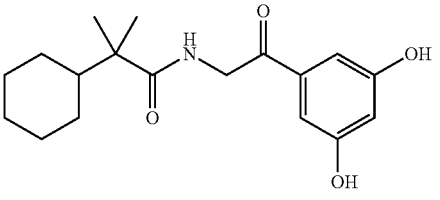 [SMILES: CC(C)(C(=O)NCC(=O)c1cc(O)cc(O)c1)C1CCCCC1] |
| 3.10 | 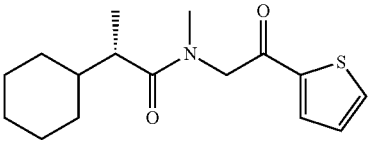 [SMILES: C[C@H](C(=O)N(C)CC(=O)c1cccs1)C1CCCCC1] |
| 3.11 | 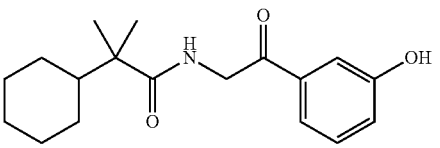 [SMILES: CC(C)(C(=O)NCC(=O)c1cccc(O)c1)C1CCCCC1] |
| 3.12 | 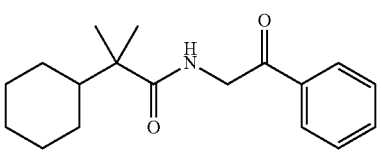 [SMILES: CC(C)(C(=O)NCC(=O)c1ccccc1)C1CCCCC1] |
| 3.13 | 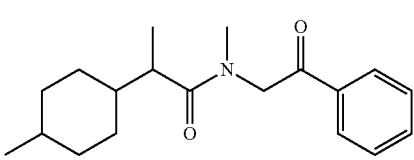 [SMILES: CC1CCC(C(C)C(=O)N(C)CC(=O)c2ccccc2)CC1] |
| 3.14 | 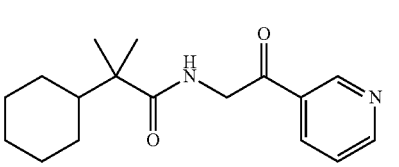 [SMILES: CC(C)(C(=O)NCC(=O)c1cccnc1)C1CCCCC1] |
| 3.15 | 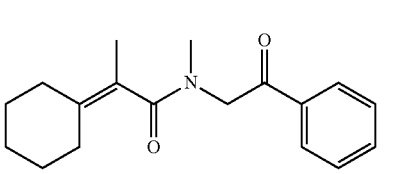 [SMILES: CC(C(=O)N(C)CC(=O)c1ccccc1)=C1CCCCC1] |
| 3.16 | 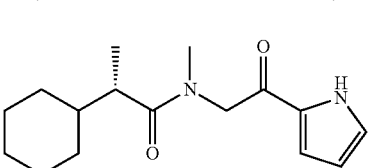 |
| 3.17 | 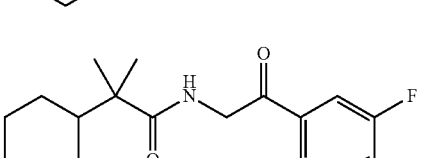 |
| 3.18 | 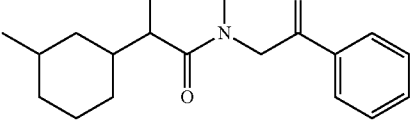 |
| 3.19 | 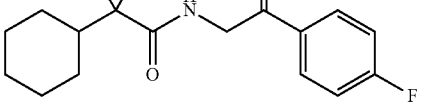 |
| 3.20 | 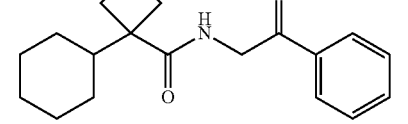 |
| 3.21 | 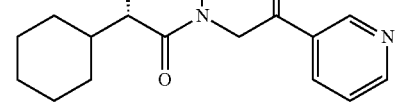 |
| 3.22 | 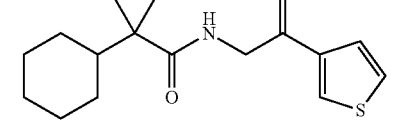 |
| 3.23 | 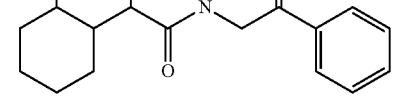 |
| 3.24 | 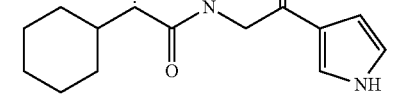 |
| 3.25 | 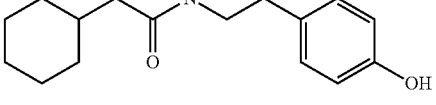 |
| 3.26 | 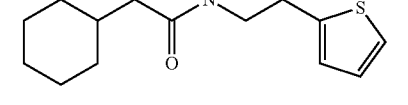 |
| 3.27 | 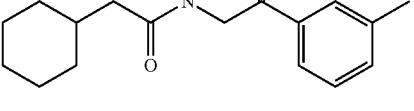 |

TABLE Y-continued

| Ex# | Structure |
|---|---|
| 3.28 | (structure) |
| 3.29 | (structure) |
| 3.30 | (structure) |
| 3.31 | (structure) |
| 3.32 | (structure) |
| 3.33 | (structure) |
| 3.34 | (structure) |
| 3.35 | (structure) |
| 3.36 | (structure) |
| 3.37 | (structure) |
| 3.38 | (structure) |
| 3.39 | (structure) |
| 3.40 | (structure) |
| 3.41 | (structure) |
| 3.42 | (structure) |
| 3.43 | (structure) |
| 3.44 | (structure) |
| 3.45 | (structure) |
| 3.46 | (structure) |
| 3.47 | (structure) |

TABLE Y-continued

| Ex# | Structure |
|---|---|
| 3.48 | 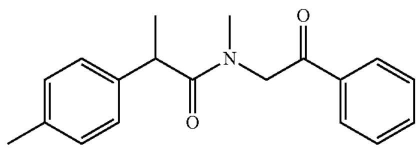 [SMILES: Cc1ccc(C(C)C(=O)N(C)CC(=O)c2ccccc2)cc1] |
| 3.49 | 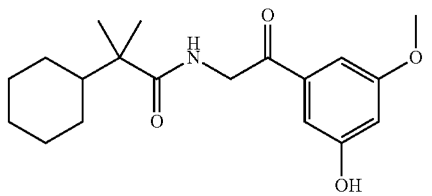 [SMILES: COc1cc(O)cc(C(=O)CNC(=O)C(C)(C)C2CCCCC2)c1] |
| 3.50 | 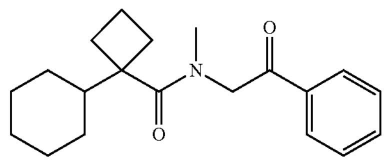 [SMILES: CN(CC(=O)c1ccccc1)C(=O)C1(C2CCCCC2)CCC1] |
| 3.51 | 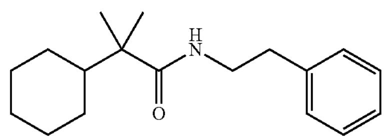 [SMILES: CC(C)(C(=O)NCCc1ccccc1)C1CCCCC1] |
| 3.52 | 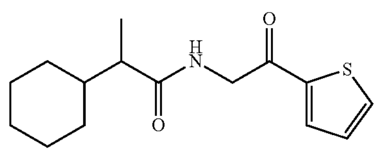 [SMILES: CC(C(=O)NCC(=O)c1cccs1)C1CCCCC1] |
| 3.53 | 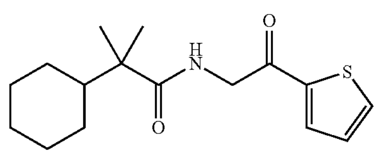 [SMILES: CC(C)(C(=O)NCC(=O)c1cccs1)C1CCCCC1] |
| 3.54 | 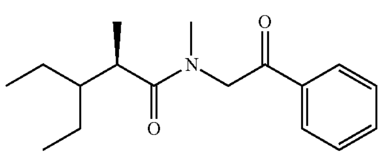 [SMILES: CCC(CC)[C@@H](C)C(=O)N(C)CC(=O)c1ccccc1] |
| 3.55 | 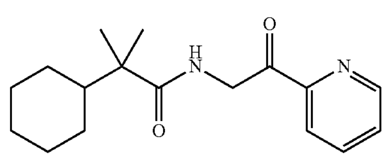 [SMILES: CC(C)(C(=O)NCC(=O)c1ccccn1)C1CCCCC1] |
| 3.56 | 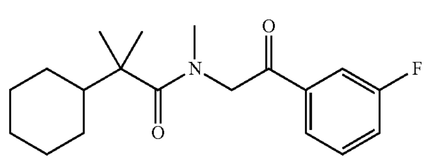 [SMILES: CN(CC(=O)c1cccc(F)c1)C(=O)C(C)(C)C1CCCCC1] |
| 3.57 | 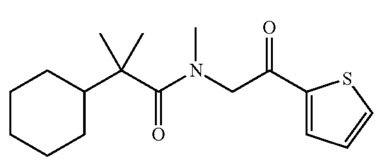 [SMILES: CN(CC(=O)c1cccs1)C(=O)C(C)(C)C1CCCCC1] |
| 3.58 | |
| 3.59 | |
| 3.60 | |
| 3.61 | |

Embodiments of the Utilities of the Present Compounds

The compounds of the present invention, or a salt or solvate thereof, can be used as modulators, e.g., agonists, of the TRPM8 receptor in personal products for modulating, e.g., inducing, chemesthetic sensations, particularly the cold or cool sensations.

The present compounds are important to the flavorings and fragrance industry because they can increase or induce/generate a cooling or cold sensation which is often associated with freshness and cleanliness.

As modulators of the TRPM8 receptor, the present compounds also have repellent effect on insects, therapeutic effect in antitumor treatments (e.g. an influencing of prostate tumors), activity in the treatment of inflammatory pain/hyperalgesia, and efficacy (as TRPM8 antagonists) in the treatment of bladder syndrome or overactive bladder.

The personal product can be provided as a composition, which comprises one or more of the present compound and optionally at least one carrier. The composition can be in any physical form, such as a solid, semi-solid, plaster, solution, suspension, lotion, cream, foam, gel, paste, emulsion, or a combination thereof. Examples of the composition include, but are not limited to, a pharmaceutical composition, an ingestible composition, a chemesthetic concentrate, a personal care composition, and a combination thereof. In one embodiment of the present invention, the composition comprises a chemesthetic sensation modulating amount of the present compound. In another embodiment of the present invention, the composition comprises a chemesthetic sensation inducing amount of the present compound. In certain embodiments, the chemesthetic sensation is a cold or cooling sensation. In one embodiment of the composition, the present compound is in a concentration ranging from about 0.0001 ppm to 100,000 ppm. In another embodiment of the composition, the present compound is in a concentration ranging from about 0.001 ppm to 10,000 ppm. In another embodiment of the composition, the present compound is in a concentration ranging from about 0.01 ppm to 1,000 ppm. In another embodiment of the composition, the present compound is in a concentration ranging from about 0.1 ppm to 500 ppm. In another embodiment of the composition, the present compound is in a concentration ranging from about 1 ppm to 500 ppm. In another embodiment of the composition, the present compound is in a concentration ranging from about 10 ppm to 500 ppm. In another embodiment of the composition, the present compound is in a concentration ranging from about 1 ppm to 400 ppm.

The present ingestible composition typically comprises one or more compounds of the present invention and at least one ingestibly acceptable carrier. The ingestible composition includes both "food or beverage products" and "non-edible products". By "food or beverage products", it is meant any edible product intended for consumption by humans or animals, including solids, semi-solids, or liquids (e.g., beverages). The term "non-edible products" or "noncomestible composition" includes nutraceutical compositions, dietary supplements, nutritional compositions, and functional food products (e.g., any fresh or processed food claimed to have a health-promoting and/or disease-preventing properties beyond the basic nutritional function of supplying nutrients).

In one embodiment, the present compounds are added to food or beverage products or formulations. Examples of food and beverage products or formulations include, but are not limited to coatings, frostings, or glazes for comestible products or any entity included in the Soup category, the Dried Processed Food category, the Beverage category, the Ready Meal category, the Canned or Preserved Food category, the Frozen Processed Food category, the Chilled Processed Food category, the Snack Food category, the Baked Goods category, the Confectionary category, the Dairy Product category, the Ice Cream category, the Meal Replacement category, the Pasta and Noodle category, and the Sauces, Dressings, Condiments category, the Baby Food category, and/or the Spreads category.

In general, the Soup category refers to canned/preserved, dehydrated or freeze dried, instant, chilled, UHT and frozen soup. For the purpose of this definition soup(s) means a food prepared from meat, poultry, fish, vegetables, grains, fruit and other ingredients, cooked in a liquid which may include visible pieces of some or all of these ingredients. It may be clear (as a broth) or thick (as a chowder), smooth, pureed or chunky, ready-to-serve, semi-condensed or condensed and may be served hot or cold, as a first course or as the main course of a meal or as a between meal snack (sipped like a beverage). Soup may be used as an ingredient for preparing other meal components and may range from broths (consommé) to sauces (cream or cheese-based soups). The dehydrated or freeze dried soups include dehydrated soup mixes, dehydrated instant soups, and dehydrated ready-to-cook soups.

The Beverage category usually means beverages, beverage mixes and concentrates, including but not limited to, carbonated and non-carbonated beverages, alcoholic and non-alcoholic beverages, ready to drink beverages, liquid concentrate formulations for preparing beverages such as sodas, and dry powdered beverage precursor mixes. The Beverage category also includes alcoholic drinks, the soft drinks, sports drinks, isotonic beverages, and hot drinks. The alcoholic drinks include, but are not limited to beer, cider/perry, FABs, wine, and spirits. The soft drinks include, but are not limited to carbonates, such as colas and non-cola carbonates; fruit juice, such as juice, nectars, juice drinks and fruit flavored drinks; bottled water, which includes sparkling water, spring water and purified/table water; functional drinks, which can be carbonated or still and include sport, energy or elixir drinks; concentrates, such as liquid and powder concentrates in ready to drink measure. The drinks, either hot or cold, include, but are not limited to coffee or ice coffee, such as fresh, instant, and combined coffee; tea or ice tea, such as black, green, white, oolong, and flavored tea; and other drinks including flavor-, malt- or plant-based powders, granules, blocks or tablets mixed with milk or water.

The Snack Food category generally refers to any food that can be a light informal meal including, but not limited to Sweet and savory snacks and snack bars. Examples of snack food include, but are not limited to fruit snacks, chips/crisps, extruded snacks, tortilla/corn chips, popcorn, pretzels, nuts and other sweet and savory snacks. Examples of snack bars include, but are not limited to granola/muesli bars, breakfast bars, energy bars, fruit bars and other snack bars.

The Baked Goods category generally refers to any edible product the process of preparing which involves exposure to heat or excessive sunlight. Examples of baked goods include, but are not limited to bread, buns, cookies, muffins, cereal, toaster pastries, pastries, waffles, tortillas, biscuits, pies, bagels, tarts, quiches, cake, any baked foods, and any combination thereof.

The Ice Cream category generally refers to frozen dessert containing cream and sugar and flavoring. Examples of ice cream include, but are not limited to: impulse ice cream; take-home ice cream; frozen yoghurt and artisanal ice cream; soy, oat, bean (e.g., red bean and mung bean), and rice-based ice creams.

The Confectionary category generally refers to edible product that is sweet to the taste. Examples of confectionary include, but are not limited to candies, gelatins, chocolate confectionery, sugar confectionery, gum, and the likes and any combination products.

The Meal Replacement category generally refers to any food intended to replace the normal meals, particularly for people having health or fitness concerns. Examples of meal replacement include, but are not limited to slimming products and convalescence products.

The Ready Meal category generally refers to any food that can be served as meal without extensive preparation or processing. The ready meal includes products that have had recipe "skills" added to them by the manufacturer, resulting in a high degree of readiness, completion and convenience. Examples of ready meal include, but are not limited to canned/preserved, frozen, dried, chilled ready meals; dinner mixes; frozen pizza; chilled pizza; and prepared salads.

The Pasta and Noodle category includes any pastas and/or noodles including, but not limited to canned, dried and chilled/fresh pasta; and plain, instant, chilled, frozen and snack noodles.

The Canned/Preserved Food category includes, but is not limited to canned/preserved meat and meat products, fish/seafood, vegetables, tomatoes, beans, fruit, ready meals, soup, pasta, and other canned/preserved foods.

The Frozen Processed Food category includes, but is not limited to frozen processed red meat, processed poultry, processed fish/seafood, processed vegetables, meat substitutes, processed potatoes, bakery products, desserts, ready meals, pizza, soup, noodles, and other frozen food.

The Dried Processed Food category includes, but is not limited to rice, breading, dessert mixes, dried ready meals, dehydrated soup, instant soup, dried pasta, plain noodles, dehydrated or ambient preparations of ready-made dishes, meals, and single serve entrees including potato and rice dishes, and instant noodles.

The Chilled Processed Food category includes, but is not limited to chilled processed meats, processed fish/seafood products, lunch kits, fresh cut fruits, ready meals, pizza, prepared salads, soup, fresh pasta and noodles.

The Sauces, Dressings and Condiments category includes, but is not limited to tomato pastes and purees, marinades, bouillon and bouillon like products in pressed tubes, tablets, or powder or granulated form, stock cubes, herbs and spices, monosodium glutamate (MSG), table sauces, soy based sauces, pasta sauces, barbecue sauces, wet/cooking sauces, dry sauces/powder mixes, ketchup, mayonnaise, mustard, salad dressings, salad toppings, vinaigrettes, dips, pickled products, liquid recipe mixes, concentrates, and other sauces, dressings and condiments.

The Baby Food category includes, but is not limited to milk- or soybean-based formula; and prepared, dried and other baby food.

The Spreads category includes, but is not limited to jams and preserves, honey, batter mixes, shelf stable spreads, chocolate spreads, nut based spreads, and yeast based spreads.

The Dairy Product category generally refers to edible product produced from mammal's milk. Examples of dairy product include, but are not limited to drinking milk products, cheese, yoghurt and sour milk drinks, and other dairy products.

Additional examples for comestible composition, particularly food and beverage products or formulations, are provided as follows. Exemplary comestible compositions include one or more confectioneries, chocolate confectionery, tablets, countlines, bagged selflines/softlines, boxed assortments, standard boxed assortments, twist wrapped miniatures, seasonal chocolate, chocolate with toys, alfajores, other chocolate confectionery, mints, standard mints, power mints, boiled sweets, pastilles, gums, jellies and chews, toffees, caramels and nougat, medicated confectionery, lollipops, liquorices, other sugar confectionery, gum, chewing gum, sugarized gum, sugar-free gum, functional gum, bubble gum, bread, packaged/industrial bread, unpackaged/artisanal bread, pastries, cakes, packaged/industrial cakes, unpackaged/artisanal cakes, cookies, chocolate coated biscuits, sandwich biscuits, filled biscuits, savory biscuits and crackers, bread substitutes, breakfast cereals, rte cereals, family breakfast cereals, flakes, muesli, other cereals, children's breakfast cereals, hot cereals, ice cream, impulse ice cream, single portion dairy ice cream, single portion water ice cream, multi-pack dairy ice cream, multi-pack water ice cream, take-home ice cream, take-home dairy ice cream, ice cream desserts, bulk ice cream, take-home water ice cream, frozen yoghurt, artisanal ice cream, dairy products, milk, fresh/pasteurized milk, full fat fresh/pasteurized milk, semi skimmed fresh/pasteurized milk, long-life/uht milk, full fat long life/uht milk, semi skimmed long life/uht milk, fat-free long life/uht milk, goat milk, condensed/evaporated milk, plain condensed/evaporated milk, flavored, functional and other condensed milk, flavored milk drinks, dairy only flavored milk drinks, flavored milk drinks with fruit juice, soy milk, sour milk drinks, fermented dairy drinks, coffee whiteners, powder milk, flavored powder milk drinks, cream, cheese, processed cheese, spreadable processed cheese, unspreadable processed cheese, unprocessed cheese, spreadable unprocessed cheese, hard cheese, packaged hard cheese, unpackaged hard cheese, yoghurt, plain/natural yoghurt, flavored yoghurt, fruited yoghurt, probiotic yoghurt, drinking yoghurt, regular drinking yoghurt, probiotic drinking yoghurt, chilled and shelf-stable desserts, dairy-based desserts, soy-based desserts, chilled snacks, fromage frais and quark, plain fromage frais and quark, flavored fromage frais and quark, savory fromage frais and quark, sweet and savory snacks, fruit snacks, chips/crisps, extruded snacks, tortilla/corn chips, popcorn, pretzels, nuts, other sweet and savory snacks, snack bars, granola bars, breakfast bars, energy bars, fruit bars, other snack bars, meal replacement products, slimming products, convalescence drinks, ready meals, canned ready meals, frozen ready meals, dried ready meals, chilled ready meals, dinner mixes, frozen pizza, chilled pizza, soup, canned soup, dehydrated soup, instant soup, chilled soup, hot soup, frozen soup, pasta, canned pasta, dried pasta, chilled/fresh pasta, noodles, plain noodles, instant noodles, cups/bowl instant noodles, pouch instant noodles, chilled noodles, snack noodles, canned food, canned meat and meat products, canned fish/seafood, canned vegetables, canned tomatoes, canned beans, canned fruit, canned ready meals, canned soup, canned pasta, other canned foods, frozen food, frozen processed red meat, frozen processed poultry, frozen processed fish/seafood, frozen processed vegetables, frozen meat substitutes, frozen potatoes, oven baked potato chips, other oven baked potato products, non-oven frozen potatoes, frozen bakery products, frozen desserts, frozen ready meals, frozen pizza, frozen soup, frozen noodles, other frozen food, dried food, dessert mixes, dried ready meals, dehydrated soup, instant soup, dried pasta, plain noodles, instant noodles, cups/bowl instant noodles, pouch instant noodles, chilled food, chilled processed meats, chilled fish/seafood products, chilled processed fish, chilled coated fish, chilled smoked fish, chilled lunch kit, chilled ready meals, chilled pizza, chilled soup, chilled/fresh pasta, chilled noodles, oils and fats, olive oil, vegetable and seed oil, cooking fats, butter, margarine, spreadable oils and fats, functional spreadable oils and fats, sauces, dressings and condiments, tomato pastes and purees, bouillon/stock cubes, stock cubes, gravy granules, liquid stocks and fonds, herbs and spices, fermented sauces, soy based sauces, pasta sauces, wet sauces, dry sauces/powder mixes, ketchup, mayonnaise, regular mayonnaise, mustard, salad dressings, regular salad dressings, low fat salad dressings, vinaigrettes, dips, pickled products, other sauces, dressings and condiments, baby food, milk formula, standard milk formula, follow-on milk formula, toddler milk formula, hypoallergenic milk formula, prepared baby food, dried baby food, other baby food, spreads, jams and preserves, honey, chocolate spreads, nut-based spreads, and yeast-based spreads. Exemplary comestible compositions also include confectioneries, bakery products, ice creams, dairy products, sweet and savory snacks, snack bars, meal replacement products, ready meals, soups, pastas, noodles, canned foods, frozen foods, dried foods, chilled foods, oils and fats, baby foods, or spreads or a mixture thereof.

In one embodiment, the pharmaceutical composition comprises one or more compounds of the present invention and at least one pharmaceutically acceptable carrier. The pharmaceutical composition includes both the prescription medications and the over-the-counter medications. The present compound may or may not be the therapeutically active ingredient in the pharmaceutical composition. The pharmaceutical composition can be used by any mode of administration known to one skilled in the art, particularly by topical administration, such as application of analgesic cream to the skin surface. In general, over the counter (OTC) product and oral hygiene product generally refer to product for household and/or personal use which may be sold without a prescription and/or without a visit to a medical professional. Examples of the OTC products include, but are not limited to vitamins and dietary supplements; topical analgesics and/or anesthetic; cough, cold and allergy remedies; antihistamines and/or allergy remedies; and combinations thereof. Vitamins and dietary supplements include, but are not limited to vitamins, dietary supplements, tonics/bottled nutritive drinks, child-specific vitamins, dietary supplements, any other products of or relating to or providing nutrition, and combinations thereof. Topical analgesics and/or anesthetic include any topical creams/ointments/gels used to alleviate superficial or deep-seated aches and pains, e.g. muscle pain; teething gel; patches with analgesic ingredient; and combinations thereof. Cough, cold and allergy remedies include, but are not limited to decongestants, cough remedies, pharyngeal preparations, medicated confectionery, antihistamines and child-specific cough, cold and allergy remedies; and combination products. Antihistamines and/or allergy remedies include, but are not limited to any systemic treatments for hay fever, nasal allergies, insect bites and stings. Examples of oral hygiene product include, but are not limited to mouth cleaning strips, toothpaste, toothbrushes, mouthwashes/dental rinses, denture care, mouth fresheners, mouth moisturizers, at-home teeth whiteners and dental floss.

As used herein, a "personal care composition" refers to a composition to be directly applied to the skin, mucosal, or other surface area of the body. Examples of personal care composition include, but are not limited to, personal paper products, such as tissue paper, napkins, and paper towel; an oral care composition, such as; toothpaste, chewing gum, breath refresher, dentifrices, and mouthwashes; a skincare or haircare composition, such as sunscreen cream, sunburn lotions, shaving cream, plasters, shampoos, conditioners, face cleaners, soaps, bath oils or bath foam, antiperspirants, and deodorant; a cosmetic composition, such as moisturizer, lip balms, foundation, etc.; an insect repellent composition; or an insecticide composition.

In one embodiment of the invention, the present compounds are provided in a chemesthetic concentrate formulation, e.g., suitable for subsequent processing to produce a ready-to-use (i.e., ready-to-serve) product. By "a chemesthetic concentrate formulation", it is meant a formulation which should be reconstituted with one or more diluting medium to become a ready-to-use composition. The term "ready-to-use composition" is used herein interchangeably with "ingestible composition", which denotes any substance that, either alone or together with another substance, can be taken by mouth whether intended for consumption or not. In one embodiment, the ready-to-use composition includes a composition that can be directly consumed by a human or animal. The chemesthetic concentrate formulation is typically used by mixing with or diluted by one or more diluting medium, e.g., any consumable or ingestible ingredient or product, to impart or modify a chemesthetic sensation to the diluting medium. Such a use process is often referred to as reconstitution. The reconstitution can be conducted in a household setting or an industrial setting. For example, a frozen fruit juice concentrate can be reconstituted with water or other aqueous medium by a consumer in a kitchen to obtain the ready-to-use fruit juice beverage. In another example, a mouthwash concentrate can be reconstituted with water or other aqueous medium by a manufacture in large industrial scales to produce the ready-to-use mouthwash. Since the chemesthetic concentrate formulation has the present compound and optionally a flavoring agent and/or flavor modifying agent in a concentration higher than the ready-to-use composition, the chemesthetic concentrate formulation is typically not suitable for being consumed directly without reconstitution. There are many benefits of using and producing a chemesthetic concentrate formulation. For example, one benefit is the reduction in weight and volume for transportation as the chemesthetic concentrate formulation can be reconstituted at the time of usage by the addition of suitable solvent, solid or liquid.

In one embodiment, the chemesthetic concentrate formulation comprises i) as chemesthetic sensation modifying ingredient, a compound of the present invention; ii) a carrier; and iii) optionally at least one adjuvant. The term "as chemesthetic sensation modifying ingredient" denotes that the compound of the present invention acts as a modulator of a chemesthetic sensation (such as, a cold or cooling sensation modulator) in the formulation. The term "carrier" denotes a usually inactive accessory substance, such as solvents, binders, or other inert medium, which is used in combination with the present compound and one or more optional adjuvants to form the formulation. For example, water or starch can be a carrier for a flavoring concentrate formulation. In some embodiments, the carrier is the same as the diluting medium for reconstituting the chemesthetic concentrate formulation; and in other embodiments, the carrier is different from the diluting medium. The term "carrier" as used herein includes, but is not limited to, ingestibly acceptable carrier.

The term "adjuvant" denotes an additive which supplements, stabilizes, maintains, or enhances the intended function or effectiveness of the active ingredient, such as the compound of the present invention. In one embodiment, the at least one adjuvant comprises one or more flavoring agents. The flavoring agent may be of any flavor known to one skilled in the art or consumers, such as the flavor of chocolate, coffee, tea, mocha, French vanilla, peanut butter, chai, or combinations thereof. In another embodiment, the at least one adjuvant comprises one or more sweeteners. In another embodiment, the at least one adjuvant comprises one or more ingredients selected from the group consisting of a emulsifier, a stabilizer, an antimicrobial preservative, an antioxidant, vitamins, minerals, fats, starches, protein concentrates and isolates, salts, and combinations thereof. Examples of emulsifiers, stabilizers, antimicrobial preservatives, antioxidants, vitamins, minerals, fats, starches, protein concentrates and isolates, and salts are described in U.S. Pat. No. 6,468,576, the contents of which are hereby incorporated by reference in its entirety for all purposes.

In one embodiment, the present chemesthetic concentrate formulation can be in a form selected from the group consisting of liquid including solution and suspension, solid, foamy material, paste, gel, cream, and a combination thereof, such as a liquid containing certain amount of solid contents. In one embodiment, the chemesthetic concentrate formulation is in form of a liquid including aqueous-based and nonaqueous-based. The present chemesthetic concentrate formulation can be carbonated or non-carbonated.

The chemesthetic concentrate formulation may further comprise a freezing point depressant, nucleating agent, or both as the at least one adjuvant. The freezing point depressant is a ingestibly acceptable compound or agent which can depress the freezing point of a liquid or solvent to which the compound or agent is added. That is, a liquid or solution containing the freezing point depressant has a lower freezing point than the liquid or solvent without the freezing point depressant. In addition to depress the onset freezing point, the freezing point depressant may also lower the water activity of the flavoring concentrate formulation. The examples of the freezing point depressant include, but are not limited to, carbohydrates, oils, ethyl alcohol, polyol, e.g., glycerol, and combinations thereof. The nucleating agent denotes a ingestibly acceptable compound or agent which is able to facilitate nucleation. The presence of nucleating agent in the flavoring concentrate formulation can improve the mouthfeel of the frozen slushes of a frozen slush and to help maintain the physical properties and performance of the slush at freezing temperatures by increasing the number of desirable ice crystallization centers. Examples of nucleating agents include, but are not limited to, calcium silicate, calcium carbonate, titanium dioxide, and combinations thereof.

In one embodiment, the chemesthetic concentrate formulation is formulated to have a low water activity for extended shelf life. Water activity is the ratio of the vapor pressure of water in a formulation to the vapor pressure of pure water at the same temperature. In one embodiment, the chemesthetic concentrate formulation has a water activity of less than about 0.85. In another embodiment, the chemesthetic concentrate formulation has a water activity of less than about 0.80. In another embodiment, the chemesthetic concentrate formulation has a water activity of less than about 0.75.

In one embodiment, the chemesthetic concentrate formulation has the present compound in a concentration that is at least 2 times of the concentration of the compound in a ready-to-use composition. In one embodiment, the chemesthetic concentrate formulation has the present compound in a concentration that is at least 5 times of the concentration of the compound in a ready-to-use composition. In one embodiment, the chemesthetic concentrate formulation has the present compound in a concentration that is at least 10 times of the concentration of the compound in a ready-to-use composition. In one embodiment, the chemesthetic concentrate formulation has the present compound in a concentration that is at least 15 times of the concentration of the compound in a ready-to-use composition. In one embodiment, the chemesthetic concentrate formulation has the present compound in a concentration that is at least 20 times of the concentration of the compound in a ready-to-use composition. In one embodiment, the chemesthetic concentrate formulation has the present compound in a concentration that is at least 30 times of the concentration of the compound in a ready-to-use composition. In one embodiment, the chemesthetic concentrate formulation has the present compound in a concentration that is at least 40 times of the concentration of the compound in a ready-to-use composition. In one embodiment, the chemesthetic concentrate formulation has the present compound in a concentration that is at least 50 times of the concentration of the compound in a ready-to-use composition. In one embodiment, the chemesthetic concentrate formulation has the present compound in a concentration that is at least 60 times of the concentration of the compound in a ready-to-use composition. In one embodiment, the chemesthetic concentrate formulation has the present compound in a concentration that is up to 100 times of the concentration of the compound in a ready-to-use composition.

The personal product can be provided as a textile product. Examples of the textile product include, but are not limited to, shirts, pants, socks, towels, and etc. The present compound can be applied to the textile product in any suitable methods known to one skilled in the art. For example, the present compound can be associated with the textile by spin-coating, imprinting, in the form of microencapsulation, direct incorporation into the textile material (e.g. extruding), covalent coupling of suitable derivatives of the modulators (via suitable spacer/linker groups, with the help of which the molecule is reversibly or irreversibly bonded to the packaging material).

The personal product can be provided as packaging materials. Examples of the packaging materials include paper and plastic wrapping, which may be in various processing forms including fibers, fabrics, and moldings. The present compound can be applied to the packaging material in any suitable methods known to one skilled in the art. For example, the present compound can be associated with the packaging material by spin-coating, imprinting, in the form of microencapsulation, direct incorporation into the packaging material (e.g. extruding), covalent coupling of suitable derivatives of the modulators (via suitable spacer/linker groups, with the help of which the molecule is reversibly or irreversibly bonded to the packaging material.

The compounds of the present invention can be used for modulating transient receptor potential channel melastatin member 8 (TRPM8) by contacting the receptor with a compound of the present invention. This modulation process can be carried out either in vitro or in vivo. In one embodiment, the compound is a TRPM8 receptor agonist.

The compounds of the present invention can also be formulated into a precursor of the above-described compositions. By "precursor", it is meant a substance or composition from which another composition, such as those described above, is formed. For example, the present compounds may be provided as a concentrated formulation or composition which may be further mixed or diluted to form another composition suitable for consumption or personal use.

The present compounds can be used to modify the chemesthetic sensation of a composition by contacting the present compounds with the composition to form a taste-modified composition. In one embodiment, the present compounds can convey or impart a cooling taste to a composition.

In one embodiment, the present invention provides a method of modulating the cold or cooling sensation of a composition comprising combining the composition with a compound of the present invention, or a salt or solvate thereof, to form a modified composition.

In one embodiment, the present invention provides a method of inducing a cold or cooling sensation in a human or animal by contacting the human or animal with a compound of the present invention.

EXAMPLES 1.1) Biological Assay

The present compounds are useful as modulators of TRPM8. The activity of TRPM8 can be readily monitored in cell based assays using fluorescent calcium-sensitive dyes, membrane potential dyes, or sodium-sensitive dyes. The activity of TRPM8 can also be monitored with electrophysiological set-ups, such as patch-clamping and two-electrode voltage clamping. A mammalian cell line derivative which stably expresses TRPM8 was used in biological assays in association with testing the present compounds with cool-tasting or -feeling properties (Servant et al. US 2007/0259354 A1 and references cited therein). Typical compound concentrations tested were 100 µM, 50 µM, 10 µM, 1 µM, and 0.5 µM. The present compounds have shown strong activity as agonists of hTRPM8. Assay results for compounds are illustrated in Table 1 below. Specifically, the Compounds listed in Table 1.1, e.g., Compounds 1.A1 to Compounds 1.A9 are the specific compounds as described herein. For example, Compounds 1.A1 is Example 1.1.

TABLE 1.1

|      | hTRPM8 EC50 Ratio | hTRPM8 EC50 (uM) | Solubility (μM) LSB | Sensory Results |
|------|-------------------|------------------|---------------------|-----------------|
| 1.A5 | 25                | 0.123            |                     |                 |
| 1.B1 | 10.5              | 0.5642           |                     |                 |
| 1.B2 | 2.1               | 2.8113           |                     |                 |
| 1.B3 | 36.0              | 0.0850           | 580                 | 15 uM < 45 uM WS-3 |
| 1.B4 | 11.4              | 0.4504           |                     |                 |
| 1.B5 | 7.0               | 0.6013           |                     |                 |
| 1.B6 | 1.3               | 3.4589           |                     |                 |
| 1.A9 | 6.1               | 0.6861           |                     |                 |
| 1.A8 | 7.0               | 0.5988           |                     |                 |
| 1.B7 | 65.2              | 0.0698           |                     |                 |
| 1.A7 | 8.5               | 0.4767           |                     |                 |
| 1.A6 | 52.5              | 0.0792           |                     |                 |
| 1.A4 | 416.0             | 0.0100           | 31                  | 5 uM > 45 uM WS-3 |
| 1.B8 | 34.0              | 0.1284           |                     |                 |
| 1.B9 | 533.0             | 0.0081           | 117                 | 5 uM > 45 uM WS-3 |
| 1.C1 | 9.1               | 0.6552           |                     |                 |
| 1.C2 | 3.7               | 1.6314           |                     |                 |
| 1.C3 | 15.5              | 0.3092           |                     |                 |
| 1.C4 | 3.8               | 1.2538           |                     |                 |
| 1.C5 | 9.0               | 0.5892           |                     |                 |
| 1.C6 | 13.3              | 0.3987           |                     |                 |
| 1.C7 | 3.9               | 1.0666           |                     |                 |
| 1.C8 | 24.5              | 0.1859           |                     |                 |
| 1.A3 | 46.0              | 0.0870           | 2316                | 10 uM~45 uM WS-3 |
| 1.C9 | 45.0              | 0.0870           | 150                 |                 |
| 1.D1 | 60.5              | 0.0747           |                     |                 |
| 1.D2 | 60.7              | 0.0742           |                     |                 |
| 1.D3 | 1.7               | 2.3914           |                     |                 |
| 1.D4 | 973.4             | 0.0031           | 792                 | 2 uM~45 uM WS-3 |
| 1.D5 | 189.0             | 0.0240           | 766                 | 5 uM~45 uM WS-3 |
| 1.D6 | 117.3             | 0.0440           |                     |                 |
| 1.A2 | 564.0             | 0.0006           | 94                  | 10 uM < 45 uM WS-3 |
| 1.D7 | 1.0               | 5.7741           |                     |                 |
| 1.D8 | 374.0             | 0.0170           | 639                 | 2 uM~45 uM WS-3 |
| 1.A1 | 100.0             | 0.0340           | 337                 | 5 uM~45 uM WS-3 |

1.2) Sensory Studies

Three typical sensory studies are described below each followed by a table summarizing sensory results of selected compounds of the invention (Tables 1.2 to 1.4).

Formulation:

All samples made with Low Sodium Buffer (LSB) pH ~7.1 and contain 0.1% ethanol.

General Protocol:

Compounds are rated on a 15 point line scale where 45 μM WS-3 (N-Ethyl-p-menthane-3-carboxamide) is ranked as a 5 in cool intensity. In most cases our compounds are tested to determine at what concentration the cooling intensity is equivalent to 45 μM WS-3. In each test, the panelist is presented with a 0 μM control sample, a 45 μM WS-3 control sample and the experimental compound sample and asked to rate the cooling intensity of each sample. Panelists are also asked to rate bitterness. In the table below there was no significant bitterness detected unless otherwise noted. Also, in the table below, n represents the number of tests completed for a given experiment (#panelists×#repetitions).

Conclusions:

Panelists found 5 μM of Compound A1 was significantly more cooling than 0 μM WS-3 (p<0.05) and not significantly different in cooling than 45 μM WS-3 (p>0.05). There were no significant bitter offtastes in any of the samples (p>0.05).

TABLE 1.2

Average Cooling, n = 30 (15 Panelists × 2 rep). Tukey's Value = 0.993 ($\alpha$ = 0.05).

| Treatment | Average | SD | St Er | Tukey (5%) |
|-----------|---------|-----|-------|------------|
| 0 μM WS-3 | 0.8 | 1.8 | 0.3 | a |
| 45 μM WS-3 | 4.4 | 2.4 | 0.4 | b |
| 5 μM Compound 1.A1 | 4.7 | 2.8 | 0.5 | b |

Conclusions:

Panelists found 10 μM of Compound A3 was significantly more cooling than 0 μM WS-3 (p<0.05) and not significantly different in cooling than 45 μM WS-3 (p>0.05). There were no significant bitter offtastes in any of the samples (p>0.05).

TABLE 1.3

Average Cooling, n = 28 (14 Panelists × 2 rep). Tukey's Value = 1.078 ($\alpha$ = 0.05).

| Treatment | Average | SD | St Er | Tukey (5%) |
|-----------|---------|-----|-------|------------|
| 0 μM WS-3 | 0.9 | 1.8 | 0.3 | a |
| 10 μM Compound 1.A3 | 4.5 | 2.6 | 0.5 | b |
| 45 μM WS-3 | 5.4 | 1.7 | 0.3 | b |

Conclusions:

Panelists found 10 μM of compound 1.A2 was significantly more cooling than 0 μM WS-3 (p<0.05) and significantly less cooling than 45 μM WS-3 (p>0.05). There were no significant bitter offtastes in any of the samples (p>0.05).

TABLE 1.4

Average Cooling, n = 28 (14 Panelists × 2 rep). Tukey's Value = 1.022 ($\alpha$ = 0.05).

| Treatment | Average | SD | St Er | Tukey (5%) |
|-----------|---------|-----|-------|------------|
| 0 μM WS-3 | 0.8 | 1.6 | 0.3 | a |
| 10 μM Compound 1.A2 | 2.7 | 2.1 | 0.4 | b |
| 45 μM WS-3 | 4.1 | 2.0 | 0.4 | c |

1.3) Preparation and Examples

Standard procedures and chemical transformation and related methods are well known to one skilled in the art, and such methods and procedures have been described, for example, in standard references such as Fiesers' Reagents for Organic Synthesis, John Wiley and Sons, New York, N.Y., 2002; Organic Reactions, vols. 1-83, John Wiley and Sons, New York, N.Y., 2006; March J. and Smith M., Advanced Organic Chemistry, 6th ed., John Wiley and Sons, New York, N.Y.; and Larock R. C., Comprehensive Organic Transformations, Wiley-VCH Publishers, New York, 1999. All texts and references cited herein are incorporated by reference in their entirety.

Reactions using compounds having functional groups may be performed on compounds with functional groups that may be protected. A "protected" compound or derivatives means derivatives of a compound where one or more reactive site or sites or functional groups are blocked with protecting groups. Protected derivatives are useful in the preparation of the compounds of the present invention or in themselves; the protected derivatives may be the biologically active agent. An example of a comprehensive text listing suitable protecting groups may be found in T. W. Greene, Protecting Groups in Organic Synthesis, 3rd edition, John Wiley & Sons, Inc. 1999.

The general synthetic schemes for the preparation of the present compounds are provided in the following Schemes 1.1 to 1.4.

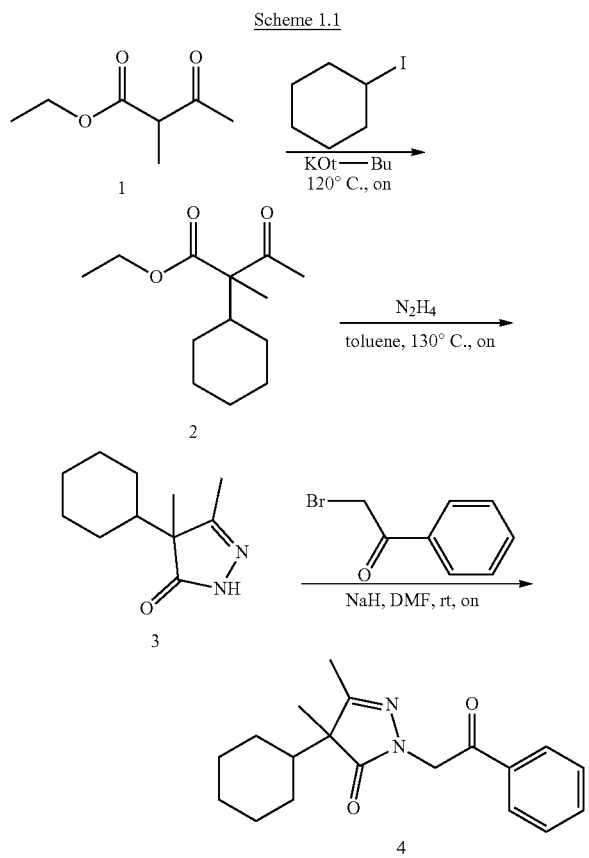

Example 1.A 4-cyclohexyl-3,4-dimethyl-1-(2-oxo-2-phenylethyl)-1H-pyrazol-5(4H)-one

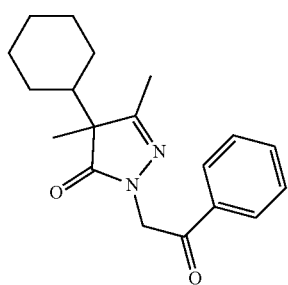 [SMILES: CC1=NN(CC(=O)c2ccccc2)C(=O)C1(C)C1CCCCC1]

Ethyl 2-cyclohexyl-2-methyl-3-oxobutanoate (Compound 2).

To the 1M solution of KOt-Bu in t-BuOH (30 mmol, 30 mL) under Nitrogen atmosphere at room temperature was added dropwise slowly ethyl 2-methyl-3-oxobutanoate (1 eq; 30 mmol; 4.27 mL). The reaction mixture was stirred at room temperature for 1 hour, and then cyclohexyl iodide was added to the resulting solution and the reaction mixture was heated at 120° C. for 24 h. A precipitate of insoluble KI was formed during the reaction. The reaction medium was allowed to cool to room temperature, and then concentrated in vacuum. The reaction was quenched with water (25 mL) and extracted with $Et_2O$ (3×20 mL). The organic layers were combined, washed with, brine (40 mL), dried over $MgSO_4$, and concentrated in vacuum, yielding 5.2 g (77%) of ethyl 2-cyclohexyl-2-methyl-3-oxobutanoate as orange-yellow oil. Crude ester was used in the next step without further purification.

4-cyclohexyl-3,4-dimethyl-1H-pyrazol-5(4H)-one (Compound 3)

To the solution of ethyl 2-cyclohexyl-2-methyl-3-oxobutanoate (Compound 2) (5.2 g; 23 mmol) in 20 mL of toluene, was added Hydrazine, 98% (1.2 eq; 27.6 mmol; 892 µL). Reaction mixture was heated at 130° C. for 18 hours with Dean-Stark adapter. The reaction medium was allowed to cool to room temperature and solvent was evaporated. The resulting residue was purified by column chromatography (Hexane/EtOAc 20%; $R^f$=0.3) utilizing a Silicycle column (120 g) to obtain the title compound (305 mg; 7%) as a yellowish crystalline solid.

4-cyclohexyl-3,4-dimethyl-1-(2-oxo-2-phenylethyl)-1H-pyrazol-5(4H)-one

To the suspension of NaH (60%; 1.2 eq; 0.62 mmol; 25 mg) in 5 mL of anhydrous DMF was added solution of 4-cyclohexyl-3,4-dimethyl-1H-pyrazol-5(4H)-one (Compound 3) (100 mg, 0.51 mmol) in 5 mL of anhydrous DMF. The reaction mixture was stirred at ambient temperature for 15 minutes and then 2-Bromoacetophenone (1.1 eq; 0.56 mmol; 112 µL) was added. The reaction mixture was stirred at room temperature for 18 hrs. Then reaction was quenched with water (15 mL) and extracted with EtOAc (3×10 mL). The organic layers were combined, washed with brine (10 mL), and dried over $MgSO_4$. Solvent was evaporated, and the resulting residue was purified by preparative HPLC using a 25 minutes $CH_3CN/H_2O$ gradient of 5-95% to give after evaporation of solvents and lyophilization the title compound (79 mg, 50% yield).

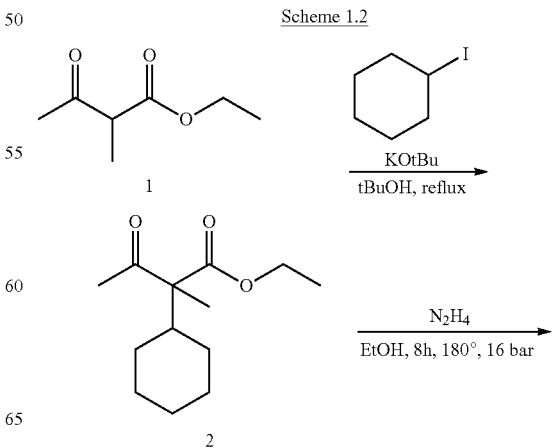

-continued

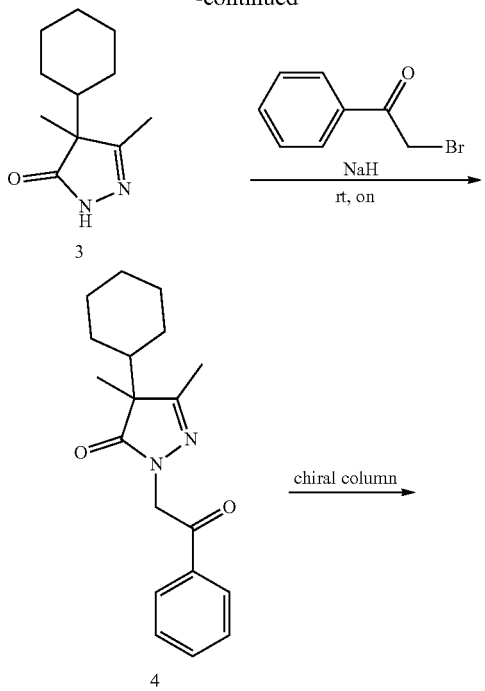

Example 1.1

4-cyclohexyl-3,4-dimethyl-1-(2-oxo-2-phenylethyl)-1H-pyrazol-5(4H)-one (Compound B11)

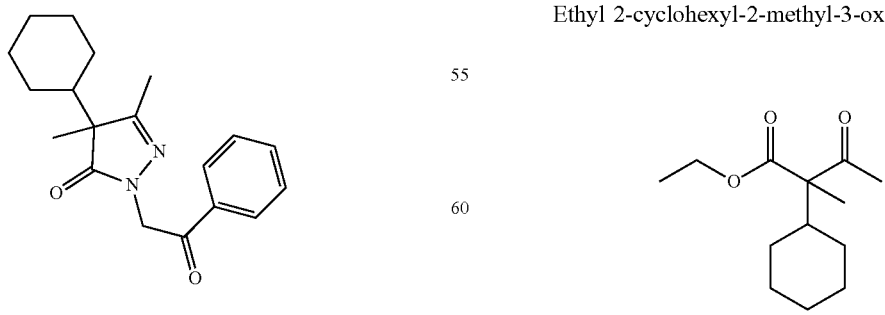

To a suspension of 60% NaH (1.2 eq; 14.77 mmol; 591 mg) in 15 mL of anhydrous DMF was added dropwise a solution of 4-cyclohexyl-3,4-dimethyl-1H-pyrazol-5(4H)-one (Example 1.1a) (2.4 g, 12.37 mmol) in 10 mL of anhydrous DMF. The reaction mixture was stirred at room temperature for 30 minutes and then was added dropwise a solution of 2-bromoacetophenone (1.1 eq; 13.6 mmol; 2.7 g). The reaction mixture was stirred at room temperature for 18 hrs. The reaction was quenched with water (30 mL) and extracted with EtOAc (3×30 mL). The organic layers were combined, washed with brine (50 mL), and dried over MgSO₄. Solvent was evaporated, and the resulting residue was purified by preparative HPLC using a 25 minutes CH₃CN/H₂O gradient of 5-95% to give after evaporation of solvents and lyophilization the 4-cyclohexyl-3,4-dimethyl-1-(2-oxo-2-phenylethyl)-1H-pyrazol-5(4H)-one (2.3 g) as a yellowish dense oil, which crystallized upon thorough drying.

¹H NMR (400 MHz, DMSO-d₆) δ 7.98 (d, J=8.0 Hz, 2H), 7.67 (t, J=8.0 Hz, 1H), 7.53 (t, J=8.0 Hz, 2H), 5.12 (s, 2H), 1.93 (s, 3H), 1.64-1.71 (m, 3H), 1.51-1.59 (m, 2H), 1.45-1.48 (m, 1H), 1.14-1.27 (m, 3H), 1.18 (s, 3H), 0.91-1.11 (m, 2H). MS 313 (MH⁺).

Example 1.1a 4-cyclohexyl-3,4-dimethyl-1H-pyrazol-5(4H)-one

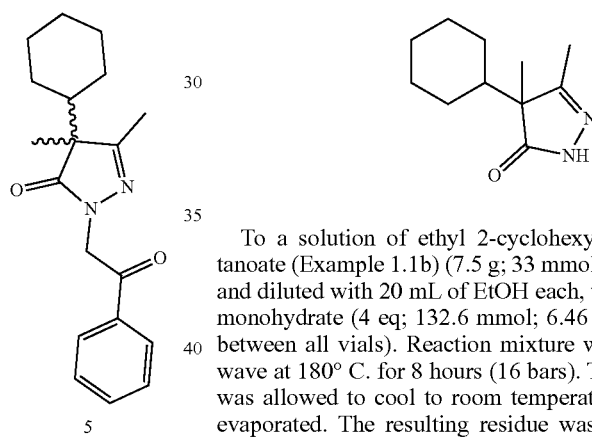

To a solution of ethyl 2-cyclohexyl-2-methyl-3-oxobutanoate (Example 1.1b) (7.5 g; 33 mmol) divided into 3 vials and diluted with 20 mL of EtOH each, was added hydrazine monohydrate (4 eq; 132.6 mmol; 6.46 mL, equally divided between all vials). Reaction mixture was heated in microwave at 180° C. for 8 hours (16 bars). The reaction medium was allowed to cool to room temperature and solvent was evaporated. The resulting residue was recrystallized from hexane to obtain the title compound (5.2 g; 81%) as a white crystalline solid.

¹H NMR (400 MHz, DMSO-d₆) δ 10.85 (s, 1H), 1.90 (s, 3H), 1.65-1.72 (m, 2H), 1.55-1.60 (m, 2H), 1.44-1.48 (m, 2H), 1.21-1.30 (m, 1H), 1.10-1.18 (m, 2H), 1.01-1.09 (m, 1H), 1.07 (s, 3H), 0.83-0.92 (m, 1H). MS 195 (MH⁺).

Example 1.1b

Ethyl 2-cyclohexyl-2-methyl-3-oxobutanoate

To 1M solution of KOt-Bu in t-BuOH (100 mmol, 100 mL) under nitrogen atmosphere at room temperature was added dropwise over 10 min ethyl 2-methyl-3-oxobutanoate (1 eq; 100 mmol; 14.25 mL). Reaction mixture was stirred at 50° C. for 1 hour, and then cyclohexyl iodide (1.2 eq; 120 mmol; 15.6 mL) was added to the resulting solution and reaction mixture was heated at 120° C. for 24 h. Precipitate of insoluble KI was formed during reaction. The reaction medium was allowed to cool to room temperature, and then concentrated under vacuum. The reaction was quenched with water (25 mL) and extracted with Et$_2$O (3×20 mL). The organic layers were combined, washed with brine (40 mL), and dried over MgSO$_4$, and concentrated under vacuum. Crude product was purified by flash column chromatography (Hexane/EtOAc 2%; R$_f$=0.6), yielding 7.5 g (33%) of ethyl 2-cyclohexyl-2-methyl-3-oxobutanoate as a light yellow oil.

$^1$H NMR (400 MHz, DMSO-d$_6$) δ 4.09 (q, J=8.0 Hz, J=8.0 Hz, 2H), 2.07-2.12 (m, 1H), 2.07 (s, 3H), 1.64-1.71 (m, 2H), 1.58-1.62 (m, 1H), 1.43-1.47 (m, 1H), 1.33-1.37 (m, 1H), 1.14-1.24 (m, 2H), 1.15 (t, J=8.0 Hz, 3H), 1.14 (s, 3H), 0.97-1.10 (m, 2H), 0.83-0.91 (m, 1H). MS 227 (MH$^+$).

Example 1.2

(+)—(S)-4-cyclohexyl-3,4-dimethyl-1-(2-oxo-2-phenylethyl)-1H-pyrazol-5(4H)-one

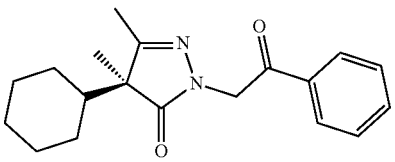 [SMILES: CC1=NN(CC(=O)c2ccccc2)C(=O)[C@@]1(C)C1CCCCC1]

Chiral separation of 4-cyclohexyl-3,4-dimethyl-1-(2-oxo-2-phenylethyl)-1H-pyrazol-5(4H)-one (Example 1.1) (3.7 g) was performed on Agilent LCMS system using a column Chiral Pak AD-H (60 min run, 15 mL/min, Hexane/IPA 10% isocratic), retention time for title compound is 56 min. After evaporation of solvents and lyophilization the desired enantiomer was obtained (1043 mg) as a yellowish glassy oil. Optical rotation was measured on Perkin Elmer polarimeter, model 341. Sample was prepared in 10 mg/mL EtOH. [α]$^{20}_D$=+114.30.

$^1$H NMR (400 MHz, DMSO-d$_6$) δ 7.98 (d, J=8.0 Hz, 2H), 7.67 (t, J=8.0 Hz, 1H), 7.53 (t, J=8.0 Hz, 2H), 5.13 (d, J=1.6 Hz, 2H), 1.93 (s, 3H), 1.64-1.71 (m, 3H), 1.51-1.59 (m, 2H), 1.45-1.48 (m, 1H), 1.17-1.27 (m, 2H), 1.14 (s, 3H), 1.11-1.17 (m, 1H), 0.91-1.12 (m, 2H). MS 313 (MH$^+$).

Example 1.3

(−)-(R)-4-cyclohexyl-3,4-dimethyl-1-(2-oxo-2-phenylethyl)-1H-pyrazol-5(4H)-one

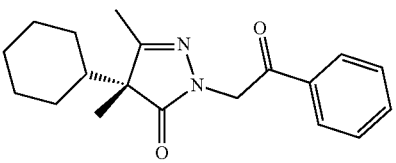 [SMILES: CC1=NN(CC(=O)c2ccccc2)C(=O)[C@]1(C)C1CCCCC1]

Prepared in a similar manner as described in Example 1.2 starting from of 4-cyclohexyl-3,4-dimethyl-1-(2-oxo-2-phenylethyl)-1H-pyrazol-5(4H)-one (Example 1.1) (3.7 g). Retention time for title compound is 34 min. The desired enantiomer was obtained (1322 mg) as a yellowish glassy oil. [α]$^{20}_D$=−113.9°.

$^1$H NMR (400 MHz, DMSO-d$_6$) δ 7.98 (d, J=8.0 Hz, 2H), 7.67 (t, J=8.0 Hz, 1H), 7.53 (t, J=8.0 Hz, 2H), 5.13 (d, J=1.6 Hz, 2H), 1.93 (s, 3H), 1.64-1.71 (m, 3H), 1.51-1.59 (m, 2H), 1.45-1.48 (m, 1H), 1.17-1.27 (m, 2H), 1.14 (s, 3H), 1.11-1.17 (m, 1H), 0.91-1.12 (m, 2H). MS 313 (MH$^+$).

Example 1.4

4-cyclohexyl-1-(2-(3-hydroxyphenyl)-2-oxoethyl)-3,4-dimethyl-1H-pyrazol-5(4H)-one

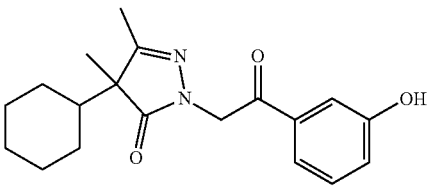 [SMILES: CC1=NN(CC(=O)c2cccc(O)c2)C(=O)C1(C)C1CCCCC1]

Prepared in a similar manner as described in Example 1.1 starting from 4-cyclohexyl-3,4-dimethyl-1H-pyrazol-5(4H)-one (1a) (400 mg, 2.06 mmol) and 2-bromo-1-(3-hydroxyphenyl)-ethanone (487 mg, 2.26 mmol) to obtain the desired 4-cyclohexyl-1-(2-(3-hydroxyphenyl)-2-oxoethyl)-3,4-dimethyl-1H-pyrazol-5(4H)-one (38.7 mg, 5%) as a white powder.

$^1$H NMR (400 MHz, DMSO-d$_6$) δ 10.0 (bs, 1H), 7.40 (d, J=8.0 Hz, 1H), 7.30 (t, J=8.0 Hz, 1H), 7.26 (s, 1H), 7.03 (d, J=8.0 Hz, 1H), 5.03 (d, 1.6 Hz, 2H), 1.91 (s, 3H), 1.63-1.69 (m, 3H), 1.51-1.59 (m, 2H), 1.45-1.48 (m, 1H), 1.17-1.27 (m, 2H), 1.13 (s, 3H), 1.11-1.17 (m, 1H), 0.91-1.12 (m, 2H). MS 329 (MH$^+$).

Example 1.5

4-cyclohexyl-1-(2-(3-fluorophenyl)-2-oxoethyl)-3,4-dimethyl-1H-pyrazol-5(4H)-one

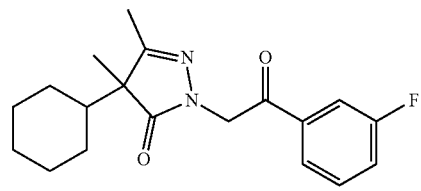 [SMILES: CC1=NN(CC(=O)c2cccc(F)c2)C(=O)C1(C)C1CCCCC1]

Prepared in a similar manner as described in Example 1.1 starting from 4-cyclohexyl-3,4-dimethyl-1H-pyrazol-5(4H)-one (1a) (97 mg, 0.5 mmol) and 2-bromo-1-(3-fluorophenyl)-ethanone (119 mg, 0.55 mmol) to obtain the desired 4-cyclohexyl-1-(2-(3-fluorophenyl)-2-oxoethyl)-3,4-dimethyl-1H-pyrazol-5(4H)-one (46 mg, 28%) as a white powder.

$^1$H NMR (400 MHz, DMSO-d$_6$) δ 7.83 (dt, J=7.6, 1.3 Hz, 1H), 7.78 (m, 1H), 7.60 (td, J=7.9, 5.8 Hz, 1H), 7.53 (tdd, J=8.4, 2.6, 1.1 Hz, 1H), 5.17 (d, J=18.0 Hz, 1H), 5.12 (d, J=18.0 Hz, 1H), 1.93 (s, 3H), 1.63-1.71 (m, 3H), 1.51-1.63

(m, 2H), 1.44-1.47 (m, 1H), 1.17-1.27 (m, 2H), 1.14 (s, 3H), 1.11-1.17 (m, 1H), 0.89-1.12 (m, 2H). MS 331 (MH+).

Example 1.6

4-cyclohexyl-3,4-dimethyl-1-(2-oxo-2-(thiophen-3-yl)ethyl)-1H-pyrazol-5(4H)-one

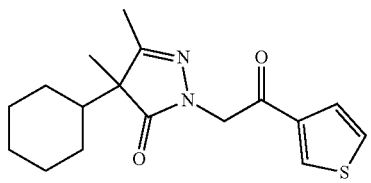 [SMILES: CC1=NN(CC(=O)c2ccsc2)C(=O)C1(C)C1CCCCC1]

Prepared in a similar manner as described in Example 1.1 starting from 4-cyclohexyl-3,4-dimethyl-1H-pyrazol-5(4H)-one (1a) (194 mg, 1 mmol) and 2-bromo-1-(thiophen-3-yl)ethanone (226 mg, 1.1 mmol) to obtain the desired 4-cyclohexyl-3,4-dimethyl-1-(2-oxo-2-(thiophen-3-yl)ethyl)-1H-pyrazol-5(4H)-one (140.4 mg, 44%) as a white powder.

$^1$H NMR (400 MHz, DMSO-$d_6$) δ 8.62 (dd, J=1.2 Hz, J=2.8 Hz, 1H), 7.67 (dd, J=2.8 Hz, J=4.8 Hz, 1H), 7.52 (dd, J=1.2 Hz, J=5.2 Hz, 1H), 5.00 (s, 2H), 1.93 (s, 3H), 1.64-1.71 (m, 3H), 1.46-1.59 (m, 3H), 1.17-1.27 (m, 2H), 1.14 (s, 3H), 1.11-1.17 (m, 1H), 0.91-1.12 (m, 2H). MS 319 (MH+).

Example 1.7

(+)-(S)-4-cyclohexyl-3,4-dimethyl-1-(2-oxo-2-(thiophen-3-yl)ethyl)-1H-pyrazol-5(4H)-one

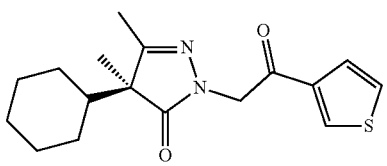 [SMILES: CC1=NN(CC(=O)c2ccsc2)C(=O)[C@@]1(C)C1CCCCC1]

Prepared in a similar manner as described in Example 1.2 starting from of 4-cyclohexyl-3,4-dimethyl-1-(2-oxo-2-(thiophen-3-yl)ethyl)-1H-pyrazol-5(4H)-one (Example 1.6) (179 mg). Retention time for title compound is 39 min. The desired enantiomer was obtained (68.4 mg) as a white powder. $[α]^{20}_D$=+104.2°.

$^1$H NMR (400 MHz, DMSO-$d_6$) δ 8.61 (dd, J=1.2 Hz, J=2.8 Hz, 1H), 7.67 (dd, J=2.8 Hz, J=4.8 Hz, 1H), 7.52 (dd, J=1.2 Hz, J=5.2 Hz, 1H), 5.00 (s, 2H), 1.93 (s, 3H), 1.64-1.71 (m, 3H), 1.46-1.59 (m, 3H), 1.17-1.27 (m, 2H), 1.14 (s, 3H), 1.11-1.17 (m, 1H), 0.91-1.12 (m, 2H). MS 319 (MH+).

Example 1.8

(−)-(R)-4-cyclohexyl-3,4-dimethyl-1-(2-oxo-2-(thiophen-3-yl)ethyl)-1H-pyrazol-5(4H)-one

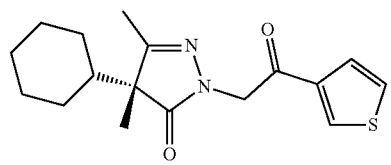 [SMILES: CC1=NN(CC(=O)c2ccsc2)C(=O)[C@]1(C)C1CCCCC1]

Prepared in a similar manner as described in Example 1.2 starting from of 4-cyclohexyl-3,4-dimethyl-1-(2-oxo-2-(thiophen-3-yl)ethyl)-1H-pyrazol-5(4H)-one (Example 1.6) (179 mg). Retention time for title compound is 20 min. The desired enantiomer was obtained (74.8 mg) as a white powder. $[α]^{20}_D$=−101.6°.

$^1$H NMR (400 MHz, DMSO-$d_6$) 8.61 (dd, J=1.2 Hz, J=2.8 Hz, 1H), 7.67 (dd, J=2.8 Hz, J=4.8 Hz, 1H), 7.52 (dd, J=1.2 Hz, J=5.2 Hz, 1H) 5.00 (s, 2H), 1.93 (s, 3H), 1.64-1.71 (m, 3H), 1.46-1.59 (m, 3H), 1.17-1.27 (m, 2H), 1.14 (s, 3H), 1.11-1.17 (m, 1H), 0.91-1.12 (m, 2H). MS 319 (MH+).

Example 1.9

4-cyclohexyl-1-(2-(4-fluorophenyl)-2-oxoethyl)-3,4-dimethyl-1H-pyrazol-5(4H)-one

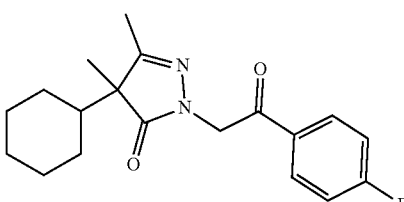

Prepared in a similar manner as described in Example 1.1 starting from 4-cyclohexyl-3,4-dimethyl-1H-pyrazol-5(4H)-one (1a) (97 mg, 0.5 mmol) and 2-bromo-1-(4-fluorophenyl)-ethanone (119 mg, 0.55 mmol) to obtain the desired 4-cyclohexyl-1-(2-(4-fluorophenyl)-2-oxoethyl)-3,4-dimethyl-1H-pyrazol-5(4H)-one (55 mg, 33%) as a white powder.

$^1$H NMR (400 MHz, DMSO-$d_6$) δ 8.07 (dd, J=5.6 Hz, J=9.2 Hz, 2H), 7.37 (t, J=9.2 Hz, 2H), 5.13 (d, J=1.6 Hz, 2H), 1.93 (s, 3H), 1.63-1.71 (m, 3H), 1.51-1.59 (m, 2H), 1.45-1.48 (m, 1H), 1.17-1.27 (m, 2H), 1.14 (s, 3H), 1.11-1.17 (m, 1H), 0.89-1.12 (m, 2H). MS 331 (MH+).

Example 1.10

4-cyclohexyl-3,4-dimethyl-1-(2-oxo-2-(thiophen-2-yl)ethyl)-1H-pyrazol-5(4H)-one

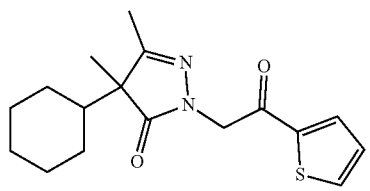 [SMILES: CC1=NN(CC(=O)c2cccs2)C(=O)C1(C)C1CCCCC1]

Prepared in a similar manner as described in Example 1.1 starting from 4-cyclohexyl-3,4-dimethyl-1H-pyrazol-5(4H)-one (1a) (97 mg, 0.5 mmol) and 2-chloro-1-(thiophen-2-yl)ethanone (88 mg, 0.55 mmol) to obtain the desired 4-cyclohexyl-3,4-dimethyl-1-(2-oxo-2-(thiophen-2-yl)ethyl)-1H-pyrazol-5(4H)-one (20.6 mg, 13%) as a white powder.

$^1$H NMR (400 MHz, DMSO-$d_6$) δ 8.10-8.07 (m, 2H), 7.28 (dd, J=4.0 Hz, J=8.0 Hz, 1H), 5.06 (s, 2H), 1.93 (s, 3H), 1.64-1.71 (m, 3H), 1.51-1.59 (m, 2H), 1.46-1.49 (m, 1H), 1.17-1.27 (m, 2H), 1.14 (s, 3H), 1.11-1.17 (m, 1H), 0.91-1.12 (m, 2H). MS 319 (MH$^+$).

Example 1.11

1-(2-(benzo[d][1,3]dioxol-5-yl)-2-oxoethyl)-4-cyclohexyl-3,4-dimethyl-1H-pyrazol-5(4H)-one

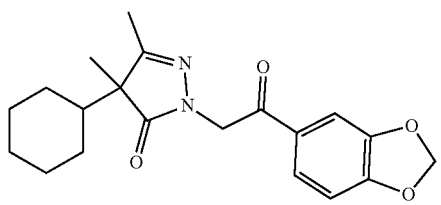 [SMILES: CC1=NN(CC(=O)c2ccc3c(c2)OCO3)C(=O)C1(C)C1CCCCC1]

Prepared in a similar manner as described in Example 1.1 starting from 4-cyclohexyl-3,4-dimethyl-1H-pyrazol-5(4H)-one (1a) (97 mg, 0.5 mmol) and 5-(bromoacetyl)-1,3-benzodioxolane (134 mg, 0.55 mmol) to obtain the desired 1-(2-(benzo[d][1,3]dioxol-5-yl)-2-oxoethyl)-4-cyclohexyl-3,4-dimethyl-1H-pyrazol-5(4H)-one (95.5 mg, 54%) as a white powder.

$^1$H NMR (400 MHz, DMSO-$d_6$) δ 7.63 (d, J=8.0 Hz, 1H), 7.46 (s, 1H), 7.05 (d, J=8.0 Hz, 1H), 6.13 (s, 2H), 5.03 (s, 2H), 1.93 (s, 3H), 1.64-1.71 (m, 3H), 1.51-1.59 (m, 2H), 1.46-1.49 (m, 1H), 1.17-1.27 (m, 2H), 1.14 (s, 3H), 1.11-1.17 (m, 1H), 0.91-1.12 (m, 2H). MS 357 (MH$^+$).

Example 1.12

4-cyclohexyl-3,4-dimethyl-1-(2-oxo-2-(1H-pyrrol-2-yl)ethyl)-1H-pyrazol-5(4H)-one

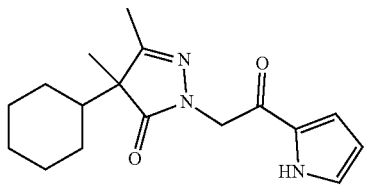 [SMILES: CC1=NN(CC(=O)c2ccc[nH]2)C(=O)C1(C)C1CCCCC1]

Prepared in a similar manner as described in Example 1.1 starting from 4-cyclohexyl-3,4-dimethyl-1H-pyrazol-5(4H)-one (1a) (400 mg, 2.06 mmol) and 2-chloro-1-(1H-pyrrol-2-yl)ethanone (326 mg, 2.26 mmol) to obtain the desired 4-cyclohexyl-3,4-dimethyl-1-(2-oxo-2-(1H-pyrrol-2-yl)ethyl)-1H-pyrazol-5(4H)-one (105.8 mg, 17%) as a white powder.

$^1$H NMR (400 MHz, DMSO-$d_6$) δ 11.92 (s, 1NH), 7.16-7.07 (m, 2H), 6.20 (dd, J=3.8 Hz, J=2.4 Hz, 1H), 4.80 (s, 2H), 1.91 (s, 3H), 1.64-1.71 (m, 3H), 1.51-1.59 (m, 2H), 1.46-1.49 (m, 1H), 1.17-1.27 (m, 2H), 1.12 (s, 3H), 1.11-1.17 (m, 1H), 0.95-1.12 (m, 2H). MS 302 (MH$^+$).

Example 1.13

4-cyclohexyl-3,4-dimethyl-1-(2-oxo-2-(pyridin-3-yl)ethyl)-1H-pyrazol-5(4H)-one

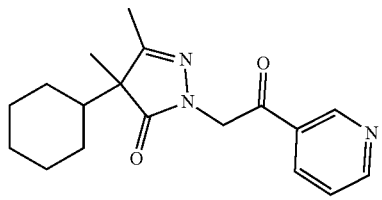 [SMILES: CC1=NN(CC(=O)c2cccnc2)C(=O)C1(C)C1CCCCC1]

Prepared in a similar manner as described in Example 1.1 starting from 4-cyclohexyl-3,4-dimethyl-1H-pyrazol-5(4H)-one (1a) (97 mg, 0.5 mmol) and 2-bromo-1-(pyridin-3-yl)ethanone hydrobromide (155 mg, 0.55 mmol) to obtain the desired 4-cyclohexyl-3,4-dimethyl-1-(2-oxo-2-(pyridin-3-yl)ethyl)-1H-pyrazol-5(4H)-one (42.5 mg, 27%) as a white powder.

$^1$H NMR (400 MHz, DMSO-$d_6$) δ 9.15 (dd, J=2.3 Hz, J=0.8 Hz, 1H), 8.82 (dd, J=4.8 Hz, J=1.7 Hz, 1H), 8.31 (dt, J=8.0 Hz, J=1.8 Hz, 1H), 7.58 (ddd, J=8.0 Hz, J=4.8 Hz, J=0.8 Hz, 1H), 5.20 (d, J=2.0 Hz, 2H), 1.93 (s, 3H), 1.63-1.71 (m, 3H), 1.51-1.59 (m, 2H), 1.44-1.47 (m, 1H), 1.17-1.27 (m, 2H), 1.14 (s, 3H), 1.11-1.17 (m, 1H), 0.89-1.12 (m, 2H). MS 314 (MH$^+$).

Example 1.14

4-cyclohexyl-1-(2-(3-methoxyphenyl)-2-oxoethyl)-3,4-dimethyl-1H-pyrazol-5(4H)-one

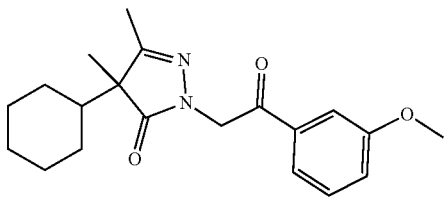 [SMILES: COc1cccc(C(=O)CN2N=C(C)C(C)(C3CCCCC3)C2=O)c1]

Prepared in a similar manner as described in Example 1.1 starting from 4-cyclohexyl-3,4-dimethyl-1H-pyrazol-5(4H)-one (1a) (97 mg, 0.5 mmol) and 2-bromo-1-(3-methoxyphenyl)-ethanone (126 mg, 0.55 mmol) to obtain the desired 4-cyclohexyl-1-(2-(3-methoxyphenyl)-2-oxoethyl)-3,4-dimethyl-1H-pyrazol-5(4H)-one (75.3 mg, 44%) as a white powder.

$^1$H NMR (400 MHz, DMSO-$d_6$) δ 7.58 (ddd, J=7.6 Hz, J=1.5 Hz, J=1.0 Hz, 1H), 7.50-7.41 (m, 2H), 7.23 (ddd, J=8.2 Hz, J=2.7 Hz, J=0.9 Hz, 1H), 5.14 (d, J=18.0 Hz, 1H), 5.08 (d, J=18.0 Hz, 1H), 3.80 (s, 3H), 1.93 (s, 3H), 1.63-1.71 (m, 3H), 1.51-1.59 (m, 2H), 1.44-1.47 (m, 1H), 1.16-1.27 (m, 2H), 1.14 (s, 3H), 1.11-1.17 (m, 1H), 0.89-1.12 (m, 2H). MS 343 (MH$^+$).

Example 1.15

4-cyclohexyl-3,4-dimethyl-1-(2-oxo-2-(pyridin-2-yl)ethyl)-1H-pyrazol-5(4H)-one

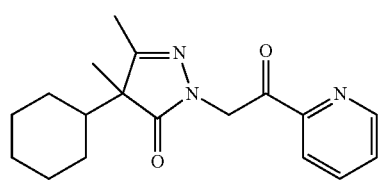 [SMILES: CC1=NN(CC(=O)c2ccccn2)C(=O)C1(C)C1CCCCC1]

Prepared in a similar manner as described in Example 1.1 starting from 4-cyclohexyl-3,4-dimethyl-1H-pyrazol-5(4H)-one (1a) (97 mg, 0.5 mmol) and 2-bromo-1-(pyridin-2-yl) ethanone hydrobromide (155 mg, 0.55 mmol) to obtain the desired 4-cyclohexyl-3,4-dimethyl-1-(2-oxo-2-(pyridin-2-yl)ethyl)-1H-pyrazol-5(4H)-one (13.6 mg, 9%) as a white powder.

$^1$H NMR (400 MHz, DMSO-$d_6$) δ 8.75 (ddd, J=4.8 Hz, J=1.7 Hz, J=0.9 Hz, 1H), 8.04 (td, J=7.7 Hz, J=1.7 Hz, 1H), 7.96 (dt, J=7.8 Hz, J=1.2 Hz, 1H), 7.72 (ddd, J=7.5 Hz, J=4.8 Hz, J=1.3 Hz, 1H), 5.22 (d, J=1.2 Hz, 2H), 1.94 (s, 3H), 1.63-1.71 (m, 3H), 1.51-1.59 (m, 2H), 1.44-1.47 (m, 1H), 1.17-1.28 (m, 2H), 1.16 (s, 3H), 1.11-1.17 (m, 1H), 0.89-1.12 (m, 2H). MS 314 (MH$^+$).

Example 1.16

4-cyclohexyl-3,4-dimethyl-1-(2-oxo-2-(pyridin-4-yl)ethyl)-1H-pyrazol-5(4H)-one

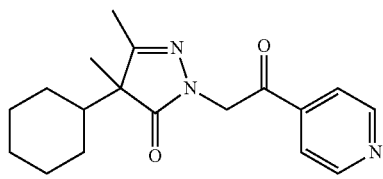 [SMILES: CC1=NN(CC(=O)c2ccncc2)C(=O)C1(C)C1CCCCC1]

Prepared in a similar manner as described in Example 1.1 starting from 4-cyclohexyl-3,4-dimethyl-1H-pyrazol-5(4H)-one (1a) (97 mg, 0.5 mmol) and 2-bromo-1-(pyridin-4-yl) ethanone hydrobromide (155 mg, 0.55 mmol) to obtain the desired 4-cyclohexyl-3,4-dimethyl-1-(2-oxo-2-(pyridin-4-yl)ethyl)-1H-pyrazol-5(4H)-one (21.7 mg, 14%) as a white powder.

$^1$H NMR (400 MHz, DMSO-$d_6$) δ 8.81 (d, J=5.6 Hz, 2H), 7.83 (d, J=6.0 Hz, 2H), 5.19 (d, J=2.8 Hz, 2H), 1.93 (s, 3H), 1.63-1.71 (m, 3H), 1.51-1.59 (m, 2H), 1.44-1.47 (m, 1H), 1.17-1.28 (m, 2H), 1.13 (s, 3H), 1.11-1.17 (m, 1H), 0.89-1.12 (m, 2H). MS 314 (MH$^+$).

Example 1.17

4-cyclohexyl-1-(2-(4-methoxyphenyl)-2-oxoethyl)-3,4-dimethyl-1H-pyrazol-5(4H)-one

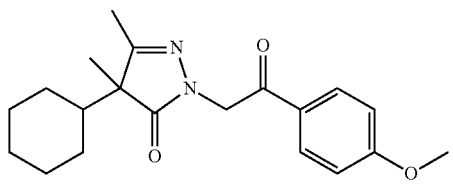 [SMILES: COc1ccc(C(=O)CN2N=C(C)C(C)(C3CCCCC3)C2=O)cc1]

Prepared in a similar manner as described in Example 1.1 starting from 4-cyclohexyl-3,4-dimethyl-1H-pyrazol-5(4H)-one (1a) (97 mg, 0.5 mmol) and 2-bromo-1-(4-methoxyphenyl)-ethanone (126 mg, 0.55 mmol) to obtain the desired 4-cyclohexyl-1-(2-(4-methoxyphenyl)-2-oxoethyl)-3,4-dimethyl-1H-pyrazol-5(4H)-one (110 mg, 64%) as a white powder.

$^1$H NMR (400 MHz, DMSO-$d_6$) δ 7.96 (d, J=8.0 Hz, 2H), 7.05 (d, J=8.0 Hz, 2H), 5.05 (s, 2H), 3.83 (s, 3H), 1.92 (s, 3H), 1.63-1.71 (m, 3H), 1.51-1.59 (m, 2H), 1.44-1.47 (m, 1H), 1.16-1.27 (m, 2H), 1.14 (s, 3H), 1.11-1.17 (m, 1H), 0.89-1.12 (m, 2H). MS 343 (MH$^+$).

Example 1.18

4-cyclohexyl-3,4-dimethyl-1-(2-oxo-2-(1H-pyrrol-3-yl)ethyl)-1H-pyrazol-5(4H)-one

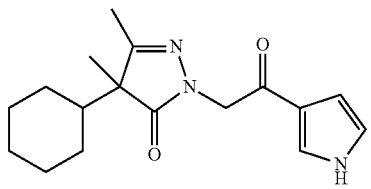 [SMILES: CC1=NN(CC(=O)c2cc[nH]c2)C(=O)C1(C)C1CCCCC1]

Prepared in a similar manner as described in Example 1.1 starting from 4-cyclohexyl-3,4-dimethyl-1H-pyrazol-5(4H)-one (1a) (97 mg, 0.5 mmol) and 2-chloro-1-(1H-pyrrol-3-yl)-ethanone (79 mg, 0.55 mmol) to obtain the desired 4-cyclohexyl-3,4-dimethyl-1-(2-oxo-2-(1H-pyrrol-3-yl)ethyl)-1H-pyrazol-5(4H)-one (35.1 mg, 23%) as a white powder.

$^1$H NMR (400 MHz, DMSO-$d_6$) δ 11.55 (s, 1NH), 7.69 (s, 1H), 6.86 (dd, J=2.8 Hz, J=1.8 Hz, 1H), 6.47 (dd, J=2.8 Hz, J=1.5 Hz, 1H), 4.76 (s, 2H), 1.91 (s, 3H), 1.64-1.71 (m, 3H), 1.51-1.59 (m, 2H), 1.46-1.49 (m, 1H), 1.17-1.28 (m, 2H), 1.13 (s, 3H), 1.11-1.17 (m, 1H), 0.94-1.12 (m, 2H). MS 302 (MH$^+$).

Example 1.19

1-(2-(3-chlorophenyl)-2-oxoethyl)-4-cyclohexyl-3,4-dimethyl-1H-pyrazol-5(4H)-one

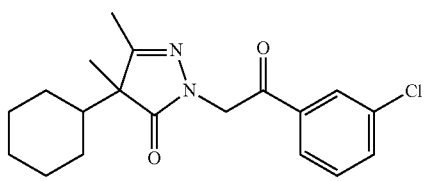 [SMILES: CC1=NN(CC(=O)c2cccc(Cl)c2)C(=O)C1(C)C1CCCCC1]

Prepared in a similar manner as described in Example 1.1 starting from 4-cyclohexyl-3,4-dimethyl-1H-pyrazol-5(4H)-one (1a) (97 mg, 0.5 mmol) and 2-bromo-1-(3-chlorophenyl)-ethanone (128 mg, 0.55 mmol) to obtain the desired 1-(2-(3-chlorophenyl)-2-oxoethyl)-4-cyclohexyl-3,4-dimethyl-1H-pyrazol-5(4H)-one (56 mg, 32%) as a white powder.

$^1$H NMR (400 MHz, DMSO-$d_6$) δ 7.99 (t, J=1.8 Hz, 1H), 7.95-7.90 (m, 1H), 7.74 (ddd, J=8.0 Hz, J=2.2 Hz, J=1.0 Hz, 1H), 7.57 (t, J=7.9 Hz, 1H), 5.17 (d, J=18.0 Hz, 1H), 5.10 (d, J=18.0 Hz, 1H), 1.93 (s, 3H), 1.63-1.71 (m, 3H), 1.51-1.59 (m, 2H), 1.44-1.47 (m, 1H), 1.16-1.27 (m, 2H), 1.13 (s, 3H), 1.11-1.17 (m, 1H), 0.89-1.12 (m, 2H). MS 347 (MH$^+$).

Example 1.20

4-cyclohexyl-3,4-dimethyl-1-(2-oxo-2-(m-tolyl)ethyl)-1H-pyrazol-5(4H)-one

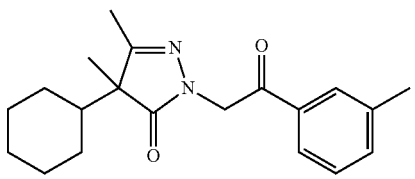 [SMILES: CC1=NN(CC(=O)c2cccc(C)c2)C(=O)C1(C)C1CCCCC1]

Prepared in a similar manner as described in Example 1.1 starting from 4-cyclohexyl-3,4-dimethyl-1H-pyrazol-5(4H)-one (1a) (97 mg, 0.5 mmol) and 2-bromo-1-(m-tolyl)ethanone (117 mg, 0.55 mmol) to obtain the desired 4-cyclohexyl-3,4-dimethyl-1-(2-oxo-2-(m-tolyl)ethyl)-1H-pyrazol-5(4H)-one (99.3 mg, 61%) as a white powder.

$^1$H NMR (400 MHz, DMSO-$d_6$) δ 7.79 (s, 1H), 7.77 (d, J=8.0 Hz, 1H), 7.48 (d, J=8.0 Hz, 1H), 7.41 (t, J=8.0 Hz, 1H), 5.12 (d, J=18.0 Hz, 1H), 5.06 (d, J=18.0 Hz, 1H), 2.36 (s, 3H), 1.93 (s, 3H), 1.63-1.71 (m, 3H), 1.51-1.59 (m, 2H), 1.44-1.47 (m, 1H), 1.16-1.27 (m, 2H), 1.14 (s, 3H), 1.11-1.17 (m, 1H), 0.89-1.12 (m, 2H). MS 327 (MH$^+$).

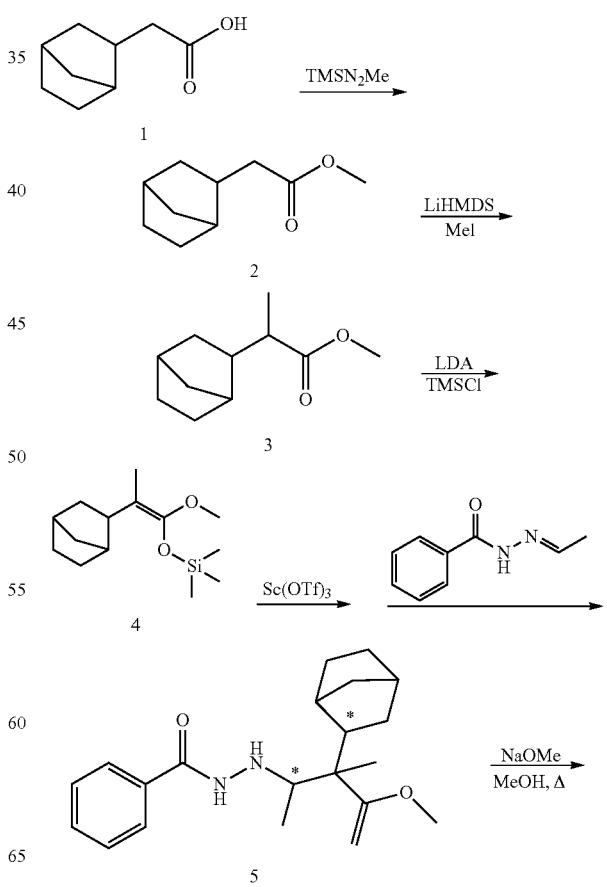

Scheme 1.3

-continued

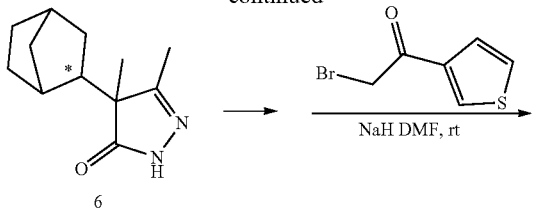

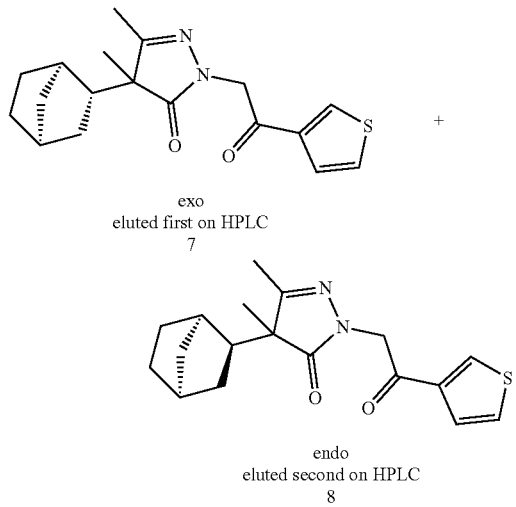

exo
eluted first on HPLC
7 endo
eluted second on HPLC
8

Example 1.21

4-((1R,2R,4S)-bicyclo[2.2.1]heptan-2-yl)-3,4-dimethyl-1-(2-oxo-2-(thiophen-3-yl)ethyl)-1H-pyrazol-5(4H)-one

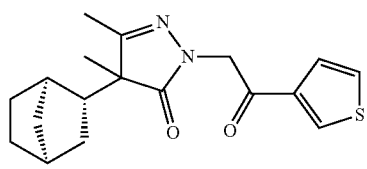 [SMILES: CC1=NN(CC(=O)c2ccsc2)C(=O)C1(C)[C@@H]1C[C@H]2CC[C@@H]1C2]

To a suspension of NaH (60%; 1.2 eq; 1.92 mmol; 77 mg) in 3 mL of anhydrous DMF at room temperature under $N_2$ atmosphere was added dropwise a solution of 4-(bicyclo[2.2.1]heptan-2-yl)-3,4-dimethyl-1H-pyrazol-5(4H)-one (Compound 6, Example 1.21a) (330 mg, 1.6 mmol) in 3 mL of anhydrous DMF. The reaction mixture was stirred at ambient temperature for 15 minutes and a solution of 2-bromo-1-(thiophen-3-yl)ethanone (1.1 eq; 1.76 mmol; 361 mg) in 2 mL of anhydrous DMF was added dropwise. The reaction mixture was stirred at room temperature for 18 hrs. The reaction was quenched with water (30 mL) and extracted with EtOAc (3×30 mL). The organic layers were combined, washed with brine (30 mL), and dried over $MgSO_4$. Solvent was evaporated, and the resulting residue was purified by preparative HPLC using a 25 minutes $CH_3CN/H_2O$ gradient of 5-95%, to give as first-eluting the desired product 4-((1R,2R,4S)-bicyclo[2.2.1]heptan-2-yl)-3,4-dimethyl-1-(2-oxo-2-(thiophen-3-yl)ethyl)-1H-pyrazol-5(4H)-one (109 mg, 21%) as a white-greenish solid. NMR analysis showed this product to be mostly related to exo-norbornyl enantiomer, as compared to the literature available for NMR spectra of exo-/endo-norborneol[i].

[i] H NMR (400 MHz, DMSO-$d_6$) δ 8.62 (dd, J=2.8, 1.3 Hz, 1H), 7.67 (dd, J=5.1, 2.8 Hz, 1H), 7.52 (dd, J=5.1, 1.3 Hz, 1H), 5.04 (d, J=18.0 Hz, 1H), 4.98 (d, J=18.0 Hz, 1H), 2.38 (bs, 1H), 2.10 (bs, 1H), 1.91 (s, 3H), 1.62 (t, J=8.0 Hz, 1H), 1.43-1.45 (m, 2H), 1.23-1.30 (m, 2H), 1.20 (s, 3H), 1.09-1.12 (m, 2H), 0.89-1.02 (m, 2H). MS 331 (MH$^+$).

Example 1.21a 4-(bicyclo[2.2.1]heptan-2-yl)-3,4-dimethyl-1H-pyrazol-5(4H)-one

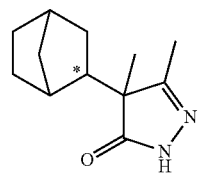

To the suspension of NaOMe (95%; 3 eq; 21.3 mmol; 1.2 g) in 50 mL of anhydrous methanol at room temperature was added solution of methyl 3-(2-benzoylhydrazinyl)-2-(bicyclo[2.2.1]heptan-2-yl)-2-methylbutanoate (Compound 5, Example 1.21b) (2.44 g, 7.09 mmol) in 5 mL of anhydrous methanol. The reaction mixture was heated at 100° C. for 18 h. Amberlite (H$^+$) resin was added to the reaction mixture until a clear solution and pH=4 were obtained. The resin was filtered off, washed with MeOH and the resulting solution was concentrated in vacuum. The residue was purified by column chromatography (DCM/EtOAc 20%; $R_f$=0.5) to obtain the title compound (438 mg; 30%) as a white powder, mixture of 2 isomers.

[1] H NMR (400 MHz, DMSO-$d_6$) δ 10.85 (s, 1H), 2.26 (bs, 0.5H), 2.15 (bs, 0.5H), 2.08 (bs, 0.5H), 1.93-1.97 (m, 0.5H), 1.87 (s, 1.5H), 1.85 (s, 1.5H), 1.62 (bs, 0.5H), 1.52-1.59 (m, 1H), 1.35-1.44 (m, 2H), 1.21-1.30 (m, 2H), 1.10 (s, 1.5H), 1.05-1.12 (m, 2H), 0.98 (s, 1.5H), 0.95 (d, J=8.0 Hz, 0.5H), 0.86 (d, J=8.0 Hz, 0.5H), 0.74-0.77 (m, 0.5H). MS 207 (MH$^+$).

Example 1.21b

Methyl 3-(2-benzoylhydrazinyl)-2-(bicyclo[2.2.1]heptan-2-yl)-2-methylbutanoate

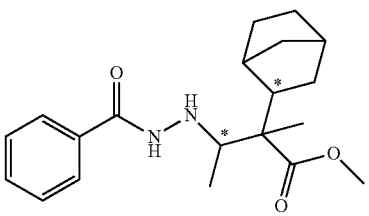 [SMILES: COC(=O)C(C)(C(C)NNC(=O)c1ccccc1)C1CC2CCC1C2]

To a solution of benzohydrazide (50 mmol, 6.8 g) in 50 mL of EtOH was added acetaldehyde (1.1 eq, 55 mmol, 3.1 mL) and the reaction mixture was stirred at room temperature for 2 h. The precipitated product was filtered off, washed with cold EtOH and dried in vacuum to afford N'-ethylidenebenzohydrazide (4 g, 50% yield) which was used further crude.

To a suspension of N'-ethylidenebenzohydrazide (1.5 g, 9.2 mmol) and scandium (III) triflate (0.1 eq, 0.92 mmol, 453 mg) in 20 mL of anhydrous acetonitrile at −20° C. was added dropwise a solution of (2-(bicyclo[2.2.1]heptan-2-yl)-1-methoxyprop-1-enyloxy)trimethylsilane (Compound 4, Example 1.21c) (1.5 eq, 13.85 mmol, 3.5 g) in 5 mL of anhydrous acetonitrile. The reaction mixture was stirred at −20° C. for 2 h, warmed to room temperature and stirred for 18 hours. The reaction was quenched with saturated NaHCO₃ solution (50 mL) and extracted with EtOAc (3×30 mL). The organic layers were combined, washed with brine (40 mL), dried over MgSO₄ and concentrated under vacuum. The resulting residue was purified by column chromatography (Hexane/EtOAc 20%; $R_f$=0.5) to obtain the title compound (2.4 g; 77%) as a white powder, mixture of four isomers.

¹H NMR (400 MHz, DMSO-d₆) δ 9.96-9.93 (m, 0.5NH), 9.91-9.88 (m, 0.5NH), 7.91-7.72 (m, 2H), 7.57-7.34 (m, 3H), 5.01 (t, J=7.6 Hz, 0.25H), 4.94 (t, J=7.6 Hz, 0.25H), 4.85 (t, J=7.6 Hz, 0.25H), 4.80 (t, J=7.6 Hz, 0.25H), 3.57 (s, 0.75H), 3.56 (s, 0.75H), 3.55 (s, 0.75H), 3.53 (s, 0.75H), 3.40-3.18 (m, 1H), 2.16 (bs, 0.5H), 2.11 (bs, 1H), 2.05-1.97 (m, 0.75H), 1.88 (t, J=7.8 Hz, 0.25H), 1.78 (t, J=8.0 Hz, 0.25H), 1.64 (t, J=7.7 Hz, 0.25H), 1.37-1.52 (m, 3H), 1.20-1.37 (m, 2H), 1.17 (s, 0.75H), 1.15-1.04 (m, 3H), 1.09 (s, 1.5H), 1.05 (s, 0.75H), 1.03-0.90 (m, 3H). MS 343 (MH⁺).

Example 1.21c (2-(bicyclo[2.2.1]heptan-2-yl)-1-methoxyprop-1-enyloxy)trimethylsilane

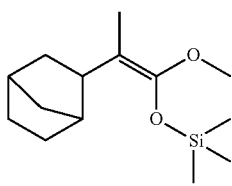 [SMILES: CO/C(O[Si](C)(C)C)=C(\C)C1CC2CCC1C2]

To a solution of diisopropylamine (23 mmol, 3.2 mL) in 20 mL of anhydrous THF at −20° C. under nitrogen atmosphere was added dropwise over 5 min 2.5M solution of n-butyllitium in hexane (23 mmol, 9.2 mL). The mixture was stirred for 15 min, and a solution of methyl 2-(bicyclo [2.2.1]heptan-2-yl)propanoate (3) (22.7 mmol, 4.13 g) in anhydrous THF (5 mL) was added. The reaction mixture was stirred at −20° C. for 1 h, and trimethylsilyl chloride (99%, 2.5 eq, 57.5 mmol, 7.3 mL) was added dropwise. The reaction mixture was slowly warmed up to room temperature and stirred for 18 hours. The formed precipitate was filtered off, filtrate was concentrated under vacuum, washed with diethyl ether and more precipitate was filtered off. The final solution was concentrated and dried under vacuum to give (2-(bicyclo[2.2.1]heptan-2-yl)-1-methoxyprop-1-enyloxy)trimethylsilane (5.5 g, 94%) as a yellow oil, mixture of E-/Z-isomers which was used further crude.

¹H NMR (400 MHz, CDCl₃) δ 3.28 (s, 3H), 2.33 (t, J=8.0 Hz, 0.7H), 2.21 (t, J=7.2 Hz, 0.3H), 2.01 (bs, 1H), 1.79 (bs, 1H), 1.31 (s, 1H), 1.27 (s, 2H), 1.21-1.28 (m, 4H), 0.96-1.12 (m, 2H), 0.87-0.91 (m, 2H), 0.01 (s, 3H), 0.00 (s, 6H).

Example 1.21d

Methyl 2-(bicyclo[2.2.1]heptan-2-yl)propanoate

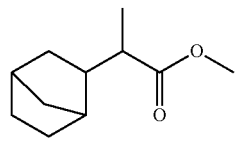

To a solution of methyl 2-(bicyclo[2.2.1]-heptan-2-yl) acetate (Example 1.21e) (6 g, 35.7 mmol) in 50 mL of anhydrous THF at −78° C. under nitrogen atmosphere was added dropwise 1M solution of LiHMDS in THF (1.15 eq, 41 mmol, 41 mL). The reaction mixture was stirred at −78° C. for 1 h, and iodomethane (1.2 eq, 42.8 mmol, 2.6 mL) was added. The reaction mixture was slowly warmed up to room temperature and stirred for 18 h. The reaction was quenched with water (50 mL) and extracted with EtOAc (3×30 mL). The organic layers were combined, washed with brine (40 mL), dried over MgSO₄ and concentrated under vacuum. The resulting residue was purified by column chromatography (Hexane/EtOAc 2%; $R_f$=0.5) to obtain the title compound (4.13 g; 64%) as a light yellow oil.

¹H NMR (400 MHz, DMSO-d₆) δ 3.54 (s, 3H), 2.12 (bs, 1H), 1.99-2.03 (m, 1H), 1.78 (bs, 1H), 1.30-1.39 (m, 4H), 1.18-1.21 (m, 1H), 0.97-1.06 (m, 4H), 0.92 (d, J=7.2 Hz, 3H). MS 183 (MH⁺).

Example 1.21e

Methyl 2-(bicyclo[2.2.1]heptan-2-yl)acetate

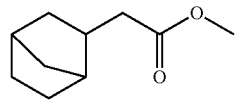

In a 250 mL round bottom flask were placed under nitrogen atmosphere 2-(bicyclo[2.2.1]heptan-2-yl)acetic acid (5 g, 32.46 mmol), anhydrous diethyl ether (40 mL) and methanol (10 mL) and the mixture was cooled to 0° C. in an ice bath. To the mixture was then added a 2M solution of (trimethylsilyl)diazomethane in diethyl ether (2 eq., 65 mmol, 32.5 mL) dropwise. After addition was complete, the mixture was warmed to room temperature and stirred for 2 h. The mixture was concentrated under vacuum to afford methyl 2-(bicyclo[2.2.1]heptan-2-yl)acetate (6 g, 100% yield) which was used further crude.

¹H NMR (400 MHz, DMSO-d₆) δ 3.55 (s, 3H), 2.25 (dd, J=8.0 Hz, J=16.0 Hz, 1H), 2.15 (bs, 1H), 2.10 (dd, J=8.0 Hz, J=15.2 Hz, 1H), 1.92 (bs, 1H), 1.74-1.81 (m, 1H), 1.39-1.45 (m, 3H), 1.27-1.30 (m, 1H), 0.97-1.14 (m, 4H). MS 169 (MH⁺).

Example 1.22

4-((1R,2S,4S)-bicyclo[2.2.1]heptan-2-yl)-3,4-dimethyl-1-(2-oxo-2-(thiophen-3-yl)ethyl)-1H-pyrazol-5(4H)-one

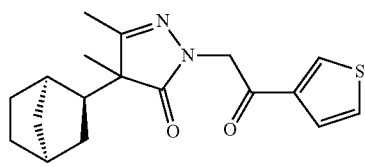 [SMILES: CC1=NN(CC(=O)c2ccsc2)C(=O)C1(C)[C@H]1C[C@H]2CC[C@@H]1C2]

Prepared in a similar manner as described in Example 1.21 starting from 4-(bicyclo[2.2.1]heptan-2-yl)-3,4-dimethyl-1H-pyrazol-5 (4H)-one (Example 1.21a) (330 mg, 1.6 mmol) and 2-bromo-1-(thiophen-3-yl)ethanone (1.1 eq; 1.76 mmol; 361 mg) and eluted second on preparative HPLC column, to obtain the desired 4-((1R,2S,4S)-bicyclo[2.2.1]heptan-2-yl)-3,4-dimethyl-1-(2-oxo-2-(thiophen-3-yl)ethyl)-1H-pyrazol-5(4H)-one (99.3 mg, 61%) as a white powder. NMR analysis showed that this product mostly related to endo-norbornyl enantiomer, as compared to the literature available NMR spectra of exo-/endo-norborneol[ii].

$^1$H NMR (400 MHz, DMSO-$d_6$) δ 8.62 (dd, J=2.8, 1.3 Hz, 1H), 7.67 (dd, J=5.1, 2.8 Hz, 1H), 7.52 (dd, J=5.1, 1.3 Hz, 1H), 5.04 (d, J=18.0 Hz, 1H), 4.98 (d, J=18.0 Hz, 1H), 2.15 (bs, 1H), 1.98-2.03 (m, 1H), 1.94 (s, 3H), 1.74 (bs, 1H), 1.66 (t, J=8.0 Hz, 1H), 1.30-1.43 (m, 2H), 1.20-1.31 (m, 2H), 1.08 (s, 3H), 1.09-1.12 (m, 2H), 0.87 (bd, J=9.0 Hz, 1H). MS 331 (MH$^+$).

Example 1.23

4-((1R,2R,4S)-bicyclo[2.2.1]heptan-2-yl)-3,4-dimethyl-1-(2-oxo-2-phenylethyl)-1H-pyrazol-5(4H)-one

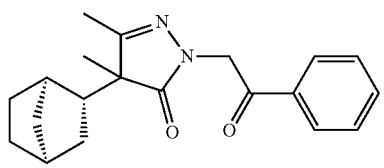 [SMILES: CC1=NN(CC(=O)c2ccccc2)C(=O)C1(C)[C@@H]1C[C@H]2CC[C@@H]1C2]

Prepared in a similar manner as described in Example 1.21 starting from 4-(bicyclo[2.2.1]heptan-2-yl)-3,4-dimethyl-1H-pyrazol-5 (4H)-one (Example 1.21a) (180 mg, 0.87 mmol) and 2-bromoacetophenone (1.1 eq; 0.96 mmol; 190 mg) and eluted first on preparative HPLC column, to obtain the desired 4-((1R,2R,4S)-bicyclo[2.2.1]heptan-2-yl)-3,4-dimethyl-1-(2-oxo-2-phenylethyl)-1H-pyrazol-5(4H)-one (126 mg, 39%) as a white powder. NMR analysis showed that this product mostly related to exo-norbornyl enantiomer, as compared to the literature available NMR spectra of exo-/endo-norborneol[iii].

$^1$H NMR (400 MHz, DMSO-$d_6$) δ 7.98 (d, J=8.0 Hz, 2H), 7.67 (t, J=8.0 Hz, 1H), 7.53 (t, J=8.0 Hz, 2H), 5.16 (d, J=18.0 Hz, 1H), 5.09 (d, J=18.0 Hz, 1H), 2.38 (bs, 1H), 2.09 (bs, 1H), 1.91 (s, 3H), 1.62 (t, J=8.0 Hz, 1H), 1.43-1.45 (m, 2H), 1.21-1.32 (m, 2H), 1.21 (s, 3H), 1.09-1.12 (m, 2H), 0.89-1.02 (m, 2H). MS 325 (MH$^+$).

Example 1.24

4-((1R,2S,4S)-bicyclo[2.2.1]heptan-2-yl)-3,4-dimethyl-1-(2-oxo-2-phenylethyl)-1H-pyrazol-5(4H)-one

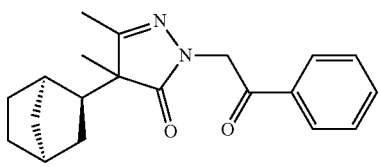 [SMILES: CC1=NN(CC(=O)c2ccccc2)C(=O)C1(C)[C@H]1C[C@H]2CC[C@@H]1C2]

Prepared in a similar manner as described in Example 1.21 starting from 4-(bicyclo[2.2.1]heptan-2-yl)-3,4-dimethyl-1H-pyrazol-5 (4H)-one (Example 1.21a) (180 mg, 0.87 mmol) and 2-bromoacetophenone (1.1 eq; 0.96 mmol; 190 mg) and eluted second on preparative HPLC column, to obtain the desired 4-((1R,2S,4S)-bicyclo[2.2.1]heptan-2-yl)-3,4-dimethyl-1-(2-oxo-2-phenylethyl)-1H-pyrazol-5(4H)-one (50 mg, 17%) as a white powder. NMR analysis showed that this product mostly related to endo-norbornyl enantiomer, as compared to the literature available NMR spectra of exo-/endo-norborneol[iv].

$^1$H NMR (400 MHz, DMSO-$d_6$) δ 7.98 (d, J=8.0 Hz, 2H), 7.67 (t, J=8.0 Hz, 1H), 7.53 (t, J=8.0 Hz, 2H), 5.16 (d, J=18.0 Hz, 1H), 5.10 (d, J=18.0 Hz, 1H), 2.15 (bs, 1H), 1.98-2.01 (m, 1H), 1.94 (s, 3H), 1.74 (bs, 1H), 1.67 (t, J=8.0 Hz, 1H), 1.37-1.43 (m, 2H), 1.20-1.31 (m, 2H), 1.14-1.09 (m, 2H), 1.09 (s, 3H), 0.88-0.85 (m, 1H). MS 325 (MH$^+$).

Example 1.25

4-((1R,2R,4S)-bicyclo[2.2.1]heptan-2-yl)-3,4-dimethyl-1-(2-oxo-2-(1H-pyrrol-2-yl)ethyl)-1H-pyrazol-5(4H)-one

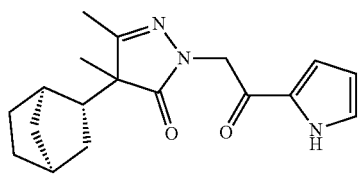 [SMILES: CC1=NN(CC(=O)c2ccc[nH]2)C(=O)C1(C)[C@@H]1C[C@H]2CC[C@@H]1C2]

Prepared in a similar manner as described in Example 1.21 starting from 4-(bicyclo[2.2.1]heptan-2-yl)-3,4-dimethyl-1H-pyrazol-5 (4H)-one (Example 1.21a) (378 mg, 1.83 mmol) and 2-chloro-1-(1H-pyrrol-2-yl)ethanone (1 eq; 1.83 mmol; 263 mg) and eluted first on preparative HPLC column, to obtain the desired 4-((1R,2R,4S)-bicyclo[2.2.1]heptan-2-yl)-3,4-dimethyl-1-(2-oxo-2-(1H-pyrrol-2-yl)ethyl)-1H-pyrazol-5(4H)-one (16.5 mg, 3%) as a white powder. NMR analysis showed that this product mostly related to exo-norbornyl enantiomer, as compared to the literature available NMR spectra of exo-/endo-norborneol[v].

$^1$H NMR (400 MHz, DMSO-$d_6$) δ 11.94 (s, 1NH), 7.09-7.13 (m, 2H), 6.20 (dd, J=3.7 Hz, J=2.4 Hz, 1H), 4.89-4.77 (m, 2H), 2.40 (bs, 1H), 2.09 (bs, 1H), 1.91 (s, 3H), 1.62 (t, J=8.0 Hz, 1H), 1.43-1.45 (m, 2H), 1.21-1.32 (m, 2H), 1.19 (s, 3H), 1.09-1.12 (m, 2H), 0.89-1.02 (m, 2H). MS 314 (MH$^+$).

Example 1.26

4-((1R,2S,4S)-bicyclo[2.2.1]heptan-2-yl)-3,4-dimethyl-1-(2-oxo-2-(1H-pyrrol-2-yl)ethyl)-1H-pyrazol-5(4H)-one

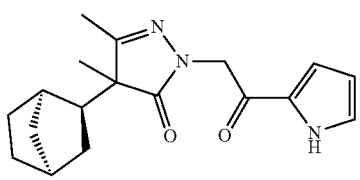 [SMILES: CC1=NN(CC(=O)c2ccc[nH]2)C(=O)C1(C)[C@H]1C[C@H]2CC[C@@H]1C2]

Prepared in a similar manner as described in Example 1.21 starting from 4-(bicyclo[2.2.1]heptan-2-yl)-3,4-dimethyl-1H-pyrazol-5 (4H)-one (Example 1.21a) (378 mg, 1.83 mmol) and 2-chloro-1-(1H-pyrrol-2-yl)ethanone (1 eq; 1.83 mmol; 263 mg) and eluted second on preparative HPLC column, to obtain the desired 4-((1R,2S,4S)-bicyclo[2.2.1] heptan-2-yl)-3,4-dimethyl-1-(2-oxo-2-(1H-pyrrol-2-yl) ethyl)-1H-pyrazol-5(4H)-one (17.4 mg, 3%) as a white powder. NMR analysis showed that this product mostly related to endo-norbornyl enantiomer, as compared to the literature available NMR spectra of exo-/endo-norborneol[vi].

$^1$H NMR (400 MHz, DMSO-d$_6$) δ 11.91 (s, 1NH), 7.09-7.13 (m, 2H), 6.20 (dd, J=3.8 Hz, J=2.4 Hz, 1H), 4.88-4.76 (m, 2H), 2.14 (bs, 1H), 1.98-2.02 (m, 1H), 1.93 (s, 3H), 1.75 (bs, 1H), 1.65 (t, J=8.0 Hz, 1H), 1.35-1.43 (m, 2H), 1.24-1.31 (m, 2H), 1.09 (s, 3H), 1.09-1.14 (m, 2H), 0.87 (d, J=8.0 Hz, 1H). MS 314 (MH$^+$).

Example 1.27

4-cyclohexyl-3-ethyl-4-methyl-1-(2-oxo-2-phenylethyl)-1H-pyrazol-5(4H)-one

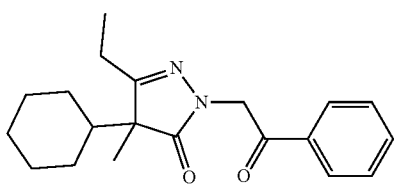 [SMILES: CCC1=NN(CC(=O)c2ccccc2)C(=O)C1(C)C1CCCCC1]

Prepared in a similar manner as described in Example 1.21 starting from 4-cyclohexyl-3-ethyl-4-methyl-1H-pyrazol-5(4H)-one (Example 1.27a) (104 mg, 0.5 mmol) and 2-bromoacetophenone (1.1 eq; 0.55 mmol; 110 mg) to obtain the desired 4-cyclohexyl-3-ethyl-4-methyl-1-(2-oxo-2-phenylethyl)-1H-pyrazol-5(4H)-one (53 mg, 32%) as a white powder.

$^1$H NMR (400 MHz, DMSO-d$_6$) δ 7.99 (d, J=8.0 Hz, 2H), 7.67 (t, J=8.0 Hz, 1H), 7.53 (t, J=8.0 Hz, 2H), 5.16 (s, 2H), 2.27-2.33 (m, 2H), 1.63-1.72 (m, 3H), 1.52-1.59 (m, 2H), 1.43 (m, 1H), 1.16-1.30 (m, 1H), 1.14 (s, 3H), 1.06-1.17 (m, 3H), 1.08 (t, J=7.6 Hz, 3H), 0.90-1.02 (m, 1H). MS 327 (MH$^+$).

Example 1.27 a 4-cyclohexyl-3-ethyl-4-methyl-1H-pyrazol-5(4H)-one

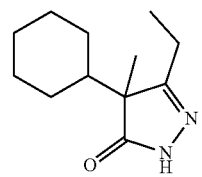

Prepared in a similar manner as described in Example 1.21a starting from methyl 3-(2-benzoylhydrazinyl)-2-cyclohexyl-2-methylpentanoate (Example 1.27b) (1.4 g, 4 mmol) and sodium methoxide (3 eq; 12 mmol; 690 mg) to obtain the desired 4-cyclohexyl-3-ethyl-4-methyl-1H-pyrazol-5(4H)-one (462 mg, 55%) as a white powder.

$^1$H NMR (400 MHz, DMSO-d$_6$) δ 10.86 (s, 1NH), 2.22 (q, J=7.6 Hz, 2H), 1.61-1.70 (m, 2H), 1.54-1.57 (m, 2H), 1.44-1.48 (m, 1H), 1.39 (m, 1H), 1.24-1.27 (m, 1H), 1.06-1.14 (m, 3H), 1.08 (t, J=7.6 Hz, 3H), 1.04 (s, 3H), 0.81-0.85 (m, 1H). MS 209 (MH$^+$).

Example 1.27 b

Methyl 3-(2-benzoylhydrazinyl)-2-cyclohexyl-2-methylpentanoate

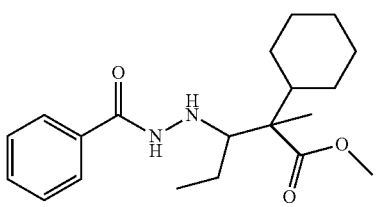 [SMILES: CCC(NNC(=O)c1ccccc1)C(C)(C(=O)OC)C1CCCCC1]

Prepared in a similar manner as described in Example 1.21b starting from ((2-cyclohexyl-1-methoxyprop-1-en-1-yl)oxy)trimethylsilane (Example 1.27c) (2.9 g, 12.35 mmol) and N'-propylidenebenzohydrazide (8.23 mmol; 1.45 g) to obtain the desired methyl 3-(2-benzoyl-hydrazinyl)2-cyclohexyl-2-methylpentanoate (462 mg, 50%) as a white powder.

$^1$H NMR (400 MHz, DMSO-d$_6$) δ 9.95 (d, J=4.0 Hz, 0.4NH), 9.92 (d, J=8.0 Hz, 0.6NH), 7.80 (t, J=8.0 Hz, 2H), 7.54-7.49 (m, 1H), 7.47-7.44 (m, 2H), 5.54 (t, J=8.0 Hz, 0.6NH), 4.96 (t, J=4.0 Hz, 0.4NH), 3.58 (s, 0.3H), 3.57 (s, 1.0H), 3.55 (s, 1.7H), 3.23-3.20 (m, 0.4H), 3.02 (t, J=8.0 Hz, 0.6H), 1.85-1.93 (m, 1H), 1.65-1.55 (m, 4H), 1.43-1.48 (m, 1H), 1.19-1.29 (m, 3H), 1.18 (s, 1.2H), 1.02-1.11 (m, 3H), 1.04 (s, 1.8H), 0.96 (t, J=7.6 Hz, 3H), 0.83-0.66 (m, 1H). MS 347 (MH$^+$).

Example 1.27 c ((2-cyclohexyl-1-methoxyprop-1-en-1-yl)oxy)trimethylsilane

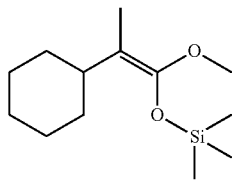 [SMILES: CO/C(O[Si](C)(C)C)=C(\C)C1CCCCC1]

Prepared in a similar manner as described in Example 1.21c starting from methyl 2-cyclohexylpropanoate (Example 1.27d) (5 g, 29.4 mmol) and trimethylsilyl chloride (99%, 2.5 eq, 75 mmol; 9.46 mL) to obtain the desired methyl ((2-cyclohexyl-1-methoxyprop-1-en-1-yl)oxy)trimethylsilane (6.23 g, 87%) as a yellow oil.

$^1$H NMR (400 MHz, CDCl$_3$) δ 3.43 (s, 1.8H), 3.42 (s, 1.2H), 1.65-1.74 (m, 3H), 1.52-1.60 (m, 2H), 1.39 (s, 1.2H), 1.36 (s, 1.8H), 1.14-1.23 (m, 5H), 1.04-1.03 (m, 1H), 0.14 (s, 3H), 0.13 (s, 6H).

Example 1.27 d

Methyl 2-cyclohexylpropanoate

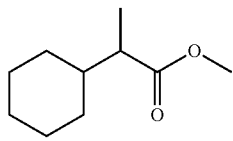

Prepared in a similar manner as described in Example 1.21d starting from methyl 2-cyclohexylacetate (5 g, 32 mmol) and methyl iodide (1.2 eq, 38.4 mmol; 2.4 mL) to obtain the desired methyl 2-cyclohexylpropanoate (5 g, 93%) as a yellow oil.

$^1$H NMR (400 MHz, CDCl$_3$) δ 3.56 (s, 3H), 2.19-2.22 (m, 1H), 1.40-1.67 (m, 6H), 1.07-1.18 (m, 3H), 1.00 (d, J=8.0 Hz, 3H), 0.96-0.85 (m, 2H). MS 171 (MH$^+$).

Example 1.28

4-cyclopentyl-3,4-dimethyl-1-(2-oxo-2-phenylethyl)-1H-pyrazol-5(4H)-one

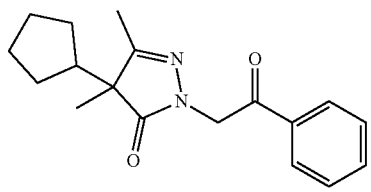 [SMILES: CC1=NN(CC(=O)c2ccccc2)C(=O)C1(C)C1CCCC1]

Prepared in a similar manner as described in Example 1.1 starting from 4-cyclopentyl-3,4-dimethyl-1H-pyrazol-5 (4H)-one (Example 1.28a) (100 mg, 0.56 mmol) and 2-bromoacetophenone (1.1 eq; 0.67 mmol; 134 mg) to obtain the desired 4-cyclopentyl-3,4-dimethyl-1-(2-oxo-2-phenylethyl)-1H-pyrazol-5(4H)-one (43 mg, 26%) as a white powder.

$^1$H NMR (400 MHz, DMSO-d$_6$) δ 7.98 (d, J=8.0 Hz, 2H), 7.67 (t, J=8.0 Hz, 1H), 7.53 (t, J=8 Hz, 2H), 5.17 (d, J=18.0 Hz, 1H), 5.11 (d, J=18.0 Hz, 1H), 2.04-2.13 (m, 1H), 1.94 (s, 3H), 1.68-1.77 (m, 1H), 1.40-1.64 (m, 6H), 1.19 (s, 3H), 1.02-1.11 (m, 1H). MS 299 (MH$^+$). MS 299 (MH$^+$).

Example 1.28a 4-cyclopentyl-3,4-dimethyl-1H-pyrazol-5(4H)-one

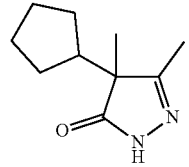

Prepared in a similar manner as described in Example 1.1a starting from ethyl 2-cyclopentyl-2-methyl-3-oxobutanoate (Example 1.28b) (950 mg, 4.48 mmol) and hydrazine (98%, 1.2 eq; 5.37 mmol; 175 μL) to obtain the desired 4-cyclopentyl-3,4-dimethyl-1H-pyrazol-5(4H)-one (217 mg, 27%) as a white powder.

$^1$H NMR (400 MHz, DMSO-d$_6$) δ 10.85 (s, 1NH), 1.99-2.03 (m, 1H), 1.88 (s, 3H), 1.61-1.65 (m, 1H), 1.39-1.55 (m, 6H), 1.08 (s, 3H), 0.87-0.91 (m, 1H). MS 181 (MH$^+$).

Example 1.28b

Ethyl 2-cyclopentyl-2-methyl-3-oxobutanoate

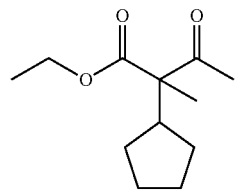

Prepared in a similar manner as described in Example 1.1b starting from ethyl 2-methyl-3-oxobutanoate (2.02 mL, 14.2 mmol) and cyclopentyl iodide (1.1 eq; 15.61 mmol; 3.06 g) to obtain the desired ethyl 2-cyclopentyl-2-methyl-3-oxobutanoate (950 mg, 32%) as a yellow oil.

$^1$H NMR (400 MHz, DMSO-d$_6$) δ 4.09 (q, J=8.0 Hz, 2H), 2.45-2.50 (m, 1H), 2.07 (s, 3H), 1.43-1.67 (m, 6H), 1.23-1.29 (m, 1H), 1.17 (s, 3H), 1.15 (t, J=8.0 Hz, 3H), 1.04-1.09 (m, 1H). MS 212 (MH$^+$).

Example 1.29

3,4-dimethyl-4-(2-methylcyclopentyl)-1-(2-oxo-2-phenylethyl)-1H-pyrazol-5(4H)-one

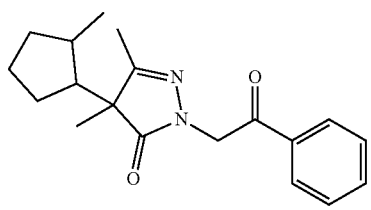 [SMILES: CC1=NN(CC(=O)c2ccccc2)C(=O)C1(C)C1CCCC1C]

Prepared in a similar manner as described in Example 1.1 starting from 3,4-dimethyl-4-(2-methylcyclopentyl)-1H-pyrazol-5(4H)-one (Example 1.29a) (130 mg, 0.67 mmol) and 2-bromoacetophenone (1.2 eq; 0.8 mmol; 160 mg) to obtain the desired 3,4-dimethyl-4-(2-methylcyclopentyl)-1-(2-oxo-2-phenylethyl)-1H-pyrazol-5(4H)-one (11.6 mg, 6%) as an oily film.

$^1$H NMR (400 MHz, DMSO-$d_6$) δ 7.99 (d, J=8.0 Hz, 2H), 7.67 (t, J=8.0 Hz, 1H), 7.53 (t, J=8 Hz, 2H), 5.05-5.20 (m, 2H), 2.22-2.28 (m, 0.5H), 2.07-2.13 (m, 0.5H), 2.04 (s, 1H), 1.99-2.00 (m, 0.5H), 1.97 (s, 1.5H), 1.94 (s, 0.5H), 1.88-1.94 (m, 0.5H), 1.40-1.81 (m, 5H), 1.22 (s, 0.75H), 1.217 (s, 0.75H), 1.21 (s, 0.75H), 1.18 (s, 0.75H), 1.08-1.18 (m, 1H), 0.95 (d, J=7.2 Hz, 0.5H), 0.88 (d, J=6.8 Hz, 1H), 0.66 (d, J=7.2 Hz, 0.5H), 0.56 (d, J=6.8 Hz, 1H). MS 313 (MH$^+$).

Example 1.29a 3,4-dimethyl-4-(2-methylcyclopentyl)-1H-pyrazol-5(4H)-one

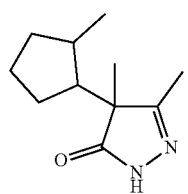

Prepared in a similar manner as described in Example 1.1a starting from ethyl 2-methyl-2-(2-methylcyclopentyl)-3-oxobutanoate (Example 1.28b) (824 mg, 3.64 mmol) and hydrazine (98%, 1.2 eq; 4.37 mmol; 141 µL to obtain the desired 3,4-dimethyl-4-(2-methylcyclopentyl)-1H-pyrazol-5(4H)-one (131 mg, 27%) as a white powder, mixture of isomers.

$^1$H NMR (400 MHz, DMSO-$d_6$) δ 10.99 (s, 0.5H), 10.89 (s, 0.25H), 10.86 (s, 0.25H), 2.34-2.20 (m, 0.4H), 2.15-2.01 (m, 0.6H), 2.00 (s, 1H), 1.99-1.93 (m, 0.8H), 1.92 (2s, 1.5H), 1.89 (s, 0.5H), 1.77-1.51 (m, 4H), 1.51-1.38 (m, 1H), 1.23-1.13 (m, 1H), 1.12 (s, 1H), 1.10 (s, 1.5H), 1.09 (s, 0.5H), 1.06-0.96 (m, 0.2H), 0.92 (d, J=6.8 Hz, 0.5H), 0.87 (d, J=6.6 Hz, 0.5H), 0.61 (d, J=7.0 Hz, 1H), 0.53 (d, J=7.1 Hz, 1H). MS 195 (MH$^+$).

Example 1.29b

Ethyl 2-methyl-2-(2-methylcyclopentyl)-3-oxobutanoate

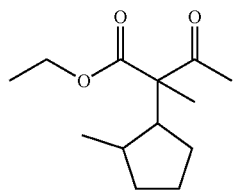 [SMILES: CCOC(=O)C(C)(C(C)=O)C1CCCC1C]

Prepared in a similar manner as described in Example 1.1b starting from ethyl 2-methyl-3-oxobutanoate (2.25 mL, 15.75 mmol) and 2-methylcyclopentyl 4-methylbenzenesulfonate (Example 1.29c) (1.1 eq; 17.32 mmol; 4.4 g) to obtain the desired ethyl 2-methyl-2-(2-methylcyclopentyl)-3-oxobutanoate (825 mg, 23%) as a yellow oil.

$^1$H NMR (400 MHz, DMSO-$d_6$) δ 4.03 (q, J=8.0 Hz, 2H), 2.29 (s, 3H), 1.91-2.04 (m, 1H), 1.69-1.85 (m, 2H), 1.69 (s, 3H), 1.40-1.67 (m, 1H), 1.45-1.59 (m, 3H), 1.31-1.42 (m, 1H), 1.17 (t, J=8.0 Hz, 3H), 1.95 (d, J=6.4 Hz, 3H). MS 227 (MH$^+$).

Example 1.29c 2-methylcyclopentyl 4-methylbenzenesulfonate

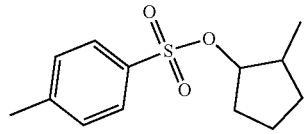 [SMILES: Cc1ccc(S(=O)(=O)OC2CCCC2C)cc1]

To a solution of 2-methylcyclopentanol (4.5 g; 45 mmol) in pyridine (14.5 mL) with ice cooling was added tosyl chloride (1.1 eq., 49.5 mmol, 9.43 g). The reaction mixture was stirred at room temperature for 18 hours. The reaction was quenched with water (30 ml) and extracted with EtOAc (3×30 ml). The organic layers were combined, washed with brine (50 ml), and dried over MgSO$_4$. The crude product was purified by flash column chromatography (Hexane/EtOAc 20%; R$_f$=0.7), yielding 8.85 g (77%) of 2-methylcyclopentyl 4-methylbenzenesulfonate as white crystals.

$^1$H NMR (400 MHz, DMSO-$d_6$) δ 7.77 (d, J=8.0 Hz, 2H), 7.44 (d, J=8.0 Hz, 2H), 4.33-4.37 (m, 1H), 2.38 (s, 3H), 1.91-1.96 (m, 1H), 1.73-1.79 (m, 2H), 1.50-1.58 (m, 3H), 1.00-1.07 (m, 1H), 0.74 (d, J=6.4 Hz, 3H).

Example 1.30

4-(cyclohexylmethyl)-3,4-dimethyl-1-(2-oxo-2-phenylethyl)-1H-pyrazol-5(4H)-one

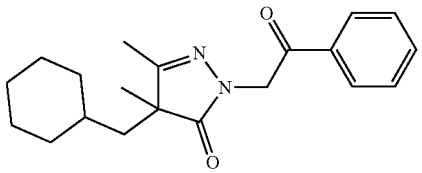 [SMILES: CC1=NN(CC(=O)c2ccccc2)C(=O)C1(C)CC1CCCCC1]

To an oven-dried, N₂-flushed, round-bottom flask were added anhydrous DMF (8 mL), 4-(cyclohexylmethyl)-3,4-dimethyl-1H-pyrazol-5(4H)-one (Example 1.30a) (170.0 mg, 0.82 mmol), and at 0° C. NaH (60%, 38.0 mg, 0.95 mmol). The reaction mixture was stirred for 15 minutes at room temperature and 2-bromo-1-phenylethanone (184.0 mg, 0.92 mmol) in anhydrous DMF (1 mL) was added dropwise at 0° C. The reaction mixture was stirred for 15 hours at room temperature and extracted with H₂O/EtOAc (3×). Combined organic phases were washed with brine, dried over MgSO₄, and solvents were evaporated. The obtained residue was loaded onto a SiO₂ column (25 g) and eluted with a hexanes/EtOAc gradient. The obtained product was further purified on preparative HPLC using a 40 minutes 5-95% CH₃CN/H₂O gradient, to obtain the desired product (131 mg, 49%).

¹H NMR (400 MHz, DMSO-d₆) δ 8.07-7.97 (m, 2H), 7.74-7.65 (m, 1H), 7.56 (t, J=7.7 Hz, 2H), 5.23 (d, J=18.0 Hz, 1H), 5.16 (d, J=18.0 Hz, 1H), 1.98 (s, 3H), 1.64-1.46 (m, 7H), 1.22-0.97 (m, 4H), 1.15 (s, 3H), 0.93-0.69 (m, 2H). MS 327 (MH⁺).

Example 1.30a 4-(cyclohexylmethyl)-3,4-dimethyl-1H-pyrazol-5(4H)-one

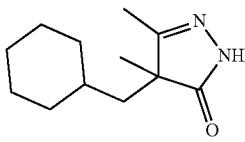

To an oven-dried, N₂-flushed, 15 mL pressure tube were added ethyl 2-(cyclohexylmethyl)-2-methyl-3-oxobutanoate (Example 1.30b) (0.5 g, 2.08 mmol), anhydrous EtOH (4 mL) and hydrazine (2 mL, 63.03 mmoL). The pressure tube was sealed and the reaction mixture was heated at 140° C. for 16 hours. The mixture was let cool down, solvents were evaporated and the obtained residue was loaded onto a SiO₂ column (40 g) and eluted with a hexanes/EtOAc gradient, to obtain the desired product (338 mg, 78%).

¹H NMR (400 MHz, CDCl₃) δ 8.35 (bs, NH), 2.00 (s, 3H), 1.74 (dd, J=14.3 Hz, J=6.8 Hz, 1H), 1.70-1.54 (m, 5H), 1.51 (dd, J=14.3 Hz, J=5.9 Hz, 1H), 1.19 (s, 3H), 1.17-0.99 (m, 4H), 0.93-0.81 (m, 2H). MS 209 (MH⁺).

Example 1.30b

Ethyl 2-(cyclohexylmethyl)-2-methyl-3-oxobutanoate

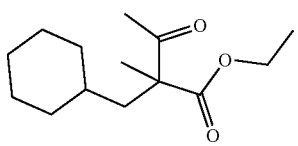 [SMILES: CCOC(=O)C(C)(CC1CCCCC1)C(C)=O]

To an oven-dried, N₂-flushed, round-bottom flask were added 1M KO-tBu/t-BuOH (8 mL), ethyl 2-methyl-3-oxobutanoate (1 g, 6.94 mmol). The reaction medium was stirred for 1 hour at room temperature and (bromomethyl)cyclohexane (1.2 mL, 8.61 mmol) was added neat and dropwise. The reaction mixture was stirred for 25 minutes at room temperature, refluxed for 21 hours at 120° C., and extracted with H₂O/EtOAc (4×). Combined organic phases were washed with brine, dried over MgSO₄, and solvents were evaporated. The obtained residue was loaded onto a SiO₂ column (80 g) and eluted with a hexanes/EtOAc gradient, to obtain the desired product (1.14 g, 68%).

¹H NMR (400 MHz, CDCl₃) δ 4.17 (q, J=7.1 Hz, 2H), 2.14 (s, 3H), 1.86 (dd, J=14.4 Hz, J=6.5 Hz, 1H), 1.68 (dd, J=14.4 Hz, J=5.4 Hz, 1H), 1.67-1.54 (m, 5H), 1.33 (s, 3H), 1.25 (t, J=7.1 Hz, 3H), 1.22-1.02 (m, 4H), 1.01-0.85 (m, 2H). MS 241 (MH⁺).

Example 1.31

4-(cyclopentylmethyl)-3,4-dimethyl-1-(2-oxo-2-phenylethyl)-1H-pyrazol-5(4H)-one

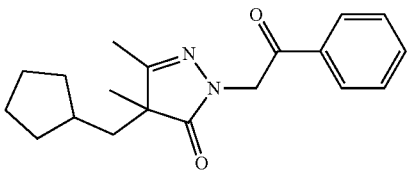 [SMILES: CC1=NN(CC(=O)c2ccccc2)C(=O)C1(C)CC1CCCC1]

Prepared in a similar manner as described in Example 1.30 from 4-(cyclopentylmethyl)-3,4-dimethyl-1H-pyrazol-5(4H)-one (Example 1.31a) (76.4 mg, 0.39 mmol) and 2-bromo-1-phenylethanone (98.0 mg, 0.49 mmol), to obtain the desired product (45.9 mg, 37%)

¹H NMR (400 MHz, CDCl₃) δ 8.00-7.91 (m, 2H), 7.64-7.55 (m, 1H), 7.54-7.41 (m, 2H), 5.13 (d, J=20.0 Hz, 1H), 5.08 (d, J=20.0 Hz, 1H), 2.03 (s, 3H), 1.93 (dd, J=14.0 Hz, J=7.1 Hz, 1H), 1.72 (dd, J=13.9 Hz, J=6.3 Hz, 1H), 1.76-1.65 (m, 2H), 1.63-1.55 (m, 2H), 1.52-1.41 (m, 3H), 1.28 (s, 3H), 1.13-0.92 (m, 2H). MS 313 (MH⁺).

Example 1.31a 4-(cyclopentylmethyl)-3,4-dimethyl-1H-pyrazol-5(4H)-one

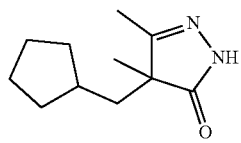

Prepared in a similar manner as described in Example 1.30a from ethyl 2-(cyclopentylmethyl)-2-methyl-3-oxobutanoate (Example 1.31b) (277.0 mg, 1.22 mmol) and hydrazine (2.0 mL, 63.03 mmol), to obtain the desired product as a yellowish oil (174.0 mg, 73%). MS 195 (MH⁺).

Example 1.31b

Ethyl 2-(cyclopentylmethyl)-2-methyl-3-oxobutanoate

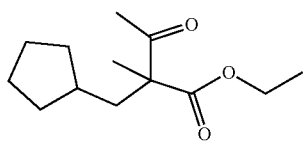 [SMILES: CCOC(=O)C(C)(CC1CCCC1)C(C)=O]

Prepared in a similar manner as described in Example 1.30b from ethyl 2-methyl-3-oxobutanoate (0.5 g, 3.47 mmol) and (bromomethyl)cyclopentane (672.0 mg, 4.12 mmol), to obtain the desired product as a yellowish oil (417.4 mg, 53%).

$^1$H NMR (400 MHz, CDCl$_3$) δ 4.16 (q, J=7.2 Hz, 2H), 2.13 (s, 3H), 2.00 (dd, J=14.2 Hz, J=6.7 Hz, 1H), 1.88 (dd, J=14.2 Hz, J=5.6 Hz, 1H), 1.78-1.64 (m, 3H), 1.62-1.52 (m, 2H), 1.52-1.40 (m, 2H), 1.34 (s, 3H), 1.25 (t, J=7.1 Hz, 3H), 1.13-0.97 (m, 2H). MS 227 (MH$^+$).

Scheme 1.4

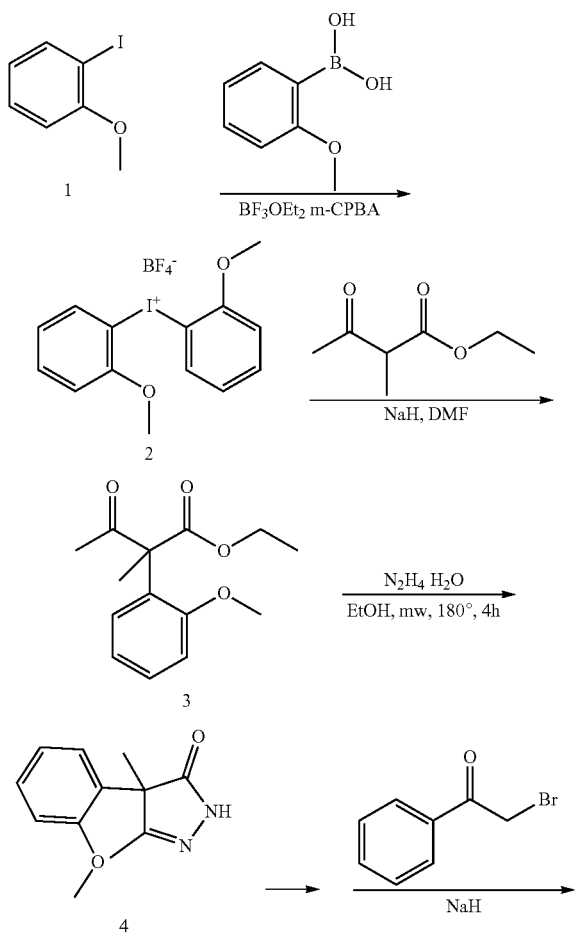

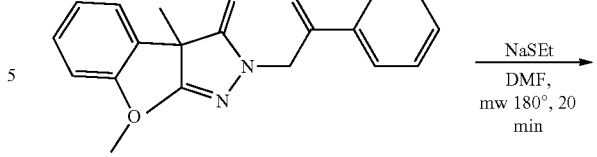

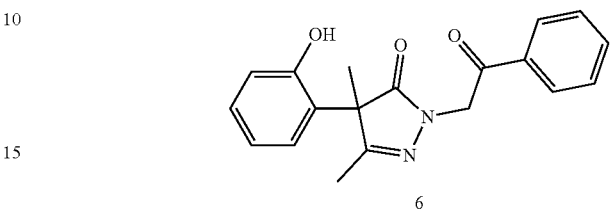

Example 1.32

4-(2-methoxyphenyl)-3,4-dimethyl-1-(2-oxo-2-phenylethyl)-1H-pyrazol-5(4H)-one

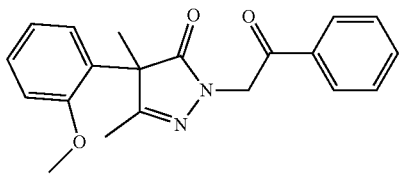 [SMILES: COc1ccccc1C1(C)C(=O)N(CC(=O)c2ccccc2)N=C1C]

Prepared in a similar manner as described in Example 1.1 starting from 4-(2-methoxy-phenyl)-3,4-dimethyl-1H-pyrazol-5(4H)-one (Compound 4, Example 1.32a) (394 mg, 1.8 mmol) and 2-bromoacetophenone (1.1 eq; 1.98 mmol; 394 mg) to obtain the desired 4-(2-methoxy-phenyl)-3,4-dimethyl-1-(2-oxo-2-phenylethyl)-1H-pyrazol-5 (4H)-one (490 mg, 81%) as a white solid.

$^1$H NMR (400 MHz, DMSO-d$_6$) δ 8.01 (d, J=8.0 Hz, 2H), 7.68 (t, J=8.0 Hz, 1H), 7.53 (t, J=8.0 Hz, 2H), 7.30 (d, J=8.0 Hz, 1H), 7.14 (t, J=8.0 Hz, 1H), 6.84 (t, J=8.0 Hz, 1H), 6.73 (d, J=8.0 Hz, 1H), 5.28 (d, J=18.0 Hz, 1H), 5.23 (d, J=18.0 Hz, 1H), 3.75 (s, 3H), 1.80 (s, 3H), 1.55 (s, 3H). MS 337 (MH$^+$).

Example 1.32a 4-(2-methoxyphenyl)-3,4-dimethyl-1H-pyrazol-5 (4H)-one

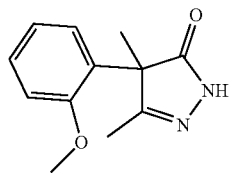 [SMILES: COc1ccccc1C1(C)C(=O)NN=C1C]

Prepared in a similar manner as described in Example 1.1a starting from ethyl 2-(2-methoxyphenyl)-2-methyl-3-oxobutanoate (Example 1.32b) (600 mg, 2.4 mmol) and hydrazine monohydrate (4 eq; 9.6 mmol; 467 µL to obtain the desired 4-(2-methoxyphenyl)-3,4-dimethyl-1H-pyrazol-5(4H)-one (394 mg, 75%) as a white solid.

$^1$H NMR (400 MHz, DMSO-$d_6$) δ 10.89 (s, 1NH), 7.34 (d, J=8.0 Hz, 1H), 7.30 (t, J=8.0 Hz, 1H), 6.99 (t, J=8.0 Hz, 1H), 6.95 (d, J=8.0 Hz, 1H), 3.60 (s, 3H), 1.58 (s, 3H), 1.42 (s, 3H). MS 219 (MH$^+$).

Example 1.32b

Ethyl 2-(2-methoxyphenyl)-2-methyl-3-oxobutanoate

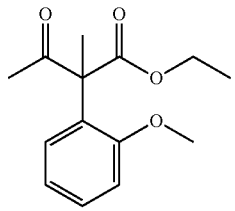 [SMILES: CCOC(=O)C(C)(C(C)=O)c1ccccc1OC]

To a suspension of NaH (60%; 1.3 eq; 4.05 mmol; 162 mg) in 25 mL of anhydrous DMF at 0° C. under nitrogen atmosphere was slowly added dropwise ethyl 2-methyl-3-oxobutanoate (1 eq; 3.11 mmol; 444 µL). The reaction mixture was stirred at 0° C. for 30 min, and a solution of bis(2-methoxyphenyl)iodonium tetrafluoroborate salt (Example 1.32c) (1.3 eq.; 4.05 mmol; 1.73 g) in 5 mL of anhydrous DMF was added dropwise, and the reaction mixture was stirred at room temperature for 18 h. The reaction was quenched with water (25 mL) and extracted with Et$_2$O (3×20 mL). The organic layers were combined, washed with brine (40 mL), dried over MgSO$_4$, and concentrated under vacuum. The resulting residue was purified by flash column chromatography (Hexane/EtOAc 5%; R$_f$=0.3) to yield 603 mg (77.5%) of ethyl 2-(2-methoxyphenyl)-2-methyl-3-oxobutanoate as a yellowish oil.

$^1$H NMR (400 MHz, DMSO-$d_6$) δ 7.30 (t, J=8.0 Hz, 1H), 7.04 (d, J=8.0 Hz, 2H), 6.94 (t, J=8.0 Hz, 1H), 4.14 (q, J=8.0 Hz, 2H), 3.71 (s, 3H), 2.08 (s, 3H), 1.52 (s, 3H), 1.15 (t, J=8.0 Hz, 3H). MS 251 (MH$^+$).

Example 1.32c

Bis(2-methoxyphenyl)iodonium thetrafluoroborate Salt

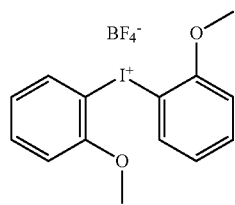 [SMILES: COc1ccccc1[I+]c1ccccc1OC ; "BF4-"]

To a solution of m-chloroperbenzoic acid (77% active oxidant; 1.11 eq.; 13.2 mmol; 2.27 g) in 40 mL of anhydrous 1,2-dichloroethane at room temperature under N$_2$ atmosphere was added a solution of 1-iodo-2-methoxybenzene (12 mmol; 1.56 mL) in 5 mL of anhydrous 1,2-dichloroethane. The reaction mixture was placed in an 80° C. pre-heated oil bath. After 1 hour, the mixture was cooled to −78° C., and a 0° C. mixture of BF$_3$.OEt$_2$ (2.5 eq.; 30 mmol; 3.77 mL) and 2-methoxyphenylboronic acid (1.11 eq.; 13.2 mmol; 2 g) dissolved in 10 mL of anhydrous DCM was added dropwise via syringe. The resulting dark solution was stirred at −78° C. for 1 hour, then slowly warmed up to room temperature and stirred for 18 h. The crude reaction mixture was loaded on a silica plug (50 g) and eluted with DCM (200 mL) to remove unreacted ArI and m-CPBA, followed by DCM/MeOH (300 mL, 20:1) to elute the product, leaving any boronic acid derivatives on the column. The latter solution was concentrated in vacuum and diethyl ether (10 mL) was added to the residue to induce a precipitation of salt, with any iodine (III) intermediates and BF$_3$ derivatives remaining in solution. The solid was filtered off, washed with diethyl ether (2×10 mL) and then dried in vacuum to give pure bis(2-methoxyphenyl)iodonium tetrafluoroborate salt as a grey powder (1.73 g, 34% yield).

$^1$H NMR (400 MHz, DMSO-$d_6$) δ 8.13 (d, J=8.0 Hz, 2H), 7.59 (t, J=8.0 Hz, 2H), 7.25 (d, J=8.0 Hz, 2H), 7.02 (t, J=8.0 Hz, 2H), 3.89 (s, 6H).

Example 1.33

4-(2-hydroxyphenyl)-3,4-dimethyl-1-(2-oxo-2-phenylethyl)-1H-pyrazol-5(4H)-one

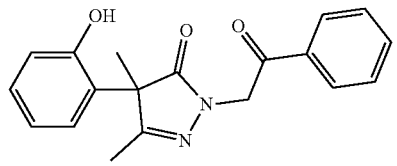 [SMILES: CC1=NN(CC(=O)c2ccccc2)C(=O)C1(C)c1ccccc1O]

To a solution of 4-(2-methoxyphenyl)-3,4-dimethyl-1-(2-oxo-2-phenylethyl)-1H-pyrazol-5(4H)-one (Example 1.32) (490 mg; 1.46 mmol) in 6 mL of anhydrous DMF, was added sodium ethanethiolate (5 eq; 7.3 mmol; 613 mg). The reaction mixture was heated under microwave irradiation at 180° C. for 20 min, diluted with 1N HCl (15 ml) and extracted with EtOAc (3×10 mL). The organic layers were combined, washed with brine (10 mL), and dried over MgSO$_4$. Solvents were evaporated, and the resulting residue was purified twice on preparative HPLC using a 25 minutes 5-95% CH$_3$CN/H$_2$O gradient, to give after evaporation of solvents and lyophilization 4-(2-hydroxyphenyl)-3,4-dimethyl-1-(2-oxo-2-phenylethyl)-1H-pyrazol-5(4H)-one as a white solid (81.7 mg; 19%).

$^1$H NMR (400 MHz, DMSO-$d_6$) δ 9.66 (bs, 1OH), 8.01 (d, J=8.0 Hz, 2H), 7.68 (t, J=8.0 Hz, 1H), 7.55 (t, J=8.0 Hz, 2H), 7.30 (d, J=8.0 Hz, 1H), 7.14 (t, J=8.0 Hz, 1H), 6.84 (t, J=8.0 Hz, 1H), 6.73 (d, J=8.0 Hz, 1H), 5.26 (d, J=18.0 Hz, 1H), 5.05 (d, J=18.0 Hz, 1H), 1.67 (s, 3H), 1.54 (s, 3H). MS 323 (MH$^+$).

Example 1.34

4-(4-methoxyphenyl)-3,4-dimethyl-1-(2-oxo-2-phenylethyl)-1H-pyrazol-5(4H)-one

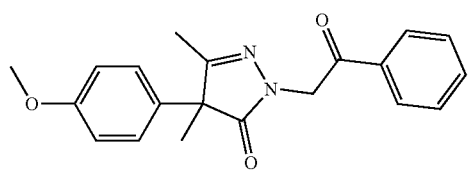 [SMILES: COc1ccc(C2(C)C(=O)N(CC(=O)c3ccccc3)N=C2C)cc1]

Prepared in a similar manner as described in Example 1.1 starting from 4-(4-methoxyphenyl)-3,4-dimethyl-1H-pyrazol-5(4H)-one (Example 1.32a) (55 mg, 0.25 mmol) and 2-bromoacetophenone (1.1 eq; 0.275 mmol; 55 mg) to obtain the desired 4-(4-methoxyphenyl)-3,4-dimethyl-1-(2-oxo-2-phenylethyl)-1H-pyrazol-5(4H)-one (30.2 mg, 36%) as a white solid.

$^1$H NMR (400 MHz, DMSO-$d_6$) δ 8.02 (d, J=8.0 Hz, 2H), 7.69 (t, J=8.0 Hz, 1H), 7.56 (t, J=8.0 Hz, 2H), 7.19 (d, J=8.0 Hz, 2H), 6.95 (d, J=8.0 Hz, 2H), 5.28 (d, J=18.0 Hz, 1H), 5.23 (d, J=18.0 Hz, 1H), 3.74 (s, 3H), 1.81 (s, 3H), 1.55 (s, 3H). MS 337 (MH$^+$).

Example 1.34a 4-(4-methoxyphenyl)-3,4-dimethyl-1H-pyrazol-5(4H)-one

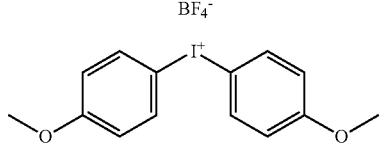

Prepared in a similar manner as described in Example 1.1a starting from ethyl 2-(4-methoxyphenyl)-2-methyl-3-oxobutanoate (Example 1.32b) (460 mg, 1.84 mmol) and hydrazine monohydrate (2 eq; 3.68 mmol; 120 μL) to obtain the desired 4-(4-methoxyphenyl)-3,4-dimethyl-1H-pyrazol-5(4H)-one (300 mg, 75%) as a white solid.

$^1$H NMR (400 MHz, DMSO-$d_6$) δ 11.06 (s, 1NH), 7.02 (d, J=8.0 Hz, 2H), 6.92 (d, J=8.0 Hz, 2H), 3.72 (s, 3H), 1.77 (s, 3H), 1.44 (s, 3H). MS 219 (MH$^+$).

Example 1.34b

Ethyl 2-(4-methoxyphenyl)-2-methyl-3-oxobutanoate

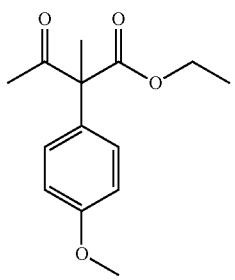 [SMILES: CCOC(=O)C(C)(C(C)=O)c1ccc(OC)cc1]

Prepared in a similar manner as described in Example 1.32b starting from ethyl 2-methyl-3-oxobutanoate (425 μL, 2.98 mmol) and bis(2-methoxyphenyl)iodonium tetrafluoroborate salt (Example 1.34c) (1.3 eq; 3.05 mmol; 1.25 g) to obtain the desired ethyl 2-(4-methoxyphenyl)-2-methyl-3-oxobutanoate (465 mg, 62%) as a colorless oily liquid.

$^1$H NMR (400 MHz, DMSO-$d_6$) δ 7.17 (d, J=8.0 Hz, 2H), 6.91 (d, J=8.0 Hz, 2H), 4.15 (q, J=8.0 Hz, 2H), 3.73 (s, 3H), 2.03 (s, 3H), 1.64 (s, 3H), 1.16 (t, J=8.0 Hz, 3H). MS 251 (MH$^+$).

Example 1.34c

Bis(4-methoxyphenyl)iodonium thetrafluoroborate Salt

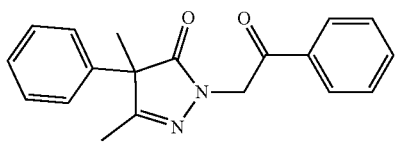 [SMILES: CC1=NN(CC(=O)c2ccccc2)C(=O)C1(C)c1ccccc1]

Prepared in a similar manner as described in Example 1.32c starting from 4-methoxyiodobenzene (1.4 mL, 6 mmol) and (4-methoxyphenyl)boronic acid (1.1 eq, 6.6 mmol, 1 g) to obtain the desired bis(2-methoxyphenyl)iodonium tetrafluoroborate salt (1.25 g, 49%) as a grey powder.

$^1$H NMR (400 MHz, DMSO-$d_6$) δ 8.10 (d, J=8.0 Hz, 4H), 7.04 (d, J=8.0 Hz, 4H), 3.76 (s, 6H).

Example 1.35

3,4-dimethyl-1-(2-oxo-2-phenylethyl)-4-phenyl-1H-pyrazol-5(4H)-one

Prepared in a similar manner as described in Example 1.1 starting from 3,4-dimethyl-4-phenyl-1H-pyrazol-5(4H)-one (Example 1.35a) (94 mg, 0.5 mmol) and 2-bromoacetophenone (1.1 eq; 0.55 mmol; 109 mg) to obtain the desired 3,4-dimethyl-1-(2-oxo-2-phenylethyl)-4-phenyl-1H-pyrazol-5(4H)-one (87 mg, 57%) as a white solid.

$^1$H NMR (400 MHz, DMSO-$d_6$) δ 8.02 (d, J=8.0 Hz, 2H), 7.69 (t, J=8.0 Hz, 1H), 7.56 (t, J=8.0 Hz, 2H), 7.41 (t, J=8.0 Hz, 2H), 7.33 (t, J=8.0 Hz, 1H), 7.28 (d, J=8.0 Hz, 2H), 5.30 (d, J=18.0 Hz, 1H), 5.24 (d, J=18.0 Hz, 1H), 1.82 (s, 3H), 1.59 (s, 3H). MS 307 (MH$^+$).

Example 1.35a 3,4-dimethyl-4-phenyl-1H-pyrazol-5(4H)-one

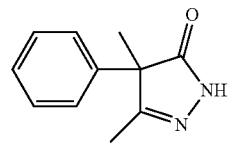

Prepared in a similar manner as described in Example 1.1a starting from ethyl 2-methyl-3-oxo-2-phenylbutanoate (Example 1.35b) (1.9 g, 8.6 mmol) and hydrazine monohydrate (2 eq; 17.27 mmol; 558 μL) to obtain the desired 3,4-dimethyl-4-phenyl-1H-pyrazol-5(4H)-one (917 mg, 57%) as a white solid.

$^1$H NMR (400 MHz, DMSO-$d_6$) δ 11.13 (s, 1NH), 7.37 (t, J=8.0 Hz, 2H), 7.30 (t, J=8.0 Hz, 1H), 7.11 (d, J=8.0 Hz, 2H), 1.78 (s, 3H), 1.48 (s, 3H). MS 189 (MH$^+$).

Example 1.35b

Ethyl 2-methyl-3-oxo-2-phenylbutanoate

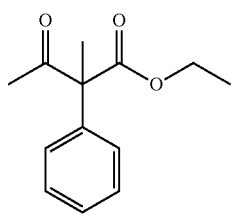 [SMILES: CCOC(=O)C(C)(C(C)=O)c1ccccc1]

Prepared in a similar manner as described in Example 1.32b starting from ethyl 3-oxo-2-phenylbutanoate (1.9 mL, 10 mmol) and methyl iodide (3 eq; 30 mmol; 1.87 mL) to obtain the desired 2-methyl-3-oxo-2-phenylbutanoate (1.9 g, 86%) as a colorless oily liquid.

$^1$H NMR (400 MHz, DMSO-$d_6$) δ 7.36 (t, J=8.0 Hz, 2H), 7.31 (d, J=8.0 Hz, 1H), 7.25 (d, J=8.0 Hz, 2H), 4.17 (q, J=8.0 Hz, 2H), 2.05 (s, 3H), 1.67 (s, 3H), 1.17 (t, J=8.0 Hz, 3H). MS 221 (MH$^+$).

Example 1.36

4-((1R,2R,4S)-bicyclo[2.2.1]heptan-2-yl)-3,4-dimethyl-1-(2-oxo-2-phenylethyl)-1H-pyrazol-5(4H)-one

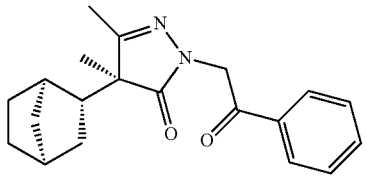 [SMILES: CC1=NN(CC(=O)c2ccccc2)C(=O)[C@@]1(C)[C@@H]1C[C@H]2CC[C@@H]1C2]

Prepared by chiral separation of example 23 using standard chiral HPLC.

$^1$H NMR (400 MHz, DMSO-$d_6$) δ 7.98 (d, J=8.0 Hz, 2H), 7.67 (t, J=8.0 Hz, 1H), 7.53 (t, J=8.0 Hz, 2H), 5.16 (d, J=18.0 Hz, 1H), 5.09 (d, J=18.0 Hz, 1H), 2.38 (bs, 1H), 2.09 (bs, 1H), 1.91 (s, 3H), 1.62 (t, J=8.0 Hz, 1H), 1.43-1.45 (m, 2H), 1.21-1.32 (m, 2H), 1.21 (s, 3H), 1.09-1.12 (m, 2H), 0.89-1.02 (m, 2H). MS 325 (MH$^+$).

NMR References

[i] Abraham R. J., et al. 1H chemical shifts in NMR: Part 23, the effect of dimethyl sulphoxide versus chloroform solvent on 1H chemical shifts. //Magn. Reson. Chem (2006), 44, p. 491-509.

[ii] Abraham R. J., et al. 1H chemical shifts in NMR: Part 23, the effect of dimethyl sulphoxide versus chloroform solvent on 1H chemical shifts. //Magn. Reson. Chem (2006), 44, p. 491-509.

[iii] Abraham R. J., et al. 1H chemical shifts in NMR: Part 23, the effect of dimethyl sulphoxide versus chloroform solvent on 1H chemical shifts. //Magn. Reson. Chem (2006), 44, p. 491-509.

[iv] Abraham R. J., et al. 1H chemical shifts in NMR: Part 23, the effect of dimethyl sulphoxide versus chloroform solvent on 1H chemical shifts. //Magn. Reson. Chem (2006), 44, p. 491-509.

[v] Abraham R. J., et al. 1H chemical shifts in NMR: Part 23, the effect of dimethyl sulphoxide versus chloroform solvent on 1H chemical shifts. //Magn. Reson. Chem (2006), 44, p. 491-509.

2.1) Biological Assay

A cell line which stably expresses hTRPM8 was used in biological assays in association with testing the present compounds with cool-tasting or -feeling properties. Typical compound concentrations tested were 100 μM, 50 μM, 10 μM, 1 μM, and 0.5 μM. The present compounds have shown activity as agonists of hTRPM8. Assay results for compounds are illustrated in the table below. $EC_{50}$ in micromoles (μM) is presented as well as the activity relative to WS3 (an established, commercially available cooling agent). $EC_{50}$ ratio is determined by taking the $EC_{50}$ of the example compound and dividing it by the $EC_{50}$ of WS3 when screened on the same day in the same screen. A value of 1 indicates the compound is equipotent to WS3 in the assay. A number greater than one indicates how many times more potent the compound is in the assay relative to WS3. It is noted that Compounds 2.A1 to 2.S6 in the table below are the Examples described in this application. For example, Compound 2.B 1 is Example 2.2.

| Compound | EC$_{50}$ (µM) | EC$_{50}$ Ratio (WS3) |
|---|---|---|
| 2.A1 | 0.135 | 54.6 |
| 2.B1 | 0.374 | 13.5 |
| 2.C1 | 0.510 | 9.9 |
| 2.D1 | 0.459 | 13.2 |
| 2.E1 | 0.898 | 8.0 |
| 2.F1 | 2.881 | 1.6 |
| 2.G1 | 4.366 | 1.2 |
| 2.H1 | 0.192 | 240.6 |
| 2.I1 | 3.312 | 1.2 |
| 2.J1 | 0.593 | 14.2 |
| 2.K1 | 0.074 | 108.0 |
| 2.L1 | 6.379 | 0.7 |
| 2.M1 | 0.321 | 32.5 |
| 2.N1 | 1.091 | 3.5 |
| 2.O1 | 0.227 | 20.5 |
| 2.P1 | 0.333 | 11.5 |
| 2.Q1 | 0.273 | 15.9 |
| 2.R1 | 5.471 | 0.7 |
| 2.S1 | 0.760 | 7.0 |
| 2.T1 | 7.195 | 0.5 |
| 2.U1 | 0.140 | 39.2 |
| 2.V1 | 1.592 | 7.1 |
| 2.W1 | 3.357 | 1.0 |
| 2.X1 | 2.039 | 2.1 |
| 2.Y1 | 1.261 | 3.1 |
| 2.Z1 | 6.678 | 0.7 |
| 2.A2 | 0.253 | 22.1 |
| 2.B2 | 10.115 | 0.5 |
| 2.C2 | 0.493 | 12.5 |
| 2.D2 | 0.087 | 85.9 |
| 2.E2 | 0.293 | 13.0 |
| 2.F2 | 11.712 | 5.4 |
| 2.G2 | 0.621 | 8.8 |
| 2.H2 | 0.447 | 10.4 |
| 2.I2 | 0.927 | 7.7 |
| 2.J2 | 0.694 | 3.9 |
| 2.K2 | 0.724 | 5.5 |
| 2.L2 | 0.547 | 9.1 |
| 2.M2 | 7.542 | 0.5 |
| 2.N2 | 0.294 | 16.5 |
| 2.O2 | 0.588 | 8.0 |
| 2.P2 | 0.006 | 2566.9 |
| 2.Q2 | 0.029 | 202.6 |
| 2.R2 | 0.866 | 5.4 |
| 7.S2 | 1.985 | 7.3 |
| 2.T2 | 2.489 | 2.1 |
| 2.U2 | 0.044 | 178.7 |
| 2.V2 | 0.053 | 83.5 |
| 2.W2 | 0.066 | 77.3 |
| 2.X2 | 0.084 | 69.7 |
| 2.Y2 | 0.089 | 54.5 |
| 2.Z2 | 0.096 | 71.5 |
| 2.A3 | 0.100 | 73.1 |
| 2.B3 | 5.279 | 2810.1 |
| 2.C3 | 0.100 | 49.1 |
| 2.D3 | 0.124 | 33.4 |
| 2.E3 | 0.127 | 53.5 |
| 2.F3 | 0.138 | 44.0 |
| 2.G3 | 0.146 | 32.6 |
| 2.H3 | 0.156 | 34.3 |
| 2.I3 | 0.163 | 33.8 |
| 2.J3 | 0.166 | 32.1 |
| 2.K3 | 0.172 | 30.1 |
| 2.L3 | 0.182 | 25.9 |
| 2.M3 | 0.192 | 240.6 |
| 2.N3 | 0.205 | 24.1 |
| 2.O3 | 0.223 | 21.6 |
| 2.P3 | 0.230 | 38.1 |
| 2.Q3 | 0.233 | 20.3 |
| 2.R3 | 0.236 | 22.8 |
| 2.S3 | 0.246 | 18.1 |
| 2.T3 | 0.268 | 22.6 |
| 2.U3 | 0.284 | 17.2 |
| 2.V3 | 0.286 | 18.6 |
| 2.W3 | 0.292 | 19.6 |
| 2.X3 | 0.305 | 21.9 |
| 2.Y3 | 0.307 | 15.3 |
| 2.Z3 | 0.381 | 12.5 |
| 2.A4 | 0.415 | 8.5 |
| 2.B4 | 0.506 | 12.5 |
| 2.C4 | 0.527 | 9.5 |
| 2.D4 | 0.557 | 7.8 |
| 2.E4 | 0.574 | 9.5 |
| 2.F4 | 0.577 | 8.0 |
| 2.G4 | 0.580 | 7.4 |
| 2.H4 | 0.625 | 8.2 |
| 2.I4 | 0.705 | 6.4 |
| 2.J4 | 0.728 | 6.4 |
| 2.K4 | 0.734 | 5.8 |
| 2.L4 | 0.766 | 6.7 |
| 2.M4 | 0.783 | 6.6 |
| 2.N4 | 0.794 | 5.9 |
| 2.O4 | 0.807 | 6.0 |
| 2.P4 | 0.827 | 7.9 |
| 2.Q4 | 0.859 | 6.2 |
| 2.R4 | 0.945 | 4.6 |
| 2.S4 | 0.968 | 5.0 |
| 2.T4 | 0.971 | 3.5 |
| 2.U4 | 1.116 | 3.0 |
| 2.V4 | 1.154 | 3.1 |
| 2.W4 | 1.165 | 4.6 |
| 2.X4 | 1.204 | 4.4 |
| 2.Y4 | 1.263 | 3.9 |
| 2.Z4 | 1.404 | 3.3 |
| 2.A5 | 1.640 | 2.1 |
| 2.B5 | 1.470 | 2.2 |
| 2.C5 | 1.484 | 2.5 |
| 2.D5 | 1.503 | 3.4 |
| 2.E5 | 1.529 | 2.9 |
| 2.F5 | 1.722 | 2.8 |
| 2.G5 | 1.836 | 2.6 |
| 7.H5 | 1.902 | 2.5 |
| 2.I5 | 2.024 | 2.5 |
| 2.J5 | 2.064 | 2.4 |
| 2.K5 | 2.074 | 2.3 |
| 2.L5 | 2.222 | 2.1 |
| 2.M5 | 2.266 | 1.9 |
| 2.N5 | 2.461 | 1.9 |
| 2.O5 | 2.526 | 1.4 |
| 2.P5 | 2.596 | 1.8 |
| 2.Q5 | 3.274 | 1.3 |
| 2.R5 | 3.297 | 1.1 |
| 2.S5 | 3.365 | 0.9 |
| 2.T5 | 3.457 | 1.0 |
| 2.U5 | 3.719 | 0.9 |
| 2.V5 | 3.863 | 1.3 |
| 2.W5 | 3.873 | 1.2 |
| 2.X5 | 3.958 | 1.1 |
| 2.Y5 | 4.199 | 0.9 |
| 2.Z5 | 4.412 | 1.5 |
| 2.A6 | 4.424 | 1.0 |
| 2.B6 | 4.429 | 0.8 |
| 2.C6 | 4.655 | 1.0 |
| 2.D6 | 5.712 | 0.6 |
| 2.E6 | 6.556 | 0.6 |
| 2.F6 | 6.639 | 0.7 |
| 2.G6 | 8.072 | 0.5 |
| 2.H6 | 8.191 | 0.8 |
| 2.I6 | 8.443 | 0.5 |
| 2.J6 | 0.0004 | 13841.0 |
| 7.K6 | 0.134 | 19.7 |
| 2.L6 | 0.152 | 27.5 |
| 2.M6 | 0.749 | 6.9 |
| 2.N6 | 0.089 | 61.9 |
| 2.O6 | 0.161 | 48.2 |
| 2.P6 | 0.059 | 84.8 |
| 2.Q6 | 0.231 | 24.4 |
| 2.R6 | 0.036 | 67.3 |
| 2.S6 | 12.667 | 0.5 |

2.2) Sensory Studies

Sensory studies were conducted for representative compounds and the results are summarized in the table below. The results are presented relative to a known concentration of WS-3.

| Compound | Sensory Results |
|---|---|
| 2.U2 | 30 uM~45 uM WS-3 |
| 2.Q2 | 30 uM~45 uM WS-3 |
| 2.K3 | 30 uM~45 uM WS-3 |
| 2.Z2 | 10 uM~45 uM WS-3 |
| 2.J3 | 15 uM~45 uM WS-3 |
| 2.T3 | 15 uM < 45 M WS-3 |
| 2.P3 | 15 uM < 45 uM WS-3 |
| 2.R3 | 15 uM~45 uM WS-3 |
| 2.P2 | 10 uM~45 uM WS-3 |
| 2.J6 | 15 uM~45 uM WS-3 |
| 2.H1 | 10 uM~60 uM WS-3 |
| 2.G3 | 15 uM < 45 uM WS-3 |
| 2.N3 | 15 uM < 45 uM WS-3 |
| 2.V2 | 10 uM~45 uM WS-3 |
| 2.A1 | 10 uM < 45 uM WS-3 |
| 2.C1 | 50 uM < 45 uM WS-3 |
| 2.K1 | 10 uM~45 uM WS-3 |
| 2.C2 | 80 uM > 45 uM WS-3 |

A more specific detailed example of the sensory evaluation of selected examples are also presented below. Data generated in this fashion was used to generate the sensory summary presented in the table above.

Line Scale test with 10 µM Compound 2.H1 in LSB at pH 7.1:
- 10 µM Compound H1 in LSB at pH 7.1 was not significantly different in average cool intensity from 60 µM 195001 (WS-3) (p<0.05)
- 10 µM Compound 2.H1 in LSB and 60 µM 195001 (WS-3) in LSB at pH 7.1 were significantly higher in cool intensity than LSB (p<0.05)

TABLE 2.1

Average cool scores, n = 10 (5 × 2 Rep) Tukey's Value = 1.14 ($\alpha$ = 0.05), 0.98 ($\alpha$ = 0.1).

| Test sample | Ave Cool | St SD | Er | Tukey (5%) | Tukey (10%) | Off-Taste (x number of panelist) |
|---|---|---|---|---|---|---|
| Low Sodium Buffer (LSB) | 1.4 | 1.7 | 0.5 | a | a | |
| 10 µM Compound 2.H1 | 3.6 | 1.6 | 0.5 | b | b | Bitter x2, Linger x2 |
| 60 µM WS-3 | 3.7 | 1.6 | 0.5 | b | b | Linger x2, Tingly |

2.3) Preparation and Examples

Standard procedures and chemical transformation and related methods are well known to one skilled in the art, and such methods and procedures have been described, for example, in standard references such as Fiesers' Reagents for Organic Synthesis, John Wiley and Sons, New York, N.Y., 2002; Organic Reactions, vols. 1-83, John Wiley and Sons, New York, N.Y., 2006; March J. and Smith M., Advanced Organic Chemistry, 6th ed., John Wiley and Sons, New York, N.Y.; and Larock R. C., Comprehensive Organic Transformations, Wiley-VCH Publishers, New York, 1999. All texts and references cited herein are incorporated by reference in their entirety.

Reactions using compounds having functional groups may be performed on compounds with functional groups that may be protected. A "protected" compound or derivatives means derivatives of a compound where one or more reactive site or sites or functional groups are blocked with protecting groups. Protected derivatives are useful in the preparation of the compounds of the present invention or in themselves; the protected derivatives may be the biologically active agent. An example of a comprehensive text listing suitable protecting groups may be found in T. W. Greene, Protecting Groups in Organic Synthesis, 3rd edition, John Wiley & Sons, Inc. 1999.

Synthesis of the examples of the present compounds are illustrated in the following schemes and procedures. One skilled in the art can readily derive the synthesis of the present compounds from the following descriptions according to the methods and principles discussed above.

Scheme 2.1. A general method for the preparation of pyrimidine diones (Example 2.1).

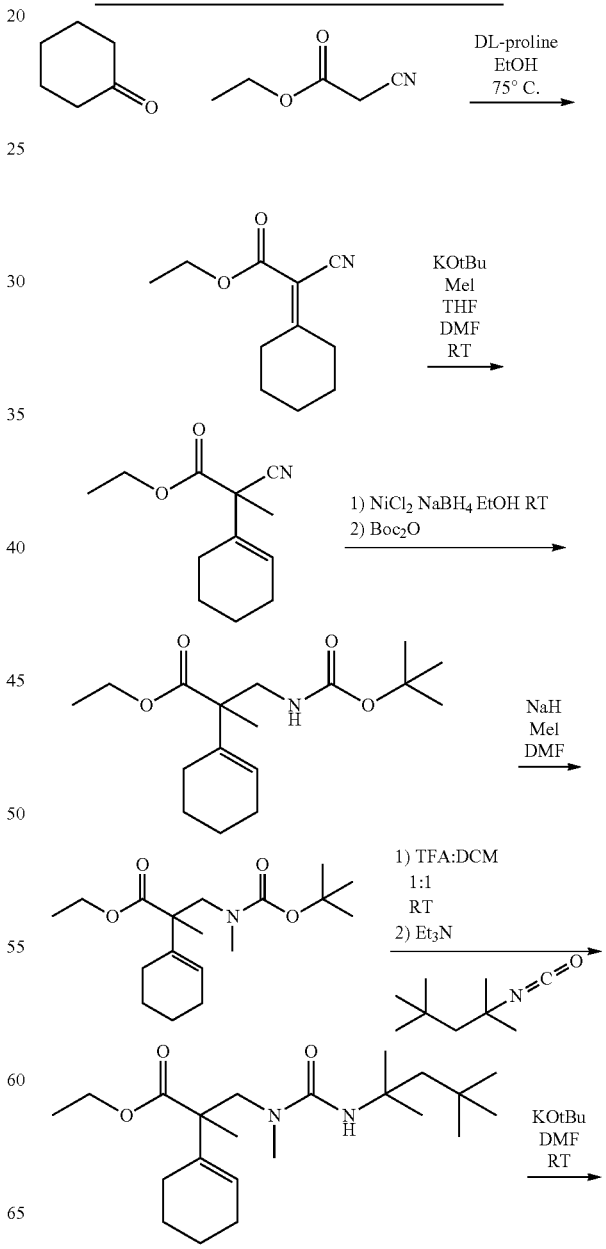

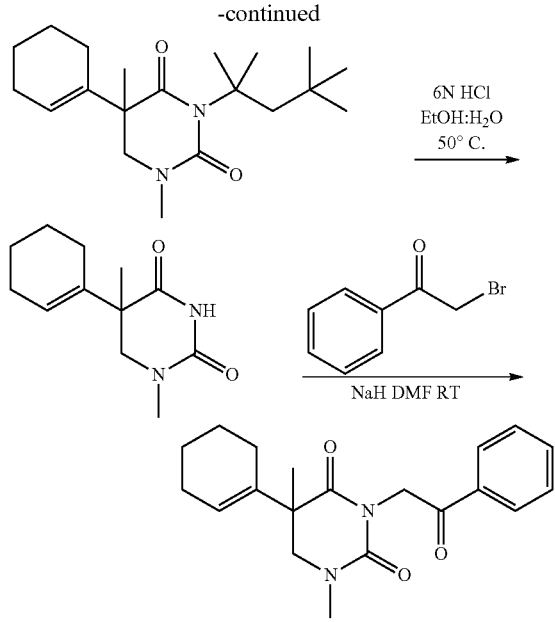

reaction mixture was extracted with DCM (3×10 mL), dried over NaCl(s), then MgSO₄, filtered, and concentrated in vacuo. The residue was purified by silica chromatography (10→60% EtOAc/hexanes gradient). The crude product was further purified on reverse phase HPLC (C$_{18}$, water/ACN gradients) to give the target compound, 109 mg (53% yield) as a hard, light-yellow gum. 1H NMR (400 MHz, DMSO-d$_6$) δ 7.977 (d of d, J=1.5 Hz, J=8.4 Hz, 2H), 7.586 (t of t, J=1.5 Hz, J=5.8 Hz, 1H), 7.474 (t of t, J=1.6 Hz, 6.2 Hz, 2H), 5.625 (m, 1H), 5.252 (d, J=17.2 Hz, 1H), 5.203 (d, J=17.2 Hz, 1H), 3.409 (d, J=12.8 Hz, 1H), 3.369 (d, J=12.8 Hz, 1H), 3.062 (s, 3H), 2.070 (m, 2H), 1.977 (m, 2H), 1.650 (m, 2H), 1.573 (m, 2H), 1.315 (s, 3H). MS 341 (MH⁺).

Example 2.1a: 5-(cyclohex-1-en-1-yl)-1,5-dimethyl-dihydropyrimidine-2,4(1H,3H)-dione 5-(cyclohex-1-en-1-yl)-1,5-dimethyl-3-(2,4,4-trimethylpentan-2-yl)dihydropyrimidine-2,4(1H,3H)-dione (Example 2.1b) (821 mg, 2.45 mmol) was placed in a 40 mL vial and dissolved in 200 proof ethanol (2.5 mL). the solution was treated with 37% HCl (2.5 mL) and stirred at room temperature for 1 hour, then heated to 50° C. for 2 hours. Volatiles were removed in vacuo (water bath=80° C.) to give 522 mg (96% yield) of a white solid. MS 223 (MH⁺).

Scheme 2.2. A general method for the preparation of pyrimidine triones (Example 2.8).

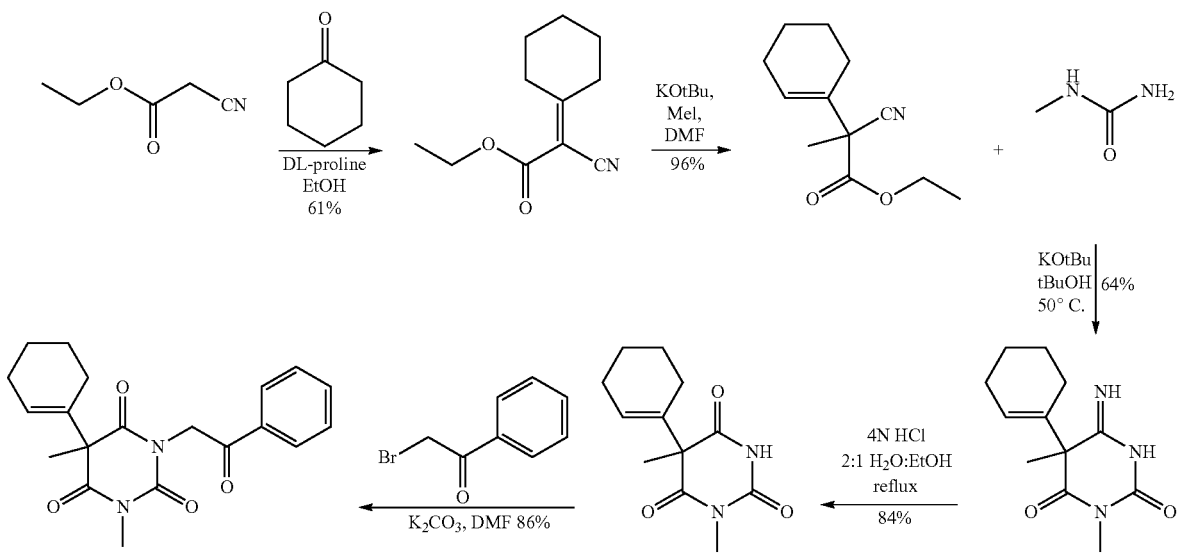

Example 2.1: 5-(cyclohex-1-en-1-yl)-1,5-dimethyl-3-(2-oxo-2-phenylethyl)dihydropyrimidine-2,4(1H,3H)-dione 5-(cyclohex-1-en-1-yl)-1,5-dimethyldihydropyrimidine-2,4(1H,3H)-dione (Example 2.1a) (133 mg, 600 μmol) and sodium hydride (60% in mineral oil, 26 mg, 660 μmol) were placed in a 40 mL vial charged with a stir bar and dry DMF (5 mL) was added via syringe under nitrogen purge with stirring. The reaction was stirred at room temperature for 5 minutes, then 2-bromo-1-phenylethanone (119 mg, 600 μmol) was added and the reaction stirred at room temperature for 1 hour. The reaction was quenched with sat. aq. NH₄Cl (1 mL) and diluted with water (25 mL). Sufficient NaHCO₃(s) was carefully added to ensure pH ~8. The Example 2.1b: 5-(cyclohex-1-en-1-yl)-1,5-dimethyl-3-(2,4,4-trimethylpentan-2-yl)dihydropyrimidine-2,4 (1H,3H)-dione Ethyl 2-(cyclohex-1-en-1-yl)-2-methyl-3-(1-methyl-3-(2,4,4-trimethylpentan-2-yl)ureido)propanoate (Example 2.1c) (1073 mg, 2.82 mmol) was placed in a 40 mL vial and dissolved in dry DMF (5 mL). KOtBu (1.0 M in THF, 2.82 mL, 2.82 mmol) was added and the reaction mixture was stirred at room temperature for 1 hour. Additional KOtBu (0.846 mmol, 0.846 mL) was added and stirred 15 minutes more at room temperature, then the solution was heated to 50° C. and stirred for 2 hours. The reaction mixture was cooled to room temperature and quenched with sat. aq. NH₄Cl (1 mL) and diluted with water (20 mL). The aqueous phase was extracted with hexanes (3×10 mL) and the combined hexane layers were washed with water (3×5 mL) and brine, then dried over MgSO$_4$, filtered, and concentrated in vacuo. The crude material was purified by silica gel flash chromatography (80 g, load in hexanes, 5→30% (15 CV) EtOAc/hexanes gradient) to afford 821 mg (87% yield) of the desired product. MS 335 (MH$^+$).

Example 2.1c: Ethyl 2-(cyclohex-1-en-1-yl)-2-methyl-3-(1-methyl-3-(2,4,4-trimethylpentan-2-yl)ureido)propanoate Ethyl 3-((tert-butoxycarbonyl)(methyl)amino)-2-(cyclohex-1-en-1-yl)-2-methylpropanoate (Example 2.1d) (1043 mg, 3.2 mmol) was placed in a 40 mL vial and both TFA (3 mL) and DCM (3 mL) were added. The resulting solution was stirred for one hour at room temperature. Then concentrated in vacuo. The crude material was partitioned between water (10 mL) and 30% ACN/DCM (10 mL), then carefully made basic with NaHCO$_3$. The layers were separated and the aqueous phase was extracted with 30% ACN/DCM (2×10 mL). The combined organic extracts were washed with brine, then dried over MgSO$_4$, filtered, and concentrated in vacuo. The crude amine was dissolved in dry DCM (2 mL) and treated with 2-isocyanato-2,4,4-trimethylpentane (546 mg, 3.52 mmol) and Et$_3$N (0.535 mL, 3.84 mmol) with stirring at room temperature for 1 hour. More 2-isocyanato-2,4,4-trimethylpentane (0.117 mL, 0.64 mmol) was added and the reaction mixture was stirred for 2 hours at room temperature. The reaction was diluted with water (10 mL) and DCM (5 mL) then acidified to pH ~0 with ~2.5 mL of 6N HCl. The resulting aqueous phase was extracted with DCM (2×10 mL), washed with brine, then dried over MgSO$_4$, filtered, and concentrated in vacuo. Ethyl 2-(cyclohex-1-en-1-yl)-2-methyl-3-(1-methyl-3-(2,4,4-trimethylpentan-2-yl)ureido)propanoate was purified by flash chromatography (5→30% EtOAc/hexanes gradient) to afford 1073 mg (88% yield). MS 381 (MH$^+$).

Example 2.1d: Ethyl 3-((tert-butoxycarbonyl)(methyl)amino)-2-(cyclohex-1-en-1-yl)-2-methylpropanoate Ethyl 3-((tert-butoxycarbonyl)amino)-2-(cyclohex-1-en-1-yl)-2-methylpropanoate (Example 2.1e) (1068 mg, 3.43 mmol) was placed in a 40 mL vial with dry DMF (10 mL) under nitrogen, then methyl iodide (321 µL, 5.14 mmol) was. NaH (60% mineral oil, 151 mg, 3.77 mmol) was added to the solution and stirred at room temperature for 1 hour under nitrogen. The reaction was quenched with sat. aq. NH$_4$Cl (1 mL), diluted with water (20 mL), extracted with DCM (3×10 mL) and the combined organic layers were washed with brine, then dried over MgSO$_4$, filtered, and concentrated in vacuo. The product was Purified by silica gel flash chromatography (, 2→10% EtOAc/hexanes gradient) to give 1043 mg of ethyl 3-((tert-butoxycarbonyl)(methyl)amino)-2-(cyclohex-1-en-1-yl)-2-methylpropanoate as a colorless oil (84% yield). MS 326 (MH$^+$).

Example 2.1e: Ethyl 3-((tert-butoxycarbonyl)amino)-2-(cyclohex-1-en-1-yl)-2-methylpropanoate Ethyl 2-cyano-2-(cyclohex-1-en-1-yl)propanoate (Example 2.1f) (2.073 g, 10.0 mmol) was placed in a 500 mL pear flask with 200 proof ethanol (40 mL), then NiCl$_2$(1.296 g, 10.0 mmol) was added. generating a yellow suspension. Next, NaBH$_4$ (1.135 g, 30.0 mmol) was added and the reaction mixture was stirred at room temperature, overnight. Boc anhydride (3.274 g, 15.0 mmol) was added to the resulting slurry and stirred at room temperature for 3 hours. The reaction was partitioned with water (100 mL), 10% citric acid (100 mL), and DCM (150 mL). Enough 6N HCl was then added to dissolve most of the nickel salts, the layers were separated, and the aqueous layer was extracted with DCM (3×50 mL). The combined organic layers were washed with brine, then dried over MgSO$_4$, filtered, and concentrated in vauco. The product was Purified by silica gel flash chromatography (1→15% EtOAc/hexanes gradient) to give 1.379 g (44% yield) of ethyl 3-((tert-butoxycarbonyl)amino)-2-(cyclohex-1-en-1-yl)-2-methylpropanoate as a nearly colorless, thick oil. MS 312 (MH$^+$).

Example 2.1f: Ethyl 2-cyano-2-(cyclohex-1-en-1-yl)propanoate

Ethyl 2-cyano-2-cyclohexylideneacetate (Example 2.1g) (19.324 g, 100.0 mmol) was placed in a 500 mL pear flask with dry DMF (100 mL) and stirred under nitrogen. KOtBu (1.0 M in THF, 110 mL, 110 mmol) was added via syringe with stirring. The resulting orange solution was stirred for about 1 minute and methyl iodide (9.359 mL, 150 mmol) was added via syringe with stirring over ~2 minutes. The reaction was stirred at room temperature under nitrogen for 3 hours then quenched with sat. aq. NH$_4$Cl solution (100 mL), diluted with water (250 mL), and extracted with hexanes (3×250 mL). The hexane layer was washed with water (4×100 mL) and aqueous NaHSO$_3$ solution (1×100 mL), then dried over MgSO$_4$, filtered, and concentrated in vacuo to afford 19.956 g (96% yield) of ethyl 2-cyano-2-(cyclohex-1-en-1-yl)propanoate as a pale yellow oil that is used without further purification (~95% pure). ($^1$H NMR). $^1$H NMR (400 MHz, DMSO-d$_6$) δ 6.007 (m, 1H), 4.258 (diastereotopic q, J=7.2 Hz, 1H), 4.261 (diastereotopic q, J=7.2 Hz, 1H), 2.119 (m, 2H), 2.028 (m, 2H), 1.682 (s, 3H), 1.61 (m, 4H), 1.311 (t, J=7.2 Hz, 3H). MS N/A (MH$^+$).

Example 2.1g: Ethyl 2-cyano-2-cyclohexylideneacetate

DL-proline (5.765 g, 50.0 mmol) was dissolved in 200 proof ethanol (500 mL), in a 1 liter pear flask, then ethyl 2-cyanoacetate (26.65 mL, 250.0 mmol) and cyclohexanone (25.883 mL, 250.0 mmol) were added via syringe with stirring. The reaction mixture was stirred overnight at room temperature, then heated to 75° C. for 6 hours, then additional cyclohexanone (12.942 mL, 125.0 mmol) was added with continued heating at 75° C. for 1 hour. The solution was cooled to room temperature, adiluted with water (100 mL) and extracted with hexanes (1×200 mL, 1×100 mL). The organic phase was then dried over MgSO$_4$, filtered, and concentrated in vacuo. Purification by vacuum distillation (short path, ~0.5 mmHg, 115° C.→124° C.) gives 29.501 g (61% yield) of ethyl 2-cyano-2-cyclohexylideneacetate as a pale yellow oil, (98% pure) ($^1$H NMR). $^1$H NMR (400 MHz, DMSO-d$_6$) δ 4.273 (q, J=7.2 Hz, 2H), 2.988 (d, J=6 Hz, 1H), 2.972 (d, J=6.4 Hz, 1H), 2.671 (d, J=6.4 Hz, 1H), 2.656 (d, J=6 Hz, 1H), 1.805 (m, 2H), 1.727 (m, 2H), 1.666 (m, 2H), 1.348 (t, J=7.2 Hz, 3H). MS N/A (MH$^+$).

Example 2.2: 5-cyclohexyl-1,5-dimethyl-3-(2-oxo-2-(pyridin-3-yl)ethyl)dihydropyrimidine-2,4(1H,3H)-dione Example 2.2 was the minor component isolated from the preparation of Example 2.3, 5-(cyclohex-1-en-1-yl)-1,5-dimethyl-3-(2-oxo-2-(pyridin-3yl)ethyl)dihydropyrimidine-2,4(1H,3H)-dione.

The mixture of 5-cyclohexyl-1,5-dimethyldihydropyrimidine-2,4(1H,3H)-dione (Example 2.2a) (minor) and 5-(cyclohex-1-en-1-yl)-1,5-dimethyldihydropyrimidine-2,4(1H,3H)-dione (Example 2.3a) (major) (204 mg, 918 μmol) and sodium hydride (60% in mineral oil, 81 mg, 2020 mol) were placed in a 40 mL vial and dissolved in dry DMF (5 mL) under nitrogen purge. The sample was stirred at room temperature for 5 minutes, then 2-bromo-1-(pyridin-3-yl)ethanone hydrobromide (258 mg, 918 μmol) was added and stirred at room temperature for 1 hour. The reaction was quenched with sat. aq. $NH_4Cl$ (1 mL), added water (25 mL) and $NaHCO_3$(s) to ensure pH ~8. The aqueous phase was extracted with DCM (3×10 mL), dried over NaCl, then $MgSO_4$, filtered, and concentrated in vacuo. The product was purified by silica gel chromatography (40→100% EtOAc/hexanes gradient). Fractions containing products were concentrated in vacuo and purified on HPLC (3 injections, 40 minute runs). The fractions containing pure products were concentrated in vacuo, then dried overnight in a vacuum oven at 50° C. to afford 140 mg (45% yield) of a hard, somewhat sticky, very light yellow gum (5-(cyclohex-1-en-1-yl)-1,5-dimethyl-3-(2-oxo-2-(pyridin-3yl)ethyl)dihydropyrimidine2,4(1H,3H)-dione, Example 2.3, and 27 mg (8.6% yield) of a hard, somewhat sticky, very light yellow gum (5-cyclohexyl-1,5-dimethyl-3-(2-oxo-2-(pyridin-3-yl)ethyl)dihydropyrimidine-2,4(1H,3H)-dione, Example 2.2, minor component). $^1H$ NMR (400 MHz, DMSO-$d_6$) (minor) δ $^1H$ NMR (400 MHz, $CDCl_3$) δ 9.20 (dd, J=2.2, 0.7 Hz, 1H), 8.81 (dd, J=4.8, 1.7 Hz, 1H), 8.24 (dt, J=8.0, 1.8 Hz, 1H), 7.45 (ddd, J=8.0, 4.8, 0.8 Hz, 1H), 5.22 (d, J=17.2 Hz, 1H), 5.16 (d, J=17.1 Hz, 1H), 3.38 (d, J=12.9 Hz, 1H), 3.21 (d, J=12.9 Hz, 1H), 3.08 (s, 3H), 1.91-1.59 (m, 8H), 1.35-1.22 (m, 3H), 1.18 (s, 3H), 1.16-1.00 (m, 3H). Melting point=N/A. MS 344 ($MH^+$). $^1H$ NMR (400 MHz, DMSO-$d_6$) (major) δ 9.205 (d of d, J=0.8 Hz, J=2.4 Hz, 1H), 8.81 (d of d, J=1.6 Hz, J=4.8 Hz, 1H), 8.244 (dt, J=2.0 Hz, J=8.0 Hz, 1H), 7.440 (ddd, J=0.8 Hz, J=4.8 Hz, J=8.0 Hz, 1H), 5.631 (m, 1H), 5.244 (d, J=17.2 Hz, 1H), 5.184 (d, J=17.2 Hz, 1H), 3.418 (d, J=13.2 Hz, 1H), 3.363 (d, J=13.2 Hz, 1H), 3.067 (s, 3H), 2.076 (m, 2H), 1.976 (m, 2H), 1.607 (m, 4H), 1.319 (s, 3H). Melting point=N/A. MS 342 ($MH^+$).

Example 2.2a: 5-cyclohexyl-1,5-dimethyldihydropyrimidine-2,4(1H,3H)-dione and Example 2.3a: 5-(cyclohex-1-en-1-yl)-1,5-dimethyldihydropyrimidine-2,4(1H,3H)-dione The mixture of 5-(cyclohex-1-en-1-yl)-1,5-dimethyl-3-(2,4,4-trimethylpentan-2-yl)dihydropyrimidine-2,4(1H,3H)-dione (Example 2.2b) (minor) and 5-(cyclohex-1-en-1-yl)-1,5-dimethyl-3-(2,4,4-trimethylpentan-2-yl)dihydropyrimidine-2,4(1H,3H)-dione (3b) (major) (821 mg, 2.45 mmol) was placed in a 40 mL vial and dissolved in 200 proof ethanol (2.5 mL). The solution was treated with 37% HCl (2.5 mL) and stirred at room temperature for 1 hour, then heated to 50° C. for 2 hours. The volatiles were removed in vacuo to give 522 mg (96% combined yield) of a white solid. MS 225 ($MH^+$) and MS 223 ($MH^+$).

Example 2.2b: 5-cyclohexyl-1,5-dimethyl-3-(2,4,4-trimethylpentan-2-yl)dihydropyrimidine-2,4(1H,3H)-dione and Example 2.3b: 5-(cyclohex-1-en-1-yl)-1,5-dimethyl-3-(2,4,4-trimethyl-pentan-2-yl)dihydropyrimidine-2,4(1H,3H)-dione A mixture of ethyl 2-cyclohexyl-2-methyl-3-(1-methyl-3-(2,4,4-trimethylpentan-2-yl)ureido)propanoate (Example 2.2c) (minor) and ethyl 2-(cyclohex-1-en-1-yl)-2-methyl-3-(1-methyl-3-(2,4,4-trimethylpentan-2-yl)ureido)propanoate (Example 2.3c) (major) (1073 mg, 2.82 mmol) was placed in a 40 mL vial and dissolved in dry DMF (5 mL). KOtBu (1.0 M in THF, 2.82 mL, 2.82 mmol) was added and stirred at room temperature for 1 hour. More KOtBu (0.846 mmol, 0.846 mL) was added and stirred a further 15 minutes at room temperature, then heated to 50° C. and stirred for 2 hours. The reaction was cooled to room temperature and quenched with saturated aqueous $NH_4Cl$ (1 mL). Added water (20 mL) and extracted with hexanes (3×10 mL). The hexanes layer was washed with water (3×5 mL), dried over NaCl, then $MgSO_4$, filtered, and concentrated in vacuo. The crude product was purified by silica gel chromatography (5→30% EtOAc/hexanes gradient) affording 821 mg (87% combined yield) of the desired product. MS 337 ($MH^+$) and MS 335 ($MH^+$).

Example 2.2c: Ethyl 2-cyclohexyl-2-methyl-3-(1-methyl-3-(2,4,4-trimethylpentan-2-yl)ureido)-propanoate and Example 2.3c: Ethyl 2-(cyclohex-1-en-1-yl)-2-methyl-3-(1-methyl-3-(2,4,4-trimethylpentan-2-yl)ureido)propanoate The mixture of ethyl 3-((tert-butoxycarbonyl)(methyl)amino)-2-cyclohexyl-2-methylpropanoate (Example 2.2d) (minor) and ethyl 3-((tert-butoxycarbonyl)(methyl)amino)-2-(cyclohex-1-en-1-yl)-2-methylpropanoate (Example 2.3d) (major) (1043 mg, 3.2 mmol) was placed in a 40 mL vial and TFA (3 mL) and DCM (3 mL) were added. The solution was stirred for one hour at room temperature. The volatiles were removed in vacuo, then the residue was partitioned between water (10 mL) and 30% ACN/DCM (10 mL). The solution was carefully made basic with $NaHCO_3$(s), and the aqueous layer was extracted with 30% ACN/DCM (2×10 mL). The combined organic extracts were dried over NaCl, then $MgSO_4$, filtered, and concentrated in vacuo. The crude mixture of amines was dissolved in dry DCM (2 mL) and treated with 2-isocyanato-2,4,4-trimethylpentane (546 mg, 3.52 mmol) and $Et_3N$ (0.535 mL, 3.84 mmol) and stirred at room temperature for 1 hour, then more 2-isocyanato-2,4,4-trimethylpentane (0.117 mL, 0.64 mmol) was added with continued Stirring for 2 hours at room temperature. The reaction was diluted with water (10 mL) and DCM (5 mL), acidified to pH ~0 with ~2.5 mL of 6N aqueous HCl and extracted with DCM (2×10 mL). The organic phase was dried over NaCl, then $MgSO_4$, filtered, and concentrated in vacuo. Purification by silica gel chromatography (5→30% EtOAc/hexanes gradient). Gave 1073 mg (88% combined yield) of the desired product. MS 383 ($MH^+$) and MS 381 ($MH^+$).

Example 2.2d: Ethyl 3-((tert-butoxycarbonyl)(methyl)amino)-2-cyclohexyl-2-methylpropanoate and 3d: Ethyl 3-((tert-butoxycarbonyl)(methyl)amino)-2-(cyclohex-1-en-1-yl)-2-methyl-propanoate A mixture of ethyl 3-((tert-butoxycarbonyl)amino)-2-cyclohexyl-2-methylpropanoate (Example 2.2e) (major) and ethyl 3-((tert-butoxycarbonyl)amino)-2-(cyclohex-1-en-1-yl)-2-methylpropanoate (Example 2.3e) (minor) (1068 mg, 3.43 mmol) was placed in a 40 mL vial with dry DMF (10 mL). The vial was flushed with nitrogen, then methyl iodide (321 μL, 5.14 mmol) was added and stirred to effect solution. NaH (60% mineral oil, 151 mg, 3.77 mmol) was added and stirred at room temperature for 1 hour under nitrogen purge. The reaction was quenched with saturated aqueous NH₄Cl (1 mL), diluted with water (20 mL), and extracted with DCM (3×10 mL). The combined organic layers were dried over NaCl, then MgSO₄, filtered, and concentrated in vacuo. Purification by silica gel chromatography (2→10% EtOAc/hexanes gradient) gave 1043 mg of the title compounds as a colorless oil (84% combined yield). MS 328 (MH⁺) and MS 326 (MH⁺).

Example 2.2e: Ethyl 3-((tert-butoxycarbonyl) amino)-2-cyclohexyl-2-methylpropanoate and 3e: Ethyl 3-((tert-butoxycarbonyl)amino)-2-(cyclohex-1-en-1-yl)-2-methylpropanoate Ethyl 2-cyano-2-(cyclohex-1-en-1-yl)propanoate (Example 2.2f) (2.073 g, 10.0 mmol) was placed in a 500 mL pear flask with a large stir bar. 200 proof ethanol (40 mL) was added, followed by NiCl₂ (1.296 g, 10.0 mmol). The reaction was stirred to get a yellow suspension. NaBH₄ (1.135 g, 30.0 mmol) was added and stirred at room temperature, capping loosely with a septum. The black precipitate was stirred overnight at room temperature then, Boc anhydride (3.274 g, 15.0 mmol) was added and stirred an additional 3 hours at room temperature. The mixture was partitioned with water (100 mL), 10% aqueous citric acid (100 mL), and DCM (150 mL). Enough 6N aqueous HCl was added to dissolve most of the nickel salts and the aqueous phase was extracted with DCM (3×50 mL). The combined DCM layers were dried over NaCl, then MgSO₄, filtered, and concentrated in vauco. Purification by silica gel chromatography (1→15% EtOAc/hexanes gradient) gave 1.379 g (44% yield) of a nearly colorless, thick oil. The product is an inseparable mixture of the target compound and the C=C bond reduction product. MS 314 (MH⁺) and MS 312 (MH⁺).

Example 2.2f: Ethyl 2-cyano-2-(cyclohex-1-en-1-yl)propanoate

Ethyl 2-cyano-2-cyclohexylideneacetate (Example 2.2g) (19.324 g, 100.0 mmol) was placed in a 500 mL pear flask with a large stir bar. Dry DMF (100 mL) was added and the flask was capped with a septum, and stirred under nitrogen. KOtBu (1.0 M in THF, 110 mL, 110 mmol) was added via syringe with stirring. The orange solution was stirred for about 1 minute, then placed the flask in a room temperature water bath and added methyl iodide (9.359 mL, 150 mmol) via syringe with stirring over ~2 minutes. The reaction mixture was stirred at room temperature under nitrogen for 3 hours, then quenched with saturated aqueous NH₄Cl solution (100 mL) and diluted with water (250 mL). The aqueous phase was extracted with hexanes (3×250 mL), washed with water (4×100 mL) and aqueous NaHSO₃ solution (1×100 mL), then dried over MgSO₄, filtered, and concentrated in vacuo affording 19.956 g (96% yield) of a light yellow oil that is ~95% pure (¹H NMR). ¹H NMR (400 MHz, DMSO-d₆) δ 6.007 (m, 1H), 4.258 (diastereotopic q, J=7.2 Hz, 1H), 4.261 (diastereotopic q, J=7.2 Hz, 1H), 2.119 (m, 2H), 2.028 (m, 2H), 1.682 (s, 3H), 1.61 (m, 4H), 1.311 (t, J=7.2 Hz, 3H). MS N/A (MH⁺).

Example 2.2g: Ethyl 2-cyano-2-cyclohexylideneacetate

DL-proline (5.765 g, 50.0 mmol) was placed in a 1 liter pear flask with a large stir bar. 200 proof ethanol (500 mL) was added followed by the addition of ethyl 2-cyanoacetate (26.65 mL, 250.0 mmol) and cyclohexanone (25.883 mL, 250.0 mmol) via syringe with stirring. The flask was capped with a yellow plug and stirred overnight at room temperature, then heated to 75° C. for 6 hours, Another portion of cyclohexanone (12.942 mL, 125.0 mmol) was added with continued heating at 75° C. for 1 hour. The reaction was cooled to room temperature, added water (100 mL), and extracted with hexanes (1×200 mL, 1×100 mL). The organic phase was dried over MgSO₄, filtered, and concentrated in vacuo. Purification by vacuum distillation on (short path, ~0.5 mmHg, 115° C.→124° C.) gave 29.501 g (61% yield) of a very light yellow oil, 98% pure (¹H NMR). ¹H NMR (400 MHz, DMSO-d₆) δ 4.273 (q, J=7.2 Hz, 2H), 2.988 (d, J=6 Hz, 1H), 2.972 (d, J=6.4 Hz, 1H), 2.671 (d, J=6.4 Hz, 1H), 2.656 (d, J=6 Hz, 1H), 1.805 (m, 2H), 1.727 (m, 2H), 1.666 (m, 2H), 1.348 (t, J=7.2 Hz, 3H). MS N/A (MH⁺).

Example 2.3: 5-(cyclohex-1-en-1-yl)-1,5-dimethyl-3-(2-oxo-2-(pyridin-3-yl)ethyl) Dihydropyrimidine-2,4(1H,3H)-dione Prepared in a similar manner to Example 2.1 using 2-bromo-1-(pyridin-3-yl)ethanone hydrobromide (258 mg, 918 μmol). Gives 140 mg (45% yield) of a pale yellow gum. ¹H NMR (400 MHz, DMSO-d₆) δ 9.205 (d of d, J=0.8 Hz, J=2.4 Hz, 1H), 8.81 (d of d, J=1.6 Hz, J=4.8 Hz, 1H), 8.244 (d of t, J=2.0 Hz, J=8.0 Hz, 1H), 7.440 (d of d of d, J=0.8 Hz, J=4.8 Hz, J=8.0 Hz, 1H), 5.631 (m, 1H), 5.244 (d, J=17.2 Hz, 1H), 5.184 (d, J=17.2 Hz, 1H), 3.418 (d, J=13.2 Hz, 1H), 3.363 (d, J=13.2 Hz, 1H), 3.067 (s, 3H), 2.076 (m, 2H), 1.976 (m, 2H), 1.607 (m, 4H), 1.319 (s, 3H). MS 342 (MH⁺).

Example 2.4: 5-cyclohexyl-1,5-dimethyl-3-(2-oxo-2-phenylethyl)dihydropyrimidine-2,4(1H,3H)-dione 5-cyclohexyl-1,5-dimethyl-3-((2-phenyl-1,3-dioxolan-2-yl)methyl)dihydropyrimidine-2,4(1H,3H)-dione (Example 2.4a) (841 mol, 325 mg) was heated in a mixture of 6N aqueous HCl and ethanol (2:1, 10 mL) at 70° C. for 6 hours. The reaction was concentrated to dryness and the residue purified by silica gel chromatography (5→80% EtOAc/hexanes gradient). Yield 93%. ¹H NMR (400 MHz, CDCl₃) δ 7.99-7.95 (m, 2H), 7.61-7.55 (m, 1H), 7.50-7.44 (m, 2H), 5.22 (d, J=17.1 Hz, 1H), 5.17 (d, J=17.1 Hz, 1H), 3.37 (d, J=12.9 Hz, 1H), 3.22 (d, J=12.9 Hz, 1H), 3.08 (s, 3H), 1.90-1.75 (m, 3H), 1.76-1.60 (m, 3H), 1.38-1.20 (m, 3H), 1.17 (s, 3H), 1.15-0.99 (m, 3H). MS 343 (MH⁺).

Example 2.4a: 5-cyclohexyl-1,5-dimethyl-3-((2-phenyl-1,3-dioxolan-2-yl)methyl)dihydro-pyrimidine-2,4(1H,3H)-dione Ethyl 3-((tert-butoxycarbonyl)(methyl)amino)-2-cyclohexyl-2-methylpropanoate (Example 2.4c) (1000 mol, 327 mg) was dissolved in DCM (3 mL) and trifluoroacetic acid (3 mL) was added. The reaction was stirred at room temperature for 30 minutes, then volatiles were removed in vacuo and the residue treated with saturated aqueous NaHCO₃(10 mL) and NaHCO₃(s) to reach pH ~8. The solution was extracted with 30% ACN/DCM (v/v) (3×10 mL), dried over NaCl, then MgSO₄, filtered, and concentrated in vacuo. The crude ethyl 2-cyclohexyl-2-methyl-3-(methylamino)propanoate was dissolved in DCM (10 mL) and treated with 2-isocyanato-2-phenyl-1,3-dioxolane (4b) (1000 mol, 205 mg) and triethylamine (1500 mol, 209 μL) and stirred at room temperature overnight. The mixture was diluted with DCM (10 mL) and extracted with 10% aqueous citric acid solution (3×5 mL). The organic phase was dried over NaCl, then MgSO$_4$, filtered, and concentrated to give a thick yellow oil that was used in next step without purification. The crude ethyl 2-cyclohexyl-2-methyl-3-(1-methyl-3-((2-phenyl-1,3-dioxolan-2-yl)methyl)ureido)propanoate (assumed 1000 mol) was dissolved in dry DMF and added KOtBu (1100 mol, 123 mg). The solution was stirred at room temperature overnight, then quenched with saturated aqueous NH$_4$Cl (2 mL), diluted with water (25 mL), and extracted with DCM (3×10 mL). The organic layers were dried over NaCl, then MgSO$_4$, filtered, and concentrated in vacuo. Purification by silica gel chromatography (10→60% EtOAc/hexanes gradient) afforded the title compound in 84% yield over 3 steps. $^1$H NMR is consistent with structure. MS 387 (MH$^+$).

Example 2.4b: 2-isocyanato-2-phenyl-1,3-dioxolane (2-phenyl-1,3-dioxolan-2-yl)methanamine (Example 2.35d) (6.0 mmol, 1075 mg) was added to a 250 mL Erlenmeyer flask with a large stir bar. DCM (25 mL) and sat. NaHCO$_3$ (25 mL) were added and stirred at 0° C. (ice bath). triphosgene (2.0 mmol, 594 mg) was added and stirred at 0° C. for 1 hour. The layers were separated and extracted the aqueous layer with DCM (3×15 mL). The organic phase was dried over NaCl, then MgSO$_4$, filtered and concentrated in vacuo to give a yellow oil that slowly solidifies at room temperature. $^1$H NMR and IR are consistent with structure. Gives 1094 mg (91% yield).

Example 2.4c: Ethyl 3-((tert-butoxycarbonyl)(methyl)amino)-2-cyclohexyl-2-methylpropanoate Ethyl 3-((tert-butoxycarbonyl)amino)-2-cyclohexyl-2-methylpropanoate (Example 2.4d) (5.71 mmol, 1789 mg) was dissolved in dry DMF (15 mL) in a 40 mL vial flushed with nitrogen. CH$_3$I (8.57 mmol, 535 µL) was added via syringe, followed by NaH (60% in mineral oil, 6.28 mmol, 251 mg) and stirred under nitrogen purge at room temperature for 1 hour. The reaction was quenched with saturated aqueous NH$_4$Cl solution (2 mL) and diluted with water (10 mL). The aqueous layer was extracted with DCM (3×10 mL) and the DCM layers dried over NaCl, then MgSO$_4$, filtered, and concentrated in vacuo. The residue was purified by silica gel chromatography (1→20% EtOAc/hexanes gradient) to afford 1675 mg (90% yield) of the title compound. $^1$H NMR is consistent with structure. MS 328 (MH$^+$)

Example 2.4d: Ethyl 3-((tert-butoxycarbonyl)amino)-2-cyclohexyl-2-methylpropanoate NiCl$_2$ (7.57 mmol, 981 mg) was added to a 250 mL round-bottomed flask with a large stir bar. A solution of ethyl 2-cyano-2-cyclohexylpropanoate (Example 2.4e) (7.57 mmol, 1585 mg) dissolved in 40 mL of ethanol (200 proof) was added to the flask. NaBH$_4$ (22.7 mmol, 860 mg) was carefully added and stirred at room temperature for 1 hour. A solution of Boc$_2$O (11.4 mmol, 2478 mg) in EtOH (200 proof) (5 mL) was added to the reaction mixture and stirred at room temperature overnight. The reaction was quenched with 50 mL of 10% aqueous citric acid solution, DCM (100 mL) was added and everything was transferred to a 500 mL Erlenmeyer flask. 6N HCl (100 mL) and con. HCl (37%) (20 mL) were added and the aqueous phase was extracted with DCM (2×100 mL). The combined organic phase was dried over NaCl, then MgSO$_4$, filtered, and concentrated in vacuo. Purification of the residue by silica gel chromatography (1→20% EtOAc/hexanes gradient) gave the title compound as a thick oil that slowly solidifies at room temperature to a waxy, whitish solid. Gives 2.373 g (75% yield from Example 2.4e). $^1$H NMR is consistent with structure. MS 314 (MH$^+$).

Example 2.4e: Ethyl 2-cyano-2-cyclohexylpropanoate

KOtBu (11.0 mmol, 1234 mg) was placed in a 40 mL vial with a stir bar and dry DMF (20 mL) and flushed with nitrogen. Ethyl 2-cyano-2-cyclohexylacetate (Example 2.4f) (10.0 mmol, 1953 mg) was added via syringe and stirred at room temperature for 2 minutes, followed by addition of CH$_3$I (15.0 mmol, 936 µL) via syringe with stirring at room temperature overnight under nitrogen. The reaction mixture was quenched with saturated aqueous NH$_4$Cl (2 mL) and added water (60 mL) and extracted with hexanes (3×50 mL). The hexanes layers were washed with water (5×10 mL), dried over NaCl, then MgSO$_4$, filtered, and concentrated in vacuo. Purification by silica gel chromatography (1→15% EtOAc/hexanes gradient). Gives 2004 mg (96% yield). $^1$H NMR is consistent with structure.

Example 2.4f: Ethyl 2-cyano-2-cyclohexylacetate

KOtBu (100.0 mmol, 11.221 g) was placed in a nitrogen-flushed 500 mL pear flask fitted with a stir bar. Dry DMF (100 mL) was added, followed by ethyl 2-cyanoacetate (100.0 mmol, 10.662 mL) via syringe. The reaction was stirred at room temperature for 5 minutes, then bromocyclohexane (100.0 mmol, 12.214 mL) was added via syringe. The reaction was stirred at room temperature overnight, then heated to 80° C. (2 h), 100° C. (2 h), then stirred over the weekend at room temperature. The reaction mixture was quenched with saturated aqueous NH$_4$Cl (10 mL) and diluted with water (300 mL), then extracted with hexanes (3×100 mL). The combined hexanes layer was washed with water (5×50 mL), dried over NaCl, then MgSO$_4$, filtered, and concentrated in vacuo. Purification by silica gel chromatography (1→15% EtOAc/hexanes gradient) gave 11.307 g (58% yield) of the title compound as a light yellow oil. $^1$H NMR is consistent with structure.

Example 2.5: 5-(cyclohex-1-en-1-yl)-3,5-dimethyl-1-(2-oxo-2-phenylethyl)dihydropyrimidine-2,4(1H, 3H)-dione The major component from this reaction is 5-(cyclohex-1-en-1-yl)-3,5-dimethyl-1-(2-oxo-2-phenylethyl)dihydropyrimidine-2,4(1H,3H)-dione (Example 2.5). The minor component isolated from the reaction mixture was 5-cyclohexyl-3,5-dimethyl-1-(2-oxo-2-phenylethyl)dihydropyrimidine-2,4(1H,3H)-dione (Example 2.7).

The mixture of 5-(cyclohex-1-en-1-yl)-1-(2-hydroxy-2-phenylethyl)-3,5-dimethyl-dihydropyrimidine-2,4(1H,3H)-dione (5a) (major) and 5-cyclohexyl-1-(2-hydroxy-2-phenylethyl)-3,5-dimethyldihydropyrimidine-2,4(1H,3H)-dione (Example 2.7a) (minor) (237 mol, 81 mg) in dry DMF (5 mL) was placed in a 40 mL vial and pyridinium dichromate (284 mol, 107 mg) was added. The reaction was stirred at room temperature for 2 days. DCM (2 mL) was added and stirred for 1 day, then more pyridinium dichromate (372 mol, 140 mg) was added and stirred at room temperature for 3 days. The reaction mixture was diluted with DCM (10 mL) and treated with 1N aqueous HCl (10 mL) and water (20 mL). The aqueous layer was extracted with DCM (2×10 mL), and the combined DCM layers were dried over NaCl, then MgSO$_4$, filtered, and concentrated in vacuo. Purification by silica gel chromatography (10→60% EtOAc/hexanes gradient), then by HPLC to give the products. The major isomer (5-(cyclohex-1-en-1-yl)-3,5-dimethyl-1-(2-oxo-2-phenylethyl)dihydropyrimidine-2,4(1H,3H)-dione, Example 2.5, is 19 mg (24% yield), minor isomer, Example 2.7, is 8 mg (10% yield). $^1$H NMR (400 MHz, CDCl$_3$) δ 8.00-7.95 (m, 2H), 7.65-7.59 (m, 1H), 7.53-7.47 (m, 2H), 5.45-5.41 (m, 1H), 5.27 (d, J=17.5 Hz, 1H), 4.39 (d, J=17.5 Hz, 1H), 3.52 (d, J=12.9 Hz, 1H), 3.30 (d, J=12.9 Hz, 1H), 3.23 (s, 3H), 2.03-1.96 (m, 2H), 1.96-1.88 (m, 2H), 1.69-1.43 (m, 4H), 1.28 (s, 3H) (major). $^1$H NMR (400 MHz, CDCl$_3$) δ 8.01-7.96 (m, 2H), 7.65-7.59 (m, 1H), 7.54-7.47 (m, 2H), 5.01 (d, J=17.5 Hz, 1H), 4.71 (d, J=17.5 Hz, 1H), 3.36 (d, J=12.7 Hz, 1H), 3.27 (d, J=12.7 Hz, 1H), 3.20 (s, 3H), 1.88-1.49 (m, 5H), 1.30-1.15 (m, 3H), 1.14 (s, 3H), 1.12-0.97 (m, 3H) (minor). MS 341 (MH$^+$) and 343 (MH$^+$), respectively.

Example 2.5a: 5-(cyclohex-1-en-1-yl)-1-(2-hydroxy-2-phenylethyl)-3,5-dimethyldihydro-pyrimidine-2,4(1H,3H)-dione A mixture ethyl 2-(cyclohex-1-en-1-yl)-3-(1-(2-hydroxy-2-phenylethyl)-3-methylureido)-2-methylpropanoate (crude sample Example 2.5b) (major) and ethyl 2-cyclohexyl-3-(1-(2-hydroxy-2-phenylethyl)-3-methylureido)-2-methylpropanoate (Example 2.7b) (minor) (300 μmol) was dissolved in dry DMF (4 mL). KOtBu (1.0 M in THF, 1.1 mmol, 1.1 mL) was added and stirred under nitrogen for 24 hours. The reaction was quenched with saturated aqueous NH$_4$Cl (1 mL) and diluted with water (25 mL), then extracted with DCM (3×10 mL), dried over NaCl, then MgSO$_4$, filtered, and concentrated in vacuo. Purification by silica gel chromatography (10→100% EtOAc/hexanes gradient) gave 81 mg (79% yield) of the desired product mixture. $^1$H NMR is consistent with structures. MS 343 (MH$^+$) and 345 (MH$^+$)

Example 2.5b: Ethyl 2-(cyclohex-1-en-1-yl)-3-(1-(2-hydroxy-2-phenylethyl)-3-methylureido)-2-methylpropanoate A mixture of ethyl 2-(cyclohex-1-en-1-yl)-3-((2-hydroxy-2-phenylethyl)amino)-2-methylpropanoate (crude sample from Example 2.5c) (major) and ethyl 2-cyclohexyl-3-((2-hydroxy-2-phenylethyl)amino)-2-methylpropanoate (Example 2.7c) (minor) (~1.0 mmol) was dissolved in DCM (5 mL) and treated with 4-nitrophenyl methylcarbamate (1.0 mmol, 196 mg), followed by triethylamine (1.5 mmol, 209 μL) and stirred at room temperature overnight. The volatiles were removed in vacuo, then the reaction was partitioned between ether (20 mL) and 1N aqueous HCl (10 mL). The organic layer was washed with 1N aqueous HCl (10 mL) followed by 1N aqueous NaOH solution (9×5 mL), then the ether extract was dried over NaCl, then MgSO$_4$, filtered, and concentrated in vacuo. Purification by silica gel chromatography (40-100% EtOAc/hexanes gradient). Gives 217 mg, contaminated with some material from the previous step. The material was carried on to the next step without further purification. $^1$H NMR is consistent with structures. MS 389 (MH$^+$) and 391 (MH$^+$)

Example 2.5c: Ethyl 2-(cyclohex-1-en-1-yl)-3-((2-hydroxy-2-phenylethyl)amino)-2-methyl-propanoate A mixture of ethyl 3-amino-2-(cyclohex-1-en-1-yl)-2-methylpropanoate (5d) (major) and ethyl 3-amino-2-cyclohexyl-2-methylpropanoate (Example 2.7d) (minor) (1.37 mmol, 290 mg) was dissolved in ethanol (200 proof, 20 mL) and 2-phenyloxirane (1.51 mmol, 172 μL) was added, followed by diisopropylethylamine (4.11 mmol, 716 μL). The reaction was stirred at room temperature for 30 minutes, then heated to 75° C. overnight. The reaction was then cooled to room temperature and stirred for 24 hours. The volatiles were removed in vacuo, then the residue was partitioned between ether (10 mL) and water (20 mL) and acidified with 6N aqueous HCl (2 mL). The organic phase was extracted with 1N aqueous HCl (5 mL), then the combined aqueous layers were made basic with NaHCO$_3$(s) and extracted with DCM (3×10 mL). The DCM layers were dried over NaCl, then MgSO$_4$, filtered, and concentrated in vacuo to give 274 mg of crude product. Conversion is about 50%. The product was carried on to the next step without further purification. $^1$H NMR is consistent with structures. MS 332 (MH$^+$) and 334 (MH$^+$)

Example 2.5d: Ethyl 3-amino-2-(cyclohex-1-en-1-yl)-2-methylpropanoate

Ethyl 2-cyano-2-(cyclohex-1-en-1-yl)propanoate (5.0 mmol, 1036 mg) (Example 2.2f) was dissolved in ethanol (200 proof, 20 mL) and NiCl$_2$ (5.0 mmol, 648 mg) was added. NaBH$_4$ (15.0 mmol, 567 mg) was added with stirring at room temperature for 2 hours. The reaction was filtered through Celite, then a 0.45 m PTFE syringe-tip filter. The mixture was concentrated to about 1 mL by rotary evaporation and the residue treated with water (50 mL) and 6N aqueous HCl (10 mL). The solution was extracted with ether (1×50 mL), then the ether layer was washed with 0.5N aqueous HCl. The combined aqueous layers were made basic with NaHCO$_3$(s) and extracted with DCM (3×50 mL) (emulsifies). The emulsion was separated from the bulk of the water layer and treated with MgSO$_4$ until dry. The DCM extract was concentrated in vacuo to give a yellow oil. Gives 742 mg (70% yield) of a mixture of the correct product and the C=C-bond reduced product. $^1$H NMR is consistent with structures. MS 212 (MH$^+$) and 214 (MH$^+$)

Example 2.6: 5-(cyclohex-1-en-1-yl)-1,5-dimethyl-3-(2-oxo-2-phenylethyl)tetrahydro-pyrimidin-2(1H)-one To a solution of 5-cyclohexenyl-1-(2-hydroxy-2-phenylethyl)-3,5-dimethyltetra-hydropyrimidin-2(1H)-one (Example 2.6a) (0.12 mmol, 40 mg) in a mixture of DCM (1.5 mL)/DMF (1.5 mL) was added pyridinium dichromate (0.12 mmol, 46 mg) in one portion. The reaction mixture was stirred at room temperature for 24 hrs. An additional 25 mg of pyridinium dichromate was added to the reaction mixture with stirring for an additional 24 hrs. When the reaction was complete, it was diluted in water and DCM and the organic phase was combined and dried in vacuo. The crude material was purified by preparative HPLC, to afford 20 mg of clean product (yield 51%). $^1$H NMR (400 MHz, DMSO-d$_6$) δ 7.970 (d, J=8.8 Hz, 2H), 7.549 (m, 1H), 7.442 (m, 2H), 5.433 (m, 1H), 4.654 (dd, J=74 Hz &7 Hz, 2H), 3.358 (m, 2H), 3.057 (m, 2H), 2.972 (s, 3H), 1.918 (m, 1H), 1.505 (m, 1H), 1.119 (s, 3H). MS 327 (MH$^+$).

Example 2.6a: 5-cyclohexenyl-1-(2-hydroxy-2-phenylethyl)-3,5-dimethyltetrahydropyrimidin-2(1H)-one In a solution of 5-cyclohexenyl-1,5-dimethyltetrahydropyrimidin-2(1H)-one (Example 2.6b) (0.48 mmol, 100 mg)

in DMF (10 mL) was added sodium hydride (60% dispersion in mineral oil, 5 eq, 2.4 mmol, 96 mg). After stirring at room temperature for 5 mins, styrene oxide (0.96 mmol, 108 µL) was added to the reaction mixture and the mixture was microwaved at 180° C. for 40 mins, then quenched with water (10 mL). The mixture was extracted with dichloromethane (DCM) (30 mL×3), and the combined organic layers were washed with brine, dried over $MgSO_4$ and concentrated in vacuo. The resulting residue was purified by mass-triggered HPLC. The fractions ionized at MS 329 were collected and concentrated. The product was obtained as a light yellow oil 40 mg (yield 25%). MS 329 ($MH^+$).

Example 2.6b: 5-cyclohexenyl-1,5-dimethyltetrahydropyrimidin-2(1H)-one

To a solution of 5-(cyclohex-1-en-1-yl)-1,5-dimethylpyrimidine-2,4,6(1H,3H,5H)-trione (Example 2.8a) (0.12 mmol, 40 mg) in a mixture of DCM (1.5 mL)/DMF (1.5 mL) was added pyridinium dichromate (0.12 mmol, 46 mg) in one portion. The reaction mixture was stirring at room temperature for 24 hrs and an additional 25 mg of pyridinium dichromate was added with stirring an additional 24 hrs. When the reaction was complete by TLC, it was worked up with water and DCM and the crude material was purified by preparative HPLC to afford 20 mg of pure product (yield 51%). $^1$H NMR (400 MHz, DMSO-$d_6$) δ 7.970 (d, J=8.8 Hz, 2H), 7.549 (m, 1H), 7.442 (m, 2H), 5.433 (m, 1H), 4.654 (dd, J=74 Hz &7 Hz, 2H), 3.358 (m, 2H), 3.057 (m, 2H), 2.972 (s, 3H), 1.918 (m, 1H), 1.505 (m, 1H), 1.119 (s, 3H). MS 327 ($MH^+$).

Example 2.7: 5-cyclohexyl-3,5-dimethyl-1-(2-oxo-2-phenylethyl)dihydropyrimidine-2,4(1H,3H)-dione Isolated as the minor component from the preparation of Example 2.5 described above.
$^1$H NMR (400 MHz, $CDCl_3$) δ 8.01-7.96 (m, 2H), 7.65-7.59 (m, 1H), 7.54-7.47 (m, 2H), 5.01 (d, J=17.5 Hz, 1H), 4.71 (d, J=17.5 Hz, 1H), 3.36 (d, J=12.7 Hz, 1H), 3.27 (d, J=12.7 Hz, 1H), 3.20 (s, 3H), 1.88-1.49 (m, 5H), 1.30-1.15 (m, 3H), 1.14 (s, 3H), 1.12-0.97 (m, 3H). MS 343 ($MH^+$).

Example 2.8: 5-(cyclohex-1-en-1-yl)-1,5-dimethyl-3-(2-oxo-2-phenylethyl)pyrimidine-2,4,6(1H,3H,5H)-trione To an oven-dried 150 mL pressure tube flushed under nitrogen, were added hexobarbital, 5-(cyclohex-1-en-1-yl)-1,5-dimethylpyrimidine-2,4,6(1H,3H,5H)-trione, (Example 2.8a) (2.7 g, 11.4 mmol) in anhydrous DMF (34 mL) and at 0° C. sodium hydride (545 mg, 13.60 mmol), and the reaction medium was stirred vigorously for a few minutes at room temperature. 2-Bromo-1-phenylethanone (2.77 g, 13.92 mmol) was then added at 0° C., the pressure tube was sealed and the reaction medium stirred for 16 hours at room temperature, followed by extraction with excess $H_2O$/EtOAc (3×). Combined organic phases were washed with brine, dried over $MgSO_4$, and solvents were evaporated. The residue was first purified by flash chromatography on silica gel and eluted with a Hexane/EtOAc gradient to obtain a yellow oil that precipitated out upon standing (4.14 g). The material was then re-purified by flash chromatography on silica gel and eluted again with a Hexane/EtOAc gradient to obtain a colorless oil that precipitated out upon standing (3.77 g), and which was taken up in EtOH 3 times successively, followed by evaporation of solvents in order to eliminate all traces of undesired solvents. Finally, the obtained white residue was re-dissolved in a small amount of EtOH, heated for dissolution, and let stand for recrystallisation in the refrigerator overnight, to obtain 3.16 g (78% yield) as a fluffy white powder. $^1$H NMR (400 MHz, $d_6$-DMSO) δ 8.09-8.04 (m, 2H), 7.76-7.70 (m, 1H), 7.62-7.56 (m, 2H), 5.81-5.76 (m, 1H), 5.36 (d, J=17.7 Hz, 1H), 5.26 (d, J=17.7 Hz, 1H), 3.19 (s, 3H), 2.09-1.93 (m, 3H), 1.90-1.78 (m, 1H), 1.55 (s, 3H), 1.63-1.44 (m, 4H). MS 355 ($MH^+$)

Example 2.8a: 5-(cyclohex-1-en-1-yl)-1,5-dimethylpyrimidine-2,4,6(1H,3H,5H)-trione The 5-(cyclohex-1-en-1-yl)-6-imino-1,5-dimethyldihydropyrimidine-2,4(1H,3H)-dione/5-(cyclohex-1-en-1-yl)-6-imino-3,5-dimethyldihydropyrimidine-2,4(1H,3H)-dione mixture (Example 2.8b) (67.00 mmol, 15.77 g) was placed in a 500 mL flask with a stir bar. 4 N HCl (250 mL) in 2:1 water/EtOH mixture (167 mL 6 N HCl+83 mL EtOH) was added and the solution was heated to reflux for 3 hours. The solution was cooled to room temperature and let stand overnight, then diluted with water (180 mL) and the crystalline solid was collected by filtration and washed with water. The material was dried by suction for ~1 hour, then on high vacuum to afford 14.41 g (91% yield) of small white crystals. $^1$H-NMR of product is consistent with structure and shows a purity >97%. MS N/A ($MH^+$).

Example 2.8b: 5-(cyclohex-1-en-1-yl)-6-imino-1,5-dimethyldihydropyrimidine-2,4(1H,3H)-dione5-(cyclohex-1-en-1-yl)-6-imino-3,5-dimethyldihydropyrimidine-2,4(1H,3H)-dione Ethyl 2-cyano-2-(cyclohex-1-en-1-yl)propanoate (129.60 mmol, 26.87 g) (Example 2.2f) and methylurea (129.60 mmol, 9.60 g) were combined in a 500 mL flask, flushed with nitrogen and placed in a room temperature water bath. tBuOK (1.0 M in tBuOH, 142.56 mmol, 143 mL) was added to a separate 250 mL, nitrogen-flushed flask, then the viscous tBuOK solution was transferred into the original solution via a large bore cannula (⅛" PTFE tubing) with continuous stirring over about 15 minutes. The reaction was stirred at room temperature for 1 hour and a heavy precipitate formed. The slurry was heated to 50° C. and stirred overnight under nitrogen, then cooled to room temperature, quenched with 6 M HCl (60 mL) and diluted with water (600 mL). The aqueous layer was extracted with hexanes (180 mL) and the hexanes was washed with water (150 mL). The combined aqueous layer was extracted with DCM (300 mL) and then again with 30% ACN/DCM mixture (300 mL). The aqueous layer was made basic with $NaHCO_3$(s) and then extracted with 30% ACN/DCM (3×300 mL). The final organic extracts were dried over NaCl, then over $MgSO_4$, filtered, and concentrated in vacuo. This gave the product as a beige solid, 15.77 g (52% yield). $^1$H-NMR of product is consistent with structure and shows a purity >97%. MS 236 ($MH^+$).

Example 2.9: 5-(cyclohex-1-en-1-yl)-1-(2-(3-methoxyphenyl)-2-oxoethyl)-3,5-dimethyl-pyrimidine-2,4,6(1H,3H,5H)-trione In a small microwave tube, were added commercially available 5-cyclohexenyl-1,5-dimethylpyrimidine-2,4,6(1H,3H,5H)-trione (30 mg, 0.127 mmol), anhydrous DMF, 2-bromo-1-(3-methoxyphenyl)ethanone (36 mg, 0.157 mmol), and K$_2$CO$_3$ (21 mg, 0.152 mmol). The tube was sealed and heated at 100° C. for 6 minutes in a microwave under very high absorbing conditions. The reaction medium was extracted with H$_2$O/EtOAc (3×). Solvents of combined organic phases were evaporated, and the residue diluted in a minimum amount of MeOH was purified by preparative HPLC using a 25 minutes CH$_3$CN/H$_2$O gradient as eluant, to obtain after solvents evaporation and drying on a lyophilizer the desired product (36.4 mg, 75%). $^1$H NMR (400 MHz, d$_6$-Acetone) δ 7.70-7.68 (m, 1H), 7.57-7.56 (m, 1H), 7.50 (t, J=7.6 Hz, 1H), 7.26 (dd, J=2.8 Hz, J=8.0 Hz, 1H), 5.84-5.83 (m, 1H), 5.40 (d, J=17.2 Hz, 1H), 5.32 (d, J=17.6 Hz, 1H), 3.89 (s, 3H), 3.26 (s, 3H), 2.10-2.03 (m, 3H), 1.98-1.90 (m, 1H), 1.67-1.51 (m, 4H), 1.61 (s, 3H). MS 385 (MH$^+$).

Example 2.10: 5-(cyclohex-1-en-1-yl)-1-(2-(3-fluorophenyl)-2-oxoethyl)-3,5-dimethyl-pyrimidine-2,4,6(1H,3H,5H)-trione Prepared in a similar manner to Example 2.9 using commercially available 5-cyclohexenyl-1,5-dimethylpyrimidine-2,4,6(1H,3H,5H)-trione (22 mg, 0.093 mmol), 2-bromo-1-(3-fluorophenyl)ethanone (22 mg, 0.101 mmol), to obtain the desired product (20.6 mg, 59%). $^1$H NMR (400 MHz, d$_6$-Acetone) δ 7.96 (dd, J=7.7, 0.6 Hz, 1H), 7.83-7.78 (m, 1H), 7.66 (td, J=8.1, 5.6 Hz, 1H), 7.50 (td, J=8.4, 2.7 Hz, 1H), 5.85-5.80 (m, 1H), 5.42 (d, J=17.6 Hz, 1H), 5.34 (d, J=17.5 Hz, 1H), 3.26 (s, 3H), 2.12-2.01 (m, 3H), 2.00-1.89 (m, 1H), 1.69-1.49 (m, 4H), 1.61 (s, 3H). MS no ionization.

Example 2.11: 5-(cyclohex-1-en-1-yl)-1,5-dimethyl-3-(2-oxo-2-(pyridin-3-yl)ethyl)pyrimidine-2,4,6(1H,3H,5H)-trione To an oven-dried, N$_2$-flushed, 150 mL pressure tube, were added 5-cyclohexenyl-1,5-dimethylpyrimidine-2,4,6(1H,3H,5H)-trione (Example 2.8a) (3.0 g, 12.7 mmol) in anhydrous DMF (40 mL) and at 0° C. sodium hydride (1.17 g, 29.3 mmol), and the reaction medium was stirred vigorously for a few minutes at room temperature. 2-Bromo-1-(pyridin-3-yl)ethanone hydrobromide (4.3 g, 15.2 mmol) was then added at 0° C., the pressure tube was sealed and the reaction medium stirred overnight at room temperature, followed by extraction with excess H$_2$O/EtOAc (3×). Combined organic phases were washed with brine, dried over MgSO$_4$, and solvents were evaporated. The residue was first purified by flash chromatography on a Silicycle column (330 g) and eluted with a DCM/EtOAc gradient to obtain a yellow oil. The material was then re-purified by flash chromatography on a Silicycle column (120 g) and eluted again with a DCM/EtOAc gradient to obtain a colourless oil which was taken in EtOH 3 times successively followed by evaporation of solvents in order to eliminate all traces of undesired solvents. Finally, the obtained oil (that precipitated out upon standing) was re-dissolved in a small amount of EtOH, heated for dissolution, and seeded with a few flakes of desired product for recrystallisation in the refrigerator overnight, to obtain after drying on the lyophilizer the desired product as a white fluffy powder (1.5 g, 33.2%).
$^1$H NMR (400 MHz, dmso) δ 9.24 (dd, J=2.3, 0.8 Hz, 1H), 8.87 (dd, J=4.8, 1.7 Hz, 1H), 8.40 (ddd, J=8.0, 2.3, 1.7 Hz, 1H), 7.62 (ddd, J=8.0, 4.8, 0.8 Hz, 1H), 5.80-5.76 (m, 1H), 5.41 (d, J=17.8 Hz, 1H), 5.31 (d, J=17.8 Hz, 1H), 3.18 (s, 3H), 2.09-1.93 (m, 3H), 1.89-1.80 (m, 1H), 1.61-1.44 (m, 4H), 1.54 (s, 3H). MS 356 (MH$^+$). Melting Point: 109-111°

C. Elemental analysis shows matching numbers with percentage differences of 0.01 for C, 0.19 for H, and 0.07 for N.

Example 2.12: 1-(2-(3-chlorophenyl)-2-oxoethyl)-5-(cyclohex-1-en-1-yl)-3,5-dimethyl-pyrimidine-2,4,6(1H,3H,5H)-trione Prepared in a similar manner to Example 2.9 using commercially available 5-cyclohexenyl-1,5-dimethylpyrimidine-2,4,6(1H,3H,5H)-trione (22 mg, 0.093 mmol), 2-bromo-1-(3-chlorophenyl)ethanone (24 mg, 0.103 mmol), to obtain the desired product (29.8 mg, 82%).
$^1$H NMR (400 MHz, d$_6$-Acetone) δ 8.09-8.03 (m, 2H), 7.77-7.72 (m, 1H), 7.63 (dd, J=8.0, 7.5 Hz, 1H), 5.85-5.80 (m, 1H), 5.42 (d, J=17.5 Hz, 1H), 5.34 (d, J=17.2 Hz, 1H), 3.26 (s, 3H), 2.11-2.01 (m, 3H), 1.99-1.89 (m, 1H), 1.68-1.50 (m, 4H), 1.61 (s, 3H). MS no ionization.

Example 2.13: 5-(cyclohex-1-en-1-yl)-1,5-dimethyl-3-(2-oxo-2-(thiophen-2-yl)ethyl)-pyrimidine-2,4,6(1H,3H,5H)-trione Prepared in a similar manner to Example 2.9 using commercially available 5-cyclohexenyl-1,5-dimethylpyrimidine-2,4,6(1H,3H,5H)-trione (20 mg, 0.085 mmol), 2-chloro-1-(thiophen-2-yl)ethanone (17 mg, 0.106 mmol), to obtain the desired product (18.1 mg, 59%). $^1$H NMR (400 MHz, d$_6$-DMSO) δ 8.20 (dd, J=3.8, 1.1 Hz, 1H), 8.11 (dd, J=4.9, 1.1 Hz, 1H), 7.31 (dd, J=4.9, 3.8 Hz, 1H), 5.78-5.73 (m, 1H), 5.27 (d, J=17.5 Hz, 1H), 5.18 (d, J=17.5 Hz, 1H), 3.16 (s, 3H), 2.06-1.90 (m, 3H), 1.88-1.75 (m, 1H), 1.52 (s, 3H), 1.60-1.40 (m, 4H). MS 361 (MH$^+$).

Example 2.14: 3-(2-(5-(cyclohex-1-en-1-yl)-3,5-dimethyl-2,4,6-trioxotetrahydropyrimidin-1(2H)-yl)acetyl)benzonitrile Prepared in a similar manner to Example 2.9 using commercially available 5-cyclohexenyl-1,5-dimethylpyrimidine-2,4,6(1H,3H,5H)-trione (100 mg, 0.423 mmol), 3-(2-bromoacetyl)benzonitrile (114 mg, 0.509 mmol), the reaction medium was also heated again for another 10 minutes at 120° C. before described work-up. The desired product was obtained (82.5 mg, 51%). $^1$H NMR (400 MHz, d$_6$-DMSO) δ 8.56 (t, J=1.5 Hz, 1H), 8.34-8.29 (m, 1H), 8.19-8.15 (m, 1H), 7.78 (t, J=7.8 Hz, 1H), 5.78-5.72 (m, 1H), 5.41 (d, J=17.9 Hz, 1H), 5.31 (d, J=17.9 Hz, 1H), 3.16 (s, 3H), 2.07-1.91 (m, 3H), 1.88-1.77 (m, 1H), 1.61-1.42 (m, 4H), 1.53 (s, 3H). MS no ionization.

Example 2.15: 5-(cyclohex-1-en-1-yl)-1,5-dimethyl-3-(2-oxo-2-(pyridin-4-yl)ethyl)pyrimidine-2,4,6(1H,3H,5H)-trione In a small oven-dried, N$_2$-flushed, pressure tube, were added commercially available 5-cyclohexenyl-1,5-dimethylpyrimidine-2,4,6(1H,3H,5H)-trione (101.7 mg, 0.430 mmol), anhydrous DMF (2 mL), NaH (46.0 mg, 1.150 mmol) and stirred for 10 minutes, followed by 2-bromo-1-(pyridin-4-yl)ethanone hydrobromide (113.7 mg, 0.405 mmol). The tube was sealed and the reaction medium was stirred vigorously for 3.5 hours and further overnight. The reaction medium was extracted with H$_2$O/EtOAc (3×). Combined organic phases were washed with brine and dried over MgSO$_4$. Solvents were evaporated and the obtained residue was dissolved in a minimum amount of MeOH, filtered, and purified by Varian preparative HPLC using a 25 minutes method and a 5-95% H$_2$O/MeOH gradient as eluant, to obtain after solvents evaporation and drying on a lyophilizer the desired product (52.5 mg, 35%). $^1$H NMR (400 MHz, d$_6$-DMSO) δ 8.86 (dd, J=4.4, 1.7 Hz, 2H), 7.93 (dd, J=4.4, 1.7 Hz, 2H), 5.80-5.71 (m, 1H), 5.39 (d, J=17.9 Hz, 1H), 5.29 (d, J=17.9 Hz, 1H), 3.18 (s, 3H), 2.09-1.90 (m, 3H), 1.90-1.78 (m, 1H), 1.61-1.42 (m, 4H), 1.54 (s, 3H). MS 356 (MH$^+$).

Example 2.16: 5-(cyclohex-1-en-1-yl)-1,5-dimethyl-3-(2-oxo-2-(pyridin-2-yl)ethyl)pyrimidine-2,4,6(1H,3H,5H)-trione Prepared in a similar manner to Example 2.15 using commercially available 5-cyclohexenyl-1,5-dimethylpyrimidine-2,4,6(1H,3H,5H)-trione (100 mg, 0.423 mmol), 2-bromo-1-(pyridin-2-yl)ethanone hydrobromide (123 mg, 0.438 mmol), to obtain the desired product (26.2 mg, 22%). $^1$H NMR (400 MHz, d$_6$-DMSO) δ 8.83-8.77 (m, 1H), 8.07 (td, J=7.7, 1.7 Hz, 1H), 8.01 (dt, J=7.8, 1.2 Hz, 1H), 7.77 (ddd, J=7.5, 4.8, 1.4 Hz, 1H), 5.81-5.77 (m, 1H), 5.46 (d, J=18.2 Hz, 1H), 5.38 (d, J=18.2 Hz, 1H), 3.18 (s, 3H), 2.09-1.94 (m, 3H), 1.91-1.79 (m, 1H), 1.62-1.44 (m, 4H), 1.54 (s, 3H). MS 356 (MH$^+$).

Example 2.17: 5-(cyclohex-2-en-1-yl)-1,5-dimethyl-3-(2-oxo-2-phenylethyl)pyrimidine-2,4,6(1H,3H,5H)-trione The suspension of 5-(cyclohex-2-enyl)-1,5-dimethylpyrimidine-2,4,6(1H,3H,5H)-trione (Example 2.17a) (106 mg, 0.45 mmol), K$_2$CO$_3$ (150 mg, 1.08 mmol) and 2-bromoacetophenone (100 mg, 0.5 mmol) in 5 mL of EtOH was heated under microwave irradiation (Biotage Personal Chemistry Emrys Optimizer) at 150° C. for 10 minutes. The reaction was diluted with water (5 mL) and purified by preparative HPLC using a 40 minutes MeOH/H$_2$O gradient of 5-95% to give after evaporation of solvents and lyophilization 30.5 mg (20% yield) of desired product as a white fluffy powder. $^1$H NMR (400 MHz, DMSO-d$_6$) δ 8.05 (d, J=8 Hz, 2H), 7.70 (t, J=8 Hz, 1H), 7.56 (t, J=8.0 Hz, 2H), 5.76 (m, 1H), 5.62 (dd, J=8 Hz, J=68 Hz, 1H), 5.35 (dd, J=8 Hz, J=20 Hz, 1H), 5.225 (dd, J=4 Hz, J=16 Hz, 1H), 3.135 (d, J=4 Hz, 3H), 2.72 (m, 1H), 1.88 (m, 2H), 1.64 (m, 2H), 1.52 (m, 1H), 1.43 (m, 1H), 1.38 (d, J=16 Hz, 3H), 1.28 (m, 1H). MS 355 (MH$^+$).

Example 2.17a: 5-(cyclohex-2-enyl)-1,5-dimethylpyrimidine-2,4,6(1H,3H,5H)-trione 11 g (43.3 mmol) of diethyl 2-(cyclohex-2-enyl)-2-methylmalonate (Example 2.17b) and 3.2 g (43.3 mmol) of methylurea were added to a cooled solution of sodium ethoxide (from sodium, 2.5 g, and absolute Ethanol, 45 mL). Reaction mixture was heated at 100° C. for 18 h, then concentrated in vacuum, residue was diluted with water and acidified with conc. HCl to pH=2. The obtained precipitate was filtered off, dried under vacuum and purified by flash chromatography using a 120 g Silicycle column (Hexane/EtOAc 20% gradient; R$_f$=0.35) to give 7.08 g (69% yield) of desired product. $^1$H NMR (400 MHz, DMSO-d$_6$) δ 11.39 (s, 1H), 5.74 (m, 1H), 5.47 (dd, J=8 Hz, J=16 Hz, 1H), 3.0.5 (d, J=4 Hz, 3H), 2.53 (m, 1H), 1.85 (m, 2H), 1.66 (m, 1H), 1.57 (m, 1H), 1.36 (m, 1H), 1.315 (d, J=4 Hz, 3H). MS 237 (MH$^+$).

Example 2.17b: Diethyl 2-(cyclohex-2-enyl)-2-methylmalonate 8.05 g (50 mmol) of 3-bromocyclohex-1-ene were added to a cooled mixture of 8.7 g (50 mmol) of diethyl 2-methylmalonate and sodium ethoxide (from sodium, 1.3 g, and absolute Ethanol, 25 mL). Reaction mixture was heated at 100° C. for 30 min, then concentrated in vacuum, residue was diluted with water and product was extracted with ether. Diethyl 2-(cyclohex-2-enyl)-2-methylmalonate was obtained (11 g; 87%) as light orange oil and used in to next step without future purification. MS 255 (MH$^+$).

Example 2.18: 5-(cyclohex-2-en-1-yl)-1-(2-(3-methoxyphenyl)-2-oxoethyl)-3,5-dimethylpyrimidine-2,4,6(1H,3H,5H)-trione Prepared in a similar manner to Example 2.17 using 5-(cyclohex-2-enyl)-1,5-dimethylpyrimi-dine-2,4,6(1H,3H,5H)-trione (17a) (106 mg, 0.45 mmol) and 2-bromo-1-(3-methoxyphenyl)ethanone (115 mg, 0.5 mmol). Gives 29 mg (17% yield) of a white powder. $^1$H NMR (400 MHz, CDCl$_3$) δ 7.56 (d, J=8 Hz, 1H), 7.49 (s, 1H), 7.41 (t, J=8 Hz, 1H), 7.17 (d, J=8 Hz, 1H), 5.86 (m, 1H), 5.70 (dd, J=12 Hz, J=44 Hz, 1H), 5.34 (dd, J=8 Hz, J=16 Hz, 1H), 5.24 (dd, J=4 Hz, J=16 Hz, 1H), 3.85 (s, 3H), 3.325 (d, J=4 Hz, 3H), 2.88 (m, 1H), 1.98 (m, 2H), 1.76 (m, 2H), 1.52 (m, 1H), 1.49 (m, 1H), 1.57 (d, J=8 Hz, 3H). MS 385 (MH$^+$).

Example 2.19: 5-(cyclohex-1-en-1-yl)-1-ethyl-5-methyl-3-(2-oxo-2-phenylethyl)pyrimidine-2,4,6(1H,3H,5H)-trione Prepared in a similar manner to Example 2.17 using 5-cyclohexenyl-1-ethyl-5-methylpyrimi-dine-2,4,6(1H,3H,5H)-trione (Example 2.19a) (75 mg, 0.3 mmol) and 2-bromoacetophenone (66 mg, 0.33 mmol). Gives 23.2 mg (21% yield) of a white powder. $^1$H NMR (400 MHz, CDCl$_3$) δ 7.98 (d, J=8 Hz, 2H), 7.62 (t, J=8 Hz, 1H), 7.50 (t, J=8 Hz, 2H), 5.83 (m, 1H), 5.31 (q, J=16 Hz, J=24 Hz, 2H), 3.97 (m, 2H), 2.11 (m, 2H), 1.97 (mm, 2H), 1.67 (s, 3H), 1.62 (m, 2H), 1.56 (m, 2H), 1.22 (t, J=8 Hz, 3H). MS 369 (MH$^+$).

Example 2.19a: 5-cyclohexenyl-1-ethyl-5-methylpyrimidine-2,4,6(1H,3H,5H)-trione Prepared in a similar manner to Example 2.17a using dimethyl 2-cyclohexenyl-2-methylmalonate (Example 2.19b) (2 g, 8.85 mmol) and ethyl urea (780 mg; 8.85 mmol). Gives 720 mg (33% yield) of a white solid. $^1$H NMR (400 MHz, DMSO-d$_6$) δ 11.44 (bs, 1H), 5.60 (m, 1H), 3.71 (m, 2H), 1.98 (m, 2H), 1.79 (m, 2H), 1.51 (m, 4H), 1.41 (s, 3H), 1.04 (t, J=8 Hz, 3H). MS 251 (MH$^+$).

Example 2.19b: Dimethyl 2-cyclohexenyl-2-methylmalonate

Prepared in a similar manner to Example 2.17b using dimethyl 2-cyclohexenylmalonate (Example 2.19c) (5.7 g, 26.8 mmol) and methyl iodide (1.67 mL, 26 mmol). Gives 4.28 g (71% yield) of a colorless oil which was used in to next step without future purification. 1H NMR (400 MHz, CDCl$_3$) δ 5.51 (m, 1H), 3.71 (s, 6H), 2.06 (m, 2H), 1.97 (m, 2H), 1.83 (m, 1H), 1.70 (m, 1H), 1.59 (m, 3H), 1.54 (m, 1H), 1.53 (s, 3H). MS 227 (MH$^+$).

Example 2.19c: Dimethyl 2-cyclohexenylmalonate

To the mixture of dimethyl malonate (11.4 mL, 100 mmol), cyclohexanone (10.3 mL; 100 mmol) and acetic anhydride (11.3 mL, 120 mmol) was added $ZnCl_2$ (4.76 g, 35 mmol) activated with aniline (1.8 mL of aniline was gradually added to $ZnCl_2$ and stirred at room temperature; resulting solid was then added to the reaction mixture). Reaction mixture was heated at 100° C. for 70 h, then was diluted with water and extracted with ether. Combined organic phases were washed with brine and dried over $MgSO_4$, and solvents were evaporated. The residue was purified by flash chromatography using a 120 g Silicycle column (Hexane/EtOAc 20% gradient, $R_f$=0.6) to obtain 5.78 g of desired product (13% yield). $^1$H NMR (400 MHz, $CDCl_3$) δ 5.68 (m, 1H), 4.02 (s, 1H), 3.74 (s, 6H), 2.08 (m, 4H), 1.85 (m, 2H), 1.59 (m, 2H). MS 213 (MH$^+$).

Example 2.20: 5-(cyclohex-1-en-1-yl)-1-ethyl-3-(2-(3-methoxyphenyl)-2-oxoethyl)-5-methylpyrimidine-2,4,6(1H,3H,5H)-trione Prepared in a similar manner to Example 2.17 using 5-cyclohexenyl-1-ethyl-5-methylpyrimidine-2,4,6(1H,3H,5H)-trione (19a) (75 mg, 0.3 mmol) and 2-bromo-1-(3-methoxy-phenyl)ethanone (76 mg, 0.33 mmol). Gives 59.5 mg (50% yield) of a white powder. $^1$H NMR (400 MHz, $CDCl_3$) δ 7.56 (d, J=8 Hz, 1H), 7.49 (t, J=4 Hz, 1H), 7.41 (t, J=8 Hz, 1H), 7.165 (dd, J=4 Hz, J=8 Hz, 1H), 5.83 (m, 1H), 5.291 (q, J=16 Hz, J=24 Hz, 2H), 3.97 (m, 2H), 2.11 (m, 2H), 2.00 (mm, 2H), 1.67 (s, 3H), 1.62 (m, 2H), 1.56 (m, 2H), 1.22 (t, J=8 Hz, 3H). MS 399 (MH$^+$).

Example 2.21: 5-(cyclohex-2-en-1-yl)-1,5-dimethyl-3-(2-oxo-2-(pyridin-3-yl)ethyl)pyrimidine-2,4,6(1H,3H,5H)-trione To the suspension of NaH (60%; 0.66 mmol; 26 mg) in 5 mL of anhydrous DMF was added solution of 5-(cyclohex-2-enyl)-1,5-dimethylpyrimidine-2,4,6(1H,3H,5H)-trione (Example 2.17a) (71 mg; 0.3 mmol) in 1 mL of anhydrous DMF. The reaction mixture was stirred at ambient temperature for 15 minutes and then 2-bromo-1-(pyridin-3-yl)ethanone hydrobromide (1 eq; 0.5 mmol; 107 mg) was added to the reaction mixture and stirred at room temperature for 18 h. The reaction was quenched with water (25 mL) and extracted with EtOAc (3×20 mL). The combined organic phases were washed with water (40 mL), brine (40 mL), and dried over $MgSO_4$ and solvents were evaporated. Crude product was purified by preparative HPLC using a 40 minutes MeOH/$H_2O$ gradient of 5-95% to give after evaporation of solvents and lyophilization 31.2 mg of product (29% yield) as a white powder. $^1$H NMR (400 MHz, $CDCl_3$) δ 9.21 (s, 1H), 8.85 (d, J=8 Hz, 1H), 8.26 (d, J=8 Hz, 1H), 7.48 (dd, J=8 Hz, J=12 Hz, 1H), 5.86 (m, 1H), 5.70 (dd, J=12 Hz, J=44 Hz, 1H), 5.35 (dd, J=8 Hz, J=16 Hz, 1H), 5.26 (dd, J=4 Hz, J=16 Hz, 1H), 3.325 (d, J=4 Hz, 3H), 2.88 (m, 1H), 1.98 (m, 2H), 1.76 (m, 2H), 1.61 (m, 2H), 1.58 (d, J=8 Hz, 3H). MS 357 (MH$^+$).

Example 2.22: 5-(cyclohex-2-en-1-yl)-1-(2-(3-fluorophenyl)-2-oxoethyl)-3,5-dimethyl-pyrimidine-2,4,6(1H,3H,5H)-trione Prepared in a similar manner to Example 2.17 using of of 5-(cyclohex-2-enyl)-1,5-dimethylpyrimi-dine-2,4,6(1H,3H,5H)-trione (Example 2.17a) (106 mg, 0.45 mmol) and 2-bromo-1-(3-fluoro-phenyl)ethanone (109 mg, 0.5 mmol). Gives 35.5 mg (21% yield) of a white powder. $^1$H NMR (400 MHz, $CDCl_3$) δ 7.76 (d, J=8 Hz, 1H), 7.66 (d, J=8 Hz, 1H), 7.505 (dd, J=8 Hz, J=20 Hz, 1H), 7.33 (t, J=8 Hz, 1H), 5.86 (m, 1H), 5.70 (dd, J=12 Hz, J=44 Hz, 1H), 5.32 (dd, J=8 Hz, J=16 Hz, 1H), 5.23 (dd, J=4 Hz, J=16 Hz, 1H), 3.32 (d, J=4 Hz, 3H), 2.88 (m, 1H), 1.98 (m, 2H), 1.76 (m, 2H), 1.52 (m, 1H), 1.49 (m, 1H), 1.57 (d, J=8 Hz, 3H). MS 385 (MH$^+$).

Example 2.23: 5-(cyclohex-1-en-1-yl)-1-ethyl-3-(2-(3-fluorophenyl)-2-oxoethyl)-5-methylpyrimidine-2,4,6(1H,3H,5H)-trione Prepared in a similar manner to Example 2.17 using 5-cyclohexenyl-1-ethyl-5-methylpyrimidine-2,4,6(1H,3H,5H)-trione (Example 2.19a) (75 mg, 0.3 mmol) and 2-bromo-1-(3-fluorophenyl)ethanone (72 mg, 0.33 mmol). Gives 20 mg (17% yield) of a white powder. $^1$H NMR (400 MHz, $CDCl_3$) δ 7.76 (d, J=8 Hz, 1H), 7.66 (d, J=8 Hz, 1H), 7.50 (m, 1H), 7.33 (t, J=8 Hz, 1H), 5.83 (m, 1H), 5.291 (q, J=16 Hz, J=24 Hz, 2H), 3.97 (m, 2H), 2.11 (m, 2H), 1.95 (mm, 2H), 1.66 (s, 3H), 1.62 (m, 2H), 1.56 (m, 2H), 1.22 (t, J=8 Hz, 3H). MS 387 (MH$^+$).

Example 2.24: 5-(cyclohex-1-en-1-yl)-1-(2-(furan-2-yl)-2-oxoethyl)-3,5-dimethylpyrimidine-2,4,6(1H,3H,5H)-trione Prepared in a similar manner to Example 2.15 using commercially available 5-cyclohexenyl-1,5-dimethylpyrimidine-2,4,6(1H,3H,5H)-trione (100 mg, 0.423 mmol), 2-bromo-1-(furan-2-yl)ethanone (123 mg, 0.651 mmol), to obtain the desired product (77.9 mg, 53%). $^1$H NMR (400 MHz, $d_6$-DMSO) δ 8.10 (dd, J=1.7, 0.7 Hz, 1H), 7.69 (dd, J=3.7, 0.6 Hz, 1H), 6.80 (dd, J=3.7, 1.7 Hz, 1H), 5.79-5.74 (m, 1H), 5.14 (d, J=17.5 Hz, 1H), 5.04 (d, J=17.5 Hz, 1H), 3.17 (s, 3H), 2.08-1.91 (m, 3H), 1.89-1.77 (m, 1H), 1.62-1.42 (m, 4H), 1.53 (s, 3H). MS 345 (MH$^+$).

Example 2.25: 5-cyclopentyl-1,5-dimethyl-3-(2-oxo-2-phenylethyl)pyrimidine-2,4,6(1H,3H,5H)-trione Prepared in a similar manner to Example 2.17 using 5-cyclopentyl-1,5-dimethylpyrimidine-2,4,6(1H,3H,5H)-trione (Example 2.25a) (67 mg, 0.3 mmol) and 2-bromoacetophenone (66 mg, 0.33 mmol). Gives 62 mg (60% yield) of a white powder. $^1$H NMR (400 MHz, $CDCl_3$) δ 7.99 (d, J=8 Hz, 2H), 7.63 (t, J=8 Hz, 1H), 7.51 (t, J=8v, 2H), 5.31 (q, J=16 Hz, J=40 Hz, 2H), 3.32 (s, 3H), 2.45 (m, 1H), 1.77 (mm, 2H), 1.63 (mm, 4H), 1.56 (m, 1H), 1.56 (s, 3H), 1.45 (m, 1H). MS 343 (MH$^+$).

Example 2.25a: 5-cyclopentyl-1,5-dimethylpyrimidine-2,4,6(1H,3H,5H)-trione

Prepared in a similar manner to Example 2.17a using diethyl 2-cyclopentyl-2-methylmalonate (Example 2.25b) (4.65 g, 19.2 mmol) and methyl urea (1.42 g; 19.2 mmol). Gives 3 g (70% yield) of a white solid. $^1$H NMR (400 MHz, DMSO-$d_6$) δ 11.34 (s, 1H), 5.60 (m, 1H), 3.05 (s, 3H), 2.15 (m, 1H), 1.46 (m, 6H), 1.32 (s, 3H), 1.28 (m, 2H). MS 237 (MH$^+$).

Example 2.25b: Diethyl 2-cyclopentyl-2-methylmalonate

Prepared in a similar manner to Example 2.17b using diethyl 2-methylmalonate (8.6 mL, 50 mmol) and bromocyclopentane (5.36 mL, 50 mmol). Gives 9.36 g (77% yield) of a colorless oil which was used in to next step without future purification. ¹H NMR (400 MHz, CDCl₃) δ 4.08 (q, J=8 Hz, J=12, 2H), 2.42 (m, 1H), 1.62 (m, 2H), 1.46 (m, 4H), 1.27 (m, 2H), 1.25 (s, 3H), 1.14 (t, J=8 Hz, 3H). MS 243 (MH⁺).

Example 2.26: 5-cyclopentyl-1-(2-(3-fluorophenyl)-2-oxoethyl)-3,5-dimethylpyrimidine-2,4,6(1H,3H,5H)-trione Prepared in a similar manner to Example 2.17 using 5-cyclopentyl-1,5-dimethyl-pyrimidine-2,4,6(1H,3H,5H)-trione (Example 2.25a) (67 mg, 0.3 mmol) and 2-bromo-1-(3-fluorophenyl)-ethanone (72 mg, 0.33 mmol). Gave 27 mg (25% yield) of a white powder. ¹H NMR (400 MHz, CDCl₃) δ 7.76 (d, J=8 Hz, 1H), 7.665 (d, J=8 Hz, 1H), 7.505 (td, J=8 Hz, J=8 Hz, 1H), 7.34 (t, J=8 Hz, 1H), 5.27 (q, J=16 Hz, J=40 Hz, 2H), 3.32 (s, 3H), 2.45 (m, 1H), 1.77 (mm, 2H), 1.63 (mm, 4H), 1.56 (m, 1H), 1.56 (s, 3H), 1.45 (m, 1H). MS 361 (MH⁺).

Example 2.27: 5-(cyclohex-1-en-1-yl)-1-ethyl-5-methyl-3-(2-oxo-2-(pyridin-3-yl)ethyl)pyrimidine-2,4,6(1H,3H,5H)-trione Prepared in a similar manner to Example 2.21 using 5-cyclohexenyl-1-ethyl-5-methylpyrimidine-2,4,6(1H,3H,5H)-trione (Example 2.19a) (75 mg, 0.3 mmol) and 2-bromo-1-(pyridin-3-yl)ethanone hydrobromide (93 mg, 0.33 mmol). Gave 52.3 mg (47% yield) of a white powder. ¹H NMR (400 MHz, CDCl₃) δ 9.215 (d, J=4 Hz, 1H), 8.85 (dd, J=1.6 Hz, J=4.8 Hz, 1H), 8.26 (dt, J=1.6 Hz, J=8.4 Hz, 1H), 7.475 (dd, J=4 Hz, J=8 Hz, 1H), 5.83 (m, 1H), 5.30 (q, J=16 Hz, J=24 Hz, 2H), 3.97 (m, 2H), 2.11 (m, 2H), 1.97 (mm, 2H), 1.67 (s, 3H), 1.62 (m, 2H), 1.56 (m, 2H), 1.22 (t, J=8 Hz, 3H). MS 370 (MH⁺).

Example 2.28: 5-(cyclohex-1-en-1-yl)-5-methyl-1-(2-oxo-2-(pyridin-3-yl)ethyl)-3-propylpyrimidine-2,4,6(1H,3H,5H)-trione Prepared in a similar manner to Example 2.21 using 5-cyclohexenyl-5-methyl-1-propylpyrimidine-2,4,6(1H,3H,5H)-trione (Example 2.28a) (79 mg, 0.3 mmol) and 2-bromo-1-(pyridin-3-yl)ethanone hydrobromide (93 mg, 0.33 mmol). Afforded 50 mg (44% yield) of a white powder. ¹H NMR (400 MHz, CDCl₃) δ 9.215 (d, J=4 Hz, 1H), 8.85 (dd, J=1.6 Hz, J=4.8 Hz, 1H), 8.26 (dt, J=1.6 Hz, J=8.4 Hz, 1H), 7.475 (dd, J=4 Hz, J=8 Hz, 1H), 5.83 (m, 1H), 5.30 (q, J=16 Hz, J=24 Hz, 2H), 3.87 (m, 2H), 2.11 (m, 2H), 1.97 (mm, 2H), 1.67 (s, 3H), 1.62 (m, 2H), 1.56 (m, 4H), 0.94 (t, J=8 Hz, 3H). MS 384 (MH⁺).

Example 2.28a: 5-cyclohexenyl-5-methyl-1-propylpyrimidine-2,4,6(1H,3H,5H)-trione Prepared in a similar manner to Example 2.17a using dimethyl 2-cyclohexenyl-2-methylmalonate (Example 2.19b) (2 g, 8.85 mmol) and propyl urea (903 mg; 8.85 mmol). Afforded 890 mg (38% yield) of a white solid. ¹H NMR (400 MHz, DMSO-d₆) δ 11.45 (bs, 1H), 5.60 (m, 1H), 3.62 (m, 2H), 1.98 (m, 2H), 1.93 (m, 1H), 1.79 (m, 2H), 1.51 (m, 5H), 1.42 (s, 3H), 0.80 (t, J=8 Hz, 3H). MS N/A (MH⁺).

Example 2.29: 5-cyclopentyl-1,5-dimethyl-3-(2-oxo-2-(pyridin-3-yl)ethyl)pyrimidine-2,4,6(1H,3H,5H)-trione Prepared in a similar manner to Example 2.21 using of 5-cyclopentyl-1,5-dimethylpyrimidine-2,4,6(1H,3H,5H)-trione (Example 2.25a) (67 mg, 0.3 mmol) and 2-bromo-1-(pyridin-3-yl)ethanone hydrobromide (93 mg, 0.33 mmol). Afforded 31.7 mg (31% yield) of a white powder. ¹H NMR (400 MHz, CDCl₃) δ 9.215 (d, J=4 Hz, 1H), 8.85 (dd, J=1.6 Hz, J=4.8 Hz, 1H), 8.26 (dt, J=1.6 Hz, J=8.4 Hz, 1H), 7.475 (dd, J=4 Hz, J=8 Hz, 1H), 5.31 (q, J=16 Hz, J=40 Hz, 2H), 3.32 (s, 3H), 2.45 (m, 1H), 1.77 (mm, 2H), 1.63 (mm, 4H), 1.56 (m, 1H), 1.56 (s, 3H), 1.45 (m, 1H). MS 344 (MH⁺).

Example 2.30: 5-(cyclopent-1-en-1-yl)-1,5-dimethyl-3-(2-oxo-2-phenylethyl)pyrimidine-2,4,6(1H,3H,5H)-trione Prepared in a similar manner to Example 2.17 using 5-cyclohexenyl-1-ethyl-5-methylpyrimidine-2,4,6(1H,3H,5H)-trione (Example 2.30a) (67 mg, 0.3 mmol) and 2-bromoacetophenone (66 mg, 0.33 mmol). Afforded 35.3 mg (35% yield) of a white powder. ¹H NMR (400 MHz, CDCl₃) δ 7.98 (d, J=8 Hz, 2H), 7.62 (t, J=8 Hz, 1H), 7.51 (t, J=8 Hz, 2H), 5.75 (m, 1H), 5.31 (q, J=16 Hz, J=32 Hz, 2H), 3.34 (s, 3H), 2.38 (m, 2H), 2.31 (m, 2H), 1.89 (m, 2H), 1.72 (s, 3H). MS 341 (MH⁺).

Example 2.30a: 5-cyclohexenyl-1-ethyl-5-methylpyrimidine-2,4,6(1H,3H,5H)-trione Prepared in a similar manner to Example 2.17a using dimethyl 2-cyclopentenyl-2-methylmalonate (Example 2.30b) (626 mg, 2.95 mmol) and methyl urea (218 mg; 2.95 mmol). Gave 208 mg (31% yield) of a white-yellowish solid. ¹H NMR (400 MHz, CDCl₃) δ 8.09 (bs, 1H), 5.66 (m, 1H), 3.29 (s, 3H), 2.37 (m, 2H), 2.28 (m, 2H), 1.89 (m, 2H), 1.66 (s, 3H). MS N/A (MH⁺).

Example 2.30b: dimethyl 2-cyclopentenyl-2-methylmalonate

Prepared in a similar manner to Example 2.17b using dimethyl 2-cyclopentenylmalonate (30c) (5.53 g, 28 mmol) and methyl iodide (1.75 mL, 28 mmol). Gave 626 mg (10% yield). ¹H NMR (400 MHz, DMSO-d₆) δ 5.58 (m, 1H), 3.64 (s, 6H), 2.29 (m, 4H), 1.81 (m, 2H), 1.48 (s, 3H). MS 213 (MH⁺).

Example 2.30c: Dimethyl 2-cyclopentenylmalonate

Prepared in a similar manner to Example 2.19c using dimethyl malonate (11.4 mL, 100 mmol) and cyclopentanone (8.85 mL, 100 mmol). Gave 5.53 g (28% yield) of a colorless oil, which was used in to the next step without purification. MS 199 (MH⁺).

Example 2.31: 5-(cyclopent-1-en-1-yl)-1,5-dimethyl-3-(2-oxo-2-(pyridin-3-yl)ethyl)pyrimidine-2,4,6(1H,3H,5H)-trione Prepared in a similar manner to Example 2.17 using 5-cyclohexenyl-1-ethyl-5-methylpyrimidine-2,4,6(1H,3H,5H)-trione (Example 2.30a) (67 mg, 0.3 mmol) and 2-bromo-1-(pyridin-3-yl)ethanone hydrobromide (93 mg, 0.33 mmol). Gave 35.4 mg (35% yield) of a white powder. ¹H NMR (400 MHz, CDCl₃) δ 9.215 (d, J=4 Hz, 1H), 8.85 (dd, J=1.6 Hz, J=4.8 Hz, 1H), 8.26 (dt, J=1.6 Hz, J=8.4 Hz, 1H), 7.475 (dd, J=4 Hz, J=8 Hz, 1H), 5.75 (m, 1H), 5.31 (q, J=16 Hz, J=32 Hz, 2H), 3.34 (s, 3H), 2.38 (m, 2H), 2.31 (m, 2H), 1.89 (m, 2H), 1.72 (s, 3H). MS 342 (MH⁺).

Example 2.32: 5-cyclohexyl-1,5-dimethyl-3-(2-oxo-2-phenylethyl)pyrimidine-2,4,6(1H,3H,5H)-trione 5-cyclohexyl-1,5-dimethylpyrimidine-2,4,6(1H,3H,5H)-trione (Example 2.32a) (453 µmol, 108 mg) and $K_2CO_3$ (680 µmol, 94 mg) were placed in a vial, dissolved in dry DMF (2 mL) and stirred at room temperature for 2 minutes. 2-Bromo-1-phenylethanone (498 µmol, 99 mg) was added and stirred at room temperature for 1 hour. 10% aqueous citric acid (10 mL) and water (10 mL) were added to precipitate the product. The product was collected by filtration and washed with water, the in ACN and concentrated to dryness. The compound was purified by silica gel chromatography (5→60% EtOAc/hexanes gradient) to give 156 mg (96% yield). $^1$H NMR (400 MHz, CDCl$_3$) δ 8.01-7.96 (m, 2H), 7.65-7.60 (m, 1H), 7.54-7.48 (m, 2H), 5.36 (d, J=17.0 Hz, 1H), 5.27 (d, J=17.0 Hz, 1H), 3.33 (s, 3H), 2.05-1.96 (m, 1H), 1.88-1.76 (m, 3H), 1.75-1.61 (m, 2H), 1.54 (s, 3H), 1.33-1.18 (m, 3H), 1.18-1.05 (m, 2H). MS 357 (MH$^+$)

Example 2.32a: 5-cyclohexyl-1,5-dimethylpyrimidine-2,4,6(1H,3H,5H)-trione

The title compound was made from ethyl 2-cyano-2-cyclohexylpropanoate (2.0 mmol, 419 mg) (Example 2.4e) in a manner similar to Example 2.8a and Example 2.8b, to afford 217 mg (46% yield over 2 steps). $^1$H NMR is consistent with structure. MS N/A (MH$^+$).

Example 2.33: 1,5-dimethyl-5-(3-methylbut-2-en-1-yl)-3-(2-oxo-2-phenylethyl)pyrimidine-2,4,6(1H,3H,5H)-trione The title compound was synthesized in a manner similar to Example 2.32 from 1,5-dimethyl-5-(3-methylbut-2-en-1-yl)pyrimidine-2,4,6(1H,3H,5H)-trione (Example 2.33a) (1.0 mmol, 224 mg), 2-bromo-1-phenylethanone (1.0 mmol, 199 mg), and $K_2CO_3$ (1.1 mmol, 152 mg). Purified by silica gel chromatography (5→30% EtOAc/hexanes gradient). Gave 293 mg (86% yield). $^1$H NMR (400 MHz, CDCl$_3$) δ 8.01-7.96 (m, 2H), 7.66-7.60 (m, 1H), 7.54-7.48 (m, 2H), 5.33 (d, J=17.1 Hz, 1H), 5.29 (d, J=17.0 Hz, 1H), 5.07-5.01 (m, 1H), 3.31 (s, 3H), 2.72 (qd, J=13.7, 7.8 Hz, 2H), 1.71 (d, J=1.0 Hz, 3H), 1.61 (s, 3H), 1.60 (d, J=1.0 Hz, 3H). MS 343 (MH$^+$)

Example 2.33a: 1,5-dimethyl-5-(3-methylbut-2-en-1-yl)pyrimidine-2,4,6(1H,3H,5H)-trione Placed 1-methylurea (3.0 mmol, 222 mg) and KOtBu (6.3 mmol, 707 mg) into a vial flushed with nitrogen. Made up a solution of diethyl 2-methyl-2-(3-methylbut-2-en-1-yl)malonate (Example 2.33b) (3.0 mmol, 727 mg) in dry DMF (6 mL) and added this solution to the reaction vial with stirring at room temperature. After 1 hour, quenched the reaction mixture with saturated aqueous NH$_4$Cl solution (1 mL) and 6N aqueous HCl (1 mL) and diluted with water (20 mL). Extracted with EtOAc (3×5 mL). Dried over NaCl, then MgSO$_4$, filtered, and concentrated to dryness. Purified by silica gel chromatography (1-10% MeOH/DCM gradient). Gave 633 mg (94% yield). $^1$H NMR is consistent with structure. MS N/A (MH$^+$).

Example 2.33b: Diethyl 2-methyl-2-(3-methylbut-2-en-1-yl)malonate

Placed NaH (60% dispersion in mineral oil, 10.0 mmol, 400 mg) into a nitrogen-flushed vial with a stir bar and suspended in dry DMF (10 mL). Added diethyl 2-methylmalonate (10.0.0 mmol, 1705 µL) dropwise with stirring under nitrogen purge. When the reaction mixture had ceased bubbling (5 minutes), added 1-bromo-3-methylbut-2-ene (10.0 mmol, 1164 µL) via syringe and stirred at room temperature for 30 minutes. Quenched with saturated aqueous NH$_4$Cl (1 mL) and diluted with water (20 mL). Extracted with ether (1×15 mL, 2×10 mL), washed the ether extracts with water (4×5 mL), dried over NaCl, then MgSO$_4$, filtered, and concentrated to dryness. Purified by silica gel chromatography (1→10% EtOAc/hexanes gradient). Gave 2117 mg (87% yield). $^1$H NMR is consistent with structure. MS N/A (MH$^+$).

Example 2.34: 1,5-dimethyl-5-(3-methylbut-2-en-1-yl)-3-(2-oxo-2-(pyridin-3-yl)ethyl)-pyrimidine-2,4,6(1H,3H,5H)-trione The title compound was synthesized in a manner similar to Example 2.32 from 1,5-dimethyl-5-(3-methylbut-2-en-1-yl)pyrimidine-2,4,6(1H,3H,5H)-trione (Example 2.33a) (1.0 mmol, 224 mg), 2-bromo-1-(pyridin-3-yl)ethanone hydrobromide (1.0 mmol, 281 mg), and $K_2CO_3$ (2.5 mmol, 346 mg). Purified by silica gel chromatography (40-100% EtOAc/hexanes gradient). Gave 118 mg (34% yield). $^1$H NMR (400 MHz, CDCl$_3$) δ 9.22 (dd, J=2.3, 0.8 Hz, 1H), 8.85 (dd, J=4.8, 1.7 Hz, 1H), 8.26 (ddd, J=8.0, 2.3, 1.8 Hz, 1H), 7.48 (ddd, J=8.0, 4.8, 0.9 Hz, 1H), 5.33 (d, J=17.1 Hz, 1H), 5.28 (d, J=17.1 Hz, 1H), 5.07-5.00 (m, 1H), 3.31 (s, 3H), 2.73 (qd, J=13.7, 7.8 Hz, 2H), 1.71 (d, J=0.9 Hz, 3H), 1.61 (s, 3H), 1.60 (d, J=0.9 Hz, 3H). MS 344 (MH$^+$).

Example 2.35: 5-benzyl-1,5-dimethyl-3-(2-oxo-2-phenylethyl)pyrimidine-2,4,6(1H,3H,5H)-trione In a 25 mL round-bottom flask, 5-benzyl-1,5-dimethyl-3-((2-phenyl-1,3-dioxolan-2-yl)methyl)pyrimidine-2,4,6(1H,3H,5H)-trione (Example 2.35a) (20 mg, 0.049 mmol) was added to a solution of 6N HCl (2 mL) and MeOH (2 mL). The reaction mixture was heated to 90° C. for 1 hr, then concentrated and purified by prep HPLC. The desired compound (5.2 mg, 17%) was isolated as a white solid. $^1$H NMR (400 MHz, CDCl$_3$) δ 7.97-7.93 (m, 2H), 7.65-7.59 (m, 1H), 7.53-7.47 (m, 2H), 7.28-7.23 (m, 4H), 7.08-7.03 (m, 1H), 5.22 (d, J=17.1 Hz, 1H), 5.04 (d, J=17.1 Hz, 1H), 3.33 (d, J=13.0 Hz, 1H), 3.28 (d, J=13.0 Hz, 1H), 3.15 (s, 3H), 1.75 (s, 3H). MS 365 (MH$^+$).

Example 2.35a: 5-benzyl-1,5-dimethyl-3-((2-phenyl-1,3-dioxolan-2-yl)methyl)pyrimidine-2,4,6(1H,3H,5H)-trione In an oven-dried, N$_2$-flushed, small round-bottom flask, were added anhydrous DMF (3.0 mL), 5-benzyl-1-methyl-3-((2-phenyl-1,3-dioxolan-2-yl)methyl)pyrimidine-2,4,6(1H,3H,5H)-trione (Example 2.35b) (30 mg, 76 mol), and the solution was cooled to 0° C. in an ice bath. NaH (6 mg, 152 µmol), and iodomethane (10 µL, 152 µmol) were added, the ice bath was removed and the reaction medium was stirred vigorously at room temperature for 2 hr, then diluted with water and extracted with EtOAc (3×10 mL). The combined organic phases were washed with brine and dried over MgSO$_4$, and the solvent was evaporated. The residue was purified by mass-triggered HPLC to obtain the pure desired product (20 mg, 64%) as a light yellow solid. MS 409 (MH$^+$). $^1$H-NMR is consistent with the structure.

Example 2.35b: 5-benzyl-1-methyl-3-((2-phenyl-1,3-dioxolan-2-yl)methyl)pyrimidine-2,4,6(1H,3H,5H)-trione In an oven-dried, $N_2$-flushed, small round-bottom flask, were added anhydrous EtOH (5.0 mL) and sodium metal (2.5 mmol, 58 mg). After stirring for 40 min, 1-methyl-3-((2-phenyl-1,3-dioxolan-2-yl)methyl)urea (Example 2.35c) (236 mg, 1 mmol) was added followed by diethyl 2-benzylmalonate (250 mg, 1 mmol). The reaction mixture was refluxed at 100° C. for 18 hrs then quenched by $H_2O$ (1 mL). The reaction mixture was concentrated, diluted with $H_2O$ (2 mL) and acidified with 1N HCl to pH ~2. The aqueous layer was extracted with DCM (3×10 mL) and the organic layer was dried over $MgSO_4$, concentrated and purified by preparative HPLC to obtain the pure product (80 mg, 20%) as a clear colorless oil. MS 395 ($MH^+$). $^1$H-NMR was consistent with the structure.

Example 2.35c: 1-methyl-3-((2-phenyl-1,3-dioxolan-2-yl)methyl)urea

In an oven-dried, $N_2$-flushed, small round-bottom flask, were added anhydrous THF (15.0 mL), 4-nitrophenyl methylcarbamate (35 g) (1.0 g, 5.09 mmol), triethylamine (850 μL, 6.1 mmol) and (2-phenyl-1,3-dioxolan-2-yl)methanamine (Example 2.35d) (1.2 g, 6.1 mmol). The resulting reaction mixture was stirred at room temperature for 18 hrs and concentrated. The residue was treated with $H_2O$ and extracted with 20% ACN in DCM (3×20 mL). The organic layer was washed with 2N NaOH, brine, dried over $MgSO_4$ and concentrated. The desired product (1.1 g, 91%) was obtained as a white solid. MS 237 ($MH^+$). $^1$H-NMR was consistent with the structure.

Example 2.35d: (2-phenyl-1,3-dioxolan-2-yl)methanamine

In an oven-dried, 500 mL round-bottom flask, were added EtOH (300 mL), 2-((2-phenyl-1,3-dioxolan-2-yl)methyl)isoindoline-1,3-dione (Example 2.35e) (18 g, 58 mmol) and hydrazine (19 mL, 580 mmol). The resulting mixture was heated up to 80° C. for 1.5 hrs. The clear solution turned cloudy and a precipitate formed. After removal of most of the EtOH, a 30% aqueous NaOH solution was added until all solids were dissolved. The aqueous layer was extracted with $Et_2O$ (3×25 mL) and the combined organic layers were dried over $MgSO_4$ and concentrated to give desired product (10.0 g, 97%) as a light yellow solid. MS 180 ($MH^+$). $^1$H-NMR is consistent with the structure.

Example 2.35e: 2-((2-phenyl-1,3-dioxolan-2-yl)methyl)isoindoline-1,3-dione

In an oven-dried, 500 mL round-bottom flask, were added benzene (250 mL), 2-(2-oxo-2-phenylethyl)isoindoline-1,3-dione (Example 2.35 f) (24 g, 90 mmol) and ethylene glycol (46.5 mL, 900 mmol) followed by p-toluenesulfonic acid (800 mg, 4.65 mmol). The resulting mixture was heated to 110° C. for 20 hrs (with Dean Stark apparatus). The reaction mixture was cooled to room temperature and benzene was removed in vacuo. The reaction mixture was quenched with $H_2O$ and extracted with $Et_2O$ (3×200 mL). The combined organic layers were dried over $MgSO_4$ and concentrated to give the desired product (23 g, 97%) as a white solid. MS 310 ($MH^+$). $^1$H-NMR is consistent with the structure.

Example 2.35f: 2-(2-oxo-2-phenylethyl)isoindoline-1,3-dione

In an oven-dried, 500 mL round-bottom flask, were added DMF (80 mL), 2-bromo-1-phenylethanone (20 g, 100 mmol) and potassium phthalimide (18.5 g, 100 mmol) was added to the suspension in three portions. The resulting mixture was stirring at r.t for 20 hrs (with Dean Stark apparatus), cooled to room temperature and the DMF was removed in vacuo. The reaction residue was diluted with $H_2O$ and extracted with DCM (3×100 mL). The combined organic layers were dried over $MgSO_4$ and concentrated to give a light yellow solid. The solid was titrated with $Et_2O$ to give the pure product (24 g, 90%) as a white solid. MS 266 ($MH^+$). $^1$H-NMR is consistent with the structure.

Example 2.35g: 4-nitrophenyl Methylcarbamate

In an oven-dried, $N_2$-flushed, 1.0 L round-bottom flask, were added anhydrous DCM (722.0 mL), 4-nitrophenyl-chloroformate (6.0 g, 29.8 mmol), anhydrous $Na_2CO_3$ (7.3 g, 68.9 mmol), and methylamine hydrochloride (2.1 g, 30.7 mmol). The reaction medium was stirred vigorously at room temperature and under $N_2$ for 8 days. The resulting heterogeneous reaction medium was filtered and the filtrate was evaporated. The obtained residue was recrystallised from EtOH to obtain the desired product as white needles (3.95 g, 68%). $^1$H NMR (400 MHz, $d_6$-DMSO) δ 8.28-8.22 (m, 2H), 7.96-7.86 (m, 1H), 7.43-7.35 (m, 2H), 2.75-2.65 (m, 3H). MS no ionization.

Example 2.36: 5-allyl-1,5-dimethyl-3-(2-oxo-2-phenylethyl)pyrimidine-2,4,6(1H,3H,5H)-trione Anhydrous DMF (3.0 mL) and 5-allyl-1,5-dimethylpyrimidine-2,4,6(1H,3H,5H)-trione (Example 2.36a) (74 mg, 0.37 mmol) were added to an oven-dried, $N_2$-flushed, small round-bottom flask and the solution was cooled to 0° C. in an ice bath. NaH (18 mg, 0.45 mmol), and 2-bromo-1-phenylethanone (90 mg, 0.45 mmol) were added, the ice bath was removed and the reaction was stirred vigorously at room temperature for 2 hr. The reaction was quenched with water (10 mL) and extracted with DCM (3×10 mL). The combined organic phases were washed with brine and dried over $MgSO_4$, and solvents were evaporated. The residue was purified by preparative HPLC affording the desired product as a clear colorless oil (35 mg, 30%). $^1$H NMR (400 MHz, $CDCl_3$) δ 8.01-7.96 (m, 2H), 7.67-7.61 (m, 1H), 7.54-7.48 (m, 2H), 5.81-5.69 (m, 1H), 5.32 (s, 2H), 5.18-5.11 (m, 2H), 3.31 (s, 3H), 2.78-2.73 (m, 2H), 1.63 (s, 3H). MS 315 ($MH^+$).

Example 2.36a: 5-allyl-1,5-dimethylpyrimidine-2,4,6(1H,3H,5H)-trione

Anhydrous DMF (10.0 mL) and 1-methylurea (74 mg, 1 mmol) were added to an oven-dried, $N_2$-flushed, small round-bottom flask and the solution was cooled to 0° C. in an ice bath. NaH (18 mg, 0.45 mmol) was added with stirring for 10 min, then diethyl 2-allyl-2-methylmalonate (Example 2.36b) (230 mg, 1 mmol) was added. The ice bath was removed and the reaction mixture was stirred vigorously at room temperature for 2 hr, then quenched with $H_2O$. The aqueous layer was acidified by 1N HCl and extracted with DCM (3×10 mL). The combined organic phase was washed with brine, dried over $MgSO_4$, and concentrated in vacuo. The residue was purified by flash chromatography using a 12 g Silicycle column and MeOH/DCM as eluant to obtain the pure product (170 mg, 93%) as a clear oil. MS 197 (M+H+). H$^1$—NMR is consistent with the structure.

Example 2.36b: Diethyl 2-allyl-2-methylmalonate

Diethyl 2-allyl-2-methylmalonate was made from diethyl 2-methylmalonate (10.0 mmol, 1705 µL) and allyl bromide (10.0 mmol, 846 µL) in a manner similar to Example 2.37b below to afford 1798 mg (84% yield) of the pure product. $^1$H NMR was consistent with structure.

Example 2.37: (E)-5-(but-2-en-1-yl)-1,5-dimethyl-3-(2-oxo-2-phenylethyl)pyrimidine-2,4,6(1H,3H,5H)-trione Anhydrous DMF (3.0 mL) and (E)-5-(but-2-en-1-yl)-1,5-dimethylpyrimidine-2,4,6(1H,3H,5H)-trione (Example 2.37a) (20 mg, 0.1 mmol), were added to an oven-dried, N$_2$-flushed, small round-bottom flask and the solution was cooled to 0° C. in an ice bath. NaH (6 mg, 0.12 mmol), and 2-bromo-1-phenylethanone (24 mg, 0.12 mmol). were added and the ice bath was removed. The reaction mixture was stirred vigorously at room temperature for 2 hr, then quenched with H$_2$O (5 mL). The aqueous layer was extracted with DCM (3×10 mL). The combined organic phase was washed with brine, dried over MgSO$_4$, and concentrated in vacuo. The residue was purified by by mass-triggered HPLC to obtain the pure desired product (10 mg, 30%) as a clear oil. $^1$H NMR (400 MHz, CDCl$_3$) δ 8.02-7.95 (m, 2H), 7.66-7.60 (m, 1H), 7.54-7.48 (m, 2H), 5.62-5.51 (m, 1H), 5.40-5.33 (m, 1H), 5.31 (d, J=1.2 Hz, 2H), 3.31 (s, 3H), 2.70 (d, J=13.5 Hz, 1H), 2.65 (d, J=13.5 Hz, 1H), 1.68-1.63 (m, 3H), 1.59 (s, 3H). MS 329 (MH$^+$).

Example 2.37a: (E)-5-(but-2-en-1-yl)-1,5-dimethylpyrimidine-2,4,6(1H,3H,5H)-trione Anhydrous DMF (8.0 mL) and 1-methylurea (111 mg, 1.5 mmol) were added to an oven-dried, N$_2$-flushed, small round-bottom flask and the solution was cooled to 0° C. in an ice bath. NaH (18 mg, 0.45 mmol) was added with stirring for 10 min, then (E)-diethyl 2-(but-2-en-1-yl)-2-methylmalonate (Example 2.37b) (342 mg, 1.5 mmol) was added The ice bath was removed and the reaction mixture was stirred vigorously at room temperature for 18 hr, then quenched with H$_2$O. The aqueous layer was acidified by 1N HCl and extracted with DCM (3×10 mL). The combined organic phase was washed with brine, dried over MgSO$_4$, and concentrated in vacuo. The residue was purified by preparative HPLC to obtain the pure product (150 mg, 30%) as a clear colorless oil. MS 211 (MH$^+$). $^1$H-NMR is consistent with the structure.

Example 2.37b: (E)-diethyl 2-(but-2-en-1-yl)-2-methylmalonate

KOtBu (10.0 mmol, 1122 mg) was placed in a 40 mL vial flushed with nitrogen and dry DMF (10 mL) was added with stirring at room temperature for 5 minutes. Diethyl 2-methylmalonate was added via syringe and stirred at room temperature an additional 5 minutes. The reaction mixture was placed in an ice-bath and cooled to 0° C. then (E)-1-bromobut-2-ene was added via syringe and stirred at 0° C., warming slowly to room temperature overnight. The reaction was quenched with sat. aqueous NH$_4$Cl (1 mL) and water (15 mL) was added. The aqueous solution was extracted with hexanes (3×10 mL), washed with brine, then dried over MgSO$_4$, filtered, and concentrated in vacuo to afford 2008 mg of product (88% yield). $^1$H NMR is consistent with structure.

Example 2.38: 5-benzyl-1,5-dimethyl-3-(2-oxo-2-(pyridin-3-yl)ethyl)pyrimidine-2,4,6(1H,3H,5H)-trione In an oven-dried, N$_2$-flushed, small round-bottom flask, were added anhydrous DMF (15.0 mL), 5-benzyl-1,5-dimethylpyrimidine-2,4,6(1H,3H,5H)-trione (38a) (480 mg, 1.95 mmol), and the solution was cooled to 0° C. in an ice bath. NaH (86 mg, 2.1 mmol), and 2-bromo-1-(pyridin-3-yl)ethanone hydrobromide (548 mg, 1.95 mmol) were added and the ice bath was removed. The reaction mixture was stirred vigorously at room temperature for 2 hr, diluted with water (15 mL) and extracted with DCM (3×20 mL). The combined organic phase was washed with brine and dried over MgSO$_4$, and solvents were evaporated. The residue was purified by mass-triggered HPLC to give the pure product (300 mg, 42%) as a clear colorless oil. $^1$H NMR (400 MHz, CDCl$_3$) δ 9.177 (m, 1H), 8.837 (m, 1H), 8.211 (m, 1H), 7.451 (m, 1H), 7.260 (m, 3H), 7.039 (m, 3H), 5.178 (d, J=16.8 Hz, 1H), 5.014 (d, J=16.8 Hz, 1H), 3.319 (d, J=12.8 Hz, 1H), 3.265 (d, J=12.8 Hz, 1H), 3.160 (s, 3H), 1.753 (s, 3H). MS 366 (MH$^+$).

Example 2.38a: 5-benzyl-1,5-dimethylpyrimidine-2,4,6(1H,3H,5H)-trione

In an oven-dried, N$_2$-flushed, small round-bottom flask, were added anhydrous DMF (10.0 mL), 1-methylurea (280 mg, 3.78 mmol), and the solution was cooled to 0° C. in an ice bath. NaH (332 mg, 8.31 mmol) was added with stirring for 10 min, then diethyl 2-benzyl-2-methylmalonate (Example 2.38b) (1.0 g, 3.78 mmol) was added. The reaction mixture was allowed to warm to room temperature with stirring for 18 hr and then quenched by H$_2$O. The aqueous layer was acidified by 1N HCl and extracted with DCM (3×15 mL). The combined organic phase was washed with brine, dried over MgSO$_4$, and solvents were evaporated. The residue was purified by flash chromatography using a 12 g Silicycle column and MeOH/DCM as eluant to obtain the pure product (900 mg, 96%) as a clear colorless oil. MS 247 (MH$^+$). $^1$H-NMR is consistent with the structure.

Example 2.38b: Diethyl 2-benzyl-2-methylmalonate

Anhydrous DMF (20.0 mL) and diethyl 2-benzylmalonate (1.5 g, 6 mmol) were placed in an oven-dried, N$_2$-flushed, 100 mL round-bottom flask and cooled to 0° C. in an ice bath. NaH (263 mg, 6.5 mmol), and iodomethane (548 µL, 6 mmol) were added and the reaction mixture was allowed to warm to room temperature. The reaction medium was stirred vigorously at room temperature for 2 hr, quenched with water (20 mL) and extracted with DCM (3×25 mL). The combined organic phase was washed with brine, dried over MgSO$_4$, and solvents were evaporated. The residue was purified by flash chromatography using a 12 g Silicycle column and EtOAc/Hexanes as eluant to obtain the pure product (1.1 g, 69%) as a clear colorless oil. MS 265 (MH$^+$). $^1$H-NMR is consistent with the structure.

Example 2.39: 5-(3-fluorobenzyl)-1,5-dimethyl-3-(2-oxo-2-phenylethyl)pyrimidine-2,4,6(1H,3H,5H)-trione In an oven-dried, N$_2$-flushed, small round-bottom flask, were added anhydrous DMF (8.0 mL) and 5-(3-fluorobenzyl)-1,5-dimethylpyrimidine-2,4,6(1H,3H,5H)-trione (Example 2.39a) (315 mg, 1.2 mmol) and the solution was cooled to 0° C. in an ice bath. NaH (53 mg, 1.32 mmol), and 2-bromo-1-phenylethanone (262 mg, 1.32 mmol) were added and the ice bath was removed. The reaction medium was stirred vigorously at room temperature for 2 hr, quenched with water (10 mL) and extracted with DCM (3×10 mL). The combined organic phase was washed with brine and dried over MgSO$_4$, and solvents were evaporated. The residue was purified by prep HPLC to give the pure product (302 mg, 65%) as a clear colorless oil. $^1$H NMR (400 MHz, CDCl$_3$) δ 7.94 (m, 2H), 7.61 (m, 1H), 7.49 (m, 2H), 7.201 (m, 1H), 6.95 (m, 1H), 6.79-6.87 (m, 2H), 5.22 (d, J=16.8 Hz, 1H), 5.09 (d, J=16.8 Hz, 1H), 3.32 (d, J=13.2 Hz, 1H), 3.19 (d, J=13.2 Hz, 1H), 3.19 (s, 3H), 1.75 (s, 3H). MS 383 (MH$^+$).

Example 2.39a: 5-(3-fluorobenzyl)-1,5-dimethylpyrimidine-2,4,6(1H,3H,5H)-trione

Anhydrous DMF (8.0 mL) and 1-methylurea (160 mg, 2.1 mmol) were placed in an oven-dried, N$_2$-flushed, small round-bottom flask and cooled to 0° C. in an ice bath. NaH (157 mg, 3.92 mmol) was added and stirred for 10 min, then dimethyl 2-(3-fluorobenzyl)-2-methylmalonate (Example 2.39b) (1.0 g, 3.78 mmol) was added. The reaction medium was stirred vigorously at room temperature for 18 hr, then quenched by H$_2$O (10 mL). The aqueous layer was acidified by 1N HCl, and extracted with DCM (3×10 mL). The combined organic phases were washed with brine and dried over MgSO$_4$, and solvents were evaporated. The residue was purified by flash chromatography using a 12 g Silicycle column and MeOH/DCM as eluant to obtain the pure product (400 mg, 40%) as a clear oil. MS 265 (MH$^+$). $^1$H-NMR is consistent with the structure.

Example 2.39b: Dimethyl 2-(3-fluorobenzyl)-2-methylmalonate

Anhydrous DMF (10.0 mL) and dimethyl 2-methylmalonate (1.0 g, 6.8 mmol), were placed in an oven-dried, N$_2$-flushed, small round-bottom flask and cooled to 0° C. in an ice bath. NaH (272 mg, 6.8 mmol) was added then 1-(bromomethyl)-3-fluorobenzene (823 μL, 6.8 mmol). The reaction medium was stirred vigorously at room temperature for 24 hr, then quenched by H$_2$O (10 mL) and extracted with DCM (3×10 mL). The combined organic phases were washed with brine and dried over MgSO$_4$, and solvents were evaporated. The residue was purified by flash chromatography using a 12 g Silicycle column and EtOAc/Hex as eluant to obtain the pure product (1.6 g, 93%) as a clear oil. MS 255 (MH$^+$). $^1$H-NMR is consistent with the structure.

Example 2.40: 5-(4-fluorobenzyl)-1,5-dimethyl-3-(2-oxo-2-phenylethyl)pyrimidine-2,4,6(1H,3H,5H)-trione Prepared in a similar manner to Example 2.39 starting with 5-(4-fluorobenzyl)-1,5-dimethylpyrimidine-2,4,6(1H,3H,5H)-trione (Example 2.40a) (157 mg, 0.6 mmol), and 2-bromo-1-phenylethanone (142 mg, 0.7 mmol) to obtain the desired product (165 mg, 72%) as a clear colorless oil. $^1$H NMR (400 MHz, CDCl$_3$) δ 7.94 (m, 2H), 7.61 (m, 1H), 7.49 (m, 2H), 7.04 (m, 2H), 6.93 (m, 2H), 5.20 (d, J=17.2 Hz, 1H), 5.09 (d, J=17.2 Hz, 1H), 3.26 (d, J=13.6 Hz, 1H), 3.30 (d, J=13.6 Hz, 1H), 3.18 (s, 3H), 1.74 (s, 3H). MS 383 (MH$^+$). MS 383 (MH$^+$).

Example 2.40a: 5-(4-fluorobenzyl)-1,5-dimethylpyrimidine-2,4,6(1H,3H,5H)-trione

Prepared in a similar manner to Example 2.39a starting with dimethyl 2-(4-fluorobenzyl)-2-methylmalonate (Example 2.40b) (500 mg, 1.96 mmol) to obtain the pure product (385 mg, 74%) as a clear oil. MS 265 (MH$^+$). $^1$H-NMR is consistent with the structure.

Example 2.40b: Dimethyl 2-(4-fluorobenzyl)-2-methylmalonate

Prepared in a similar manner to Example 2.39b starting with dimethyl 2-(4-fluorobenzyl)malonate (1.0 g, 4.1 mmol) to obtain the pure product (800 mg, 77%) as a clear oil. MS 255 (MH$^+$). $^1$H-NMR is consistent with the structure.

Example 2.41: 2-(5-(cyclohex-1-en-1-yl)-3,5-dimethyl-2,4,6-trioxotetrahydropyrimidin-1(2H)-yl)-N-phenylacetamide 5-(Cyclohex-1-en-1-yl)-1,5-dimethylpyrimidine-2,4,6(1H,3H,5H)-trione (Example 2.8a) (500 μmol, 118 mg) was placed in a vial with dry DMF (5 mL). K$_2$CO$_3$ (750 μmol, 104 mg), was added and the reaction was stirred for 1 minute at room temperature. 2-chloro-N-phenylacetamide (550 μmol, 93 mg) was added and stirred at room temperature for 2 hours, then diluted with water (30 mL) and stirred to precipitate the product. The precipitate was collected by filtration, washed with water, and dissolved in DCM (10 mL). The solution was dried with NaCl, then MgSO$_4$, filtered, and concentrated in vacuo. Purification by silica gel chromatography (10→60% EtOAc/hexanes gradient) gave 166 mg (90% yield). $^1$H NMR (400 MHz, d$_6$-DMSO) δ 10.22 (s, 1H), 7.55-7.49 (m, 2H), 7.33-7.26 (m, 2H), 7.07-7.01 (m, 1H), 5.79-5.74 (m, 1H), 4.62 (d, J=16.2 Hz, 1H), 4.48 (d, J=16.2 Hz, 1H), 3.16 (s, 3H), 2.06-1.89 (m, 3H), 1.86-1.75 (m, 1H), 1.51 (s, 3H), 1.60-1.38 (m, 4H). MS 370 (MH$^+$).

Example 2.42: 5-((1S,4R)-bicyclo[2.2.1]heptan-2-yl)-1,5-dimethyl-3-(2-oxo-2-phenylethyl) imidazolidine-2,4-dione To an oven dried, N$_2$-flushed, small round bottom flask was added 5-bicyclo[2.2.1]heptan-2-yl)-5-methyl-3-(2-oxo-2-phenylethyl)imidazolidine-2,4-dione (Example 2.42a) (0.89 g, 2.70 mmol), Cs$_2$CO$_3$ (1.30 g, 4.0 mmol), 3 mL anhydrous DMF and methyl iodide (0.460 g, 3.2 mmol). The reaction mixture was stirred vigorously at ambient temperature for 24 hours where it was diluted with 50 mL ethyl acetate and washed with water (2×50 mL), brine (1×50 mL) and dried with Na$_2$SO$_4$. The solvent was evaporated and the residue purified by column chromatography utilizing an 80 g Silicycle column and elution with 0-40% ethyl acetate/hexanes to afford a mixture of diastereomers. The diastereomers were separated by HPLC utilizing a 40 minute method to afford the title compound (0.147 g) as a semi-solid. The residue was concentrated from EtOH 3× and dried on the lyophilizer for 48 h to afford the title compound as a white solid. $^1$H-NMR (400 MHz, DMSO-d$_6$) δ 8.05-8.03 (m, 2H), 7.74-7.70 (m, 1H), 7.59-7.56 (m, 2H), 4.97 (s, 2H), 2.81 (s, 3H), 2.39-2.37 (m, 1H), 2.18-2.16 (m, 1H), 1.85-1.80 (m, 1H), 1.50-1.47 (m, 2H), 1.44 (s, 3H), 1.38-1.32 (m, 1H), 1.27-1.13 (m, 4H), 1.02-0.99 (m, 1H); MS 341 (MH$^+$).

Example 2.42a: 5-bicyclo[2.2.1]heptan-2-yl)-5-methyl-3-(2-oxo-2-phenylethyl)imidazolidine-2,4-dione To an oven dried, $N_2$-flushed, small round bottom flask was added 5-bicyclo[2.2.1]heptan-2-yl)-5-methylimidazolidine-2,4-dione (Example 2.42b) (1.7 g, 8.31 mmol), 10 mL DMF, $K_2CO_3$ (1.72 g, 12.5 mmol) and bromoacetophenone (1.65 g, 8.31 mmol). The flask was sealed and the reaction mixture was stirred at ambient temperature for 18 hrs. The reaction was quenched with water (25 mL) and extracted with EtOAc (3×20 mL). The organic layers were combined, washed with water (40 mL), brine (40 mL), and dried over $Na_2SO_4$. Solvent was evaporated, and the resulting residue was purified by column chromatography utilizing a Silicycle column (40 g) and elution with 10%-40% ethyl acetate/hexanes. The title compound was isolated 1.9 g (71%) as a mixture of diastereomers. $^1$H-NMR (400 MHz, DMSO-d$_6$) δ 8.4 (s, 1H), 8.37 (s, 1H), 8.07-8.02 (m, 4H), 7.74-7.69 (m, 2H), 7.60-7.55 (m, 4H), 4.94 (s, 2H), 4.91 (s, 2H), 2.28-2.26 (m, 1H), 2.21-2.18 (m, 2H), 2.12-2.10 (m, 1H), 1.77-1.70 (m, 2H), 1.50-1.34 (m, 12H), 1.27-1.21 (m, 5H), 1.13-0.99 (m, 5H); MS 327 (MH$^+$).

Example 2.42b: 5-bicyclo[2.2.1]heptan-2-yl)-5-methylimidazolidine-2,4-dione

To a 150 mL pressure tube, were added $H_2O$ (30 mL), commercially available 1-bicyclo[2.2.1]hept-2-ylethanone (5.3 g, 38.4 mmol) in MeOH (50 mL), $(NH_4)_2CO_3$ (11.4 g, 119.1 mmol), and KCN (2.75 g, 42.3 mmol) in $H_2O$ (10 mL) drop-wise over 5 minutes. The tube was sealed and heated at 55° C. for 24 hours. The reaction medium was allowed to cool to room temperature. 20 mL $H_2O$ was added and the reaction was cooled to 0° C. for two hours. The white precipitate was filtered and washed with cold $H_2O$ and dried to obtain the title compound 8.0 g (quantitative) as a white crystalline solid consisting of two diastereomers. $^1$H NMR (400 MHz, DMSO-d$_6$) δ 10.5 (br s, 2H), 7.92-7.87 (m, 2H), 2.17-2.15 (m, 3H), 1.77-1.76 (m, 1H), 1.67-1.59 (m, 2H), 1.47-1.34 (m, 8H), 1.25 (s, 3H), 1.21-1.18 (m, 2H), 1.13-1.05 (m, 7H), 1.01-0.96 (m, 2H); MS 209 (MH$^+$).

Example 2.43: 5-cyclohexyl-3-(2-(3-hydroxyphenyl)-2-oxoethyl)-1,5-dimethylimidazolidine-2,4-dione In an oven-dried, $N_2$-flushed, small round-bottom flask, were added anhydrous DMF (6.0 mL), 5-cyclohexyl-1,5-dimethylimidazolidine-2,4-dione (47a) (199.9 mg, 951 mol), NaH (40.0 mg, 1000 mol), and after about 10 minutes vigorous stirring 2-bromo-1-(3-hydroxyphenyl)ethanone (225.0 mg, 1047 μmol). The reaction medium was stirred vigorously overnight, diluted with water and extracted with excess EtOAc (3×). The combined organic phases were washed with brine and dried over MgSO$_4$, and solvents were evaporated. The residue was diluted in a minimum amount of MeOH was purified by preparative HPLC using a 40 minutes $CH_3CN/H_2O$ gradient as eluant to obtain the pure desired product (148.0 mg, 45%). $^1$H NMR (400 MHz, d$_6$-DMSO) δ 9.91 (s, 1H), 7.53-7.46 (m, 1H), 7.37 (t, J=7.9 Hz, 1H), 7.33-7.31 (m, 1H), 7.11-7.07 (m, 1H), 4.87 (d, J=0.9 Hz, 2H), 2.81 (s, 3H), 1.79-1.66 (m, 4H), 1.66-1.56 (m, 2H), 1.38 (s, 3H), 1.37-1.28 (m, 1H), 1.26-1.11 (m, 2H), 1.11-0.86 (m, 2H). MS 345 (MH$^+$).

Example 2.44: 5-cyclopentyl-1,5-dimethyl-3-(2-oxo-2-phenylethyl)imidazolidine-2,4-dione In an oven-dried, $N_2$-flushed, small round-bottom flask, were added anhydrous DMF (3.3 mL), 5-cyclopentyl-5-methyl-3-(2-oxo-2-phenylethyl)imidazolidine-2,4-dione (Example 2.44a) (102.7 mg, 342 μmol), $K_2CO_3$ (58.0 mg, 420 mol), and MeI (100 μL, 1606 μmol). The reaction medium was stirred vigorously at room temperature for 21 hours, diluted with water and extracted with EtOAc (3×). The combined organic phases were washed with brine and dried over MgSO$_4$, and solvents were evaporated. The residue was purified by preparative HPLC using a $CH_3CN/H_2O$ gradient as eluant to obtain the pure desired product (38 mg, 36%) as an oily film. $^1$H NMR (400 MHz, DMSO-d$_6$) δ 8.05-8.03 (m, 2H), 7.73-7.69 (m, 1H), 7.59-7.56 (m, 2H), 4.97 (s, 2H), 2.84 (s, 3H), 2.35-2.31 (m, 1H), 1.85-1.73 (m, 1H), 1.68-1.46 (m, 6H), 1.42 (s, 3H), 1.34-1.24 (m, 1H). MS 315 (MH$^+$).

Example 2.44a: 5-cyclopentyl-5-methyl-3-(2-oxo-2-phenylethyl)imidazolidine-2,4-dione In an oven-dried, $N_2$-flushed, small round-bottom flask, were added anhydrous DMF (20.0 mL), 5-cyclopentyl-5-methylimidazolidine-2,4-dione (Example 2.44b) (1.0 g, 5.5 mmol), $K_2CO_3$ (925 mg, 6.7 mmol), and 2-bromo-1-phenylethanone (1.15 g, 5.8 mmol). The reaction medium was stirred vigorously at room temperature for 19 hours, diluted with water and extracted with EtOAc (3×25 mL). The combined organic phases were washed with brine and dried over MgSO$_4$, and solvents were evaporated. The residue was purified by flash chromatography using a 120 g Silicycle column and a Hexanes/EtOAc gradient as eluant to obtain the pure desired product (1.1 g, 67%) as a white powder. $^1$H NMR (400 MHz, DMSO-d$_6$) δ 8.41 (s, 1H), 8.04-8.02 (m, 2H), 7.71-7.68 (m, 1H), 7.58-7.54 (m, 2H), 4.90 (s, 2H), 2.22-2.14 (m, 1H), 1.76-1.72 (m, 1H), 1.62-1.45 (m, 5H), 1.43-1.28 (m, 2H), 1.35 (s, 3H). MS 301 (MH$^+$).

Example 2.44b: 5-cyclopentyl-5-methylimidazolidine-2,4-dione

In a $N_2$-flushed 150 mL pressure tube, were added $H_2O$ (32 mL), 1-cyclopentylethanone (3.0 g, 26.7 mmol) in MeOH (40 mL), $(NH_4)_2CO_3$ (8 g, 82.9 mmol), and KCN (1.44 g, 29.4 mmol) in $H_2O$ (10 mL) was added dropwise over a few minutes. The tube was sealed and heated at 50° C. for 50 hours. The reaction medium was allowed to cool down and the obtained white precipitate was filtered and washed with a little cold $H_2O$ and dried to obtain a first crop of the desired pure product (2.81 g, 58%). Further precipitate formed in the mother liquors and was filtered and washed as above to obtain a second crop of pure desired compound (716 mg, 14.7%). $^1$H NMR (400 MHz, DMSO-d$_6$) δ 10.50 (s, 1H), 7.96 (s, 1H), 2.11-2.02 (m, 1H), 1.72-1.66 (m, 1H), 1.56-1.41 (m, 5H), 1.33-1.24 (m, 1H), 1.24 (s, 3H), 1.16-1.08 (m, 1H). MS 183 (MH$^+$).

Example 2.45: 5-cyclopentyl-1,5-dimethyl-3-(2-oxo-2-(pyridin-3-yl)ethyl)imidazolidine-2,4-dione In an oven-dried, $N_2$-flushed, small round-bottom flask, were added anhydrous DMF (3.0 mL), 5-cyclopentyl-1,5-dimethylimidazolidine-2,4-dione (Example 2.45a) (65.7 mg, 335 μmol), and at 0° C. NaH (38.0 mg, 950 mol), and 2-bromo-1-(pyridin-3-yl)ethanone hydrobromide (119 mg, 424 mol). The reaction medium was stirred vigorously at room temperature overnight, diluted with water and extracted with EtOAc (3×10 mL). Combined organic phases were washed with brine and dried over MgSO$_4$, and solvents were evaporated. The residue was purified by flash chromatography using a 12 g Silicycle column and a DCM/EtOAc gradient as eluant to obtain the pure product (63.8 mg, 60%) as an oily film. $^1$H NMR (400 MHz, CDCl$_3$) δ 9.21 (s, br, 1H), 8.85 (s, br, 1H), 8.32 (s, br, 1H), 7.54 (s, br, 1H), 4.92 (s, 2H), 2.94 (s, 3H), 2.32-2.25 (m, 1H), 1.93-1.55 (m, 7H), 1.52 (s, 3H), 1.44-1.34 (m, 1H). MS 316 (MH$^+$).

Example 2.45a: 5-cyclopentyl-1,5-dimethylimidazolidine-2,4-dione

In a N$_2$-flushed round-bottom flask, were added anhydrous CH$_3$CN (7.7 mL), 5-cyclopentyl-3-(4-methoxybenzyl)-1,5-dimethylimidazolidine-2,4-dione (Example 2.45b) (243.4 mg, 769 μmol), and at 0° C. an ice-cooled solution of ammonium cerium IV nitrate (886.0 mg, 1616 mol) in H$_2$O (4.6 mL) was added dropwise. The reaction medium was monitored by TLC, stirred vigorously at room temperature overnight, diluted with brine and extracted with EtOAc (3×15 mL). The combined organic phases were washed again with brine and dried over MgSO$_4$, and solvents were evaporated. The residue was purified by flash chromatography using a 40 g Silicycle column and a Hexanes/EtOAc gradient as eluant to obtain the pure desired product (72.1 mg, 48%). $^1$H NMR (400 MHz, DMSO-d$_6$) δ 10.78 (s, 1H), 2.72 (s, 3H), 2.26-2.18 (m, 1H), 1.74-1.66 (m, 1H), 1.63-1.45 (m, 6H), 1.31 (s, 3H), 1.09-1.01 (m, 1H). MS 197 (MH$^+$).

Example 2.45b: 5-cyclopentyl-3-(4-methoxybenzyl)-1,5-dimethylimidazolidine-2,4-dione In an oven-dried, N$_2$-flushed, small round-bottom flask, were added anhydrous DMF (4.0 mL), 5-cyclopentyl-3-(4-methoxybenzyl)-5-methylimidazolidine-2,4-dione (Example 2.45c) (287.5 mg, 951 μmol), and NaH (49.0 mg, 1225 mol), and MeI (100 μL, 1606 μmol). The reaction medium was stirred vigorously at room temperature overnight, then diluted with water and extracted with EtOAc (3×10 mL). The combined organic phases were washed with brine and dried over MgSO$_4$, and solvents were evaporated. The residue was purified by flash chromatography using a 40 g Silicycle column and a Hexanes/EtOAc gradient as eluant to obtain the pure desired product (253.6 mg, 84%). $^1$H NMR (400 MHz, CDCl$_3$) δ 7.32 (d, J=8.0, 2H), 6.82 (d, J=8.4, 2H), 4.58 (s, 2H), 3.78 (s, 3H), 2.86 (s, 3H), 2.25-2.16 (m, 1H), 1.79-1.72 (m, 1H), 1.65-1.43 (m, 6H), 1.37 (s, 3H), 1.01-0.92 (m, 1H). MS 317 (MH$^+$).

Example 2.45c: 5-cyclopentyl-3-(4-methoxybenzyl)-5-methylimidazolidine-2,4-dione In an oven-dried, N$_2$-flushed, small round-bottom flask, were added anhydrous DMF (4.0 mL), 5-cyclopentyl-5-methylimidazolidine-2,4-dione (Example 2.44b) (200 mg, 1.10 mmol), K$_2$CO$_3$ (232 mg, 1.68 mmol), KI (18 mg, 0.11 mmol) and 1-(bromomethyl)-4-methoxybenzene (240 μL, 1.67 mmol). The reaction medium was stirred vigorously at room temperature overnight, diluted with water and extracted with EtOAc (3×10 mL). The combined organic phases were washed with brine and dried over MgSO$_4$, and solvents were evaporated. The residue was purified by flash chromatography using a 40 g Silicycle column and a Hexanes/EtOAc gradient as eluant to obtain the pure desired product (287.5 mg, 87%). $^1$H NMR (400 MHz, CDCl$_3$) δ 7.32 (d, J=8.4, 2H), 6.83 (d, J=8.4, 2H), 4.57 (s, 2H), 3.79 (s, 3H), 2.28-2.19 (m, 1H), 1.85-1.78 (m, 1H), 1.64-1.40 (m, 6H), 1.40 (s, 3H), 1.13-1.04 (m, 1H). MS 303 (MH$^+$).

Example 2.46: 1,5-dimethyl-5-(2-methylbenzyl)-3-(2-oxo-2-phenylethyl)imidazolidine-2,4-dione Prepared in a similar manner as described in Example 2.45 starting from 1,5-dimethyl-5-(2-methylbenzyl)imidazolidine-2,4-dione (Example 2.46a) (0.075 g, 0.33 mmol), and 2-bromo-1-phenylethanone (0.063 g, 0.33 mmol), to obtain the pure desired product as a white solid (80 mg, 70%). $^1$H NMR (400 MHz, DMSO-d$_6$) δ 8.01-7.99 (m, 2H), 7.71-7.67 (m, 1H), 7.14-7.08 (m, 3H), 7.03-7.00 (m, 1H), 4.78 (s, 2H), 3.14 (d, J=14.6 Hz, 1H), 3.05 (d, J=14.6 Hz, 1H), 2.90 (s, 3H), 2.28 (s, 3H) 1.54 (s, 3H); MS 351 (MH$^+$).

Example 2.46a: 1,5-dimethyl-5-(2-methylbenzyl)imidazolidine-2,4-dione

Prepared in a similar manner as described in Example 2.45a starting from 3-(4-methoxybenzyl)-1,5-dimethyl-5-(2-methylbenzyl)imidazolidine-2,4-dione (Example 2.46b) (0.47 g, 1.33 mmol) in 5 mL CH$_3$CN and CAN (1.9 g, 3.46 mmol) in 1 mL H$_2$O, to obtain the pure desired product as a beige solid (256 mg, 80%). $^1$H NMR (400 MHz, DMSO-d$_6$) δ 10.5 (s, 1H), 7.13-7.05 (m, 3H), 6.93-6.91 (m, 1H), 3.01 (d, J=14.5 Hz, 1H), 2.93 (d, J=14.5 Hz, 1H), 2.83 (s, 3H), 2.28 (s, 3H), 1.42 (s, 3H); MS 233 (MH$^+$).

Example 2.46b: 3-(4-methoxybenzyl)-1,5-dimethyl-5-(2-methylbenzyl)imidazolidine-2,4-dione To a solution of 3-(4-methoxybenzyl)-5-(2-methylbenzyl)imidazolidine-2,4-dione (Example 2.46c) (0.89 g, 2.74 mmol) in 7 mL DMF was added NaH (0.30 g, 8.23 mmol). The mixture was stirred for 0.5 h at ambient temperature then methyl iodide (0.7 mL, 10.94 mmol) was added neat via syringe. The reaction was stirred for 12 h at ambient temperature when it was determined to be complete by LCMS. The mixture was diluted with 25 mL H$_2$O and extracted with ethyl acetate (3×10 mL). The combined organic phases were washed with H$_2$O (1×10 mL), and brine (1×10 mL) and dried with Na$_2$SO$_4$ and the solvent was removed. The compound was dissolved in a minimum amount of DCM and loaded onto a 40 g Silicycle column purged with hexanes. A gradient from 0 to 70% ethyl acetate:hexanes was run to afford the desired product as a yellow oil (0.70 g, 73%). $^1$H NMR (400 MHz, DMSO-d$_6$) δ 7.15-7.07 (m, 2H), 7.00-6.96 (m, 1H), 6.85-6.83 (m, 1H), 6.86-6.66 (m, 2H), 6.55-6.53 (m, 2H), 4.32 (d, J=15.4 Hz, 1H), 4.20 (d, J=15.4 Hz, 1H), 3.70 (s, 3H), 3.08 (d, J=14.6 Hz, 1H), 3.00 (d, J=14.6 Hz, 1H), 2.93 (s, 3H), 2.24 (s, 3H), 1.47 (s, 3H); MS 353 (MH$^+$).

Example 2.46c: 3-(4-methoxybenzyl)-5-(2-methylbenzyl)imidazolidine-2,4-dione

To a suspension of (S)-5-(2-methylbenzyl)imidazolidine-2,4-dione (Example 2.46d) (0.73 g, 3.6 mmol) and K$_2$CO$_3$ (0.54 g, 3.9 mmol) in 2 mL DMF was added 1-(chloromethyl)-4-methoxybenzene (0.53 mL, 3.9 mmol). The reaction was stirred for 12 h at ambient temperature where it was determined to be complete by TLC. 10 mL H$_2$O was added with stirring and the white precipitate was collected by vacuum filtration to afford the desired product (0.9 g, 77%). ¹H NMR (400 MHz, DMSO-d₆) δ 8.30 (s, 1H), 7.14-7.11 (m, 3H), 7.08-7.03 (m, 1H), 6.93-6.90 (m, 2H), 6.81-6.77 (m, 2H), 4.45-4.31 (m, 3H), 3.72 (s, 3H), 3.04 (dd, J=14.4, 4.7 Hz, 1H), 2.93 (dd, J=14.4, 6.3 Hz, 1H), 2.27 (s, 3H); MS 325 (MH⁺).

Example 2.46d:
(S)-5-(2-methylbenzyl)imidazolidine-2,4-dione

To a 50 mL round bottom flask was added (S)-2-amino-3-(o-tolyl)propanoic acid (0.94 g, 5.30 mmol). 2M HCl (2.65 mL, 5.3 mmol) was added followed by 8 mL H₂O. The mixture was stirred with gentle heating until homogeneous. KOCN was added portion-wise as a solid. Stir at reflux for 2 h. Cool to room temperature and add concentrated HCl until the pH is approximately 2. Stir the suspension at reflux for 3 h. The reaction was cooled to room temperature and the precipitate was filtered and dried to afford the desired product as an off white solid (0.73 g, 67%). ¹H NMR (400 MHz, DMSO-d₆) δ 10.54 (s, 1H), 7.92 (s, 1H), 7.17-7.09 (m, 4H), 4.32-4.29 (m, 1H), 3.01 (dd, J=14.4, 4.7 Hz, 1H), 2.86 (dd, J=14.4, 6.9 Hz, 1H), 2.28 (s, 3H).

Example 2.47: 5-cyclohexyl-1,5-dimethyl-3-(2-oxo-2-phenylethyl)imidazolidine-2,4-dione Prepared in a similar manner as described in Example 2.44 starting from 5-cyclohexyl-1,5-dimethylimidazolidine-2,4-dione (230 mg, 1.09 mmol) (Example 2.47a) and 2-bromo-1-phenylethanone (258 mg, 1.30 mmol) to obtain the desired product (75 mg, 21%) as a white solid. ¹H NMR (400 MHz, DMSO-d₆) δ 7.95 (d, J=8 Hz, 2H), 7.49 (t, J=4 Hz, 2H), 8.30 (m, 2H), 4.91 (s, 2H), 2.91 (s, 3H), 1.66 (m, =7H), 1.46 (s, 3H), 1.04 (m, 4H). MS 329 (MH⁺).

Example 2.47a:
5-cyclohexyl-1,5-dimethylimidazolidine-2,4-dione

Prepared in a similar manner as described in Example 2.45a starting from 5-cyclohexyl-3-(4-methoxybenzyl)-1,5-dimethylimidazolidine-2,4-dione (12.4 mmol, 4.1 g) (Example 2.47b) and a solution of ammonium cerium nitrate (17.6 g, 32.2 mmol) in water (92 mL) to obtain the desired product (2.1 g, 80%) as a light brown solid. ¹H NMR (400 MHz, DMSO-d₆) δ 8.79 (s, 1H), 2.03 (s, 3H), 1.59 (m, 6H), 1.40 (s, 3H), 0.88 (m, 5H). MS 211 (MH⁺).

Example 2.47b: 5-cyclohexyl-3-(4-methoxybenzyl)-1,5-dimethylimidazolidine-2,4-dione Prepared in a similar manner as described in Example 2.45b starting from 5-cyclohexyl-3-(4-methoxybenzyl)-5-methylimidazolidine-2,4-dione (Example 2.47c) (16 mmol, 5 g) and MeI (18.9 mmol, 1.17 mL) to obtain the desired product (4.5 g, 85%). ¹H NMR is consistent with the structure. MS 331 (MH⁺).

Example 2.47c: 5-cyclohexyl-3-(4-methoxybenzyl)-5-methylimidazolidine-2,4-dione

Prepared in a similar manner as described in Example 2.46c starting from 5-cyclohexyl-5-methylimidazolidine-2,4-dione (3.8 g, 19.3 mmol) (Example 2.47d) and para-methoxyl benzyl chloride (3.2 mL, 23.6 mmol) to obtain the desired product (6 g, 98%) as a clear oil. ¹H NMR (400 MHz, DMSO-d₆) δ 7.30 (d, J=2H), 6.82 (d, 2H), 5.39 (s, 1H), 4.56 (s, 2H), 3.78 (s, 3H), 1.60 (m, 5H), 1.35 (s, 3H), 0.80 (s, 6H). MS 317 (MH⁺).

Example 2.47d:
5-cyclohexyl-5-methylimidazolidine-2,4-dione

Prepared in a similar manner as described in Example 2.44b starting from 1-cyclohexylethanone (3 g, 23.8 mmol), (NH₄)₂CO₃ (7.1 g, 73.9 mmol), and KCN (1.28 g, 26.1 mmol) to obtain the desired product (3.5 g, 75%) as a white solid. ¹H NMR (400 MHz, DMSO-d₆) δ 10.53 (s, 1H), 7.89 (s, 1H), 1.75-1.58 (m, 4H), 1.50-1.38 (m, 2H), 1.21 (s, 3H), 1.19-1.11 (m, =2H), 1.08-0.90 (m, 3H). MS 197 (MH⁺).

Example 2.48: 5-((1S,4R)-bicyclo[2.2.1]heptan-2-yl)-1,5-dimethyl-3-(2-oxo-2-(1H-pyrrol-2-yl)ethyl)imidazolidine-2,4-dione To an oven dried, N₂-flushed, small round bottom flask was added 5-bicyclo[2.2.1]heptan-2-yl)-1,5-dimethylimidazolidine-2,4-dione (Example 2.54a) (1.04 g, 4.70 mmol), K₂CO₃ (0.97 g, 7.00 mmol), and 5 mL DMF. The suspension was stirred at ambient temperature, and 2-bromo-1-(1H-pyrrol-2-yl)ethanone (Example 2.48a) (0.88 g, 7.70 mmol) was added as a solid. The reaction was stirred for 3 hours when it was determined to be complete by LCMS. 15 mL water was added and the mixture was extracted with ethyl acetate (3×15 mL). The combined organic layers were washed with water (1×30 mL), brine (1×30 mL) and dried with Na₂SO₄. The solvent was removed and the residue was concentrated into a 40 mL vial. The vial contained approximately 1 gram of crude material. The residue was dissolved in a total of 20 mL of acetonitrile and water and purified by HPLC utilizing a 40 minute method to afford the title compound (0.085 g) as a white solid. The residue was concentrated from ethanol 3 times. Two diastereomers separated during chromatography. The first compound to elute, shown here, is the most potent. ¹H-NMR (400 MHz, DMSO-d₆) δ 12.04 (s, 1H) 7.19-7.16 (m, 2H), 6.26-6.24 (m, 1H), 4.68 (s, 2H), 2.80 (s, 3H), 2.40 (s, 1H), 2.14 (s, 1H), 1.84-1.80 (m, 1H), 1.49-1.47 (m, 2H), 1.42 (s, 3H), 1.33-1.31 (m, 2H), 1.27-1.25 (m, 1H), 1.16-1.13 (m, 2H), 1.00-0.98 (m, 1H); MS 330 (MH⁺).

Example 2.48a:
2-bromo-1-(1H-pyrrol-2-yl)ethanone

To a solution of bromoacetyl bromide (5 mL, 56.4 mmol) in 150 mL chloroform was added a solution of pyrolle (2.6 mL, 37.5 mmol) and 2,6-lutidine (9 mL, 75 mmol) in 40 mL chloroform via addition funnel. The reaction was stirred for 24 h at ambient temperature. The reaction was washed with 1 M HCl (1×100 mL) and saturated sodium bicarbonate (1×100 mL) and dried with Na₂SO₄. The solvent was evaporated and the residue was purified by column chromatography utilizing a Silicycle column (120 g) and elution with DCM. The title compound was isolated 2.7 g (25%) as a dark grey solid. ¹H-NMR (400 MHz, DMSO-d₆) δ 12.03 (s, 1H), 7.19-7.15 (m, 2H), 6.25-6.23 (m, 1H), 4.54 (s, 2H).

Example 2.49: 5-cyclohexyl-3-(2-(3,5-dihydroxyphenyl)-2-oxoethyl)-1,5-dimethyl-imidazolidine-2,4-dione Prepared in a similar manner to Example 2.43 using 5-cyclohexyl-1,5-dimethylimidazolidine-2,4-dione (47a) (100.0 mg, 476 mol), and 2-bromo-1-(3,5-dihydroxyphenyl)

ethanone (Example 2.49a) (124 mg, 537 mol), to obtain the desired product (61.9 mg, 36%). $^1$H NMR (400 MHz, d$_6$-DMSO) δ 9.78 (s, 2H), 6.82 (d, J=2.2 Hz, 2H), 6.52 (t, J=2.2 Hz, 1H), 4.80 (d, J=18.2 Hz, 1H), 4.75 (d, J=18.1 Hz, 1H), 2.81 (s, 3H), 1.79-1.65 (m, 4H), 1.65-1.56 (m, 2H), 1.37 (s, 3H), 1.36-1.27 (m, 1H), 1.26-1.12 (m, 2H), 1.11-1.01 (m, 1H), 0.98-0.86 (m, 1H). MS 361 (MH$^+$).

Example 2.49a: 2-bromo-1-(3,5-dihydroxyphenyl)ethanone

Copper bromide (3.17 g, 13.5 mmol) was suspended in EtOAc (26 mL) and commercially available 1-(3,5-dihydroxyphenyl)ethanone (1.0 g, 6.6 mmol) dissolved in DCM (12 mL) was added. The reaction medium was heated at 70° C. for 16 hours and filtered hot through a celite pad further washed with EtOAc. Solvents were evaporated and the brown residue was purified by flash-chromatography using a Silicycle column (80 g) and a DCM/EtOAc gradient as eluant, to obtain after evaporation of solvents and drying the desired product (896.1 mg, 59%). $^1$H NMR (400 MHz, d$_6$-DMSO) δ 6.82 (d, J=2.2 Hz, 2H), 6.49 (t, J=2.2 Hz, 1H), 5.76 (s, 2H), 4.80 (s, 2H). MS no ionization.

Example 2.50: 3-(2-(3-aminophenyl)-2-oxoethyl)-5-cyclohexyl-1,5-dimethylimidazolidine-2,4-dione In a small round-bottom flask flushed with N$_2$, were added 5-cyclohexyl-1,5-dimethyl-3-(2-(3-nitrophenyl)-2-oxoethyl)imidazolidine-2,4-dione (Example 2.50a) (100.0 mg, 268 mol) in EtOH/H$_2$O (1.1 mL/1.1 mL) followed by NH$_4$Cl (100.0 mg, 1.87 mmol) and iron powder (200.0 mg, 3.58 mmol). The reaction medium was refluxed for 2 hours, and filtered through a celite pad. The filtrate was concentrated under vacuum and partitioned between EtOAc and brine and extracted with EtOAc (3×10 mL). Combined organic phases were dried over MgSO$_4$, and solvents were evaporated. The residue was purified by flash chromatography (12 g Silicycle column and DCM/EtOAc gradient as eluant), followed by a 40 minutes preparative HPLC run using a H$_2$O/ACN gradient as eluant to obtain the desired product. $^1$H NMR (400 MHz, d$_6$-DMSO) δ 7.19-7.18 (m, 2H), 7.13-7.12 (m, 1H), 6.87-6.84 (m, 1H), 5.39 (s, 2H), 4.79 (s, 2H), 2.79 (s, 3H), 1.74-1.68 (m, 4H), 1.63-1.56 (m, 2H), 1.38 (s, 3H), 1.36-1.28 (m, 1H), 1.24-1.13 (m, 2H), 1.10-0.99 (m, 1H), 0.98-0.92 (m, 1H). MS 344 (MH$^+$).

Example 2.50a: 5-cyclohexyl-1,5-dimethyl-3-(2-(3-nitrophenyl)-2-oxoethyl)imidazolidine-2,4-dione Prepared in a similar manner as described in Example 2.43 using 5-cyclohexyl-1,5-dimethylimidazolidine-2,4-dione (Example 2.47a) (500.0 mg, 2.38 mmol), and 2-bromo-1-(3-nitrophenyl)ethanone (641.0 mg, 2.627 mmol). The residue was purified by flash-chromatography using a Silicycle column (120 g) and a Hexanes/EtOAc gradient as eluant, to obtain after evaporation of solvents and drying the desired product (765.7 mg, 86%). $^1$H NMR (400 MHz, d$_6$-DMSO) δ 8.73-8.70 (m, 1H), 8.55-8.51 (m, 1H), 8.49-8.45 (m, 1H), 7.88 (t, J=8.0 Hz, 1H), 5.10 (s, 2H), 2.82 (s, 3H), 1.79-1.66 (m, 4H), 1.66-1.54 (m, 2H), 1.39 (s, 3H), 1.37-1.28 (m, 1H), 1.25-1.12 (m, 2H), 1.09-1.00 (m, 1H), 0.96-0.88 (m, 1H). MS 374 (MH$^+$).

Example 2.51: 5-((1S,2S,4S)-bicyclo[2.2.2]oct-5-en-2-yl)-15-dimethyl-3-(2-oxo-2-phenylethyl) imidazolidine-2,4-dione Prepared in a similar manner as described in Example 2.44 starting from 5-((1S,2S,4S)-bicyclo[2.2.2]oct-5-en-2-yl)-1,5-dimethyl-3-(2-oxo-2-phenylethyl)imidazolidine-2,4-dione (Example 2.51a) (109 mg, 0.32 mmol) and methyliodide (22 μL, 0.35 mmol) to obtain the desired product as a white powder (70 mg, 62% yield). $^1$H NMR (400 MHz, DMSO-d$_6$) δ 8.01 (d, J=8 Hz, 2H), 7.69 (t, J=8 Hz, 1H), 7.55 (t, J=8 Hz, 2H), 6.11 (t, J=8 Hz, 1H), 5.95 (t, J=8 Hz, 1H), 4.88 (q, J=16 Hz, J=36 Hz, 2H), 2.79 (s, 3H), 2.48 (m, 1H), 2.29 (m, 1H), 2.15 (t, J=8 Hz, 1H), 1.39-1.62 (m, 4H), 1.28 (s, 3H), 1.12 (m, 2H). MS 353 (MH$^+$).

Example 2.51a: 5-((1S,2S,4S)-bicyclo[2.2.2]oct-5-en-2-yl)-5-methyl-3-(2-oxo-2-phenylethyl) imidazolidine-2,4-dione Prepared in a similar manner as described in Example 2.44a starting from 5-(bicyclo[2.2.2]oct-5-en-2-yl)-5-methylimidazolidine-2,4-dione (Example 2.51b) (220 mg, 1 mmol) and 2-bromoacetophenone (200 mg, 1 mmol). The product eluted first (Rf=0.55) on a flash chromatography 120 g Silicycle column and, after evaporation of solvents, was obtained as a white powder (109 mg, 32% yield). $^1$H NMR (400 MHz, DMSO-d$_6$) δ 8.01 (d, J=8 Hz, 2H), 7.95 (s, 1H), 7.69 (t, J=8 Hz, 1H), 7.55 (t, J=8 Hz, 2H), 6.16 (m, 2H), 4.852 (d, J=1.6 Hz, 2H), 2.66 (m, 1H), 1.99 (t, J=8 Hz, 1H), 1.39-1.56 (m, 4H), 1.30 (s, 3H), 1.09 (m, 3H). MS 338 (MH$^+$).

Example 2.51b: 5-(bicyclo[2.2.2]oct-5-en-2-yl)-5-methylimidazolidine-2,4-dione

Prepared in a similar manner as described in Example 2.44b starting from 1-(bicyclo[2.2.2]oct-5-en-2-yl)ethanone (Example 2.51c) (1 g, 6.67 mmol)) to obtain product as a white powder of mixture of 2 pairs of diastereomers (1.3 g, 89% yield). $^1$H NMR (400 MHz, DMSO-d$_6$) δ 10.43 (bs, 1H), 7.42-7.56 (2s, 1H), 6.10 (m, 1.4H), 5.96 (t, J=8 Hz, 0.6H), 2.60 (m, 0.4H), 2.44 (m, 0.6H), 2.15 (m, 0.6H), 1.89 (m, 1H), 1.67 (t, J=8 Hz, 1H), 1.36-1.51 (m, 2.6H), 1.18 (s, 1H), 1.12 (m, 2.4H), 1.06 (s, 2H), 0.93 (m, 0.4H). MS 221 (MH$^+$).

Example 2.51c: 1-(bicyclo[2.2.2]oct-5-en-2-yl)ethanone

To the solution of cyclohexadiene (1.78 mL, 18.75 mmol) in 15 mL of dry DCM cooled to 0° C. under N$_2$ atmosphere was added methylvinylketone (7.63 mL, 93.75 mmol), following SnCl$_4$ (2.19 mL, 18.75 mmol) dropwise over 30 min period. The reaction mixture was stirred at 0° C. for 1 h, then poured in to 100 mL of saturated NaHCO$_3$ and extracted with DCM (3×50 mL). The combined organic phases were washed with brine and dried over MgSO$_4$, and solvents were evaporated. The residue was purified by flash chromatography using a 120 g Silicycle column and a Hexanes/Et$_2$O gradient as eluant to obtain the pure ketone (2.1 g, 75%) as a colorless liquid. $^1$H NMR (400 MHz, CDCl$_3$) δ 6.27 (t, J=8 Hz, 1H), 6.10 (t, J=8 Hz, 1H), 2.90 (m, 1H), 2.67 (t, J=8 Hz, 1H), 2.60 (m, 1H), 2.11 (s, 3H), 1.66 (m, 2H), 1.59 (m, 1H), 1.50 (m, 1H), 1.28 (m, 1H), 1.24 (m, 1H). MS N/A (MH$^+$).

Example 2.52: 5-cyclohexyl-1,5-dimethyl-3-(2-oxo-2-(thiophen-3-yl)ethyl)imidazolidine-2,4-dione In an oven-dried, N$_2$-flushed, small round-bottom flask, were added anhydrous DMF (8.0 mL), 5-cyclohexyl-1,5-dimethylimidazolidine-2,4-dione (Example 2.47a) (150 mg, 714 umol), and cooled to 0° C. Next, NaH (35 mg, 856 umol), and 2-bromo-1-(thiophen-3-yl)ethanone (175 mg, 856 µmol) were added and the reaction medium was allowed to warm to room temperature and stirred vigorously for 1.5 hr. The solution was extracted with $H_2O$/EtOAc (3×) and the combined organic phases were washed with brine, dried over $MgSO_4$, and concentrated in vacuo. The residue was purified by flash chromatography using a 12 g Silicycle column and EtOAc/Hex gradient as eluant to obtain the pure desired product (20 mg, 8.4%) as a light yellow oil. $^1$H NMR (400 MHz, $CDCl_3$) δ 8.15 (dd, J=2.8, 1.3 Hz, 1H), 7.56 (dd, J=5.1, 1.3 Hz, 1H), 7.37 (dd, J=5.1, 2.9 Hz, 1H), 4.81 (s, 2H), 2.91 (s, 3H), 1.89-1.64 (m, 6H), 1.54-1.42 (m, 1H), 1.48 (s, 3H), 1.29-0.99 (m, 4H).

Example 2.53: 5-((1s,4s)-bicyclo[2.2.2]octan-2-yl)-1,5-dimethyl-3-(2-oxo-2-phenylethyl) imidazolidine-2,4-dione Prepared in a similar manner as described in Example 2.44 starting from 5-((1S,4S)-bicyclo[2.2.2]octan-2-yl)-5-methyl-3-(2-oxo-2-phenylethyl)imidazolidine-2,4-dione (Example 2.53a) (60 mg, 0.18 mmol) and methyliodide (12 µL, 0.19 mmol) to obtain product as a white powder (38 mg, 62% yield). $^1$H NMR (400 MHz, DMSO-$d_6$) δ 8.01 (d, J=8 Hz, 2H), 7.69 (t, J=8 Hz, 1H), 7.55 (t, J=8 Hz, 2H), 4.97 (s, 2H), 2.89 (s, 3H), 2.02 (t J=8 Hz, 1H), 1.82 (m, 1H), 1.61 (m, 3H), 1.28-1.46 (m, 8H), 1.38 (s, 3H). MS 355 (MH$^+$).

Example 2.53a: 5-((1S,4S)-bicyclo[2.2.2]octan-2-yl)-5-methyl-3-(2-oxo-2-phenylethyl) imidazolidine-2,4-dione Prepared in a similar manner as described in Example 2.44a starting from 5-(bicyclo[2.2.2]octan-2-yl)-5-methyl-imidazolidine-2,4-dione (Example 2.53b) (222 mg, 1 mmol) and 2-bromoacetophenone (219 mg, 1.1 mmol). When purified by flash chromatography the product eluted second ($R_f$=0.5) on a 120 g Silicycle column and, after evaporation of solvents, was obtained as a white powder (65.8 mg, 19% yield). $^1$H NMR (400 MHz, DMSO-$d_6$) δ 8.60 (s, 1H), 8.01 (d, J=8 Hz, 2H), 7.69 (t, J=8 Hz, 1H), 7.55 (t, J=8 Hz, 2H), 4.90 (s, 2H), 1.94 (t, J=8 Hz, 1H), 1.85 (m, 1H), 1.67 (m, 2H), 1.35-1.50 (m, 9H), 1.28 (s, 3H). MS 341 (MH$^+$).

Example 2.53b: 5-(bicyclo[2.2.2]octan-2-yl)-5-methylimidazolidine-2,4-dione

Prepared in a similar manner as described in Example 2.44b starting from 1-(bicyclo[2.2.2]octan-2-yl)ethanone (Example 2.53c) (1 g, 6.67 mmol) to obtain product as a white powder and a mixture of 2 pairs of diastereomers (1.15 g, 78% yield). $^1$H NMR (400 MHz, DMSO-$d_6$) δ 10.03 (bs, 1H), 7.68 and 8.05 (2s, 1H), 2.380 (m, 0.5H), 2.06 (m, 0.5H), 1.95 (m, 0.5H), 1.59-1.82 (m, 4H), 1.55 (m, 2H), 1.31-1.53 (m, 5.5H), 1.305 (d, J=4 Hz, 3H), 1.20 (s, 1.5H), 1.16 (s, 3H). MS 221 (MH$^+$).

Example 2.53c: 1-(bicyclo[2.2.2]octan-2-yl)ethanone

A solution of 1-(bicyclo[2.2.2]oct-5-en-2-yl)ethanone (Example 2.51c) (1 g, 6.67 mmol) in 50 mL of EtOAc was hydrogenated on 10% Pd/C (57 mg) in Parr shaker at 20 psi at room temperature for 5 h. Then reaction mixture was filtered trough Celite pad and the filtrate was concentrated in vacuum to obtain 90% clean ketone as a colorless oil (1 g, 100%). $^1$H NMR (400 MHz, $CDCl_3$) δ 2.64 (m, 1H), 2.13 (s, 3H), 2.04 (m, 1H), 1.94 (m, 1H), 1.65 (m, 3H), 1.46-1.55 (m, 4H), 1.37-1.43 (m, 3H). MS N/A (MH$^+$).

Example 2.54: 5-((bicyclo[2.2.1]heptan-2-yl)-3-(2-(3-hydroxyphenyl)-2-oxoethyl)-1,5-dimethylimidazolidine-2,4-dione To an oven dried, $N_2$-flushed, small round bottom flask was added 5-bicyclo[2.2.1]heptan-2-yl)-1,5-dimethylimidazolidine-2,4-dione (Example 2.54a) (0.86 g, 3.87 mmol), $K_2CO_3$ (0.80 g, 5.80 mmol), and 3 mL DMF. The suspension was stirred at 50° C. and a solution of 2-bromo-1-(3-hydroxyphenyl)ethanone (0.83 g, 3.87 mmol) in 1 mL of DMF was added drop-wise over 5 minutes. The reaction was stirred for 2 hours when it was determined to be complete by LCMS. 10 mL of water was added and the mixture was extracted with ethyl acetate (3×10 mL). The combined organic layers were washed with water (1×20 mL), brine (1×20 mL) and dried with $Na_2SO_4$. The solvent was evaporated and the residue purified by column chromatography utilizing an 40 g Silicycle column and elution with 0-40% ethyl acetate/hexanes to afford a mixture of diastereomers. The diastereomers were separated by HPLC utilizing a 40 minute method to afford the title compound (0.100 g) as a white solid. The compound was concentrated from ethanol three times. The compound was then recrystallized from ethanol/water to afford 84 mg of the title compound as a white solid. $^1$H-NMR (400 MHz, DMSO-$d_6$) δ 9.10 (s, 1H), 7.51-7.49 (m, 1H), 7.39-7.35 (m, 1H), 7.33-7.32 (m, 1H), 7.10-7.08 (m, 1H), 4.89 (s, 2H), 2.81 (s, 3H), 2.37 (s, 1H), 2.17 (s, 1H), 1.84-1.81 (m, 1H), 1.49-1.47 (m, 2H), 1.43 (s, 3H), 1.37-1.32 (m, 1H), 1.27-1.14 (m, 4H), 1.02-0.99 (m, 1H); MS 357 (MH$^+$).

Example 2.54a: 5-bicyclo[2.2.1]heptan-2-yl)-1,5-dimethylimidazolidine-2,4-dione

To an oven dried, $N_2$-flushed, small round bottom flask was added 5-bicyclo[2.2.1]heptan-2-yl)-3-(4-methoxybenzyl)-1,5-dimethylimidazolidine-2,4-dione (Example 2.54b) (2.04 g, 5.96 mmol), 15 mL acetonitrile, 6 mL water and ceric ammonium nitrate (5.30 g 9.67 mmol). The reaction was stirred 24 hours at ambient temperature were it was determined to be ca. 85% complete by LCMS. The solvent was removed and the residue was dissolved in 50 mL ethyl acetate. The organic layer was washed with 1 M HCl (1×25 mL), water (1×25 mL), brine (1×25 mL) and dried with $Na_2SO_4$. The solvent was evaporated, and the resulting residue was purified by column chromatography utilizing a Silicycle column (40 g) and elution with 10-40% ethyl acetate/hexanes. The title compound was isolated (1.13 g, 84%) as a mixture of diastereomers. $^1$H-NMR (400 MHz, DMSO-$d_6$) δ 10.81 (s, 2H), 2.71-2.70 (m, 6H), 2.23-2.21 (m, 2H), 2.14 (s, 1H), 1.87-1.71 (m, 4H) 1.47-1.45 (m, 4H), 1.34-1.11 (m, 14H), 1.03-0.94 (m, 3H); MS 223 (MH$^+$).

Example 2.54b: 5-bicyclo[2.2.1]heptan-2-yl)-3-(4-methoxybenzyl)-1,5-dimethylimidazo-lidine-2,4-dione To an oven dried, $N_2$-flushed, small round bottom flask was added 5-bicyclo[2.2.1]heptan-2-yl)-3-(4-methoxybenzyl)-5-methylimidazolidine-2,4-dione (Example 2.54c) (3.4 g, 10.4 mmol), 10 mL of anhydrous DMF, and NaH (0.7 g, 20.7 mmol). The reaction was stirred ambient temperature for 30 minutes and methyl iodide (2 mL, 31.2 mmol) was added. The reaction was stirred for one hour at ambient temperature when it was determined to by complete by LCMS and TLC. 30 mL water was added the mixture was extracted with ethyl acetate (3×10 mL). The combined extracts were washed with water (1×20 mL), brine (1×20 mL) and dried with $Na_2SO_4$. The solvent was evaporated, and the resulting residue was purified by column chromatography utilizing a Silicycle column (80 g) and elution with 0-50% ethyl acetate/hexanes. The title compound was isolated 2.0 g (57%) as a mixture of diastereomers. $^1$H-NMR (400 MHz, DMSO-$d_6$) δ 7.19-7.16 (m, 4H), 6.89-6.86 (m, 4H), 4.46 (s, 4H), 3.72-3.71 (m, 6H), 2.78 (s, 3H), 2.76 (s, 3H), 2.21 (s, 1H), 2.14 (s, 1H), 2.0 (s, 1H), 1.83-1.72 (m, 4H), 1.44-1.35 (m, 7H), 1.27-1.23 (m, 5H), 1.14-1.04 (m, 5H), 0.95-0.90 (m, 2H), 0.82-0.77 (m, 1H), 0.72-0.69 (m, 1H); MS 343 (MH$^+$).

Example 2.54c: 5-bicyclo[2.2.1]heptan-2-yl)-3-(4-methoxybenzyl)-5-methyl-imidazolidine-2,4-dione To an oven dried, $N_2$-flushed, small round bottom flask was added 5-bicyclo[2.2.1]heptan-2-yl)-5-methylimidazolidine-2,4-dione (Example 2.42b) (2.67 g, 12.8 mmol), 7 mL DMF, $K_2CO_3$ (2.65 g, 19.2 mmol) and 4-methoxybenzyl chloride (1.75 mL, 12.8 mmol). The vial was sealed and the reaction mixture was stirred at ambient temperature for 12 hrs. The reaction was quenched with water (25 mL) and extracted with EtOAc (3×20 mL). The organic layers were combined, washed with water (40 mL), brine (40 mL), and dried over $Na_2SO_4$. The solvent was evaporated, and the resulting residue was purified by column chromatography utilizing a Silicycle column (40 g) and elution with 0-50% ethyl acetate/hexanes. The title compound was isolated 3.4 g (81%) as a mixture of diastereomers. $^1$H-NMR (400 MHz, DMSO-$d_6$) δ 8.31 (s, 1H), 8.27 (s, 1H) 7.23-7.15 (m, 4H), 6.89-6.86 (m, 4H), 4.45 (s, 2H), 4.42-4.40 (m, 2H), 3.73-3.72 (m, 6H), 2.15-2.10 (m, 3H), 1.72-1.64 (m, 2H), 1.59-1.58 (m, 1H), 1.44-1.24 (m, 1H), 1.14-1.01 (m, 9H), 0.96-0.88 (m, 2H); MS 329 (MH$^+$).

Example 2.55: 5-((1S,2R,4R)-bicyclo[2.2.1]heptan-2-yl)-3-(2-(3-hydroxyphenyl)-2-oxoethyl)-1,5-dimethylimidazolidine-2,4-dione The title compound was isolated during the purification of 54. Compound 55 eluted after compound 54 on the HPLC during the separation of the diastereomers. The procedure is identical to that of 54. $^1$H-NMR (400 MHz, DMSO-$d_6$) δ 9.95 (s, 1H), 7.52-7.49 (m, 1H), 7.39-7.35 (m, 1H), 7.33-7.32 (m, 1H), 7.10-7.07 (m, 1H), 4.88 (s, 2H), 2.83 (s, 3H), 2.21 (s, 1H), 2.01 (s, 1H), 1.89-1.85 (m, 2H), 1.48-1.47 (m, 2H), 1.35-1.29 (m, 4H), 1.20-1.14 (m, 3H), 0.97-0.95 (m, 1H); MS 357 (MH$^+$).

Example 2.56: 5-cyclohexyl-3-(2-(4-hydroxyphenyl)-2-oxoethyl)-1,5-dimethylimidazolidine-2,4-dione Prepared in a similar manner as described in Example 2.43 using 5-cyclohexyl-1,5-dimethylimidazolidine-2,4-dione (Example 2.47a) (102.3 mg, 476 mol), and commercially available 2-chloro-1-(4-hydroxyphenyl)ethanone (90.0 mg, 528 mol), to obtain the desired product (47.6 mg, 28%). $^1$H NMR (400 MHz, $d_6$-DMSO) δ 10.47 (s, 1H), 7.91 (d, J=8.8 Hz, 2H), 6.88 (d, J=8.8 Hz, 2H), 4.85 (d, J=18.1 Hz, 1H), 4.80 (d, J=18.0 Hz, 1H), 2.81 (s, 3H), 1.78-1.66 (m, 4H), 1.65-1.57 (m, 2H), 1.38 (s, 3H), 1.36-1.27 (m, 1H), 1.25-1.13 (m, 2H), 1.10-1.01 (m, 1H), 1.00-0.88 (m, 1H). MS 345 (MH$^+$).

Example 2.57: 5-((1S,4S)-bicyclo[2.2.2]oct-5-en-2-yl)-1,5-dimethyl-3-(2-oxo-2-phenylethyl) imidazolidine-2,4-dione Prepared in a similar manner as described in Example 2.44 starting from 5-((1S,4S)-bicyclo[2.2.2]oct-5-en-2-yl)-5-methyl-3-(2-oxo-2-phenylethyl)imidazolidine-2,4-dione (Example 2.57a) (191 mg, 0.56 mmol) and methyliodide (39 µL, 0.62 mmol) to obtain product as a white powder (118 mg, 60% yield). $^1$H NMR (400 MHz, DMSO-$d_6$) δ 8.02 (d, J=8 Hz, 2H), 7.69 (t, J=8 Hz, 1H), 7.56 (t, J=8 Hz, 2H), 6.19 (t, J=8 Hz, 1H), 5.98 (t, J=8 Hz, 1H), 4.955 (q, J=16 Hz, J=30 Hz, 2H), 2.71 (s, 3H), 2.51 (m, 2H), 2.13 (t, J=8 Hz, 1H), 1.70 (t, J=8 Hz, 1H), 1.43 (m, 2H), 1.29 (s, 3H), 1.16 (m, 3H). MS 353 (MH$^+$).

Example 2.57a: 5-((1S,4S)-bicyclo[2.2.2]oct-5-en-2-yl)-5-methyl-3-(2-oxo-2-phenylethyl) imidazolidine-2,4-dione Prepared in a similar manner as described in Example 2.44a starting from 5-(bicyclo[2.2.2]oct-5-en-2-yl)-5-methylimidazolidine-2,4-dione (Example 2.51b) (220 mg, 1 mmol) and 2-bromoacetophenone (200 mg, 1 mmol). When purified by flash chromatography the product eluted second on a 120 g Silicycle column (Rf=0.5) and, after evaporation of solvents, was obtained as a white powder (191.3 mg, 57% yield). $^1$H NMR (400 MHz, DMSO-$d_6$) δ 8.07 (s, 1H), 8.03 (d, J=8 Hz, 2H), 7.69 (t, J=8 Hz, 1H), 7.56 (t, J=8 Hz, 2H), 6.15 (t, J=8 Hz, 1H), 6.05 (t, J=8 Hz, 1H), 4.91 (s, 2H), 2.52 (m, 1H), 2.41 (m, 1H), 2.02 (t, J=8 Hz, 1H), 1.72 (t, J=8 Hz, 1H), 1.41 (m, 2H), 1.17 (s, 3H), 1.09 (m, 3H). MS 338 (MH$^+$).

Example 2.58: 5-cyclohexenyl-1,5-dimethyl-3-(2-oxo-2-phenylethyl)imidazolidine-2,4-dione Prepared in a similar manner as described in Example 2.44 starting from 5-cyclohexenyl-5-methyl-3-(2-oxo-2-phenylethyl)imidazolidine-2,4-dione (Example 2.58a) (92.2 mg, 295 umol) and MeI (50.0 µL, 803 µmol) to obtain the desired product (28.1 mg, 29%) as an oily film. $^1$H NMR (400 MHz, DMSO-$d_6$) δ 7.96-7.94 (m, 2H), 7.62-7.59 (m, 1H), 7.50-7.47 (m, 2H), 5.93 (s, br, 1H), 4.93 (s, 2H), 2.79 (s, 3H), 2.20-2.08 (m, 2H), 1.99-1.87 (m, 2H), 1.74-1.65 (m, 2H), 1.65-1.53 (m, 2H), 1.58 (s, 3H). MS 327 (MH$^+$).

Example 2.58a: 5-cyclohexenyl-5-methyl-3-(2-oxo-2-phenylethyl)imidazolidine-2,4-dione Prepared in a similar manner as described in Example 2.44a starting from a crude mixture containing 5-cyclohexenyl-5-methylimidazolidine-2,4-dione (Example 2.58b) (300 mg, 1.54 mmol) and 2-bromo-1-phenylethanone (378 mg, 1.90 mmol) to obtain the desired product (92.2 mg, 19% over 2 steps 58a and 58b). MS 313 (MH$^+$).

Example 2.58b: 5-cyclohexenyl-5-methylimidazolidine-2,4-dione

Prepared in a similar manner as described in Example 2.44b starting from 1-cyclohexenylethanone (1 g, 8.1 mmol) to obtain product that was used as a crude mixture without further purification.

Example 2.59: 3-(2-(3-hydroxyphenyl)-2-oxoethyl)-1,5-dimethyl-5-(2-methylcyclopentyl) Imidazolidine-2,4-dione Prepared in a similar manner as described in Example 2.44 starting from 1,5-dimethyl-5-(2-methylcyclopentyl)imidazolidine-2,4-dione (Example 2.59a) (105 mg, 0.5 mmol) and 2-bromo-1-(3-hydroxyphenyl)ethanone (107 mg, 0.5 mmol). Gives 81.6 mg (47% yield) of a white powder of mixture of 4 pairs of diastereomers. $^1$H NMR (400 MHz, DMSO-$d_6$) δ 9.95 (bs, 1H), 7.47 (d, J=8 Hz, 1H), 7.34 (t, J=8 Hz, 1H), 7.30 (s, 1H), 7.07 (d, J=8 Hz, 1H), 4.87 (t, J=4 Hz, 2H), 2.80-2.86 (4s, 3H), 2.00-2.4 (m, 1H), 1.82 (m, 2H), 1.65 (m, 2H), 1.49 (m, 1H), 1.39-1.41 (4s, 3H), 1.35 (m, 1H), 1.17 (m, 1H), 0.66-0.98 (4d, J=8 Hz, 3H). MS 345 (MH$^+$).

Example 2.59a: 1,5-dimethyl-5-(2-methylcyclopentyl)imidazolidine-2,4-dione

Prepared in a similar manner as described in Example 2.45a starting from 3-(4-methoxybenzyl)-1,5-dimethyl-5-(2-methylcyclopentyl)imidazolidine-2,4-dione (Example 2.59b) (818 mg, 2.48 mmol) and a solution of ammonium cerium nitrate (3.53 g, 6.45 mmol) in water (15 mL) to obtain product as a white powder of mixture of 4 pairs of diastereomers (435 mg, 83% yield). $^1$H NMR (400 MHz, DMSO-$d_6$) δ 10.78 (bs, 1H), 2.69-2.75 (4s, 3H), 1.96-2.19 (m, 1H), 1.80 (m, 2H), 1.65 (m, 2H), 1.44 (m, 2H), 1.28-1.31 (4s, 3H), 1.14 (m, 1H), 0.63-0.93 (4d, J=8 Hz, 3H). MS 211 (MH$^+$).

Example 2.59b: 3-(4-methoxybenzyl)-1,5-dimethyl-5-(2-methylcyclopentyl)imidazolidine-2,4-dione Prepared in a similar manner as described in Example 2.45b starting from 3-(4-methoxybenzyl)-5-methyl-5-(2-methylcyclopentyl)imidazolidine-2,4-dione (Example 2.59c) (913 mg, 2.88 mmol) and methyl iodide (270 μL, 4.33 mmol) to obtain product as a colorless oil of mixture of 4 pairs of diastereomers (818 mg, 86% yield). $^1$H NMR (400 MHz, DMSO-$d_6$) δ 6.87 (d, J=8 Hz, 2H), 6.56 (d, J=8 Hz, 2H), 4.15 (s, 2H), 3.40 (s, 3H), 2.47-2.52 (4s, 3H), 1.75-1.90 (m, 1H), 1.55 (m, 1H), 1.32 (m, 2H), 1.13 (m, 2H), 1.00-1.04 (4s, 3H), 0.95 (m, 0.5H), 0.80 (m, 1H), 0.66 (m, 0.5H), 0.01-0.56 (4d, J=8 Hz, 3H). MS 331 (MH$^+$).

Example 2.59c: 3-(4-methoxybenzyl)-5-methyl-5-(2-methylcyclopentyl)imidazolidine-2,4-dione Prepared in a similar manner as described in Example 2.45c starting from 5-methyl-5-(2-methylcyclopentyl)imidazolidine-2,4-dione (Example 2.59d) (585 mg, 2.69 mmol) and 4-methoxybenzyl chloride (438 μL, 3.22 mmol) to obtain product as a white powder of mixture of 4 pairs of diastereomers (850 mg, 100% yield). $^1$H NMR (400 MHz, DMSO-$d_6$) δ 8.35 (s, 1H), 7.15 (d, J=8 Hz, 2H), 6.85 (d, J=8 Hz, 2H), 4.41 (s, 2H), 3.70 (s, 3H), 1.96-2.25 (m, 1H), 1.52-1.80 (m, 3H), 1.39 (m, 3H), 1.22-1.30 (4s, 3H), 1.13 (m, 1H), 0.47-0.72 (4d, J=8 Hz, 3H). MS 317 (MH$^+$).

Example 2.59d: 5-methyl-5-(2-methylcyclopentyl)imidazolidine-2,4-dione

Prepared in a similar manner as described in Example 2.44b starting from 1-(2-methylcyclopentyl)ethanone (Example 2.59e) (988 mg, 7.84 mmol) to obtain product as a white powder of mixture of 4 pairs of diastereomers (790 mg, 51% yield). $^1$H NMR (400 MHz, DMSO-$d_6$) δ 10.00 (bs, 1H), 7.90 (s, 1H), 1.39-1.86 (m, 8H), 1.19-1.26 (4s, 3H), 1.13 (m, 1H), 0.71-0.98 (4d, J=8 Hz, 3H). MS 197 (MH$^+$).

Example 2.59e: 1-(2-methylcyclopentyl)ethanone

To 1 g (7.81 mmol) of 2-methylcyclopentanecarboxylic acid in 10 mL dry ether under N$_2$ atmosphere at −20° C. was added dropwise over 20 minutes 1.5 M ethereal solution of methyllitium (10.42 mL, 15.62 mmol). Reaction mixture was stirred at 0° C. for 30 min, then gradually warmed up to room temperature and stirred 18 h. Resulting cloudy solution was poured in to mixture of 50 mL ice-water and 50 mL of 1N HCl and then product was extracted with ether (3×50 mL). Organic fractions were washed with water, saturated NaHCO$_3$, water, dried over MgSO$_4$ and concentrated in vacuum yielded 988 mg of 1-(2-methylcyclopentyl)-ethanone as a colorless oil consisting of two pairs of diastereomers (2:1 ratio by NMR analysis). Crude ketone was used in the next step without further purification. $^1$H NMR (400 MHz, DMSO-$d_6$) δ 2.95 (m, 0.2H), 2.38 (m, 0.8H), 2.075 (d, J=4 Hz, 3H), 2.03 (m, 1H), 1.76 (m, 2H), 1.54 (m, 3H), 1.3 (m, 0.4H), 1.14 (m, 0.6H), 0.69-0.97 (2d, J=8 Hz, 3H). MS N/A (MH$^+$).

Example 2.60: 3-(2-(3-hydroxyphenyl)-2-oxoethyl)-5-(2-methoxyphenyl)-1,5-dimethyl-imidazolidine-2,4-dione In an oven-dried, N$_2$-flushed, small round-bottom flask, were added anhydrous DMF (3.0 mL), 5-(2-methoxyphenyl)-1,5-dimethylimidazolidine-2,4-dione (Example 2.60a) (234 mg, 1 mmol), and at 0° C. NaH (120 mg, 3 mmol), and 2-bromo-1-(3-hydroxylphenyl)ethanone (256 mg, 1.2 mmol). The reaction medium was stirred vigorously at room temperature overnight, poured in water (20 mL) and extracted with EtOAc (3×20 mL). Combined organic phases were washed with brine and dried over MgSO$_4$, and solvents were evaporated. The residue was purified by HPLC to obtain the pure desired product (80 mg, 22%) as a white solid. $^1$H NMR (400 MHz, CDCl$_3$) δ 7.45 (dt, J=7.6, 1.7 Hz, 2H), 7.39 (ddd, J=8.3, 7.5, 1.6 Hz, 1H), 7.31-7.26 (m, 3H), 7.07-7.00 (m, 2H), 6.91 (dd, J=8.3, 1.0 Hz, 1H), 6.87 (s, 1H), 5.03 (s, 2H), 3.79 (s, 3H), 2.66 (s, 3H), 1.94 (s, 3H). MS 316 (MH$^+$).

Example 2.60a: 5-(2-methoxyphenyl)-1,5-dimethyl-imidazolidine-2,4-dione

In a N$_2$-flushed round-bottom flask, were added anhydrous CH$_3$CN (15 mL), 3-(4-methoxybenzyl)-5-(2-methoxyphenyl)-1,5-dimethylimidazolidine-2,4-dione (Example 2.60b) (531 mg, 1.5 mmol), and at 0° C. dropwise an ice-cooled solution of ammonium cerium IV nitrate (2145.0 mg, 3.9 mmol) in H$_2$O (9 mL). The reaction medium was monitored by TLC, stirred vigorously at room temperature overnight, and extracted with brine/EtOAc (3×). Combined organic phases were washed again with brine and dried over MgSO$_4$, and solvents were evaporated. The residue was purified by flash chromatography using a 40 g Silicycle column and a Hexanes/EtOAc gradient as eluant to obtain

Example 2.60b: 3-(4-methoxybenzyl)-5-(2-methoxyphenyl)-1,5-dimethylimidazolidine-2,4-dione In an oven-dried, $N_2$-flushed, small round-bottom flask, were added anhydrous DMF (4.0 mL), 3-(4-methoxybenzyl)-5-(2-methoxyphenyl)-5-methylimidazolidine-2,4-dione (Example 2.60c) (680 mg, 2 mmol), and NaH (100.0 mg, 2.5 umol), and MeI (186 µL, 3 mmol). The reaction medium was stirred vigorously at room temperature overnight, poured in water (20 mL) and extracted with $H_2O$/EtOAc (3×). Combined organic phases were washed with brine and dried over $MgSO_4$, and solvents were evaporated. The residue was purified by flash chromatography using a 40 g Silicycle column and a Hexanes/EtOAc gradient as eluant to obtain the pure desired product (566.4 mg, 80%). $^1$H NMR is consistent with structure. MS 355 (MH$^+$).

Example 2.60c: 3-(4-methoxybenzyl)-5-(2-methoxyphenyl)-5-methylimidazolidine-2,4-dione In an oven-dried, $N_2$-flushed, small round-bottom flask, were added anhydrous DMF (10.0 mL), 5-(2-methoxyphenyl)-5-methylimidazolidine-2,4-dione (Example 2.60d) (1980 mg, 9.0 mmol), $K_2CO_3$ (2.48 g, 18 mmol), KI (180 mg, 1.1 mmol) and 1-(bromomethyl)-4-methoxybenzene (1.35 mL, 10 mmol). The reaction medium was stirred vigorously at room temperature overnight, poured in water (100 mL) and extracted with $H_2O$/EtOAc (3×). Combined organic phases were washed with brine and dried over $MgSO_4$, and solvents were evaporated. The residue was purified by flash chromatography using a 40 g Silicycle column and a Hexanes/EtOAc gradient as eluant to obtain the pure desired product (2.45 g, 80%). $^1$H NMR is consistent with structure. MS 341 (MH$^+$).

Example 2.60d: 5-(2-methoxyphenyl)-5-methylimidazolidine-2,4-dione

In a 40 mL roundbottom vial, were added $H_2O$ (20 mL), 2-methoxyacetophenone (1.5 g, 10 mmol) in EtOH (10 mL), $(NH_4)_2CO_3$ (3.36 g, 35 mmol), and KCN (1.0.2 g, 15 mmol) in $H_2O$ (10 mL) dropwise over a few minutes. The reaction mixture was stirred and heated at 50° C. until judged complete by LCMS analysis. The reaction medium was allowed to cool down, the obtained white precipitate was filtered and washed with a little cold $H_2O$ and dried to obtain the desired pure product (2.0 g, 90%). $^1$H NMR is consistent with structure. MS 221 (MH$^+$).

Example 2.61: 5-((1R,2S,4R)-bicyclo[2.2.2]octan-2-yl)-1,5-dimethyl-3-(2-oxo-2-phenylethyl) imidazolidine-2,4-dione Prepared in a similar manner as described in Example 2.44 starting from 5-((1R,2S,4S)-bicyclo[2.2.2]octan-2-yl)-5-methyl-3-(2-oxo-2-phenylethyl)imidazolidine-2,4-dione (Example 2.61a) (65.8 mg, 0.19 mmol) and methyl iodide (13 µL, 0.21 mmol) to obtain product as a white powder (40 mg, 62% yield). $^1$H NMR (400 MHz, DMSO-d$_6$) δ 8.01 (d, J=8 Hz, 2H), 7.69 (t, J=8 Hz, 1H), 7.55 (t, J=8 Hz, 2H), 4.95 (s, 2H), 2.75 (s, 3H), 2.08 (t J=8 Hz, 1H), 1.98 (t J=8 Hz, 1H), 1.57 (m, 2H), 1.47 (m, 4H), 1.37 (s, 3H), 1.24-1.37 (m, 5H). MS 355 (MH$^+$).

Example 2.61a: 5-((1R,2S,4R)-bicyclo[2.2.2]octan-2-yl)-5-methyl-3-(2-oxo-2-phenylethyl) imidazolidine-2,4-dione Prepared in a similar manner as described in Example 2.44a starting from 5-(bicyclo[2.2.2]octan-2-yl)-5-methylimidazolidine-2,4-dione (Example 2.53b) (222 mg, 1 mmol) and 2-bromoacetophenone (219 mg, 1.1 mmol). When purified by flash chromatography the product eluted first (R$_f$=0.55) on a 120 g Silicycle column and, after evaporation of solvents, was obtained as a white powder (60 mg, 18% yield). $^1$H NMR (400 MHz, DMSO-d$_6$) δ 8.27 (s, 1H), 8.01 (d, J=8 Hz, 2H), 7.69 (t, J=8 Hz, 1H), 7.55 (t, J=8 Hz, 2H), 4.91 (s, 2H), 1.89 (t, J=8 Hz, 1H), 1.67 (m, 2H), 1.56 (m, 1H), 1.35-1.50 (m, 8H), 1.33 (s, 3H), 1.28 (m, 1H). MS 341 (MH$^+$).

Example 2.62: 5-cyclohexyl-1,5-dimethyl-3-(2-oxo-2-(1H-pyrrol-2-yl)ethyl)imidazolidine-2,4-dione Prepared in a similar manner as described in Example 2.45 starting from 5-cyclohexyl-1,5-dimethylimidazolidine-2,4-dione (68 mg, 0.32 mmol) (Example 2.47a) and 2-chloro-1-(1H-pyrrol-2-yl)ethanone (55 mg, 0.38 mmol) to obtain the desired product (21 mg, 20%) as a light purple oil. $^1$H NMR (400 MHz, DMSO-d$_6$) δ 9.345 (s, 1H), 7.045 (m, 1H), 6.991 (m, 1H), 6.299 (m, 1H), 4.752 (s, 2H), 2.903 (s, 3H), 1.600 (m, 6H), 1.461 (s & m, 4H), 1.027 (m, 4H). MS 318 (MH$^+$).

Example 2.63: 5-cyclohexyl-1,5-dimethyl-3-(2-oxo-2-(pyridin-3-yl)ethyl)imidazolidine-2,4-dione Prepared in a similar manner as described in Example 2.45 starting from 5-cyclohexyl-1,5-dimethylimidazolidine-2,4-dione (266 mg, 1.26 mmol) (Example 2.47a) and 3-(bromoacetyl)-pyridine hydrobromide (424 mg, 1.5 mmol) to obtain the desired product (60 mg, 14%) as a clear oil. $^1$H NMR (400 MHz, DMSO-d$_6$) δ 9.187 (s, 1H), 8.827 (d, J=4.8 Hz, 1H), 8.222 (d, J=8 Hz 1H), 7.444 (dd, J=8.4 Hz & 4.4 Hz, 1H), 4.911 (s, 2H), 2.918 (s, 3H), 1.657 (m, 6H), 1.485 (s & m, 4H), 1.029 (m, 4H). MS 330 (MH$^+$).

Example 2.64: 1,5-dimethyl-5-(2-methylcyclopentyl)-3-(2-oxo-2-phenylethyl) imidazolidine-2,4-dione Prepared in a similar manner as described in Example 2.44 starting from 5-methyl-5-(2-methylcyclopentyl)-3-(2-oxo-2-phenylethyl)imidazolidine-2,4-dione (Example 2.64a) (242 mg, 0.77 mmol) and methyl iodide (58 µL, 0.92 mmol) to obtain product as a white powder of mixture of 4 pairs of diastereomers (103.7 mg, 41% yield). $^1$H NMR (400 MHz, DMSO-d$_6$) δ 8.02 (d, J=8 Hz, 2H), 7.69 (t, J=8 Hz, 1H), 7.55 (t, J=8 Hz, 2H), 4.95 (s, 2H), 2.81-2.86 (3s, 3H), 2.34 (m, 1H), 1.88 (m, 2H), 1.65 (m, 2H), 1.49 (m, 2H), 1.37-1.43 (3s, 3H), 1.16 (m, 1H), 0.83-0.98 (3d, J=8 Hz, 3H). MS 329 (MH$^+$).

Example 2.64a: 5-methyl-5-(2-methylcyclopentyl)-3-(2-oxo-2-oxo-2-phenylethyl)imidazolidine-2,4-dione Prepared in a similar manner as described in Example 2.44a starting from 5-methyl-5-(2-methylcyclopentyl)imidazolidine-2,4-dione (Example 2.59d) (196 mg, 1 mmol) and 2-bromoacetophenone (200 mg, 1 mmol) to obtain product as a white powder of mixture of 4 pairs of diastereomers (242.7 mg, 77% yield). $^1$H NMR (400 MHz, DMSO-d$_6$) δ 8.44 (bs, 1H), 8.03 (d, J=8 Hz, 2H), 7.69 (t, J=8 Hz, 1H), 7.56 (t, J=8 Hz, 2H), 4.91 (d, J=8 Hz, 2H), 1.96-2.19 (m, 1H), 1.80 (m, 2H), 1.65 (m, 2H), 1.48 (m, 2H), 1.32-1.36 (3s, 3H), 1.17 (m, 1H), 1.03-0.78 (3d, J=8 Hz, 3H). MS 315 (MH$^+$).

Example 2.65: 5-(cyclohex-1-en-1-yl)-1,5-dimethyl-3-(2-oxo-2-phenylethyl)pyrimidine-2,4,6(1H,3H,5H)-trione To an oven-dried 150 mL pressure tube flushed under nitrogen, were added hexobarbital (2.7 g, 11.4 mmol) in anhydrous DMF (34 mL) and at 0° C. sodium hydride (545 mg, 13.60 mmol), and the reaction medium was stirred vigorously for a few minutes at room temperature. 2-Bromo-1-phenylethanone (2.77 g, 13.92 mmol) was then added at 0° C., the pressure tube was sealed and the reaction medium stirred for 16 hours at room temperature, followed by extraction with excess H$_2$O/EtOAc (3×). Combined organic phases were washed with brine, dried over MgSO$_4$, and solvents were evaporated. The residue was first purified by flash chromatography on silica gel and eluted with a Hexane/EtOAc gradient to obtain a yellow oil that precipitated out upon standing (4.14 g). The material was then re-purified by flash chromatography on silica gel and eluted again with a Hexane/EtOAc gradient to obtain a colorless oil that precipitated out upon standing (3.77 g), and which was taken up in EtOH 3 times successively, followed by evaporation of solvents in order to eliminate all traces of undesired solvents. Finally, the obtained white residue was re-dissolved in a small amount of EtOH, heated for dissolution, and let stand for recrystallisation in the refrigerator overnight, to obtain 3.16 g (78% yield) as a fluffy white powder. $^1$H NMR (400 MHz, d$_6$-DMSO) δ 8.09-8.04 (m, 2H), 7.76-7.70 (m, 1H), 7.62-7.56 (m, 2H), 5.81-5.76 (m, 1H), 5.36 (d, J=17.7 Hz, 1H), 5.26 (d, J=17.7 Hz, 1H), 3.19 (s, 3H), 2.09-1.93 (m, 3H), 1.90-1.78 (m, 1H), 1.55 (s, 3H), 1.63-1.44 (m, 4H). MS 355 (MH$^+$)

Example 2.66: 1,5-dimethyl-5-(2-methylcyclopentyl)-3-(2-oxo-2-(1H-pyrrol-2-yl)ethyl) imidazolidine-2,4-dione Prepared in a similar manner as described in Example 2.44 starting from 1,5-dimethyl-5-(2-methylcyclopentyl) imidazolidine-2,4-dione (Example 2.59a) (105 mg, 0.5 mmol) and 2-bromo-1-(1H-pyrrol-2-yl)ethanone (Example 2.48a) (103 mg, 0.55 mmol) to obtain product as a white powder of mixture of 4 pairs of diastereomers (136 mg, 86% yield). $^1$H NMR (400 MHz, DMSO-d$_6$) δ 11.99 (bs, 1H), 7.15 (s, 2H), 6.22 (s, 1H), 4.65 (s, 2H), 2.79-2.85 (4s, 3H), 2.36 (m, 1H), 1.88 (m, 2H), 1.65 (m, 2H), 1.46 (m, 2H), 1.37-1.43 (4s, 3H), 1.16 (m, 1H), 0.66-0.98 (4d, J=8 Hz, 3H). MS 318 (MH$^+$).

Example 2.67: 5-((1R,4S)-bicyclo[2.2.1]heptan-2-yl)-1,5-dimethyl-3-(2-oxo-2-(1H-pyrrol-2-yl)ethyl) imidazolidine-2,4-dione The title compound was isolated during the purification of 48. Compound 67 eluted after compound 48 on the HPLC during the separation of the diastereomers. The procedure is identical to that of 48. $^1$H-NMR (400 MHz, DMSO-d$_6$) δ 11.99 (s, 1H), 7.17 (s, 2H), 6.25 (s, 1H), 4.67 (s, 2H), 2.82 (s, 3H), 2.20 (s, 1H), 2.03 (s, 1H), 1.89-1.84 (m, 2H), 1.47-1.44 (m, 2H), 1.33-1.29 (m, 4H), 1.22-1.13 (m, 3H), 0.96-0.94 (m, 1H); MS 330 (MH$^+$).

Example 2.68: 5-cyclohexyl-1-ethyl-5-methyl-3-(2-oxo-2-phenylethyl)imidazolidine-2,4-dione In an oven-dried, N$_2$-flushed, small round-bottom flask, were added anhydrous DMF (8.0 mL), 5-cyclohexyl-1-ethyl-5-methylimidazolidine-2,4-dione (Example 2.68a) (40 mg, 178 mol) and the solution was cooled to 0° C. NaH (9 mg, 178 umol), and 2-bromo-1-phenylethanone (44 mg, 178 mol) were added, the ice bath was removed and the reaction medium was stirred vigorously for 2 hr warming to room temperature. The resulting mixture was extracted with H$_2$O/EtOAc (3×) and the combined organic phases were washed with brine, dried over MgSO$_4$, and concentrated in vacuo. The residue was purified by preparative HPLC. The pure product was obtained as a clear oil (20 mg, 33%). $^1$H NMR (400 MHz, CDCl$_3$) δ 7.95 (d, J=6.8 Hz, 2H), 7.59 (t, J=6.4 Hz, 1H), 7.47 (t, J=5.6 Hz, 2H), 4.90 (s, 2H), 3.26 (d & sextet, J=44.8 Hz & 7.2 Hz, 2H), 1.67-1.82 (m, 7H), 1.51 (s, 3H), 1.28 (t, J=6.4 Hz, 3H), 1.03-1.24 (m, 4H) MS 343 (MH$^+$).

Example 2.68a: 5-cyclohexyl-1-ethyl-5-methylimidazolidine-2,4-dione

In a N$_2$-flushed round-bottom flask, were added anhydrous CH$_3$CN (16 mL), 5-cyclohexyl-1-ethyl-3-(4-methoxybenzyl)-5-methylimidazolidine-2,4-dione (Example 2.68b) (562 mg, 1.6 mmol), and the solution was cooled to 0° C. in an ice bath. An ice-cooled solution of ammonium cerium IV nitrate (2.3 g, 4.2 mmol) in H$_2$O (12 mL) was added dropwise and the reaction medium was monitored by TLC. The solution was allowed to warm to room temperature with continued vigorous stirring overnight. Acetonitrile was removed in vacuo, the residue was treated with H$_2$O and 30% CH$_3$CN in DCM. The organic layer was dried, concentrated and purified by flash chromatography using a 40 g Silicycle column and a Hexanes/EtOAc gradient as eluant to obtain the pure product (300 mg, 83%). MS 225 (MH$^+$). $^1$H-NMR was consistent with the structure.

Example 2.68b: 5-cyclohexyl-1-ethyl-3-(4-methoxybenzyl)-5-methylimidazolidine-2,4-dione To a suspension of 5-cyclohexyl-3-(4-methoxybenzyl)-5-methylimidazolidine-2,4-dione (Example 2.47c) (500 mg, 1.65 mmol) and NaH (80 mg, 1.98 mmol) in 10 mL DMF was added ethyl bromide (147 μL, 1.98 mmol). The reaction was stirred for 18 h at ambient temperature. Additional NaH and ethyl bromide were added. The resulting mixture was stirring 3 more hours, then the mixture was treated with EtOAc and H$_2$O. The organic layer was dried and concentrated to give a yellow oil. The crude product was purified by flash chromatography using a 12 g Silicycle column and EtOAc/Hex gradient as eluant to obtain the pure product (352 mg, 64%) as a light yellow oil. MS 345 (MH$^+$). $^1$H-NMR was consistent with the structure.

Example 2.69: 5-(cyclohex-1-en-1-yl)-1,5-dimethyl-3-(2-oxo-2-(1H-pyrrol-2-yl)ethyl) imidazolidine-2,4-dione Prepared in a similar manner as described in Example 2.60 starting from 5-(cyclohex-1-en-1-yl)-1,5-dimethylimidazolidine-2,4-dione (Example 2.69a) (42 mg, 0.2 mmol) and 2-bromo-1-(1H-pyrrol-2-yl)ethanone (45 mg, 0.22 mmol) to obtain the desired product (12 mg, 20%) as a white solid. $^1$H NMR is consistent with structure. MS 316 (MH$^+$).

Example 2.69a 5-(cyclohex-1-en-1-yl)-1,5-dimethylimidazolidine-2,4-dione

Prepared in a similar manner as described in Example 2.60a starting from 5-(cyclohex-1-en-1-yl)-3-(4-methoxybenzyl)-1,5-dimethylimidazolidine-2,4-dione (Example 2.69b) (328 mg, 1 mmol) to obtain the desired product (104 mg, 50%) as a white solid. $^1$H NMR is consistent with structure. MS 329 (MH$^+$).

Example 2.69b 5-(cyclohex-1-en-1-yl)-3-(4-methoxybenzyl)-1,5-dimethylimidazolidine-2,4-dione Prepared in a similar manner as described in Example 2.60b starting from 5-(cyclohex-1-en-1-yl)-3-(4-methoxybenzyl)imidazolidine-2,4-dione (69c) (600 mg, 2 mmol) to obtain the product (540 mg, 82%) as a white solid. $^1$H NMR is consistent with structure. MS 329 (MH$^+$).

Example 2.69c 5-(cyclohex-1-en-1-yl)-3-(4-methoxybenzyl)imidazolidine-2,4-dione Prepared in a similar manner as described in Example 2.60c starting from 5-(cyclohex-1-en-1-yl)imidazolidine-2,4-dione (Example 2.69d) (720 mg, 4 mmol) to obtain the desired product (900 mg, 75%) as a white solid. $^1$H NMR is consistent with structure. MS 301 (MH$^+$).

Example 2.69d: 5-(cyclohex-1-en-1-yl)imidazolidine-2,4-dione

Prepared in a similar manner as described in Example 2.60d starting from cyclohex-1-enecarbaldehyde (1100 mg, 10 mmol) to obtain the desired product (800 mg, 44%) as a white solid. $^1$H NMR is consistent with structure. MS 181 (MH$^+$).

Example 2.70: 5-(2-methoxyphenyl)-1,5-dimethyl-3-(2-oxo-2-phenylethyl)imidazolidine-2,4-dione In an oven-dried, $N_2$-flushed, small round-bottom flask, were added anhydrous DMF (3.0 mL), 5-(2-methoxyphenyl)-5-methyl-3-(2-oxo-2-phenylethyl)imidazolidine-2,4-dione (Example 2.70a) (170 mg, 0.5 mmol), $K_2CO_3$ (138.0 mg, 1 mmol), and MeI (38 µL, 1.2 mmol). The reaction medium was stirred vigorously at room temperature for 21 hours, poured in water (20 mL) and extracted with EtOAc (3×). Combined organic phases were washed with brine and dried over $MgSO_4$, and solvents were evaporated. The residue was purified by preparative HPLC using a $CH_3CN$/$H_2O$ gradient as eluant to obtain the pure desired product (76 mg, 43%) as an oily film. $^1$H NMR (400 MHz, DMSO-$d_6$) δ 8.11-8.05 (m, 2H), 7.71 (t, J=7.4 Hz, 1H), 7.57 (dd, J=11.6, 4.3 Hz, 2H), 7.50 (dd, J=8.0, 1.6 Hz, 1H), 7.45-7.37 (m, 1H), 7.08-6.99 (m, 2H), 5.05 (s, 2H), 3.72 (s, 3H), 3.31 (s, 3H), 1.77 (s, 3H). MS 353 (MH$^+$).

Example 2.70a: 5-(2-methoxyphenyl)-5-methyl-3-(2-oxo-2-phenylethyl)imidazolidine-2,4-dione In an oven-dried, $N_2$-flushed, small round-bottom flask, were added anhydrous DMF (4.0 mL), 5-(2-methoxyphenyl)-5-methylimidazolidine-2,4-dione (Example 2.60d) (220 mg, 1.0 mmol), $K_2CO_3$ (276 mg, 2.0 mmol), and 2-bromo-1-phenylethanone (199 mg, 1.0 mmol). The reaction medium was stirred vigorously at room temperature for 19 hours, poured in water (20 mL) and extracted with EtOAc (3×). Combined organic phases were washed with brine and dried over $MgSO_4$, and solvents were evaporated. The residue was purified by flash chromatography using a 40 g Silicycle column and a Hexanes/EtOAc gradient as eluant to obtain the pure desired product (300 mg, 89%) as a white powder. $^1$H NMR (400 MHz, CDCl$_3$) δ 8.02-7.95 (m, 2H), 7.66-7.60 (m, 1H), 7.57 (dd, J=7.7, 1.6 Hz, 1H), 7.54-7.48 (m, 2H), 7.34 (ddd, J=8.2, 7.5, 1.7 Hz, 1H), 7.02-6.94 (m, 2H), 6.46 (s, 1H), 5.05-4.93 (m, 2H), 3.92 (s, 3H), 1.90 (d, J=6.6 Hz, 3H). MS 339 (MH$^+$).

Example 2.71: 5-(2-hydroxyphenyl)-1,5-dimethyl-3-(2-oxo-2-phenylethyl)imidazolidine-2,4-dione In an oven-dried, $N_2$-flushed, small round-bottom flask, were added anhydrous methanol (5.0 mL), 5-(2-benzyloxy)-1,5-dimethyl-3-(2-oxo-2-phenylethyl)imidazolidine-2,4-dione (Example 2.120) (86 mg, 0.2 mmol), 10% Pd/C (25 mg), and the reaction medium was stirred vigorously and hydrogenated with hydrogen balloon at room temperature overnight. The reaction mixture was filtered through plug of Celite and the solvent was evaporated. The residue was purified by HPLC to obtain the pure product (20 mg, 30%) as a white powder. $^1$H NMR (400 MHz, CDCL$_3$) δ 8.00-7.93 (m, 2H), 7.66-7.58 (m, 1H), 7.54-7.45 (m, 2H), 7.32-7.19 (m, 2H), 6.98 (td, J=7.7, 1.2 Hz, 1H), 6.90 (dd, J=8.0, 1.1 Hz, 1H), 4.99 (s, 2H), 2.85 (s, 3H), 1.98 (s, 3H).

Example 2.72: 5-cyclohexyl-3-(2-(4-fluorophenyl)-2-oxoethyl)-1,5-dimethyl-imidazolidine-2,4-dione Prepared in a similar manner as described in Example 2.44 starting from 5-cyclohexyl-1,5-dimethylimidazolidine-2,4-dione (Example 2.47a) (210 mg, 1 mmol) and 2-bromo-1-(3-fluorophenyl)ethanone (260 mg, 1.2 mmol) to obtain the desired product (280 mg, 81%) as a white powder. $^1$H NMR (400 MHz, DMSO-$d_6$) δ 8.11 (dd, J=5.6 Hz, J=8.8 Hz, 2H), 7.39 (t, J=8 Hz, 2H), 4.94 (s, 2H), 2.79 (s, 3H), 1.73-1.67 (m, 4H), 1.61-1.58 (m, 2H), 1.36 (s, 3H), 1.34-1.30 (m, 1H), 1.21-1.13 (m, 2H), 1.04-1.00 (m, 1H), 0.92-0.88 (m, 1H).

Example 2.73: 5-(cyclohex-1-en-1-yl)-1,5-dimethyl-3-(2-oxo-2-(pyridin-3-yl)ethyl) Imidazolidine-2,4-dione Prepared in a similar manner as described in Example 2.60 starting from 5-(cyclohex-1-en-1-yl)-1,5-dimethylimidazolidine-2,4-dione (Example 2.69a) (52 mg, 0.25 mmol) and 2-bromo-1-(pyridin-3-yl)ethanone hydrochloride (84 mg, 0.3 mmol) to obtain the product (35 mg, 43%) as a light yellow solid. $^1$H NMR (400 MHz, CDCl$_3$) δ 9.23-9.15 (m, 1H), 8.84 (dd, J=4.8, 1.7 Hz, 1H), 8.28-8.17 (m, 1H), 7.47 (ddd, J=8.0, 4.8, 0.8 Hz, 1H), 5.98-5.92 (m, 1H), 4.94 (s, 2H), 2.81 (s, 3H), 2.15 (dd, J=7.6, 5.1 Hz, 2H), 1.91 (d, J=4.2 Hz, 2H), 1.77-1.53 (m, 7H). MS 328 (MH$^+$).

Example 2.74: 5-(2-ethoxyphenyl)-1,5-dimethyl-3-(2-oxo-2-phenylethyl)imidazolidine-2,4-dione Prepared in a similar manner as described in Example 2.44 starting from 5-(2-ethoxyphenyl)-5-methyl-3-(2-oxo- 2-phenylethyl)imidazolidine-2,4-dione (Example 2.74a) (319 mg, 0.9 mmol) and methyl iodide (67 μL, 1.08 mmol) to obtain product as a white powder (81 mg, 25% yield). $^1$H NMR (400 MHz, DMSO-d$_6$) δ 8.08 (d, J=8 Hz, 2H), 7.71 (t, J=8 Hz, 1H), 7.57 (t, J=8 Hz, 2H), 7.49 (d, J=8 Hz, 1H), 7.38 (t, J=8 Hz, 1H), 5.01 (q, J=16 Hz, J=56 Hz, 2H), 3.945 (q, J=8 Hz, J=12 Hz, 2H), 2.48 (s, 3H), 1.78 (s, 3H), 1.22 (t, J=8 Hz, 3H). MS 367 (MH$^+$).

Example 2.74a: 5-(2-ethoxyphenyl)-5-methyl-3-(2-oxo-2-phenylethyl)imidazolidine-2,4-dione Prepared in a similar manner as described in Example 2.44a starting from 5-(2-ethoxyphenyl)-5-methylimidazolidine-2,4-dione (Example 2.74b) (234 mg, 1 mmol) and 2-bromoacetophenone (200 mg, 1 mmol) to obtain product as a white powder (320 mg, 91% yield). $^1$H NMR (400 MHz, DMSO-d$_6$) δ 8.38 (s, 1H), 8.07 (d, J=8 Hz, 2H), 7.70 (t, J=8 Hz, 1H), 7.57 (t, J=8 Hz, 2H), 7.44 (d, J=8 Hz, 1H), 7.33 (t, J=8 Hz, 1H), 6.96 (m, 2H), 4.95 (q, J=18 Hz, J=40 Hz, 2H), 3.95 (q, J=8 Hz, J=12 Hz, 2H), 3.31 (s, 3H), 1.75 (s, 3H), 1.25 (t, J=8 Hz, 3H). MS 352 (MH$^+$).

Example 2.74b: 5-(2-ethoxyphenyl)-5-methylimidazolidine-2,4-dione

Prepared in a similar manner as described in Example 2.44b starting from 1-(2-ethoxy phenyl)ethanone (984 mg, 6 mmol) to obtain product as a white powder (1.3 g, 93% yield). $^1$H NMR (400 MHz, DMSO-d$_6$) δ 10.51 (s, 1H), 7.87 (s, 1H), 7.36 (d, J=8 Hz, 2H), 7.30 (t, J=8 Hz, 1H), 6.96 (m, 2H), 3.95 (m, 2H), 1.61 (s, 3H), 1.26 (t, J=8 Hz, 3H). MS 235 (MH$^+$).

Example 2.75: 5-((1R,4S)-bicyclo[2.2.1]heptan-2-yl)-1,5-dimethyl-3-(2-oxo-2-phenylethyl) imidazolidine-2,4-dione The title compound was isolated during the purification of 42. Compound 75 eluted after compound 42 on the HPLC during the separation of the diastereomers. The procedure is identical to that of 42. $^1$H-NMR (400 MHz, DMSO-d$_6$) δ 8.05-8.03 (s, 2H), 7.73-7.69 (m, 1H), 7.59-7.56 (m, 2H), 4.97 (s, 2H), 2.83 (s, 3H), 2.21 (s, 1H), 2.02 (s, 1H), 1.89-1.86 (m, 2H), 2.02 (s, 1H), 1.89-1.86 (m, 2H), 1.49-1.47 (m, 2H), 1.35-1.29 (m, 4H), 1.19-1.14 (m, 3H), 0.97-0.95 (m, 1H); MS 341 (MH$^+$).

Example 2.76: 5-(2-isopropoxyphenyl)-1,5-dimethyl-3-(2-oxo-2-phenylethyl) imidazolidine-2,4-dione Prepared in a similar manner as described in Example 2.70 starting from 5-(2-isopropoxyphenyl)-5-methyl-3-(2-oxo-2-phenylethyl)imidazolidine-2,4-dione (Example 2.76a) (183 mg, 0.5 mmol) and MeI (40 μL, 0.6 mmol) to obtain the desired product (100 mg, 53%) as a white solid. $^1$H NMR (400 MHz, CDCl$_3$) δ 8.00 (dd, J=8.4, 1.3 Hz, 2H), 7.61 (d, J=7.4 Hz, 1H), 7.55-7.47 (m, 2H), 7.45 (dd, J=7.8, 1.6 Hz, 1H), 7.38-7.30 (m, 1H), 6.98 (td, J=7.6, 1.1 Hz, 1H), 6.87 (d, J=8.1 Hz, 1H), 4.99 (d, J=2.1 Hz, 2H), 4.67-4.57 (m, 1H), 2.62 (s, 3H), 1.93 (s, 3H), 1.27 (dd, J=13.3, 6.0 Hz, 6H). MS 381 (MH$^+$).

Example 2.76a: 5-(2-isopropoxyphenyl)-5-methyl-3-(2-oxo-2-phenylethyl)imidazolidine-2,4-dione Prepared in a similar manner as described in Example 2.70a starting from 5-(2-isopropoxyphenyl)-5-methylimidazolidine-2,4-dione (Example 2.76b) (264 mg, 1 mmol) and 2-bromo-1-phenylethanone (199 mg, 1.0 mmol) to obtain the desired product (283 mg, 77%) as a white solid. $^1$H NMR is consistent with structure. MS 367 (MH$^+$).

Example 2.76b: 5-(2-isopropoxyphenyl)-5-methyl-imidazolidine-2,4-dione

Prepared in a similar manner as described in Example 2.60d starting from 1-(2-isopropoxyphenyl)ethanone (1424 mg, 8 mmol) to obtain the desired product (1.7 g, 86%) as a white solid. $^1$H NMR is consistent with structure. MS 249 (MH$^+$).

Example 2.77: 5-cycloheptyl-1,5-dimethyl-3-(2-oxo-2-phenylethyl)imidazolidine-2,4-dione Prepared in a similar manner as described in Example 2.70 starting from 5-cycloheptyl-5-methyl-3-(2-oxo-2-phenylethyl)imidazolidine-2,4-dione (Example 2.77a) (50 mg, 0.15 mmol) and MeI (12 μL, 0.2 mmol) to obtain the desired product (20 mg, 39%) as a white solid. $^1$H NMR (400 MHz, CDCl$_3$) δ 8.02-7.93 (m, 2H), 7.66-7.58 (m, 1H), 7.49 (ddd, J=6.7, 4.6, 1.1 Hz, 2H), 4.91 (s, 2H), 2.91 (s, 3H), 1.91-1.63 (m, 6H), 1.62 (s, 1H), 1.61-1.53 (m, 3H), 1.53-1.50 (m, 4H), 1.41-1.25 (m, 2H). MS 343 (MH$^+$).

Example 2.77a: 5-cycloheptyl-5-methyl-3-(2-oxo-2-phenylethyl)imidazolidine-2,4-dione Prepared in a similar manner as described in Example 2.70a starting from 5-cycloheptyl-5-methylimidazolidine-2,4-dione (Example 2.77b) (105 mg, 0.5 mmol) and 2-bromo-1-phenylethanone (100 mg, 0.5 mmol) to obtain the desired product (80 mg, 49%) as a white solid. $^1$H NMR (400 MHz, CDCl$_3$) δ 8.02-7.92 (m, 2H), 7.67-7.58 (m, 1H), 7.50 (ddd, J=8.0, 6.8, 1.1 Hz, 2H), 5.49 (s, 1H), 4.91 (s, 2H), 1.98-1.88 (m, 2H), 1.81-1.65 (m, 3H), 1.62-1.55 (m, 3H), 1.52 (d, J=4.6 Hz, 3H), 1.51-1.36 (m, 4H), 1.29-1.17 (m, 1H). MS 329 (MH$^+$).

Example 2.77b: 5-cycloheptyl-5-methylimidazolidine-2,4-dione

Prepared in a similar manner as described in Example 2.60d starting from 1-cycloheptyl-ethanone (600 mg, 4.28 mmol) to obtain the desired product (250 mg, 28%) as a white solid. $^1$H NMR is consistent with structure. MS 211 (MH$^+$).

Example 2.78: 3-(2-(4-aminophenyl)-2-oxoethyl)-5-cyclohexyl-1,5-dimethyl-imidazolidine-2,4-dione To a solution of 5-cyclohexyl-1,5-dimethyl-3-(2-(4-nitrophenyl)-2-oxoethyl) imidazolidine-2,4-dione (Example 2.78a) (240 mg, 0.64 mmol) in MeOH (5 mL) was added Pd/C (10%, 48 mg) under N$_2$. The resulting mixture was stirring at room temperature for 2 hrs. The mixture was filtered through celite and concentrated and the resulting crude material was purified by mass-triggered HPLC. The desired product (120 mg, 54%) was obtained as a clear colorless oil. $^1$H NMR (400 MHz, DMSO-d$_6$) δ 7.68 (d, J=8.8 Hz, 2H), 6.55 (d, J=8.8 Hz, 2H), 6.20 (s, 2H), 4.69 (s, 2H), 2.78 (s, 3H), 1.56-1.73 (m, 6H), 0.91-1.29 (m&s, 8H). MS 344 (MH$^+$).

Example 2.78a: 5-cyclohexyl-1,5-dimethyl-3-(2-(4-nitrophenyl)-2-oxoethyl)imidazolidine-2,4-dione In an oven-dried, N$_2$-flushed, small round-bottom flask, were added anhydrous DMF (8.0 mL), 5-cyclohexyl-1,5-dimethylimidazolidine-2,4-dione (Example 2.47a) (210 mg, 1.0 mmol), and the solution was cooled to 0° C. in an ice bath. NaH (48 mg, 1.2 mmol), and 2-bromo-1-(4-nitrophenyl)ethanone (293 mg, 1.2 mmol) was added the ice bath was removed and the reaction medium was stirred vigorously at room temperature for 1.5 hr. The mixture was diluted with water and extracted with EtOAc (3×10 mL). The combined organic phases were washed with brine and dried over MgSO$_4$, and solvents were evaporated. The residue was purified by flash chromatography using a 12 g Silicycle column and EtOAc/Hex gradient as eluant to obtain the pure product (300 mg, 80%) as a light yellow oil. MS 374 (MH$^+$). $^1$H-NMR is consistent with the structure.

Example 2.79: 5-(6,6-dimethylbicyclo[3.1.1]hept-2-en-2-yl)-1,5-dimethyl-3-(2-oxo-2-phenylethyl)imidazolidine-2,4-dione Prepared in a similar manner as described in Example 2.44 starting from 5-(6,6-dimethy bicyclo[3.1.1]hept-2-en-2-yl)-1,5-dimethylimidazolidine-2,4-dione (Example 2.79a) (24.5 mg, 0.1 mmol) and 2-bromoacetophenone (24 mg, 0.12 mmol). Gives 3.1 mg (8% yield) of product as a white powder. On HPLC this isomer elutes first. $^1$H NMR (400 MHz, DMSO-d$_6$) δ 7.95 (d, J=8 Hz, 2H), 7.61 (t, J=8 Hz, 1H), 7.49 (t, J=8 Hz, 2H), 5.79 (m, 1H), 4.92 (s, 2H), 2.82 (s, 3H), 2.29-2.44 (m, 3H), 2.17 (t, J=4 Hz, 1H), 2.10 (m, 1H), 1.63 (s, 3H), 1.29 (s, 3H), 1.14 (d, J=8 Hz, 1H), 0.84 (s, 3H). MS 367 (MH$^+$).

Example 2.79a: 5-(6,6-dimethylbicyclo[3.1.1]hept-2-en-2-yl)-1,5-dimethylimidazolidine-2,4-dione Prepared in a similar manner as described in Example 2.45a starting from 5-(6,6-dimethylbicyclo[3.1.1]hept-2-en-2-yl)-3-(4-methoxybenzyl)-1,5-dimethylimidazolidine-2,4-dione (Example 2.79b) (470 mg, 1.27 mmol) and a solution of ammonium cerium nitrate (1.82 g, 3.32 mmol) in water (10 mL) to obtain product as a white powder of mixture of 2 pairs of diastereomers (24.5 mg, 8% yield). $^1$H NMR (400 MHz, DMSO-d$_6$) δ 10.81 (bs, 1H), 5.69 (m, 1H), 2.56-2.57 (2s, 3H), 2.20-2.38 (m, 3H), 2.04 (m, 1H), 1.67-1.77 (m, 1H), 1.38-1.39 (2s, 3H), 1.19-1.21 (2s, 3H), 0.98 (m, 1H), 0.68-0.75 (2s, 3H). MS 249 (MH$^+$).

Example 2.79b: 5-(6,6-dimethylbicyclo[3.1.1]hept-2-en-2-yl)-3-(4-methoxybenzyl)-1,5-dimethylimidazolidine-2,4-dione Prepared in a similar manner as described in Example 2.45b starting from 5-((1R,5S)-6,6-dimethylbicyclo[3.1.1]hept-2-en-2-yl)-3-(4-methoxybenzyl)imidazolidine-2,4-dione (Example 2.79c) (552 mg, 1.62 mmol) and methyl iodide (222 μL, 3.56 mmol) to obtain product as a colorless oil of mixture of 2 pairs of diastereomers 2:1 ratio (471.3 mg, 79% yield). $^1$H NMR (400 MHz, DMSO-d$_6$) δ 7.16 (d, J=8 Hz, 1.3H), 7.13 (d, J=8 Hz, 0.7H), 6.85 (d, J=8 Hz, 2H), 5.70 (dm, J=12 Hz, 1H), 4.44 (m, 2H), 3.69-3.70 (2s, 3H), 2.61-2.63 (2s, 3H), 2.16-2.30 (m, 3H), 1.98 (m, 1H), 1.60 (t, J=4 Hz, 0.3H), 1.45 (t, J=4 Hz, 0.7H), 1.41 (s, 3H), 1.14 (s, 1H), 0.96 (s, 2H), 0.92 (m, 1H), 0.69 (s, 1H), 0.55 (s, 2H). MS 369 (MH$^+$).

Example 2.79c: 5-((1R,5S)-6,6-dimethylbicyclo[3.1.1]hept-2-en-2-yl)-3-(4-methoxybenzyl)-imidazolidine-2,4-dione Prepared in a similar manner as described in Example 2.45c starting from 5-((1R,5S)-6,6-dimethylbicyclo[3.1.1]hept-2-en-2-yl)imidazolidine-2,4-dione (Example 2.79d) (1.21 g, 5.5 mmol) and 4-methoxybenzyl chloride (896 μL, 6.6 mmol) to obtain product as a yellowish powder (552.4 mg, 30% yield). $^1$H NMR (400 MHz, DMSO-d$_6$) δ 9.97 (s, 1H), 7.16 (d, J=8 Hz, 2H), 6.85 (d, J=8 Hz, 2H), 4.45 (s, 2H), 3.94 (t, J=4 Hz, 1H), 3.69 (s, 3H), 2.32-2.40 (m, 3H), 1.85-1.97 (m, 3H), 1.30 (d, J=8 Hz, 1H), 1.23 (s, 3H), 0.65 (s, 3H). MS 341 (MH$^+$).

Example 2.79d: 5-((1R,5S)-6,6-dimethylbicyclo[3.1.1]hept-2-en-2-yl)imidazolidine-2,4-dione Prepared in a similar manner as described in Example 2.44b starting from (1R)-(−)-myrtenal (1.5 g, 10 mmol) to obtain product as a white powder (1.87 g, 85% yield). $^1$H NMR (400 MHz, DMSO-d$_6$) δ 10.72 (s, 1H), 9.63 (s, 1H), 3.90 (t, J=4 Hz, 1H), 2.31-2.37 (m, 3H), 1.85-1.97 (m, 3H), 2.30 (d, J=8 Hz, 1H), 1.21 (s, 3H), 0.65 (s, 3H). MS 221 (MH$^+$).

Example 2.80: 1,5-dimethyl-5-(3-methylcyclohexyl)-3-(2-oxo-2-phenylethyl) imidazolidine-2,4-dione Prepared in a similar manner as described in Example 2.44 starting from 5-methyl-5-(3-methylcyclohexyl)-3-(2-oxo-2-phenylethyl)imidazolidine-2,4-dione (Example 2.80a) (534 mg, 1.63 mmol) and methyl iodide (122 μL, 1.95 mmol) to obtain product as a white powder of mixture of 4 pairs of diastereomers (236 mg, 42% yield). $^1$H NMR (400 MHz, DMSO-d$_6$) δ 8.02 (d, J=8 Hz, 2H), 7.69 (t, J=8 Hz, 1H), 7.55 (t, J=8 Hz, 2H), 4.94 (s, 2H), 2.80 (t, J=8 Hz, 3H), 1.86-2.08 (m, 1H), 1.39-1.80 (m, 5H), 1.35-1.38 (2s, 3H), 1.15-1.40 (m, 3H), 0.87-1.03 (m, 1H), 0.95 (dd, J=2.8 Hz, J=7.4 Hz, 1H), 0.86 (t, J=8 Hz, 2H), 0.57-0.74 (m, 1H). MS 329 (MH$^+$).

Example 2.80a: 5-methyl-5-(3-methylcyclohexyl)-3-(2-oxo-2-phenylethyl)imidazolidine-2,4-dione Prepared in a similar manner as described in Example 2.44a starting from 5-methyl-5-(3-methylcyclohexyl)imidazolidine-2,4-dione (Example 2.80b) (420 mg, 2 mmol) and 2-bromoacetophenone (478 mg, 2.4 mmol) to obtain product as a white powder of mixture of 4 pairs of diastereomers (540 mg, 82% yield). $^1$H NMR (400 MHz, DMSO-d$_6$) δ 8.35 (d, J=8 Hz, 1H), 8.02 (d, J=8 Hz, 2H), 7.69 (t, J=8 Hz, 1H), 7.55 (t, J=8 Hz, 2H), 4.90 (s, 2H), 1.96-2.05 (m, 0.5H), 1.41-1.77 (m, 5H), 1.17-1.36 (m, 2.5H), 1.28-1.31 (4s, 3H), 0.97 (m, 1H), 0.83-0.94 (4d, J=6 Hz, 3H), 0.73 (m, 1H). MS 329 (MH$^+$).

Example 2.80b: 5-methyl-5-(3-methylcyclohexyl) imidazolidine-2,4-dione

Prepared in a similar manner as described in Example 2.44b starting from 1-(3-methylcyclohexyl)-ethanone (Example 2.80c) (2.72 g, 19.44 mmol) to obtain product as a white powder of mixture of 4 pairs of diastereomers (2.52 g, 62% yield). $^1$H NMR (400 MHz, DMSO-d$_6$) δ 10.41 (bs, 1H), 7.78 (s, 1H), 1.96-2.05 (m, 0.5H), 1.63-1.72 (m, 1.5H), 1.57 (m, 1H), 1.48 (m, 1H), 1.22-1.38 (m, 3H), 1.14-1.18 (4s, 3H), 0.14-1.22 (m, 1H), 0.80-0.92 (4d, J=6 Hz, 3H), 0.60-0.73 (m, 1H). MS 211 (MH⁺).

Example 2.80c: 1-(3-methylcyclohexyl)-ethanone

Prepared in a similar manner as described in Example 2.59e starting from 3-methylcyclohexane-carboxylic acid (2.87 mL, 20 mmol) to obtain product as a colorless oil consisting of two pairs of diastereomers (2:1 ratio by NMR analysis) (2.72 g, 97% yield). $^1$H NMR (400 MHz, CDCl$_3$) δ 2.53 (m, 0.3H), 2.30 (m, 0.7H), 2.07 (2s, 3H), 1.72-1.83 (m, 3H), 1.59-1.64 (m, 1H), 1.49 (m, 1H), 1.36 (m, 1H), 1.15-1.26 (m, 1H), 0.96-1.12 (m, 1H0, 0.85-0.86 (2s, 3H), 0.76-0.83 (m, 1H). MS N/A (MH⁺).

Example 2.81: 5-cyclohexyl-3-(2-(3,4-dihydroxyphenyl)-2-oxoethyl)-1,5-dimethyl-imidazolidine-2,4-dione Prepared in a similar manner as described in Example 2.43 using 5-cyclohexyl-1,5-dimethylimidazolidine-2,4-dione (Example 2.47a) (100.0 mg, 476 mol), and commercially available 2-chloro-1-(3,4-dihydroxyphenyl)ethanone (100.0 mg, 536 μmol), to obtain the desired product (47.6 mg, 28%). $^1$H NMR (400 MHz, d$_6$-DMSO) δ 7.45 (dd, J=8.3, 2.2 Hz, 1H), 7.34 (d, J=2.1 Hz, 1H), 6.84 (d, J=8.3 Hz, 1H), 4.78 (s, 2H), 2.81 (s, 3H), 1.78-1.66 (m, 4H), 1.65-1.57 (m, 2H), 1.37 (s, 3H), 1.36-1.28 (m, 1H), 1.26-1.12 (m, 2H), 1.10-0.91 (m, 2H). MS 361 (MH⁺).

Example 2.82: 3-(2-(benzo[d][1,3]dioxol-5-yl)-2-oxoethyl)-5-cyclohexyl-1,5-dimethylimidazolidine-2,4-dione Prepared in a similar manner as described in Example 2.43 using 5-cyclohexyl-1,5-dimethylimidazolidine-2,4-dione (Example 2.47a) (100.0 mg, 476 umol), and commercially available 1-(benzo[d][1,3]dioxol-5-yl)-2-bromoethanone (144.0 mg, 592 umol), to obtain the desired product. $^1$H NMR (400 MHz, d$_6$-DMSO) δ 7.70 (dd, J=8.2, 1.8 Hz, 1H), 7.51 (d, J=1.7 Hz, 1H), 7.09 (d, J=8.2 Hz, 1H), 6.17 (s, 2H), 4.87 (s, 2H), 2.81 (s, 3H), 1.79-1.66 (m, 4H), 1.65-1.56 (m, 2H), 1.38 (s, 3H), 1.37-1.28 (m, 1H), 1.25-1.12 (m, 2H), 1.10-1.00 (m, 1H), 0.99-0.87 (m, 1H). MS 374 (MH⁺).

Example 2.83: 5-cyclohexyl-1,5-dimethyl-3-(2-oxo-2-(pyridin-4-yl)ethyl)imidazolidine-2,4-dione Prepared in a similar manner as described in Example 2.45 starting from 5-cyclohexyl-1,5-dimethylimidazolidine-2,4-dione (68 mg, 0.32 mmol) (Example 2.47a) and 4-(bromoacetyl)-pyridine hydrobromide (108 mg, 0.38 mmol) to obtain the desired product (30 mg, 23%) as a light yellow oil. $^1$H NMR (400 MHz, DMSO-d$_6$) δ 8.84 (d, J=4.4 Hz, 2H), 7.73 (d, J=4.4 Hz, 2H), 4.88 (s, 2H), 2.91 (s, 3H), 1.665 (m, 6H), 1.47 (s & m, 4H), 1.01 (m, 4H). MS 330 (MH⁺).

Example 2.84: 1,5-dimethyl-5-(4-methylcyclohexyl)-3-(2-oxo-2-phenylethyl)imidazolidine-2,4-dione Prepared in a similar manner as described in Example 2.105 starting from 1,5-dimethyl-5-(4-methylcyclohexyl)-3-((2-phenyl-1,3-dioxolan-2-yl)methyl)imidazolidine-2,4-dione (Example 2.84a) (386 mg, 1 mmol) to obtain product as a colorless oily film consisting of two pairs of diastereomers (2:1 ratio by NMR analysis) (20 mg, 6% yield). $^1$H NMR (400 MHz, DMSO-d$_6$) δ 8.01 (d, J=8 Hz, 2H), 7.69 (t, J=8 Hz, 1H), 7.55 (t, J=8 Hz, 2H), 4.94 (m, 2H), 2.80 (s, 2H), 2.79 (s, 1H), 1.88 (m, 1H), 1.52-1.71 (m, 3H), 1.30-1.48 (m, 4H), 1.37 (s, 3H), 1.16 (m, 1H), 0.87-1.05 (m, 1H), 0.83 (m, 3H). MS 343 (MH⁺).

Example 2.84a: 1,5-dimethyl-5-(4-methylcyclohexyl)-3-((2-phenyl-1,3-dioxolan-2-yl)methyl)-imidazolidine-2,4-dione Prepared in a similar manner as described in Example 2.95b starting from 5-(4-methylcyclohexyl)-3-((2-phenyl-1,3-dioxolan-2-yl)methyl)imidazolidine-2,4-dione (Example 2.84b) (395 mg, 1.1 mmol) to obtain product as a colorless oil consisting of two pairs of diastereomers (386 mg, 90% yield). MS 387 (MH⁺).

Example 2.84b: 5-(4-methylcyclohexyl)-3-((2-phenyl-1,3-dioxolan-2-yl)methyl)imidazolidine-2,4-dione Prepared in a similar manner as described in Example 2.95c starting from methyl 2-(4-methyl-cyclohexyl)-2-(3-((2-phenyl-1,3-dioxolan-2-yl)methyl)ureido)acetate (84c) (460 mg, 1.18 mmol) to obtain product as a white solid (398.6 mg, 94% yield). $^1$H NMR (400 MHz, DMSO-d$_6$) δ 7.31-7.37 (m, 5H), 3.89 (m, 2H), 3.67 (m, 4H), 1.88 (m, 1H), 1.52-1.71 (m, 3H), 1.30-1.48 (m, 4H), 1.16 (m, 1H), 0.87-1.05 (m, 1H), 0.85 (m, 3H). MS 359 (MH⁺).

Example 2.84c: Methyl 2-(4-methylcyclohexyl)-2-(3-((2-phenyl-1,3-dioxolan-2-yl)methyl)ureido)acetate Prepared in a similar manner as described in Example 2.95d starting from methyl 2-amino-2-(4-methylcyclohexyl)acetate (Example 2.84d) (225 mg, 1.21 mmol) and 2-(isocyanatomethyl)-2-phenyl-1,3-dioxolane (373 mg, 1.82 mmol) to obtain product as a colorless oil (461.6 mg, 98% yield). $^1$H NMR (400 MHz, DMSO-d$_6$) δ 7.27-7.39 (m, 5H), 6.38 (d, J=8 Hz, 1H), 6.03 (q, J=6 Hz, J=12 Hz, 1H), 4.11 (t, J=8 Hz, 0.5H), 4.01 (m, 2.5H), 3.73 (m, 2H), 3.58 (s, 3H), 3.40 (m, 1H), 3.30 (m, 1H), 1.63 (m, 2H), 1.34-1.49 (m, 3H), 1.13-1.30 (m, 3H), 0.98 (m, 1H), 0.85 (m, 1H), 0.88 (d, J=8 Hz, 1.5H), 0.82 (d, J=8 Hz, 1.5H). MS 391 (MH⁺).

Example 2.84d: Methyl 2-amino-2-(4-methylcyclohexyl)acetate

Prepared following Scheme A.

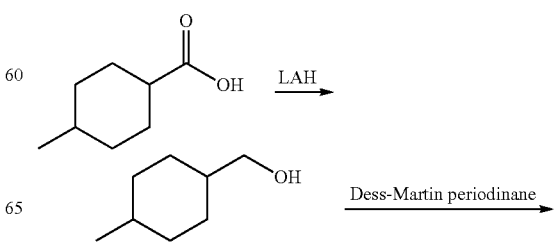

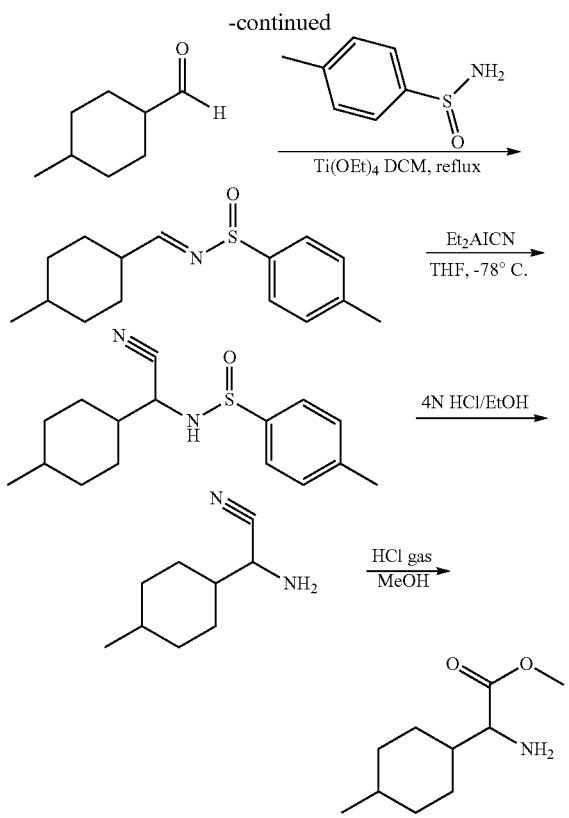

Example 2.84d-1: Methyl 2-amino-2-(4-methylcyclohexyl)acetate

2-Amino-2-(4-methylcyclohexyl)acetonitrile hydrochloride (Example 2.84d-2) (335 mg, 1.77 mmol) in 200 mL of MeOH was saturated with HCl gas and then heated at 90° C. for 18 h. Reaction mixture was concentrated in vacuum; residue was washed with saturated NaHCO$_3$ and product was extracted with EtOAc (3×20 mL). Combined organic fractions were washed with brine, dried over MgSO$_4$ and solvent was removed in vacuum to obtain product as a colorless oil (227 mg, 69% yield). $^1$H NMR (400 MHz, DMSO-d$_6$) δ 3.58 (s, 3H), 3.12 (dd, J=6 Hz, J=40 Hz, 1H), 1.65 (m, 2H), 1.34-1.49 (m, 3H), 1.13-1.30 (m, 3H), 0.98 (m, 1H), 0.85 (m, 1H), 0.87 (d, J=8 Hz, 1.5H), 0.82 (d, J=8 Hz, 1.5H). MS 186 (MH$^+$).

Example 2.84d-2: 2-amino-2-(4-methylcyclohexyl)acetonitrile hydrochloride

N-(cyano(4-methylcyclohexyl)methyl)-4-methylbenzenesulfinamide (Example 2.84d-3) (730.7 mg, 2.52 mmol) in 35 mL MeOH was heated at 110° C. for 18 h with 4N HCl in dioxane (36.5 mL, 146 mmol). Then reaction mixture was concentrated in vacuum, residue was diluted with water (20 mL) and saturated NaHCO$_3$(10 mL) and then extracted with EtOAc (3×20 mL). Combined organic fractions were washed with brine, dried over MgSO$_4$ and solvent was removed in vacuum. To the residue was added 10 mL of 4N HCl in dioxane and reaction mixture was concentrated in vacuum again. Obtained product was washed with ether, filtered off and dried in vacuum to give 335 mg of product as a white powder (79% yield). $^1$H NMR (400 MHz, D$_2$O) δ 4.30 (dd, J=6 Hz, J=32 Hz, 1H), 1.90 (m, 0.5H), 1.73-1.85 (m, 1H), 1.62-1.70 (m, 2.5H), 1.07-1.54 (m, 5H), 0.86 (m, 1H), 0.79 (d, J=8 Hz, 1.5H), 0.73 (d, J=8 Hz, 1.5H). MS 153 (MH$^+$).

Example 84d-3: N-(cyano(4-methylcyclohexyl)methyl)methylbenzenesulfinamide

To a solution of diethylaluminum cyanide (1M in Toluene, 11.4 mL, 11.4 mmol) in 10 mL of anhydrous THF at −78° C. under N$_2$ was added isopropanol (4.56 mL, 7.6 mmol), warmed up to room temperature and stirred 30 min. Obtained solution was cannulated to the solution of (E)-4-methyl-N-((4-methylcyclohexyl)methylene)benzenesulfinamide (84d-4) (Example 2.2g, 7.6 mmol) in 40 mL of anhydrous THF cooled to −78° C. under N$_2$. Then reaction mixture was gradually warmed up to room temperature and stirred for 18 h. Obtained yellow solution was cooled to −78° C. and saturated NH$_4$Cl (50 mL) was added dropwise. Reaction mixture was warmed up to room temperature, and then filtered trough Celite. Filtrate was extracted with EtOAc (3×20 mL). Combined organic fractions were washed with brine, dried over MgSO$_4$ and solvent was removed in vacuum. Crude product was purified by flash chromatography using a 80 g Silicycle column (Hexane/EtOAc 20% gradient; R$_f$=0.3) to give 730.7 mg (33% yield) of product as a yellow oil. $^1$H NMR (400 MHz, DMSO-d$_6$) δ 7.51 (d, J=8 Hz, 2H), 7.43 (t, J=8 Hz, 1H), 7.38 (d, J=8 Hz, 2H), 4.10 (dt, J=8 Hz, J=48 Hz, 1H), 2.36 (s, 3H), 1.79 (m, 1H), 1.67 (m, 2H), 1.38-1.59 (m, 4H), 1.23-1.33 (m, 2H), 0.96-1.09 (m, 1H), 0.87 (d, J=8 Hz, 1.5H), 0.83 (d, J=8 Hz, 1.5H). MS 291 (MH$^+$).

Example 2.84d-4: (E)-4-Methyl-N-((4-methylcyclohexyl)methylene)benzenesulfinamide To the solution of 4-methylcyclohexanecarbaldehyde (Example 2.84d-5) (4.37 g, 34.68 mmol), (S)-(+)-p-Toluenesulfinamide (3.58 g, 23 mol) in 50 mL of anhydrous DCM was added Titanium (IV) ethoxide (14.46 mL, 69 mmol) and reaction mixture was heated at 40° C. for 18 h. Reaction mixture was diluted with water (40 mL) and 100 mL of DCM was added and resulting mixture was filtered trough Celite. Filtrate was extracted with DCM, combined organic phases were washed with H$_2$O and brine, dried over MgSO$_4$ and solvent was removed in vacuum. Crude product was purified by flash chromatography using a 120 g Silicycle column (Hexane/EtOAc 20% gradient; R$_f$=0.6) to give 5.83 g (64% yield) of (E)-4-methyl-N-((4-methylcyclohexyl)-methylene)benzenesulfinamide as a fluorescented yellow oil. MS 264 (MH$^+$).

Example 2.84d-5: 4-Methylcyclohexanecarbaldehyde

To a solution of (4-methylcyclohexyl)methanol (Example 2.84d-6) (4.83 g, 37.7 mmol) in 200 mL of anhydrous DCM was added Dess-Martin periodinane (24 g, 56.6 mol) and reaction mixture was stirred at room temperature for 2.5 h. Then reaction mixture was diluted with 1N NaOH and washed with it until all precipitate dissolved (~600 mL). Basic solution was extracted with DCM, combined organic fractions were washed with brine, dried over MgSO$_4$ and concentrated in vacuum. To the residue was added 50 mL of ether, formed precipitate was filtered off and filtrate was concentrated in vacuum to give a product as colorless oil, which was used in to next step without purification (5.74 g, 100% yield). ¹H NMR (400 MHz, CDCl₃) δ 9.64 (s, 1H), 2.32 (m, 1H), 1.87-2.03 (m, 2H), 1.75 (m, 1H), 1.49-1.53 (m, 4H), 1.39 (m, 1H), 0.84 (m, 1H), 0.85 (d, J=8 Hz, 1H), 0.81 (d, J=8 Hz, 2H). MS N/A (MH⁺).

Example 2.84d-6: (4-Methylcyclohexyl)methanol

To a solution of 4-methylcyclohexanecarboxylic acid (5 g, 35.21 mmol, mix of cis- and trans-isomers) in 20 mL of anhydrous THF at −20° C. under N₂ was added portionwise LiAlH₄ (95% powder, 1.4 g, 35.2 mmol). Reaction mixture was gradually warmed up to room temperature and stirred for 18 h. Then cooled to −20° C. and added H₂O (1.4 mL), then 15% NaOH (1.4 mL), and then H₂O (4 mL). Reaction mixture was allowed to stir at room temperature another 30 min, then anhydrous Na₂SO₄ was added (~10 g) and reaction mixture was diluted with ether (50 mL) and filtered. Filtrate was concentrated in vacuum to obtain crude product as colorless oil mixture of 2 pair of diastereomers 2:1 ratio 90% clean by LCMS analysis (4.83 g, 100%). ¹H NMR (400 MHz, CDCl₃) δ 3.74 (m, 0.5H), 3.53 (d, J=8 Hz, 1.4H), 3.44 (d, J=8 Hz, 0.6H), 1.85 (m, 0.5H), 1.61-1.76 (m, 3H), 1.40-1.53 (m, 4H), 1.22-1.28 (m, 2H), 0.92 (m, 1H), 0.91 (d, J=8 Hz, 2H), 0.88 (d, J=8 Hz, 1H). MS N/A (MH⁺).

Example 2.85: 1,5-dimethyl-3-(2-oxo-2-phenyl-ethyl)-5-(pentan-3-yl)imidazolidine-24-dione In an oven-dried, N₂-flushed, small round-bottom flask, were added anhydrous DMF (20 mL), 5-methyl-3-(2-oxo-2-phenylethyl)-5-(pentan-3-yl)imidazolidine-2,4-dione (Example 2.85a) (778 mg, 2.57 mmol), K₂CO₃ (532 mg, 3.85 mmol), and MeI (546 mg, 3.85 mmol). The reaction medium was stirred vigorously at room temperature for 21 hours, diluted with water and extracted with EtOAc (3×20 mL). The combined organic phases were washed with brine and dried over MgSO₄, and solvents were evaporated. The residue was purified by flash chromatography using a 12 g Silicycle column and a Hexanes/EtOAc gradient as eluant to obtain the pure product (750 mg, 86%) as an oily film. ¹H NMR (400 MHz, CDCl₃) δ 7.95 (d, J=8.4 Hz, 2H), 7.47 (t, J=7.2 Hz, 1H), 7.26 (t, J=7.2 Hz, 2H), 4.92 (s, 2H), 2.91 (s, 3H), 1.72 (m, 1H), 1.25-1.57 (s&m, 7H), 0.95 (t&t, J=7.6 Hz, 7.6 Hz, 6H). MS 317 (MH⁺).

Example 2.85a: 5-methyl-3-(2-oxo-2-phenylethyl)-5-(pentan-3-yl)imidazolidine-2,4-dione In an oven-dried, N₂-flushed, small round-bottom flask, were added anhydrous DMF (8 mL), 5-methyl-5-(pentan-3-yl) imidazolidine-2,4-dione (Example 2.85b) (600 mg, 3.26 mmol), K₂CO₃ (675 mg, 4.89 mmol), and 2-bromo-1-phenylethanone (973 mg, 4.89 mmol). The reaction mixture was stirred vigorously at room temperature for 19 hours, diluted with water and extracted with EtOAc (3×10 mL). The combined organic phases were washed with brine and dried over MgSO₄, and solvents were evaporated. The residue was purified by flash chromatography using a 12 g Silicycle column and a Hexanes/EtOAc gradient as eluant to obtain the pure product (778 mg, 52%) as a white powder. MS 303 (MH⁺). ¹H-NMR is consistent with the structure.

Example 2.85b: 5-methyl-5-(pentan-3-yl)imidazolidine-2,4-dione

In a N₂-flushed 150 mL pressure tube, were added H₂O (20 mL), 3-ethylpentan-2-one (2.0 g, 17.5 mmol) in MeOH (20 mL), (NH₄)₂CO₃ (5.21 g, 54.3 mmol), and KCN (1.25 g, 19.2 mmol) in H₂O (7 mL) was added dropwise over a few minutes. The tube was sealed and heated at 50° C. for 48 hours. The reaction medium was allowed to cool to room temperature and the obtained white precipitate was filtered and washed with cold H₂O, then dried to obtain the pure product (3.3 g, 93%). MS 185 (MH⁺). ¹H-NMR is consistent with the structure.

Example 2.86: 5-cyclohexyl-1,5-dimethyl-3-(2-oxo-2-(thiophen-2-yl)ethyl)imidazolidine-2,4-dione Prepared in a similar manner as described in Example 2.45 starting from 5-cyclohexyl-1,5-dimethylimidazolidine-2,4-dione (68 mg, 0.32 mmol) (Example 2.47a) and 2-bromo-acetylthiophenone (79 mg, 0.38 mmol) to obtain the desired product (6 mg, 6%) as a light yellow oil. ¹H NMR (400 MHz, DMSO-d₆) δ 7.788 (d, J=4 Hz, 1H), 7.699 (d, J=4.4 Hz), 7.161 (dd, J=4.4 Hz & 4 Hz) 4.847 (S, 2H), 2.906 (s, 3H), 1.659 (m, 6H), 1.471 (s, 3H), 1.037 (m, 5H). MS 335 (MH⁺).

Example 2.87: 5-cyclohexyl-1,5-dimethyl-3-(2-(1-methyl-1H-pyrazol-4-yl)-2-oxoethyl) imidazolidine-2,4-dione Prepared in a similar manner as described in Example 2.45 starting from 5-cyclohexyl-1,5-dimethylimidazolidine-2,4-dione (Example 2.47a) (0.109 g, 0.520 mmol), K₂CO₃ (0.086 g, 0.62 mmol), and 2-bromo-1-(1-methyl-1H-pyrazol-4-yl)ethanone (0.126 g, 0.62 mmol) in 0.5 mL DMF. The title compound was obtained as white solid 70 mg (41%). ¹H-NMR (400 MHz, DMSO-d₆) δ 8.51 (s, 1H), 8.04 (s, 1H), 4.64 (s, 2H), 3.90 (s, 3H), 2.80 (s, 3H), 1.76-1.57 (m, 6H), 1.39-1.28 (m, 4H), 1.23-0.90 (m, 4H); MS 333 (MH⁺).

Example 2.88: 5-((1S,4S)-bicyclo[2.2.1]hept-5-en-2-yl)-1,5-dimethyl-3-(2-oxo-2-phenylethyl) imidazolidine-2,4-dione Prepared in a similar manner as described in Example 2.70 starting from 5-(bicyclo[2.2.1]hept-5-en-2-yl)-5-methyl-3-(2-oxo-2-phenylethyl)imidazolidine-2,4-dione (Example 2.88a) (162 mg, 0.5 mmol) and MeI (40 μL, 0.6 mmol) to obtain the desired product (eluted second on HPLC) (50 mg, 39%) as a white solid. ¹H NMR (400 MHz, CDCl₃) δ 7.98-7.93 (m, 2H), 7.64-7.58 (m, 1H), 7.53-7.45 (m, 2H), 6.12 (dd, J=5.7, 3.1 Hz, 1H), 5.87 (dd, J=5.7, 2.9 Hz, 1H), 4.87 (q, J=17.4 Hz, 2H), 2.99 (s, 3H), 2.87 (s, 1H), 2.80 (s, 1H), 2.60-2.52 (m, 1H), 1.83 (dd, J=9.5, 3.8 Hz, 1H), 1.78-1.70 (m, 1H), 1.49-1.40 (m, 4H), 1.29 (d, J=8.3 Hz, 1H). MS 339 (MH⁺).

Example 2.88a: 5-(bicyclo[2.2.1]hept-5-en-2-yl)-5-methyl-3-(2-oxo-2-phenylethyl) imidazolidine-2,4-dione Prepared in a similar manner as described in Example 2.70a starting from 5-(bicyclo[2.2.1]hept-5-en-2-yl)-5-methylimidazolidine-2,4-dione (Example 2.88b) (248 mg, 1 mmol) and 2-bromo-1-phenylethanone (199 mg, 1 mmol) to obtain the desired product (250 mg, 77%) as a white solid (mixture of 2 isomers). First isomer: ¹H NMR (400 MHz, CDCl₃) δ 7.99 (d, J=1.2 Hz, 1H), 7.98-7.93 (m, 2H), 7.64-7.58 (m, 1H), 7.53-7.45 (m, 2H), 6.12 (dd, J=5.7, 3.1 Hz, 1H), 5.87 (dd, J=5.7, 2.9 Hz, 1H), 4.87 (q, J=17.4 Hz, 2H), 2.99 (s, 3H), 2.87 (s, 1H), 2.80 (s, 1H), 2.60-2.52 (m, 1H), 1.83 (dd, J=9.5, 3.8 Hz, 1H), 1.78-1.70 (m, 1H), 1.49-1.40 (m, 3H), 1.29 (d, J=8.3 Hz, 1H).

Second isomer: $^1$H NMR (400 MHz, CDCl$_3$) δ 8.00-7.90 (m, 2H), 7.66-7.58 (m, 1H), 7.49 (tt, J=6.7, 1.1 Hz, 2H), 6.32 (dd, J=5.7, 3.1 Hz, 1H), 6.01 (dd, J=5.7, 2.8 Hz, 1H), 5.19 (s, 1H), 4.88 (d, J=1.5 Hz, 2H), 3.10 (s, 1H), 2.92 (s, 1H), 2.76-2.67 (m, 1H), 1.86 (ddd, J=12.0, 9.2, 3.9 Hz, 1H), 1.57 (s, 3H), 1.52-1.43 (m, 1H), 1.34 (d, J=8.4 Hz, 1H), 1.00 (ddd, J=11.9, 4.9, 2.6 Hz, 1H). MS 325 (MH$^+$).

Example 2.88b: 5-(bicyclo[2.2.1]hept-5-en-2-yl)-5-methylimidazolidine-2,4-dione Prepared in a similar manner as described in Example 2.60d starting from 1-(bicyclo[2.2.1]hept-5-en-2-yl)ethanone (1360 mg, 10 mmol) to obtain the desired product (1.3 g, 63%) as a white solid. MS 207 (MH$^+$).

Example 2.89: 5-cyclopentyl-1-ethyl-5-methyl-3-(2-oxo-2-phenylethyl)imidazolidine-2,4-dione Prepared in a similar manner as described in Example 2.45 starting from 5-cyclopentyl-1-ethyl-5-methylimidazolidine-2,4-dione (Example 2.89a) (85 mg, 0.40 mmol), and 2-bromo-1-phenylethanone (96 mg, 0.48 mmol), to obtain the pure product as a clear oil (60 mg, 45%). $^1$H NMR (400 MHz, CDCl$_3$) δ 7.99-7.92 (m, 2H), 7.64-7.56 (m, 1H), 7.52-7.44 (m, 2H), 4.91 (s, 2H), 3.45 (dq, J=14.5, 7.2 Hz, 1H), 3.31 (dq, J=14.3, 7.2 Hz, 1H), 2.28 (tt, J=9.9, 7.9 Hz, 1H), 2.00-1.88 (m, 1H), 1.77-1.51 (m, 9H), 1.47-1.36 (m, 1H), 1.29 (t, J=7.2 Hz, 3H).

Example 2.89a: 5-cyclopentyl-1-ethyl-5-methylimidazolidine-2,4-dione

Prepared in a similar manner as described in Example 2.45a starting from 5-cyclopentyl-1-ethyl-3-(4-methoxybenzyl)-5-methylimidazolidine-2,4-dione (Example 2.89b) (0.075 g, 0.33 mmol), and a solution of ammonium cerium nitrate (1.52 g, 2.77 mmol) in water (8 mL), to obtain the pure product as a light brown solid (180 mg, 81%). MS 211 (MH$^+$).

Example 2.89b: 5-cyclopentyl-1-ethyl-3-(4-methoxybenzyl)-5-methylimidazolidine-2,4-dione Prepared in a similar manner as described in Example 2.45b starting from 5-cyclopentyl-3-(4-methoxybenzyl)-5-methylimidazolidine-2,4-dione (Example 2.45c) (500 mg, 1.65 mmol), and ethyl bromide (147 μL, 1.98 mmol), to obtain the pure desired product as a clear oil (352 mg, 64%). MS 331 (MH$^+$).

Example 2.90: 1,5-dimethyl-5-((1s,4s)-4-methylcyclohexyl)-3-(2-oxo-2-phenylethyl) imidazolidine-2,4-dione Prepared in a similar manner as described in Example 2.105 starting from 1,5-dimethyl-5-(4-methylcyclohexyl)-3-((2-phenyl-1,3-dioxolan-2-yl)methyl)imidazolidine-2,4-dione (Example 2.84a) (386 mg, 1 mmol) to obtain product as a colorless oily film. On HPLC this isomer eluted first (42.5 mg, 12% yield). $^1$H NMR (400 MHz, DMSO-d$_6$) δ 8.02 (d, J=8 Hz, 2H), 7.69 (t, J=8 Hz, 1H), 7.55 (t, J=8 Hz, 2H), 4.95 (d, J=16 Hz, J=24 Hz, 2H), 2.79 (s, 3H), 1.88 (m, 1H), 1.52-1.71 (m, 2H), 1.39-1.57 (m, 5H), 1.37 (s, 3H), 1.29-1.37 (m, 1H), 1.14 (m, 1H). MS 343 (MH$^+$).

Example 2.91: 5-(2-methoxy-5-methylphenyl)-1,5-dimethyl-3-(2-oxo-2-phenylethyl) imidazolidine-2, 4-dione Prepared in a similar manner as described in Example 2.70 starting from 5-(2-methoxy-5-methylphenyl)-5-methyl-3-(2-oxo-2-phenylethyl)imidazolidine-2,4-dione (Example 2.91a) (117 mg, 0.5 mmol) and MeI (40 μL, 0.6 mmol) to obtain the desired product (100 mg, 55%) as a white solid. $^1$H NMR (400 MHz, CDCl$_3$) δ 8.03-7.95 (m, 2H), 7.61 (t, J=7.4 Hz, 1H), 7.50 (t, J=7.7 Hz, 2H), 7.22 (d, J=1.7 Hz, 1H), 7.16 (d, J=8.3 Hz, 1H), 6.79 (d, J=8.3 Hz, 1H), 5.10-4.95 (m, 2H), 3.75 (s, 3H), 2.64 (s, 3H), 2.33 (s, 3H), 1.90 (s, 3H). MS 367 (MH$^+$).

Example 2.91a: 5-(2-methoxy-5-methylphenyl)-5-methyl-3-(2-oxo-2-phenylethyl)imidazolidine-2,4-dione Prepared in a similar manner as described in Example 2.70a starting from 5-(2-methoxy-5-methylphenyl)-5-methylimidazolidine-2,4-dione (Example 2.91b) (234 mg, 1 mmol) and 2-bromo-1-phenylethanone (199 mg, 1 mmol) to obtain the desired product (250 mg, 71%) as a white solid. $^1$H NMR is consistent with structure. MS 353 (MH$^+$).

Example 2.91b: 5-(2-methoxy-5-methylphenyl)-5-methylimidazolidine-2,4-dione

Prepared in a similar manner as described in Example 2.60d starting from 1-(2-methoxy-5-methylphenyl)ethanone (820 mg, 5 mmol) to obtain the desired product (800 mg, 68%) as a white solid. $^1$H NMR is consistent with structure. MS 235 (MH$^+$).

Example 2.92: 1,5-dimethyl-5-(3-methylcyclopentyl)-3-(2-oxo-2-phenylethyl)imidazolidine-2,4-dione Prepared in a similar manner as described in Example 2.44 starting from 5-methyl-5-(3-methylcyclopentyl)-3-(2-oxo-2-phenylethyl)imidazolidine-2,4-dione (Example 2.92a) (209 mg, 0.67 mmol) and methyl iodide (50 μL, 0.80 mmol) to obtain product as a white powder of mixture of 2 pairs of diastereomers 2:1 ratio (72.4 mg, 33% yield). $^1$H NMR (400 MHz, DMSO-d$_6$) δ 8.02 (d, J=8 Hz, 2H), 7.69 (t, J=8 Hz, 1H), 7.55 (t, J=8 Hz, 2H), 4.95 (s, 2H), 2.80-2.81 (2s, 3H), 2.38 (m, 1H), 1.89 (m, 2H), 1.70 (m, 2H), 1.58 (m, 1H), 1.43 (m, 1H), 1.38 (d, J=4 Hz, 3H), 1.06 (m, 1H), 0.93 (d, J=8 Hz, 2H), 0.91 (d, J=8 Hz, 1H). MS 329 (MH$^+$).

Example 2.92a: 5-methyl-5-(3-methylcyclopentyl)-3-(2-oxo-2-oxo-2-phenylethyl)imidazolidine-2,4-dione Prepared in a similar manner as described in Example 2.44a starting from 5-methyl-5-(3-methyl-cyclopentyl)imidazolidine-2,4-dione (Example 2.92b) (196 mg, 1 mmol) and 2-bromoacetophenone (200 mg, 1 mmol) to obtain product as a white powder of mixture of 4 pairs of diastereomers (209 mg, 67% yield). $^1$H NMR (400 MHz, DMSO-d$_6$) δ 8.42 (bs, 1H), 8.02 (d, J=8 Hz, 2H), 7.69 (t, J=8 Hz, 1H), 7.55 (t, J=8 Hz, 2H), 4.90 (d, J=2.8 Hz, 2H), 2.25 (m, 1H), 1.84 (m, 2H), 1.70 (m, 2H), 1.58 (m, 1H), 1.45 (m, 1H), 1.31 (d, J=4 Hz, 3H), 1.06 (m, 1H), 0.97 (d, J=8 Hz, 2H), 0.91 (d, J=8 Hz, 1H). MS 315 (MH$^+$).

Example 2.92b: 5-methyl-5-(3-methylcyclopentyl)imidazolidine-2,4-dione

Prepared in a similar manner as described in Example 2.44b starting from 1-(3-methyl-cyclopentyl)ethanone (Example 2.92c) (1.25 g, 9.92 mmol) to obtain product as a white powder of mixture of 2 pairs of diastereomers (375 mg, 19% yield). $^1$H NMR (400 MHz, DMSO-d$_6$) δ 10.45 (bs, 1H), 7.95 (s, 1H), 2.13 (m, 1H), 1.64-1.84 (m, 4H), 1.13-1.52 (m, 2H), 1.198 (d, J=4 Hz, 3H), 1.02 (m, 1H), 0.94 (d, J=8 Hz, 1.5H), 0.90 (d, J=8 Hz, 1.5H). MS 197 (MH$^+$).

Example 2.92c: 1-(3-methyl-cyclopentyl)ethanone

Prepared in a similar manner as described in Example 2.59e starting from 3-methylcyclopentane-carboxylic acid (Example 2.92d) (1.62 g, 12.65 mmol) to obtain product as a colorless oil, the mixture of 2 pairs of diastereomers (2:1 ratio by NMR analysis) (375 mg, 19% yield). $^1$H NMR (400 MHz, DMSO-d$_6$) δ 2.95 (m, 0.7H), 2.65 (m, 0.3H), 2.06 (s, 3H), 2.03 (m, 1H), 1.62-1.96 (m, 5H), 1.52 (m, 1H), 1.14 (m, 1H), 0.90-0.94 (2d, J=8 Hz, 3H). MS N/A (MH$^+$).

Example 2.92d: 3-methylcyclopentane-carboxylic Acid

4-Methylcyclohexanone (5.6 g, 50 mmol) was added to a mixture of 30% H$_2$O$_2$ (5.1 mL, 50 mmol) and selenium (IV) dioxide (111 mg, 1 mmol) in 60 mL anhydrous t-BuOH and reaction mixture was heated at 80° C. for 18 h. Small particles of selenium were filtered off, reaction mixture was concentrated in vacuum and residue was diluted with saturated K$_2$CO$_3$ (~50 mL) and extracted with ether (3×25 mL). Aqueous phase was acidified with conc. HCl to pH=2 and extracted with ether (3×25 mL). Solvent was removed in vacuo and residue was distilled at 143-145° C./30 Torr to obtain the product as a colorless oil, the mixture of 2 pairs of diastereomers (2:1 ratio by NMR analysis) (1 g, 15.6%). $^1$H NMR (400 MHz, DMSO-d$_6$) δ 11.90 (s, 1H), 2.64 (m, 1H), 1.80-1.97 (m, 2H), 1.65-7.78 (m, 3H), 1.08-1.25 (m, 2H), 0.94 (d, J=8 Hz, 2H), 0.92 (d, J=8 Hz, 1H). MS N/A (MH$^+$).

Example 2.93: 5-(cyclohex-3-en-1-yl)-1,5-dimethyl-3-(2-oxo-2-phenylethyl)imidazolidine-2,4-dione Prepared in a similar manner as described in Example 2.60 starting from 5-(cyclohex-3-en-1-yl)-1,5-dimethylimidazolidine-2,4-dione (Example 2.93a) (52 mg, 0.25 mmol) and 2-bromo-1-phenylethanone (50 mg, 0.25 mmol) to obtain the desired product (40 mg, 49%) as a white solid. $^1$H NMR is consistent with structure. $^1$H NMR (400 MHz, CDCl$_3$) δ 8.01-7.89 (m, 2H), 7.66-7.57 (m, 1H), 7.49 (ddd, J=8.4, 1.6, 0.5 Hz, 2H), 5.69 (s, 2H), 4.92 (d, J=3.2 Hz, 2H), 2.98-2.87 (m, 3H), 2.53-2.36 (m, 1H), 2.22-1.94 (m, 4H), 1.92-1.73 (m, 1H), 1.53 (d, J=6.6 Hz, 3H), 1.39-1.24 (m, 1H). MS 327 (MH$^+$).

Example 2.93a 5-(cyclohex-3-en-1-yl)-1,5-dimethylimidazolidine-2,4-dione

Prepared in a similar manner as described in Example 2.60a starting from 5-(cyclohex-3-en-1-yl)-3-(4-methoxybenzyl)-1,5-dimethylimidazolidine-2,4-dione (Example 2.93b) (328 mg, 1 mmol) to obtain the desired product (104 mg, 50%) as a white solid. $^1$H NMR is consistent with structure. MS 329 (MH$^+$).

Example 2.93b 5-(cyclohex-3-en-1-yl)-3-(4-methoxybenzyl)-1,5-dimethylimidazolidine-2,4-dione Prepared in a similar manner as described in Example 2.60b starting from 5-(cyclohex-3-en-1-yl)-3-(4-methoxybenzyl)imidazolidine-2,4-dione (Example 2.93c) (600 mg, 2 mmol) to obtain the desired product (540 mg, 82%) as a white solid. $^1$H NMR is consistent with structure. MS 329 (MH$^+$).

Example 2.93c 5-(cyclohex-3-en-1-yl)-3-(4-methoxybenzyl)imidazolidine-2,4-dione

Prepared in a similar manner as described in Example 2.60c starting from 5-(cyclohex-3-en-1-yl)imidazolidine-2,4-dione (Example 2.93d) (720 mg, 4 mmol) to obtain the desired product (900 mg, 75%) as a white solid. $^1$H NMR is consistent with structure. MS 301 (MH$^+$).

Example 2.93d: 5-(cyclohex-3-en-1-yl)imidazolidine-2,4-dione

Prepared in a similar manner as described in Example 2.60d starting from cyclohex-3-enecarbaldehyde (1100 mg, 10 mmol) to obtain the desired product (800 mg, 44%) as a white solid. $^1$H NMR is consistent with structure. MS 181 (MH$^+$).

Example 2.94: 5-(cyclopentylmethyl)-1,5-dimethyl-3-(2-oxo-2-phenylethyl)imidazolidine-2,4-dione Prepared in a similar manner as described in Example 2.105 starting from 5-(cyclopentylmethyl)-1,5-dimethyl-3-((2-phenyl-1,3-dioxolan-2-yl)methyl)imidazolidine-2,4-dione (Example 2.94a) (60 mg, 0.16 mmol) to obtain product as a colorless oily film (20 mg, 38% yield). $^1$H NMR (400 MHz, DMSO-d$_6$) δ 8.03 (d, J=8 Hz, 2H), 7.69 (t, J=8 Hz, 1H), 7.55 (t, J=8 Hz, 2H), 4.97 (s, 2H), 2.80 (s, 3H), 1.82 (m, 2H), 1.69 (m, 1H), 1.38-1.64 (m, 6H), 1.34 (s, 3H), 1.01 (m, 2H). MS 329 (MH$^+$).

Example 2.94a: 5-(cyclopentylmethyl)-1,5-dimethyl-3-((2-phenyl-1,3-dioxolan-2-yl)methyl)imidazolidine-2,4-dione Prepared in a similar manner as described in Example 2.105a starting from 1,5-dimethyl-3-((2-phenyl-1,3-dioxolan-2-yl)methyl)imidazolidine-2,4-dione (Example 2.105b) (100 mg, 0.34 mmol) to obtain product as a colorless oil (60 mg, 47% yield). MS 373 (MH$^+$).

Example 2.95: 5-(cyclohex-2-en-1-yl)-1,5-dimethyl-3-(2-oxo-2-(pyridin-3-yl)ethyl) imidazolidine-2,4-dione To a 20 mL scintillation vial was added 5-(cyclohex-2-en-1-yl)-1,5-dimethyl-imidazolidine-2,4-dione (Example 2.95a) (108 mg, 0.5 mmol) (Example 2.95a) in dry DMF (5 mL). Sodium hydride (52 mg, 1.30 mmol) was added to the solution followed by 2-bromo-1-(pyridin-3-yl)ethanone hydrobromide (167 mg, 0.60 mmol). The reaction mixture was stirred at room temperature for 24 hr then partitioned between DCM (10 mL) and water (10 mL) and extracted with DCM three times (10 mL each) and the combined organic layers were dried over MgSO$_4$ and concentrated. The resulting oil was purified by preparative HPLC. The fractions containing pure product were concentrated in vacuo and dried on the lyophilizer to obtain the product as a white solid (40 mg, 24% yield). $^1$H NMR (400 MHz, CDCl$_3$) δ 9.19 (d, J=2 Hz, 1H), 8.84 (dd, J=2 Hz, J=4 Hz, 1H), 8.24 (tt, J=2 Hz, J=4 Hz, 1H), 7.46 (q, J=4 Hz, J-2 Hz, 1H), 5.88 (m, 1H), 5.69 (m, 1H), 4.92 (d, J=2 Hz, 2H), 2.94 (s, 3H), 2.65 (m, 1H), 2.01 (m, 2H), 1.85 (m, 2H), 1.70 (m, 2H), 1.56 (s, 3H). MS 328 (MH$^+$).

Example 2.95a: 5-(cyclohex-2-en-1-yl)-1,5-dimethylimidazolidine-2,4-dione

In a N$_2$-flushed round-bottom flask, were added anhydrous CH$_3$CN (15 mL), 5-(cyclohex-2-en-1-yl)-3-(4-methoxybenzyl)-1,5-dimethylimidazolidine-2,4-dione (Example 2.95b) (580 mg, 1.77 mmol), and the solution was cooled to 0° C. in an ice bath. An ice-cooled solution of ammonium cerium IV nitrate (2531.0 mg, 4.6 mmol) in H$_2$O (9 mL) was added dropwise and stirred at room temperature overnight. The mixture was diluted with brine (15 mL) and extracted with EtOAc (3×20 mL). The combined organic phase was washed again with brine and dried over MgSO$_4$, and solvents were evaporated. The obtained compound was used for the next step without further purification. Yield: (312 mg, 84%). MS 209 (MH$^+$).

Example 2.95b: 5-(cyclohex-2-en-1-yl)-3-(4-methoxybenzyl)-1,5-dimethylimidazolidine-2,4-dione To a 20 mL scintillation vial was added 5-(cyclohex-2-en-1-yl)-3-(4-methoxybenzyl)-5-methylimidazolidine-2,4-dione (Example 2.95c) (565 mg, 1.8 mmol) in dry DMF (5 mL). Sodium hydride (152 mg, 3.80 mmol) was added followed by the addition of methyl iodide (237 mL, 3.8 mmol). The reaction mixture was stirred at room temperature for 24 hr, then partitioned between ethyl acetate (20 mL) and water (20 mL). The aqueous layer was extracted with ethyl acetate three times (10 mL each time) and the combined organic layer was dried over MgSO$_4$ and concentrated. The crude compound was purified by preparative HPLC and the fractions containing pure product were concentrated in vacuo. The obtained compound was used for the next step without further purification. MS 329 (MH$^+$).

Example 2.95c: 5-(cyclohex-2-en-1-yl)-3-(4-methoxybenzyl)-5-methylimidazolidine-2,4-dione Tert-butyl 2-(cyclohex-2-en-1-yl)-2-(3-(4-methoxybenzyl)ureido)propanoate (Example 2.95d) (700 mg, 1.8 mmol) in dry DMF (3 mL) was added to a 20 mL scintillation vial, then potassium tert-butoxide (246 mg, 2.2 mmol) was added and the reaction mixture was stirred at ambient temperature overnight. The reaction mixture was partitioned between etyl acetate (20 mL) and water (20 mL) and the aqueous layer was extracted with ethyl acetate (3×10 mL). The combined organic layers were dried over MgSO$_4$ and concentrated. The compound was used for the next step without further purification. Yield: (565 mg, 100%). MS 315 (MH$^+$)

Example 2.95d: tert-butyl 2-(cyclohex-2-en-1-yl)-2-(3-(4-methoxybenzyl)ureido)propanoate To a 20 mL scintillation vial was added t-butyl 2-amino-2-(cyclohex-2-en-1-yl)propanoate (Example 2.95e) (640 mg, 2.84 mmol) in dry THF (5 mL). Then p-methoxybenzylisocyanate (463 mg, 2.84 mmol) was added and the reaction mixture was stirred at ambient temperature overnight. The solvent was evaporated, and the residue was purified by flash chromatography on Biotage 40 g silica column with 10%~50% EtOAc/Hex gradient. The final product was obtained as a white solid (700 mg, 64% yield). $^1$H NMR (400 MHz, CDCl$_3$) δ 7.23 (d, J=8 Hz, 2H), 6.85 (d, J=8 Hz, 2H), 5.79 (m, 1H), 5.55 (m, 1H), 4.66 (m, 1H), 4.26 (m, =2H), 3.79 (s, 3H), 2.70 (m, 1H), 1.94 (m, 1H), 1.77 (m, 1H), 1.62 (d J=4 Hz, 3H), 1.44 (d J=4 Hz, 9H). MS 389 (MH$^+$)

Example 2.95e: tert-butyl 2-amino-2-(cyclohex-2-en-1-yl)propanoate

To a 20 mL scintillation vial was added (E)-tert-butyl 2-((4-chlorobenzylidene)amino)-propanoate (Example 2.95f) (1.34 g, 5.0 mmol) in dry toluene (5 mL). Then cesium hydroxide (840 mg, 5.0 mmol) was added followed by 3-bromocyclohex-1-ene (890 mg, 5.5 mmol). The reaction mixture was stirred at 50° C. for 24 hr, then partitioned between DCM (10 mL) and water (10 mL). The aqueous layer was extracted with DCM (3×10 mL) and the combined organic layers were dried over MgSO$_4$ and concentrated. The resulting oil was dissolved in 5 mL of THF and citric acid (5 mL, 0.5M) was added. The reaction mixture was stirred overnight, then THF was evaporated and the solution was extracted with hexane. The aqueous phase was basified with Na$_2$CO$_3$ and extracted with DCM. DCM was evaporated and the residue was purified by preparative HPLC to give the desired product (Yield: 640 mg, 57%). $^1$H NMR (400 MHz, CDCl$_3$) δ 5.84 (m, 1H), 5.42-5.65 (dd, J=Hz, 1H), 2.43 (m, 1H), 1.98 (m, 2H), 1.78 (m, 2H), 1.63 (m, =1H), 1.52 (m, 3H), 1.47 (s, 9H), 1.30 (s, 3H), 1.22 (s, 2H). MS 226 (MH$^+$)

Example 2.95f: (E)-tert-butyl 2-((4-chlorobenzylidene)amino)propanoate

To a 100 mL roundbottom flask was added t-Butyl-alanine (5.8 g, 0.04 mol) and p-chlorobenzaldehyde (5.6 g, 0.04 mol) in dry methanol (40 mL). Anhydrous sodium sulfate (11.36 g, 0.08 mol) was added and the reaction mixture was stirred at room temperature for 24 hr. The solvent was evaporated and the residue was partitioned between DCM (40 mL) and water (40 mL). The aqueous layer was extracted with DCM (3×10 mL) and the combined organic layers were dried over MgSO$_4$ and concentrated. The resulting oil was used for the next step without further purification. Yield: 9.6 g (90%). $^1$H NMR (400 MHz, CDCl$_3$) δ 8.26 (s, 1H), 7.72 (d, J=8 Hz, 2H), 7.38 (d, J=8 Hz, 2H), 4.04 (q, J=8 Hz, 1H), 1.48 (d, J=4 Hz, 3H), 1.47 (s, 9H)

Example 2.96: 5-cyclohexyl-1,5-dimethyl-3-(2-oxo-2-(1H-pyrrol-3-yl)ethyl)imidazolidine-2,4-dione In an oven-dried, N$_2$-flushed, small round-bottom flask, were added anhydrous DMF (8.0 mL), 5-cyclohexyl-1,5-dimethylimidazolidine-2,4-dione (Example 2.47a) (128 mg, 0.61 mmol), and the reaction mixture was cooled to 0° C. NaH (30 mg, 0.73 mmol), and 2-bromo-1-(1H-pyrrol-3-yl)ethanone (105 mg, 0.73 mmol) were added. The ice bath was removed and the reaction medium was stirred vigorously at room temperature for 18 hr. The reaction was quenched with water and extracted with DCM (3×10 mL). The combined organic phases were washed with brine and dried over MgSO$_4$, and solvents were evaporated. The residue was purified by flash chromatography using a 12 g Silicycle column and MeOH/DCM gradient as eluant to obtain the pure desired product (30 mg, 15%) as a clear oil. $^1$H NMR (400 MHz, CDCl$_3$) δ 9.56 (s, 1H), 7.37-7.39 (m, 1H), 6.73-6.74 (m, 1H), 6.58-6.60 (m, 1H), 4.70 (s, 2H), 2.88 (s, 3H), 1.39-1.80 (s & m, 10H), 1.04-1.28 (m, 4H). MS 318 (MH$^+$).

Example 2.97: 1,5-dimethyl-5-((1r,4r)-4-methylcyclohexyl)-3-(2-oxo-2-phenylethyl) imidazolidine-2,4-dione Prepared in a similar manner as described in Example 2.105 starting from 1,5-dimethyl-5-(4-methylcyclohexyl)-3-((2-phenyl-1,3-dioxolan-2-yl)methyl)imidazolidine-2,4-dione (Example 2.84a) (386 mg, 1 mmol) to obtain product as a colorless oily film. On HPLC this isomer eluted second (60.5 mg, 18% yield). $^1$H NMR (400 MHz, DMSO-d$_6$) δ 8.02 (d, J=8 Hz, 2H), 7.69 (t, J=8 Hz, 1H), 7.55 (t, J=8 Hz, 2H), 4.93 (s, 2H), 2.79 (s, 3H), 1.78-1.86 (m, 0.5H), 1.52-1.71 (m, 4.5H), 1.39-1.50 (m, 1H), 1.37 (s, 3H), 1.21 (m, 1H), 0.85-1.02 (m, 3H), 0.83 (d, J=8 Hz, 3H). MS 343 (MH$^+$).

Example 2.98: 5-cyclohexyl-1,5-dimethyl-3-(2-oxo-2-(pyridin-2-yl)ethyl)imidazolidine-2,4-dione Prepared in a similar manner as described in Example 2.45 starting from 5-cyclohexyl-1,5-dimethylimidazolidine-2,4-dione (Example 2.47a) (159 mg, 0.75 mmol) and 2-(bromoacetyl)-pyridine hydrobromide (256 mg, 0.91 mmol) to obtain the desired product (82 mg, 30%) as a light yellow oil. $^1$H NMR (400 MHz, DMSO-d$_6$) δ 8.68 (d, J=5.2 Hz, 1H), 8.01 (d, J=7.6 Hz, 1H), 7.82 (t, J=8 Hz, 1H), 7.50 (dd, J=7.2 Hz & 6.0 Hz), 5.19 (s, 2H), 2.92 (s, 3H), 1.66 (m, 6H), 1.48 (m, 4H), 1.07 (m, 4H). MS 330 (MH$^+$).

Example 2.99: 5-cyclopentyl-1-ethyl-5-methyl-3-(2-oxo-2-(pyridin-3-yl)ethyl)imidazolidine-2,4-dione Prepared in a similar manner as described in Example 2.45 starting from 5-cyclopentyl-1-ethyl-5-methylimidazolidine-2,4-dione (Example 2.89a) (100 mg, 0.47 mmol), and 3-(bromoacetyl)-pyridine hydrobromide (267 mg, 0.952 mmol), to obtain the pure product as a light yellow oil (50 mg, 32%). $^1$H NMR (400 MHz, cdcl$_3$) δ 9.19 (dd, J=2.3, 0.8 Hz, 1H), 8.83 (dd, J=4.8, 1.7 Hz, 1H), 8.24 (ddd, J=8.0, 2.2, 1.8 Hz, 1H), 7.46 (ddd, J=8.0, 4.8, 0.9 Hz, 1H), 4.92 (s, 2H), 3.46 (dq, J=14.5, 7.2 Hz, 1H), 3.32 (dq, J=14.4, 7.2 Hz, 1H), 2.35-2.24 (m, 1H), 2.00-1.88 (m, 1H), 1.79-1.52 (m, 9H), 1.49-1.34 (m, 1H), 1.30 (t, J=7.2 Hz, 3H).

Example 2.100: 5-cyclohexyl-3-(2-(2-fluorophenyl)-2-oxoethyl)-1,5-dimethylimidazolidine-2,4-dione Anhydrous DMF (8.0 mL), and 5-cyclohexyl-1,5-dimethylimidazolidine-2,4-dione (Example 2.47a) (55 mg, 0.26 mmol) were added to an oven-dried, N$_2$-flushed, small round-bottom flask and the solution was cooled to 0° C. in an ice bath. NaH (15 mg, 0.31 mmol), and 2-bromo-1-(2-fluorophenyl)ethanone (105 mg, 0.73 mmol) were added and the reaction was stirred vigorously at room temperature for 3 hr. The reaction was quenched with water (10 mL) and extracted with DCM (3×10 mL). The combined organic phase was washed with brine, dried over MgSO$_4$, and solvents were evaporated. The residue was purified by preparative HPLC to obtain the pure product (15 mg, 16%) as a clear colorless oil. $^1$H NMR (400 MHz, CDCl$_3$) δ 7.95 (t, J=8 Hz, 1H), 7.57-7.61 (m, 1H), 7.16-7.28 (m, 2H), 4.84 (d, J=3.6 Hz, 2H), 2.01 (s, 3H), 1.46-1.86 (s&m, 10H), 1.04-1.25 (m, 4H). MS 347 (MH$^+$).

Example 2.101: 5-(2-methoxyphenyl)-1,5-dimethyl-3-(2-oxo-2-(1H-pyrrol-2-yl)ethyl) imidazolidine-2,4-dione Prepared in a similar manner as described in Example 2.60 starting from 5-(2-methoxyphenyl)-1,5-dimethylimidazolidine-2,4-dione (Example 2.60a) (234 mg, 1 mmol) and 2-bromo-1-(1H-pyrrol-2-yl)ethanone (224 mg, 1.2 mmol) to obtain the desired product (40 mg, 12%) as an oily film. $^1$H NMR (400 MHz, CDCl$_3$) δ 9.32 (s, 1H), 7.43 (dd, J=7.7, 1.6 Hz, 1H), 7.37 (ddd, J=8.2, 7.5, 1.6 Hz, 1H), 7.09-6.99 (m, 3H), 6.89 (dd, J=8.3, 1.1 Hz, 1H), 6.33 (dt, J=3.9, 2.5 Hz, 1H), 4.86 (d, J=1.5 Hz, 2H), 3.77 (s, 3H), 2.62 (s, 3H), 1.88 (s, 3H). MS 342 (MH$^+$).

Example 2.102: 5-cyclohexyl-3-(2-(3-fluorophenyl)-2-oxoethyl)-1,5-dimethylimidazolidine-2,4-dione Prepared in a similar manner as described in Example 2.45 starting from 5-cyclohexyl-1,5-dimethylimidazolidine-2,4-dione (Example 2.47a) (68 mg, 0.32 mmol) and bromoacetyl 3-fluorophenone (108 mg, 0.38 mmol) to obtain the desired product (15 mg, 13%) as a light yellow oil. $^1$H NMR (400 MHz, DMSO-d$_6$) δ 7.73 (m, 1H), 7.63 (m, 1H), 7.46 (m, 1H), 7.26 (m, 1H), 4.88 (s, 2H), 2.91 (s, 3H), 1.66 (m, 6H), 1.48 (s & m, 4H), 1.03 (m, 4H). MS 347 (MH$^+$).

Example 2.103: 5-(2-methoxy-4-methylphenyl)-1,5-dimethyl-3-(2-oxo-2-phenylethyl) imidazolidine-2,4-dione Prepared in a similar manner as described in Example 2.70 starting from 5-(2-methoxy-4-methylphenyl)-5-methyl-3-(2-oxo-2-phenylethyl)imidazolidine-2,4-dione (Example 2.103a) (117 mg, 0.5 mmol) and MeI (40 μL, 0.6 mmol) to obtain the desired product (100 mg, 55%) as a white solid. $^1$H NMR (400 MHz, CDCl$_3$) δ 8.03-7.97 (m, 2H), 7.65-7.57 (m, 1H), 7.54-7.45 (m, 2H), 7.30 (d, J=7.9 Hz, 1H), 6.83 (dd, J=7.9, 0.8 Hz, 1H), 6.71 (s, 1H), 5.02 (d, J=2.9 Hz, 2H), 3.77 (s, 3H), 2.63 (s, 3H), 2.36 (s, 3H), 1.88 (s, 3H). MS 367 (MH$^+$).

Example 2.103a: 5-(2-methoxy-4-methylphenyl)-5-methyl-3-(2-oxo-2-phenylethyl) imidazolidine-2,4-dione Prepared in a similar manner as described in Example 2.70a starting from 5-(2-methoxy-4-methylphenyl)-5-methylimidazolidine-2,4-dione (Example 2.103b) (234 mg, 1 mmol) and 2-bromo-1-phenylethanone (199 mg, 1 mmol) to obtain the desired product (250 mg, 71%) as a white solid. $^1$H NMR is consistent with structure. MS 353 (MH$^+$).

Example 2.103b: 5-(2-methoxy-4-methylphenyl)-5-methylimidazolidine-2,4-dione

Prepared in a similar manner as described in Example 2.60d starting from 1-(2-methoxy-4-methylphenyl)ethanone (820 mg, 5 mmol) to obtain the desired product (800 mg, 68%) as a white solid. $^1$H NMR is consistent with structure. MS 235 (MH$^+$).

Example 2.104: 5-(2,4-dimethoxyphenyl)-1,5-dimethyl-3-(2-oxo-2-phenylethyl)imidazolidine-2,4-dione Prepared in a similar manner as described in Example 2.44 starting from 5-(2,4-dimethoxyphenyl)-5-methyl-3-(2-oxo-2-phenylethyl)imidazolidine-2,4-dione (Example 2.104a) (307 mg, 0.83 mmol) and methyl iodide (62 μL, 1.0 mmol) to obtain product as a white powder (63 mg, 20% yield). $^1$H NMR (400 MHz, DMSO-$d_6$) δ 8.07 (d, J=8 Hz, 2H), 7.70 (t, J=8 Hz, 1H), 7.57 (t, J=8 Hz, 2H), 7.37 (d, J=8 Hz, 1H), 6.59 (d, J=8 Hz, 1H), 6.57 (s, 1H), 5.02 (s, 2H), 3.76 (s, 3H), 3.69 (s, 3H), 2.47 (s, 3H), 1.72 (s, 3H). MS 383 (MH$^+$).

Example 2.104a: 5-(2,4-dimethoxyphenyl)-5-methyl-3-(2-oxo-2-phenylethyl)imidazolidine-2,4-dione Prepared in a similar manner as described in Example 2.44a starting from 5-(2,4-dimethoxy-phenyl)-5-methylimidazolidine-2,4-dione (Example 2.104b) (250 mg, 1 mmol) and 2-bromoacetophenone (200 mg, 1 mmol) to obtain product as a white powder (307.5 mg, 84% yield). $^1$H NMR (400 MHz, DMSO-$d_6$) δ 8.33 (s, 1H), 8.06 (d, J=8 Hz, 2H), 7.70 (t, J=8 Hz, 1H), 7.57 (t, J=8 Hz, 2H), 7.32 (d, J=8 Hz, 1H), 6.57 (s, 1H), 6.52 (d, J=8 Hz, 1H), 4.97 (s, 2H), 3.75 (s, 3H), 3.71 (s, 3H), 1.70 (s, 3H). MS 368 (MH$^+$).

Example 2.104b: 5-(2,4-dimethoxy-phenyl)-5-methylimidazolidine-2,4-dione

Prepared in a similar manner as described in Example 2.44b starting from 1-(2,4-dimethoxyphenyl)ethanone (1.08 g, 6 mmol) to obtain product as a white powder (1.07 g, 71% yield). $^1$H NMR (400 MHz, DMSO-$d_6$) δ 10.46 (s, 1H), 7.84 (s, 1H), 7.25 (d, J=8 Hz, 1H), 6.55 (s, 1H), 6.49 (d, J=8 Hz, 2H), 3.74 (s, 3H), 3.67 (s, 3H), 1.57 (s, 3H). MS 251 (MH$^+$).

Example 2.105: 5-(cyclohexylmethyl)-1,5-dimethyl-3-(2-oxo-2-phenylethyl)imidazolidine-2,4-dione To 5-(cyclohexylmethyl)-1,5-dimethyl-3-((2-phenyl-1,3-dioxolan-2-yl)methyl) imidazolidine-2,4-dione (Example 2.105a) (53.2 mg, 138 μM) was added EtOH (2 mL) and HCl 6N (4 mL) and the reaction mixture was refluxed under $N_2$ for 2 hours. The reaction mixture was diluted with water (10 mL), extracted with $Et_2O$ (3×10 mL) and the combined organic phase was washed with brine, dried over $MgSO_4$, and concentrated, to afford the pure product (45.1 mg, 97%) as a colourless oily film. $^1$H NMR (400 MHz, CDCl$_3$) δ 7.96-7.94 (m, 2H), 7.61-7.57 (m, 1H), 7.49-7.45 (m, 2H), 4.95 (d, J=17.6, 1H), 4.90 (d, J=17.6, 1H), 2.88 (s, 3H), 1.82 (dd, J=6.4, J=15.2, 1H), 1.65-1.56 (m, 6H), 1.43 (s, 3H), 1.34-1.17 (m, 3H), 1.14-1.06 (m, 1H), 1.00-0.85 (m, 2H). MS 343 (MH$^+$).

Example 2.105a: 5-(cyclohexylmethyl)-1,5-dimethyl-3-((2-phenyl-1,3-dioxolan-2-yl)methyl) imidazolidine-2,4-dione In an oven-dried, $N_2$-flushed, small round-bottom flask, were added anhydrous DMF (5.0 mL), 1,5-dimethyl-3-((2-phenyl-1,3-dioxolan-2-yl)methyl)imidazolidine-2,4-dione (Example 2.105b) (140 mg, 482 umol), and at 0° C. NaH (30.0 mg, 750 mol), and after a few minutes stirring at room temperature (bromomethyl)cyclohexane (100 μL, 723 μmol). The reaction medium was stirred vigorously at room temperature for 4 hours and extracted with $H_2O$/EtOAc (3×). Combined organic phases were washed with brine and dried over $MgSO_4$, and solvents were evaporated. The residue was purified by flash chromatography using a 40 g Silicycle column and a DCM/EtOAc gradient as eluant to obtain the pure product (53.2 mg, 29%). $^1$H NMR (400 MHz, CDCl$_3$) δ 7.57-7.55 (m, 2H), 7.36-7.30 (m, 3H), 4.01-3.98 (m, 2H), 3.88 (d, J=4.0, 2H), 3.79-3.72 (m, 2H), 2.82 (s, 3H), 1.79 (dd, J=6.4, J=14.8, 1H), 1.64-1.49 (m, 5H), 1.50 (dd, J=5.2, J=14.4, 1H), 1.24 (s, 3H), 1.19-1.04 (m, 4H), 0.96-0.85 (m, 2H). MS 387 (MH$^+$).

Example 2.105b: 1,5-dimethyl-3-((2-phenyl-1,3-dioxolan-2-yl)methyl)imidazolidine-2,4-dione In an oven-dried, $N_2$-flushed, small round-bottom flask, were added anhydrous DMF (13.0 mL), 1-methyl-3-((2-phenyl-1,3-dioxolan-2-yl)methyl)imidazolidine-2,4-dione (Example 2.105c) (500 mg, 1.8 mmol), and at 0° C. NaH (80.0 mg, 2.0 mmol), and after 15 minutes stirring MeI (200 μL, 3.21 mmol). The reaction medium was stirred vigorously at room temperature overnight and extracted with $H_2O$/EtOAc (3×). Combined organic phases were washed with brine and dried over $MgSO_4$, and solvents were evaporated. The residue was purified by flash chromatography using a 80 g Silicycle column and a DCM/EtOAc gradient as eluant to obtain the pure product (140 mg, 27%). $^1$H NMR (400 MHz, DMSO-$d_6$) δ 7.38-7.33 (m, 5H), 3.96-3.92 (m, 3H), 3.73-3.65 (m, 4H), 2.78 (s, 3H), 1.20 (d, J=6.8, 3H). MS 291 (MH$^+$).

Example 2.105c: 1-methyl-3-((2-phenyl-1,3-dioxolan-2-yl)methyl)imidazolidine-2,4-dione In a 250 mL round-bottom flask, equipped with a 40 mL Dean-Stark trap, a reflux condenser, and a drying tube were added 1-methyl-3-(2-oxo-2-phenylethyl)imidazolidine-2,4-dione (Example 2.105d) (7.74 g, 33.3 mmol), anhydrous benzene (150.0 mL), ethylene glycol (3 mL, 53.2 mmol), and p-toluenesulfonic acid (128 mg, 0.74 mmol). The reaction mixture was heated at 135° C. (oil bath temperature) overnight, and the reaction was monitored by LCMS and $^1$H-NMR showing at that point 40% product. Benzene (150.0 mL, and 60 mL) and ethylene glycol (56 mL, 992 mmol and 40 mL, 709 mmol) were added again twice as well as p-toluenesulfonic acid (256 mg, 1.49 mmol) once and the reaction mixture was further refluxed another night to allow the reaction to go to completion (by $^1$H-NMR). The reaction mixture was extracted with saturated NaHCO$_3$/EtOAc (3×). Combined organic phases were washed with brine and dried over $MgSO_4$, and solvents were evaporated to obtain after drying the pure product (8.2 g, 89%). $^1$H NMR (400 MHz, CDCl$_3$) δ 7.58-7.55 (m, 2H), 7.39-7.33 (m, 3H), 4.04-4.00 (m, 2H), 3.90 (s, 2H), 3.84 (s, 2H), 3.80-3.77 (m, 2H). MS 277 (MH$^+$).

Example 2.105d: 1-methyl-3-(2-oxo-2-phenylethyl)imidazolidine-2,4-dione

In an oven-dried, $N_2$-flushed, 500 mL round-bottom flask, were added anhydrous DMF (260.0 mL), commercially available 1-methylimidazolidine-2,4-dione (10 g, 87.6 mmol), $K_2CO_3$ (13.3 g, 96.2 mmol), and 2-bromo-1-phenylethanone (20.9 g, 105.0 mmol). The reaction medium was stirred vigorously at room temperature overnight and extracted with $H_2O$/EtOAc (2×) and $H_2O$/Hexanes (1×).

Combined organic phases were washed with brine and dried over MgSO$_4$, and solvents were evaporated. The residue was purified by flash chromatography using a 330 g Silicycle column and a Hexanes/EtOAc gradient followed by DCM/EtOAc gradient as eluants to obtain the pure product (7.74 g, 38%). $^1$H-NMR (400 MHz, CDCl$_3$) δ 7.98-7.96 (m, 2H), 7.65-7.61 (m, 1H), 7.52-7.48 (m, 2H), 4.94 (s, 2H), 4.03 (s, 2H), 3.06 (s, 3H). MS 233 (MH$^+$).

Example 2.106: 5-(cyclobutylmethyl)-1,5-dimethyl-3-(2-oxo-2-phenylethyl)imidazolidine-2,4-dione Prepared in a similar manner as described in Example 2.105 starting from 5-(cyclobutylmethyl)-1,5-dimethyl-3-((2-phenyl-1,3-dioxolan-2-yl)methyl)imidazolidine-2,4-dione (Example 2.137), except the reaction medium was only heated at 50° C. for 1 hour, to obtain the desired product (31.9 mg). $^1$H NMR (400 MHz, d$_6$-DMSO) δ 8.07-8.03 (m, 2H), 7.75-7.69 (m, 1H), 7.61-7.55 (m, 2H), 4.99 (d, J=18.1 Hz, 1H), 4.94 (d, J=18.1 Hz, 1H), 2.80 (s, 3H), 2.24-2.14 (m, 2H), 1.97-1.85 (m, 2H), 1.85-1.77 (m, 2H), 1.76-1.54 (m, 3H), 1.33 (s, 3H). MS 315 (MH$^+$).

Example 2.107: 5-(cyclohex-2-en-1-yl)-1,5-dimethyl-3-(2-oxo-2-phenylethyl)imidazolidine-2,4-dione To a 20 mL scintillation vial was added 5-(cyclohex-2-en-1-yl)-1,5-dimethyl-imidazolidine-2,4-dione (Example 2.95a) (108 mg, 0.5 mmol) in dry DMF (5 mL) with potassium carbonate (140 mg, 1.0 mmol). Next, alpha-bromoacetophenone (120 mg, 0.60 mmol) was added and the reaction mixture was stirred at room temperature for 24 hr. DCM (10 mL) and water (10 mL) were added and the aqueous layer was extracted with DCM (10 mL×3). The combined organic layers were dried over MgSO$_4$ and concentrated in vacuo. The resulting oil was purified by preparative HPLC. The fractions containing pure product were concentrated in vacuo giving a white solid (40 mg) (24% yield). $^1$H NMR (400 MHz, CDCL$_3$) δ 7.96 (dd, J=2 Hz, J=8 Hz, 2H), 7.61 (t, J=8 Hz, 1H), 7.49 (t, J=8 Hz, 2H), 5.88 (m, 1H), 5.73 (m, 1H), 4.92 (s, 2H), 2.94 (s, 3H)., 2.65 (m, 1H), 2.01 (m, 2H), 1.85 (m, 2H), 1.61 (m, 2H), 1.55 (s, 3H). MS 327 (MH$^+$).

Example 2.108: 5-((1R,4R)-bicyclo[2.2.1]hept-5-en-2-yl)-1,5-dimethyl-3-(2-oxo-2-phenylethyl) imidazolidine-2,4-dione Prepared in a similar manner as described in Example 2.70 starting from 5-(bicyclo[2.2.1]hept-5-en-2-yl)-5-methyl-3-(2-oxo-2-phenylethyl)imidazolidine-2,4-dione (Example 2.88a) (162 mg, 0.5 mmol) and MeI (40 μL, 0.6 mmol) to obtain the desired product (eluted first on HPLC) (65 mg, 39%) as a white solid. $^1$H NMR (400 MHz, CDCl$_3$) δ 7.98-7.93 (m, 2H), 7.64-7.58 (m, 1H), 7.53-7.45 (m, 2H), 6.12 (dd, J=5.7, 3.1 Hz, 1H), 5.87 (dd, J=5.7, 2.9 Hz, 1H), 4.87 (q, J=17.4 Hz, 2H), 2.99 (s, 3H), 2.87 (s, 1H), 2.80 (s, 1H), 2.60-2.52 (m, 1H), 1.83 (dd, J=9.5, 3.8 Hz, 1H), 1.78-1.70 (m, 1H), 1.49-1.40 (m, 4H), 1.29 (d, J=8.3 Hz, 1H). MS 339 (MH$^+$).

Example 2.109: 5-cyclohexyl-3-(2-(furan-2-yl)-2-oxoethyl)-1,5-dimethylimidazolidine-2,4-dione Prepared in a similar manner to Example 2.43 using 5-cyclohexyl-1,5-dimethylimidazolidine-2,4-dione (Example 2.47a) (100.0 mg, 476 umol), and commercially available 2-bromo-1-(furan-2-yl)ethanone (129 mg, 683 umol), to obtain the desired product. $^1$H NMR (400 MHz, d$_6$-DMSO) δ 8.10 (dd, J=1.7, 0.7 Hz, 1H), 7.66 (dd, J=3.7, 0.7 Hz, 1H), 6.80 (dd, J=3.7, 1.7 Hz, 1H), 4.75 (s, 2H), 2.82 (s, 3H), 1.79-1.66 (m, 4H), 1.66-1.56 (m, 2H), 1.38 (s, 3H), 1.37-1.28 (m, 1H), 1.26-1.13 (m, 2H), 1.06 (dd, J=15.2, 9.9 Hz, 1H), 1.00-0.87 (m, 1H). MS 319 (MH$^+$).

Example 2.110: 5-(2-fluorophenyl)-1,5-dimethyl-3-(2-oxo-2-phenylethyl)imidazolidine-2,4-dione Prepared in a similar manner as described in Example 2.44 starting from 5-(2-fluorophenyl)-5-methyl-3-(2-oxo-2-phenylethyl)imidazolidine-2,4-dione (Example 2.110a) (245 mg, 0.75 mmol) and methyl iodide (56 μL, 0.9 mmol) to obtain the desired product as a white powder (121.5 mg, 48% yield). $^1$H NMR (400 MHz, DMSO-d$_6$) δ 8.06 (d, J=8 Hz, 2H), 7.71 (t, J=8 Hz, 1H), 7.62 (t, J=8 Hz, 1H), 7.57 (t, J=8 Hz, 2H), 7.49 (m, 1H), 7.32 (t, J=8 Hz, 1H), 7.255 (dd, J=8 Hz, J=12 Hz, 1H), 5.07 (s, 2H), 2.62 (s, 3H), 1.86 (s, 3H). MS 341 (MH$^+$).

Example 2.110a: 5-(2-fluorophenyl)-5-methyl-3-(2-oxo-2-phenylethyl)imidazolidine-2,4-dione Prepared in a similar manner as described in Example 2.44a starting from 5-(2-fluorophenyl)-5-methylimidazolidine-2,4-dione (Example 2.110b) (208 mg, 1 mmol) and 2-bromoacetophenone (239 mg, 1.2 mmol) to obtain the desired product as a white powder (246 mg, 75% yield). $^1$H NMR (400 MHz, DMSO-d$_6$) δ 8.85 (s, 1H), 8.06 (d, J=8 Hz, 2H), 7.70 (t, J=8 Hz, 1H), 7.59 (m, 3H), 7.45 (m, 1H), 7.23 (m, 2H), 5.02 (s, 2H), 1.82 (s, 3H). MS 327 (MH$^+$).

Example 2.110b: 5-(2-fluorophenyl)-5-methylimidazolidine-2,4-dione

Prepared in a similar manner as described in Example 2.44b starting from 1-(2-fluorophenyl)-ethanone (728 μL, 6 mmol) to obtain the desired product as a white powder (966 mg, 77% yield). $^1$H NMR (400 MHz, DMSO-d$_6$) δ 10.85 (s, 1H), 8.31 (s, 1H), 7.51 (t, J=8 Hz, 1H), 7.415 (dd, J=8 Hz, J=12 Hz, 1H), 7.20 (m, 2H), 1.69 (s, 3H). MS 209 (MH$^+$).

Example 2.111: 1,5-dimethyl-5-(2-methylcyclohexyl)-3-(2-oxo-2-phenylethyl) imidazolidine-2,4-dione Prepared in a similar manner as described in Example 2.44 starting from 5-methyl-5-(2-methyl-cyclohexyl)-3-(2-oxo-2-phenylethyl)imidazolidine-2,4-dione (Example 2.111a) (499 mg, 1.52 mmol) and methyl iodide (114 μL, 1.83 mmol) to obtain the desired product as a white powder of mixture of 4 pairs of diastereomers (179 mg, 34% yield). $^1$H NMR (400 MHz, DMSO-d$_6$) δ 8.02 (d, J=8 Hz, 2H), 7.69 (t, J=8 Hz, 1H), 7.55 (t, J=8 Hz, 2H), 4.94 (d, J=6 Hz, 2H), 2.81 (s, 1H), 2.79 (s, 2H), 1.55-2.01 (m, 5H), 1.39-1.80 (m, 5H), 1.45 (m, 2H), 1.41 (s, 2H), 1.38 (s, 1H), 1.33 (m, 2H), 1.19 (m, 1H), 0.95 (d, J=8 Hz, 1H), 0.76 (d, J=8 Hz, 2H). MS 343 (MH$^+$).

Example 2.111a: 5-methyl-5-(2-methylcyclohexyl)-3-(2-oxo-2-phenylethyl)imidazolidine-2,4-dione Prepared in a similar manner as described in Example 2.44a starting from 5-methyl-5-(2-methyl-cyclohexyl)imidazolidine-2,4-dione (111b) (420 mg, 2 mmol) and 2-bromoacetophenone (478 mg, 2.4 mmol) to obtain the desired product as a white powder of mixture of 4 pairs of diastereomers (499 mg, 76% yield). $^1$H NMR (400 MHz, DMSO-$d_6$) δ 8.37 (s, 0.3H), 8.03 (s, 0.7H), 8.02 (d, J=8 Hz, 2H), 7.69 (t, J=8 Hz, 1H), 7.55 (t, J=8 Hz, 2H), 4.91 (s, 2H), 1.97-2.12 (m, 1H), 1.63-1.84 (m, 2H), 1.34-1.59 (m, 5H), 1.32 (s, 1H), 1.31 (s, 2H), 1.26 (m, 1H), 1.13 (m, 1H), 0.90 (t, J=8 Hz, 3H). MS 329 (MH$^+$).

Example 2.111b: 5-methyl-5-(2-methylcyclohexyl) imidazolidine-2,4-dione

Prepared in a similar manner as described in Example 2.44b starting from 1-(2-methylcyclohexyl)-ethanone (Example 2.111c) (3 g, 21.43 mmol) to obtain the desired product as a white powder of mixture of 4 pairs of diastereomers (2.51 g, 56% yield). $^1$H NMR (400 MHz, DMSO-$d_6$) δ 10.56 (bs, 1H), 7.90 (s, 0.3H), 7.56 (s, 0.7H), 1.91-2.09 (m, 1H), 1.30-1.75 (m, 7H), 1.21 (s, 1H), 1.20 (s, 2H), 0.95-1.17 (m, 2H), 0.86 (d, J=8 Hz, 2H), 0.82 (d, J=8 Hz, 0.6H), 0.74 (d, J=8 Hz, 0.3H), 0.72 (d, J=8 Hz, 0.1H). MS 211 (MH$^+$).

Example 2.111c: 1-(2-methylcyclohexyl)-ethanone

Prepared in a similar manner as described in Example 2.59e starting from 2-methylcyclohexane-carboxylic acid (cis- and trans-mixture of isomers) (2.815 mL, 20 mmol) to obtain the desired product as a colorless oil consisting of two pairs of diastereomers (2:1 ratio by NMR analysis) (3 g, 97% yield). $^1$H NMR (400 MHz, CDCl$_3$) δ 2.45 (dt, J=4 Hz, J=12 Hz, 1H), 2.23 (m, 1H), 2.03 (s, 3H), 1.45-1.66 (m, 5H), 1.35 (m, 2H), 1.14 (m, 2H), 0.76 (d, J=8 Hz, 3H). MS N/A.

Example 2.112: 5-cyclohexyl-1,5-dimethyl-3-(2-oxo-2-(1H-pyrazol-4-yl)ethyl) imidazolidine-2,4-dione To an oven dried, N$_2$-flushed, small round bottom flask was added 3-(2-(1-(tert-butyl)-1H-pyrazol-4-yl)-2-hydroxyethyl)-5-cyclohexyl-1,5-dimethylimidazolidine-2,4-dione (Example 2.112a) followed by 2 mL DCM and Dess-Martin periodinane (0.240 g, 0.56 mmol). The reaction was stirred for 2 hours. 10 mL ether, 5 mL saturated NaHCO$_3$, and 5 mL saturated Na$_2$S$_2$O$_3$ were added and the mixture was stirred for 1 hour. The layers were separated and the organic layer was washed with 5 mL saturated NaHCO$_3$, brine and dried with Na$_2$SO$_4$. The solvent was evaporated, and the residue was purified by column chromatography utilizing a Silicycle column (12 g) and elution with 0-70% ethyl acetate/hexanes. 130 mg of 3-(2-(1-(tert-butyl)-1H-pyrazol-4-yl)-2-oxo-ethyl)-5-cyclohexyl-1,5-dimethylimidazolidine-2,4-dione was isolated as an off white semi-solid.

The compound was dissolved in 1 mL dioxane and 1 mL concentrated HCl and stirred at 100° C. until the deprotection was complete. The reaction mixture was neutralized with saturated NaHCO$_3$, and extracted with ethyl acetate (3×10 mL). The combined organics were dried with Na$_2$SO$_4$. The solvent was evaporated, and the residue was purified by column chromatography utilizing a Silicycle column (12 g) and elution with 20-100% ethyl acetate/hexane to afford 23 mg (20%) of the title compound as an off white solid. $^1$H-NMR (400 MHz, DMSO-$d_6$) δ 13.54 (s, 1H), 8.58 (s, 1H), 8.04 (s, 1H), 4.66 (s, 2H), 2.79 (s, 3H), 1.81-1.52 (m, 6H), 1.42-1.23 (m, 4H), 1.22-0.86 (m, 4H); MS 319 (MH$^+$).

Example 2.112a: 3-(2-(1-(tert-butyl)-1H-pyrazol-4-yl)-2-hydroxyethyl)-5-cyclohexyl-1,5-dimethylimidazolidine-2,4-dione To an oven dried, N$_2$-flushed, small round bottom flask was added 4-bromo-1-(tert-butyl)-1H-pyrazole (0.396 g, 1.95 mmol). The flask was sealed and purged with nitrogen. 5 mL anhydrous THF was added and the reaction was cooled to −78° C. n-Butyl lithium (0.93 mL, 2.24 mmol) was added and the reaction was stirred at −78° C. for 30 minutes. 2-(4-cyclohexyl-3,4-dimethyl-2,5-dioxoimidazolidin-1-yl) acetaldehyde (112b) (0.446 g, 1.77 mmol) in 3 mL was then added to the flask at at −78° C. The reaction was stirred for 2 hours at −78° C. and quenched with water. The mixture was extracted with ethyl acetate (3×10 mL). The combined organics were dried with Na$_2$SO$_4$. The solvent was evaporated, and the residue was purified by column chromatography utilizing a Silicycle column (12 g) and elution with 20-100% ethyl acetate/hexane to afford 200 mg (50%) of product as an off white solid.

Example 2.112 b: 2-(4-cyclohexyl-3,4-dimethyl-2,5-dioxoimidazolidin-1-yl)acetaldehyde 3-allyl-5-cyclohexyl-1,5-dimethylimidazolidine-2,4-dione (Example 2.112c) (12.1 g, 48.3 mmol) was added to a 250 mL round bottom flask followed by 150 mL DCM. The flask was cooled to −78° C. under nitrogen for five minutes. The nitrogen and septum were removed and ozone was bubbled through the solution for 1 h when the reaction turned blue. The reaction was purged with nitrogen for 20 minutes. Dimethyl sulfide (30.0 g, 483.0 mmol) was added and the reaction was stirred overnight. The solvent was evaporated, and the residue was purified by column chromatography utilizing a Silicycle column (100 g) and elution with 0-50% ethyl acetate/hexane to afford 7.5 g (61%) of the title compound as an oil. $^1$H-NMR (400 MHz, DMSO-$d_6$) δ 9.47 (s, 1H), 4.34 (s, 2H), 2.76 (s, 3H), 1.78-1.47 (m, 6H), 1.41-1.23 (m, 4H), 1.22-0.97 (m, 3H), 0.85 (m, 1H).

Example 2.112c: 3-allyl-5-cyclohexyl-1,5-dimethyl-imidazolidine-2,4-dione

To an oven dried, N$_2$-flushed, 250 mL round bottom flask was added 5-cyclohexyl-5-methylimidazolidine-2,4-dione (Example 2.47d) (10.1 g, 51.5 mmol), K$_2$CO$_3$ (7.8 g, 56.6 mmol), 50 mL DMF and allyl bromide (4.4 mL, 51.5 mmol). The reaction was stirred at ambient temperature for 2 hours and water was added with stirring. The white precipitate was filtered and dried to afford 12.48 g (97%) of 3-allyl-5-cyclohexyl-5-methylimidazolidine-2,4-dione as a white solid.

To an oven dried, N$_2$-flushed, 250 mL round bottom flask was added 3-allyl-5-cyclohexyl-5-methylimidazolidine-2,4-dione (12.4 g, 52.5 mmol), cesium carbonate (26.0 g, 78.7 mmol), 75 mL DMF and methyl iodide (5 mL, 68.3 mmol) neat. After stirring 24 hours at ambient temperature the reaction was 70% complete. 150 mL water was added and the mixture was extracted with ethyl acetate (3×50 mL). The combined organics were washed with water (1×100 mL), brine and dried with Na$_2$SO$_4$. The residue was re-subjected to the above conditions until the reaction was complete. The reaction workup was identical the procedure above. 12.2 grams (93%) of the title compound was isolated as an oil. $^1$H-NMR (400 MHz, DMSO-$d_6$) δ 5.87-5.67 (m, 1H), 5.09 (ddq, J=22.0, 17.2, 1.6 Hz, 2H), 4.07-3.86 (m, 2H), 2.78 (s, 3H), 1.80-1.46 (m, 6H), 1.41-1.25 (m, 4H), 1.24-0.96 (m, 3H), 0.78-0.68 (m, 1H); MS 251 (MH+).

Example 2.113: 5-cyclohexyl-3-(2-(3-methoxyphenyl)-2-oxoethyl)-1,5-dimethyl-imidazolidine-2,4-dione Prepared in a similar manner as described in Example 2.43 using 5-cyclohexyl-1,5-dimethylimidazolidine-2,4-dione (Example 2.47a) (100.0 mg, 476 μmol), and commercially available 2-bromo-1-(3-methoxyphenyl)ethanone (117.0 mg, 686 mol), to obtain the desired product. $^1$H NMR (400 MHz, d$_6$-DMSO) δ 7.66-7.62 (m, 1H), 7.53-7.46 (m, 2H), 7.30-7.26 (m, 1H), 4.95 (s, 2H), 3.83 (s, 3H), 2.82 (s, 3H), 1.79-1.66 (m, 4H), 1.66-1.57 (m, 2H), 1.38 (s, 3H), 1.37-1.29 (m, 1H), 1.26-1.13 (m, 2H), 1.10-1.01 (m, 1H), 0.98-0.87 (m, 1H). MS 359 (MH+).

Example 2.114: 5-cyclohexyl-3-(2-(3-hydroxy-4-methoxyphenyl)-2-oxoethyl)-1,5-dimethylimidazolidine-2,4-dione Prepared in a similar manner as described in Example 2.43 using 5-cyclohexyl-1,5-dimethylimidazolidine-2,4-dione (Example 2.47a) (107.0 mg, 509 μmol), and 2-bromo-1-(3-hydroxy-4-methoxyphenyl)ethanone (114a) (137.0 mg, 559 μmol), to obtain the desired product (59.7 mg, 31%). $^1$H NMR (400 MHz, d$_6$-DMSO) δ 9.54 (s, 1H), 7.58 (dd, J=8.5, 2.2 Hz, 1H), 7.35 (d, J=2.2 Hz, 1H), 7.06 (d, J=8.6 Hz, 1H), 4.85 (d, J=18.0 Hz, 1H), 4.80 (d, J=18.0 Hz, 1H), 3.86 (s, 3H), 2.81 (s, 3H), 1.79-1.66 (m, 4H), 1.65-1.57 (m, 2H), 1.38 (s, 3H), 1.37-1.28 (m, 1H), 1.25-1.12 (m, 2H), 1.10-1.01 (m, 1H), 0.99-0.88 (m, 1H). MS 375 (MH+).

Example 2.114a: 2-bromo-1-(3-hydroxy-4-methoxyphenyl)ethanone

Prepared in a similar manner as described in Example 2.49a using commercially available 1-(3-hydroxy-4-methoxyphenyl)ethanone (1.0 g, 6.0 mmol), to obtain the desired product (881.1 mg, 60%). $^1$H NMR (400 MHz, d$_6$-DMSO) δ 9.48 (s, 1H), 7.54 (dd, J=8.5, 2.2 Hz, 1H), 7.37 (d, J=2.2 Hz, 1H), 7.04 (d, J=8.5 Hz, 1H), 4.79 (s, 2H), 3.86 (s, 3H). MS no ionization.

Example 2.115: 5-(cyclohex-3-en-1-yl)-1,5-dimethyl-3-(2-oxo-2-(1H-pyrrol-2-yl)ethyl)imidazolidine-2,4-dione Prepared in a similar manner as described in Example 2.60 starting from 5-(cyclohex-3-en-1-yl)-1,5-dimethylimidazolidine-2,4-dione (Example 2.93a) (42 mg, 0.2 mmol) and 2-bromo-1-(1H-pyrrol-2-yl)ethanone (45 mg, 0.22 mmol) to obtain the desired product (12 mg, 20%) as a white solid. $^1$H NMR (400 MHz, CDCl$_3$) δ δ 9.32 (s, 1H), 7.07 (m, 1H) 7.05 (m, 1H), 6.33 (dt, J=3.9, 2.5 Hz, 1H), 5.69 (s, 2H), 4.92 (d, J=3.2 Hz, 2H), 2.98-2.87 (m, 3H), 2.53-2.36 (m, 1H), 2.22-1.94 (m, 4H), 1.92-1.73 (m, 1H), 1.53 (d, J=6.6 Hz, 3H), 1.39-1.24 (m, 1H). MS 327 (MH+).

Example 2.116: 5-cyclohexyl-1,5-dimethyl-3-(2-oxo-2-(1H-pyrazol-5-yl)ethyl) imidazolidine-2,4-dione To an oven dried, N$_2$-flushed 25 mL round bottom flask was added 1-((2-(trimethylsilyl)ethoxy)methyl)-1H-pyrazole (Example 2.116a) (0.330 g, 1.67 mmol). The flask was sealed and purged with nitrogen. 3 mL anhydrous THF was added and the flask was cooled to −78° C. 1.8 M n-butyl lithium (0.930 mL, 1.67 mmol) was added and the reaction was stirred at −78° C. for 30 minutes. 2-(4-Cyclohexyl-3,4-dimethyl-2,5-dioxoimidazolidin-1-yl)-N-methoxy-N-methylacetamide (116b) (0.451 g, 1.45 mmol) in 1 mL THF was added to the solution at −78° C. and the reaction was stirred for 4 hours. The reaction was quenched at −78° C. with 1 mL water. The mixture was extracted with ethyl acetate (3×10 mL) and dried with Na$_2$SO$_4$. The solvent was removed to afford 50 mg of 5-cyclohexyl-1,5-dimethyl-3-(2-oxo-2-(1-((2-(trimethylsilyl)ethoxy)methyl)-1H-pyrazol-5-yl)ethyl)imidazolidine-2,4-dione. The residue was dissolved in 1 mL dioxane and 1 mL 6 M HCl and heated at 50° C. for 4 h. The solvent was evaporated and the residue was purified by HPLC chromatography using acetonitrile and water as eluents to afford 4 mg of the title compound as a white solid. $^1$H-NMR (400 MHz, DMSO-d$_6$) δ 7.92 (s, 1H), 6.79 (s, 1H), 4.78 (s, 2H), 2.79 (s, 3H), 1.77-1.54 (m, 6H), 1.39-0.75 (m, 8H); MS 319 (MH+).

Example 2.116a: 1-((2-(trimethylsilyl)ethoxy)methyl)-1H-pyrazole

Example 2.116b: 2-(4-cyclohexyl-3,4-dimethyl-2,5-dioxoimidazolidin-1-yl)-N-methoxy-N-methylacetamide To an oven dried, N$_2$-flushed 100 mL round bottom flask was added 5-cyclohexyl-5-methylimidazolidine-2,4-dione (Example 2.47d) (6.77 g, 32.9 mmol), K$_2$CO$_3$ (6.80 g, 49.3 mmol) 32 mL of anhydrous DMF and commercially available 2-chloro-N-methoxy-N-methylacetamide (4.74 g, 34.5 mmol). The reaction was stirred at 50° C. for 12 h. The reaction was cooled and 70 mL water was added with stirring. The precipitate was filtered and dried to afford 8.9 g (92%) of 2-(4-cyclohexyl-4-methyl-2,5-dioxoimidazolidin-1-yl)-N-methoxy-N-methylacetamide as a white solid.

To an oven dried, N$_2$-flushed 100 mL round bottom flask was added 2-(4-cyclohexyl-4-methyl-2,5-dioxoimidazolidin-1-yl)-N-methoxy-N-methylacetamide (8.90 g, 29.9 mmol), Cs$_2$CO$_3$ (13.65 g, 41.9 mmol), 30 mL DMF and methyl iodide (2 mL, 31.4 mmol). The reaction was stirred for 24 hours and 60 mL water was added. The mixture was extracted with ether (3×50 mL). The combined organic layers were washed with water (1×100 mL), brine and dried with Na$_2$SO$_4$. The solvent was evaporated, and the residue was purified by column chromatography utilizing a Silicycle column (120 g) and elution with 20-70% ethyl acetate/hexane to afford 8.2 g (88%) of the title compound as a white solid. $^1$H-NMR (400 MHz, DMSO-d$_6$) δ 4.28 (s, 2H), 3.73 (s, 3H), 3.10 (s, 3H), 2.78 (s 3H), 1.79-1.49 (m, 6H), 1.39-1.25 (m, 4H), 1.23-0.82 (m, 4H); MS 312 (MH+).

Example 2.117: 5-cyclohexyl-1,5-dimethyl-3-(2-oxo-2-(m-tolyl)ethyl)imidazolidine-2,4-dione Prepared in a similar manner as described in Example 2.43 using 5-cyclohexyl-1,5-dimethylimidazolidine-2,4-dione (Example 2.47a) (100.0 mg, 476 μmol), and commercially available 2-bromo-1-m-tolylethanone (146.0 mg, 685 μmol), to obtain the desired product (109.6 mg, 67%). $^1$H NMR (400 MHz, d$_6$-DMSO) δ 7.87-7.80 (m, 2H), 7.53 (d, J=7.5 Hz, 1H), 7.46 (t, J=7.6 Hz, 1H), 4.95 (d, J=18.1 Hz, 1H), 4.90 (d, J=18.1 Hz, 1H), 2.82 (s, 3H), 2.39 (s, 3H), 1.79-1.66 (m, 4H), 1.66-1.57 (m, 2H), 1.38 (s, 3H), 1.37-

1.28 (m, 1H), 1.25-1.13 (m, 2H), 1.10-1.01 (m, 1H), 0.99-0.87 (m, 1H). MS 343 (MH+).

Example 2.118: 5-cyclohexyl-3-(2-(1-ethyl-1H-pyrazol-4-yl)-2-oxoethyl)-15-dimethyl-imidazolidine-2,4-dione Prepared in a similar manner as described in Example 2.45 starting from 5-cyclohexyl-1,5-dimethylimidazolidine-2,4-dione (Example 2.47a) (0.143 g, 0.67 mmol), $K_2CO_3$ (0.141 g, 1.02 mmol), 0.5 mL DMF and 2-bromo-1-(1-ethyl-1H-pyrazol-4-yl)ethanone (Example 2.118a) (0.145 g, 0.67 mmol) to afford 0.107 g (46%) of the title compound as a white solid. $^1$H-NMR (400 MHz, DMSO-$d_6$) δ 8.56 (s 1H), 8.05 (s, 1H), 4.65 (s, 2H), 4.19 (q, J=7.3 Hz, 2H), 2.80 (s, 3H), 1.80-1.54 (m, 6H), 1.48-1.26 (m, 7H), 1.25-0.85 (m, 4H); MS 347 (MH+).

Example 2.118a: 2-bromo-1-(1-ethyl-1H-pyrazol-4-yl)ethanone

To an oven dried, 100 mL round bottom flask was added ethyl 1H-pyrazole-4-carboxylate (3.2 g, 22.8 mmol), $Cs_2CO_3$ (8.9 g, 27.4 mmol), 20 mL DMF and ethyl iodide (2 mL, 23.9 mmol). The reaction was stirred for 50° C. for 12 h. 20 mL water was added and the mixture was extracted with ethyl acetate (3×10 mL). The combined organic layers were washed with water (1×20 mL), brine and dried with $Na_2SO_4$ to afford 3.6 grams of ethyl 1-ethyl-1H-pyrazole-4-carboxylate as an oil.

To a 100 mL round bottom flask was added ethyl 1-ethyl-1H-pyrazole-4-carboxylate (3.6 g, 21.4 mmol), 20 mL methanol and 10 M NaOH (8.6 mL, 85.6 mmol). The reaction was refluxed for 2 hours and cooled to room temperature. The pH was adjusted to approximately 2 with 6 M HCl. The white precipitate was collected and dried to afford 2.4 g (80%) of 1-ethyl-1H-pyrazole-4-carboxylic acid as a white solid. $^1$H-NMR (400 MHz, DMSO-$d_6$) δ 12.27 (s, 1H), 8.25 (s, 1H), 7.78 (s, 1H), 4.15 (q, J=10 Hz, 3H), 1.36 (t, J=10 Hz, 4H)

To an oven dried, $N_2$-flushed 100 mL round bottom flask was added 1-ethyl-1H-pyrazole-4-carboxylic acid (0.978 g, 6.98 mmol), 10 mL DCM, oxalyl chloride (2.4 mL, 27.9 mmol) and 1 drop of DMF. The reaction was stirred for 1 h at 45° C. The solvent was removed. Toluene was added and evaporated 2 times. The residue was dissolved in 10 mL acetonitrile and cooled to 0° C. Trimethylsilyldiazomethane (10.5 mL, 20.9 mmol) was added and the reaction as stirred for 12 h at ambient temperature. The solution was cooled to 0° C. and 2.2 mL of HBr was added. The reaction was stirred for 1 hour and the solvent was evaporated. The residue was dissolved in 20 mL ethyl acetate and washed with saturated $NaHCO_3$, brine and dried with $Na_2SO_4$ to afford 1.3 grams of 2-bromo-1-(1-ethyl-1H-pyrazol-4-yl)ethanone (118a) as an oil. MS 217 (MH+). The compound was used without any further purification.

Example 2.119: 5-((2S,5R)-2-isopropyl-5-methylcyclohexyl)-1-(2-oxo-2-phenylethyl) imidazolidine-2,4-dione Prepared in a similar manner as described in Example 2.44 from 5-((2S,5R)-2-isopropyl-5-methylcyclohexyl) imidazolidine-2,4-dione (Example 2.119a) (107.1 mg, 449 μmol), $K_2CO_3$ (107.0 mg, 774 μmol), and 2-bromo-1-phenylethanone (97.5 mg, 490 μmol), to obtain the desired compound (22.5 mg, 14%). $^1$H NMR (400 MHz, $d_6$-DMSO) δ 8.79 (s, 1H), 8.09-8.00 (m, 2H), 7.74-7.69 (m, 1H), 7.61-7.55 (m, 2H), 4.95 (s, 2H), 1.77-1.64 (m, 3H), 1.63-1.53 (m, 3H), 1.45-1.32 (m, 3H), 1.03-0.91 (m, 2H), 0.88 (d, J=6.4 Hz, 3H), 0.84 (d, J=3.7 Hz, 3H), 0.82 (d, J=3.5 Hz, 3H). MS—Does not ionize well.

Example 2.119a: 5-((2S,5R)-2-isopropyl-5-methyl-cyclohexyl)imidazolidine-2,4-dione Prepared in a similar manner as described in Example 2.44b from (1R,2S,5R)-2-isopropyl-5-methylcyclohexanecarbaldehyde (Example 2.119b) (752.3 mg, 4.47 mmol), except the reaction medium was heated at 55° C. for 18 hours only and the work-up was a combination of precipitate filtration and extraction using $H_2O$/EtOAc, to obtain the desired compound (691.9 mg, 65%) which was used without further purification. The proton NMR is consistent with the structure, showing also additional peaks related to starting material. MS no ionization.

Example 2.119b: (1R,2S,5R)-2-isopropyl-5-methylcyclohexanecarbaldehyde

To a suspension of (methoxymethyl)triphenylphosphonium chloride (9.33 g, 19.45 mmol) in dry THF (60 mL) at 0° C., was added a 2 M solution of n-BuLi in hexanes (13.61 mL, 27.22 mmol) via syringe over 10 min. The red solution was stirred for 30 min at 0° C. and (−)-menthone (3.00 g, 19.45 mmol) was added over 5 min. The reaction mixture was stirred for 10 h at room temperature and then quenched with 1 N HCl, extracted with diethyl ether (3×), dried over anhydrous magnesium sulfate and concentrated partially under reduced pressure. The residue was filtered to remove the solid triphenyl phosphine oxide and the filtrate was concentrated under reduced pressure. The enol ether obtained was then dissolved in 20 mL of chloroform and 3 mL of 12 N HCl was added. The solution was stirred 4 h at room temperature and chloroform was evaporated. Diethyl ether and water were added and the aqueous phase was extracted with diethyl ether (2×) and the combined organic layers were dried over anhydrous magnesium sulfate and concentrated under reduced pressure. The residue was purified by flash chromatography eluting with ethyl acetate: hexanes (1:20) to yield 2.76 g (84%) of the desired aldehyde. $^1$H NMR (CDCl$_3$, 400 MHz): δ 9.49 (d, 1H, J=4.4 Hz), 2.24 (tt, 1H, J=11.5, 4.4 Hz), 1.82-1.63 (m, 4H), 1.54 (tt, 1H, J=11.8, 3.2 Hz), 1.47-1.26 (m, 2H), 1.17-0.88 (m, 2H), 0.92 (d, 6H, J=6.5 Hz), 0.80 (d, 3H, J=7.5 Hz). MS 168 (MH+)

Example 2.120: 5-(2-(benzyloxy)phenyl)-1,5-dimethyl-3-(2-oxo-2-phenylethyl) imidazolidine-2,4-dione Prepared in a similar manner as described in Example 2.70 starting from 5-(2-benzyloxy)-5-methyl-3-(2-oxo-2-phenylethyl)imidazolidine-2,4-dione (Example 2.120a) (207 mg, 0.5 mmol) and MeI (40 μL, 0.6 mmol) to obtain the desired product (100 mg, 47%) as a white solid. $^1$H NMR (400 MHz, CDCl$_3$) δ 7.76 (dt, J=3.6, 1.4 Hz, 2H), 7.59 (t, J=7.4 Hz, 1H), 7.54-7.49 (m, 2H), 7.49-7.34 (m, 7H), 7.09-6.98 (m, 2H), 4.94 (dd, J=79.2, 10.0 Hz, 2H), 3.97 (dd, J=55.6, 17.8 Hz, 2H), 2.64 (s, 3H), 1.88 (s, 3H). MS 429 (MH+).

Example 2.120a: 5-(2-benzyloxy)-5-methyl-3-(2-oxo-2-phenylethyl)imidazolidine-2,4-dione Prepared in a similar manner as described in Example 2.70a starting from 5-(2-benzyloxy)-5-methylimidazolidine-2,4-dione (296 mg, 1 mmol) and 2-bromo-1-phenylethanone (199 mg, 1 mmol) to obtain the desired 5-(2-benzyloxy)-5-methyl-3-(2-oxo-2-phenylethyl)imidazolidine-2,4-dione (250 mg, 71%) as a white solid. $^1$H NMR is consistent with structure. MS 415 (MH$^+$).

Example 2.120b: 5-(2-benzyloxy)-5-methylimidazolidine-2,4-dione

Prepared in a similar manner as described in Example 2.60d starting from 1-(2-(benzyloxy)phenyl)ethanone (1130 mg, 5 mmol) to obtain the desired product (1 g, 68%) as a white solid. MS 297 (MH$^+$).

Example 2.121: (5S,6S,9R)-6-isopropyl-9-methyl-3-(2-oxo-2-phenylethyl)-1,3-diazaspiro[4.5]decane-2,4-dione Prepared in a similar manner as described in Example 2.44a starting from (5S,6S,9R)-6-isopropyl-9-methyl-1,3-diazaspiro[4.5]decane-2,4-dione (0.35 g, 1.58 mmol), triethylamine (0.41 g, 3.15 mmol) and 2-bromo-1-phenylethanone (0.33 g, 1.66 mmol) in 2 mL of DCM to afford 137 mg (25%) of the title compound as a white solid. $^1$H-NMR (400 MHz, DMSO-d$_6$) δ 8.79 (s, 1H), 8.06-8.04 (m, 2H), 7.73-7.70 (m, 1H), 7.60-7.56 (m, 2H), 4.95 (s, 2H), 1.75-1.23 (m, 8H), 1.02-0.79 (m, 10H); MS 343 (MH$^+$).

Example 2.121a: (5S,6S,9R)-6-isopropyl-9-methyl-1,3-diazaspiro[4.5]decane-2,4-dione Prepared in a similar manner as described in Example 2.44b starting from (−)-menthone (1.46 g, 9.5 mmol), (NH$_4$)$_2$CO$_3$ (2.82 g, 30 mmol) and KCN (0.68 g, 10.5 mmol) in 12 mL of methanol and 9 mL H$_2$O to obtain the 1.6 grams (76%) of the title compound as a white solid. $^1$H-NMR (400 MHz, DMSO-d$_6$) δ 10.53 (s, 1H), 8.29 (s, 1H), 1.69-1.41 (m, 6H), 1.33-1.22 (m, 2H), 0.93-0.76 (m, 10H); MS 225 (MH$^+$).

Example 2.122: 5-((1R,5S)-6,6-dimethylbicyclo[3.1.1]hept-2-en-2-yl)-1,5-dimethyl-3-(2-oxo-2-phenylethyl)imidazolidine-2,4-dione Prepared in a similar manner as described in Example 2.44 starting from 5-(6,6-dimethylbicyclo-[3.1.1]hept-2-en-2-yl)-1,5-dimethylimidazolidine-2,4-dione (Example 2.138a) (24.5 mg, 0.1 mmol) and 2-bromoacetophenone (24 mg, 0.12 mmol). Gives 11.5 mg (31.4% yield) of product as a white powder. On HPLC this isomer eluted second. $^1$H NMR (400 MHz, DMSO-d$_6$) δ 7.95 (d, J=8 Hz, 2H), 7.61 (t, J=8 Hz, 1H), 7.49 (t, J=8 Hz, 2H), 5.79 (m, 1H), 4.92 (s, 2H), 2.80 (s, 3H), 2.46 (m, 1H), 2.37 (m, 2H), 2.17 (t, J=4 Hz, 1H), 2.12 (m, 1H), 1.63 (s, 3H), 1.33 (s, 3H), 1.07 (d, J=8 Hz, 1H), 0.77 (s, 3H). MS 367 (MH$^+$).

Example 2.123: 5-(2-chlorobenzyl)-1,5-dimethyl-3-(2-oxo-2-phenylethyl)imidazolidine-2,4-dione 5-(2-chlorobenzyl)-1,5-dimethylimidazolidine-2,4-dione (Example 2.123a)(249 mol, 63 mg) and K$_2$CO$_3$ (374 μmol, 52 mg) were placed in a vial with dry DMF (2 mL) and stirred for 1 minute. 2-bromo-1-phenylethanone (274 mol, 55 mg) was added and stirred at room temperature overnight. The reaction was quenched with 10% citric acid/water solution (10 mL) and an additional 20 mL of water was added. The reaction mixture was extracted with DCM (3×10 mL), washed with brine, then dried over MgSO$_4$, filtered, and concentrated in vacuo. The final product was purified by silica gel flash chromatography (10→60% EtOAc/hexanes gradient). to give a 61% yield of product. $^1$H NMR (400 MHz, d$_6$-DMSO) δ 8.02-7.98 (m, 2H), 7.71-7.66 (m, 1H), 7.57-7.51 (m, 2H), 7.44-7.39 (m, 1H), 7.28-7.25 (m, 2H), 7.25-7.20 (m, 1H), 4.86 (d, J=18.2 Hz, 1H), 4.81 (d, J=18.1 Hz, 1H), 3.26 (d, J=2.7 Hz, 2H), 2.87 (s, 3H), 1.52 (s, 3H). MS 371 (MH$^+$).

Example 2.123a: 5-(2-chlorobenzyl)-1,5-dimethylimidazolidine-2,4-dione 5-(2-chlorobenzyl)-3-(4-methoxybenzyl)-1,5-dimethylimidazolidine-2,4-dione (Example 2.123b) (250 mol, 93 mg) was dissolved in ACN (2.5 mL) and water (0.5 mL). Ceric ammonium nitrate (525 mol, 288 mg) was added and the mixture was allowed to stir at room temperature overnight. Additional ceric ammonium nitrate (125 mol, 69 mg) was added with stirring at room temperature overnight. Saturated NaHCO$_3$/water solution (10 mL) was added and stirred at room temperature for 30 minutes, then the salts were filtered off and washed with a 50:50 mixture of water:ACN. The filtrate was concentrated to dryness and the residue extracted with hot THF (3×5 mL). THF was removed in vacuo to give a light orange solid, 63 mg, ~90% pure by $^1$H NMR (balance is unreacted starting material). Used in the subsequent step without further purification.

Example 2.123b: 5-(2-chlorobenzyl)-3-(4-methoxybenzyl)-1,5-dimethylimidazolidine-2,4-dione 5-(2-chlorobenzyl)-3-(4-methoxybenzyl)imidazolidine-2,4-dione (Example 2.123c) (895 μmol, 309 mg) and NaH (60% dispersion in mineral oil, 1.97 mmol, 79 mg) were added to a vial with dry DMF (2 mL) under nitrogen. The reaction was stirred for 10 minutes until bubbling ceased then MeI (2.24 mmol, 140 μL) was added and the reaction was stirred overnight at room temperature. Water (30 mL) was slowly added followed by 10% citric acid/water solution (5 mL). The resulting precipitate was filtered, washed with water and dried in a vacuum oven overnight at 50° C. to give a beige solid, 319 mg, 96% yield. MS 373 (MH$^+$). $^1$H NMR is consistent with structure.

Example 2.123c: 5-(2-chlorobenzyl)-3-(4-methoxybenzyl)imidazolidine-2,4-dione 5-(2-chlorobenzyl)imidazolidine-2,4-dione (Example 2.123d) (1.0 mmol, 225 mg), dry DMF (2 mL) and K$_2$CO$_3$ (1.0 mmol, 139 mg) were combined in a vial and stirred at room temperature for 1 minute, then 4-methoxybenzyl chloride (1.0 mmol, 136 μL) was added and stirred 48 h at room temperature. Water (30 mL) was added and the resulting precipitate was filtered and washed with water, then dried in a vacuum oven overnight at 50° C. to afford 309 mg of product as a white solid, 90% yield. MS 345 (MH$^+$). $^1$H NMR is consistent with structure.

Example 2.123d: 5-(2-chlorobenzyl)imidazolidine-2,4-dione

Prepared in a similar manner to Example 2.46d from L-2-amino-3-(2-chlorophenyl) propanoic acid (4.63 mmol, 923 mg). 715 mg of a white solid, 65% yield. MS 225 (MH$^+$). $^1$H NMR is consistent with structure.

Example 2.124: 3-(2-(3-chlorophenyl)-2-oxoethyl)-5-cyclohexyl-1,5-dimethyl-imidazolidine-2,4-dione In an oven-dried, $N_2$-flushed, small round-bottom flask, were added anhydrous DMF (8.0 mL), 5-cyclohexyl-1,5-dimethylimidazolidine-2,4-dione (Example 2.47a) (62 mg, 0.29 mmol), and at 0° C. NaH (15 mg, 0.35 mmol), and 2-bromo-1-(3-chlorophenyl)ethanone (82 mg, 0.35 mmol). The reaction medium was stirred vigorously at room temperature for 3 hr, and extracted with $H_2O$/DCM (3×). Combined organic phases were washed with brine and dried over $MgSO_4$, and solvents were evaporated. The residue was purified by prep HPLC to obtain the pure product (30 mg, 28%) as a clear oil. $^1$H NMR (400 MHz, $CDCl_3$) δ 7.93 (t, J=2.0 Hz, 1H), 7.57 (d, J=7.6 Hz, 1H), 7.82 (dt, J=7.6 Hz & 0.8 Hz, 1H), 7.42 (t, J=8 Hz, 1H), 4.87 (s, 2H), 2.91 (s, 3H), 1.45-1.86 (s&m, 10H), 1.02-1.24 (m, 4H). MS 363 (MH$^+$).

Example 2.125: 1,5-dimethyl-3-(2-oxo-2-(pyridin-3-ethyl)-5-phenethylimidazolidine-2,4-dione Prepared in a similar manner as described in Example 2.45 starting from 1,5-dimethyl-5-phenethylimidazolidine-2,4-dione (Example 2.125a) (153 mg, 0.66 mmol) and 3-(bromoacetyl)-pyridine hydrobromide (222 mg, 0.79 mmol), to obtain the pure desired product as a light yellow oil (30 mg, 13%). $^1$H NMR (400 MHz, DMSO-$d_6$) δ 9.20 (d, J=1.6 Hz, 1H), 8.83 (dd, J=4.4 Hz, 1H), 8.23 (d, J=8.4 Hz, 1H), 7.45 (dd, J=8 Hz & 4.8 Hz, 1H), 7.27 (m, 2H), 7.17 (m, 3H), 4.91 (s, 2H), 2.90 (s, 3H), 2.62 (m, 1H), 2.53 (m, 1H), 2.24 (m, 1H), 1.80 (m, 1H), 1.48 (s, 3H). MS 352 (MH$^+$).

Example 2.125a: 1,5-dimethyl-5-phenethylimidazolidine-2,4-dione

Prepared in a similar manner as described in Example 2.45a starting from 3-(4-methoxybenzyl)-1,5-dimethyl-5-phenethylimidazolidine-2,4-dione (Example 2.125b) (2.75 mmol, 640 g) and a solution of ammonium cerium nitrate (3.9 g, 7.15 mmol) in water (20 mL), to obtain the pure product as a light brown solid (320 mg, 80%). The reaction mixture had stirred at room temperature for 18 hrs. Both LCMS and analytical TLC showed completion of the reaction (no MS ionization). After ACN was evaporated, the resulting water layer was extracted with 30% ACN in DCM (30 mL×3). The organic layers were combined, washed with brine, and then dried over $MgSO_4$. After the solvent was evaporated, the resulting light brown oil was purified on Biotage 40 g silica column with elute 10%~40% EtOAc/Hex (Rf~0.2 in 30% EtOAc/Hex).

Example 2.125b: 3-(4-methoxybenzyl)-1,5-dimethyl-5-phenethylimidazolidine-2,4-dione Prepared in a similar manner as described in Example 2.45b starting from 3-(4-methoxybenzyl)-5-phenethylimidazolidine-2,4-dione (Example 2.125c) (2.96 mmol, 961 mg) in DMF (15 mL) (125c), and methyl bromide (7.1 mmol, 442 mL), to obtain the pure product as a white solid (640 mg, 61%). MS 353 (MH$^+$).

Example 2.125c: 3-(4-methoxybenzyl)-5-phenethyl-imidazolidine-2,4-dione

Prepared in a similar manner as described in Example 2.45c starting from (S)-5-phenethylimidazolidine-2,4-dione (Example 2.125d) (900 mg, 4.4 mmol) in DMF (25 mL) (Example 2.125d), and para-methoxyl benzyl chloride (1.1 eq, 4.8 mmol, 657 µL), to obtain the pure product as a white solid (961 mg, 67%). $^1$H NMR (400 MHz, DMSO-$d_6$) δ 8.45 (s, 1H), 7.25 (m, 2H), 7.16 (m, 3H), 6.85 (m, 2H), 4.38 (dd, J=20 Hz & 15.2, 2H), 3.70 (s, 3H), 2.57 (m, 2H), 1.98 (s, 1H), 1.79 (m, 1H).

Example 2.125d: (S)-5-phenethylimidazolidine-2,4-dione

Prepared in a similar manner as described in Example 2.46d starting from α-homo-phenylalanine (5.18 mmol, 930 mg) in water (25 mL), HCl (0.4 mL), and potassium cyanate (26 mmol, 2.1 g), to obtain the pure product as a white solid (979 mg, 92%). $^1$H NMR (400 MHz, DMSO-$d_6$) δ 12.50 (s, 1H), 7.24 (m, 2H), 7.15 (m, 3H), 6.33 (d, J=8.4 Hz, 1H), 4.00 (m, 1H), 2.55 (m, 2H), 1.89 (m, 1H), 1.76 (m, 1H).

Example 2.126: 5-(2-methoxy-4,5-dimethylphenyl)-1,5-dimethyl-3-(2-oxo-2-phenylethyl)imidazolidine-2,4-dione Prepared in a similar manner as described in Example 2.44 starting from 5-(2-methoxy-4,5-dimethylphenyl)-5-methyl-3-(2-oxo-2-phenylethyl)imidazolidine-2,4-dione (Example 2.126a) (284 mg, 0.77 mmol) and methyl iodide (58 µL, 0.93 mmol) to obtain product as a white powder (144 mg, 49% yield). $^1$H NMR (400 MHz, DMSO-$d_6$) δ 8.07 (d, J=8 Hz, 2H), 7.70 (t, J=8 Hz, 1H), 7.57 (t, J=8 Hz, 2H), 7.21 (s, 1H), 6.83 (s, 1H), 5.02 (s, 2H), 3.65 (s, 3H), 2.47 (s, 3H), 2.21 (s, 3H), 2.19 (s, 3H), 1.73 (s, 3H). MS 381 (MH$^+$).

Example 2.126a: 5-(2-methoxy-4,5-dimethylphenyl)-5-methyl-3-(2-oxo-2-phenylethyl)imidazolidine-2,4-dione Prepared in a similar manner as described in Example 2.44a starting from 5-(2-methoxy-4,5-dimethylphenyl)-5-methylimidazolidine-2,4-dione (Example 2.126b) (248 mg, 1 mmol) and 2-bromoacetophenone (200 mg, 1 mmol) to obtain product as a white powder (284 mg, 78% yield). $^1$H NMR (400 MHz, DMSO-$d_6$) δ 8.33 (s, 1H), 8.06 (d, J=8 Hz, 2H), 7.69 (t, J=8 Hz, 1H), 7.55 (t, J=8 Hz, 1H), 7.15 (s, 1H), 6.82 (s, 1H), 4.97 (s, 2H), 3.68 (s, 3H), 2.19 (s, 3H), 2.16 (s, 3H), 1.70 (s, 3H). MS 367 (MH$^+$).

Example 2.126b: 5-(2-methoxy-4,5-dimethylphenyl)-5-methylimidazolidine-2,4-dione Prepared in a similar manner as described in Example 2.44b starting from 1-(2-methoxy-4,5-dimethylphenyl)ethanone (1068 mg, 6 mmol) to obtain product as a white powder (1.35 g, 91% yield). $^1$H NMR (400 MHz, DMSO-$d_6$) δ 10.49 (s, 1H), 7.83 (s, 1H), 7.08 (s, 1H), 6.81 (s, 1H), 3.64 (s, 3H), 2.18 (s, 3H), 2.14 (s, 3H), 1.58 (s, 3H). MS 249 (MH$^+$).

Example 2.127: 1,5-dimethyl-3-(2-oxo-2-phenyl-ethyl)-5-(pyridin-2-yl)imidazolidine-2,4-dione Prepared in a similar manner as described in Example 2.70 starting from 5-methyl-3-(2-oxo-2-phenylethyl)-5-(pyridin-2-yl)imidazolidine-2,4-dione (Example 2.127a) (155 mg, 0.5 mmol) and MeI (40 µL, 0.6 mmol) to obtain the desired product (100 mg, 62%) as a white solid. $^1$H NMR (400 MHz, $CDCl_3$) δ 8.65 (ddd, J=4.8, 1.8, 0.9 Hz, 1H), 8.02-7.95 (m, 2H), 7.83-7.75 (m, 1H), 7.67-7.56 (m, 2H), 7.55-7.47 (m, 2H), 7.30 (ddd, J=7.5, 4.8, 1.1 Hz, 1H), 5.10-4.93 (m, 2H), 2.85 (s, 3H), 1.99 (s, 3H). MS 324 (MH$^+$).

Example 2.127a: 5-methyl-3-(2-oxo-2-phenylethyl)-5-(pyridin-2-yl)imidazolidine-2,4-dione Prepared in a similar manner as described in Example 2.70a starting from 5-methyl-5-(pyridin-2-yl)imidazolidine-2,4-dione (Example 2.127b) (191 mg, 1 mmol) and 2-bromo-1-phenylethanone (199 mg, 1 mmol) to obtain the product (200 mg, 65%) as a light yellow solid. $^1$H NMR (400 MHz, CDCl$_3$) δ 8.62-8.55 (m, 1H), 7.96 (dd, J=8.4, 1.3 Hz, 2H), 7.79-7.71 (m, 2H), 7.61 (d, J=7.4 Hz, 1H), 7.49 (dd, J=11.7, 4.3 Hz, 2H), 7.33-7.27 (m, 1H), 6.46 (s, 1H), 4.96 (s, 2H), 1.91 (s, 3H). MS 310 (MH$^+$).

Example 2.127b: 5-methyl-5-(pyridin-2-yl)imidazolidine-2,4-dione

Prepared in a similar manner as described in Example 2.60d starting from 1-(pyridin-2-yl)ethanone (1210 mg, 10 mmol) to obtain the product (1 g, 52%) as a light yellow solid. $^1$H NMR is consistent with structure. MS 192 (MH$^+$).

Example 2.128: (5S,6S,9R)-6-isopropyl-1,9-dimethyl-3-(2-oxo-2-phenylethyl)-1,3-diazaspiro[4.5]decane-2,4-dione Prepared in a similar manner as described in Example 2.44 starting from (5S,6S,9R)-6-isopropyl-9-methyl-1,3-diazaspiro[4.5]decane-2,4-dione (Example 2.121) (0.13 g, 0.38 mmol), K$_2$CO$_3$ (0.080 g, 0.570 mmol) and methyl iodide (0.070 g, 0.49 mmol) in 5 mL DMF to afford 21 mg (16%) of the title compound as a white solid. $^1$H-NMR (400 MHz, DMSO-d$_6$) δ 8.05-8.03 (m, 2H), 7.74-7.70 (m, 1H), 7.60-7.86 (m, 2H), 5.01 (s, 2H), 3.11 (s, 3H), 1.94-1.71 (m, 6H), 1.60-1.46 (m, 2H), 1.08-0.98 (m, 1H), 0.86-0.80 (m, 6H); MS 357 (MH$^+$).

Example 2.129: 5-cyclopentyl-3-(2-(3-fluorophenyl)-2-oxoethyl)-1,5-dimethylimidazolidine-2,4-dione Prepared in a similar manner as described in Example 2.45 starting from 5-cyclopentyl-1,5-dimethylimidazolidine-2,4-dione (Example 2.45a) (87 mg, 443 umol), and 2-bromo-1-(3-fluorophenyl)ethanone (118 mg, 544 mol), to obtain the pure product as an oily film. $^1$H NMR (400 MHz, CDCl$_3$) δ 7.73-7.70 (m, 1H), 7.63-7.60 (m, 1H), 7.48-7.43 (m, 1H), 7.31-7.26 (m, 1H), 4.87 (s, 2H), 2.91 (s, 3H), 2.31-2.22 (m, 1H), 1.89-1.81 (m, 1H), 1.72-1.51 (m, 6H), 1.48 (s, 3H), 1.42-1.35 (m, 1H). MS 333 (MH$^+$).

Example 2.130: 5-cyclohexyl-1,5-dimethyl-3-(2-oxo-2-(pyrimidin-5-yl)ethyl) imidazolidine-2,4-dione Anhydrous DCM (3.0 mL), 5-cyclohexyl-3-(2-hydroxy-2-(pyrimidin-5-yl)ethyl)-1,5-dimethylimidazolidine-2,4-dione (Example 2.130a) (52 mg, 0.16 mmol), and pyridinium dichromate (88 mg, 0.23 mmol) were added to a N$_2$-flushed, small round-bottom flask. After stirring at room temperature for 18 hrs. the reaction mixture was diluted with H$_2$O and DCM. The organic layer was dried over MgSO$_4$, and solvents were evaporated. The residue was purified by mass-triggered HPLC to obtain the desired product (20 mg, 40%) as a white solid.
$^1$H NMR (400 MHz, CDCl$_3$) δ 9.42 (s, 1H), 9.26 (s, 2H), 4.89 (s, 2H), 2.92 (s, 3H), 1.45-1.86 (s & m, 10H), 1.01-1.26 (m, 4H). MS 331 (MH$^+$).

Example 2.130a: 5-cyclohexyl-3-(2-hydroxy-2-(pyrimidin-5-v)ethyl)-1,5-dimethylimidazolidine-2,4-dione In an oven-dried, N$_2$-flushed, small round-bottom flask, was added 5-bromopyrimidine (229 mg, 1.44 mmol) in THF (20 mL) at room temperature The solution was cooled down to −78° C., then nBuLi was added dropwise. After stirring for 2 min at −78° C., 2-(4-cyclohexyl-3,4-dimethyl-2,5-dioxoimidazolidin-1-yl)acetaldehyde (Example 2.112b) in THF (2 mL) (275 mg, 1.09 mmol) was added dropwise over 5 mins. The resulting reaction mixture was stirred at −78° C. for 1 hr and quenched with cold water (10 mL). The mixture was extracted with DCM (3×25 mL) and the combined organic layer was dried over MgSO$_4$, and concentrated. The residue was purified by mass-triggered HPLC to obtain the desired product (100 mg, 30%) as a clear oil. MS 333 (MH$^+$). H$^1$-NMR is consistent with the structure.

Example 2.131: 5-cyclobutyl-1,5-dimethyl-3-(2-oxo-2-phenylethyl)imidazolidine-2,4-dione Prepared in a similar manner as described in Example 2.44 starting from 5-cyclobutyl-5-methyl-3-(2-oxo-2-phenylethyl)imidazolidine-2,4-dione (Example 2.131a) (0.10 g, 0.37 mmol), K$_2$CO$_3$ (0.61 g, 0.44 mmol) and methyl iodide (0.062 g, 0.44 mmol) in 0.5 mL DMF to afford 63 mg (57%) of the title compound as a semi-solid. $^1$H-NMR (400 MHz, DMSO-d$_6$) δ 8.07-8.04 (m, 2H), 7.74-7.70 (m, 1H) 7.60-7.56 (m, 2H), 4.99 (s, 2H), 2.85-2.75 (m, 4H), 2.37-2.30 (m, 1H), 1.89-1.73 (m, 4H), 1.66-1.62 (m, 1H), 1.29 (s, 3H); MS 301 (MH$^+$).

Example 2.131a: 5-cyclobutyl-5-methyl-3-(2-oxo-2-phenylethyl)imidazolidine-2,4-dione Prepared in a similar manner as described in Example 2.44a starting from 5-cyclobutyl-5-methylimidazolidine-2,4-dione (Example 2.131b) (0.202 g, 1.2 mmol), diisopropylethylamine (0.31 g, 2.4 mmol), and bromoacetophenone (0.26 g, 1.3 mmol) in 2 mL DMF to afford 210 mg (61%) of the title compound as an off white semi-solid. $^1$H-NMR (400 MHz, DMSO-d$_6$) δ 8.53 (s, 1H), 8.03-8.00 (m, 2H), 7.71-7.61 (m, 1H), 7.57-7.53 (m, 2H), 4.89 (s, 2H), 2.65-2.58 (m, 1H), 1.96-1.63 (m, 6H), 1.21 (s, 3H); MS 287 (MH$^+$).

Example 2.131b: 5-cyclobutyl-5-methylimidazolidine-2,4-dione

Prepared in a similar manner as described in Example 2.44b starting from 1-cyclobutylethanone (2.19 g, 22.3 mmol), (NH$_4$)$_2$CO$_3$ (6.64 g, 69.2 mmol) and KCN (1.60 g, 24.5 mmol) in 30 mL MeOH and 20 mL of H$_2$O to afford 3.4 g (91%) of the title compound as a white solid. $^1$H-NMR (400 MHz, DMSO-d$_6$) δ 8.03 (s, 1H), 2.58-2.50 (m, 1H), 1.87-1.62 (m, 6H), 1.16 (s, 3H); MS 169 (MH$^+$).

Example 2.132: 5-((3R,5R,7R)-adamantan-1-yl)-1,5-dimethyl-3-(2-oxo-2-phenylethyl) imidazolidine-2,4-dione Prepared in a similar manner as described in Example 2.70 starting from 5-((3R,5R,7R)-adamantan-1-yl)-5- methyl-3-(2-oxo-2-phenylethyl)imidazolidine-2,4-dione (Example 2.132a) (155 mg, 0.5 mmol) and MeI (40 µL, 0.6 mmol) to obtain the desired product (100 mg, 62%) as a white solid. $^1$H NMR (400 MHz, CDCl$_3$) δ 7.96 (dd, J=8.4, 1.3 Hz, 2H), 7.61 (t, J=7.4 Hz, 1H), 7.49 (t, J=7.7 Hz, 2H), 4.90 (d, J=0.7 Hz, 2H), 3.02 (s, 3H), 2.04 (s, 3H), 1.98-1.90 (m, 3H), 1.75-1.58 (m, 9H), 1.47 (s, 3H). MS 324 (MH$^+$).

Example 2.132a: 5-((3R,5R,7R)-adamantan-1-yl)-5-methyl-3-(2-oxo-2-phenylethyl) imidazolidine-2,4-dione Prepared in a similar manner as described in Example 2.70a starting from 5-((3R,5R,7R)-adamantan-1-yl)-5-methylimidazolidine-2,4-dione (Example 2.132b) (191 mg, 1 mmol) and 2-bromo-1-phenylethanone (199 mg, 1 mmol) to obtain the desired product (200 mg, 65%) as a light yellow solid. $^1$H NMR (400 MHz, CDCl$_3$ δ 7.99-7.93 (m, 2H), 7.64-7.58 (m, 1H), 7.50 (dd, J=8.2, 7.1 Hz, 2H), 5.41 (s, 1H), 4.89 (s, 2H), 2.11-2.01 (m, 3H), 1.93 (dd, J=11.9, 1.7 Hz, 3H), 1.81 (d, J=2.9 Hz, 1H), 1.68 (d, J=16.1 Hz, 6H), 1.55-1.51 (m, 2H), 1.48 (s, 3H). MS 310 (MH$^+$).

Example 2.132b: 5-((3r,5r,7r)-adamantan-1-yl)-5-methylimidazolidine-2,4-dione

Prepared in a similar manner as described in Example 2.60d starting from 1-((3R,5R,7R)-adamantan-1-yl)ethanone (1780 mg, 10 mmol) to obtain the product (1.6 g, 65%) as a white solid. $^1$H NMR is consistent with structure. MS 249 (MH$^+$).

Example 2.133: 5-(2,5-diethoxyphenyl)-1,5-dimethyl-3-(2-oxo-2-phenylethyl) imidazolidine-2,4-dione Prepared in a similar manner as described in Example 2.44 starting from 5-(2,5-diethoxyphenyl)-5-methyl-3-(2-oxo-2-phenylethyl)imidazolidine-2,4-dione (Example 2.133a) (294 mg, 0.74 mmol) and methyl iodide (55 µL, 0.89 mmol) to obtain product as a white powder (200.6 mg, 66% yield). $^1$H NMR (400 MHz, DMSO-d$_6$) δ 8.07 (d, J=8 Hz, 2H), 7.70 (t, J=8 Hz, 1H), 7.57 (t, J=8 Hz, 2H), 7.00 (s, 1H), 6.92 (s, 2H), 4.99 (q, J=18 Hz, J=52 Hz, 2H), 3.99 (q, J=8 Hz, J=16 Hz, 2H), 3.88 (q, J=8 Hz, J=12 Hz, 2H), 2.49 (s, 3H), 1.76 (s, 3H), 1.30 (t, J=8 Hz, 3H), 1.19 (t, J=8 Hz, 3H). MS 411 (MH$^+$).

Example 2.133a: 5-(2,5-diethoxyphenyl)-5-methyl-3-(2-oxo-2-phenylethyl)imidazolidine-2,4-dione Prepared in a similar manner as described in Example 2.44a starting from 5-(2,5-diethoxyphenyl)-5-methylimidazolidine-2,4-dione (Example 2.133b) (278 mg, 1 mmol) and 2-bromoacetophenone (239 mg, 1.2 mmol) to obtain product as a white powder (294 mg, 74% yield). $^1$H NMR (400 MHz, DMSO-d$_6$) δ 8.38 (s, 1H), 8.07 (d, J=8 Hz, 2H), 7.70 (t, J=8 Hz, 1H), 7.57 (t, J=8 Hz, 1H), 6.95 (s, 1H), 6.89 (s, 2H), 4.94 (q, J=20 Hz, J=40 Hz, 2H), 3.97 (q, J=8 Hz, J=16 Hz, 2H), 3.88 (q, J=8 Hz, J=12 Hz, 2H), 1.73 (s, 3H), 1.29 (t, J=8 Hz, 3H), 1.22 (t, J=8 Hz, 3H). MS 397 (MH$^+$).

Example 2.133b: 5-(2,5-diethoxyphenyl)-5-methyl-imidazolidine-2,4-dione

Prepared in a similar manner as described in Example 2.44b starting from 1-(2,5-diethoxyphenyl)-ethanone (1248 mg, 6 mmol) to obtain product as a white powder (1.45 g, 87% yield). $^1$H NMR (400 MHz, DMSO-d$_6$) δ 10.51 (s, 1H), 7.87 (s, 1H), 6.87 (m, 3H), 3.95 (q, J=8 Hz, J=16 Hz, 2H), 3.87 (dq, J=8 Hz, J=12v, J=20 Hz, 2H), 1.58 (s, 3H), 1.28 (t, J=8v, 3H), 1.23 (t, J=8 Hz, 3H). MS 279 (MH$^+$).

Example 2.134: 5-(cyclopropylmethyl)-1,5-dimethyl-3-(2-oxo-2-phenylethyl) imidazolidine-2,4-dione Prepared in a similar manner as described in Example 2.105 starting from 5-(cyclopropylmethyl)-1,5-dimethyl-3-((2-phenyl-1,3-dioxolan-2-yl)methyl)imidazolidine-2,4-dione (Example 2.134a) (49.0 mg, 142 umol), except the reaction medium was only heated at 50° C. for 1 hour, to obtain the desired product (42.0 mg, 98%). $^1$H NMR (400 MHz, d$_6$-DMSO) δ 8.08-8.02 (m, 2H), 7.75-7.68 (m, 1H), 7.62-7.53 (m, 2H), 5.00 (s, 2H), 2.85 (s, 3H), 1.88 (dd, J=14.7, 6.1 Hz, 1H), 1.52 (dd, J=14.6, 7.6 Hz, 1H), 1.34 (s, 3H), 0.60-0.50 (m, 1H), 0.44-0.33 (m, 2H), 0.11-0.05 (m, 1H), 0.04--0.02 (m, 1H). MS 301 (MH$^+$).

Example 2.134a: 5-(cyclopropylmethyl)-1,5-dimethyl-3-((2-phenyl-1,3-dioxolan-2-yl)methyl)imidazolidine-2,4-dione Prepared in a similar manner as described in Example 2.105a starting from 1,5-dimethyl-3-((2-phenyl-1,3-dioxolan-2-yl)methyl)imidazolidine-2,4-dione (Example 2.105b) (148.8 mg, 513 mol) and (bromomethyl)cyclopropane (61 µL, 624 umol), except the extracted material was purified by a 40 minutes preparative HPLC run using a CH$_3$CN/H$_2$O gradient as eluant, to obtain the desired product. $^1$H NMR (400 MHz, CDCl$_3$) δ 7.59-7.56 (m, 2H), 7.38-7.31 (m, 3H), 4.03-3.96 (m, 2H), 3.93 (d, J=0.6 Hz, 2H), 3.82-3.75 (m, 2H), 2.88 (s, 3H), 1.73 (dd, J=14.5, 5.2 Hz, 1H), 1.60-1.52 (m, 1H), 1.27 (s, 3H), 0.46-0.36 (m, 2H), 0.34-0.25 (m, 1H), 0.12--0.02 (m, 2H). MS 345 (MH$^+$).

Example 2.135: (S)-5-benzyl-1,5-dimethyl-3-(2-oxo-2-phenylethyl)imidazolidine-2,4-dione Prepared in a similar manner as described in Example 2.44 starting from (S)-5-benzyl-5-methyl-3-(2-oxo-2-phenylethyl)imidazolidine-2,4-dione (Example 2.135a) (0.15 mmol, 47 g) in DMF (5 mL) (Example 2.136a) and iodomethane (0.34 mmol, 20 µL), to obtain the pure desired product as a yellow oil (7 mg, 14%). $^1$H NMR (400 MHz, DMSO-d$_6$) δ 7.88 (m, 2H), 7.59 (m, 1H), 7.44 (m, 2H), 7.25 (m, 3H), 7.09 (m, 2H), 4.61 (dd, J=21 Hz & 17 Hz, 2H), 2.96 (dd, J=85 Hz & 14 Hz, 2H), 3.00 (s, 3H), 1.57 (s, 3H). No ionization.

Example 2.135a: (S)-5-benzyl-5-methyl-3-(2-oxo-2-phenylethyl)imidazolidine-2,4-dione Prepared in a similar manner as described in Example 2.44 starting from (S)-5-benzyl-5-methylimidazolidine-2,4-dione (Example 2.135b) (100 mg, 0.49 mmol) (Example 2.135b) in dry DMF (10 mL) α-bromoacetophenone (118 mg, 0.59 mmol), to obtain the pure product as a light yellow oil (47 mg, 29%). MS 324 (MH$^+$)

Example 2.135b: (S)-5-benzyl-5-methylimidazolidine-2,4-dione

Prepared in a similar manner as described in Example 2.46d starting from α-methylphenylalanine (2 mmol, 358 mg), water (10 mL), concentrated hydrochloric acid (0.2 mL) and potassium cyanate (10 mmol, 810 mg), to obtain the pure product as a white solid (200 mg, 50%). MS 205 (MH+).

Example 2.136: 5-(2-fluorobenzyl)-1,5-dimethyl-3-(2-oxo-2-phenylethyl)imidazolidine-2,4-dione To a 20 mL scintillation vial was added 5-(2-fluorobenzyl)-1,5-dimethylimidazolidine-2,4-dione (Example 2.136a) (90 mg, 0.38 mmol) in dry DMF (2 mL) and potassium carbonate (140 mg, 1.0 mmol) followed by alpha-bromoacetophenone (100 mg, 0.50 mmol). The reaction mixture was stirred at room temperature for 24 hr, then partitioned between DCM (10 mL) and water (10 mL). The aqueous layer was extracted with DCM (10 mL×3) and the combined organic layer was dried over $MgSO_4$ and concentrated. The resulting oil was purified by prep HPLC. The fractions containing pure product were concentrated in vacuo and dried in lyophilizer to afford the product as a white solid (40 mg, 30% yield). $^1$H NMR (400 MHz, $CDCL_3$) δ 7.91 (d, J=8 Hz, 2H), 7.60 (t, J=8 Hz, 1H), 7.47 (t, J=8 Hz, 2H), 7.23 (m, 1H), 7.16 (m, 1H), 7.03 (m, 2H), 4.74 (dd, J=20 Hz, J=8 Hz, 2H), 3.17 (dd, J=16 Hz, J=24 Hz, 2H), 2.98 (d, J=2 Hz, 3H), 1.64 (s, 3H). MS 355 (MH+).

Example 2.136a: 5-(2-fluorobenzyl)-1,5-dimethyl-imidazolidine-2,4-dione

In a $N_2$-flushed round-bottom flask, were added anhydrous $CH_3CN$ (10 mL), 5-(2-fluorobenzyl)-3-(4-methoxybenzyl)-1,5-dimethylimidazolidine-2,4-dione (Example 2.136b) (249 mg, 0.7 mmol), and the solution was cooled to 0° C. in an ice bath ammonium cerium IV nitrate (1000.0 mg, 1.8 mmol) in $H_2O$ (6 mL) was added dropwise and the reaction mixture was stirred vigorously at room temperature overnight. The solution was diluted with brine and extracted with EtOAc (3×10 mL). The combined organic phase was washed again with brine, dried over $MgSO_4$, and concentrated. The resulting compound was used for the next step without further purification. Yield: (90 mg, 54%). MS 237 (MH+)

Example 2.136b: 5-(2-fluorobenzyl)-3-(4-methoxybenzyl)-1,5-dimethylimidazolidine-2,4-dione To a 20 mL scintillation vial were added 5-(2-fluorobenzyl)-3-(4-methoxybenzyl)-imidazolidine-2,4-dione (Example 2.136c) (249 mg, 0.76 mmol) in dry DMF (3 mL) followed by sodium hydride (91 mg, 2.28 mmol) and methyl iodide (190 μL, 3.0 mmol). The reaction mixture was stirred at room temperature for 24 hr then partitioned between DCM (10 mL) and water (10 mL). The aqueous layer was extracted with DCM three times (10 mL each time) and the combined organic layers were dried over $MgSO_4$ and concentrated. The resulting oil was purified by preparative HPLC. The fractions containing pure product were concentrated in vacuo and dried in lyophilizer. Yield: 249 mg (92%). MS 357 (MH+).

Example 2.136c: 5-(2-fluorobenzyl)-3-(4-methoxybenzyl)imidazolidine-2,4-dione

To a 20 mL scintillation vial was added 5-(2-fluorobenzyl)imidazolidine-2,4-dione (Example 2.136d) (168 mg, 0.81 mmol) in dry DMF (3 mL) followed by potassium carbonate (223 mg, 1.6 mmol) and 4-Br-benzylchloride (126 mg, 0.81 mmol). The reaction mixture was stirring at room temperature for 24 hr and the reaction mixture was partitioned between DCM (10 mL) and water (10 mL). The aqueous layer was extracted with DCM three times (10 mL×3) and the combined all organic layers were dried over $MgSO_4$ and concentrated. The resulting oil was purified by preparative HPLC. The fractions containing pure product were concentrated in vacuo and dried in lyophilizer. Yield: 249 mg (93%). MS 329 (MH+).

Example 2.136d: 5-(2-fluorobenzyl)imidazolidine-2,4-dione

A mixture of o-F-phenylalanine hydrochloride (220 mg, 1 mmol) and KNCO (405 mg, 5 mmol) in 5 mL of $H_2O$ was refluxed for 2 hr. After cooling, conc. HCl (1.6 mL) was added to the reaction mixture and the whole was refluxed for another 30 min. Crystals precipitated after reaction mixture cooled and were collected by filtration. Yield: 168 mg (81%). $^1$H NMR (400 MHz, DMSO-$d_6$) δ 10.53 (s, 1H), 7.92 (s, 1H), 7.27 (m, 2H), 7.12 (m, 2H), 4.29 (t, J=4.8 Hz, 1H), 2.96 (m, 2H). MS 209 (MH+).

Example 2.137: 5-(cyclobutylmethyl)-1,5-dimethyl-3-((2-phenyl-1,3-dioxolan-2-yl)methyl)imidazolidine-2,4-dione Prepared in a similar manner as described in Example 2.105a starting from 1,5-dimethyl-3-((2-phenyl-1,3-dioxolan-2-yl)methyl)imidazolidine-2,4-dione (Example 2.105b) (150.0 mg, 517 mol) and (bromomethyl)cyclobutane (70 μL, 623 umol), except the extracted material was purified by mass-spectroscopy-triggered preparative HPLC, to obtain the desired product. $^1$H NMR (400 MHz, $d_6$-DMSO) δ 7.43-7.32 (m, 5H), 3.99-3.93 (m, 2H), 3.76-3.64 (m, 4H), 2.70 (s, 3H), 2.00-1.90 (m, 1H), 1.82-1.73 (m, 3H), 1.73-1.50 (m, 5H), 1.15 (s, 3H). MS 359 (MH+).

Example 2.138: 5-((1S,2S,5S)-6,6-dimethylbicyclo[3.1.1]heptan-2-yl)-1,5-dimethyl-3-(2-oxo-2-(1H-pyrrol-2-yl)ethyl)imidazolidine-2,4-dione Prepared in a similar manner as described in Example 2.44 starting from 5-(6,6-dimethylbicyclo-[3.1.1]heptan-2-yl)-1,5-dimethylimidazolidine-2,4-dione (Example 2.138a) (94 mg, 0.376 mmol) and 2-bromo-1-(1H-pyrrol-2-yl)ethanone (78 mg, 0.56 mmol). Gives 82.8 mg (62% yield) of product as a white powder. On HPLC this isomer was eluted second. $^1$H NMR (400 MHz, DMSO-$d_6$) δ 11.95 (s, 1H), 7.15 (s, 2H), 6.22 (s, 1H), 4.615 (q, J=16 Hz, J=20 Hz, 2H), 2.70 (s, 3H), 2.30 (t, J=8 Hz, 1H), 1.94-2.07 (m, 2H), 1.66-1.77 (m, 4H), 1.48 (m, 1H), 1.34 (s, 3H), 1.27 (d, J=8 Hz, 1H), 1.17 (s, 3H), 0.78 (s, 3H). MS 358 (MH+).

Example 2.138a: 5-(6,6-dimethylbicyclo-[3.1.1]heptan-2-yl)-1,5-dimethylimidazolidine-2,4-dione Prepared in a similar manner as described in Example 2.45a starting from 5-(6,6-dimethylbicyclo-[3.1.1]heptan-2-yl)-3-(4-methoxybenzyl)-1,5-dimethylimidazolidine-2,4-dione (Example 2.138b) (620 mg, 1.67 mmol) and a solution of ammonium cerium nitrate (2.388 g, 4.35 mmol) in water (10 mL) to obtain product as a white powder of mixture of 2 pairs of diastereomers (285 mg, 68% yield). $^1$H NMR (400 MHz, DMSO-$d_6$) δ 10.72 (s, 1H), 2.58 (s, 3H), 2.21 (t, J=8 Hz, 1H), 1.94-2.04 (mm, 2H), 1.67-1.76 (mm, 3H), 1.559 (t, J=6, 1H), 1.43 (m, 1H), 1.30 (d, J=8 Hz, 1H), 1.23 and 1.24 (2s, 3H), 1.16 and 1.17 (2s, 3H), 0.76 (s, 3H). MS 251 (MH+).

Example 2.138b: 5-(6,6-dimethylbicyclo-[3.1.1] heptan-2-yl)-3-(4-methoxybenzyl)-1,5-dimethylimidazolidine-2,4-dione Prepared in a similar manner as described in Example 2.45b starting from 5-(6,6-dimethylbicyclo-[3.1.1]heptan-2-yl)-3-(4-methoxybenzyl)imidazolidine-2,4-dione (Example 2.138c) (539 mg, 1.57 mmol) and Methyliodide (216 µL, 3.46 mmol) to obtain product as a colorless oil of mixture of 2 pairs of diastereomers 6:1 ratio (620 mg, 100% yield). $^1$H NMR (400 MHz, DMSO-$d_6$) δ 7.14 (d, J=8 Hz, 2H), 6.86 (d, J=8 Hz, 2H), 4.40 and 4.43 (2s, 2H), 3.69 and 3.70 (2s, 3H), 2.80 (s, 0.4H), 2.64 (s, 2.6H), 2.24 (m, 1H), 1.98 (m, 1H), 1.50-1.68 (m, 4H), 1.35-1.41 (m, 2H), 1.27 (s, 2.6H), 1.24 (s, 0.4H), 1.11 (s, 0.4H), 1.06 (s, 2.6H), 1.45 (d, J=6 Hz, 1H), 0.73 (s, 3H). MS 371 (MH+).

Example 2.138c: 5-(6,6-dimethylbicyclo[3.1.1]heptan-2-yl)-3-(4-methoxybenzyl)imidazolidine-2,4-dione Prepared in a similar manner as described in Example 2.46c starting from 5-(6,6-dimethylbicyclo-[3.1.1]heptan-2-yl)imidazolidine-2,4-dione (Example 2.138d) (808.5 mg, 3.64 mmol) and 4-methoxybenzyl chloride (543 µL, 4 mmol) to obtain product as a white powder (539 mg, 43% yield) of mixture of 2 pairs of diastereomers 2:1 ratio. $^1$H NMR (400 MHz, DMSO-$d_6$) δ 8.36 (s, 0.3H), 8.16 (s, 0.7H), 7.14 (d, J=8 Hz, 2H), 6.85 (d, J=8 Hz, 2H), 4.39 (m, 2H), 3.96 (m, 1H), 3.69 (s, 2H), 3.70 (s, 1H), 2.27 (m, 1H), 1.95 (m, 1H), 1.88 (t, J=5.2, 1H), 1.62-1.75 (m, 4H), 1.28-1.48 (m, 3H), 1.14 (s, 2H), 1.08 (s, 1H), 0.75 (s, 2H), 0.73 (s, 1H). MS 343 (MH+).

Example 2.138d: 5-(6,6-dimethylbicyclo-[3.1.1] heptan-2-yl)imidazolidine-2,4-dione Prepared in a similar manner as described in Example 2.44b starting from (1S,2S,5S)-6,6-dimethylbicyclo[3.1.1] heptane-2-carbaldehyde (Example 2.138e) (893.6 mg, 5.88 mmol) to obtain product as a white powder (808.5 mg, 62% yield). $^1$H NMR (400 MHz, DMSO-$d_6$) δ 10.49 (s, 1H), 7.79 (s, 1H), 3.86 (d, J=6.4 Hz, 1H), 2.25 (m, 1H), 2.01 (m, 1H), 1.91 (t, J=5.2, 1H), 1.62-1.75 (mm, 4H), 1.34-1.53 (mm, 4H), 1.16 (s, 3H), 0.77 (s, 3H). MS 223 (MH+).

Example 2.138e: (1S,2S,5S)-6,6-dimethylbicyclo[3.1.1]heptane-2-carbaldehyde

To a mixture of oxalyl chloride (1 mL, 11 mmol) in 25 mL of anhydrous DCM under $N_2$ atmosphere cooled to –70° C. was added dropwise anhydrous DMSO (1.56 mL, 22 mmol) in 5 mL of anhydrous DCM. Reaction mixture was allowed to stir for 2 minutes and then added ((1S,2S,5S)-(–)-trans-myrtanol (1.58 mL, 10 mmol) in 10 mL anhydrous DCM within 5 min. Reaction mixture was stirred for 15 min and then was added $Et_3N$ (6.95 mL, 50 mmol). Reaction mixture was stirred additional 5 min, then warmed up to room temperature. Formed white precipitate was poured in to 50 mL of water and extracted with DCM (3×20 mL). Combined organic fractions were washed with brine, dried over $MgSO_4$ and concentrated in vacuum. Crude aldehydes 90% clean by LCMS analysis was used in to next step without purification (1.47 g, 97% yield, as colorless oil). $^1$H NMR (400 MHz, DMSO-$d_6$) δ 9.55 (s, 1H), 2.72 (m, 2H), 2.20 (t, J=8, 1H), 2.00-2.09 (m, 2H), 1.78-1.86 (m, 3H), 1.49-1.57 (m, 1H), 1.21 (s, 3H), 0.83 (s, 3H). MS N/A.

Example 2.139: 2-(4-cyclohexyl-3,4-dimethyl-2,5-dioxoimidazolidin-1-yl)-N-phenylacetamide Prepared in a similar manner to Example 2.45 from 5-cyclohexyl-1,5-dimethyl-imidazolidine-2,4-dione (Example 2.47a) (204 µmol, 43 mg) and 2-chloro-N-phenylacetamide (265 µmol, 45 mg). White solid, 54 mg, 77% yield. $^1$H NMR (400 MHz, $d_6$-DMSO) δ 10.22 (s, 1H), 7.54-7.50 (m, 2H), 7.32-7.26 (m, 2H), 7.07-7.01 (m, 1H), 4.17 (s, 2H), 2.78 (s, 3H), 1.79-1.47 (m, 6H), 1.33 (s, 3H), 1.38-0.82 (m, 6H). MS 344 (MH+).

Example 2.140: 5-((1S,4R)-bicyclo[2.2.1]heptan-2-yl)-3-(2-(3-hydroxyphenyl)-2-oxoethyl)-1,5-dimethylimidazolidine-2,4-dione The two enantiomers of Example 2.54 (55 mg, 154 umol) were separated by chiral chromatography utilizing hexane/isopropanol/methanol as the solvent system. The most potent enantiomer was the second compound to elute. Twenty purified fractions were combined and the solvents evaporated. The residue was dissolved in ethanol and evaporated three times to remove undesirable solvents. The material was dissolved in ethanol and filtered through a cotton plug. The ethanol was removed and the compound was dried on the lyophilizer and vacuum oven at 40° C. to obtain the desired pure enantiomer (24.8 mg, 45%). $^1$H-NMR (400 MHz, DMSO-$d_6$) δ 10.01 (br s, 1H), 7.49-7.47 (m, 1H), 7.38-7.34 (m, 1H), 7.32-7.31 (m, 1H), 7.10-7.07 (m, 1H), 4.88 (s, 2H), 2.81 (s, 3H), 2.37 (s, 1H), 2.17 (s, 1H), 1.84 (m, 1H), 1.50-1.47 (m, 2H), 1.43 (s, 3H), 1.37-1.31 (m, 1H), 1.27-1.21 (m, 2H), 1.16-1.14 (m, 2H), 1.02-0.99 (m, 1H); MS 357 (MH+).

Example 2.141: 5-(2-ethoxyphenyl)-1-ethyl-5-methyl-3-(2-oxo-2-phenylethyl)imidazolidine-2,4-dione Prepared in a similar manner as described in Example 2.70 starting from 5-(2-hydroxyphenyl)-5-methyl-3-(2-oxo-2-phenylethyl)imidazolidine-2,4-dione (Example 2.141a) (32 mg, 0.1 mmol) and EtBr (17 µL, 0.23 mmol) to obtain the desired product (5 mg, 13%) as a white solid. $^1$H NMR (400 MHz, CDCl$_3$) δ 8.00 (dt, J=8.5, 1.7 Hz, 2H), 7.66-7.58 (m, 1H), 7.54-7.43 (m, 3H), 7.39-7.31 (m, 1H), 7.01 (td, J=7.6, 1.1 Hz, 1H), 6.85 (dd, J=8.2, 0.9 Hz, 1H), 5.00 (d, J=0.8 Hz, 2H), 4.11-3.85 (m, 2H), 3.13 (qd, J=7.2, 1.6 Hz, 2H), 1.95 (s, 3H), 1.36 (t, J=7.0 Hz, 4H), 0.92 (t, J=7.2 Hz, 3H). MS 381 (MH+).

Example 2.141a: 5-(2-hydroxyphenyl)-5-methyl-3-(2-oxo-2-phenylethyl)imidazolidine-2,4-dione Prepared in a similar manner as described in Example 2.70a starting from 2-(4-methyl-2,5-dioxoimidazolidin-4-yl)phenyl acetate (Example 2.141b) (248 mg, 1 mmol) and 2-bromo-1-phenylethanone (199 mg, 1 mmol) to obtain the product (100 mg, 31%) as a white solid. $^1$H NMR is consistent with structure. MS 325 (MH+).

Example 2.141b: 2-(4-methyl-2,5-dioxoimidazolidin-4-yl)phenyl Acetate

Prepared in a similar manner as described in Example 2.60d starting from 2-acetylphenyl acetate (890 mg, 5 mmol) to obtain the desired product (0.8 g, 64%) as a white solid. MS 249 (MH+).

Example 2.142: 5-((1S,4S)-bicyclo[2.2.2]oct-5-en-2-yl)-3-(2-(3-hydroxyphenyl)-2-oxoethyl)-1,5-dimethylimidazolidine-2,4-dione Prepared in a similar manner as described in Example 2.45 starting from 5-(bicyclo[2.2.2]oct-5-en-2-yl)-1,5-dimethylimidazolidine-2,4-dione (Example 2.142a) (210 mg, 0.89 mmol) and 2-bromo-1-(3-hydroxyphenyl)ethanone (193 mg, 0.9 mmol). Gives 96.7 mg (29% yield) of product as a yellowish oily film as a mixture of 2 pairs of diastereomers 2:1 ratio. $^1$H NMR (400 MHz, DMSO-$d_6$) δ 9.97 (bs, 1H), 7.47 (d, J=8 Hz, 2H), 7.36 (t, J=8 Hz, 1H), 7.31 (s, 1H), 7.06 (d, J=8 Hz, 1H), 6.15 (dt, J=8 Hz, J=32 Hz, 1H), 5.96 (m, 1H), 4.86 (m, 2H), 2.78 (s, 2H), 2.71 (s, 1H), 2.49 (m, 1H), 2.29 (m, 1H), 2.14 (m, 1H), 1.39-1.73 (m, 4H), 1.29 (s, 1H), 1.27 (s, 2H), 1.11-1.21 (m, 2H). MS 369 (MH+).

Example 2.142a: 5-(bicyclo[2.2.2]oct-5-en-2-yl)-1,5-dimethylimidazolidine-2,4-dione Prepared in a similar manner as described in Example 2.45a starting from 5-(bicyclo[2.2.2]oct-5-en-2-yl)-3-(4-methoxybenzyl)-1,5-dimethylimidazolidine-2,4-dione (Example 2.142b) (1.325 g, 3.74 mmol) and a solution of ammonium cerium nitrate (5.33 g, 9.73 mmol) in water (15 mL) to obtain product as a white powder of mixture of 2 pairs of diastereomers (419 mg, 48% yield). $^1$H NMR (400 MHz, DMSO-$d_6$) δ 10.76 (s, 0.4H), 10.60 (s, 0.6H), 6.12 (m, 1H), 5.91 (dt, J=8 Hz, J=32 Hz, 1H), 2.67 (s, 2H), 2.60 (s, 1H), 2.25 (m, 1H), 2.01 (m, 1H), 2.14 (m, 1H), 1.26-1.73 (m, 5H), 1.19 (s, 1H), 1.16 (s, 2H), 1.10-1.15 (m, 2H). MS 235 (MH+).

Example 2.142b: 5-(bicyclo[2.2.2]oct-5-en-2-yl)-3-(4-methoxybenzyl)-1,5-dimethylimidazolidine-2,4-dione Prepared in a similar manner as described in Example 2.45b starting from 5-(bicyclo[2.2.2]oct-5-en-2-yl)-3-(4-methoxybenzyl)-5-methylimidazolidine-2,4-dione (Example 2.142c) (1.48 g, 4.35 mmol) and methyl iodide (326 µL, 5.22 mmol) to obtain product as a colorless oil of mixture of 2 pairs of diastereomers (1325 mg, 86% yield). MS 355 (MH+).

Example 2.142c: 5-(bicyclo[2.2.2]oct-5-en-2-yl)-3-(4-methoxybenzyl)-5-methylimidazolidine-2,4-dione Prepared in a similar manner as described in Example 2.46c starting from 5-(bicyclo[2.2.2]oct-5-en-2-yl)-5-methylimidazolidine-2,4-dione (Example 2.51b) (1077 mg, 4.89 mmol) and 4-methoxybenzyl chloride (730 µL, 5.38 mmol) to obtain product as a white powder (1.48 g, 89% yield) of mixture of 2 pairs of diastereomers 2:1 ratio. $^1$H NMR (400 MHz, DMSO-$d_6$) δ 7.99 (s, 0.4H), 7.88 (s, 0.6H), 7.16 (m, 2H), 6.86 (m, 2H), 6.09 (m, 1H), 5.80 (m, 1H), 4.39 (m, 2H), 3.70 (s, 3H), 2.56 (m, 0.5H), 2.40 (m, 0.5H), 1.92 (m, 1.5H), 1.66 (m, 1H), 1.35-1.47 (m, 2.5H), 1.20 (s, 1H), 1.11 (s, 2H), 1.08 (m, 2H), 0.93 (m, 1H). MS 341 (MH+).

Example 2.143: 5-((1S,4S)-bicyclo[2.2.2]oct-5-en-2-yl)-1,5-dimethyl-3-(2-oxo-2-(1H-pyrrol-2-yl)ethyl)imidazolidine-2,4-dione Prepared in a similar manner as described in Example 2.44 starting from 5-(bicyclo[2.2.2]oct-5-en-2-yl)-1,5-dimethylimidazolidine-2,4-dione (Example 2.142a) (210 mg, 0.89 mmol) and 2-bromo-1-(1H-pyrrol-2-yl)ethanone (185 mg, 0.98 mmol). Gives 131 mg (43% yield) of product as a yellowish oily film as a mixture of 3 pairs of diastereomers. $^1$H NMR (400 MHz, DMSO-$d_6$) δ 12.0 (bs, 1H), 7.16 (m, 2H), 6.22 (m, 1H), 6.15 (dt, J=8 Hz, J=32 Hz, 1H), 5.96 (m, 1H), 4.65 (m, 2H), 2.84 (s, 0.5H), 2.78 (s, 2H), 2.70 (s, 0.5H), 2.62 (m, 0.5H), 2.43 (m, 0.5H), 2.28 (m, 1H), 2.13 (m, 1H), 1.93 (m, 0.5H), 1.39-1.66 (m, 3.5H), 1.45 (s, 0.5H), 1.27 (s, 0.5H), 1.26 (s, 2H), 1.11-1.21 (m, 2H). MS 342 (MH+).

Example 2.144: 5-(bicyclo[2.2.2]octan-2-yl)-3-(2-(3-hydroxyphenyl)-2-oxoethyl)-1,5-dimethyl imidazolidine-2,4-dione Prepared in a similar manner as described in Example 2.45 starting from 5-(bicyclo[2.2.2]octan-2-yl)-1,5-dimethylimidazolidine-2,4-dione (Example 2.144a) (150 mg, 0.635 mmol) and 2-bromo-1-(3-hydroxyphenyl)ethanone (136 mg, 0.635 mmol). Gives 57.5 mg (29% yield) of product as a yellowish oily film as a mixture of 2 pairs of diastereomers 1:1 ratio. $^1$H NMR (400 MHz, DMSO-$d_6$) δ 9.93 (bs, 1H), 7.46 (t, J=8 Hz, 1H), 7.34 (t, J=8 Hz, 1H), 7.305 (s, 1H), 7.06 (d, J=8 Hz, 1H), 4.88 (s, 1H), 4.86 (s, 1H), 2.88 (s, 1.5H), 2.75 (s, 1.5H), 1.95-2.09 (m, 2H), 1.81 (m, 1H), 1.56-1.65 (m, 2H), 1.39-1.53 (m, 6H), 1.37 (s, 1.5H), 1.36 (s, 1.5H), 1.24-1.34 (m, 2H). MS 371 (MH+).

Example 2.144a: 5-(bicyclo[2.2.2]octan-2-yl)-1,5-dimethylimidazolidine-2,4-dione Prepared in a similar manner as described in Example 2.45a starting from 5-(bicyclo[2.2.2]octan-2-yl)-3-(4-methoxybenzyl)-1,5-dimethylimidazolidine-2,4-dione (Example 2.144b) (614 mg, 1.72 mmol) and a solution of ammonium cerium nitrate (2.46 g, 4.48 mmol) in water (15 mL) to obtain product as a white powder of mixture of 2 pairs of diastereomers 1:1 ratio (303 mg, 75% yield). $^1$H NMR (400 MHz, DMSO-$d_6$) δ 10.81 (s, 0.5H), 10.75 (s, 0.5H), 2.78 (s, 1.5H), 2.63 (s, 1.5H), 1.89-1.98 (m, 2H), 1.81 (m, 1H), 1.53-1.60 (m, 2H), 1.18-1.44 (m, 8H), 1.27 (s, 1.5H), 1.25 (s, 1.5H). MS 237 (MH+).

Example 2.144b: 5-(bicyclo[2.2.2]octan-2-yl)-3-(4-methoxybenzyl)-1,5-dimethylimidazolidine-2,4-dione Prepared in a similar manner as described in Example 2.45b starting from 5-(bicyclo[2.2.2]octan-2-yl)-3-(4-methoxybenzyl)-5-methylimidazolidine-2,4-dione (Example 2.144c) (852 mg, 2.49 mmol) and methyl iodide (187 µL, 3 mmol) to obtain product as a colorless oil of mixture of 2 pairs of diastereomers (614.5 mg, 69% yield). MS 357 (MH+).

Example 2.144c: 5-(bicyclo[2.2.2]octan-2-yl)-3-(4-methoxybenzyl)-5-methylimidazolidine-2,4-dione Prepared in a similar manner as described in Example 2.46c starting from 5-(bicyclo[2.2.2]octan-2-yl)-5-methylimidazolidine-2,4-dione (Example 2.51b) (927 mg, 4.17 mmol) and 4-methoxybenzyl chloride (623 μL, 4.59 mmol) to obtain product as a white powder (852 mg, 60% yield) of mixture of 2 pairs of diastereomers 1:1 ratio. $^1$H NMR (400 MHz, DMSO-d$_6$) δ 8.52 (s, 0.5H), 8.18 (s, 0.5H), 7.16 (m, 2H), 6.86 (d, J=8 Hz, 2H), 4.39 (m, 2H), 3.70 (s, 1.5H), 3.69 (s, 1.5H), 1.84 (m, 1H), 1.26-1.66 (m, 10H), 1.24 (s, 1.5H), 1.19 (s, 1.5H), 1.02-1.17 (m, 2H). MS 343 (MH$^+$).

Example 2.145: (R)-5-((1R,2S,4R)-bicyclo[2.2.2] octan-2-yl)-3-(2-(3-hydroxyphenyl)-2-oxoethyl)-1,5-dimethylimidazolidine-2,4-dione Prepared in a similar manner as described in Example 2.45 starting from 5-(bicyclo[2.2.2]octan-2-yl)-1,5-dimethylimidazolidine-2,4-dione (Example 2.144a) (150 mg, 0.635 mmol) and 2-bromo-1-(3-hydroxyphenyl)ethanone (136 mg, 0.635 mmol). Gives 28.5 mg (12% yield) of product as a yellowish oily film. This isomer was eluted second on HPLC column. $^1$H NMR (400 MHz, DMSO-d$_6$) δ 9.93 (bs, 1H), 7.42 (d, J=8 Hz, 1H), 7.30 (t, J=8 Hz, 1H), 7.27 (s, 1H), 7.03 (d, J=8 Hz, 1H), 4.85 (s, 1H), 2.74 (s, 3H), 1.95-2.09 (m, 2H), 1.56-1.65 (m, 2H), 1.39-1.53 (m, 6H), 1.36 (s, 3H), 1.24-1.34 (m, 3H). MS 371 (MH$^+$).

Example 2.146: 5-((1S,4S)-bicyclo[2.2.2]octan-2-yl)-1,5-dimethyl-3-(2-oxo-2-(1H-pyrrol-2-yl)ethyl) imidazolidine-2,4-dione Prepared in a similar manner as described in Example 2.44 starting from 5-(bicyclo[2.2.2]octan-2-yl)-1,5-dimethylimidazolidine-2,4-dione (Example 2.144a) (150 mg, 0.635 mmol) and 2-bromo-1-(1H-pyrrol-2-yl)ethanone (131 mg, 0.69 mmol). Gives 14.7 mg (7% yield) of product as a yellowish oily film. On HPLC this isomer eluted first. $^1$H NMR (400 MHz, DMSO-d$_6$) δ 12.01 (bs, 1H), 7.15 (s, 2H), 6.22 (m, 1H), 4.67 (s, 1H), 2.88 (s, 3H), 2.03 (m, 1H), 1.83 (m, 1H), 1.58-1.66 (m, 3H), 1.37-1.52 (m, 7H), 1.36 (s, 3H), 1.22-1.34 (m, 1H). MS 344 (MH$^+$).

Example 2.147: (R)-5-((1R,2S,4R)-bicyclo[2.2.2] octan-2-yl)-1,5-dimethyl-3-(2-oxo-2-(1H-pyrrol-2-yl)ethyl)imidazolidine-2,4-dione Prepared in a similar manner as described in Example 2.44 starting from 5-(bicyclo[2.2.2]octan-2-yl)-1,5-dimethylimidazolidine-2,4-dione (Example 2.144a) (150 mg, 0.635 mmol) and 2-bromo-1-(1H-pyrrol-2-yl)ethanone (131 mg, 0.69 mmol). Gives 35.7 mg (16% yield) of product as a yellowish oily film. On HPLC this isomer was the second to elute. $^1$H NMR (400 MHz, DMSO-d$_6$) δ 11.95 (bs, 1H), 7.15 (m, 2H), 6.22 (m, 1H), 4.65 (s, 1H), 2.74 (s, 3H), 2.04 (m, 2H), 1.51-1.66 (m, 3H), 1.37-1.52 (m, 5H), 1.35 (s, 3H), 1.19-1.32 (m, 3H). MS 344 (MH$^+$).

Example 2.148: 5-(bicyclo[2.2.2]octan-2-yl)-1,5-dimethyl-3-(2-oxo-2-(1H-pyrrol-2-yl)ethyl)imidazolidine-2,4-dione Prepared in a similar manner as described in Example 2.44 starting from 5-(bicyclo[2.2.2]octan-2-yl)-1,5-dimethylimidazolidine-2,4-dione (Example 2.144a) (150 mg, 0.635 mmol) and 2-bromo-1-(1H-pyrrol-2-yl)ethanone (131 mg, 0.69 mmol). Gives 89.4 mg (41% yield) of product as a yellowish oily film as a mixture of 2 pairs of diastereomers 2:1 ratio. $^1$H NMR (400 MHz, DMSO-d$_6$) δ 12.0 (bs, 1H), 7.15 (m, 2H), 6.22 (m, 1H), 4.67 (s, 1H), 4.65 (s, 1H), 2.88 (s, 2H), 2.75 (s, 1H), 2.03 (m, 2H), 1.83 (m, 1H), 1.51-1.66 (m, 3H), 1.37-1.52 (m, 5H), 1.36 (s, 2H), 1.35 (s, 1H), 1.22-1.34 (m, 2H). MS 344 (MH$^+$).

Example 2.149: 5-(but-3-en-2-yl)-1,5-dimethyl-3-(2-oxo-2-phenylethyl)imidazolidine-2,4-dione Prepared in a similar manner as described in Example 2.105 starting from 5-(but-3-en-2-yl)-1,5-dimethyl-3-((2-phenyl-1,3-dioxolan-2-yl)methyl)imidazolidine-2,4-dione (Example 2.149a) (80 mg, 0.23 mmol) to obtain product as a colorless oily film (51 mg, 74% yield). $^1$H NMR (400 MHz, DMSO-d$_6$) δ 8.03 (d, J=8 Hz, 2H), 7.69 (t, J=8 Hz, 1H), 7.55 (t, J=8 Hz, 2H), 5.53 (m, 1H), 5.03-5.26 (m, 2H), 4.96 (s, 2H), 2.80 (s, 3H), 2.39 (m, 1H), 1.60 (d, J=8 Hz, 2.5H), 1.39 (s, 0.4H), 1.34 (s, 2.6H), 1.07 (d, J=8 Hz, 0.25H), 0.92 (d, J=8 Hz, 0.25H). MS 345 (MH$^+$).

Example 2.149a: 5-(but-3-en-2-yl)-1,5-dimethyl-3-((2-phenyl-1,3-dioxolan-2-yl)methyl) imidazolidine-2,4-dione Prepared in a similar manner as described in Example 2.105a starting from 1,5-dimethyl-3-((2-phenyl-1,3-dioxolan-2-yl)methyl)imidazolidine-2,4-dione (Example 2.105b) (100 mg, 0.34 mmol) to obtain product as a colorless oil (80 mg, 68% yield). MS 345 (MH$^+$).

3.1) Biological Assay

The present compounds are useful as modulators of TRPM8. The activity of TRPM8 can be readily monitored in cell based assays using fluorescent calcium-sensitive dyes, membrane potential dyes, or sodium-sensitive dyes. The activity of TRPM8 can also be monitored with electrophysiological set-ups, such as patch-clamping and two-electrode voltage clamping. A mammalian cell line derivative which stably expresses TRPM8 was used in biological assays in association with testing the present compounds with cool-tasting or -feeling properties (Servant et al. US 2007/0259354 A1 and references cited therein). Typical compound concentrations tested were 50 μM, 20 μM, 10 μM, 5 μM, 2 μM, 1 μM, 0.5 μM, 0.1 μM, 0.05 μM, 0.01 μM, and other concentration points in between. The present compounds have shown strong activity as agonists of hTRPM8. Assay results for compounds are illustrated in Table 1 below. Specifically, the Compounds listed in Table 3.1, i.e., Compounds 3.A1 to Compounds 3.D1 are the specific compounds as described above.

TABLE 3.1

| Example | EC50 (uM) | EC50 Ratio (WS3) | Observed [m/z + 1] |
|---|---|---|---|
| 3.A1 | 0.013 | 581.6 | 304.2 |
| 3.A2 | 0.010 | 577.8 | 288.2 |
| 3.A3 | 0.028 | 221.2 | 320.2 |
| 3.A4 | 0.041 | 132.4 | 294.1 |
| 3.A5 | 0.056 | 116.2 | 306.2 |
| 3.A6 | 0.080 | 99.6 | 306.2 |
| 3.A7 | 0.056 | 86.8 | 288.2 |
| 3.A8 | 0.061 | 84.4 | 300.2 |
| 3.A9 | 0.087 | 66.5 | 320.2 |
| 3.A10 | 0.059 | 62.5 | 294.1 |
| 3.B1 | 0.105 | 45.5 | 304.2 |
| 3.B2 | 0.138 | 38.1 | 288.2 |
| 3.B3 | 0.363 | 34.1 | 302.2 |
| 3.B4 | 0.230 | 26.5 | 289.2 |
| 3.B5 | 0.161 | 25.0 | 286.2 |
| 3.B6 | 0.193 | 20.6 | 277.2 |
| 3.B7 | 0.257 | 18.6 | 306.2 |

TABLE 3.1-continued

| Example | EC50 (uM) | EC50 Ratio (WS3) | Observed [m/z + 1] |
|---|---|---|---|
| 3.B8 | 0.420 | 16.3 | 302.2 |
| 3.B9 | 0.398 | 15.3 | 306.2 |
| 3.B10 | 0.309 | 13.7 | 314.2 |
| 3.C1 | 0.254 | 13.0 | 289.2 |
| 3.C2 | 0.471 | 12.3 | 294.1 |
| 3.C3 | 0.591 | 11.6 | 302.2 |
| 3.C4 | 0.449 | 10.0 | 277.2 |
| 3.C5 | 0.504 | 9.4 | 304.2 |
| 3.C6 | 0.489 | 9.2 | 294.1 |
| 3.C7 | 0.662 | 8.2 | 302.2 |
| 3.C8 | 1.369 | 5.5 | 302.2 |
| 3.C9 | 0.621 | 5.3 | 290.2 |
| 3.C10 | 0.954 | 4.7 | 274.2 |
| 3.D1 | 1.085 | 4.7 | 296.2 |
| 3.D2 | 1.914 | 4.5 | 276.2 |
| 3.D3 | 1.035 | 4.5 | 274.2 |
| 3.D4 | 1.427 | 4.3 | 318.2 |
| 3.D5 | 2.181 | 4.1 | 288.2 |
| 3.D6 | 2.348 | 3.9 | 282.1 |
| 3.D7 | 1.026 | 3.9 | 300.2 |
| 3.D8 | 1.395 | 3.9 | 274.2 |
| 3.D9 | 2.348 | 3.8 | 276.2 |
| 3.D10 | 2.362 | 3.5 | 300.1 |
| 3.E1 | 1.555 | 3.1 | 282.1 |
| 3.E2 | 1.337 | 2.8 | 308.1 |
| 3.E3 | 1.942 | 2.8 | 272.1 |
| 3.E4 | 1.781 | 2.7 | 300.2 |
| 3.E5 | 1.211 | 2.5 | 280.1 |
| 3.E6 | 4.468 | 2.5 | 296.1 |
| 3.E7 | 2.156 | 1.9 | 320.2 |
| 3.E8 | 4.740 | 1.9 | 296.1 |
| 3.E9 | 3.161 | 1.8 | 334.2 |
| 3.E10 | 2.923 | 1.7 | 308.1 |
| 3.F1 | 2.385 | 1.6 | 274.2 |
| 3.F2 | 1.784 | 1.6 | 280.1 |
| 3.F3 | 2.863 | 1.4 | 280.2 |
| 3.F4 | 5.938 | 1.4 | 276.2 |
| 3.F5 | 3.084 | 1.4 | 289.2 |
| 3.F6 | 3.213 | 1.3 | 320.2 |
| 3.F7 | 3.507 | 1.2 | 308.1 |
| 3.F8 | 4.173 | 1.1 | 290.2 |
| 3.F9 | 3.391 | 1.0 | 286.2 |
| 3.F10 | 6.103 | 1.0 | 318.2 |
| 3.G1 | 6.242 | 1.0 | 275.2 |

3.2) Sensory Studies

Two typical sensory studies are described below each followed by a table summarizing sensory results of selected compounds of the invention (Tables 3.2 and 3.3).

Formulation:

All samples made with Low Sodium Buffer (LSB) pH ~7.1 and contain 0.1% ethanol.

General Protocol:

The test is a cool line scale test with timed 30 seconds interval. Compounds are rated on a 15 point line scale where 45 µM WS-3 (N-Ethyl-p-menthane-3-carboxamide) is ranked as a 5 in cool intensity. The present compound was tested to determine at what concentration the cooling intensity is equivalent to 45 µM WS-3. In each test, the panelist was presented with a 0 µM control sample, a 45 µM WS-3 control sample and the experimental compound sample and asked to rate the cooling intensity of each sample. Panelists were also asked to rate bitterness. In the table below there was no significant bitterness detected unless otherwise noted. Also, in the table below, n represents the number of tests completed for a given experiment (#panelists×#repetitions).

Conclusions:

Panelists found 5 µM COMPOUND 3.2 was significantly more cooling than 0 µM WS-3 (p<0.05) and not significantly different in cooling than 45 µM WS-3 (p<0.05). There were no significant bitter offtastes in any of the samples (p<0.05).

TABLE 3.2

Average Cooling, n = 30 (15 Panelists × 2 rep).
Tukey's Value = 0.926 (α = 0.05).

| Treatment | Average | SD | St Er | Tukey (5%) |
|---|---|---|---|---|
| 0 µM WS-3 | 0.7 | 1.5 | 0.3 | a |
| 5 µM Compound 3.2 | 4.0 | 1.8 | 0.3 | b |
| 45 µM WS-3 | 4.5 | 1.5 | 0.3 | b |

TABLE 3.3

Average Bitterness, n = 30 (15 Panelists × 2 rep).
Tukey's Value = 0.317 (α = 0.05).

| Treatment | Average | SD | St Er | Tukey (5%) |
|---|---|---|---|---|
| 0 µM WS-3 | 0.2 | 0.5 | 0.1 | a |
| 5 µM Compound 3.2 | 0.4 | 0.8 | 0.1 | a |
| 45 µM WS-3 | 0.5 | 1.1 | 0.2 | a |

Table 3.4 summarizes addition sensory studies that were conducted on these compounds.

TABLE 3.4

Summary or related sensory results.

| Example | Sensory result | n |
|---|---|---|
| 3.A1 | Panelists found 5 uM 58758115 was significantly more cooling than 0 uM WS-3 (p < 0.05) and not significantly different in cooling 45 uM WS-3 (p > 0.05) | 24 |
| 3.A2 | Panelists found 5 uM 57962022 was significantly more cooling than 0 uM WS-3 (p < 0.05) and not significantly different in cooling 45 uM WS-3 (p > 0.05) | 30 |
| 3.A6 | Panelists found 5 uM 58751264 was significantly more cooling than 0 uM WS-3 (p < 0.05) and not significantly different in cooling 45 uM WS-3 (p > 0.05) | 20 |
| 3.B2 | Panelists found 5 uM 58750445 was significantly more cooling than 0 uM WS-3 (p < 0.05) and not significantly different in cooling 45 uM WS-3 (p > 0.05) | 24 |
| 3.C2 | Panelists found 7 uM 59227831 was significantly more cooling than 0 uM WS-3 (p < 0.05) and not significantly different in cooling than 45 uM WS-3 (p > 0.05) | 32 |

3.3) Preparation and Examples

Standard procedures and chemical transformation and related methods are well known to one skilled in the art, and such methods and procedures have been described, for example, in standard references such as Fiesers' Reagents for Organic Synthesis, John Wiley and Sons, New York, N.Y., 2002; Organic Reactions, vols. 1-83, John Wiley and Sons, New York, N.Y., 2006; March J. and Smith M., Advanced Organic Chemistry, 6th ed., John Wiley and Sons, New York, N.Y.; and Larock R. C., Comprehensive Organic Transformations, Wiley-VCH Publishers, New York, 1999. All texts and references cited herein are incorporated by reference in their entirety.

Reactions using compounds having functional groups may be performed on compounds with functional groups that may be protected. A "protected" compound or derivatives means derivatives of a compound where one or more reactive site or sites or functional groups are blocked with protecting groups. Protected derivatives are useful in the preparation of the compounds of the present invention or in themselves; the protected derivatives may be the biologically active agent. An example of a comprehensive text listing suitable protecting groups may be found in T. W. Greene, Protecting Groups in Organic Synthesis, 3rd edition, John Wiley & Sons, Inc. 1999.

The example compounds were prepared according to two main schemes; the following compounds were prepared according to the general procedures outlined in Scheme 3.1 as described herein below.

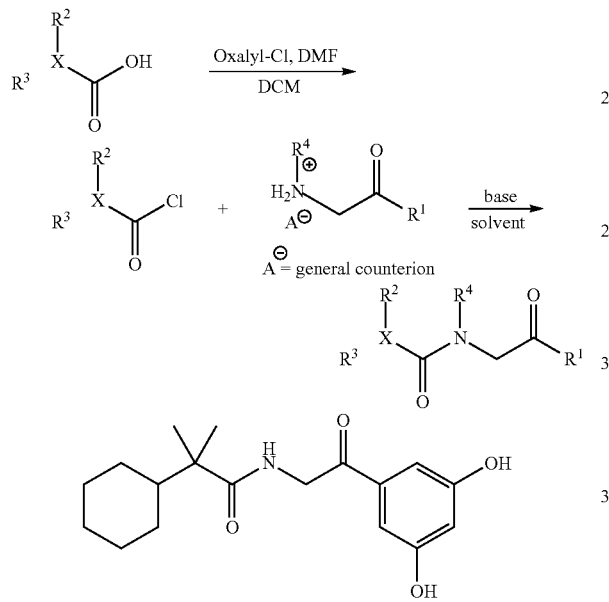

2-cyclohexyl-N-(2-(3,5-dihydroxyphenyl)-2-oxoethyl)-2-methylpropanamide. Example 3.9

2-Cyclohexyl-N-(2-(3,5-dimethoxyphenyl)-2-oxoethyl)-2-methylpropanamide (1.7 mmol, 542 mg) was dissolved in dichloromethane (DCM). 1.0 M $BBr_3$ in DCM (2.5 mmol, 2.5 mL) was added drop wise at −78° C. The resulting mixture was allowed to warm to room temperature with stirring overnight. The reaction was quenched with $H_2O$ (10 mL) and the aqueous layer was extracted with DCM (50 mL×3). The organic layers were combined, washed with brine, dried over $MgSO_4$ and concentrated. The resulting residue oil was purified by preparative HPLC to give 2-cyclohexyl-N-(2-(3,5-dihydroxyphenyl)-2-oxoethyl)-2-methylpropanamide as a white solid 100 mg (yield 18%). $^1$H NMR (400 MHz, DMSO-d6) δ 9.618 (s, 2H), 7.649 (t, J=5.2 Hz, 1H), 6.766 (s, 1H), 6.760 (s, 1H), 6.441 (t, J=2 Hz, 1H), 4.350 (d, J=5.6 Hz, 2H), 1.507-1.711 (m, 6H), 0.997 (s, 6H), 0.837-1.203 (m, 5H). MS 320 (MH$^+$)

2-cyclohexyl-N-(2-(3,5-dimethoxyphenyl)-2-oxoethyl)-2-methylpropanamide. Example 3.9a 2-Amino-1-(3,5-dimethoxyphenyl)ethanone hydrochloride (3.9 mmol, 900 mg) was dissolved in DCM (15 mL) and cooled to 0° C. 2-cyclohexyl-2-methylpropanoyl chloride (3.9 mmol, 733 mg) was added followed by the addition of triethylamine (15.6 mmol, 2.17 mL) in DCM (5 mL). The resulting mixture was allowed to warm to room temperature with stirring overnight. Water was added (10 mL) and the aqueous layer was extracted three times with DCM (50 mL×3). The combined organic layers were washed with brine, dried over $MgSO_4$ and concentrated. The resulting oil was purified by flash chromatography (Biotage 40 g silica column, 0%~40% EtOAc/Hex gradient) to afford 2-cyclohexyl-N-(2-(3,5-dimethoxyphenyl)-2-oxoethyl)-2-methylpropanamide as clear oil 592 mg (yield 43%). $^1$H NMR (400 MHz, DMSO-d6) δ 7.755 (t, J=5.6 Hz, 1H), 7.073 (s, 1H), 7.068 (s, 1H), 6.741 (t, J=2 Hz, 1H), 4.452 (d, J=5.2 Hz, 2H), 3.786 (s, 6H), 1.502-1.700 (m, 6H), 0.992 (s, 6H), 0.845-1.189 (m, 5H). MS 348 (MH$^+$).

2-amino-1-(3,5-dimethoxyphenyl)ethanone Hydrochloride. Example 3.9b

A solution of tert-butyl (2-(3,5-dimethoxyphenyl)-2-oxoethyl)carbamate (1.8 mmol, 531 mg) in EtOAc (15 mL) was cooled to 0° C. and 4.0N HCl solution in dioxane (3.7 mmol, 0.91 mL) was added dropwise. The resulting mixture was stirred at room temperature for 48 h and concentrated. The product was used into the next step without purification. MS 196 (MH$^+$)

Tert-butyl (2-(3,5-dimethoxyphenyl)-2-oxoethyl)carbamate. Example 3.9c t-Butyl (2-(methoxy(methyl)amino)-2-oxoethyl)carbamate (3.0 mmol, 700 mg) in dry THF (8 mL) was cooled to −15° C. and a 2.0 M solution of isopropylmagnesium chloride in dry THF (3.0 mmol, 1.5 mL) was added dropwise. The resulting mixture was stirred at −15° C. for 15 minutes before being used in the reaction described below.

1-Bromo-3,5-dimethoxybenzene (3.9 mmol, 850 mg) in dry THF (10 mL) I was cooled to −78° C. and 2.5 M n-butyllithium in hexane (3.9 mmol, 1.6 mL) was added drop wise. The reaction was stirred for 5 minutes and the solution prepared above was added drop wise by cannula at −78° C. The resulting mixture was stirred overnight, quenched with water (5 mL) and concentrated. Water was added (20 mL) and the mixture was extracted with EtOAc (50 mL×4). The organic layers were combined, washed with brine (50 mL), dried over $MgSO_4$ and concentrated. The resulting oil was purified by flash chromatography (Biotage 40 g silica column, 0% to 30% gradient EtOAc in Hex) to give 540 mg of tert-butyl (2-(3,5-dimethoxyphenyl)-2-oxoethyl)carbamate as a colorless oil. (yield 47%). MS 296 (MH$^+$).

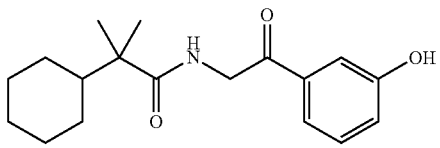 [SMILES: CC(C)(C(=O)NCC(=O)c1cccc(O)c1)C1CCCCC1]

2-cyclohexyl-2-methyl-N-(2-oxo-2-phenylethyl) propanamide. Example 3.11

To a solution of 2-(3-hydroxyphenyl)-2-oxoethanaminium chloride (Example 3.11c) (0.19 g, 1 mmol) in DCM (5 mL) was added a solution of 2-cyclohexyl-2-methylpropanoyl chloride (0.19 g, 1 mmol) in DCM (2 mL) and triethylamine (0.3 mL, 2 mmol). The reaction was stirred at room temperature overnight then concentrated. The crude product was dissolved in DCM and purified by flash chromatography (Silicycle XXg column, 0-20% DCM/EtOAc gradient). The material was further purified by preparative HPLC to afford ~50 mg of 2-cyclohexyl-2-methyl-N-(2-oxo-2-phenylethyl)propanamide as a white solid. MS (M+H)=304. $^1$H NMR (400 MHz, dmso) δ 0.85-0.97 (m, 2H), 1.01 (s, 6H), 1.04-1.25 (m, 3H), 1.49-1.77 (m, 6H), 4.44 (d, J=5.5 Hz, 2H), 7.01-7.04 (m, 1H), 7.28-7.30 (m, 1H), 7.32 (t, J=7.9 Hz, 1H), 7.42-7.44 (m, 1H), 9.81 (s, 1H).

2-cyclohexyl-2-methylpropanoyl Chloride. Example 3.11a

To a round bottom flask equipped with a gas bubbler was added 2-cyclohexyl-2-methylpropanoic acid (Example 3.11b) (1.3 g, 7.5 mmol) and DCM (10 mL). Oxalyl chloride (1 mL, 11.3 mmol) was added followed by a few drops of DMF at room temperature. The resulting solution was stirred at room temperature until gas evolution ceased (~1 h). The mixture was concentrated 3 times from DCM and the resulting acid chloride was used without further purification for the coupling above.

2-cyclohexyl-2-methylpropanoic Acid. Example 3.11b

2-Methyl-2-phenylpropanoic acid (10 g, 61 mmol), acetic acid (60 mL) and 5 wt % Rh/Al$_2$O$_3$ (2.0 g) were combined in a glass beaker. The beaker was placed in the stainless steel pressure reactor and the reaction medium was stirred under H$_2$ atmosphere (110 psi) overnight. The reaction mixture was filtered thru celite and washed with ethyl acetate then concentrated. The residue was dissolved in diethyl ether, washed with water (50 mL×4), and brine (50 mL×2), dried over MgSO$_4$ and concentrated to give 2-cyclohexyl-2-methylpropanoic acid as a white solid (~10 g, 95% yield). UPLC MS (M−H)=169; $^1$H NMR (400 MHz, DMSO-d$_6$) δ 12.01 (s, 1H), 1.72 (dt, J=12.2, 2.7 Hz, 2H), 1.67-1.51 (m, 3H), 1.47 (dt, J=11.9, 3.0 Hz, 1H), 1.25-1.01 (m, 3H), 1.00 (s, 6H), 0.98-0.87 (m, 2H).

2-(3-hydroxyphenyl)-2-oxoethanaminium Chloride. Example 3.11c

To a 0° C. stirring solution of 2-bromo-1-(3-hydroxyphenyl)ethanone (5.00 g; 23.25 mmol) in DMF (10.0 mL) was added sodium azide (1.59 g; 24.41 mmol) and the reaction was stirred overnight allowing to reach room temperature. The reaction mixture was concentrated and suspended in ethyl acetate then washed with water (20 mL), brine (20 mL) and dried over magnesium sulfate. Solvent was evaporated and the crude azide was dissolved in a 1.25 M solution of hydrochloric acid in ethanol (30.0 mL). Palladium on charcoal (500 mg of 10% dispersion) was added and the reaction was stirred overnight under Hydrogen. The mixture was filtered through Celite and washed with ethanol. The filtrate was evaporated and dried under vacuum to give 2.534 g of 2-(3-hydroxyphenyl)-2-oxoethanaminium chloride (13.48 mmol, 58%). The material was used without further purification in the next step.

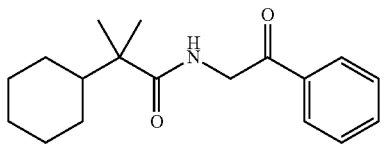 [SMILES: CC(C)(C(=O)NCC(=O)c1ccccc1)C1CCCCC1]

2-cyclohexyl-2-methyl-N-(2-oxo-2-phenylethyl) propanamide. Example 3.12

Prepared in a similar manner as described in Example 3.9a starting from 2-(3-hydroxyphenyl)-2-oxoethanaminium chloride (Example 3.11c) (2.94 mmol) and 2-amino-1-phenylethanone hydrochloride (555 mg, 3.23 mmol) to give 466.5 mg of the title compound, (55%). $^1$H NMR (400 MHz, DMSO-d$_6$) δ 7.98 (d, J=8.4, 2H), 7.78 (t, J=5.5 Hz, 1H), 7.65 (t, J=7.4 Hz, 1H), 7.53 (t, J=7.6 Hz, 2H), 4.50 (d, J=5.5 Hz, 2H), 1.79-1.65 (m, 2H), 1.65-1.47 (m, 4H), 1.25-1.03 (m, 3H), 1.01 (s, 6H), 0.99-0.84 (m, 2H). MS 288 (MH$^+$).

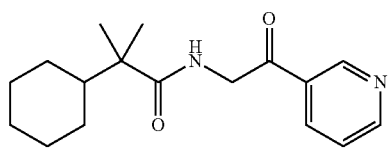 [SMILES: CC(C)(C(=O)NCC(=O)c1cccnc1)C1CCCCC1]

2-cyclohexyl-2-methyl-N-(2-oxo-2-(pyridin-3-yl) ethyl)propanamide. Example 3.14

To a stirred solution of 2-cyclohexyl-2-methylpropanoyl chloride (Example 3.11a) (0.46 mmol, 86 mg) and 2-amino-1-(pyridin-3-yl)ethanone hydrochloride (0.46 mmol, 80 mg) in DCM (5 mL) at 0° C. was added triethylamine (1.4 mmol, 195 μL). The resulting mixture was stirred overnight warming to room temperature, then quenched with water and extracted with DCM (50 mL×3). The combined organic layers were washed with brine, dried over MgSO$_4$ and concentrated. The resulting oil residue was purified by preparative HPLC to give the title compound as a colorless oil (45 mg; yield 34%). $^1$H NMR (400 MHz, CDCl$_3$) δ 9.207 (s, 1H), 8.837 (d, J=4.4 Hz, 1H), 8.242 (dt, J=8 Hz & 1.6 Hz, 1H), 7.456 (dd, J=8 Hz & 5.2 Hz, 1H), 6.685 (s, 1H), 4.770 (d, J=4.4 Hz, 2H), 1.591-1.777 (m, 6H), 1.180 (s, 6H), 0.965-1.335 (m, 5H). MS 289 (MH$^+$)

2-amino-1-(pyridin-3-yl)ethanone Hydrochloride

A solution of tert-butyl (2-oxo-2-(pyridin-3-yl)ethyl)carbamate (0.46 mmol, 108 mg) in EtOAc (6 mL) at 0° C. was treated with 4.0 N HCl in dioxane (0.70 mmol, 174 μL). The resulting mixture was stirred at room temperature for 48 h and concentrated. The resulting product was used into the next step without further purification. MS 137 (MH$^+$).

Tert-butyl (2-oxo-2-(pyridin-3-yl)ethyl)carbamate

To a solution of 3-bromopyridine (4.0 mmol, 627 mg) in THF (20 mL) at −78° C. was added a 2.5 M solution of n-butyllithium in hexane (4.0 mmol, 1.6 mL). The reaction was stirred for 10 minutes and t-butyl (2-(methoxy(methyl) amino)-2-oxoethyl)carbamate (4.0 mmol, 932 mg) was added in one portion. The resulting mixture was stirred at −78° C. for 30 minutes then allowed to warm to room temperature overnight. The reaction was quenched with water (5 mL) and diluted with EtOAc (50 mL) and H₂O (20 mL). The aqueous layer was extracted with EtOAc (50 mL×3) and the combined organic layers were washed with brine (50 mL), dried over MgSO₄ and concentrated. The resulting oil was purified by flash chromatography (Biotage 40 g silica column, 20% to 50% EtOAc in Hex gradient) to give Tert-butyl (2-oxo-2-(pyridin-3-yl)ethyl)carbamate as a colorless oil 210 mg (yield 22%). ¹H NMR (400 MHz, DMSO-d6) δ 9.110 (d, J=2.4 Hz, 1H), 8.781 (dd, J=1.6 Hz & 4.8 Hz, 1H), 8.242 (dt, J=8 Hz & 2 Hz, 1H), 7.538 (dd, J=8 Hz & 4.8 Hz, 1H), 7.155 (t, J=6 Hz, 1H), 4.436 (d, J=5.6 Hz, 2H), 0.362 (s, 9H). MS 289 (MH⁺).

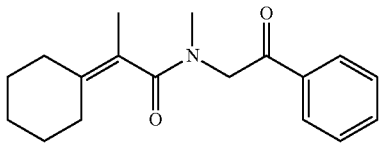 [SMILES: CC(C(=O)N(C)CC(=O)c1ccccc1)=C1CCCCC1]

2-cyclohexylidene-N-methyl-N-(2-oxo-2-phenylethyl)propanamide. Example 3.15

2-Cyclohexylidenepropanoic acid (227 mg, 1.47 mmol, 1.0 eq) was dissolved in DCM (25 mL) and cooled to 0° C. followed by the addition of oxalyl chloride (0.134 mL, 1.54 mmol, 1.05 eq) and DMF (3 drops, catalytic). The mixture was stirred and allowed to warm to room temperature. The reaction was stirred an additional hour after gas evolution had ceased then the reaction was concentrated and re-diluted in DCM (20 mL). 2-(Methylamino)-1-phenylethanone hydrochloride salt (409 mg, 2.21 mmol, 1.5 eq) was added followed by the slow addition of a solution of pyridine (0.297 mL, 3.68 mmol, 2.5 eq) in DCM (10 mL). The reaction mixture was allowed to stir at room temperature overnight then concentrated. The crude mixture was partitioned between ethyl acetate and 1.0 N HCl (25 mL each). The layers were separated and the organic layer was washed with 1.0 N NaOH (25 mL), brine (25 mL), dried over sodium sulfate and concentrated. The crude material was purified by HPLC (MeCN/water) to obtain 130 mg of the desired compound (31%). ¹H NMR (400 MHz, DMSO-d6): δ, ppm: 8.05 (t, 1H, J=5.6 Hz), 7.99 (m, 2H), 7.66 (t, 1H, J=6.0 Hz), 7.54 (t, 2H, J=8.0 Hz, 4.57 (d, 2H, J=5.6 Hz), 2.22 (m, 2H), 2.12 (m, 2H), 1.75 (s, 3H), 1.51 (m, 6H).

2-cyclohexylidenepropanoic Acid. Example 3.15a

Methyl 2-bromopropanoate (1.0 eq, 10 g, 59.9 mmol) and triethylphosphite (5.0 eq, 299.5 mmol, 51.5 mL) were combined neat and heated to 110° C. with stirring overnight. The reaction mixture was concentrated, azeotroped with toluene 3×, and dried under high vacuum. The resulting phosphonate was obtained in quantitative yield and was used directly in the following reaction: The phosphonate (1.0 eq, 10.0 g, 44.6 mmol) was dissolved in anhydrous THF (100 mL) and cooled to 0° C. To this mixture, n-BuLi (2.5 M in Hexanes, 18.7 mL, 46.8 mmol, 1.05 eq) was added dropwise. The mixture was stirred for 2 hours at 0° C., then cyclohexanone (1.0 eq, 44.6 mmol, 4.6 mL) was added. The mixture was stirred at 0° C. gradually warming to ambient temperature over 72 hours. The reaction was quenched with saturated aqueous ammonium chloride (500 mL) and concentrated. The remaining aqueous layer was extracted with ethyl acetate (2×200 mL) to give 16.8 g of the crude ester as a yellow oil which was purified by flash column chromatography (hex/ethyl acetate gradient). 3.7 g of a pale yellow oil was obtained as mixture of methyl and ethyl esters in about 1.4:1 molar ratio (21.25 mmol, 48% yield). The isolated mixed ester (3.2 g, 18.36 mmol) was dissolved in ethanol (50 mL) and solid sodium hydroxide (1.0 g, 25 mmol) was added. The mixture was refluxed until reaction was complete. Ethanol was subsequently removed and the residue was partitioned between ethyl acetate (50 mL) and a 1.0 N solution of HCl (50 mL). The aqueous layer was acidified with 6.0 N HCl until acidic and extracted with ethyl acetate (50 mL) again. Combined organic layers were washed with brine and dried over magnesium sulfate. The crude material was purified by flash column chromatography (hex/ethyl acetate gradient) to afford 2.0 g (71% yield) of the desired isomer as a yellow oil in 90% purity by ¹H-NMR. ¹H NMR (400 MHz, DMSO-d6): δ, ppm: 12.18 (s, 1H), 2.40 (m, 2H), 2.17 (m, 2H), 1.77 (s, 3H), 1.52 (m, 6H).

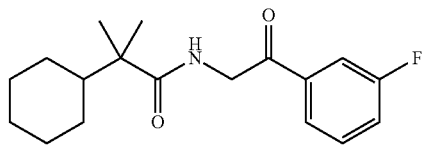

2-cyclohexyl-N-(2-(3-fluorophenyl)-2-oxoethyl)-2-methylpropanamide. Example 3.17

To a solution of commercial 2-amino-1-(3-fluorophenyl)ethanone (0.08 g, 0.5 mmol) in DCM (5.0 mL) was added a solution of 2-cyclohexyl-2-methylpropanoyl chloride (Example 3.11a) (0.09 g, 0.5 mmol) in DCM (2.0 mL) and triethylamine (0.15 mL, 1.0 mmol). The reaction was stirred at room temperature overnight then concentrated. The crude product was dissolved in DCM and purified by flash chromatography (silicycle column, DCM/EtOAc gradient 0-20%) to afford 2-cyclohexyl-N-(2-(3-fluorophenyl)-2-oxoethyl)-2-methylpropanamide as a white solid. MS (M+H)=306. ¹H NMR (400 MHz, DMSO-d6): δ 7.80-7.89 (m, 2H), 7.73-7.77 (ddd, J=9.8, 2.6, 1.5 Hz, 1H), 7.59 (td, J=8.0, 5.8 Hz, 1H), 7.51 (tdd, J=8.4, 2.6, 1.0 Hz, 1H), 4.48 (d, J=5.4 Hz, 2H), 1.49-1.75 (m, 6H), 1.02-1.24 (m, 3H), 1.00 (s, 6H), 0.84-0.99 (m, 2H),

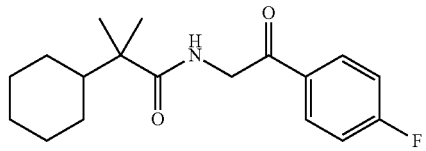 [SMILES: CC(C)(C(=O)NCC(=O)c1ccc(F)cc1)C1CCCCC1]

2-cyclohexyl-N-(2-(4-fluorophenyl)-2-oxoethyl)-2-methylpropanamide. Example 3.19

Prepared in a similar manner as of Example 3.9a from 2-amino-1-(4-fluorophenyl)ethanone hydrochloride (Example 3.19a) (0.32 mmol, 60 mg) and 2-cyclohexyl-2-methylpropanoyl chloride (Example 3.11b) (0.32 mmol, 60 mg). The product was obtained as a white solid 40 mg (yield 41%). ¹H NMR (400 MHz, DMSO-d6) δ 8.021 (dd, J=8.4 Hz & 5.6 Hz, 2H), 7.768 (t, J=5.2 Hz, 1H), 7.315 (t, J=8.8 Hz, 2H), 4.450 (d, J=5.6 Hz, 2H), 1.491~1.692 (m, 6H), 0.985 (s, 6H), 0.809~1.176 (m, 5H). MS 306 (MH⁺).

2-amino-1-(4-fluorophenyl)ethanone Hydrochloride. Example 3.19a

Prepared in a similar manner as of Example 3.9b from tert-butyl (2-(4-fluorophenyl)-2-oxoethyl)carbamate (Example 3.19b) (0.32 mmol, 81 mg). The 60 mg (quant.) of the product were obtained and used into the next step without further purification.

Tert-butyl (2-(4-fluorophenyl)-2-oxoethyl)carbamate. Example 3.19b

Prepared in a similar manner as of Example 3.9c from t-butyl (2-(methoxy(methyl)amino)-2-oxoethyl)carbamate (2.0 mmol, 467 mg), isopropylmagnesium chloride 2.0 M in THF (2.0 mmol, 1.0 mL), and 1-bromo-4-fluorobenzene (2.6 mmol, 850 mg). The final product was obtained as a white solid 290 mg. (yield 57%). ¹H NMR (400 MHz, DMSO-d6) δ 8.025 (dd, J=9.2 Hz & 5.6 Hz, 2H), 7.327 (t, J=9.2 Hz, 1H), 7.067 (t, J=6 Hz, 2H), 4.397 (d, J=6 Hz, 2H), 1.371 (s, 9H). MS 254 (MH⁺)

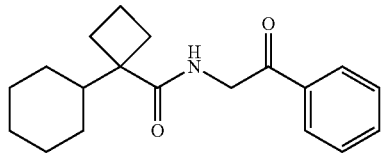 [SMILES: O=C(CNC(=O)C1(C2CCCCC2)CCC1)c1ccccc1]

1-cyclohexyl-N-methyl-N-(2-oxo-2-phenylethyl) cyclobutanecarboxamide. Example 3.20

To a solution of 2-(methylamino)-1-phenylethanone hydrochloride (90 mg, 0.50 mmol) in DCM (5.0 mL) was added a solution of 1-cyclohexylcyclobutanecarbonyl chloride (100 mg, 0.50 mmol) in DCM (2 mL) and triethylamine (0.170 mL, 1 mmol). The reaction was stirred at room temperature overnight then concentrated. The crude product was dissolved in DCM and purified by flash chromatography (silicycle column, DCM/EtOAc gradient 0-20%) to afford 1-cyclohexyl-N-methyl-N-(2-oxo-2-phenylethyl)cyclobutanecarboxamide as a white solid. MS (M+H)=314. ¹H NMR (400 MHz, dmso) δ 7.94-8.04 (m, 2H), 7.62-7.72 (m, 1H), 7.50-7.60 (m, 2H), 4.75 (s, 2H), 2.89 (s, 3H), 2.31-2.40 (m, 2H), 1.91-2.30 (m, 2H), 1.53-1.84 (m, 8H), 0.95-1.35 (m, 5H).

1-cyclohexylcyclobutanecarbonyl Chloride. Example 3.20a

A solution of 1-cyclohexylcyclobutanecarboxylic acid (200 mg, 1.0 mmol) in DCM (5.0 mL) was treated with oxalyl chloride (0.150 mL, 1.7 mmol) followed by a few drops of DMF at room temperature. The resulting solution was stirred at room temperature until gas evolution ceased (~1 h). The mixture was concentrated from DCM (3×10 mL) and used without further purification for the coupling above described.

1-cyclohexylcyclobutanecarboxylic Acid. Example 3.20b

1-Phenylcyclobutanecarboxylic acid (800 mg, 4.5 mmol), acetic acid (10 mL) and 5% wt Rh/Al₂O₃ (200 mg) were added to a glass beaker and placed in the stainless steel pressure reactor under H₂ atmosphere (110 psi) for 72 hours with stirring. The reaction mixture was filtered through celite and washed with EtOAc then concentrated. The residue was dissolved in ether and washed with water (50 mL×4), and brine (50 mL×2), dried over MgSO₄ and concentrated to give 1-cyclohexylcyclobutanecarboxylic acid. UPLC MS (M–H)=181. ¹H NMR indicated the purity was greater than 90%.

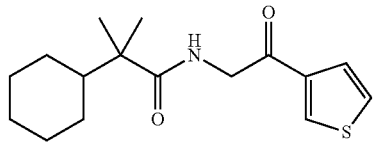 [SMILES: CC(C)(C(=O)NCC(=O)c1ccsc1)C1CCCCC1]

2-cyclohexyl-2-methyl-N-(2-oxo-2-(thiophen-3-yl) ethyl)propanamide. Example 3.22

2-Cyclohexyl-2-methylpropanoic acid (Example 3.11b) (17.9 g, 105 mmol) in anhydrous DCM (100 mL) was chilled to 0° C. and DMF (0.387 mL, 5.0 mmol) was added followed by oxalyl chloride (9.6 mL, 110 mmol). The mixture was stirred and allowed to warm to room temperature overnight. The mixture was concentrated and redissolved in anhydrous DCM (100 mL). 2-amino-1-(thiophen-3-yl)ethanone hydrochloride (17.75 g, 99.9 mmol) was added and cooled in an ice bath followed by the drop wise addition of a solution of triethylamine in 50 mL DCM (26.6 mL, 199.8 mmol). The reaction was allowed to stir and warm to room temperature for 5 hours. The reaction was concentrated and partitioned between ethyl acetate (500 mL) and water (500 mL). The aqueous layer was extracted with ethyl acetate (200 mL) and the combined organic layers were washed with brine, dried over sodium sulfate and concentrated. Purification by flash chromatography (Hex/EtOAc gradient), produced 25.1 g of 2-cyclohexyl-2-methyl-N-(2-oxo-2-(thiophen-3-yl)ethyl)propanamide as a light yellow solid. The solids were washed with hexanes and filtered after being chilled in the freezer to afford 24.4 g of off white solid. The solids were stirred vigorously in hot hexanes and filtered at room temperature (3×200-250 mL) to afford 22.1 g of desired product in high purity as a white solid. ¹H NMR (400 MHz, DMSO-d6): δ, ppm: 8.58 (dd, 1H, J₁=1.6 Hz, J₂=2.8 Hz), 7.77 (t, 1H, J=5.6 Hz), 7.65 (dd, 1H, J₁=5.2 Hz, J₂=2.8 Hz)), 7.53 (dd, 1H, J₁=5.2 Hz, J₂=1.2 Hz), 4.40 (d, 2H, J=5.6 Hz), 1.61 (m, 6H), 1.15 (m, 3H), 1.02 (s, 6H), 0.91 (m, 2H), 2-amino-1-(thiophen-3-yl)ethanone Hydrochloride. Example 3.22a A solution of Tert-butyl (2-oxo-2-(thiophen-3-yl)ethyl) carbamate (15.7 g, 64.9 mmol) in dioxane was treated with a solution of 4.0 M hydrochloric acid in dioxane (65 mL). The reaction mixture was stirred at room temperature overnight. The mixture was diluted with hexanes (100 mL), cooled to –5° C. and filtered. The precipitate was washed with hexanes (3×25 mL) and air dried to afford 9.94 g of the desired HCl salt as an off white solid. ¹H NMR (400 MHz, DMSO-d6): δ, ppm: 6.86 (t, broad, 1H, J=6.0 Hz), 3.82 (d, 2H, J=6.4 Hz), 3.67 (s, 3H), 3.08 (s, 3H), 1.38 (s, 9H).

Tert-butyl (2-oxo-2-(thiophen-3-yl)ethyl)carbamate

To flame dried magnesium turnings (9.72 g, 400 mmol) in a 500 mL round bottom flask, anhydrous THF (150 mL) was added at room temperature under nitrogen. The mixture was cooled in an ice bath and 1,2-dibromoethane (200 mmol, 17.2 mL) was added in 3 portions 10-15 minutes apart. The mixture was allowed to stir and gradually warm to room temperature. Once bubbling had ceased (~3 hours), the mixture was cooled to 0° C. and 3-bromothiophene (14.0 mL, 150 mmol) was added. A 2.0M solution of n-BuLi in THF (56.0 mL, 140 mmol) was added slowly via syringe. The mixture was allowed to warm to room temperature with stirring for 2 h. In another 1 L flask, tert-butyl (2-(methoxy (methyl)amino)-2-oxoethyl)carbamate (21.8 g, 100 mmol) was dissolved in THF (500 mL) and charged with a 2.0M solution of i-PrMgCl in THF (50 mL, 100 mmol) at −40° C. This mixture was stirred until complete dissolution. Upon complete dissolution, the prepared Grignard was transferred via syringe at −40° C. The mixture was allowed to stir overnight warming to room temperature. The reaction mixture was cooled in an ice bath and quenched with 500 mL of aqueous saturated ammonium chloride solution. Most of the organics were evaporated and the remaining mixture was extracted with ethyl acetate (2×500 mL). The combined organic layer was washed with brine, dried over sodium sulfate and concentrated. This crude material was purified by flash chromatography (Hex/EtOAc gradient) to give 15.7 g of Tert-butyl (2-oxo-2-(thiophen-3-yl)ethyl)carbamate as a light yellow oil that eventually solidified upon standing. ¹H NMR (400 MHz, DMSO-d6): δ, ppm: 8.56 (dd, 1H, J1=1.2 Hz, J2=2.8 Hz), 7.65 (dd, 1H, J1=2.8 Hz, J2=5.2 Hz), 7.52 (dd, 1H, J1=1.2 Hz, J2=5.2 Hz), 7.09 (t, 1H, J=6.0 Hz), 4.32 (d, 2H, J=6.0 Hz), 1.39 (s, 9H).

The following compounds were prepared according to the general procedures outlined in Scheme 3.2 as described herein below.

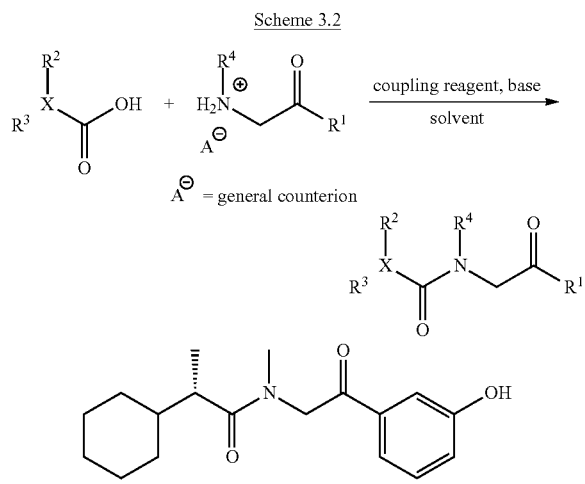

Scheme 3.2

(+)-(S)-2-cyclohexyl-N-(2-(3-hydroxyphenyl)-2-oxoethyl)-N-methylpropanamide. Example 3.1

To a solution of (+)-(S)-2-cyclohexyl-N-(2-(3-methoxyphenyl)-2-oxoethyl)-N-methylpropanamide (Example 3.1a) (331 mg; 1.04 mmol) in 20 mL of DCM at −78° C., under $N_2$ atmosphere was added 1.0 M $BBr_3$ solution in DCM (1.5 eq; 1.56 mL; 1.56 mmol). The reaction mixture was slowly warmed to room temperature and stirred for 18 h; then poured into saturated $NaHCO_3$ (20 mL) and extracted with DCM (3×20 mL). The combined organic phases were dried over $MgSO_4$ and solvent was evaporated. The residue was purified by preparative HPLC (25 minute 5-95% $CH_3CN$/$H_2O$ gradient) to give the desired compound (45 mg; 14%) as a white powder. ¹H-NMR spectrum in DMSO-$d_6$ indicates a mixture of rotamers (~1:2). ¹H NMR (DMSO-$d_6$) δ: 9.85 (s, 1H), 7.47 (ddd, J=7.8, 1.5, 1.0 Hz, 0.3H), 7.41 (ddd, J=7.7, 1.6, 1.1 Hz, 0.7H), 7.38-7.31 (m, 1.3H), 7.29 (dd, J=2.5, 1.6 Hz, 0.7H), 7.07 (ddd, J=8.0, 2.6, 1.0 Hz, 0.3H), 7.04 (ddd, J=8.0, 2.6, 1.0 Hz, 0.7H), 5.07 (d, J=19.3 Hz, 0.3H), 4.95 (d, J=19.3 Hz, 0.3H), 4.81 (d, J=17.7 Hz, 0.7H), 4.71 (d, J=17.6 Hz, 0.7H), 3.06 (s, 2H), 2.81 (s, 1H), 2.70-2.58 (m, 0.7H), 2.29-2.19 (m, 0.3H), 1.82-1.30 (m, 6H), 1.47-1.35 (m, 1H), 1.27-1.01 (m, 3H), 0.97 (d, J=6.8 Hz, 2H), 0.88 (d, J=6.7 Hz, 1H), 1.06-0.74 (m, 1H). MS 304 (MH⁺). [α]²⁰_D=+470 (EtOH, 1 mg/mL).

(+)-(S)-2-cyclohexyl-N-(2-(3-methoxyphenyl)-2-oxoethyl)-N-methylpropanamide. Example 3.1a To a solution of (S)-2-cyclohexylpropanoic acid (Example 3.2a) (234 mg; 1.5 mmol) in anhydrous DMF (10 mL) at room temperature were added HATU (1.3 eq.; 741 mg, 1.95 mmol) and HOAt (0.6 M in DMF; 2 eq.; 5 mL, 3.0 mmol). The reaction mixture was stirred for 15 min and 1-(3-methoxyphenyl)-2-(methylamino)ethanone hydrochloride (Example 3.1b) (1.3 eq.; 420 mg; 1.95 mmol) and $Et_3N$ (1.5 eq.; 312 μL, 2.25 mmol) were added. The reaction mixture was stirred at room temperature overnight. The reaction medium was diluted with $H_2O$ (20 mL) and extracted with EtOAc (3×15 mL). The combined organic phases were dried over $MgSO_4$ and solvent was evaporated. The residue was purified by flash chromatography (hexane/EtOAc gradient), to obtain (+)-(S)-2-cyclohexyl-N-(2-(3-methoxyphenyl)-2-oxoethyl)-N-methylpropanamide as a yellow oil (332 mg, 69%). ¹H-NMR spectrum in d⁶-DMSO indicates a mixture of rotamers (~1:2). ¹H NMR (DMSO-$d_6$) δ: 7.63 (ddd, J=7.6, 1.6, 1.0 Hz, 0.3H), 7.57 (ddd, J=7.7, 1.6, 1.0 Hz, 0.7H), 7.54-7.41 (m, 2H), 7.27 (ddd, J=8.3, 2.7, 1.0 Hz, 0.3H), 7.23 (ddd, J=8.3, 2.7, 1.0 Hz, 0.7H), 5.13 (d, J=19.4 Hz, 0.3H), 5.03 (d, J=19.4 Hz, 0.3H), 4.87 (d, J=17.7 Hz, 0.7H), 4.77 (d, J=17.7 Hz, 0.7H), 3.84 (s, 1H), 3.82 (s, 2H), 3.07 (s, 2H), 2.82 (s, 1H), 2.70-2.58 (m, 0.7H), 2.29-2.22 (m, 0.3H), 1.81-1.49 (m, 6H), 1.49-1.29 (m, 1H), 1.28-1.01 (m, 3H), 0.97 (d, J=6.8 Hz, 2H), 0.89 (d, J=6.7 Hz, 1H), 0.95-0.71 (m, 1H). MS 318 (MH⁺).

1-(3-methoxyphenyl)-2-(methylamino)ethanone hydrochloride Example 3.1b

To a solution of tert-butyl-(2-(3-methoxyphenyl)-2-oxoethyl)(methyl)carbamate (Example 3.1c) (2.5 g, 9.0 mmol) in anhydrous EtOAc (20 mL) flushed with $N_2$ and cooled to 0° C. was added 4.0 M HCl in dioxane (4.5 eq.; 10.0 mL, 40.0 mmol) and the reaction medium was stirred for 20 h gradually warming to room temperature. The heterogeneous solution was filtered, the white powder was washed with cold EtOAc (2×10 mL) and dried under vacuum to obtain the 1-(3-methoxyphenyl)-2-(methylamino)ethanone as a pale yellow solid (1.57 g, 81%). ¹H NMR (DMSO-$d_6$) δ: 9.38 (s, 2H), 7.58 (ddd, J=7.7, 1.6, 1.1 Hz, 1H), 7.52 (t, J=7.9

Hz, 1H), 7.48 (dd, J=2.6, 1.5 Hz, 1H), 7.31 (ddd, J=8.1, 2.7, 1.1 Hz, 1H), 4.76 (s, 2H), 3.84 (s, 3H), 2.61 (s, 3H). MS 180 (MH+).

Tert-butyl-(2-(3-methoxyphenyl)-2-oxoethyl) (methyl)carbamate. Example 3.1c

To a solution of tert-butyl-(2-(methoxy(methyl)amino)-2-oxoethyl)(methyl)carbamate (Example 3.1d) (2.32 g, 10.0 mmol) in 20 mL of anhydrous THF under N₂ atmosphere was added (3-methoxy-phenyl)magnesium bromide (1.0 M solution in THF; 2.1 eq; 21.0 mL; 21.0 mmol) drop wise, maintaining the temperature between 25-45° C. The reaction was stirred at room temperature overnight and the obtained heterogeneous solution was quenched with saturated NH₄Cl (50 mL) and acidified with 1N HCl to pH=5-6. The reaction was extracted with EtOAc (3×50 mL). The combined organic phases were washed with brine, dried over MgSO₄ and solconcentrated. The residue was purified by flash chromatography using a hexane/EtOAc gradient, to obtain the desired compound as a yellow oil (2.5 g, 89%). ¹H-NMR spectrum in DMSO-d₆ indicates a mixture of rotamers (~1:1). ¹H NMR (DMSO-d₆) δ: 7.56 (tt, J=7.8, 1.2 Hz, 1H), 7.50-7.43 (m, 2H), 7.24 (ddd, J=8.2, 2.7, 1.0 Hz, 1H), 4.71 (s, 1H), 4.70 (s, 1H), 3.82 (s, 3H), 2.86 (s, 1.5H), 2.83 (s, 1.5H), 1.41 (s, 4.5H), 1.27 (s, 4.5H). MS 180 (MH+).

Tert-Butyl (2-(methoxy(methyl)amino)-2-oxoethyl) (methyl)carbamate. Example 3.1d To a solution of 2-((tert-butoxycarbonyl)(methyl)amino) acetic acid (25.0 g, 132.0 mmol) in 300 mL of anhydrous THF under N₂ atmosphere was added CDI (1.2 eq; 25.7 g; 159.0 mmol) portionwise over 10 min. The reaction mixture was stirred at room temperature for 2 h and N,O-dimethyl-hydroxylamine hydrochloride (1.2 eq.; 15.5 g; 159 mmol) and Et₃N (1.2 eq; 22.0 mL; 159.0 mmol) were added. The resulting mixture was stirred overnight at room temperature. The precipitated salts were filtered off and the filtrate was concentrated. The residue was diluted with H₂O (300 mL) and extracted with EtOAc (3×100 mL). Combined organic phases were washed with 10% KHSO₄ (3×50 mL), saturated NaHCO₃ (50 mL), water and brine, then dried over MgSO₄ and concentrated. This gave tert-Butyl (2-(methoxy(methyl) amino)-2-oxoethyl)(methyl)carbamate as a colorless oil (29 g, 95%). ¹H-NMR spectrum in DMSO-d₆ indicates a mixture of rotamers (~1:1). ¹H NMR (DMSO-d₆) δ: 4.08 (s, 1H), 4.07 (s, 1H), 3.68 (s, 1.5H), 3.66 (s, 1.5H), 3.10 (s, 1.5H), 3.09 (s, 1.5H), 2.82 (s, 1.5H), 2.78 (s, 1.5H), 1.39 (s, 4.5H), 1.33 (s, 4.5H). MS 132 (MH+).

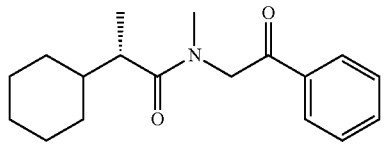 [SMILES: C[C@H](C(=O)N(C)CC(=O)c1ccccc1)C1CCCCC1]

(S)-2-Cyclohexyl-N-methyl-N-(2-oxo-2-phenyl-ethyl)propanamide. Example 3.2

To an oven-dried, N₂-flushed round-bottom flask were added anhydrous DMF (80 mL) and (S)-2-cyclohexylpropanoic acid (Example 3.2a) (1.57 g, 10 mmol). The reaction mixture was cooled to 0° C. and HATU (5.0 g, 13 mmol), HOAt (2.72 g, 20 mmol), 2-(methylamino)-1-phenyletha-none hydrochloride (Example 3.2b) (1.95 g, 10.5 mmol), and Et₃N (6.4 mL, 46.1 mmol) were added. The reaction was stirred at room temperature overnight, diluted with H₂O (100 mL) and extracted and EtOAc (3×100 mL). The combined organic phases were washed with an ice-cold solution of 0.5% aqueous citric acid (50 mL), saturated NaHCO₃(50 mL), water (50 mL), and brine (50 mL), then dried over MgSO₄ and concentrated. The residue was purified by flash chromatography (hexane/EtOAc gradient), to obtain the desired compound as a yellow oil (2.83 g, 98%). ¹H-NMR in DMSO-d₆ indicates a ~2:1 mixture of rotamers unresolved at 80° C. LCMS, ¹H-NMR, ¹³C-NMR indicate a purity of greater than 98%.
¹H NMR (400 MHz, DMSO-d₆) δ 8.03 (d, J=8.4 Hz, 0.6H), 7.97 (d, J=8.4 Hz, 1.4H), 7.74-7.62 (m, 1H), 7.62-7.46 (m, 2H), 5.15 (d, J=19.3 Hz, 0.3H), 5.03 (d, J=19.3 Hz, 0.3H), 4.88 (d, J=17.7 Hz, 0.7H), 4.78 (d, J=17.7 Hz, 0.8H), 3.08 (s, 2H), 2.82 (s, 1H), 2.71-2.57 (m, 0.8H), 2.34-2.19 (m, 0.3H), 1.81-1.50 (m, 5H), 1.50-1.29 (m, 1H), 1.29-1.02 (m, 3H), 0.97 (d, J=8.0, 2H), 0.96-0.77 (m, 2H), 0.90 (d, J=4.0, 1H). MS 288 (MH+). Chiral analysis showed the compound was optically pure (ee >99%)

(S)-2-Cyclohexylpropanoic Acid. Example 3.2(a)

(S)-2-Phenylpropanoic acid (4.92 g, 3.3 mmol), glacial acetic acid (60 mL) and 5% Rh/Al₂O₃(1.0 g) were placed in a glass beaker and the beaker was placed in a stainless steel pressure reactor under H₂ atmosphere (110 psi) for 72 h with stirring and intermittent pressure re-adjustments. The reaction medium was filtered over Celite, washed with AcOH and EtOAc and concentrated. The resulting oil was dissolved in Et₂O and washed with H₂O (4×50 mL) and brine (2×50 mL), dried over MgSO₄ and concentrated, to obtain the desired product as an off-white powder (4.85 g, 95%).
¹H NMR (400 MHz, DMSO-d₆) δ 12.02 (s, 1H), 2.11 (pseudo p, J=7.0 Hz, 1H), 1.75-1.53 (m, 5H), 1.52-1.37 (m, 1H), 1.27-1.02 (m, 3H), 1.00-0.81 (m, 2H), 0.99 (d, J=7.0 Hz, 3H). Optical rotation+0.212 (10 mg/mL EtOH, 20° C.).

2-(Methylamino)-1-phenylethanone Hydrochloride. Example 3.2(b)

In a round-bottom flask, tert-butyl methyl(2-oxo-2-phenylethyl)carbamate (Example 3.2c) (1.44 g, 5.76 mmol) was flushed with N₂ and diluted with EtOAc (18 mL). 4M HCl/dioxane (10 mL, 40 mmol) was added at 0° C. and the reaction medium was stirred for 20 h warming to room temperature. The flask was then cooled to 0° C. and the heterogeneous solution was filtered. The white powder was washed with cold EtOAc (3×10 mL) and dried under vacuum to obtain the 2-(Methylamino)-1-phenylethanone hydrochloride as a off white powder (0.94 g, 87%).
¹H NMR (400 MHz, DMSO-d₆) δ 9.00 (s, 2H), 8.00 (d, J=7.2 Hz, 2H), 7.76 (t, J=7.4 Hz, 1H), 7.67-7.56 (m, 2H), 4.78 (s, 2H), 2.64 (s, 3H). MS 150 (MH+).

Tert-butyl methyl(2-oxo-2-phenylethyl)carbamate. Example 3.2(c)

To an oven-dried, N₂-flushed round-bottom flask was added 1M phenylmagnesium bromide in anhydrous THF (17.8 mL, 17.8 mmol). A solution of tert-butyl methyl(2-morpholino-2-oxoethyl)carbamate (Example 3.2d) (2.2 g, 8.5 mmol) in anhydrous THF (10 mL) was added drop wise over 10 minutes and the reaction was stirred at room temperature overnight and quenched with saturated NH₄Cl (15 mL). Water was added (10 mL) and the reaction medium was extracted with EtOAc (3×25 mL). The combined organic phases were washed with brine, dried over MgSO₄ and concentrated. The residue was purified by flash chromatography (hexane/EtOAc gradient), to obtain the title compound as a white solid (1.44 g, 68%). ¹H-NMR in DMSO-d₆ indicates a ~1:1 mixture of rotamers. ¹H NMR (400 MHz, DMSO-d₆) δ 8.02-7.91 (m, 2H), 7.67 (t, J=7.4 Hz, 1H), 7.61-7.50 (m, 2H), 4.72 (s, 1H), 4.71 (s, 1H), 2.86 (s, 1.5H), 2.84 (s, 1.5H), 1.41 (s, 4.5H), 1.27 (s, 4.5H). MS 150 ([M-Boc+H]⁺)

Tert-butyl methyl(2-morpholino-2-oxoethyl)carbamate. Example 3.2(d)

To an oven-dried, N₂-flushed round-bottom flask were added anhydrous DMF (100 mL) and 2-((tert-butoxycarbonyl)(methyl)amino)acetic acid (5.0 g, 26.4 mmol). CDI (5.1 g, 31.5 mmol) was added in 4 portions over 10 minutes and reaction was stirred for 1 h at room temperature. Morpholine (2.8 mL, 31.5 mmol) was added and the reaction was stirred overnight at room temperature. The resulting solution was extracted with EtOAc (3×100 mL) and DCM/ACN (3×100 mL). The combined organic phases were washed with ice-cold 1N HCl (100 mL), water (100 mL) and brine (50 mL), the dried over MgSO₄ and concentrated, to obtain the desired compound (2.2 g, 32%) as a a ~1:1 mixture of rotamers by ¹H-NMR. ¹H NMR (400 MHz, DMSO-d₆) δ 4.02 (s, 1H), 4.00 (s, 1H), 3.59-3.51 (m, 4H), 3.46-3.36 (m, 4H), 2.78 (s, 1.5H), 2.75 (s, 1.5H), 1.39 (s, 4.5H), 1.33 (s, 4.5H). MS 159 ([M-Boc+H]+).

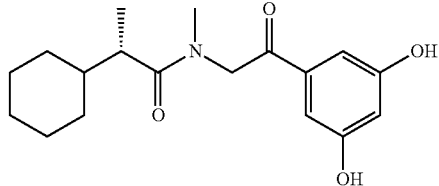 [SMILES: C[C@H](C(=O)N(C)CC(=O)c1cc(O)cc(O)c1)C1CCCCC1]

(S)-2-cyclohexyl-N-(2-(3,5-dihydroxyphenyl)-2-oxoethyl)-N-methylpropanamide. Example 3.3

Prepared in a similar manner as described in Example 3.1 starting from (S)-2-cyclohexyl-N-(2-(3,5-dimethoxyphenyl)-2-oxoethyl)-N-methylpropanamide (Example 3.3a) (95 mg, 0.27 mmol) to obtain the title compound (28 mg, 32%) as an white powder. ¹H-NMR spectrum in DMSO-d₆ indicates a mixture of rotamers (~1:2). ¹H NMR (DMSO-d₆) δ: 9.67 (s, 2H), 6.83 (d, J=2.2 Hz, 0.6H), 6.77 (d, J=2.2 Hz, 1.4H), 6.50 (t, J=2.2 Hz, 0.3H), 6.47 (t, J=2.2 Hz, 0.7H), 4.99 (d, J=19.2 Hz, 0.3H), 4.86 (d, J=19.3 Hz, 0.3H), 4.73 (d, J=17.6 Hz, 0.7H), 4.64 (d, J=17.6 Hz, 0.7H), 3.04 (s, 2H), 2.79 (s, 1H), 2.68-2.58 (m, 0.7H), 2.27-2.15 (m, 0.3H), 1.80-1.48 (m, 6H), 1.48-1.28 (m, 1H), 1.26-0.99 (m, 3H), 0.96 (d, J=6.8 Hz, 2H), 0.87 (d, J=6.7 Hz, 1H), 0.94-0.73 (m, 1H). MS 320 (MH⁺).

(S)-2-cyclohexyl-N-(2-(3,5-dimethoxyphenyl)-2-oxoethyl)-N-methylpropanamide. Example 3.3a Prepared in a similar manner as described in Example 3.1a starting from (S)-2-cyclohexyl-propanoic acid (156 mg; 1 mmol) and 1-(3,5-dimethoxyphenyl)-2-(methylamino)ethanone hydrochloride (Example 3.3b) (320 mg; 1.3 mmol) to obtain the desired compound (106 mg, 30%) as a white powder. ¹H-NMR spectrum in DMSO-d6 indicates a mixture of rotamers (~1:2). ¹H NMR (DMSO-d₆) δ: 7.15 (d, J=2.3 Hz, 0.6H), 7.09 (d, J=2.3 Hz, 1.4H), 6.82 (t, J=2.3 Hz, 0.3H), 6.78 (t, J=2.3 Hz, 0.7H), 5.11 (d, J=19.5 Hz, 0.3H), 5.01 (d, J=19.4 Hz, 0.3H), 4.85 (d, J=17.8 Hz, 0.7H), 4.75 (d, J=17.8 Hz, 0.7H), 3.82 (s, 1H), 3.81 (s, 3H), 3.06 (s, 3H), 2.81 (s, 1H), 2.70-2.58 (m, 0.7H), 2.29-2.19 (m, 0.3H), 1.77-1.51 (m, 6H), 1.49-1.30 (m, 1H), 1.26-1.01 (m, 3H), 0.97 (d, J=6.8 Hz, 2H), 0.89 (d, J=6.6 Hz, 1H), 0.87-0.72 (m, 1H). MS 348 (MH⁺).

1-(3,5-dimethoxyphenyl)-2-(methylamino)ethanone Hydrochloride. Example 3.3b

Prepared in a similar manner as described in Example 3.1b starting from tert-butyl (2-(3,5-dimethoxyphenyl)-2-oxoethyl)(methyl)carbamate (3.66 g; 11.86 mmol) to obtain the desired compound as a white powder (1.152 g, 67%). ¹H NMR (DMSO-d₆) δ: 9.22 (s, 2H), 7.11 (d, J=2.3 Hz, 2H), 6.87 (t, J=2.3 Hz, 1H), 4.74 (s, 2H), 3.83 (s, 6H), 2.61 (s, 3H). MS 210 (MH⁺).

Tert-butyl (2-(3,5-dimethoxyphenyl)-2-oxoethyl)(methyl)carbamate. Example 3.3c

Prepared in a similar manner as described in Example 3.1c starting from tert-butyl (2-(methoxy(methyl)amino)-2-oxoethyl)(methyl)carbamate (Example 3.1d) (1.624 g, 7.0 mmol) and (3,5-dimethoxyphenyl)magnesium bromide (0.5 M solution in THF; 29.4 mL; 14.7 mmol) to obtain the desired compound as an colorless oil (2.1 g, 98%). ¹H-NMR spectrum in DMSO-d6 indicates a mixture of rotamers (~1:1). ¹H NMR (DMSO-d₆) δ: 7.09 (d, J=2.3 Hz, 1H), 7.06 (d, J=2.3 Hz, 1H), 6.79 (t, J=2.2 Hz, 1H), 4.69 (s, 1H), 4.68 (s, 1H), 3.81 (s, 6H), 2.85 (s, 1H), 2.82 (s, 2H), 1.41 (s, 4.5H), 1.28 (s, 4.5H). MS 210 (MH⁺).

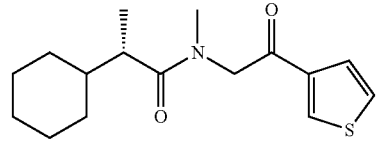 [SMILES: C[C@H](C(=O)N(C)CC(=O)c1ccsc1)C1CCCCC1]

(S)-2-cyclohexyl-N-methyl-N-(2-oxo-2-(thiophen-3-yl)ethyl)propanamide. Example 3.4

Prepared in a similar manner as described in Example 3.1a starting from (S)-2-cyclohexyl-propanoic acid (78 mg; 0.5 mmol) and 2-(methylamino)-1-(thiophen-3-yl)ethanone hydrochloride (Example 3.4a) (124 mg; 0.65 mmol) to obtain the title compound (53 mg, 36%) as an white powder. ¹H-NMR spectrum in DMSO-d₆ indicates a mixture of rotamers (~1:2). ¹H NMR (DMSO-d₆) δ: 8.63 (dd, J=2.8, 1.3 Hz, 0.3H), 8.56 (dd, J=2.8, 1.3 Hz, 0.7H), 7.69 (dd, J=5.1, 2.8 Hz, 0.3H), 7.66 (dd, J=5.1, 2.8 Hz, 0.7H), 7.57 (dd, J=5.1, 1.3 Hz, 0.3H), 7.52 (dd, J=5.1, 1.3 Hz, 0.7H), 5.02 (d, J=19.3 Hz, 0.3H), 4.89 (d, J=19.3 Hz, 0.3H), 4.77 (d, J=17.6 Hz, 0.7H), 4.67 (d, J=17.6 Hz, 0.7H), 3.07 (s, 2H), 2.82 (s, 1H), 2.70-2.58 (m, 0.7H), 2.32-2.20 (m, 0.3H), 1.81-1.49 (m, 6H), 1.49-1.30 (m, 1H), 1.27-1.01 (m, 3H), 0.97 (d, J=6.8 Hz, 2H), 0.89 (d, J=6.7 Hz, 1H), 0.95-0.71 (m, 1H). MS 294 (MH+).

2-(methylamino)-1-(thiophen-3-yl)ethanone Hydrochloride. Example 3.4a

Prepared in a similar manner as described in Example 3.1b starting from tert-butyl methyl(2-oxo-2-(thiophen-3-yl)ethyl)carbamate (Example 3.4b) (1.64 g; 6.45 mmol) to obtain the desired compound as a white powder (1.08 g, 87%). $^1$H-NMR (DMSO-$d_6$) δ: 9.25 (s, 2H), 8.66 (dd, J=2.8, 1.3 Hz, 1H), 7.74 (dd, J=5.1, 2.8 Hz, 1H), 7.57 (dd, J=5.1, 1.3 Hz, 1H), 4.62 (s, 2H), 2.60 (s, 3H). MS 156 (MH+).

Tert-butyl methyl(2-oxo-2-(thiophen-3-yl)ethyl)carbamate. Example 3.4b

Prepared in a similar manner as described in Example 3.1c starting from tert-butyl (2-(methoxy(methyl)amino)-2-oxoethyl)(methyl)carbamate (Example 3.1d) (1.83 g, 7.88 mmol) and thiophen-3-ylmagnesium iodide (0.3 M solution in THF; 55 mL; 16.56 mmol) to obtain the desired compound as a white powder (1.64 g, 82%). $^1$H-NMR spectrum in DMSO-$d_6$ indicates a mixture of rotamers (~1:1). $^1$H NMR (DMSO-$d_6$) δ: 8.56 (ddd, J=2.9, 1.8, 1.2 Hz, 1H), 7.67 (dd, J=5.1, 2.8 Hz, 1H), 7.53 (td, J=4.9, 1.3 Hz, 1H), 4.60 (s, 1H), 4.59 (s, 1H), 2.86 (s, 1.5H), 2.83 (s, 1.5H), 1.41 (s, 4.5H), 1.27 (s, 4.5H). MS 156 (MH+).

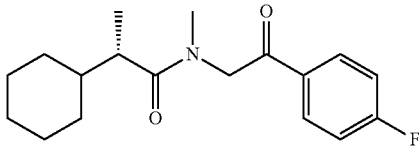 [SMILES: C[C@H](C(=O)N(C)CC(=O)c1ccc(F)cc1)C1CCCCC1]

(+)-(S)-2-cyclohexyl-N-(2-(4-fluorophenyl)-2-oxo-ethyl)-N-methylpropanamide. Example 3.5

Prepared in a similar manner as described in Example 3.1a starting from (S)-2-cyclohexyl-propanoic acid (78 mg; 0.5 mmol) and 1-(4-fluorophenyl)-2-(methylamino)ethanone hydrochloride (Example 3.5a) (132 mg; 0.65 mmol) to obtain the desired compound (60 mg, 40%) as a white powder. $^1$H-NMR spectrum in DMSO-$d_6$ indicates a mixture of rotamers (~1:2). $^1$H NMR (DMSO-$d_6$) δ: 8.12 (dd, J=8.9, 5.5 Hz, 0.6H), 8.06 (dd, J=8.9, 5.5 Hz, 1.4H), 7.41 (t, J=8.9 Hz, 0.6H), 7.37 (t, J=8.9 Hz, 1.4H), 5.14 (d, J=19.3 Hz, 0.3H), 5.02 (d, J=19.3 Hz, 0.3H), 4.86 (d, J=17.7 Hz, 0.7H), 4.76 (d, J=17.7 Hz, 0.7H), 3.07 (s, 2H), 2.81 (s, 1H), 2.70-2.58 (m, 0.7H), 2.32-2.20 (m, 0.3H), 1.80-1.49 (m, 6H), 1.50-1.30 (m, 1H), 1.25-1.00 (m, 3H), 0.97 (d, J=6.8 Hz, 2H), 0.89 (d, J=6.7 Hz, 1H), 0.95-0.71 (m, 1H). MS 306 (MH+). 1-(4-fluorophenyl)-2-(methylamino)ethanone hydrochloride. Example 3.5a Prepared in a similar manner as described in Example 3.1b starting from tert-butyl (2-(4-fluorophenyl)-2-oxoethyl)(methyl)carbamate (Example 3.5b) (1.42 g; 5.33 mmol) to obtain the desired compound as a white powder (1.03 g, 95%). $^1$H NMR (DMSO-$d_6$) δ: 9.15 (s, 2H), 8.09 (dd, J=8.9, 5.4 Hz, 2H), 7.46 (t, J=8.8 Hz, 2H), 4.76 (s, 2H), 2.62 (s, 3H). MS 168 (MH+).

Tert-butyl (2-(4-fluorophenyl)-2-oxoethyl)(methyl)carbamate. Example 3.5b

Prepared in a similar manner as described in Example 3.1c starting from tert-butyl (2-(methoxy(methyl)amino)-2-oxoethyl)(methyl)carbamate (Example 3.1d) (1.624 g, 7.0 mmol) and (4-fluorophenyl)magnesium bromide (1.0 M solution in THF; 14.7 mL; 14.7 mmol) to obtain the desired compound as a white powder (1.42 g, 76%). $^1$H-NMR spectrum in DMSO-$d_6$ indicates a mixture of rotamers (~1:1). $^1$H NMR (DMSO-$d_6$) δ: 8.06 (ddd, J=8.8, 5.5, 3.2 Hz, 2H), 7.38 (t, J=8.9 Hz, 2H), 4.71 (s, 0.8H), 4.70 (s, 1.2H), 2.86 (s, 1.3H), 2.83 (s, 1.7H), 1.41 (s, 4H), 1.26 (s, 5H). MS 168 (MH+).

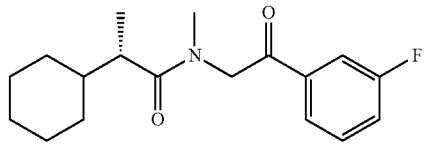 [SMILES: C[C@H](C(=O)N(C)CC(=O)c1cccc(F)c1)C1CCCCC1]

(S)-2-cyclohexyl-N-(2-(3-fluorophenyl)-2-oxoethyl)-N-methylpropanamide. Example 3.6

Prepared in a similar manner as described in Example 3.1a starting from (S)-2-cyclohexyl-propanoic acid (156 mg; 1 mmol) and 1-(3-fluorophenyl)-2-(methylamino)ethanone hydrochloride (Example 3.6a) (265 mg; 1.3 mmol) to obtain the desired compound as a white powder (123 mg, 40%). $^1$H-NMR spectrum in DMSO-$d_6$ indicates a mixture of rotamers (~1:2). $^1$H NMR (DMSO-$d_6$) δ: 7.87 (dt, J=7.7, 1.3 Hz, 0.3H), 7.86-7.80 (m, 1H), 7.75 (ddd, J=9.8, 2.6, 1.5 Hz, 0.7H), 7.67-7.48 (m, 2H), 5.16 (d, J=19.5 Hz, 0.3H), 5.05 (d, J=19.5 Hz, 0.3H), 4.87 (d, J=17.8 Hz, 0.7H), 4.77 (d, J=17.7 Hz, 0.7H), 3.08 (s, 2H), 2.81 (s, 1H), 2.70-2.58 (m, 0.7H), 2.33-2.21 (m, 0.3H), 1.82-1.49 (m, 6H), 1.49-1.30 (m, 1H), 1.28-1.01 (m, 3H), 0.96 (d, J=6.8 Hz, 2H), 0.89 (d, J=6.6 Hz, 1H), 0.95-0.72 (m, 1H). MS 306 (MH+). $[α]^{20}_D$=+470 (EtOH, 1 mg/mL).

1-(3-fluorophenyl)-2-(methylamino)ethanone hydrochloride. Example 3.6a

Prepared in a similar manner as described in Example 3.1b starting from tert-butyl (2-(3-fluorophenyl)-2-oxoethyl)(methyl)carbamate (Example 3.6b) (1.59 g; 5.94 mmol) to obtain the title compound as a white powder (0.97 g, 80%). $^1$H NMR (DMSO-$d_6$) δ: 9.34 (s, 2H), 7.85 (dt, J=7.5, 1.4 Hz, 1H), 7.83-7.78 (m, 1H), 7.71-7.59 (m, 2H), 4.77 (s, 2H), 2.62 (s, 3H). MS 168 (MH+).

Tert-butyl (2-(3,5-dimethoxyphenyl)-2-oxoethyl)(methyl)carbamate. Example 3.6b Prepared in a similar manner as described in Example 3.1c starting from tert-butyl (2-(methoxy(methyl)amino)-2-oxoethyl)(methyl)carbamate (Example 3.1d) (1.624 g, 7.0 mmol) and (3-fluorophenyl)magnesium bromide (1.0 M solution in THF; 14.7 mL; 14.7 mmol) to obtain the title compound as a colorless oil (1.59 g, 85%). $^1$H-NMR spectrum in DMSO-$d_6$ indicates a mixture of rotamers (~1:1). $^1$H NMR (DMSO-$d_6$) δ: 7.85-7.79 (m, 1H), 7.75 (ddd, J=9.7, 2.6, 1.5 Hz, 1H), 7.61 (td, J=8.0, 5.6 Hz, 1H), 7.53 (tdd, J=8.4, 2.6, 1.0 Hz, 1H), 4.73 (s, 1H), 4.72 (s, 1H), 2.86 (s, 1.4H), 2.83 (s, 1.6H), 1.41 (s, 4.3H), 1.27 (s, 4.7H). MS 168 (MH⁺).

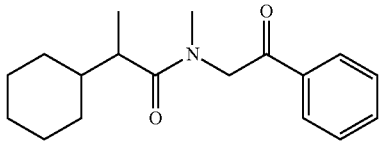 [SMILES: CC(C(=O)N(C)CC(=O)c1ccccc1)C1CCCCC1]

2-Cyclohexyl-N-methyl-N-(2-oxo-2-phenylethyl)propanamide. Example 3.7

To an oven-dried, $N_2$-flushed round-bottom flask were added anhydrous DMF (6 mL), 2-cyclohexylpropanoic acid (210 mg, 1.3 mmol), HATU (633 mg, 1.7 mmol), HOAt (349 mg, 2.6 mmol), 2-(methylamino)-1-phenylethanone hydrochloride (Example 3.2b) (269 mg, 1.4 mmol) and $Et_3N$ (0.8 mL, 5.8 mmol). The reaction medium was stirred at room temperature overnight and diluted with water (50 mL). The reaction medium was extracted with EtOAc (3×50 mL) and the combined organic phases were washed with brine, dried over $MgSO_4$, and concentrated. The crude product was purified by preparative HPLC ($CH_3CN/H_2O$ gradient) and lyophilized to obtain the desired racemic mixture (289 mg, 75% yield) as a colorless oil. ¹H-NMR spectrum in DMSO-$d_6$ indicates a ~2:1 mixture of rotamers and matches description of pure (S)-enantiomer (Example 3.2).

¹H NMR (400 MHz, DMSO-$d_6$) δ 8.03 (d, J=7.1 Hz, 0.7H), 7.97 (d, J=7.1 Hz, 1.3H), 7.73-7.64 (m, 1H), 7.60-7.51 (m, 2H), 5.15 (d, J=19.3 Hz, 0.3H), 5.03 (d, J=19.3 Hz, 0.3H), 4.88 (d, J=17.7 Hz, 0.7H), 4.78 (d, J=17.7 Hz, 0.7H), 3.08 (s, 2H), 2.82 (s, 1H), 2.71-2.58 (m, 0.8H), 2.30-2.20 (m, 0.3H), 1.82-1.49 (m, 5H), 1.49-1.30 (m, 1H), 1.29-1.00 (m, 3H), 0.97 (d, J=6.8 Hz, 2H), 0.95-0.75 (m, 2H), 0.89 (d, J=6.7 Hz, 1H). MS 288 (MH⁺).

2-Cyclohexylpropanoic Acid (2). Example 3.7a

In a 250 mL round bottom flask under $N_2$ at 0° C. was placed NaH (1408 mg, 35.2 mmol) and diisopropylamine (4965 µL, 35.2 mmol) in 60 mL anhydrous THF. 2-cyclohexylacetic acid (5 g, 32.5 mmol) in 10 mL anhydrous THF was added the reaction mixture drop-wise via syringe. The reaction mixture was stirred at 0° C. for 30 min, then heated at 42° C. for 15 min. The mixture was then cooled to −20° C. and 1.6 M butyllithium in hexane (24.2 mL, 38.72 mmol) was added dropwise. The reaction mixture was warmed to 0° C. and stirred for 15 min, then heated at 35° C. for 30 min and a yellowish solution was obtained. The solution was cooled again to 0° C. and MeI (2.2 mL, 35.2 mmol) was added drop wise over 20 minutes. The reaction mixture was stirred at 0° C. for 30 min, then heated at 35° C. for 1 h, and left stirring at room temperature overnight. The reaction mixture was diluted with $H_2O$ (100 mL) and extracted with ether (3×30 mL). The aqueous phase was acidified with 6N HCl to pH=1 and extracted with EtOAc (3×60 mL). The combined organic fractions were washed with brine (100 mL), dried over $MgSO_4$ and concentrated under vacuum. The obtained crude yellow solid (4.8 g, 87.5%) was 90% clean by ¹H-NMR analysis and was used in the next step without further purification.

¹H NMR (DMSO-$d_6$) δ: 11.97 (s, 1H), 2.10 (pseudo p, J=6.9 Hz, 1H), 1.74-1.53 (m, 6H), 1.50-1.41 (m, 1H), 1.27-1.02 (m, 2H), 0.99 (d, J=7.0 Hz, 3H), 0.95-0.85 (m, 2H).

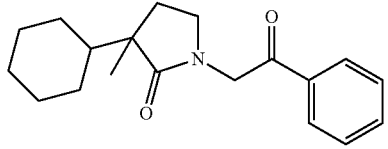 [SMILES: CC1(C2CCCCC2)CCN(CC(=O)c2ccccc2)C1=O]

3-cyclohexyl-3-methyl-1-(2-oxo-2-phenylethyl)pyrrolidin-2-one. Example 3.8

To a suspension of NaH (60% in mineral oil; 78 mg; 1.95 mmol) in 10 mL of anhydrous DMF was added a solution of 3-cyclohexyl-3-methylpyrrolidin-2-one (Example 3.8a) (235 mg; 1.3 mmol) in 5 mL of anhydrous DMF dropwise. The reaction mixture was stirred at room temperature for 30 min and a solution of bromoacetophenone (310 mg; 1.56 mmol) in 5 mL of DMF was added dropwise. The reaction medium was stirred at room temperature for 18 h and then was diluted with $H_2O$ (30 mL) and extracted with EtOAc (3×20 mL). The combined organic phases were washed with brine, dried over $MgSO_4$ and concentrated. The residue was purified by preparative HPLC (25 minutes 5-95% $CH_3CN/H_2O$), to give the desired compound (24 mg; 6%) as a white powder. ¹H NMR (400 MHz, DMSO-$d_6$) δ 0.81-1.05 (m, 2H), 1.07 (s, 3H), 1.09-1.25 (m, 2H), 1.42 (tt, J=12.0, 3.2 Hz, 1H), 1.48-1.65 (m, 2H), 1.63-1.81 (m, 5H), 1.98-2.10 (m, 1H), 3.20-3.29 (m, 1H), 4.07-4.18 (m, 1H), 4.71 (d, J=17.9 Hz, 1H), 4.77 (d, J=18.0 Hz, 1H), 7.55 (t, J=8.0 Hz, 2H), 7.68 (t, J=8.0 Hz, 1H), 7.99 (dd, J=8.4, 1.3 Hz, 2H). MS 300 (MH⁺).

3-cyclohexyl-3-methylpyrrolidin-2-one. Example 3.8a

A solution of ethyl 3-cyano-2-cyclohexyl-2-methylpropanoate (Example 3.8b) (2.5 g; 11.2 mmol) and $CoCl_2.6H_2O$ (1.33 g; 5.6 mmol) in 60 mL of THF/$H_2O$ (2:1) was stirred under $N_2$ and cooled to 0° C. To this reaction, $NaBH_4$ (2.13 g; 56 mmol) was added portion wise. The resulting mixture was stirred at room temperature for 72 h then quenched with aqueous 28% $NH_4OH$ (5 mL). The precipitated inorganic materials were filtered off trough Celite, which was washed with a THF/$H_2O$ mixture. The filtrate was concentrated under vacuum and the residue was extracted with DCM (3×50 mL). The combined organic phases were washed with brine, dried over $MgSO_4$ and concentrated. The crude material was purified by flash chromatography (DCM/MeOH gradient), to obtain the desired compound as a light green powder (465 mg, 23%). ¹H NMR (DMSO-$d_6$) δ: 0.77-0.92 (m, 1H), 0.97 (s, 3H), 0.99-1.27 (m, 3H), 1.34 (tt, J=11.8, 3.1 Hz, 1H), 1.44-1.51 (m, 1H), 1.51-1.83 (m, 6H), 1.93-2.04 (m, 1H), 3.02-3.16 (m, 2H), 7.45 (s, 1H). MS 182 (MH⁺).

Ethyl 3-cyano-2-cyclohexyl-2-methylpropanoate. Example 3.8b

A solution of diisopropylamine (3.4 mL; 24 mmol) in anhydrous THF was stirred under $N_2$ and cooled to −78° C. n-Butyllithium (2.5 M in hexane; 9.6 mL; 24 mmol) was added dropwise and the reaction was stirred 30 minutes, then a solution of ethyl 2-cyclohexylpropanoate (Example 3.8c) (4.05 g; 22 mmol) in 5 mL anhydrous THF was added drop wise. The reaction mixture was stirred at −78° C. for 1 h, then a solution of bromoacetonitrile (1.76 mL; 26.4 mmol) in 10 mL of anhydrous THF was added slowly over 30 min. Stirring was continued overnight while the reaction was allowed to warm to room temperature. The reaction was quenched with 1N HCl (100 mL) and extracted with ether (3×50 mL). The combined organic phases were washed with saturated NaHCO$_3$(100 mL), brine (50 mL), dried over MgSO$_4$ and concentrated. The residue was purified on silica gel using Hexane/EtOAc gradient to afford Ethyl 3-cyano-2-cyclohexyl-2-methylpropanoate as a colorless oil (2.51 g, 51%). $^1$H NMR (DMSO-d$_6$) δ: 0.89-1.17 (m, 5H), 1.18 (s, 3H), 1.20 (t, J=7.1 Hz, 3H), 1.49-1.65 (m, 4H), 1.67-1.77 (m, 2H), 2.68 (d, J=16.7 Hz, 1H), 2.77 (d, J=16.7 Hz, 1H), 4.04-4.21 (m, 2H). MS 224 (MH$^+$).

Ethyl 2-cyclohexylpropanoate. Example 3.8c

LiHMDS (1M in THF; 58 mL; 58 mmol) was added drop wise to a stirred solution of ethyl 2-cyclohexylacetate (9 mL; 50 mmol) in anhydrous THF (20 mL), at −78° C. The mixture was stirred at −78° C. for 1 h then MeI (3.75 mL; 60.0 mmol) was added. The mixture was allowed to gradually warm to room temperature, stirred an additional 18 h, then quenched with H$_2$O (100 mL) and extracted with EtOAc (3×50 mL). The combined organic phases were washed with brine, dried over MgSO$_4$ and concentrated. The residue was purified on silica gel using Hexane/EtOAc gradient to obtain ethyl 2-cyclohexylpropanoate as a colorless oil (8.75 g, 95%). $^1$H NMR (DMSO-d$_6$) δ: 0.83-1.00 (m, 2H), 1.01 (d, J=7.0 Hz, 3H), 1.05-1.25 (m, 2H), 1.17 (t, J=7.1 Hz, 3H), 1.40-1.51 (m, 1H), 1.51-1.74 (m, 6H), 2.19 (pseudo p, J=7.1 Hz, 1H), 3.97-4.11 (m, 2H). MS 185 (MH$^+$).

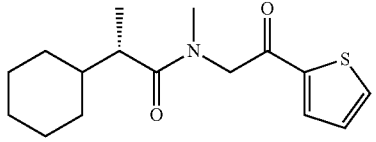 [SMILES: C[C@H](C(=O)N(C)CC(=O)c1cccs1)C1CCCCC1]

(S)-2-cyclohexyl-N-methyl-N-(2-oxo-2-(thiophen-2-yl)ethyl)propanamide. Example 10

Prepared in a similar manner as described in Example 3.1a starting from (S)-2-cyclohexyl-propanoic acid (78 mg; 0.5 mmol) and 2-(methylamino)-1-(thiophen-2-yl)ethanone hydrochloride (Example 3.6a) (124 mg; 0.65 mmol) to obtain the desired compound (146 mg, 93%) as a white powder. $^1$H-NMR spectrum in DMSO-d$_6$ indicates a mixture of rotamers (~1:2). $^1$H NMR (DMSO-d$_6$) δ: 8.13-8.06 (m, 0.6H), 8.06-8.01 (m, 1.4H), 7.31 (dd, J=4.9, 3.8 Hz, 0.3H), 7.27 (dd, J=4.9, 3.8 Hz, 0.7H), 5.07 (d, J=19.1 Hz, 0.3H), 4.95 (d, J=19.1 Hz, 0.3H), 4.81 (d, J=17.5 Hz, 0.7H), 4.72 (d, J=17.5 Hz, 0.7H), 3.08 (s, 2H), 2.82 (s, 1H), 2.70-2.58 (m, 0.7H), 2.34-2.24 (m, 0.3H), 1.82-1.48 (m, 6H), 1.48-1.30 (m, 1H), 1.26-1.01 (m, 3H), 0.97 (d, J=6.8 Hz, 2H), 0.90 (d, J=6.7 Hz, 1H), 0.95-0.73 (m, 1H). MS 294 (MH$^+$).

2-(methylamino)-1-(thiophen-2-yl)ethanone Hydrochloride. Example 3.10a

Prepared in a similar manner as described in Example 3.1b starting from tert-butyl methyl(2-oxo-2-(thiophen-2-yl) ethyl)carbamate (Example 3.6b) (1.64 g; 6.45 mmol) to obtain the desired compound as a white powder (1.04 g, 84%). $^1$H NMR (DMSO-d$_6$) δ: 9.28 (s, 2H), 8.19 (dd, J=4.9, 1.1 Hz, 1H), 8.07 (dd, J=3.9, 1.1 Hz, 1H), 7.34 (dd, J=4.9, 3.9 Hz, 1H), 4.68 (s, 2H), 2.61 (s, 3H). MS 156 (MH$^+$).

Tert-butyl methyl(2-oxo-2-(thiophen-2-yl)ethyl)carbamate. Example 3.10b

Prepared in a similar manner as described in Example 3.1c starting from tert-butyl (2-(methoxy(methyl)amino)-2-oxoethyl)(methyl)carbamate (Example 3.1d) (1.62 g, 7.0 mmol) and thiophen-2-ylmagnesium bromide (1.0 M solution in THF; 14.7 mL; 14.7 mmol) to obtain the desired compound as a light-brown oil (1.64 g, 92%). $^1$H-NMR spectrum in DMSO-d$_6$ indicates a mixture of rotamers (~1:1). $^1$H NMR (DMSO-d$_6$) δ: 8.05 (dd, J=4.9, 1.1 Hz, 1H), 8.01 (ddd, J=5.8, 3.8, 1.1 Hz, 1H), 7.27 (ddd, J=4.8, 3.9, 0.6 Hz, 1H), 4.65 (s, 1H), 4.63 (s, 1H), 2.87 (s, 1.5H), 2.84 (s, 1.5H), 1.41 (s, 4.5H), 1.26 (s, 4.5H). MS 156 (MH$^+$).

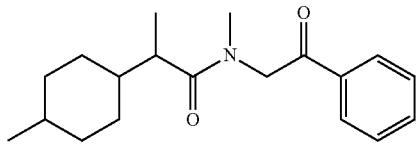 [SMILES: CC1CCC(C(C)C(=O)N(C)CC(=O)c2ccccc2)CC1]

N-Methyl-2-(4-methylcyclohexyl)-N-(2-oxo-2-phenylethyl)propanamide. Example 3.13

To an oven-dried, N$_2$-flushed round-bottom flask were added anhydrous DMF (12 mL) and 2-(4-methylcyclohexyl) propanoic acid (Example 3.13a) (237.1 mg, 1.39 mmol). The reaction was cooled to 0° C. and HATU (722 mg, 1.90 mmol), HOAt (397 mg, 2.92 mmol), 2-(methylamino)-1-phenylethanone hydrochloride (Example 3.2b) (347 mg, 1.87 mmol), and NEt$_3$ (900 μL, 6.49 mmol) were added. The reaction medium was stirred at room temperature overnight, then diluted with H$_2$O (20 mL) and extracted with EtOAc (3×25 mL). the combined organic phases were washed with brine (30 mL), dried over MgSO$_4$ and concentrated. The obtained mixture of 4 stereoisomers was purified and separated as follows: a preparative HPLC using a CH$_3$CN/H$_2$O gradient followed by lyophilization returned two fractions FI and FII, which were the two expected pairs of cis and trans diastereomers. The two pairs of enantiomers were further resolved on a chiral column into the single components cis-R, cis-S, trans-R and trans-S (for all of them: MS 302 (MH$^+$)).

FI: $^1$H NMR spectrum in d$^6$-DMSO indicates a ~1:2-1:3 mixture of rotamers.

$^1$H NMR (400 MHz, DMSO-d$_6$) δ 8.03 (d, J=8.0 Hz, 0.5H), 7.97 (d, J=7.1 Hz, 1.3H), 7.72-7.65 (m, 1H), 7.61-7.51 (m, 2H), 5.15 (d, J=19.2 Hz, 0.3H), 5.09 (d, J=19.3 Hz, 0.3H), 4.89 (d, J=17.7 Hz, 0.7H), 4.79 (d, J=17.7 Hz, 0.7H), 3.11 (s, 2H), 2.89-2.81 (m, 0.6H), 2.83 (s, 1H), 2.49-2.39 (m, 0.3H), 1.74-1.50 (m, 2H), 1.50-1.12 (m, 7H), 0.98 (d, J=6.8 Hz, 2H), 0.92 (d, J=6.9 Hz, 2H), 0.89 (d, J=6.7 Hz, 1H), 0.81 (d, J=7.0 Hz, 1H). MS 302 (MH$^+$).

FII: $^1$H NMR spectrum in d$^6$-DMSO indicates a ~1:2 mixture of rotamers.

$^1$H NMR (400 MHz, DMSO-d$_6$) δ 8.03 (d, J=7.1 Hz, 0.5H), 7.97 (d, J=7.1 Hz, 1.3H), 7.72-7.64 (m, 1H), 7.60-

7.51 (m, 2H), 5.15 (d, J=19.3 Hz, 0.3H), 5.02 (d, J=19.4 Hz, 0.3H), 4.87 (d, J=17.6 Hz, 0.7H), 4.79 (d, J=17.6 Hz, 0.7H), 3.07 (s, 2H), 2.82 (s, 1H), 2.68-2.57 (m, 0.8H), 2.29-2.19 (m, 0.3H), 1.83-1.49 (m, 4H), 1.48-1.12 (m, 3H), 1.05-0.99 (m, 0.7H), 0.97 (d, J=6.8 Hz, 2H), 0.95-0.91 (m, 0.7H), 0.89 (d, J=6.7 Hz, 1H), 0.88-0.86 (m, 0.4H), 0.85 (d, J=6.5 Hz, 2H), 0.82 (d, J=6.5 Hz, 1H), 0.80 (d, J=2.7 Hz, 0.3H). MS 302 (MH$^+$).

2-(4-Methylcyclohexyl)propanoic Acid. Example 3.13a

Prepared in a similar fashion as described in Example 3.2a from 2-(p-tolyl)propanoic acid (1.02 g, 6.23 mmol), glacial acetic acid (60 mL), and 5% wt Rh/Al$_2$O$_3$(500 mg), under H$_2$ pressure for 24 h, to obtain the desired product as an off-white powder (992 mg, 94%). $^1$H-NMR spectrum in DMSO-d$_6$ indicates an approximate 1.4:1.0 trans/cis diastereomeric mixture. $^1$H NMR (400 MHz, DMSO-d$_6$) δ 12.00 (s, 1H), 2.28 (dq, J=8.6, 7.0 Hz, 0.7H), 2.10 (pseudo p, J=7.0 Hz, 0.5H), 1.70-1.61 (m, 1.8H), 1.61-1.55 (m, 0.5H), 1.51 (dq, J=7.4, 4.1 Hz, 0.7H), 1.48-1.41 (m, 1H), 1.41-1.37 (m, 1.8H), 1.37-1.33 (m, 1.1H), 1.33-1.20 (m, 1.8H), 1.07-1.02 (m, 0.4H), 1.01 (d, J=7.2 Hz, 1.45H), 0.99 (d, J=6.8 Hz, 1.45H), 0.98-0.95 (m, 0.3H), 0.94-0.90 (m, 0.5H), 0.88 (d, J=6.9 Hz, 1.9H), 0.84 (d, J=6.5 Hz, 1.4H).

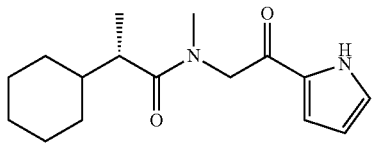

(S)-2-cyclohexyl-N-methyl-N-(2-oxo-2-(1H-pyrrol-2-yl)ethyl)propanamide. Example 3.16

A 1.0 M solution of TBAF in THF (0.300 mL, 0.300 mmol) was added to a stirred solution of (S)-2-cyclohexyl-N-methyl-N-(2-oxo-2-(1-tosyl-1H-pyrrol-2-yl)ethyl)propanamide (Example 3.16) (127 mg, 0.300 mmol) in THF (3.0 mL) and stirring was continued overnight. Water (0.100 mL) was added and stirring continued for 5 minutes. All the volatiles were evaporated and the obtained crude was purified by column chromatography (Hex/EtOAc gradient). In this way, 47 mg (57%) of (S)-2-cyclohexyl-N-methyl-N-(2-oxo-2-(1H-pyrrol-2-yl)ethyl)propanamide were obtained. $^1$H-NMR spectrum in DMSO-d$_6$ indicates a mixture of rotamers (~1:2). $^1$H NMR (DMSO-d$_6$) δ 11.99 (br s, 0.3H), 11.87 (br s, 0.7H), 7.14-7.12 (m, 0.7H), 7.10-7.08 (m, 0.7H), 7.03-7.02 (m, 0.7H), 6.24-6.22 (m, 0.3H), 6.21-6.19 (m, 0.7H), 4.76 (d, J=18.8 Hz, 0.3H), 4.70 (d, J=18.8 Hz, 0.3H), 4.67 (d, J=17.2 Hz, 0.7H), 4.49 (d, J=17.2 Hz, 0.7H), 3.06 (s, 2H), 2.82 (s, 1H), 2.70-2.58 (m, 0.7H), 2.30-2.21 (m, 0.3H), 1.83-1.49 (m, 5H), 1.48-1.28 (m, 1H), 1.26-1.03 (m, 3H), 1.02-0.77 (m, 5H), (S)-2-cyclohexyl-N-methyl-N-(2-oxo-2-(1-tosyl-1H-pyrrol-2-yl)ethyl)propanamide. Example 3.16a Prepared in a similar manner as described in Example 3.1a starting from (S)-2-cyclohexyl-propanoic acid (156 mg; 1.0 mmol) and 2-(methylamino)-1-(1-tosyl-1H-pyrrol-2-yl)ethanone hydrochloride (Example 3.16b) (427 mg; 1.3 mmol) to obtain the desired compound (250 mg, 58%) as a white powder. $^1$H-NMR spectrum in DMSO-d$_6$ indicates a mixture of rotamers (~1:2). $^1$H NMR (DMSO-d$_6$) δ: 7.96 (dd, J=3.2, 1.6 Hz, 0.3H), 7.91 (dd, J=3.2, 1.7 Hz, 0.7H), 7.87 (t, J=8.4 Hz, 2H), 7.55 (dd, J=3.9, 1.7 Hz, 0.3H), 7.47 (dd, J=3.8, 1.7 Hz, 0.7H), 7.42 (td, J=8.7, 0.6 Hz, 2H), 6.56 (dd, J=3.8, 3.2 Hz, 0.3H), 6.50 (dd, J=3.8, 3.2 Hz, 0.7H), 4.79 (d, J=19.1 Hz, 0.3H), 4.73 (d, J=19.1 Hz, 0.3H), 4.64 (d, J=17.3 Hz, 0.7H), 4.44 (d, J=17.2 Hz, 0.7H), 2.96 (s, 2H), 2.72 (s, 1H), 2.64-2.54 (m, 0.7H), 2.38 (s, 2H), 2.37 (s, 1H), 2.10-1.98 (m, 0.3H), 1.76-1.48 (m, 6H), 1.46-0.93 (m, 4H), 0.91 (d, J=6.8 Hz, 2H), 0.76 (d, J=6.7 Hz, 1H), 0.96-0.62 (m, 1H). MS 431 (MH$^+$).

2-(methylamino)-1-(1-tosyl-1H-pyrrol-2-yl)ethanone hydrochloride Example 3.16b

Prepared in a similar manner as described in Example 3.2b starting from tert-butyl methyl(2-oxo-2-(1-tosyl-1H-pyrrol-2-yl)ethyl)carbamate (Example 3.16c) (1.24 g; 3.15 mmol) to obtain the desired compound (0.58 g, 56%) as a white powder. $^1$H NMR (DMSO-d$_6$) δ: 8.91 (s, 2H), 8.07 (dd, J=3.2, 1.7 Hz, 1H), 7.92 (d, J=8.4 Hz, 2H), 7.56 (dd, J=3.9, 1.7 Hz, 1H), 7.48 (dd, J=8.6, 0.8 Hz, 2H), 6.62 (dd, J=3.9, 3.2 Hz, 1H), 4.49 (s, 2H), 2.51 (s, 3H), 2.41 (s, 3H). MS 293 (MH$^+$).

Tert-butyl methyl(2-oxo-2-(1-tosyl-1H-pyrrol-2-yl)ethyl)carbamate. Example 3.16c To a solution of 2-bromo-1-tosyl-1H-pyrrole (4.0 g, 13.3 mmol) in 10 mL of anhydrous THF under N$_2$ atmosphere at 0° C. was added i-propylmagnesium chloride, lithium chloride complex (1.3 M solution in THF; 11.3 mL; 14.7 mmol) over 10 minutes. The reaction medium was stirred at 0° C. for 1 h, then added to the solution of tert-butyl (2-(methoxy(methyl)amino)-2-oxoethyl)(methyl)carbamate (Example 3.2d) (1.5 g, 6.3 mmol) in 20 mL of anhydrous THF over 10 minutes maintaining the temperature between 25-45° C. The reaction was stirred at room temperature overnight and the obtained heterogeneous solution was quenched with saturated NH$_4$Cl (50 mL) and acidified with 1 N HCl to pH=5-6. The reaction medium was extracted with EtOAc (3×50 mL). The combined organic phases were washed with brine, dried over MgSO$_4$ and concentrated. The residue was purified on silica gel using a hexane/EtOAc gradient, to obtain the desired title compound as an orange-yellow oil (1.24 g, 23%). $^1$H-NMR spectrum in DMSO-d$_6$ indicates a mixture of rotamers (~2:1). $^1$H NMR (DMSO-d$_6$) δ: 7.93 (m, 1H), 7.84 (m, 2H), 7.48-7.39 (m, 2.4 H), 7.34 (dd, J=3.3, 1.8 Hz, 0.6H), 6.24-6.19 (m, 1H), 4.43 (s, 0.6H), 4.39 (s, 1.4H), 2.74 (s, 1H), 2.73 (s, 2H), 2.37 (s, 3H), 1.37 (s, 3H), 1.12 (s, 6H). MS 293 (MH$^+$).

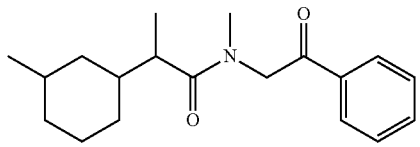 [SMILES: CC1CCCC(C(C)C(=O)N(C)CC(=O)c2ccccc2)C1]

N-Methyl-2-(3-methylcyclohexyl)-N-(2-oxo-2-phenylethyl)propanamide. Example 3.18

To an oven-dried, N$_2$-flushed round-bottom flask were added anhydrous DMF (6.0 mL) and 2-(3-methylcyclohexyl)propanoic acid (Example 3.18a) (134 mg, 0.79 mmol). The solution was cooled to 0° C. and HATU (389 mg, 1.02 mmol), HOAt (214 mg, 1.57 mmol), 2-(methylamino)-1-phenylethanone hydrochloride (Example 3.2b) (161 mg, 0.87 mmol), and NEt₃ (491 μL, 3.54 mmol) were added. The reaction medium was stirred at room temperature overnight, then diluted with H₂O (10 mL) and extracted with EtOAc (3×10 mL). The combined organic phases were washed with brine (15 mL), dried over MgSO₄ and concentrated. The obtained residue was purified by preparative HPLC using a CH₃CN/H₂O gradient and lyophilized to give the desired mixture of 8 stereoisomers (112 mg, 47%). Further separation on a chiral column only allowed to isolate 3 fractions F1, F2, F3 (302 (MH⁺)).

¹H-NMR spectrum in DMSO-d₆ indicates a mixture of 4 diastereomeric pairs, 3 of which may appear as a mixture of rotamers (~1:1) based on the NMe signals.

¹H NMR (400 MHz, DMSO-d₆) δ 8.03 (d, J=8.3 Hz, 0.6H), 7.97 (d, J=8.4 Hz, 1.3H), 7.73-7.64 (m, 1H), 7.60-7.51 (m, 2H), 5.21-4.74 (m, 2H), 3.17 (s, 0.1H), 3.16 (s, 0.1H), 3.10 (s, 0.2H), 3.09 (s, 0.2H), 3.07 (s, 1.6H), 2.83 (s, 0.4H), 2.82 (s, 0.4H), 2.68-2.58 (m, 0.6H), 2.34-2.21 (m, 0.3H), 1.82-1.57 (m, 4H), 1.57-1.36 (m, 2H), 1.36-1.07 (m, 2H), 0.99-0.94 (m, 2H), 0.92-0.80 (m, 4H), 0.79-0.72 (m, 1H), 0.71-0.41 (m, 1H). MS 302 (MH⁺).

2-(3-Methylcyclohexyl)propanoic Acid. Example 3.18a

Prepared in a similar fashion as described in Example 3.2a from 2-(m-tolyl)propanoic acid (0.5 g, 3.05 mmol), glacial acetic acid (40 mL) and 5% wt Rh/Al₂O₃ (483 mg), under H₂ pressure for 24 h, to obtain the desired product as an off-white powder (442 mg, 85%). ¹H-NMR spectrum in DMSO-d₆ indicates a mixture of diastereoisomers, 1H NMR (400 MHz, DMSO-d₆) δ 11.99 (s, 1H), 2.30-2.19 (m, 0.3H), 2.10 (td, J=7.0, 5.5 Hz, 0.9H), 1.73-1.64 (m, 1.4H), 1.64-1.56 (m, 2H), 1.56-1.52 (m, 0.5H), 1.52-1.42 (m, 1.4H), 1.42-1.27 (m, 1.3H), 1.26-1.15 (m, 1.4H), 1.01-0.98 (m, 2.9H), 0.94-0.90 (m, 0.3H), 0.90-0.83 (m, 3.3H), 0.77 (td, J=12.1, 3.5 Hz, 0.9H), 0.72-0.53 (m, 0.8H).

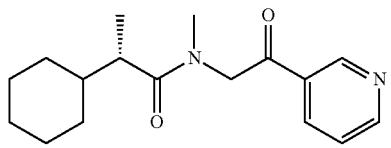 [SMILES: C[C@H](C(=O)N(C)CC(=O)c1cccnc1)C1CCCCC1]

(S)-2-cyclohexyl-N-methyl-N-(2-oxo-2-(pyridin-3-yl)ethyl)propanamide. Example 3.21

Prepared in a similar manner as described in Example 3.1a starting from (S)-2-cyclohexyl-propanoic acid (0.25 mmol, 39 mg) to obtain 15 mg of the desired compound as a clear oil (yield 21%). ¹H NMR (400 MHz, CDCl₃) δ 9.167 (d, J=2 Hz, 1H), 8.789 (dd, J=2 Hz & 4.8 Hz, 1H), 8.233 (dt, J=8 Hz & 4.8 Hz, 1H), 7.412 (dd, J=8 Hz & 4.8 Hz, 1H), 4.834 (d, J=17.2, 1H), 4.743 (d, J=17.2, 1H), 3.169 (s, 3H), 2.565 (m, 1H), 1.566-1.870 (m, 7H), 1.108 (s, 3H), 0.868-1.301 (m, 4H). MS 289 (MH⁺).

2-(methylamino)-1-(pyridin-3-yl)ethanone Hydrochloride. Example 3.21a

Prepared in a similar manner as described in Example 3.9b starting from tert-butyl methyl(2-oxo-2-(pyridin-3-yl)ethyl)carbamate (0.40 mmol, 100 mg), 4.0 N HCl in dioxane (2.70 mmol, 0.675 mL) and EtOAc (6.0 mL) to obtain 55 mg of the desired compound as yellow solids (yield 72%). MS 151 (MH⁺).

Tert-butyl methyl(2-oxo-2-(pyridin-3-yl)ethyl)carbamate. Example 3.21b

Prepared in a similar manner as described in Example 3.9c starting from 3-bromopyridine (2.0 mmol, 316 mg) and tert-butyl (2-(methoxy(methyl)amino)-2-oxoethyl)(methyl)carbamate (2.0 mmol, 464 mg) to obtain 200 mg of the desired compound as a clear oil (yield 40%). MS 251 (MH⁺).

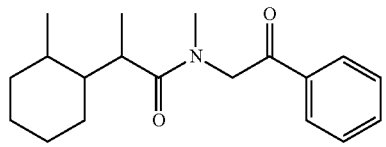 [SMILES: CC1CCCCC1C(C)C(=O)N(C)CC(=O)c1ccccc1]

N-Methyl-2-(2-methylcyclohexyl)-N-(2-oxo-2-phenylethyl)propanamide. Example 3.23

To an oven-dried, N₂-flushed round-bottom flask were added anhydrous DMF (6.0 mL) and 2-(2-methylcyclohexyl)propanoic acid (Example 3.23a) (113 mg, 0.66 mmol). The solution was cooled to 0° C. and HATU (328 mg, 0.86 mmol), HOAt (181 mg, 1.33 mmol), 2-(methylamino)-1-phenylethanone hydrochloride (Example 3.2b) (186 mg, 1.00 mmol), and Et₃N (620 μL, 4.47 mmol) were added. The reaction mixture was stirred at room temperature overnight then diluted with H₂O (10 mL) and extracted with EtOAc (3×15 mL). the combined organic phases were washed with brine (10 mL), dried over MgSO₄ and concentrated. The obtained residue was purified by preparative HPLC using a CH₃CN/H₂O gradient and lyophilized to afford the desired mixture of diastereoisomers (65 mg, 32%). Further separation on a chiral column only allowed to isolate 3 fractions F1, F2, F3 (MS 302 (MH⁺)). ¹H-NMR spectrum in DMSO-d₆ indicates a mixture of 3 major diastereomeric pairs. ¹H NMR (400 MHz, DMSO-d₆) δ 8.03 (d, J=7.1 Hz, 0.4H), 7.97 (d, J=7.1 Hz, 1.6H), 7.72-7.64 (m, 1H), 7.60-7.51 (m, 2H), 5.11 (d, J=20.0 Hz, 0.2H), 5.05 (d, J=20.0 Hz, 0.2H), 4.89 (d, J=20.0 Hz, 0.7H), 4.86 (d, J=16.0 Hz, 0.1H), 4.80 (d, J=16.0 Hz, 0.1H), 4.80 (d, J=20.0 Hz, 0.7H), 3.10 (s, 0.3H), 3.08 (s, 2.0H), 2.83 (s, 0.7H), 2.70-2.59 (m, 1H), 2.25-2.16 (m, 0.3H), 2.03-1.93 (m, 0.8H), 1.93-1.85 (m, 0.3H), 1.64-1.51 (m, 3H), 1.50-1.29 (m, 4H), 1.27-1.02 (m, 2H), 1.00 (d, J=6.8 Hz, 0.3H), 0.96 (d, J=6.7 Hz, 2H), 0.87 (d, J=4.0 Hz, 2H), 0.87 (d, J=4.0 Hz, 0.6H), 0.83 (d, J=7.2 Hz, 0.3H), 0.68 (d, J=7.1 Hz, 0.6H). MS 302 (MH⁺).

2-(2-Methylcyclohexyl)propanoic Acid. Example 3.23a

Prepared in a similar fashion as described in Example 3.2a from 2-(o-tolyl)propanoic acid (543 mg, 3.31 mmol), glacial acetic acid (40 mL) and 5% wt Rh/Al₂O₃ (474 mg), to obtain the desired product under H₂ pressure for 24 h, as an off-white powder (481 mg, 85%). ¹H-NMR spectrum in DMSO-d₆ indicates a mixture of diastereoisomers, showing one major set of signals and two less prevalent ones. ¹H NMR (400 MHz, DMSO-d₆) δ 12.01 (s, 1H), 2.11-2.05 (m, 0.2H), 2.05-1.99 (m, 0.8H), 1.98-1.91 (m, 0.9H), 1.69-1.58 (m, 1.1H), 1.58-1.49 (m, 1.3H), 1.49-1.39 (m, 1.9H), 1.39-1.32 (m, 1.8H), 1.32-1.25 (m, 1.2H), 1.21-1.09 (m, 2H), 1.03 (d, J=6.9 Hz, 0.4H), 1.00 (d, J=6.9 Hz, 2.5H), 0.89-0.81 (m, 0.6H), 0.78 (d, J=7.1 Hz, 2.5H).

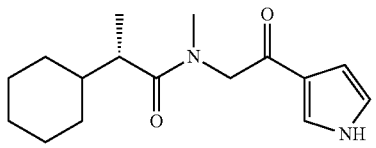 [SMILES: C[C@H](C(=O)N(C)CC(=O)c1cc[nH]c1)C1CCCCC1]

(S)-2-cyclohexyl-N-methyl-N-(2-oxo-2-(1H-pyrrol-3-yl)ethyl)propanamide. Example 3.24

Prepared in a similar manner as described in Example 3.16 from (S)-2-cyclohexyl-N-methyl-N-(2-oxo-2-(1-tosyl-1H-pyrrol-3-yl)ethyl)propanamide (Example 3.24a) (94 mg, 0.2256 mmol) to give 28 mg (45% yield) of the desired product (S)-2-cyclohexyl-N-methyl-N-(2-oxo-2-(1H-pyrrol-3-yl)ethyl)propanamide. ¹H-NMR spectrum in DMSO-d₆ indicates a mixture of rotamers (~1:1.5). ¹H NMR (DMSO-d₆) δ 11.57 (br s, 0.4H), 11.43 (br s, 0.6H), 7.72 (br s, 0.4H), 7.63 (br s, 0.6H), 6.88 (br s, 0.4H), 6.85 (br s, 0.6H), 6.51 (br s, 0.4H), 6.46 (br s, 0.6H), 4.78 (d, J=19.0 Hz, 0.4H), 4.64 (d, J=19.0 Hz, 0.4H), 4.60 (d, J=17.0 Hz, 0.6H), 4.50 (d, J=17.0 Hz, 0.6H), 3.03 (br s, 1.8H), 2.80 (br s, 1.2H), 2.68-2.58 (m, 0.6H), 2.27-2.17 (m, 0.4H), 1.88-0.72 (m, 14H)

(S)-2-cyclohexyl-N-methyl-N-(2-oxo-2-(1-tosyl-1H-pyrrol-3-yl)ethyl)propanamide. Example 3.24a Prepared in a similar manner as described in Example 3.2a starting from (S)-2-cyclohexyl-propanoic acid (156 mg; 1.0 mmol) and 2-(methylamino)-1-(1-tosyl-1H-pyrrol-3-yl)ethanone hydrochloride (Example 3.24b) (427 mg; 1.3 mmol) to obtain the desired compound (181 mg, 42%) as an white powder. ¹H-NMR spectrum in DMSO-d₆ indicates a mixture of rotamers (~1:2). ¹H NMR (DMSO-d₆) δ: 8.35 (dd, J=2.1, 1.6 Hz, 0.3H), 8.25 (dd, J=2.1, 1.6 Hz, 0.7H), 7.97 (d, J=8.4 Hz, 2H), 7.53-7.47 (m, 2.3H), 7.46 (dd, J=3.3, 2.1 Hz, 0.7H), 6.72 (dd, J=3.3, 1.6 Hz, 0.3H), 6.67 (dd, J=3.3, 1.6 Hz, 0.7H), 4.89 (d, J=19.2 Hz, 0.3H), 4.79 (d, J=19.3 Hz, 0.3H), 4.64 (d, J=17.6 Hz, 0.7H), 4.53 (d, J=17.6 Hz, 0.7H), 3.02 (s, 2H), 2.77 (s, 1H), 2.65-2.56 (m, 0.7H), 2.40 (s, 3H), 2.29-2.17 (m, 0.3H), 1.92-1.45 (m, 6H), 1.45-1.23 (m, 1H), 1.23-1.01 (m, 3H), 0.94 (d, J=6.8 Hz, 2H), 0.86 (d, J=6.7 Hz, 1H), 0.95-0.70 (m, 1H). MS 431 (MH⁺).

2-(methylamino)-1-(1-tosyl-1H-pyrrol-3-yl)ethanone Hydrochloride. Example 3.24b

Prepared in a similar manner as described in Example 3.2b starting from tert-butyl methyl(2-oxo-2-(1-tosyl-1H-pyrrol-3-yl)ethyl)carbamate (Example 3.24c) (1.1 g; 2.8 mmol) to obtain the desired compound (0.58 g, 56%) as a white powder. ¹H NMR (DMSO-d₆) δ: 9.16 (s, 2H), 8.39 (d, J=1.7 Hz, 1H), 8.38 (d, J=1.7 Hz, 1H), 7.99 (d, J=8.4 Hz, 2H), 7.54 (dd, J=3.4, 2.1 Hz, 1H), 7.51 (d, J=8.0 Hz, 2H), 6.74 (dd, J=3.4, 1.6 Hz, 1H), 4.49 (s, 2H), 2.56 (s, 3H), 2.40 (s, 3H). MS 293 (MH⁺).

Tert-butyl methyl(2-oxo-2-(1-tosyl-1H-pyrrol-3-yl)ethyl)carbamate. Example 3.24c Prepared in a similar manner as described in Example 3.16c starting from tert-butyl (2-(methoxy(methyl)amino)-2-oxoethyl)(methyl)carbamate (Example 3.2d) (1.62 g, 7.0 mmol) and 3-bromo-1-tosyl-1H-pyrrole (Example 3.24d) (4.5 g; 15 mmol) to obtain the desired compound as a yellow-orange oil (1.1 g, 18%). ¹H-NMR spectrum in DMSO-d₆ indicates a mixture of rotamers (~1:1). ¹H NMR (DMSO-d₆) δ: 8.24 (dt, J=5.3, 1.9 Hz, 1H), 7.95 (dd, J=8.4, 2.7 Hz, 2H), 7.50-7.42 (m, 3H), 6.67 (ddd, J=6.6, 3.3, 1.6 Hz, 1H), 4.45 (s, 1H), 4.44 (s, 1H), 2.79 (s, 1.3H), 2.77 (s, 1.7H), 2.37 (s, 3H), 1.37 (s, 4H), 1.20 (s, 5H). MS 293 (MH⁺).

3-bromo-1-tosyl-1H-pyrrole. Example 3.24d

To a stirring solution of 1-tosyl-1-H-pyrrole (Example 3.24e) (29 g; 131 mmol) in 500 mL of glacial AcOH was added a solution of Br₂ (7.0 mL; 138 mmol) in 60 mL of glacial AcOH dropwise over 30 minutes. Reaction mixture was heated at 130° C. for 4 h and then concentrated under vacuum. The residue was purified on silica gel using a hexane/DCM gradient, to obtain 3-bromo-1-tosyl-1H-pyrrole as a yellow solid (13.2 g, 34%). ¹H NMR (DMSO-d₆) δ: 7.90 (d, J=8.4 Hz, 2H), 7.59 (dd, J=2.4, 1.6 Hz, 1H), 7.45 (d, J=8.7 Hz, 2H), 7.38 (dd, J=3.4, 2.4 Hz, 1H), 6.45 (dd, J=3.3, 1.6 Hz, 1H), 2.37 (s, 3H). MS 301 (MH⁺).

1-tosyl-1H-pyrrole. Example 3.24e

To a suspension of NaOH (18 g; 0.60 mol) in 100 mL of DCE was added freshly distilled 1-H-pyrrole (10 mL; 0.15 mol). The reaction mixture was stirred at room temperature for 30 min, then a solution of p-toluene-sulfonyl chloride (1.22 eq; 35 g; 0.18 mol) in 40 mL of DCE was added dropwise via addition funnel at 0° C. The reaction mixture was then warmed to room temperature and stirred for 18 h. The reaction was diluted with H₂O (100 mL) and extracted with DCM (3×50 mL). The combined organic phases were dried over MgSO₄ and solvent was evaporated, to obtain the product as a white powder (29.0 g, 88%), which was 90% pure by ¹H-NMR analysis and used in the next step without further purification. ¹H NMR (DMSO-d₆) δ: 7.84 (d, J=8.4 Hz, 2H), 7.43 (d, J=8.7 Hz, 2H), 7.32 (t, J=2.0 Hz, 2H), 6.34 (t, J=2.0 Hz, 2H), 2.37 (s, 3H). MS: the compound did not ionize.

All of the Examples listed in Table Y, including Examples 3.25 to 3.61, were prepared through procedures outlined in Scheme 3.1 or procedures which are similar to the ones described in the Examples above, such as Examples 3.1 to 3.24.

The patents and publications listed herein describe the general skill in the art and are hereby incorporated by reference in their entireties for all purposes and to the same extent as if each was specifically and individually indicated to be incorporated by reference. In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings.

What is claimed is:

1. A compound having structural Formula (Ib):

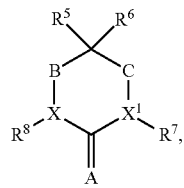

or a salt or solvate thereof; wherein
$R^5$ or $R^6$ is selected from $C_1$-$C_3$ alkyl, and the remaining $R^5$ or $R^6$ is selected from the group consisting of optionally substituted $C_3$-$C_8$ cycloalkyl and optionally substituted $C_3$-$C_8$ cycloalkenyl;
X and $X^1$ are N;
$R^7$ is $C_1$-$C_3$ alkyl;
$R^8$ is represented by (a) or (b):

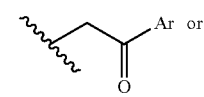

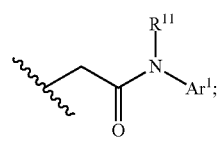

A is O;
B is $CH_2$, or C=O;
C is $CH_2$, or C=O;
Ar and $Ar^1$ are independently optionally substituted phenyl, or optionally substituted heteroaryl; and
$R^{11}$ is selected from the group consisting of hydrogen or optionally substituted $C_1$-$C_4$ alkyl.

2. A compound of claim 1, selected from the group consisting of:

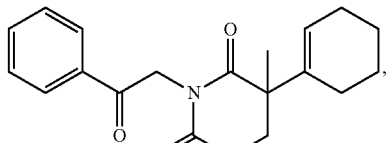

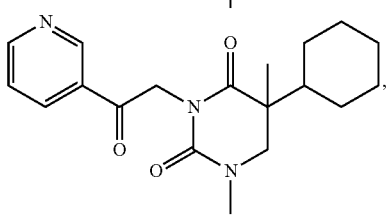

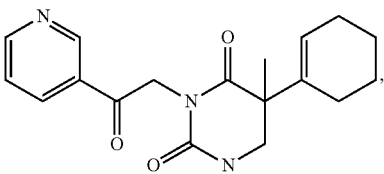

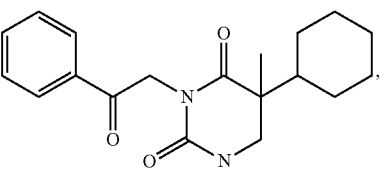

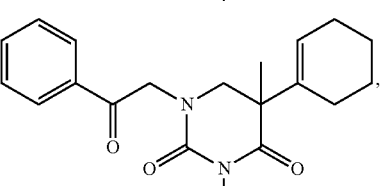

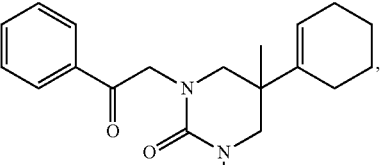

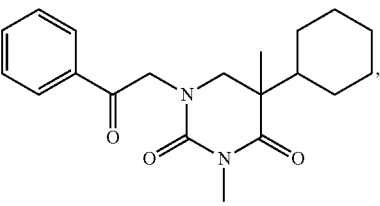

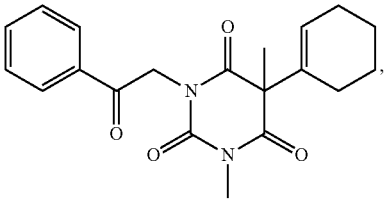

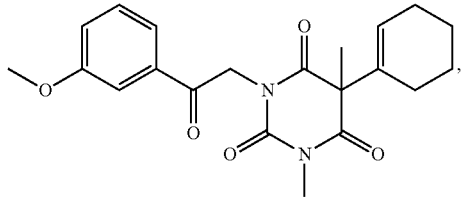

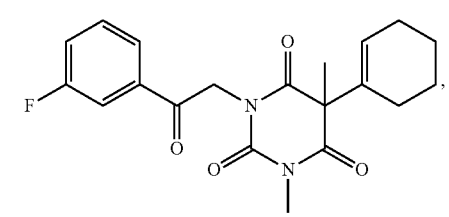

233
-continued
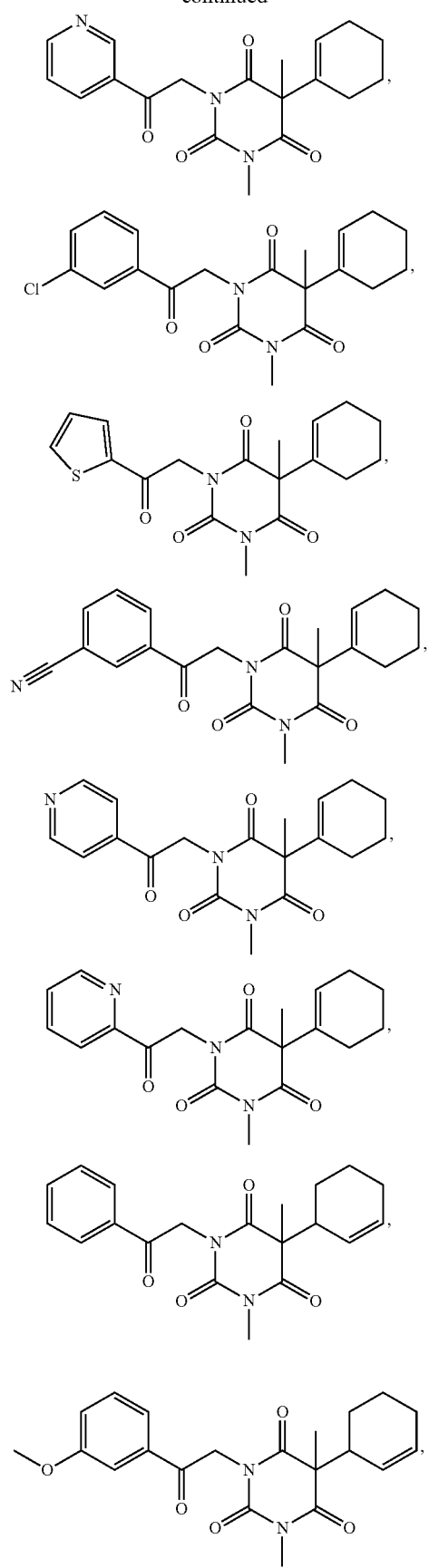
234
-continued
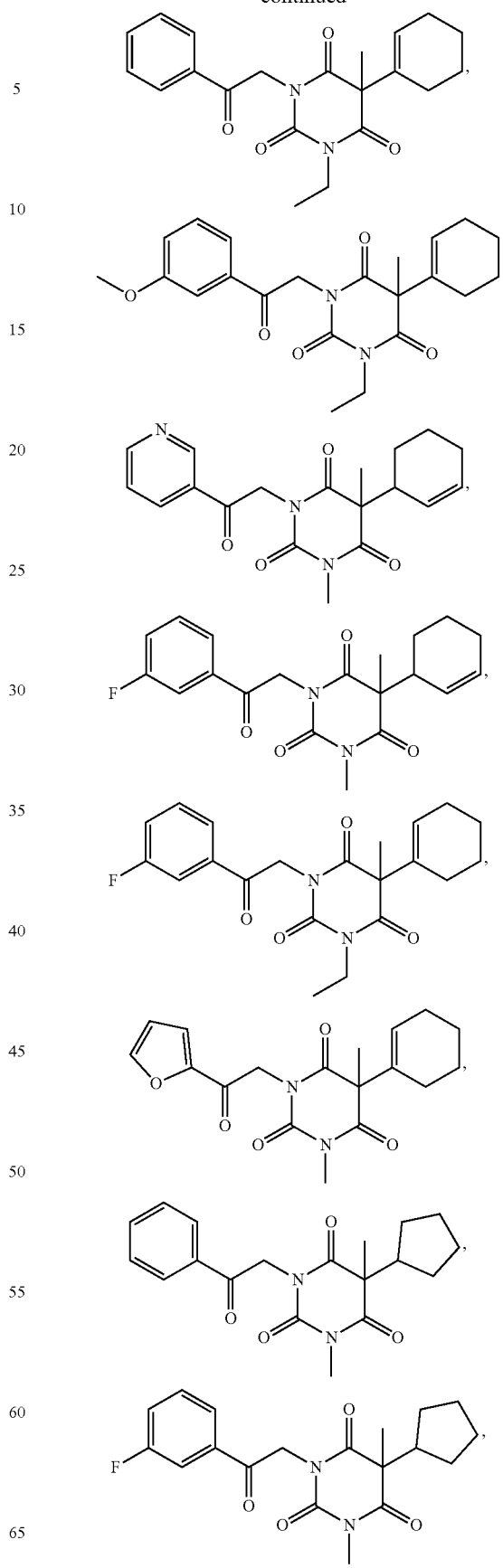

235
-continued
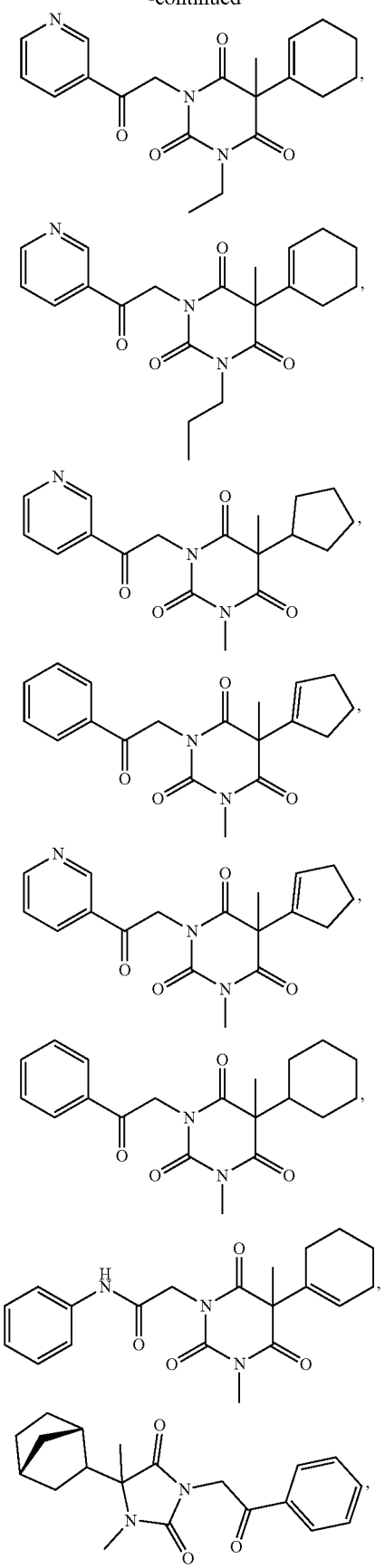
236
-continued
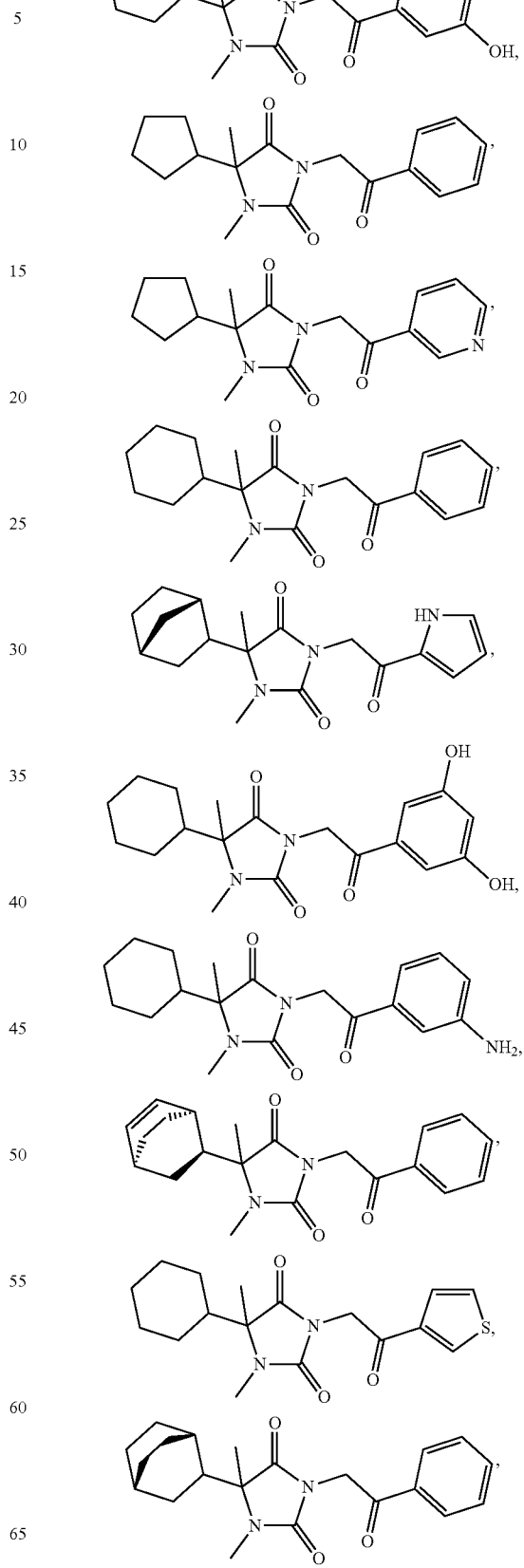

-continued
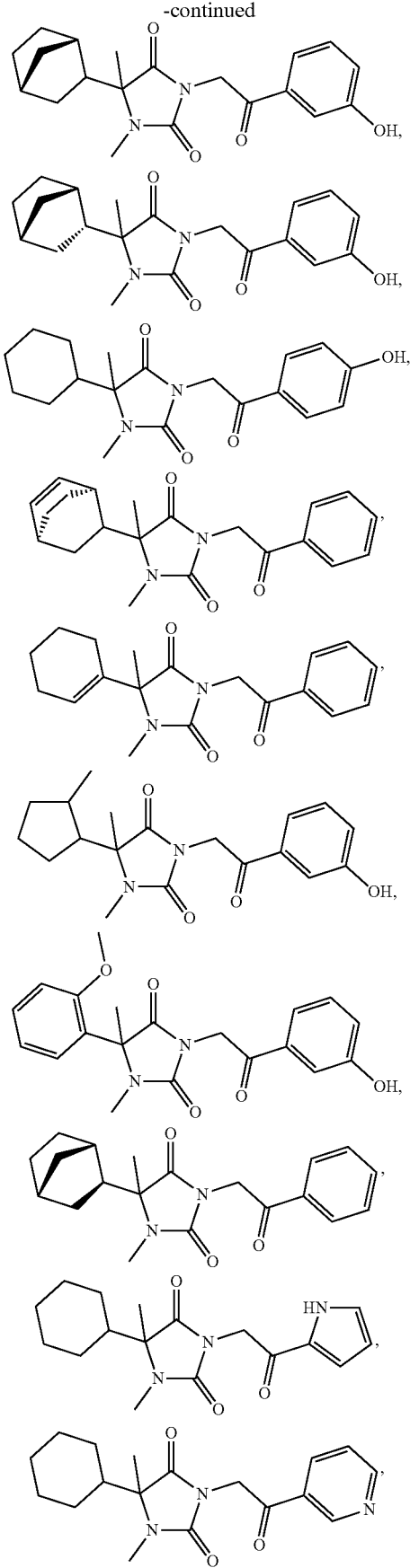
-continued
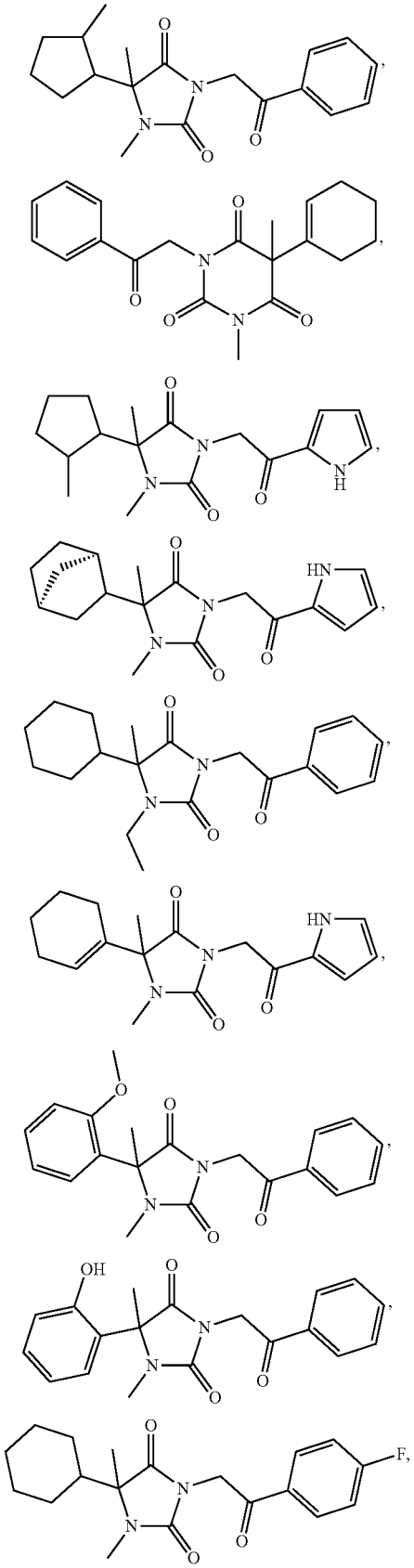

239
-continued
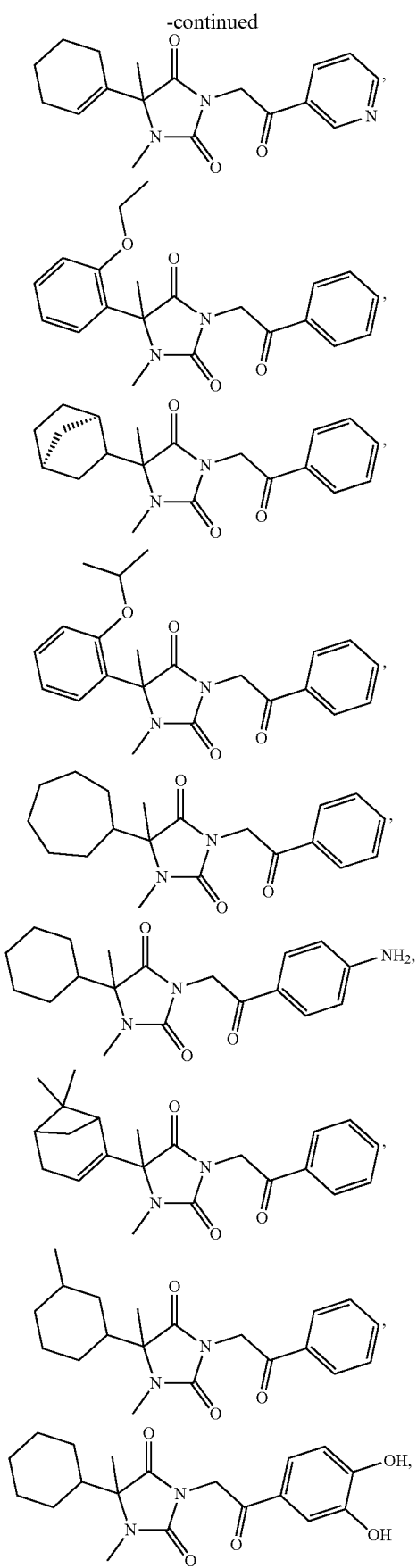
240
-continued
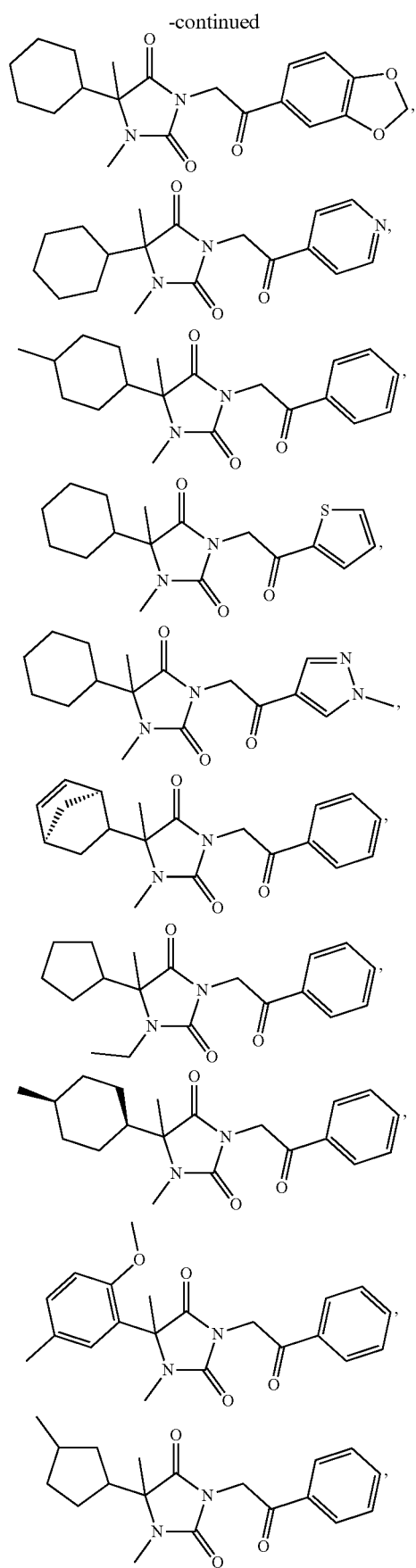

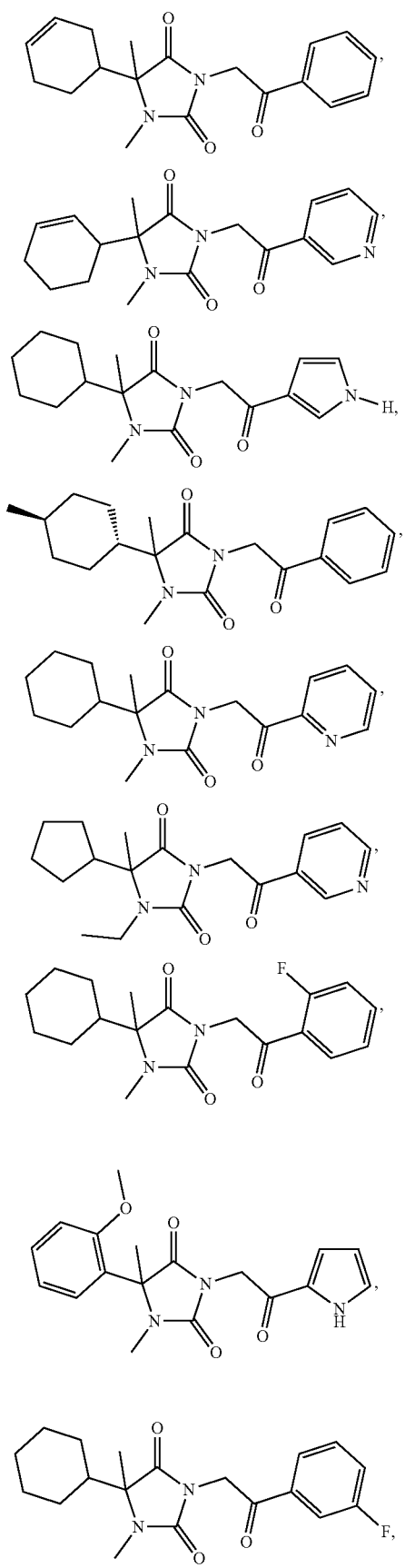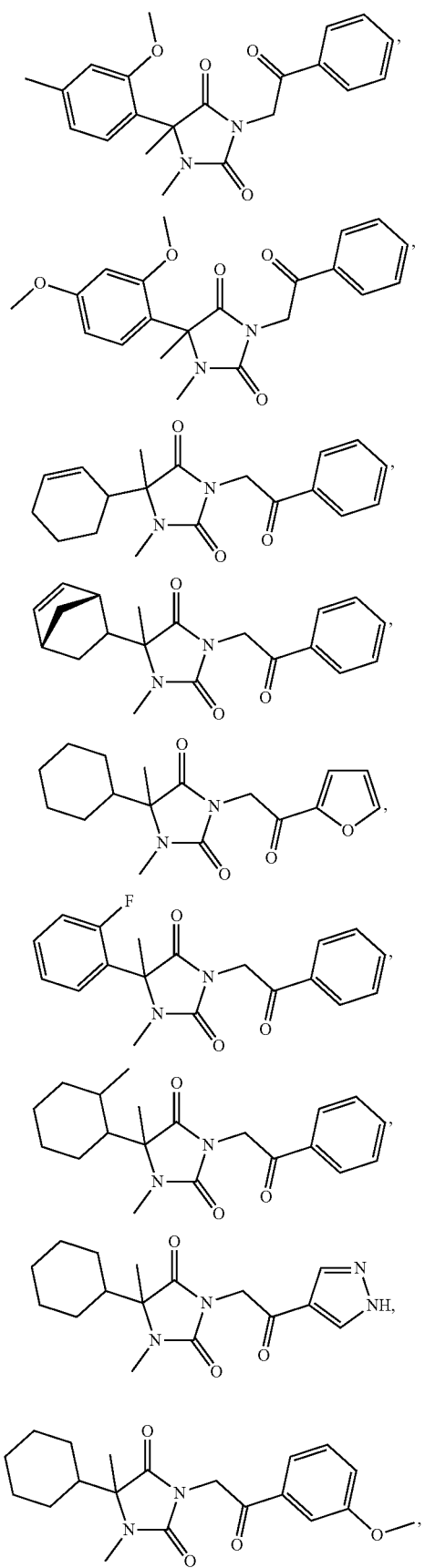

243
-continued
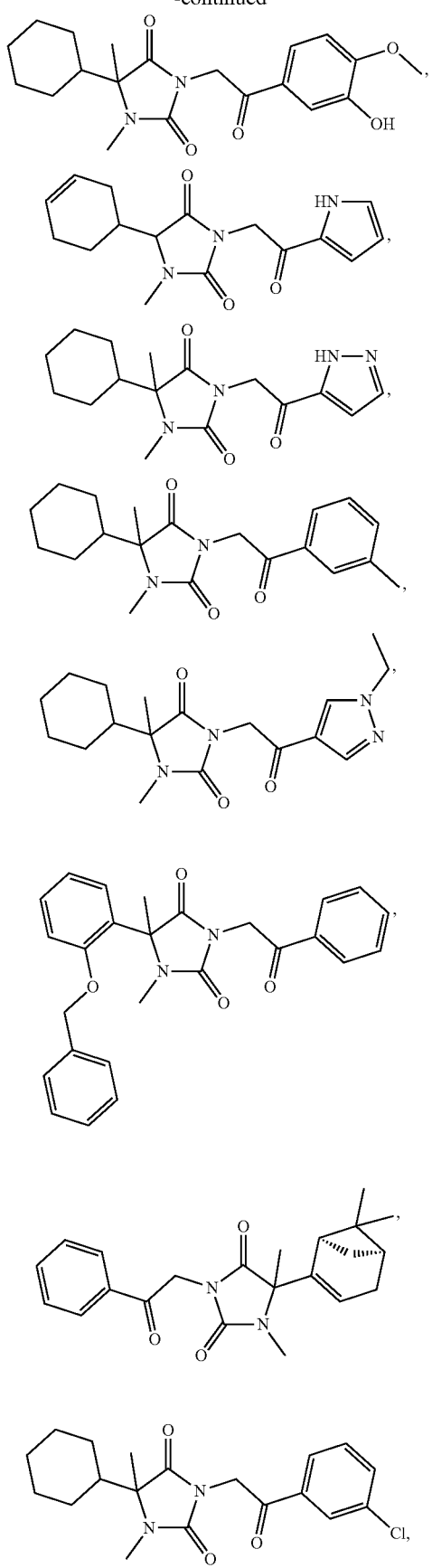
244
-continued
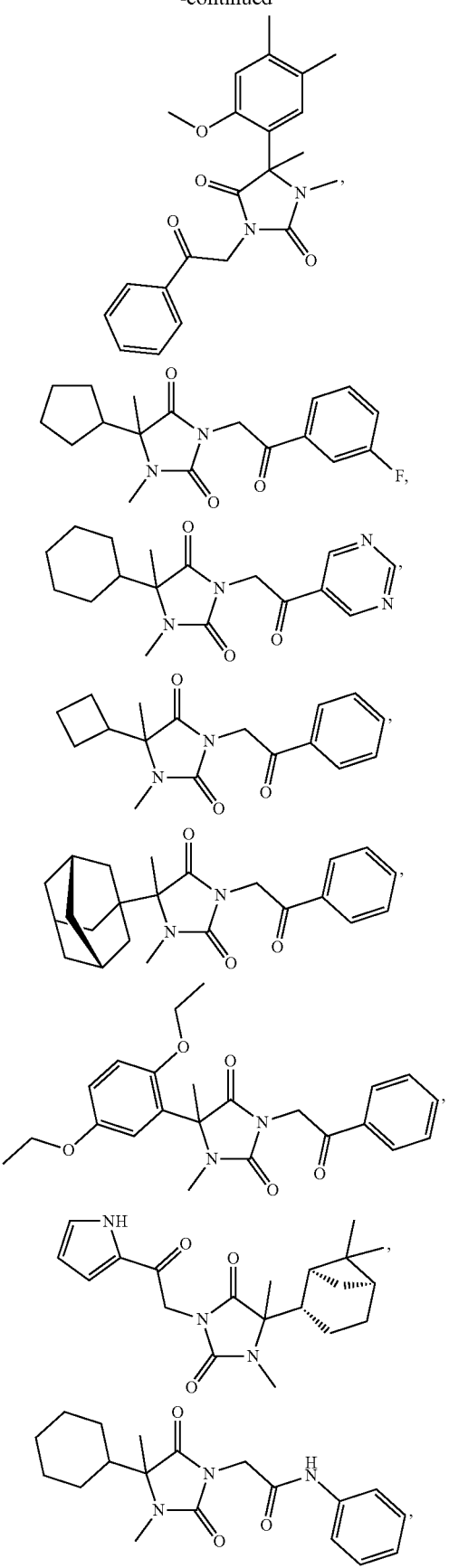

245
-continued

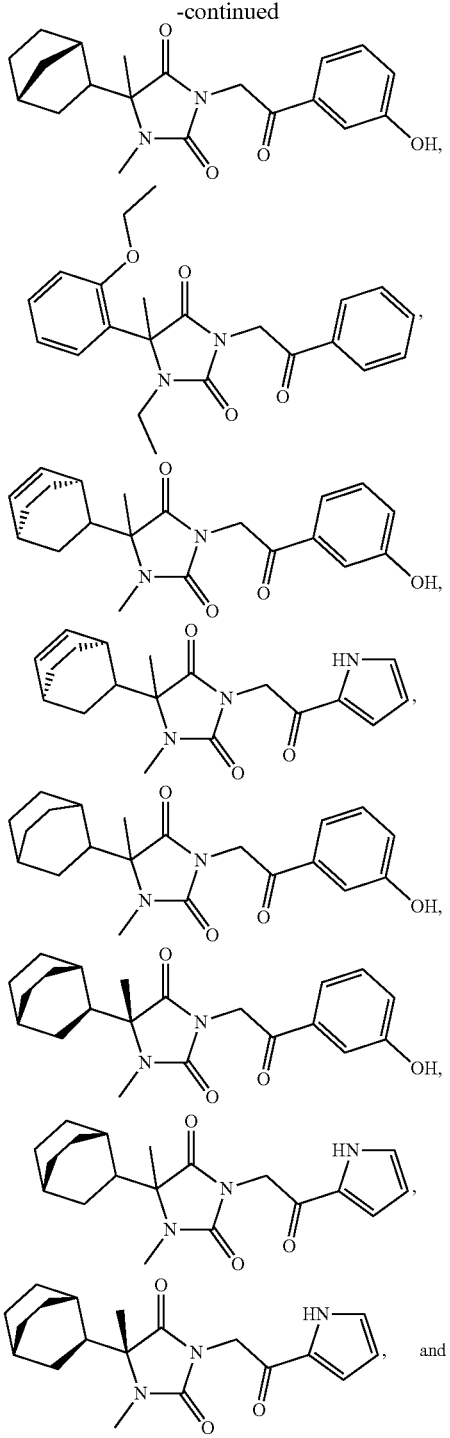

246
-continued

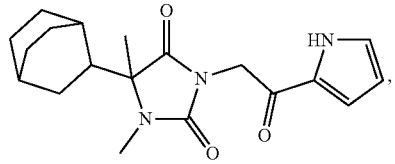

or a salt or solvate thereof.

3. The compound of claim 1, wherein the compound is

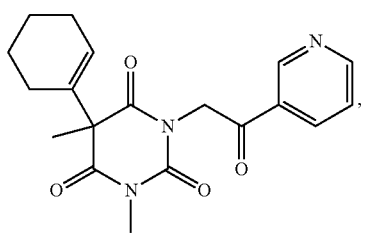 [SMILES: CN1C(=O)N(CC(=O)c2cccnc2)C(=O)C(C)(C2=CCCCC2)C1=O]

or a salt or solvate thereof.

4. A composition comprising a compound of claim 1, or a salt or solvate thereof; and at least one carrier.

5. The composition of claim 4, which is an ingestible composition or personal care composition.

6. The composition of claim 5, wherein the ingestible composition is a food or beverage.

7. The composition of claim 4, wherein the compound in the composition is in a concentration ranging from about 1 ppm to about 500 ppm.

8. The composition of claim 4, which is a textile product or a packaging material.

9. The composition of claim 5, wherein the composition is in the form of a solid, semisolid, plaster, solution, suspension, lotion, cream, foam, gel, paste, emulsion, or a combination thereof.

10. The compound of claim 1 or a salt or solvate thereof for use in a method of modulating transient receptor potential channel melastatin member 8 (TRPM8).

11. The compound of claim 1 or a salt or solvate thereof for use in either a) a method of modulating the cooling sensation of a composition, or b) a method of inducing a cooling sensation in a human or animal.

12. The compound of claim 10 or a salt or solvate thereof, wherein the compound is a TRPM8 receptor agonist.

* * * * *

UNITED STATES PATENT AND TRADEMARK OFFICE
CERTIFICATE OF CORRECTION

PATENT NO. : 11,028,052 B2  
APPLICATION NO. : 16/574657  
DATED : June 8, 2021  
INVENTOR(S) : Lyudmyla Chumakova Page 1 of 1

It is certified that error appears in the above-identified patent and that said Letters Patent is hereby corrected as shown below:

In the Claims

In Column 231, Line 48, Claim 2, delete "compound of claim 1," and insert --compound--.

Signed and Sealed this  
Second Day of November, 2021

Drew Hirshfeld  
*Performing the Functions and Duties of the*  
*Under Secretary of Commerce for Intellectual Property and*  
*Director of the United States Patent and Trademark Office*